US011925116B2

(12) United States Patent
Song et al.

(10) Patent No.: US 11,925,116 B2
(45) Date of Patent: Mar. 5, 2024

(54) COMPOUND FOR ORGANIC ELECTRONIC ELEMENT, ORGANIC ELECTRONIC ELEMENT USING THE SAME, AND AN ELECTRONIC DEVICE THEREOF

(71) Applicant: DUK SAN NEOLUX CO., LTD., Cheonan-si (KR)

(72) Inventors: Hyun Ju Song, Cheonan-si (KR); Jae Ho Kim, Cheonan-si (KR); Junggeun Lee, Cheonan-si (KR); Ki Hwan Yoon, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 0 days.

(21) Appl. No.: 18/318,279

(22) Filed: May 16, 2023

(65) Prior Publication Data

US 2023/0292612 A1 Sep. 14, 2023

Related U.S. Application Data

(63) Continuation-in-part of application No. 18/180,625, filed on Mar. 8, 2023, which is a continuation-in-part (Continued)

(30) Foreign Application Priority Data

Oct. 26, 2020 (KR) ........................ 10-2020-0139441

(51) Int. Cl.
*H10K 85/60* (2023.01)
*C07D 251/24* (2006.01)

(Continued)

(52) U.S. Cl.
CPC ....... *H10K 85/6574* (2023.02); *C07D 251/24* (2013.01); *C09K 11/06* (2013.01); *H10K 85/626* (2023.02); *H10K 85/631* (2023.02); *H10K 85/653* (2023.02); *H10K 85/654* (2023.02); *H10K 85/6572* (2023.02); *H10K 85/6576* (2023.02); *C07B 2200/05* (2013.01); *C09K 2211/1018* (2013.01); *H10K 50/11* (2023.02);

(Continued)

(58) Field of Classification Search
None
See application file for complete search history.

(56) References Cited

U.S. PATENT DOCUMENTS

2014/0367654 A1 12/2014 Kim et al.
2015/0303379 A1 10/2015 Lee et al.

(Continued)

FOREIGN PATENT DOCUMENTS

KR 10-2009-0079134 A 7/2009
KR 10-2016-0111780 A 9/2016

(Continued)

OTHER PUBLICATIONS

SciFinder Search, 4 pages, Apr. 7, 2021.
STN Search, 351 pages, Apr. 7, 2021.

*Primary Examiner* — Vu A Nguyen
(74) *Attorney, Agent, or Firm* — Vorys, Sater, Seymour and Pease LLP; Mih Suhn Koh

(57) ABSTRACT

Provide are a compound capable of improving the light-emitting efficiency, stability, and lifespan of an element, an organic electronic element using same, and an electronic device thereof.

16 Claims, 4 Drawing Sheets

Related U.S. Application Data of application No. 17/212,886, filed on Mar. 25, 2021, now Pat. No. 11,678,577, which is a continuation of application No. 17/096,790, filed on Nov. 12, 2020, now Pat. No. 11,063,226.

(51) Int. Cl.

| | |
|---|---|
| ***C09K 11/06*** | (2006.01) |
| ***H10K 50/11*** | (2023.01) |
| ***H10K 50/15*** | (2023.01) |
| ***H10K 50/16*** | (2023.01) |
| ***H10K 50/18*** | (2023.01) |
| ***H10K 101/10*** | (2023.01) |
| ***H10K 101/00*** | (2023.01) |

(52) U.S. Cl.

CPC ............. *H10K 50/15* (2023.02); *H10K 50/16* (2023.02); *H10K 50/18* (2023.02); *H10K 2101/10* (2023.02); *H10K 2101/90* (2023.02)

(56) References Cited

U.S. PATENT DOCUMENTS

2016/0133674 A1 5/2016 Lee et al.
2018/0072695 A1 3/2018 Byun et al.
2018/0123048 A1 5/2018 So et al.
2018/0151806 A2 5/2018 Park et al.
2018/0261774 A1 9/2018 Park et al.
2022/0131083 A1* 4/2022 Lee .................... H10K 85/6574
2023/0189639 A1* 6/2023 Lee ...................... C07D 495/04
257/40

FOREIGN PATENT DOCUMENTS

WO 2017/171420 A1 10/2017
WO 2019/124902 A1 6/2019
WO WO-2021101247 A1 * 5/2021 ........... C07D 405/12

* cited by examiner

COMPOUND FOR ORGANIC ELECTRONIC ELEMENT, ORGANIC ELECTRONIC ELEMENT USING THE SAME, AND AN ELECTRONIC DEVICE THEREOF

CROSS-REFERENCE TO RELATED APPLICATIONS

This application is a Continuation-In-Part of U.S. patent application Ser. No. 18/180,625 filed on Mar. 8, 2023, which was a Continuation-In-Part of U.S. patent application Ser. No. 17/212,886 filed on Mar. 25, 2021, which was a Continuation of U.S. patent application Ser. No. 17/096,790 filed on Nov. 12, 2020, now U.S. Pat. No. 11,063,226 issued on Jul. 13, 2021, which claims the benefit of priority from Korean Patent Application No. 10-2020-0139441 filed on Oct. 26, 2020, the contents of each of which are incorporated herein by reference in its entirety.

BACKGROUND

Technical Field

The present invention relates to a compound for an organic electronic element, an organic electronic element using the same, and an electronic device thereof.

Background Art

In general, organic light emitting phenomenon refers to a phenomenon that converts electric energy into light energy by using an organic material. An organic electronic element using an organic light emitting phenomenon usually has a structure including an anode, a cathode, and an organic material layer interposed therebetween.

Here, in order to increase the efficiency and stability of the organic electronic element, the organic material layer is often composed of a multi-layered structure composed of different materials, and for example, may include a hole injection layer, a hole transport layer, an emitting layer, an electron transport layer, an electron injection layer and the like.

A material used as an organic material layer in an organic electronic element may be classified into a light emitting material and a charge transport material, such as a hole injection material, a hole transport material, an electron transport material, an electron injection material and the like depending on its function. And the light emitting material can be classified into a high molecular weight type and a low molecular weight type according to the molecular weight, and according to the light emission mechanism, it can be classified into a fluorescent material derived from a singlet excited state of an electron and a phosphorescent material derived from a triplet excited state of an electron. Also, the light emitting material may be divided into blue, green, and red light emitting materials and yellow and orange light emitting materials necessary for realizing a better natural color according to the emission color.

However, when only one material is used as a light emitting material, due to intermolecular interaction, the maximum emission wavelength shifts to a longer wavelength, and there are problems in that the color purity is lowered or the device efficiency is reduced due to the emission attenuation effect, therefore in order to increase color purity and increase luminous efficiency through energy transfer, a host/dopant system may be used as a light emitting material. The principle is that when a small amount of a dopant having a smaller energy band gap than that of the host forming the emitting layer is mixed in the emitting layer, excitons generated in the emitting layer are transported to the dopant to emit light with high efficiency. At this time, since the wavelength of the host moves to the wavelength band of the dopant, light having a desired wavelength can be obtained according to the type of dopant used.

Currently, the portable display market is a large-area display, and the size thereof is increasing, and thus, more power consumption than the power consumption required for the existing portable display is required. Therefore, power consumption has become a very important factor for a portable display having a limited power supply such as a battery, and the problem of efficiency and lifespan must also be solved.

Efficiency, lifespan, and driving voltage are related to each other, and when the efficiency is increased, the driving voltage is relatively decreased, and as the driving voltage is decreased, crystallization of organic materials due to Joule heating generated during driving decreases, and consequently, the lifespan tends to increase. However, the efficiency cannot be maximized simply by improving the organic material layer. This is because, when the energy level and T1 value between each organic material layer, and the intrinsic properties (mobility, interfacial properties, etc.) of materials are optimally combined, long lifespan and high efficiency can be achieved at the same time.

Therefore, while delaying the penetration and diffusion of metal oxide from the anode electrode (ITO) into the organic layer, which is one of the causes of shortening the lifespan of the organic electronic element, it should have stable characteristics against Joule heating generated during device driving, and OLED devices are mainly formed by a deposition method, and it is necessary to develop a material that can withstand a long time during deposition, that is, a material with strong heat resistance.

That is, in order to fully exhibit the excellent characteristics of an organic electronic element, it should be preceded that the material constituting the organic material layer in the device, such as a hole injection material, a hole transport material, a light emitting material, an electron transport material, an electron injection material, etc., is supported by a stable and efficient material. But the development of a stable and efficient organic material layer material for an organic electronic element has not yet been sufficiently made. Therefore, the development of new materials is continuously required, and in particular, the development of a host material for the emitting layer is urgently required.

DETAILED DESCRIPTION OF THE INVENTION

Summary

In order to solve the problems of the above-mentioned background art, the present invention has revealed a compound having a novel structure, and when this compound is applied to an organic electronic element, it has been found that the luminous efficiency, stability and lifespan of the element can be significantly improved.

Accordingly, an object of the present invention is to provide a novel compound, an organic electronic element using the same, and an electronic device thereof.

Technical Solution

In one aspect, the present invention provides an organic electronic element comprising a first electrode; a second electrode; and an organic material layer formed between the first electrode and the second electrode, wherein the organic material layer includes an emitting layer, wherein the emitting layer is a phosphorescent emitting layer, and comprises a first host compound represented by Formula 1 and a second host compound represented by Formula 4 or Formula 5.

Formula 1

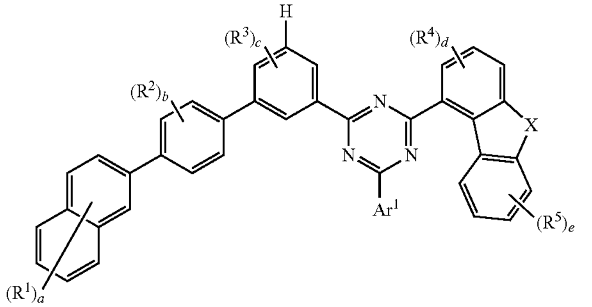

Formula 4

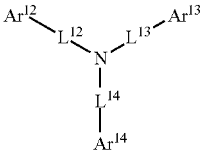

Formula 5

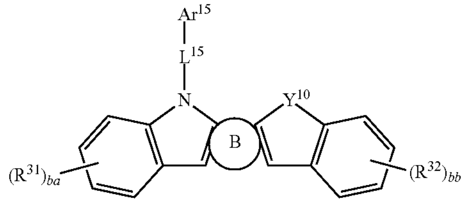

In another aspect, the present invention provides an electronic device comprising the organic electronic element.

In another aspect, the present invention provides a compound represented by Formula 1. Formula 1

Formula 1

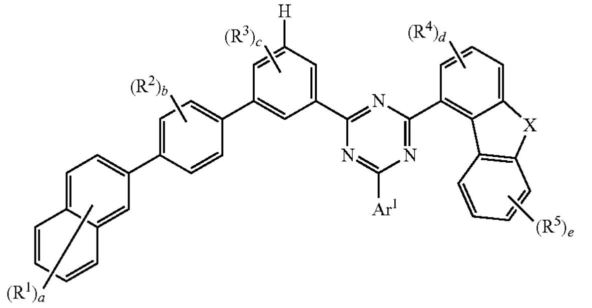

Effects of the Invention

By using the compound according to the present invention, high luminous efficiency, low driving voltage and high heat resistance of the element can be achieved, and color purity and lifespan of the element can be greatly improved.

Figure 1:
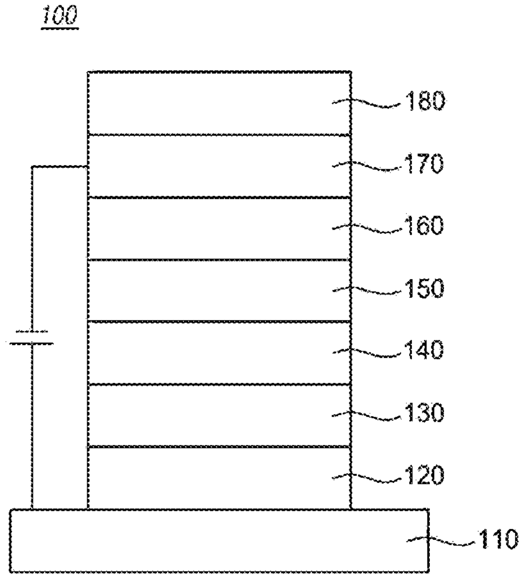
FIG. 1 to FIG. 3 are exemplary views of an organic electroluminescent device according to the present invention.

| | |
|---|---|
| 100, 200, 300: organic electronic element | 110: the first electrode |
| 120: hole injection layer | 130: hole transport layer |
| 140: emitting layer | 150: electron transport layer |
| 160: electron injection layer | 170: second electrode |
| 180: light efficiency enhancing Layer | 210: buffer layer |
| 220: emitting auxiliary layer | 320: first hole injection layer |
| 330: first hole transport layer | 340: first emitting layer |
| 350: first electron transport layer | 360: first charge generation layer |
| 361: second charge generation layer | 420: second hole injection layer |
| 430: second hole transport layer | 440: second emitting layer |
| 450: second electron transport layer | CGL: charge generation layer |
| ST1: first stack | ST2: second stack |

DETAILED DESCRIPTION

Hereinafter, some embodiments of the present invention will be described in detail. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if a component is described as being "connected", "coupled", or "connected" to another component, the component may be directly connected or connected to the other component, but another component may be "connected", "coupled" or "connected" between each component.

As used in the specification and the accompanying claims, unless otherwise stated, the following is the meaning of the term as follows.

Unless otherwise stated, the term "halo" or "halogen", as used herein, includes fluorine, bromine, chlorine, or iodine.

Unless otherwise stated, the term "alkyl" or "alkyl group", as used herein, has a single bond of 1 to 60 carbon atoms, and means saturated aliphatic functional radicals including a linear alkyl group, a branched chain alkyl group, a cycloalkyl group (alicyclic), an cycloalkyl group substituted with a alkyl or an alkyl group substituted with a cycloalkyl.

Unless otherwise stated, the term "alkenyl" or "alkynyl", as used herein, has double or triple bonds of 2 to 60 carbon atoms, but is not limited thereto, and includes a linear or a branched chain group.

Unless otherwise stated, the term "cycloalkyl", as used herein, means alkyl forming a ring having 3 to 60 carbon atoms, but is not limited thereto.

Unless otherwise stated, the term "alkoxyl group", "alkoxy group" or "alkyloxy group", as used herein, means an alkyl group bonded to oxygen radical, but is not limited thereto, and has 1 to 60 carbon atoms.

Unless otherwise stated, the term "aryloxyl group" or "aryloxy group", as used herein, means an aryl group bonded to oxygen radical, but is not limited thereto, and has 6 to 60 carbon atoms.

The terms "aryl group" and "arylene group" used in the present invention have 6 to 60 carbon atoms, respectively, unless otherwise specified, but are not limited thereto. In the present invention, an aryl group or an arylene group means a single ring or multiple ring aromatic, and includes an aromatic ring formed by an adjacent substituent joining or participating in a reaction.

For example, the aryl group may be a phenyl group, a biphenyl group, a fluorene group, or a spirofluorene group.

The prefix "aryl" or "ar" means a radical substituted with an aryl group. For example, an arylalkyl may be an alkyl substituted with an aryl, and an arylalkenyl may be an alkenyl substituted with aryl, and a radical substituted with an aryl has a number of carbon atoms as defined herein.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substituted with an arylcarbonyl, wherein the arylcarbonyl may be a carbonyl substituted with an aryl.

Unless otherwise stated, the term "heterocyclic group", as used herein, contains one or more heteroatoms, but is not limited thereto, has 2 to 60 carbon atoms, includes any one of a single ring or multiple ring, and may include heteroaliphadic ring and heteroaromatic ring. Also, the heterocyclic group may also be formed in conjunction with an adjacent group.

Unless otherwise stated, the term "heteroatom", as used herein, represents at least one of N, O, S, P, or Si.

Also, the term "heterocyclic group" may include a ring including $SO_2$ instead of carbon consisting of cycle. For example, "heterocyclic group" includes the following compound.

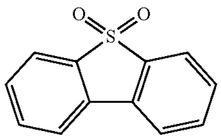 [SMILES: O=S1(=O)c2ccccc2-c2ccccc21]

Unless otherwise stated, the term "fluorenyl group" or "fluorenylene group", as used herein, means a monovalent or divalent functional group, in which R, R' and R" are all hydrogen in the following structures, and the term "substituted fluorenyl group" or "substituted fluorenylene group" means that at least one of the substituents R, R', R" is a substituent other than hydrogen, and include those in which R and R' are bonded to each other to form a spiro compound together with the carbon to which they are bonded.

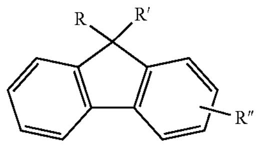

The term "spiro compound", as used herein, has a 'spiro union', and a spiro union means a connection in which two rings share only one atom. At this time, atoms shared in the two rings are called 'spiro atoms', and these compounds are called 'monospiro-', 'di-spiro-' and 'tri-spiro-', respectively, depending on the number of spiro atoms in a compound.

Unless otherwise stated, the term "aliphatic", as used herein, means an aliphatic hydrocarbon having 1 to 60 carbon atoms, and the term "aliphatic ring", as used herein, means an aliphatic hydrocarbon ring having 3 to 60 carbon atoms.

Unless otherwise stated, the term "ring", as used herein, means an aliphatic ring having 3 to 60 carbon atoms, or an aromatic ring having 6 to 60 carbon atoms, or a hetero ring having 2 to 60 carbon atoms, or a fused ring formed by the combination of them, and includes a saturated or unsaturated ring.

Other hetero compounds or hetero radicals other than the above-mentioned hetero compounds include, but are not limited thereto, one or more heteroatoms.

Also, unless expressly stated, as used herein, "substituted" in the term "substituted or unsubstituted" means substituted with one or more substituents selected from the group consisting of deuterium, halogen, an amino group, a nitrile group, a nitro group, a $C_1$-$C_{20}$ alkyl group, a $C_1$-$C_{20}$ alkoxyl group, a $C_1$-$C_{20}$ alkylamine group, a $C_1$-$C_{20}$ allylthiophene group, a $C_6$-$C_{20}$ arylthiopen group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group, but is not limited to these substituents.

Also, unless there is an explicit explanation, the formula used in the present invention is the same as the definition of the substituent by the exponent definition of the following formula.

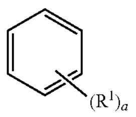

Here, when a is an integer of 0, the substituent $R^1$ is absent, when a is an integer of 1, the sole substituent $R^1$ is linked to any one of the carbon constituting the benzene ring, when a is an integer of 2 or 3, each is combined as follows, where $R^1$ may be the same or different from each other, when a is an integer of 4 to 6, it is bonded to the carbon of the benzene ring in a similar manner, while the indication of the hydrogen bonded to the carbon forming the benzene ring is omitted.

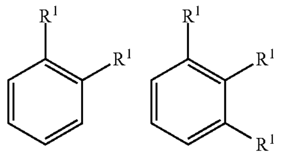

(a = 2) (a = 3)

Bond-Dissociation Energy is a calculation of the binding energy for an acyclic bond in a molecule. For this purpose, the electric potential energy of the target molecule is calculated and the electrical potential energy is calculated for each by dividing it into 2 radical molecules based on the non-cyclic bond, and Bond-dissociation energy can be expressed as:

$$E_{BD}=E_A^{rod}+E_B^{rad}-E_{AB}^{mol}$$

All calculations are performed assuming an electrically neutral state, and Bond-dissociation energy is calculated by proceeding with molecular Geometric Optimization calculation.

$E_{BD}$ =

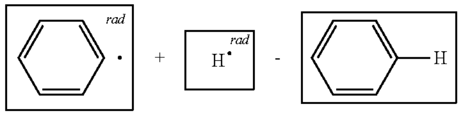

Hereinafter, a laminated structure of an organic electronic element including the compound of the present invention will be described with reference to FIGS. 1 to 3.

In adding reference numerals to the components of each figures, it should be noted that the same components have the same numerals as much as possible even if they are displayed on different figures. In addition, in describing the present invention, if it is determined that a detailed description of a related known configuration or function may obscure the gist of the present invention, the detailed description will be omitted.

Figure 2:
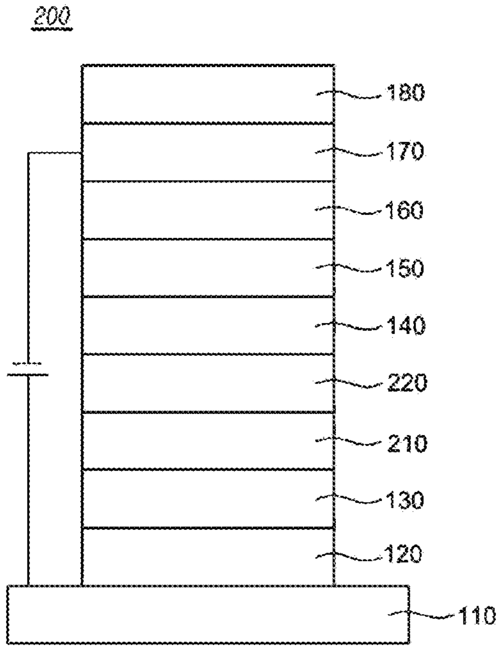
Figure 3:
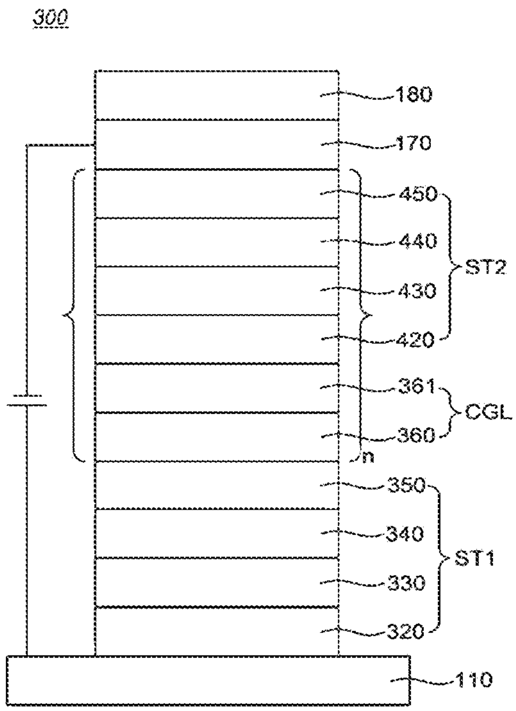
Figure 4:
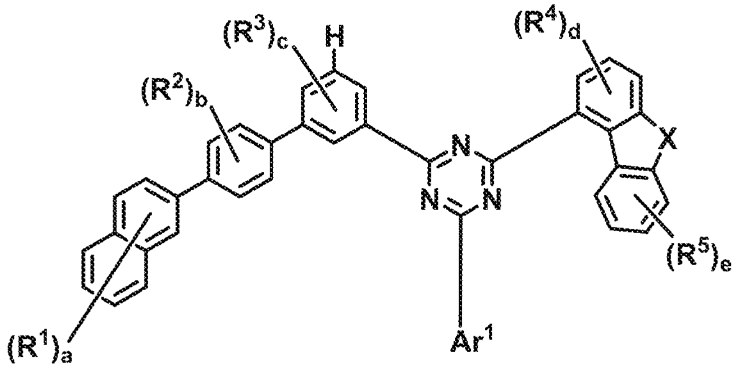
FIG. 4 shows a formula according to one aspect of the present invention.

FIGS. 1 to 3 are exemplary views of an organic electronic element according to an embodiment of the present invention.

Referring to FIG. 1, an organic electronic element (100) according to an embodiment of the present invention comprises a first electrode (110), a second electrode (170) formed on a substrate (not shown), and an organic layer formed between the first electrode (110) and the second electrode (170).

The first electrode (110) may be an anode, the second electrode (170) may be a cathode, and in the case of an inverted type, the first electrode may be a cathode and the second electrode may be an anode.

The organic material layer may include a hole injection layer (120), a hole transport layer (130), an emitting layer (140), an electron transport layer (150), and an electron injection layer (160). Specifically, a hole injection layer (120), a hole transport layer (130), an emitting layer (140), an electron transport layer (150), and an electron injection layer (160) may be sequentially formed on the first electrode (110).

Preferably, a light efficiency enhancing layer (180) may be formed on at least one surface of the first electrode (110) and the second electrode (170), the surface being opposite to the organic material layer, and when the light efficiency enhancing layer (180) is formed, the light efficiency of the organic electronic element may be improved.

For example, the light efficiency enhancing layer (180) may be formed on the second electrode (170), and in the case of a top emission organic light emitting device, the light efficiency enhancing layer (180) is formed, thereby reducing optical energy loss due to surface plasmon polaritons (SPPs) in the second electrode (170), and in the case of a bottom emission organic light emitting device, the light efficiency enhancing layer (180) may function as a buffer for the second electrode (170).

A buffer layer (210) or an emitting auxiliary layer (220) may be further formed between the hole transport layer (130) and the emitting layer (140), which will be described with reference to FIG. 2.

Referring to FIG. 2, an organic electric device (200) according to another embodiment of the present invention includes a hole injection layer (120), a hole transport layer (130), a buffer layer (210), an emitting auxiliary layer (220), an emitting layer (140), an electron transport layer (150), an electron injection layer (160), a second electrode (170), sequentially formed on the first electrode (110), and a light efficiency enhancing layer (180) formed on the second electrode.

Although not shown in FIG. 2, an electron transport auxiliary layer may be further formed between the emitting layer (140) and the electron transport layer (150).

Also, according to another embodiment of the present invention, the organic material layer may have a plurality of stacks including a hole transport layer, an emitting layer and an electron transport layer. This will be described with reference to FIG. 3.

Referring to FIG. 3, in the organic electronic element (300) according to another embodiment of the present invention, 2 or more sets of stacks (ST1 and ST2) made of a multi-layered organic material layer may be formed between the first electrode (110) and the second electrode (170), and a charge generation layer (CGL) may be formed between the stacks of organic material layers.

Specifically, the organic electronic element according to an embodiment of the present invention may include a first electrode (110), a first stack (ST1), a charge generation layer (CGL), a second stack (ST2), and a second electrode (170) and a light efficiency enhancing layer (180).

The first stack (ST1) is an organic material layer formed on the first electrode (110) and may include a first hole injection layer (320), a first hole transport layer (330), a first emitting layer (340), and a first electron transport layer (350), and the second stack (ST2) may include a second hole injection layer (420), a second hole transport layer (430), a second emitting layer (440), and a second electron transport layer (450). As described above, the first stack and the second stack may be organic material layers having the same laminated structure, but may be organic material layers having different laminated structures.

A charge generation layer (CGL) may be formed between the first stack (ST1) and the second stack (ST2). The charge generation layer (CGL) may include a first charge generation layer (360) and a second charge generation layer (361). The charge generation layer (CGL) is formed between the first emitting layer (340) and the second emitting layer (440) to increase the current efficiency generated in each emitting layer and smoothly distribute charge.

When a plurality of emitting layers are formed by the multilayer stack structure method as shown in FIG. 3, an organic electronic element that emits white light by a mixing effect of light emitted from each emitting layer can be manufactured, as well as an organic electronic element that emits light of various colors.

The compounds represented by Formula 1, Formula 4 and 5 of the present invention may be used as a material for a hole injection layer (120, 320, 420), a hole transport layer (130, 330, 430), a buffer layer (210), an emitting auxiliary layer (220), and an electron transport layer (150, 350, 450), the electron injection layer (160), the emitting layer (140, 340, 440), or the light efficiency enhancing layer (180), but preferably, as a host of the emitting layers (140, 340, 440).

Otherwise, even if the same or similar core is used, the band gap, the electrical characteristics, the interface characteristics, and the like may vary depending on which substituent is bonded at which position, therefore it is necessary to study the selection of the core and the combination of sub-substituents bonded thereto, and in particular, when the optimal combination of energy levels and T1 values of each organic material layer and unique properties of materials (mobility, interfacial characteristics, etc.) is achieved, a long lifespan and high efficiency can be achieved at the same time.

The organic light emitting device according to an embodiment of the present invention may be manufactured using various deposition methods. It can be manufactured using a vapor deposition method such as PVD or CVD. For example, an anode (110) is formed by depositing a metal or a conductive metal oxide or an alloy thereof on a substrate, and after forming an organic material layer including the hole injection layer(120), the hole transport layer(130), the emitting layer(140), the electron transport layer(150) and the electron injection layer(160) thereon, the organic electroluminescent device according to an embodiment of the present invention can be manufactured by depositing a material that can be used as a cathode (170) thereon. Also, an emitting auxiliary layer (220) may be further formed between the hole transport layer(130) and the emitting layer(140), and an electron transport auxiliary layer (not shown) may be further formed between the emitting layer(140) and the electron transport layer (150), and as described above, may be formed in a stack structure.

Also, the organic material layer may be manufactured with a smaller number of layers by using various polymer materials and not by a deposition method, but by a solution process or a solvent process, such as a spin coating process, a nozzle printing process, an inkjet printing process, a slot coating process, a dip coating process or a roll-to-roll process, doctor blading process, screen printing process, or a thermal transfer method, etc. Since the organic material layer according to the present invention can be formed by various methods, the scope of the present invention is not limited by the forming method.

In addition, the organic electronic element according to an embodiment of the present invention may be selected from the group consisting of an organic electroluminescent device, an organic solar cell, an organic photoreceptor, an organic transistor, a monochromatic lighting device, and a quantum dot display device.

Another embodiment of the present invention may comprise an electronic device comprising a display device including the organic electronic element of the present invention; and a control unit for driving the display device. At this time, the electronic device may be a current or future wired/wireless communication terminal, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, an organic electronic element according to an aspect of the present invention will be described.

The present invention provides an organic electronic element comprising a first electrode, a second electrode, and an organic material layer formed between the first electrode and the second electrode, wherein the organic material layer comprises an emitting layer, wherein the emitting layer comprises a first host compound represented by Formula 1 and a second host compound represented by Formula 4 or Formula 5 as the phosphorescent emitting layer.

Formula 1

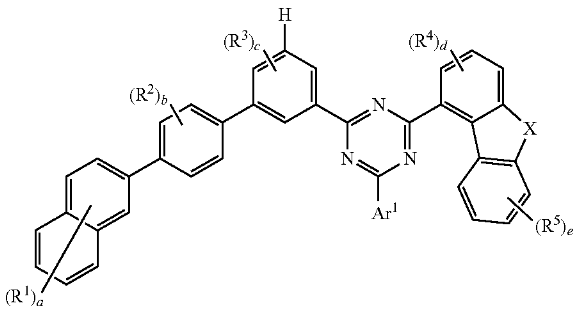

Formula 4

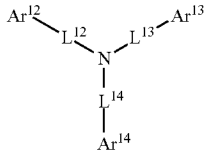

Formula 5

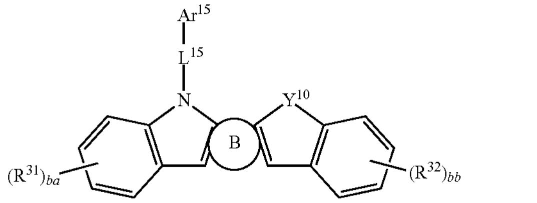

In Formula 1, Formula 4 and Formula 5, each symbol may be defined as follows.

In Formula 1, $R^1$, $R^2$ and $R^3$ are each the same or different, and each independently hydrogen; or deuterium;

$R^4$ and $R^5$ are each the same or different, and each independently selected from the group consisting of hydrogen; deuterium; a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring; a $C_3$-$C_{60}$ aliphatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; and a $C_6$-$C_{30}$ aryloxy group; or an adjacent plurality of $R^4$ and plurality of $R^5$ may be bonded to each other to form a ring.

When $R^4$ and $R^5$ are an aryl group, it is preferably an $C_6$-$C_{30}$ aryl group, more preferably an $C_6$-$C_{25}$ aryl group, for example, it may be phenyl, biphenyl, terphenyl, naphthalene, phenanthrene and the like.

When $R^4$ and $R^5$ are a heterocyclic group, it is preferably a $C_2$-$C_{30}$ heterocyclic group, and more preferably a $C_2$-$C_{24}$ heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, etc.

When $R^4$ and $R^5$ are a fused ring group, it is preferably a fused ring group of a $C_3$-$C_{30}$ aliphatic ring and an $C_6$-$C_{30}$ aromatic ring, and more preferably a fused ring group of an $C_3$-$C_{24}$ aliphatic ring and an $C_6$-$C_{24}$ aromatic ring.

When $R^4$ and $R^5$ are an aliphatic ring group, it is preferably a $C_3$-$C_{30}$ aliphatic ring group, more preferably a $C_3$-$C_{24}$ aliphatic ring group.

When $R^4$ and $R^5$ are an alkyl group, it is preferably a $C_1$-$C_{30}$ alkyl group, and more preferably a $C_1$-$C_{24}$ alkyl group.

When $R^4$ and $R^5$ are an alkoxyl group, it is preferably a $C_1$-$C_{24}$ alkoxyl group.

When $R^4$ and $R^5$ are an aryloxy group, it is preferably a $C_6$-$C_{24}$ aryloxy group.

X is O or S, $Ar^1$ is each independently selected from the group consisting of a $C_6$-$C_{60}$ aryl group; a fluorenyl group; a $C_2$-$C_{60}$ heterocyclic group including at least one hetero atom of O, N, S, Si or P; and a fused ring group of a $C_3$-$C_{60}$ aliphatic ring and a $C_6$-$C_{60}$ aromatic ring;

When $Ar^1$ is an aryl group, it is preferably an $C_6$-$C_{30}$ aryl group, more preferably an $C_6$-$C_{25}$ aryl group, for example, it may be phenyl, biphenyl, terphenyl, naphthalene, phenanthrene and the like.

When $Ar^1$ is a heterocyclic group, it is preferably a $C_2$-$C_{30}$ heterocyclic group, and more preferably a $C_2$-$C_{24}$ heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, etc.

When $Ar^1$ is a fused ring group, it is preferably a fused ring group of a $C_3$-$C_{30}$ aliphatic ring and an $C_6$-$C_{30}$ aromatic ring, and more preferably a fused ring group of an $C_3$-$C_{24}$ aliphatic ring and an $C_6$-$C_{24}$ aromatic ring.

a is an integer from 0 to 7, b and e are each independently an integer from 0 to 4, c and d are each independently an integer from 0 to 3, In Formula 4 and Formula 5, Ring B is an $C_6$-$C_{20}$ aryl group, $Y^{10}$ is O, S, $CR^{51}R^{52}$ or $NR^{53}$, $Ar^{12}$, $Ar^{13}$ and $Ar^{14}$ are each independently selected from the group consisting of an $C_6$-$C_{60}$ aryl group; a fluorenyl group; a $C_2$-$C_{60}$ heterocyclic group including at least one heteroatom of O, N, S, Si or P; and a fused ring group of a $C_3$-$C_{60}$ aliphatic ring and a $C_6$-$C_{60}$ aromatic ring;

When $Ar^{12}$, $Ar^{13}$ and $Ar^{14}$ are an aryl group, it is preferably an $C_6$-$C_{30}$ aryl group, more preferably an $C_6$-$C_{25}$ aryl group, for example, it may be phenyl, biphenyl, terphenyl, naphthalene, phenanthrene and the like.

When $Ar^{12}$, $Ar^{13}$ and $Ar^{14}$ are a heterocyclic group, it is preferably a $C_2$-$C_{30}$ heterocyclic group, and more preferably a $C_2$-$C_{24}$ heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, etc.

When $Ar^{12}$, $Ar^{13}$ and $Ar^{14}$ are a fused ring group, it is preferably a fused ring group of a $C_3$-$C_{30}$ aliphatic ring and an $C_6$-$C_{30}$ aromatic ring, and more preferably a fused ring group of an $C_3$-$C_{24}$ aliphatic ring and an $C_6$-$C_{24}$ aromatic ring.

$Ar^{15}$ is each independently selected from the group consisting of an $C_6$-$C_{60}$ aryl group; a fluorenyl group; a $C_2$-$C_{60}$ heterocyclic group including at least one heteroatom of O, N, S, Si or P; and a fused ring group of a $C_3$-$C_{60}$ aliphatic ring and a $C_6$-$C_{60}$ aromatic ring; and -L"-$NR^fR^g$;

When $Ar^{15}$ is an aryl group, it is preferably an $C_6$-$C_{30}$ aryl group, more preferably an $C_6$-$C_{25}$ aryl group, for example, it may be phenyl, biphenyl, terphenyl, naphthalene, phenanthrene and the like.

When $Ar^{15}$ is a heterocyclic group, it is preferably a $C_2$-$C_{30}$ heterocyclic group, and more preferably a $C_2$-$C_{24}$ heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, etc.

When $Ar^{15}$ is a fused ring group, it is preferably a fused ring group of a $C_3$-$C_{30}$ aliphatic ring and an $C_6$-$C_{30}$ aromatic ring, and more preferably a fused ring group of an $C_3$-$C_{24}$ aliphatic ring and an $C_6$-$C_{24}$ aromatic ring.

$L^{12}$, $L^{13}$, $L^{14}$, $L^{15}$ and L" are each independently selected from the group consisting of single bond; a $C_6$-$C_{60}$ arylene group; a fluorenylene group; a fused ring group of a $C_3$-$C_{60}$ aliphatic ring and a $C_6$-$C_{60}$ aromatic ring; a $C_2$-$C_{60}$ heterocyclic group including at least one heteroatom of O, N, S, Si or P;

When $L^{12}$, $L^{13}$, $L^{14}$, $L^{15}$ and L" are an arylene group, an arylene group, it is preferably an $C_6$-$C_{30}$ arylene group, more preferably an $C_6$-$C_{25}$ arylene group, for example, it may be phenylene, biphenylene, naphthylene, terphenylene, anthracenylene, and the like.

When $L^{12}$, $L^{13}$, $L^{14}$, $L^{15}$ and L" are a heterocyclic group, it is preferably a $C_2$-$C_{30}$ heterocyclic group, and more preferably a $C_2$-$C_{24}$ heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, etc.

When $L^{12}$, $L^{13}$, $L^{14}$, $L^{15}$ and L" are a fused ring group, it is preferably a fused ring group of an $C_3$-$C_{30}$ aliphatic ring and an $C_6$-$C_{30}$ aromatic ring, and more preferably a fused ring group of an $C_3$-$C_{24}$ aliphatic ring and an $C_6$-$C_{24}$ aromatic ring.

$R^{31}$ and $R^{32}$ are each the same or different, and each independently selected from the group consisting of hydrogen; deuterium; halogen; cyano group; nitro group; a $C_6$-$C_{60}$ aryl group; fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; or an adjacent plurality of $R^{31}$ or a plurality of $R^{32}$ may be bonded to each other to form a ring, When $R^{31}$ and $R^{32}$ are an aryl group, it is preferably a $C_6$-$C_{30}$ aryl group, more preferably an $C_6$-$C_{25}$ aryl group, for example, it may be phenyl, biphenyl, terphenyl, naphthalene, phenanthrene and the like.

When $R^{31}$ and $R^{32}$ are a heterocyclic group, it is preferably a $C_2$-$C_{30}$ heterocyclic group, and more preferably a $C_2$-$C_{24}$ heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, etc.

When $R^{31}$ and $R^{32}$ are a fused ring group, it is preferably a fused ring group of a $C_3$-$C_{30}$ aliphatic ring and an $C_6$-$C_{30}$ aromatic ring, and more preferably a fused ring group of an $C_3$-$C_{24}$ aliphatic ring and an $C_6$-$C_{24}$ aromatic ring.

$R^{51}$, $R^{52}$ and $R^{53}$ are each independently selected from the group consisting of a $C_6$-$C_{60}$ aryl group; fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{60}$ alkenyl group; a $C_2$-$C_{60}$ alkynyl group; a $C_1$-$C_{50}$ alkoxy group; and a $C_6$-$C_{60}$ aryloxy group; or $R^{51}$ and $R^{52}$ may be bonded to each other to form a ring;

When $R^{51}$, $R^{52}$ and $R^{53}$ are an aryl group, it is preferably an $C_6$-$C_{30}$ aryl group, more preferably an $C_6$-$C_{25}$ aryl group, for example, it may be phenyl, biphenyl, terphenyl, naphthalene, phenanthrene and the like.

When $R^{51}$, $R^{52}$ and $R^{53}$ are a heterocyclic group, it is preferably a $C_2$-$C_{30}$ heterocyclic group, and more preferably a $C_2$-$C_{24}$ heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, etc.

When $R^{51}$, $R^{52}$ and $R^{53}$ are a fused ring group, it is preferably a fused ring group of an $C_3$-$C_{30}$ aliphatic ring and an $C_6$-$C_{30}$ aromatic ring, and more preferably a fused ring group of an $C_3$-$C_{24}$ aliphatic ring and an $C_6$-$C_{24}$ aromatic ring.

When $R^{51}$, $R^{52}$ and $R^{53}$ are an alkyl group, it is preferably a $C_1$-$C_{30}$ alkyl group, and more preferably a $C_1$-$C_{24}$ alkyl group.

When $R^{51}$, $R^{52}$ and $R^{53}$ are an alkenyl group, it is preferably a $C_2$-$C_{30}$ alkenyl group, and more preferably a $C_2$-$C_{24}$ alkenyl group.

When $R^{51}$, $R^{52}$ and $R^{53}$ are an alkynyl group, it is preferably a $C_2$-$C_{30}$ alkynyl group, and more preferably a $C_2$-$C_{24}$ alkynyl group.

When $R^{51}$, $R^{52}$ and $R^{53}$ are an alkoxyl group, it is preferably a $C_1$-$C_{24}$ alkoxyl group.

When $R^{51}$, $R^{52}$ and $R^{53}$ are an aryloxy group, it is preferably a $C_6$-$C_{24}$ aryloxy group.

$R^f$ and $R^g$ are each independently selected from the group consisting of a $C_6$-$C_{60}$ aryl group; fluorenyl group; a $C_2$-$C_{60}$ heterocyclic group including at least one heteroatom of O, N, S, Si or P; and a $C_3$-$C_{60}$ aliphatic ring;

When $R^f$ and $R^g$ are an aryl group, it is preferably an $C_6$-$C_{30}$ aryl group, more preferably an $C_6$-$C_{25}$ aryl group, for example, it may be phenyl, biphenyl, terphenyl, naphthalene, phenanthrene and the like.

When $R^f$ and $R^g$ are a heterocyclic group, it is preferably a $C_2$-$C_{30}$ heterocyclic group, and more preferably a $C_2$-$C_{24}$ heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, etc.

When $R^f$ and $R^g$ are an aliphatic ring, it is preferably a $C_3$-$C_{30}$ aliphatic groups, more preferably $C_3$-$C_{24}$ aliphatic groups.

ba and bb are each independently integers from 0 to 4, wherein the aryl group, arylene group, heterocyclic group, fluorenyl group, fluorenylene group, aliphatic ring group, fused ring group, alkyl group, alkenyl group, alkynyl group, alkoxyl group and aryloxy group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxy group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; $C_3$-$C_{20}$ cycloalkyl group; $C_7$-$C_{20}$ arylalkyl group; and $C_8$-$C_{20}$ arylalkenyl group; also the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

Also, $Ar^1$ is represented by any one of Formulas (Ar-1) to (Ar-12).

Formula (Ar-1)

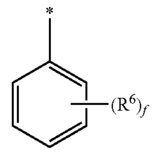

Formula (Ar-2)

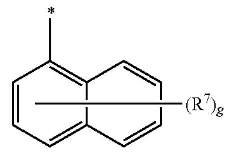

Formula (Ar-3)

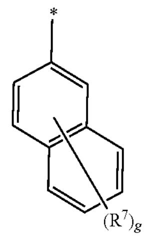

Formula (Ar-4)

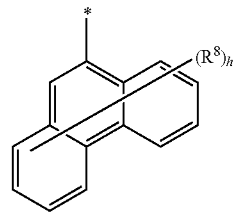

Formula (Ar-5)

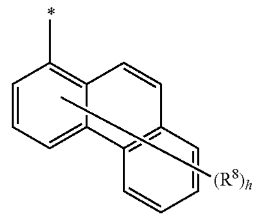

Formula (Ar-6)

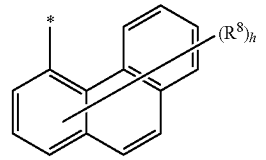

-continued

Formula (Ar-7)

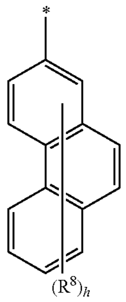

Formula (Ar-8)

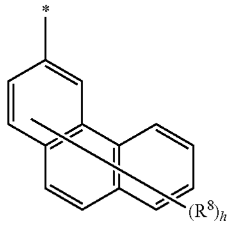

Formula (Ar-9)

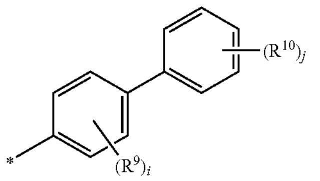

Formula (Ar-10)

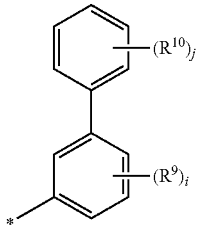

Formula (Ar-11)

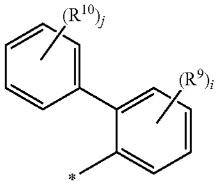

Formula (Ar-12)

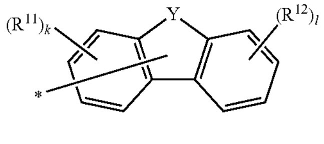

Wherein, $R^6$, $R^7$, $R^8$, $R^9$, $R^{10}$, $R^{11}$ and $R^{12}$ are the same as the definition of $R^4$, or an adjacent plurality of $R^6$, or plurality of $R^7$, or plurality of $R^8$, or plurality of $R^9$, or plurality of $R^{10}$, or plurality of $R^{11}$, or plurality of $R^{12}$ may be bonded to each other to form a ring, $R^6$, $R^7$, $R^8$, $R^9$, $R^{10}$, $R^{11}$ and $R^{12}$ are more preferably hydrogen; deuterium; $C_6$-$C_{20}$ aryl group; or $C_6$-$C_{20}$ aryl group substituted with deuterium;

Y is O, S, $CR^{13}R^{14}$, $NR^{15}$ or $SiR^{16}R^{17}$, provided that when Y is bonded to Formula 1, it is -$L^1$-N, $R^{13}$, $R^{14}$, $R^{15}$, $R^{16}$ and $R^{17}$ are each independently selected from the group consisting of hydrogen; deuterium; a $C_1$-$C_{50}$ alkyl group; a $C_6$-$C_{60}$ aryl group; and a $C_2$-$C_{60}$ heterocyclic group including at least one hetero atom of O, N, S, Si or P; alternatively, $R^{13}$ and $R^{14}$ or $R^{16}$ and $R^{17}$ may be bonded to each other to form a spiro, When $R^{13}$, $R^{14}$, $R^{15}$, $R^{16}$ and $R^{17}$ are an alkyl group, it is preferably a $C_1$-$C_{30}$ alkyl group, and more preferably a $C_1$-$C_{24}$ alkyl group.

When $R^{13}$, $R^{14}$, $R^{15}$, $R^{16}$ and $R^{17}$ are an aryl group, it is preferably an $C_6$-$C_{30}$ aryl group, more preferably an $C_6$-$C_{25}$ aryl group, for example, it may be phenyl, biphenyl, terphenyl, naphthalene, phenanthrene and the like.

When $R^{13}$, $R^{14}$, $R^{15}$, $R^{16}$ and $R^{17}$ are a heterocyclic group, it is preferably a $C_2$-$C_{30}$ heterocyclic group, and more preferably a $C_2$-$C_{24}$ heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, etc.

$L^1$ is each independently selected from the group consisting of single bond; a $C_6$-$C_{60}$ arylene group; a fluorenylene group; a fused ring group of a $C_3$-$C_{60}$ aliphatic ring and a $C_6$-$C_{60}$ aromatic ring; a $C_2$-$C_{60}$ heteroarylene group including at least one heteroatom of O, N, S, Si or P;

When $L^1$ is an arylene group, it is preferably an $C_6$-$C_{30}$ arylene group, more preferably an $C_6$-$C_{25}$ arylene group, for example, it may be phenylene, biphenylene, naphthylene, terphenylene, anthracenylene, and the like.

When $L^1$ is a fused ring group, it is preferably a fused ring group of an $C_3$-$C_{30}$ aliphatic ring and an $C_6$-$C_{30}$ aromatic ring, and more preferably a fused ring group of an $C_3$-$C_{24}$ aliphatic ring and an $C_6$-$C_{24}$ aromatic ring.

When $L^1$ is a heteroarylene group, it is preferably a $C_2$-$C_{30}$ heteroarylene group, and more preferably a $C_2$-$C_{24}$ heteroarylene group.

f and j are each independently an integer from 0 to 5, g is an integer from 0 to 7, h is an integer from 0 to 9, i, k and l are an integer from 0 to 4,

* means the position to be bonded.

Also, Formula Ar-12 is preferably represented by any one of Formula Ar-12-1 to Formula Ar-12-5.

Formula Ar-12-1

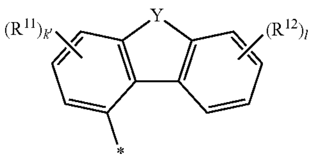

Formula Ar-12-2

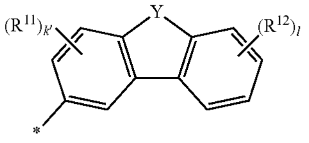

Formula Ar-12-3

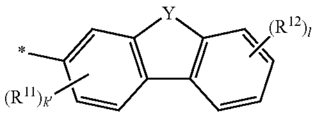

Formula Ar-12-4

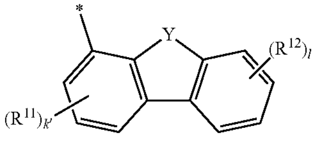

-continued

Formula Ar-12-5

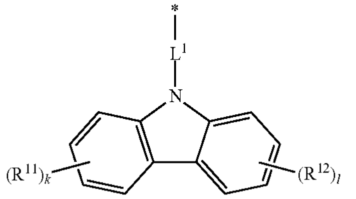

Wherein,

Y, $R^{11}$, $R^{12}$, k, l and * are the same as defined in Ar-12-1, k' is an integer from 0 to 3.

Also, Formula 4 is represented by any one of Formulas 4-1 to 4-3.

<Formula 4-1>

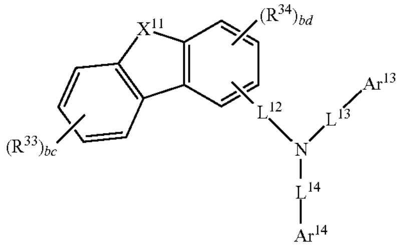

<Formula 4-2>

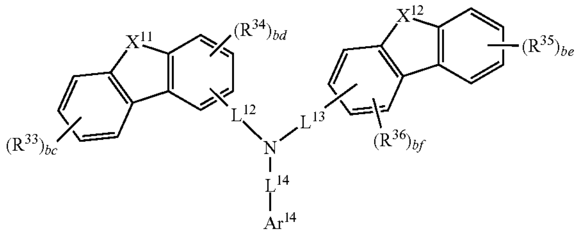

<Formula 4-3>

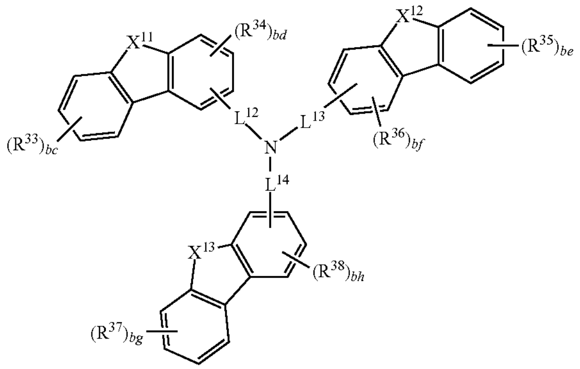

Wherein, $Ar^{13}$, $Ar^{14}$, $L^{12}$, $L^{13}$ and $L^{14}$ are the same as defined in Formula 4, $X^{11}$, $X^{12}$ and $X^{13}$ are the same as the definition of $Y^{10}$, $R^{33}$, $R^{34}$, $R^{35}$, $R^{36}$, $R^{37}$ and $R^{38}$ are the same as the definition of $R^{31}$, or an adjacent plurality of $R^{33}$, or plurality of $R^{34}$, or plurality of $R^{35}$, or plurality of $R^{36}$, or plurality of $R^{37}$, or plurality of $R^{38}$ may be bonded to each other to form a ring, bc, be and bg are each independently an integer from 0 to 4, bd, bf and bh are each independently an integer from 0 to 3.

Also, Formula 5 is represented by any one of Formulas 5-1 to 5-6.

<Formula 5-1>

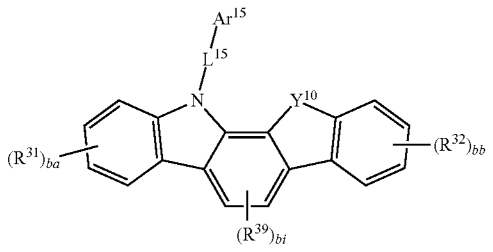

<Formula 5-2>

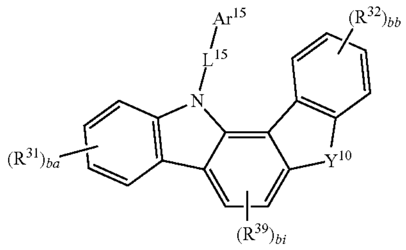

<Formula 5-3>

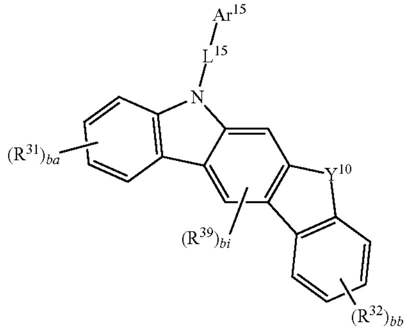

<Formula 5-4>

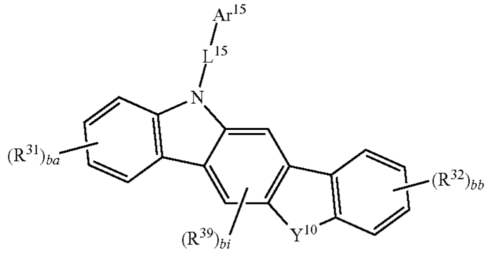

<Formula 5-5>

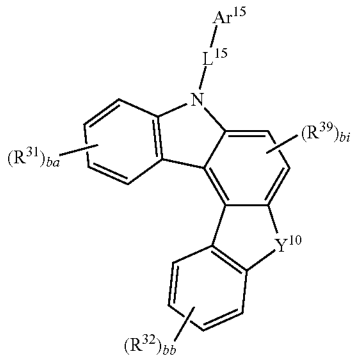

-continued

<Formula 5-6>

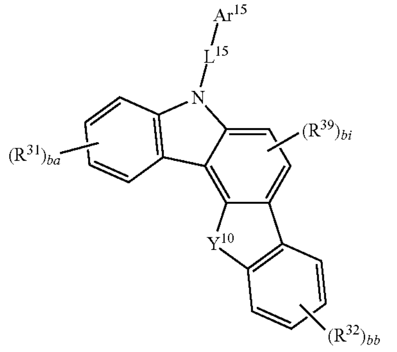

Wherein, $Y^{10}$, $R^{31}$, $R^{32}$, $Ar^{15}$, $L^{15}$, ba and bb are the same as defined in Formula 5, $R^{39}$ is the same as the definition of $R^{31}$, bi is an integer from 0 to 2.

Also, Formula 5 is represented by any one of Formulas 5-7 to 5-9.

<Formula 5-7>

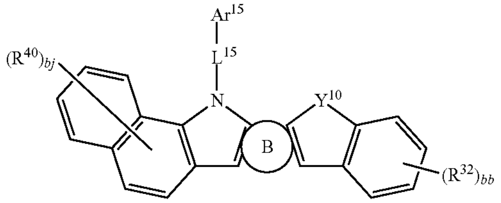

<Formula 5-8>

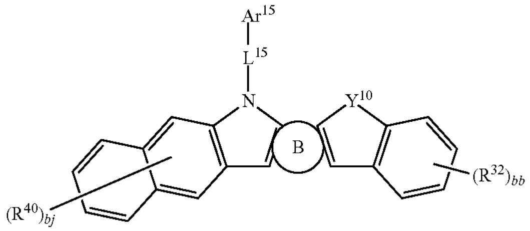

<Formula 5-9>

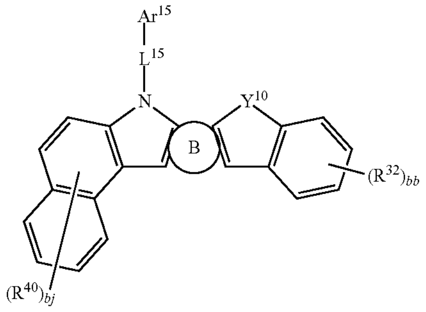

Wherein, $Y^{10}$, Ring B, $R^{32}$, bb, $L^{15}$ and $Ar^{15}$ are the same as defined in Formula 5, $R^{40}$ is the same as the definition of $R^{31}$, bj is an integer from 0 to 6.

Also, Formula 5 is represented by any one of Formulas 5-10 to 5-12.

<Formula 5-10>

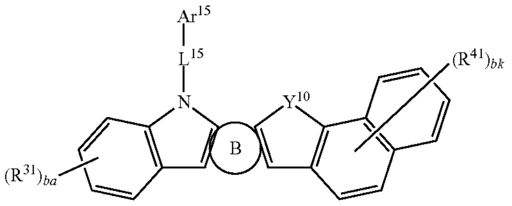

<Formula 5-11>

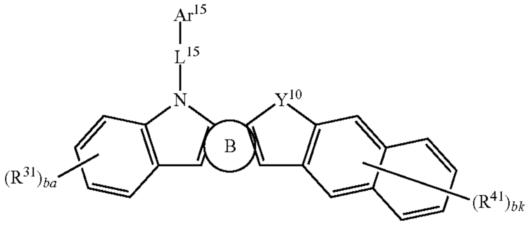

<Formula 5-12>

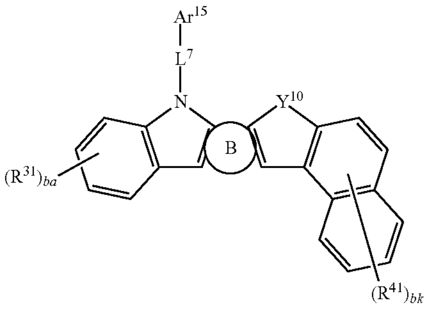

Wherein, $Y^{10}$, Ring B, $R^{31}$, ba, $L^{15}$ and $Ar^{15}$ are the same as defined in Formula 5, $R^{41}$ is the same as the definition of $R^{31}$, bk is an integer from 0 to 6.

Also, Formula 5 is represented by any one of Formulas 5-13 to 5-18.

<Formula 5-13>

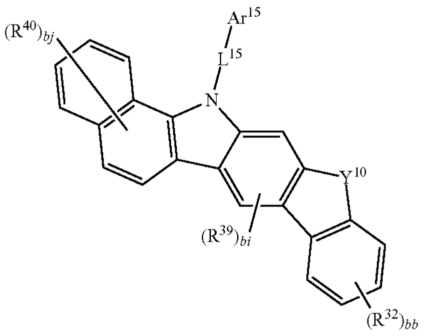

-continued

<Formula 5-14>

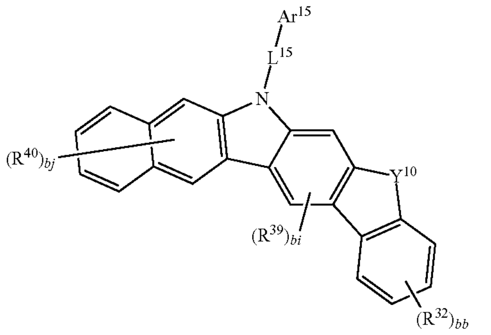

<Formula 5-15>

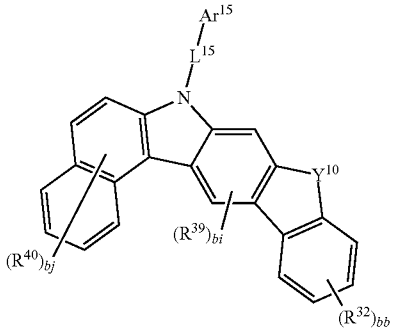

<Formula 5-16>

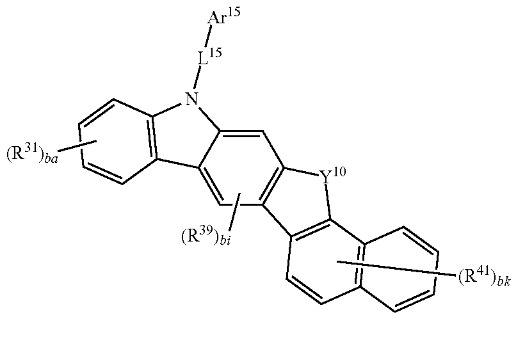

<Formula 5-17>

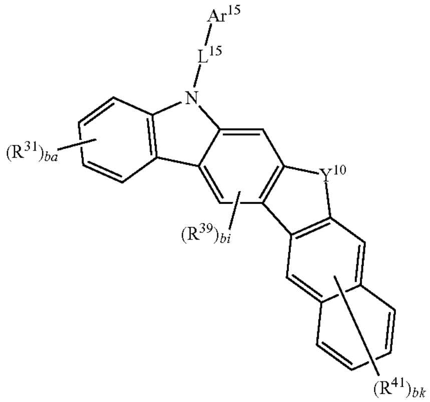

-continued

<Formula 5-18>

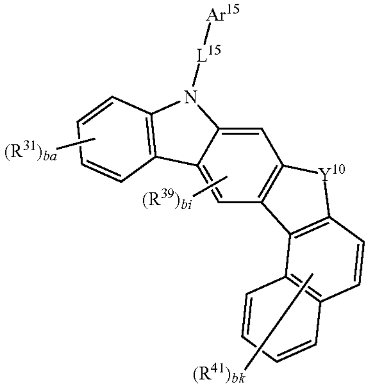

Wherein, $Y^{10}$, $R^{31}$, $R^{32}$, ba, bb, $L^{15}$ and $Ar^{15}$ are the same as defined in Formula 5, $R^{39}$, $R^{40}$ and $R^{41}$ are the same as the definition of $R^{31}$ bi is an integer from 0 to 2, bj and bk are each independently an integer from 0 to 6.

Also, Formula 5 is represented by Formula 5-19.

<Formula 5-19>

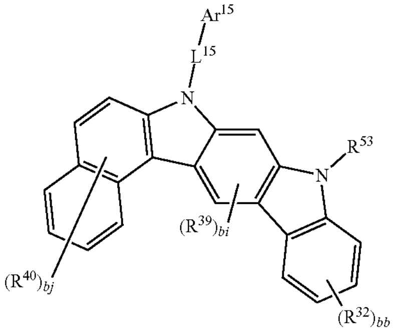

Wherein, $R^{31}$, $R^{53}$, bb, $L^{15}$ and $Ar^{15}$ are the same as defined in Formula 5, $R^{39}$ and $R^{40}$ are the same as the definition of $R^{31}$, bi is an integer from 0 to 2, bj is an integer from 0 to 6.

Also, Formula 1 is represented by any one of the following compounds P-1 to P-107.

P-1
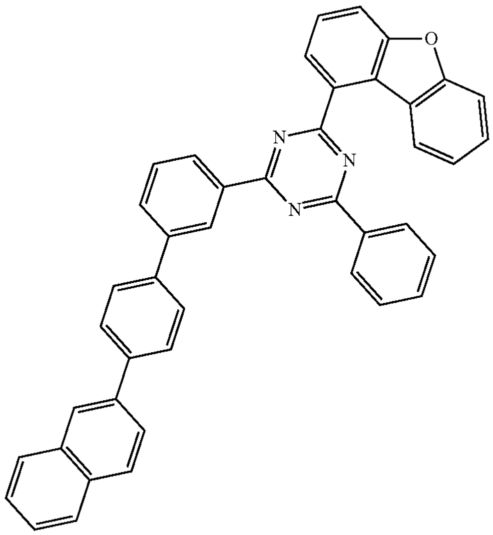
P-2
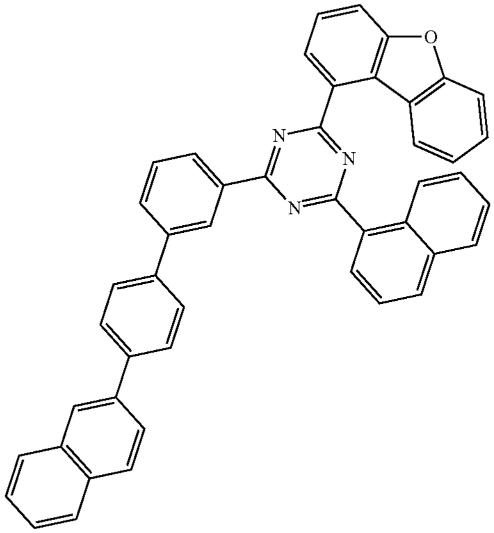
P-3
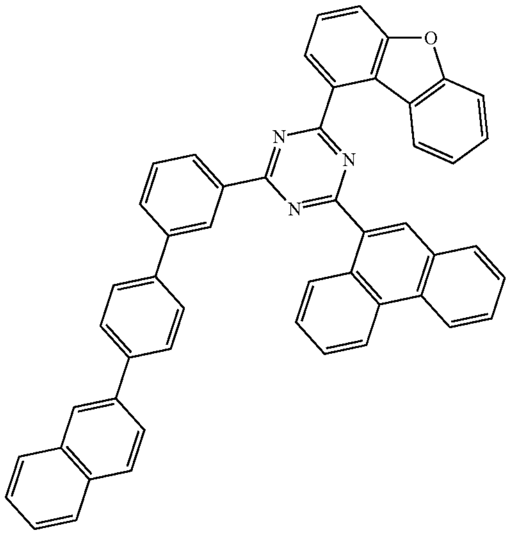
-continued
P-4
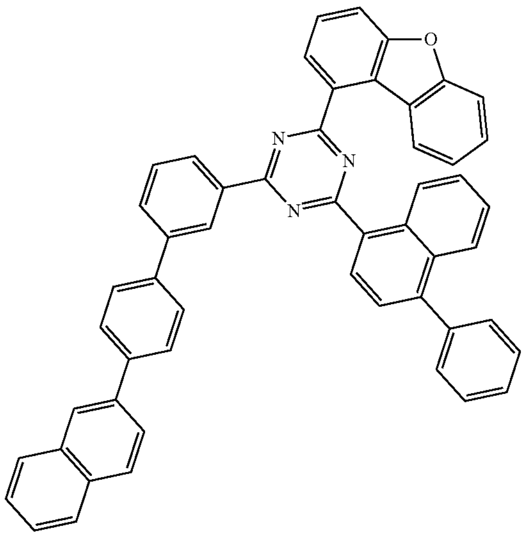
P-5
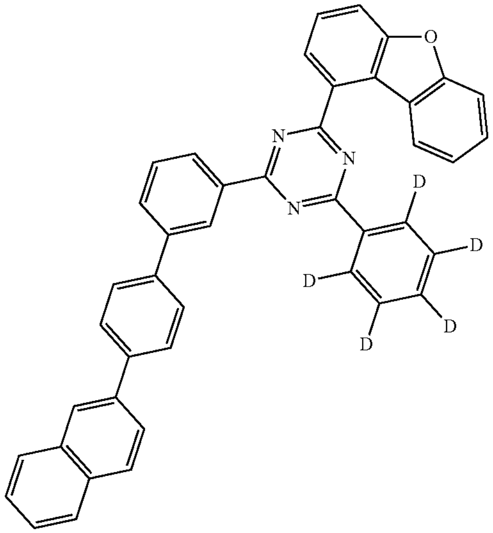
P-6
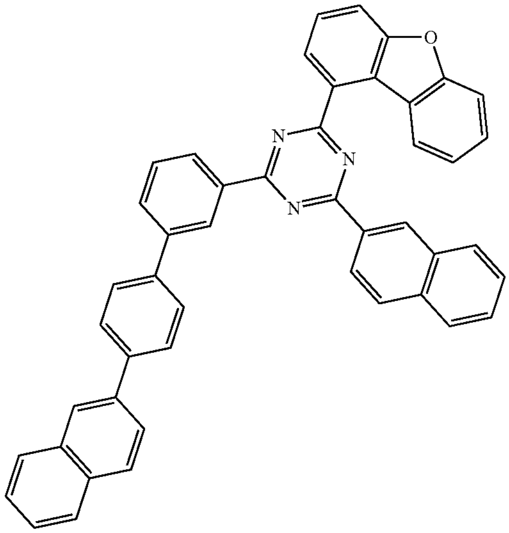

-continued
P-7
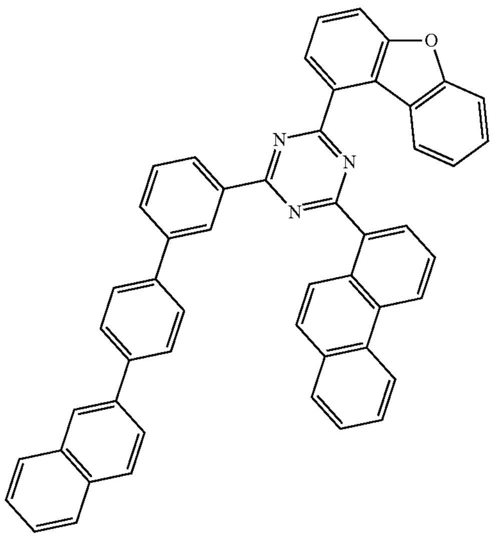
P-8
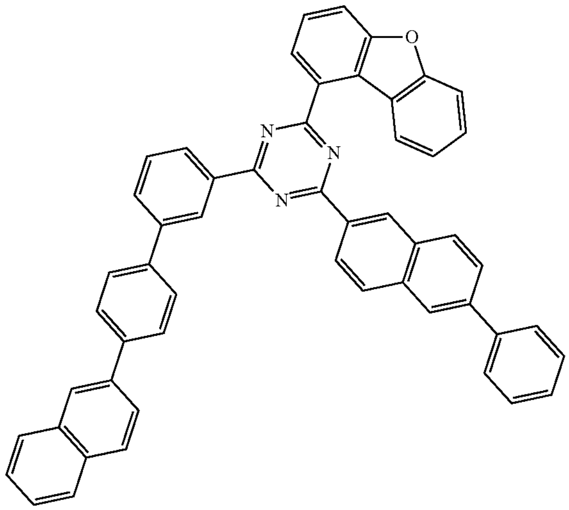
P-9
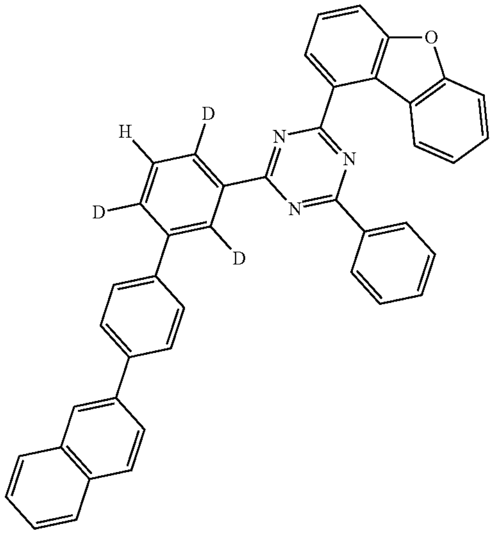
-continued
P-10
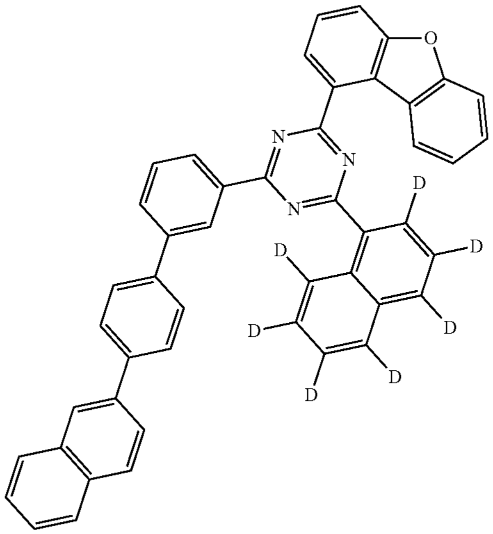
P-11
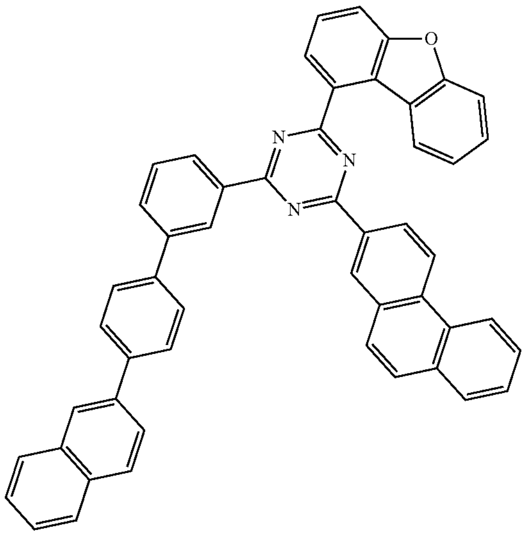
P-12
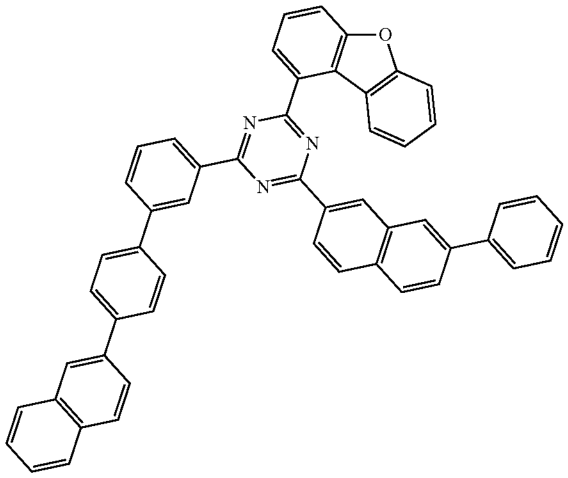

-continued
P-13
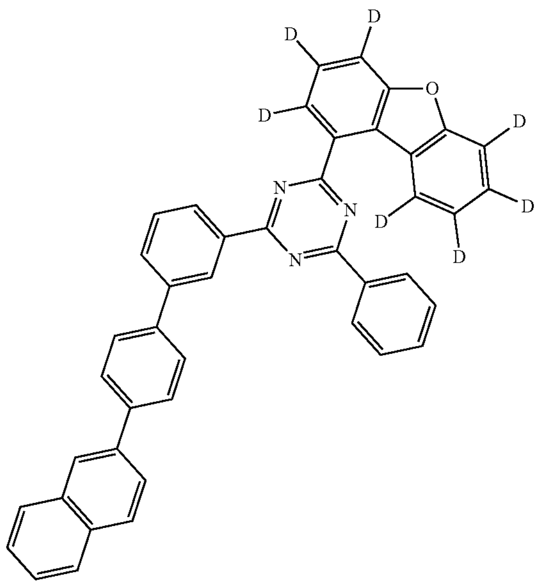
P-14
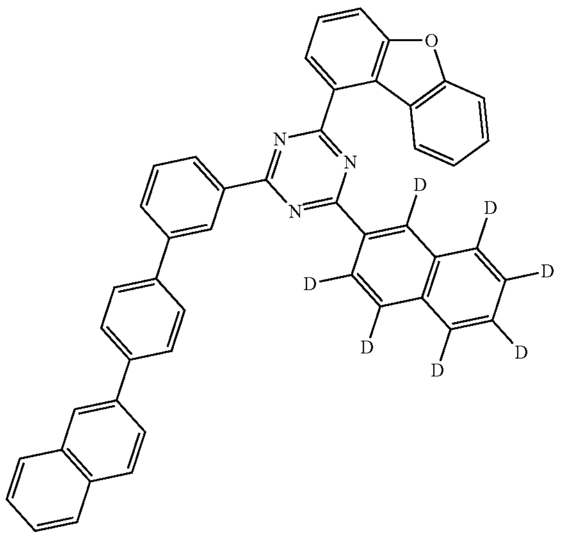
-continued
P-15
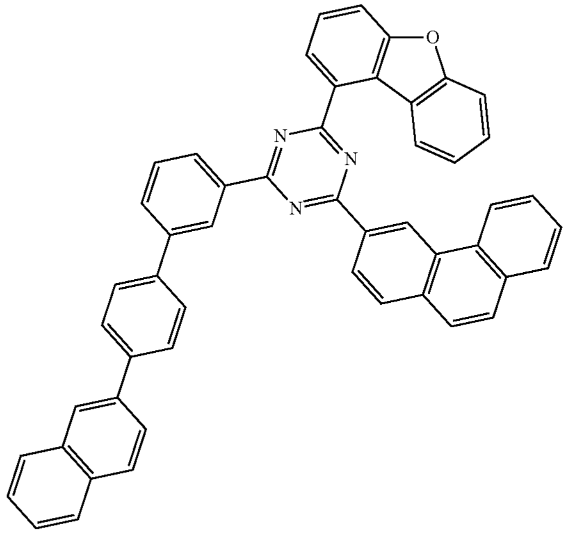
P-16
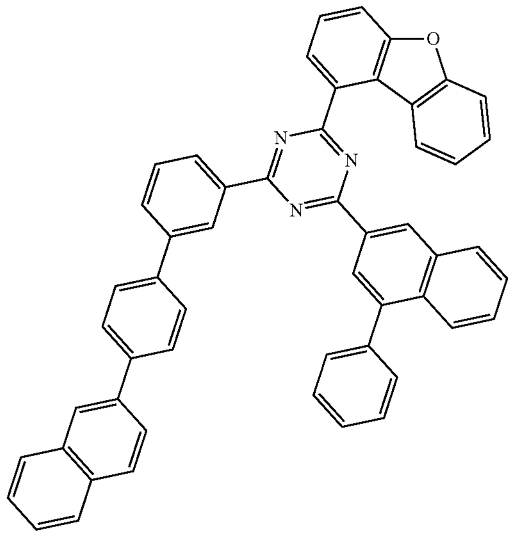

-continued
P-17
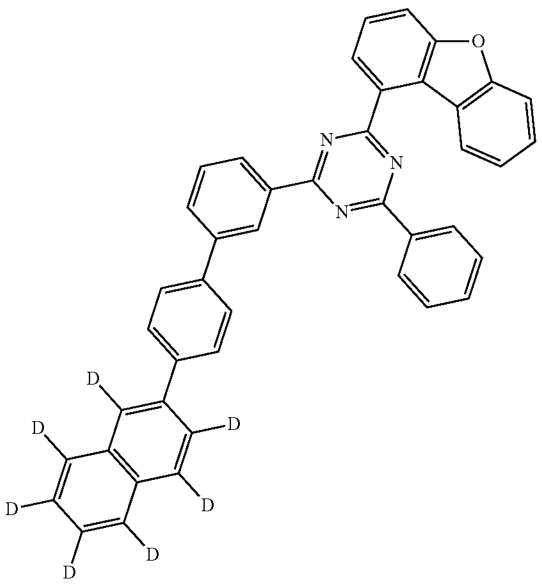
P-18
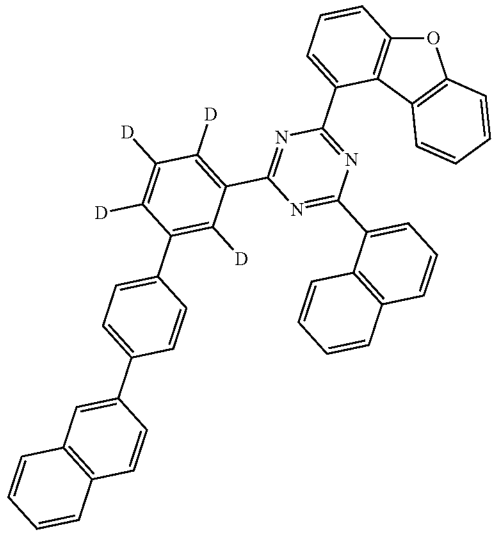
-continued
P-19
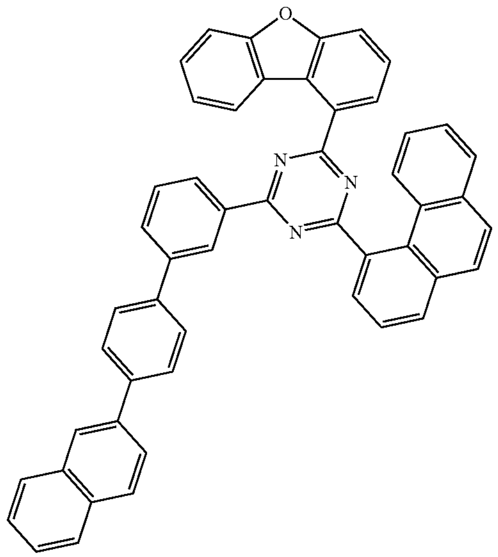
P-20
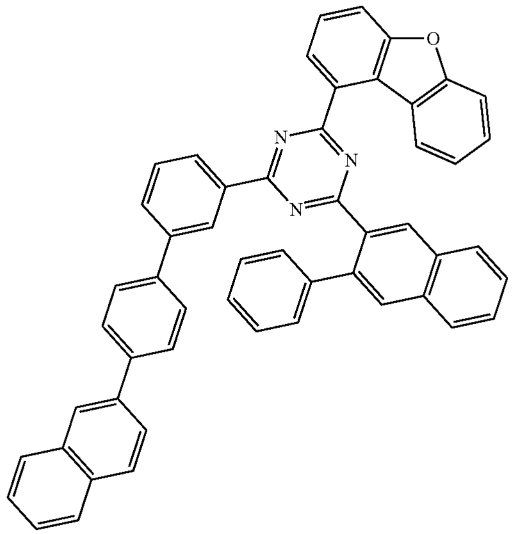

-continued
P-21
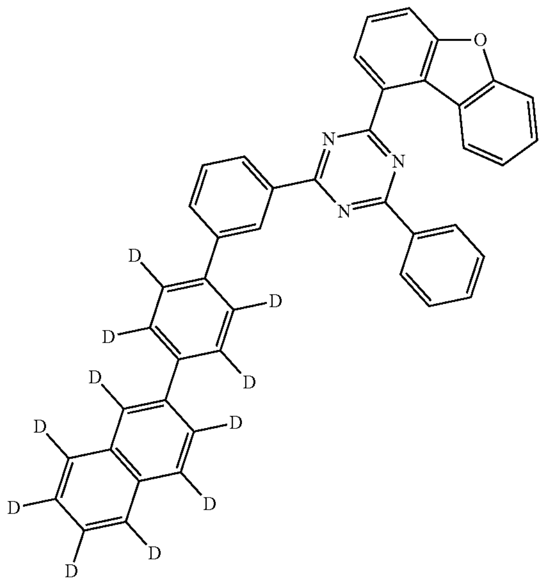
P-22
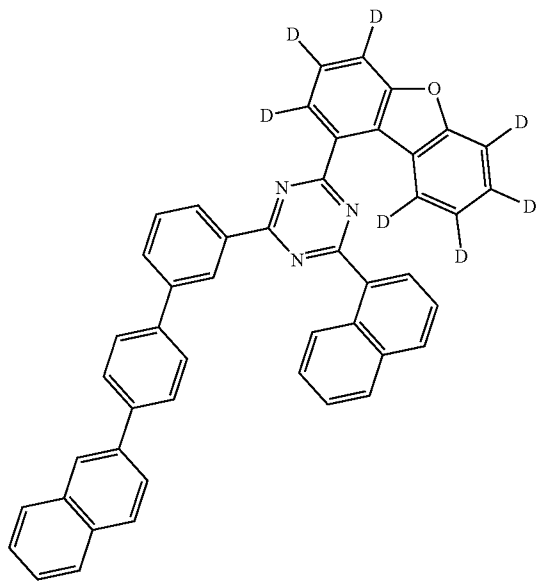
-continued
P-23
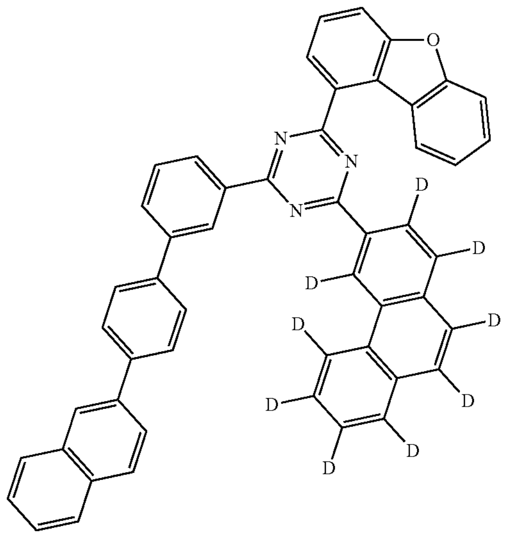
P-24
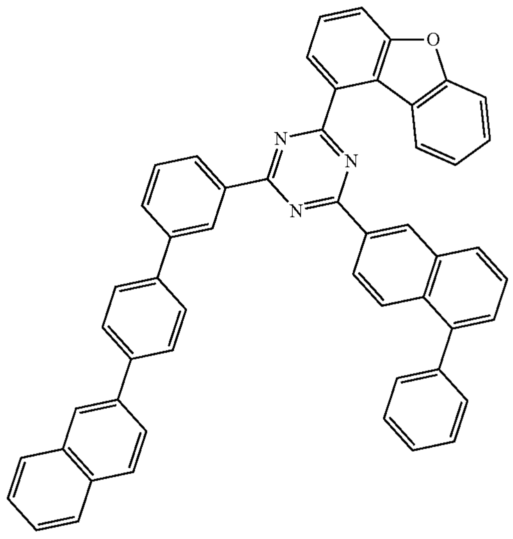

-continued
P-25
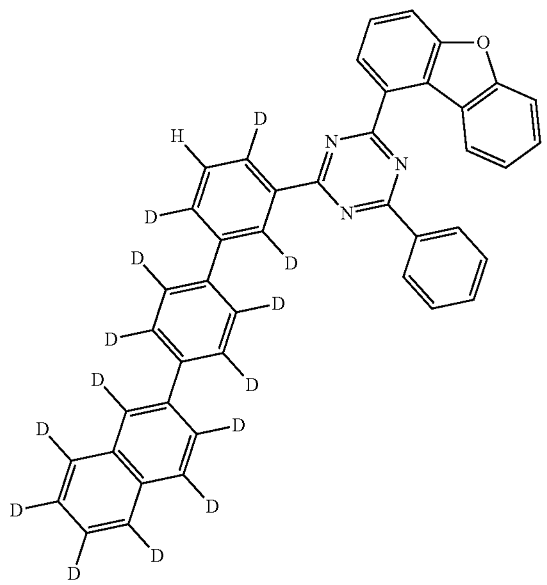
P-26
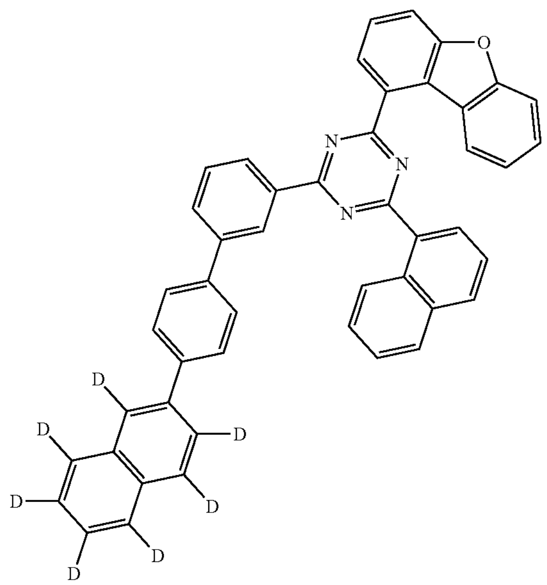
-continued
P-27
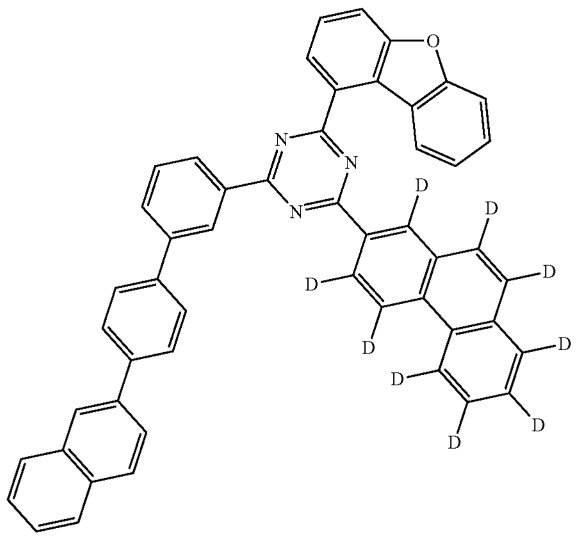
P-28
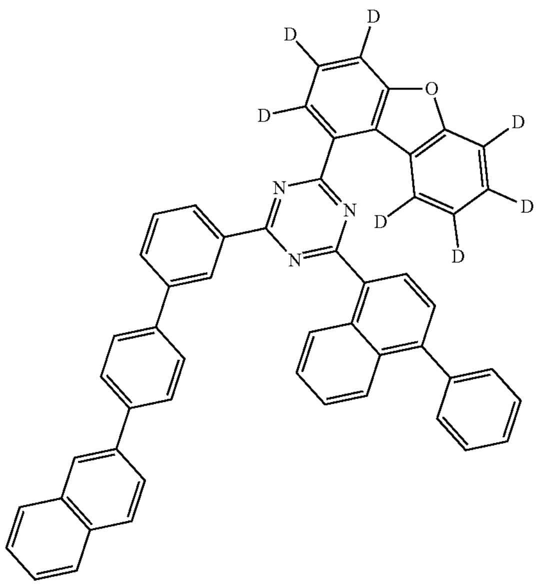

-continued
P-29
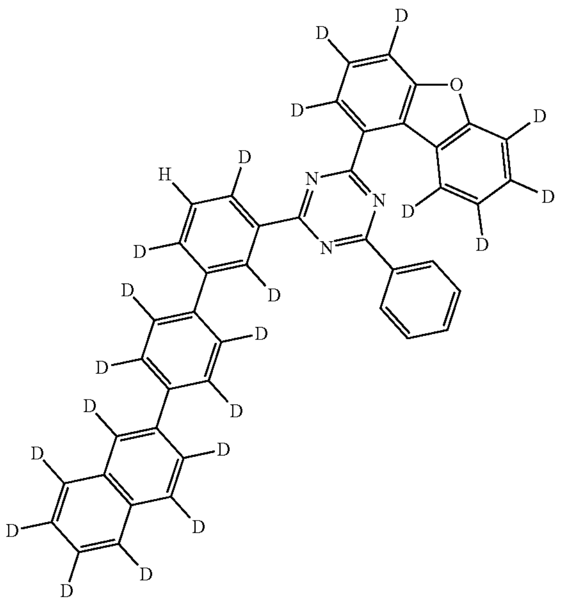
P-30
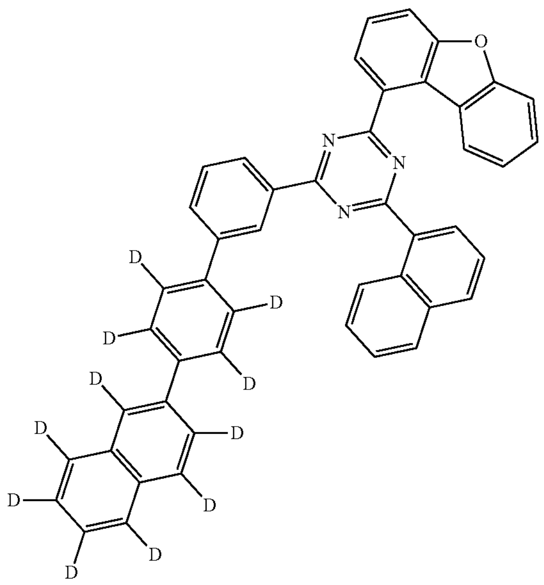
-continued
P-31
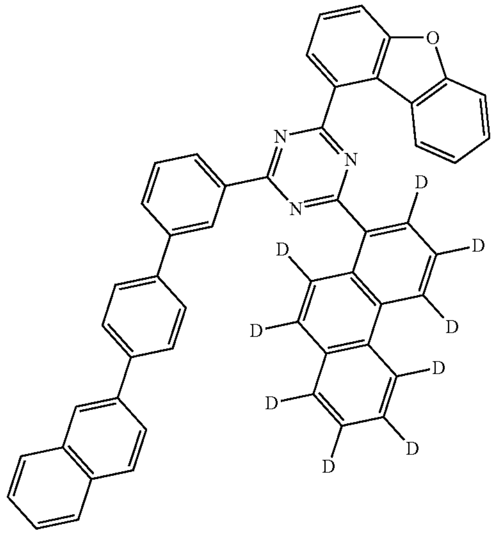
P-32
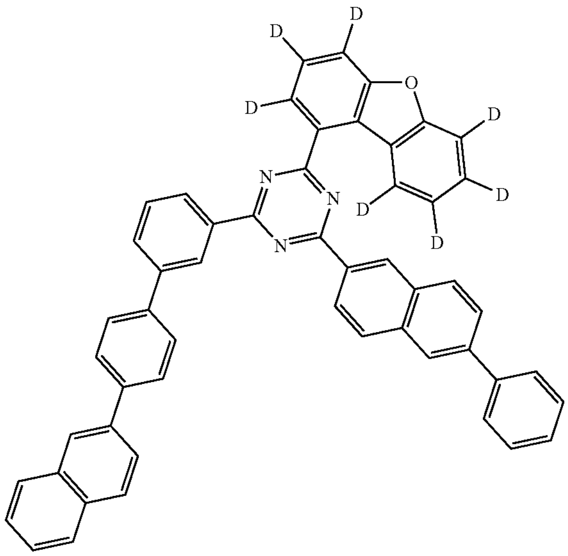

P-33
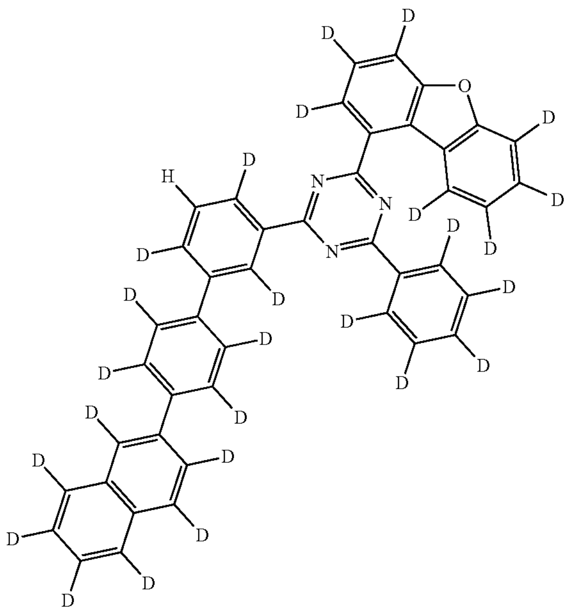
P-34
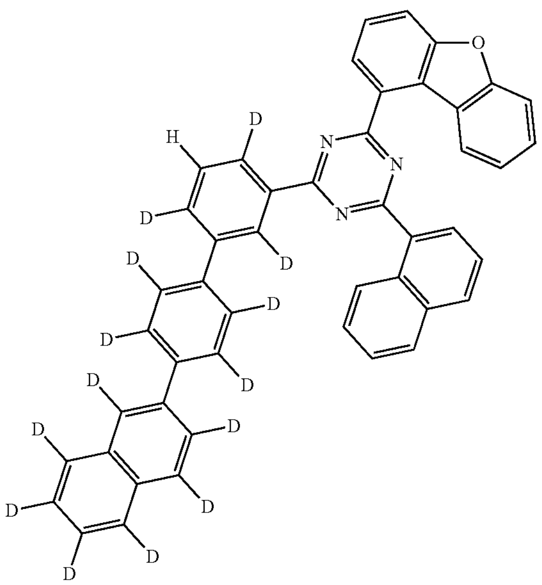
P-35
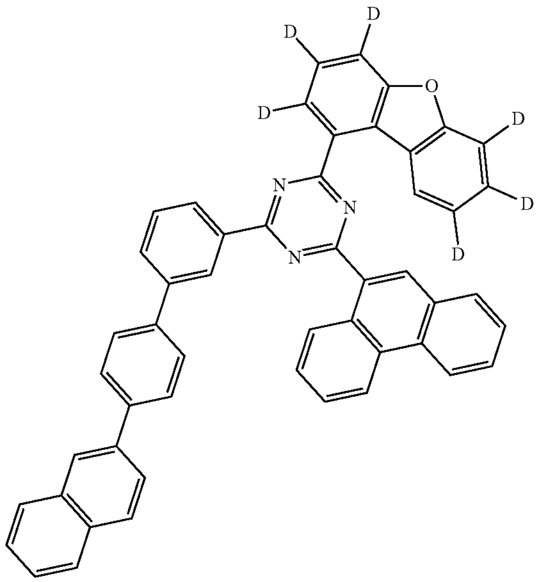
P-36
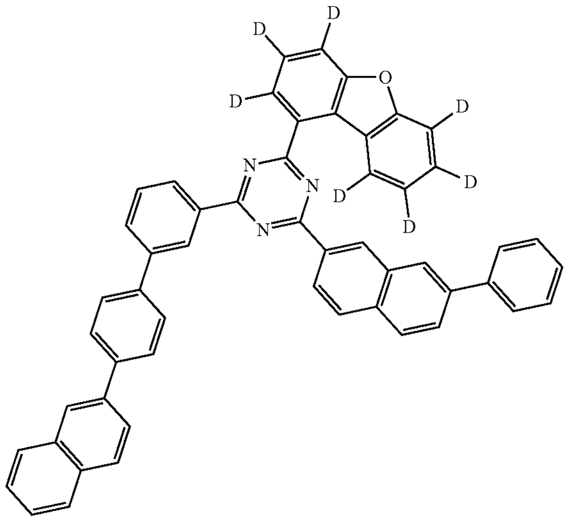

-continued
P-37
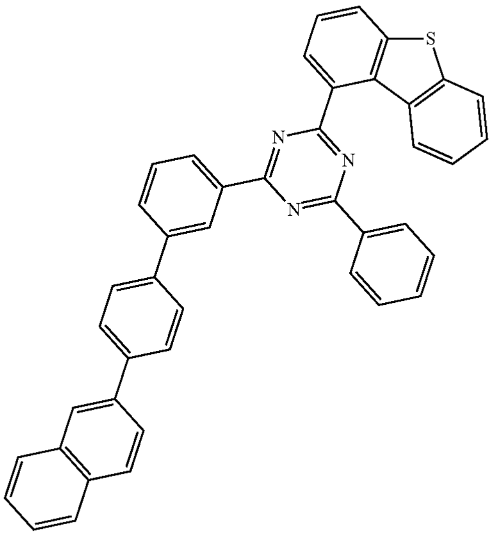
P-38
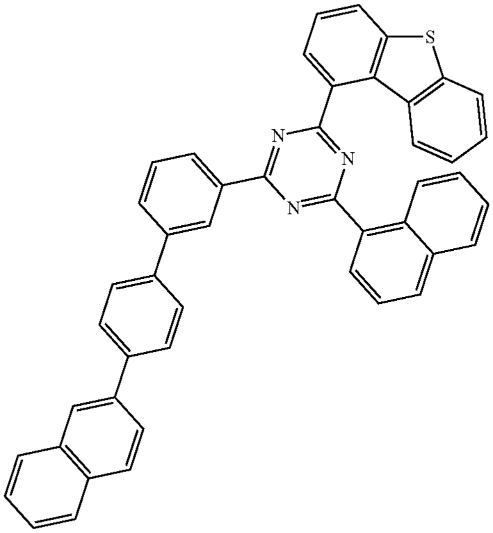
P-39
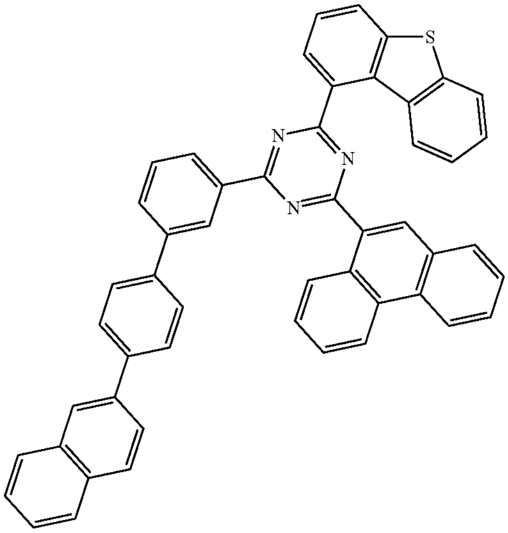
-continued
P-40
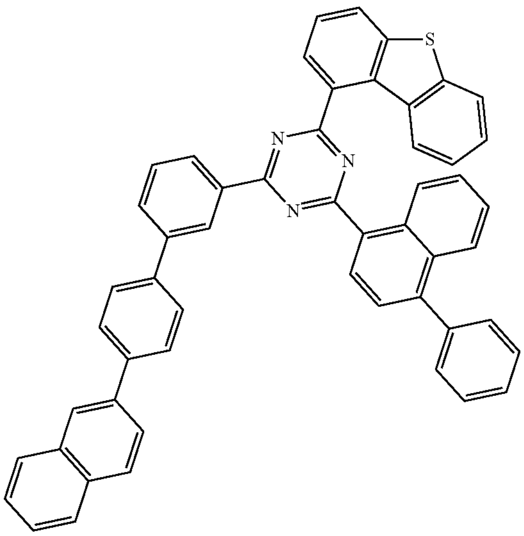
P-41
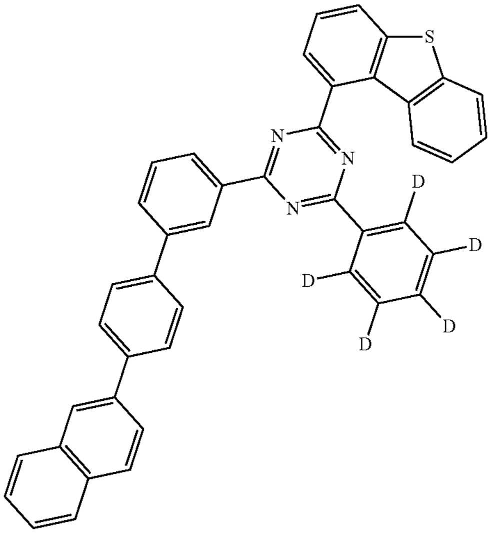
P-42
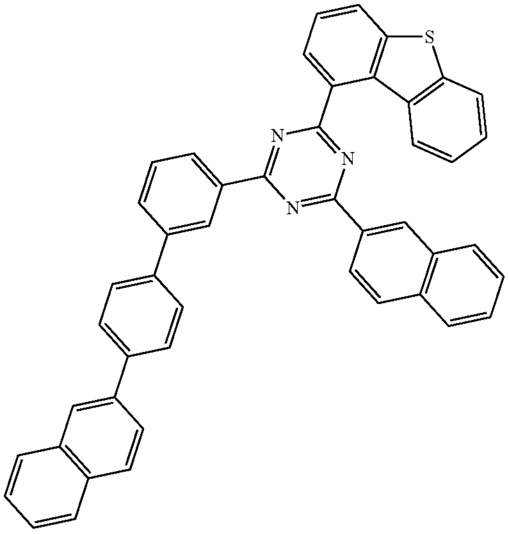

-continued
P-43
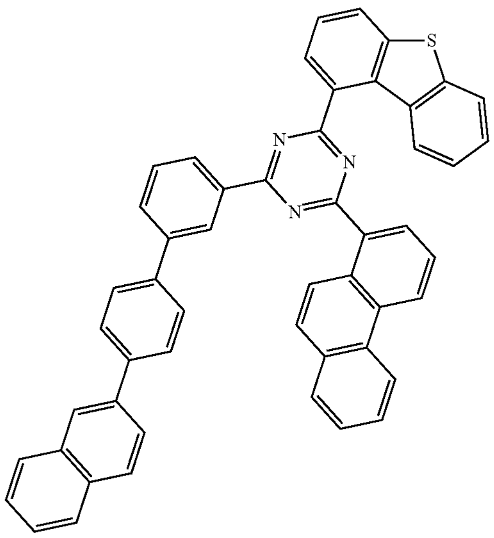
P-44
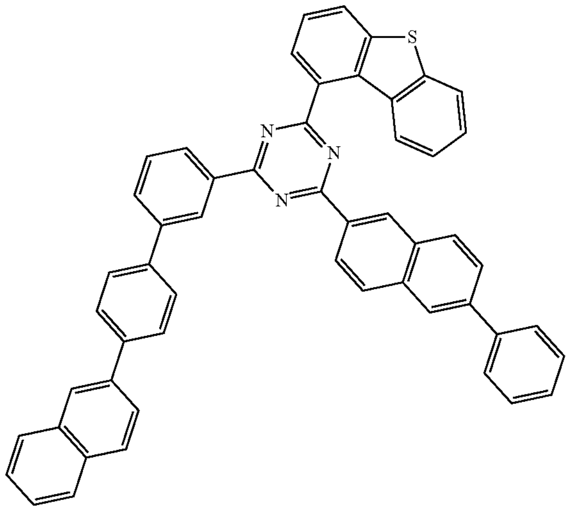
P-45
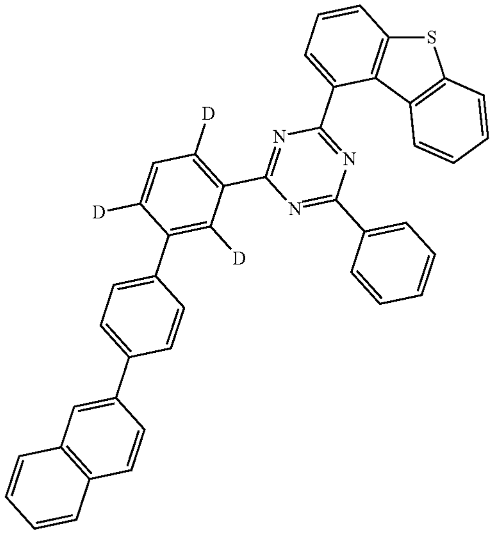
-continued
P-46
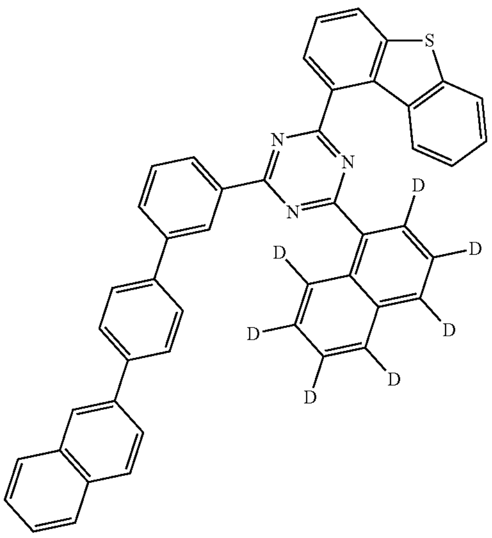
P-47
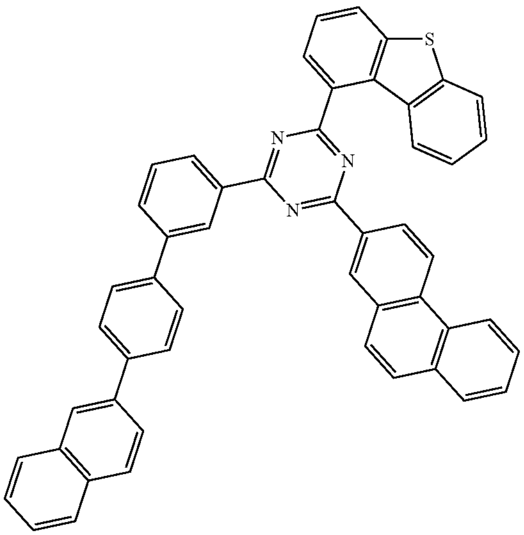
P-48
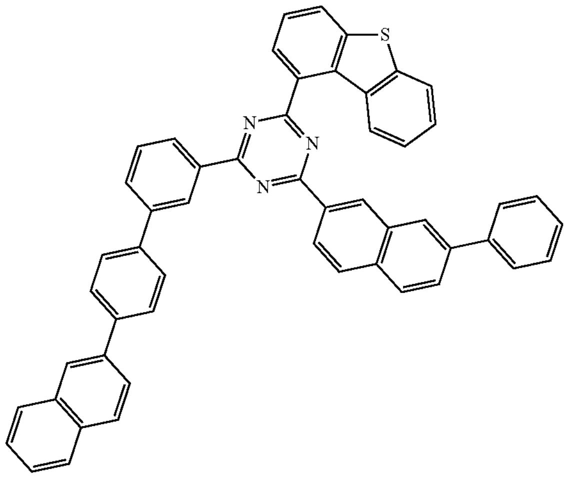

-continued
P-49
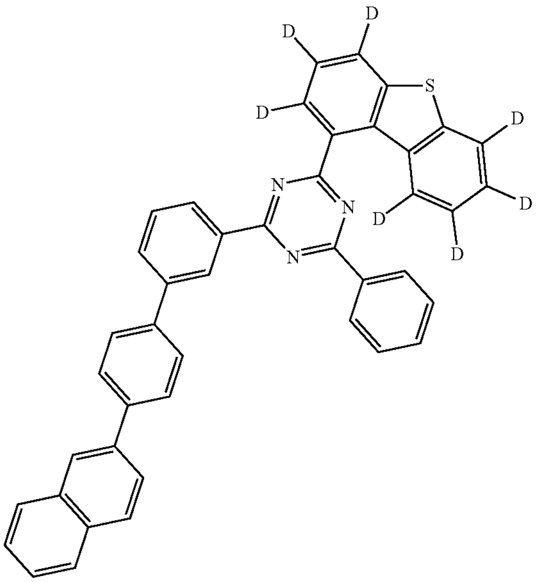
P-50
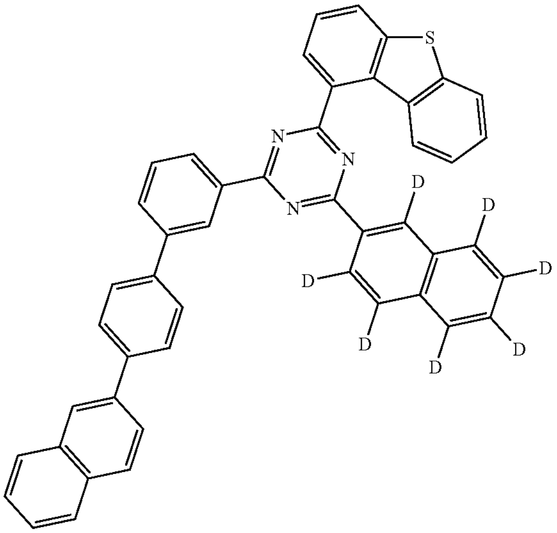
-continued
P-51
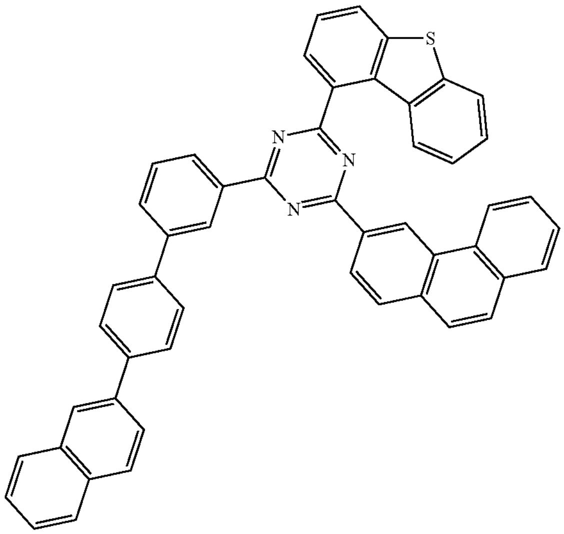
P-52
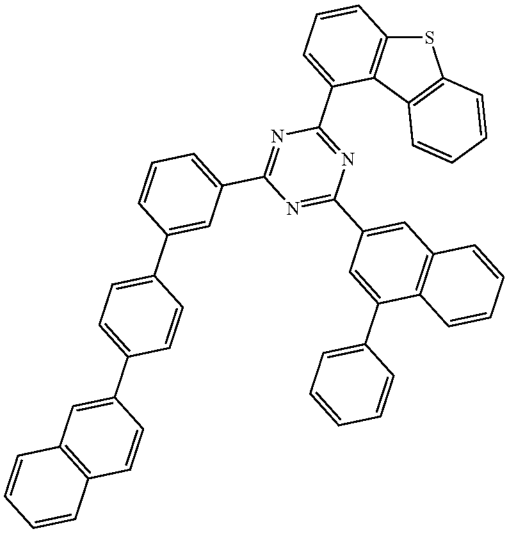
P-53
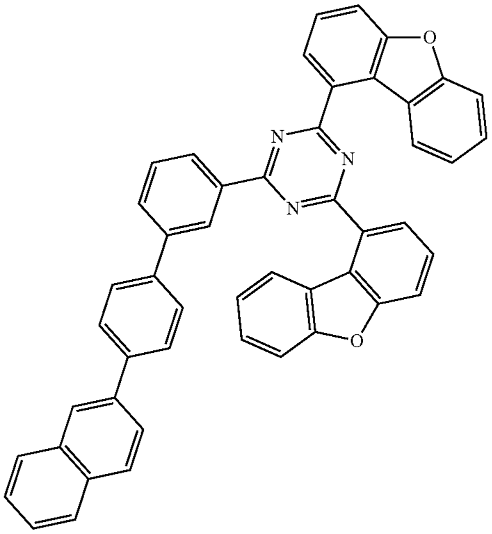

-continued
P-54
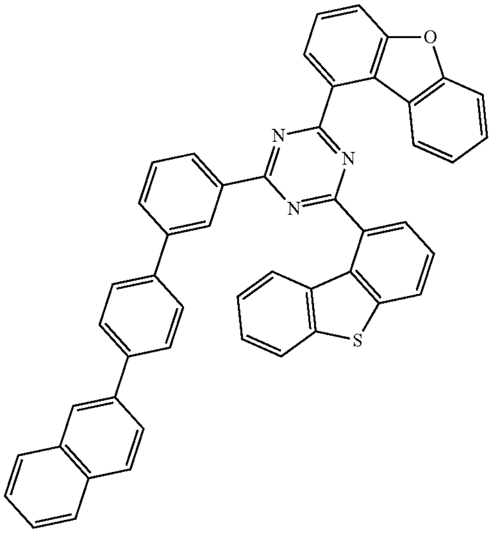
P-55
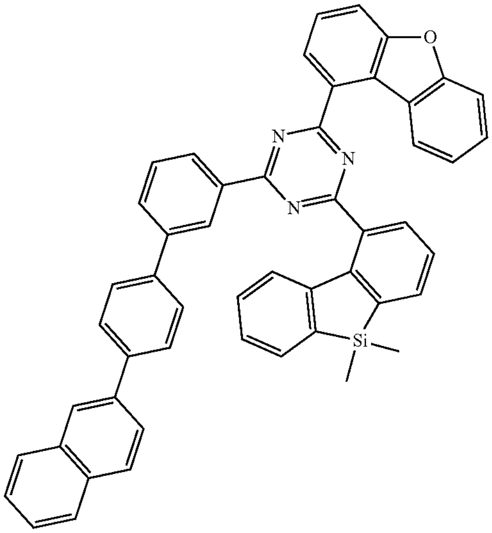
P-56
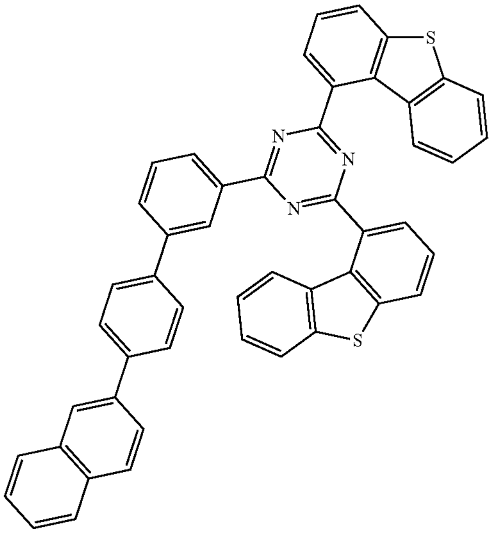
-continued
P-57
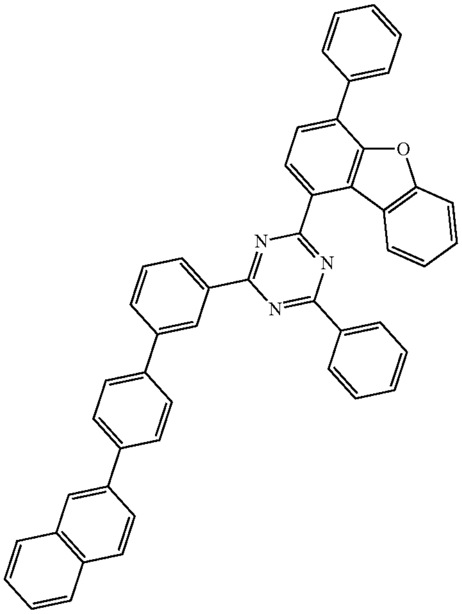
P-58
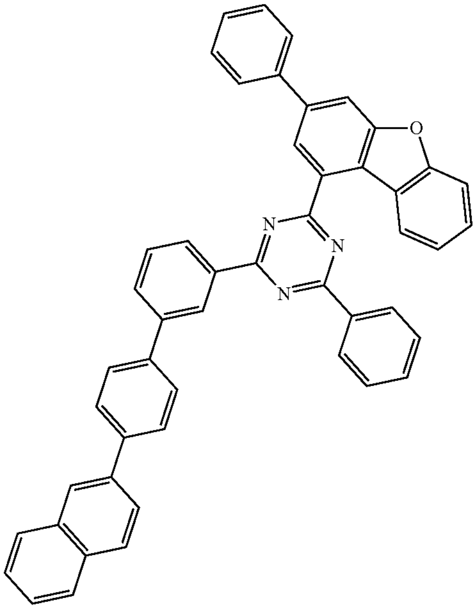

-continued
P-59
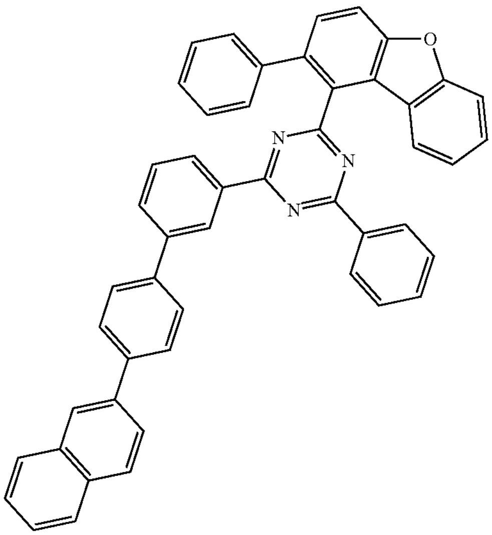
P-60
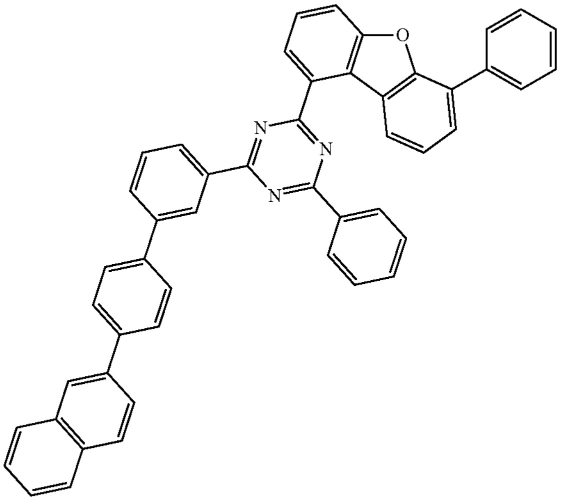
P-61
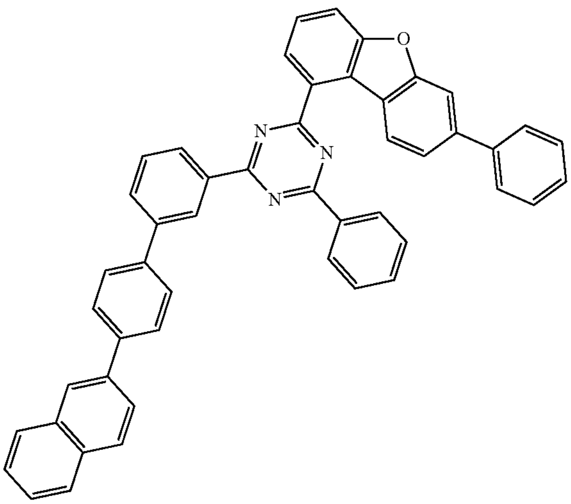
-continued
P-62
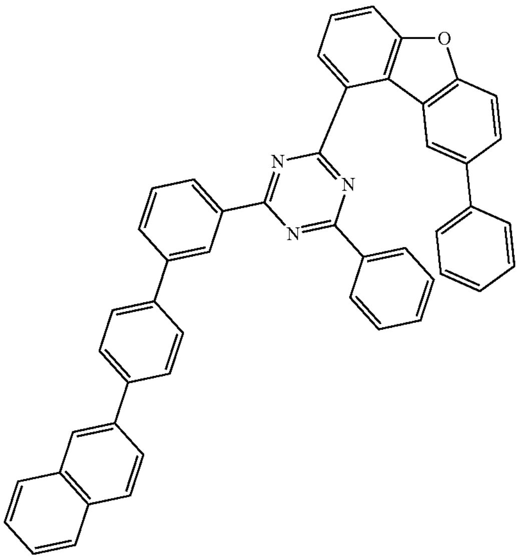
P-63
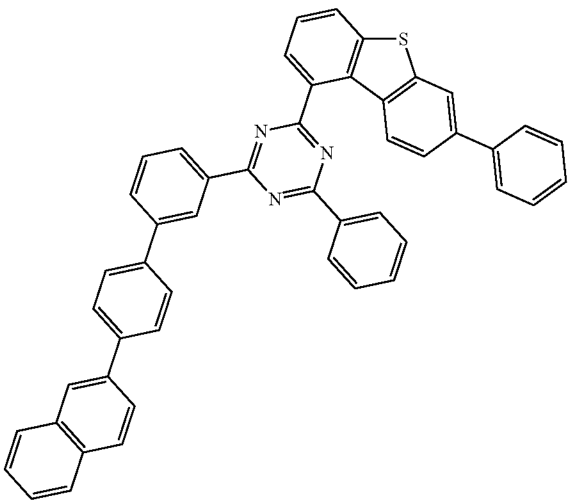

-continued
P-64
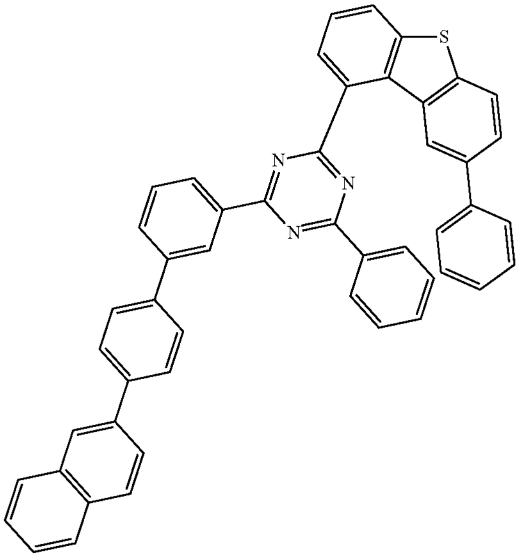
P-65
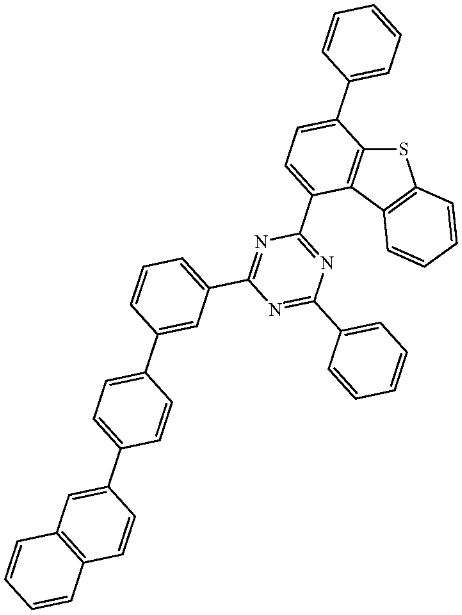
-continued
P-66
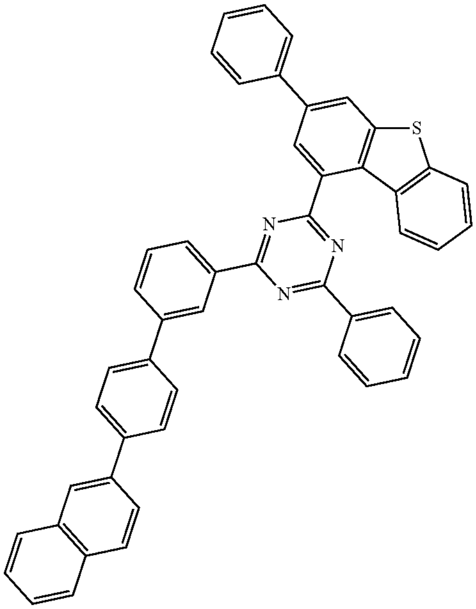
P-67
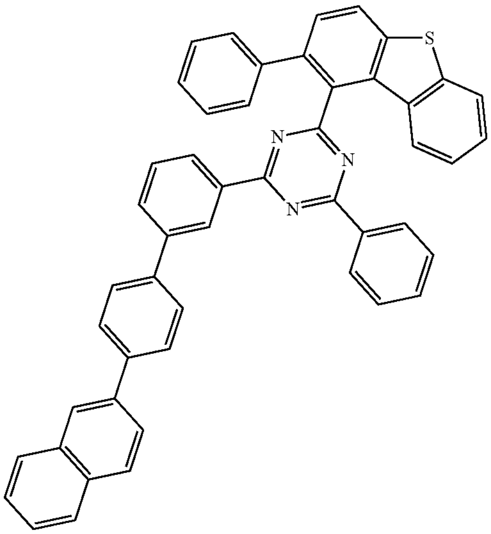

-continued
P-68
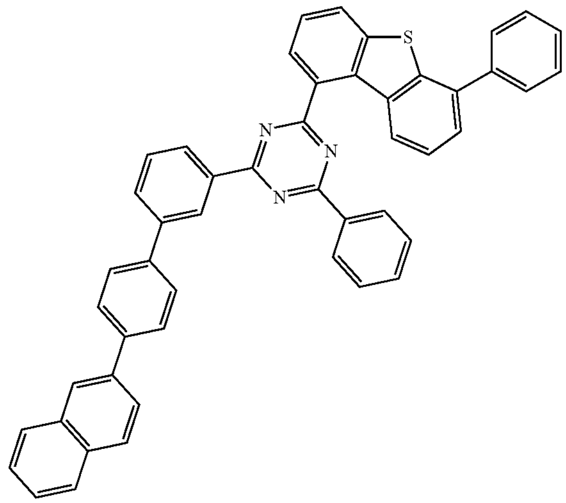
P-69
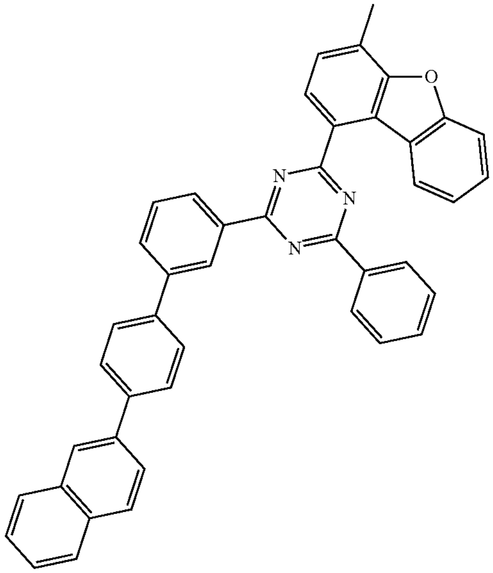
-continued
P-70
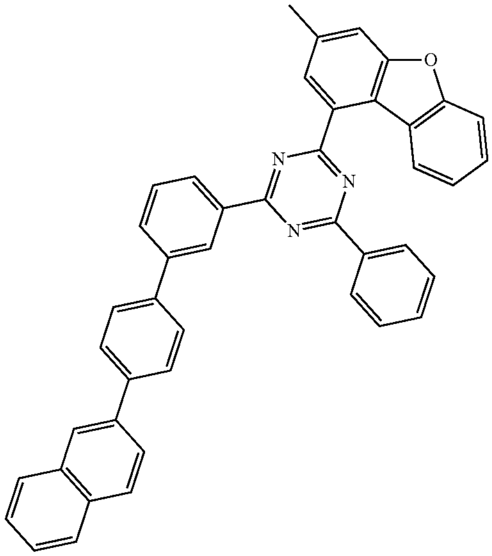
P-71
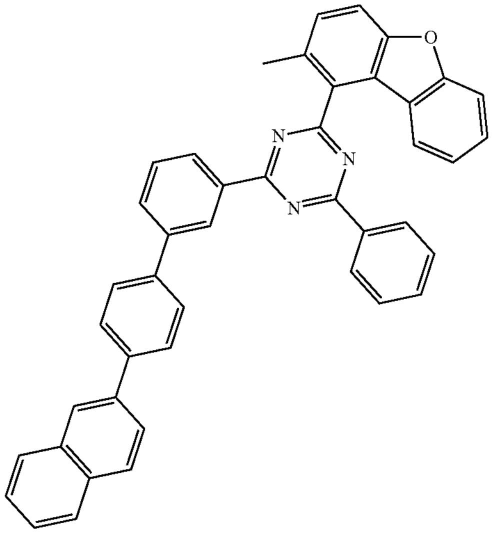

-continued
P-72
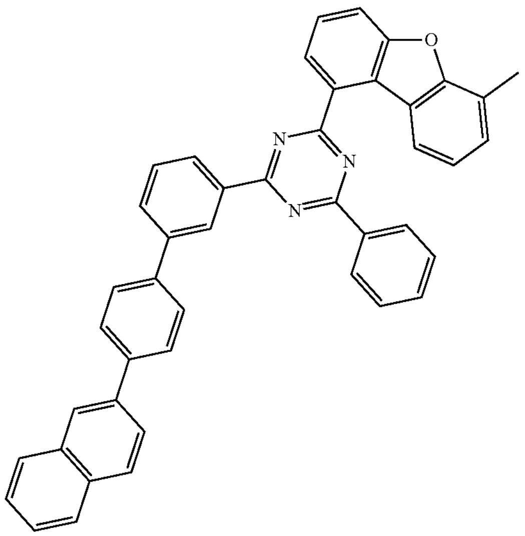
P-73
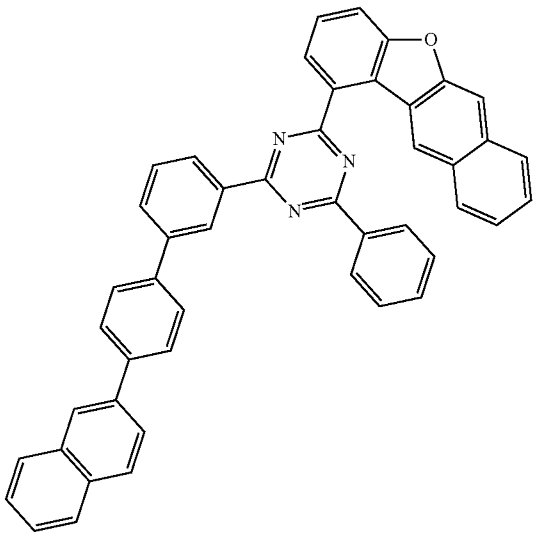
P-74
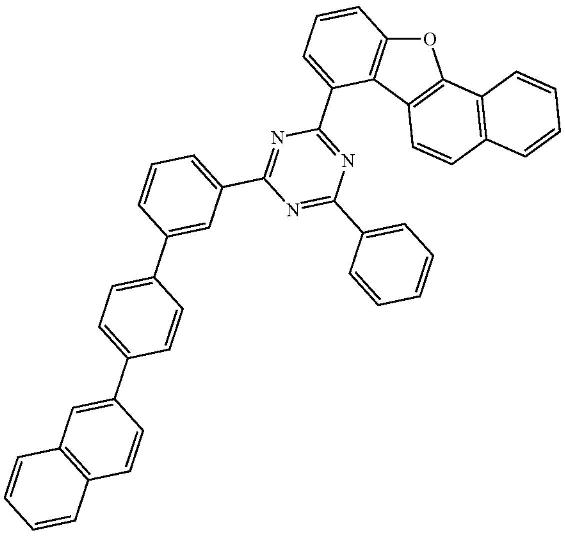
-continued
P-75
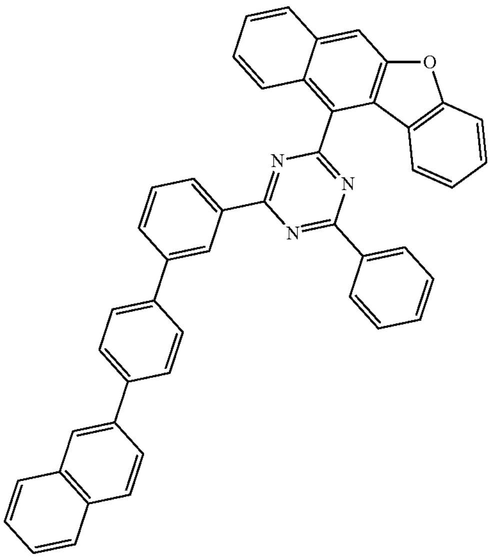
P-76
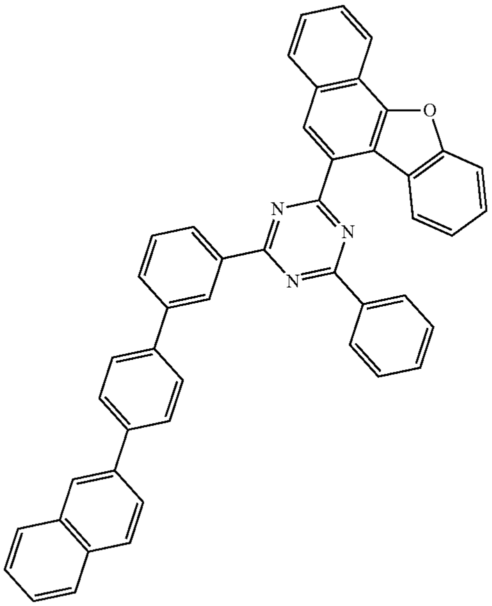

-continued
P-77
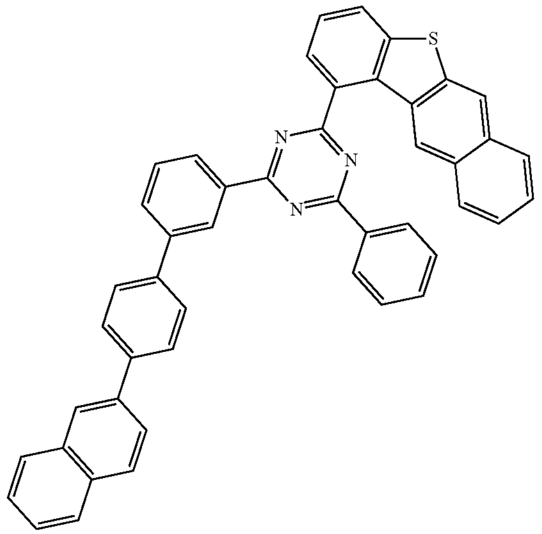
P-78
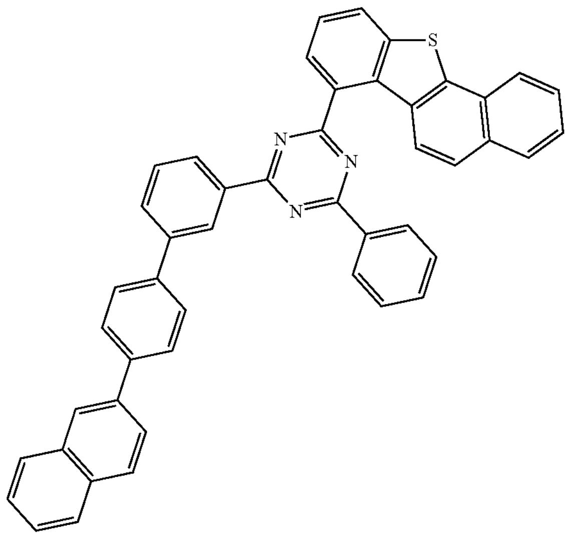
-continued
P-79
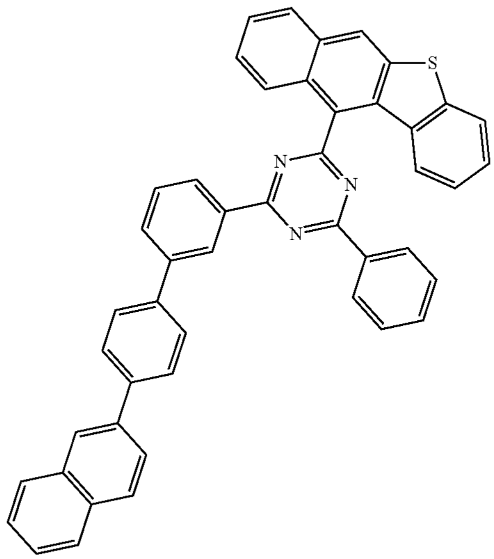
P-80
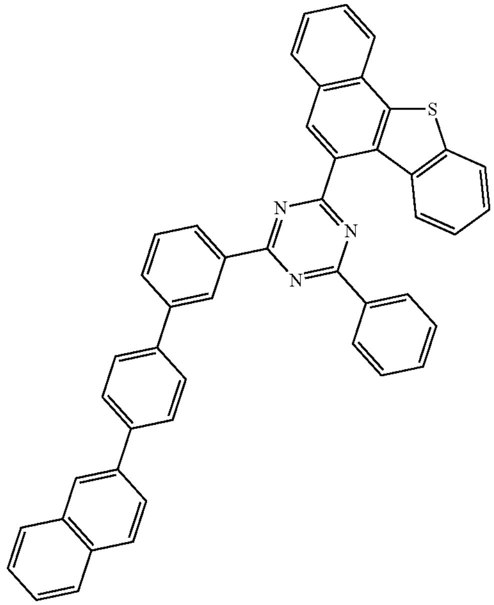

-continued
P-81
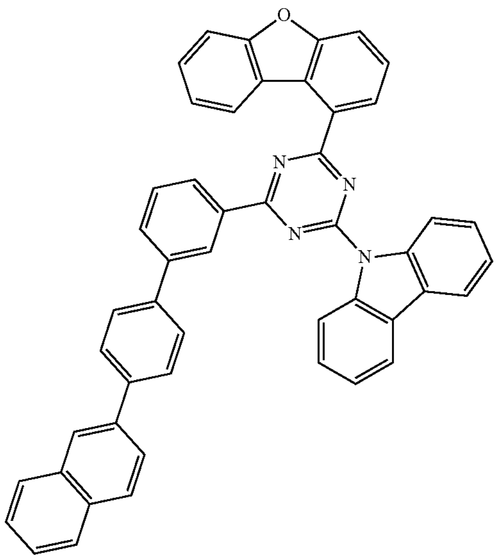
P-82
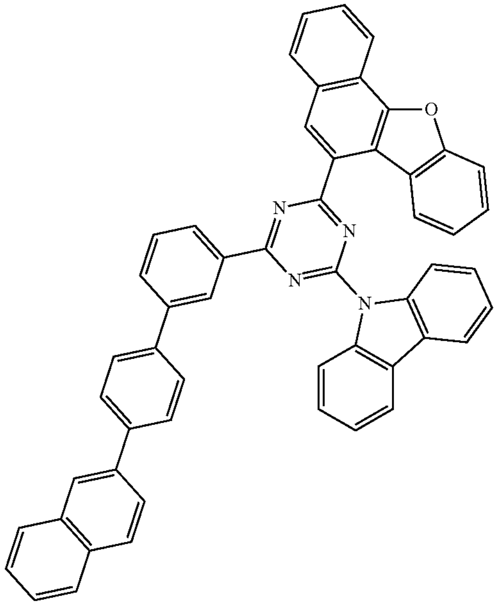
-continued
P-83
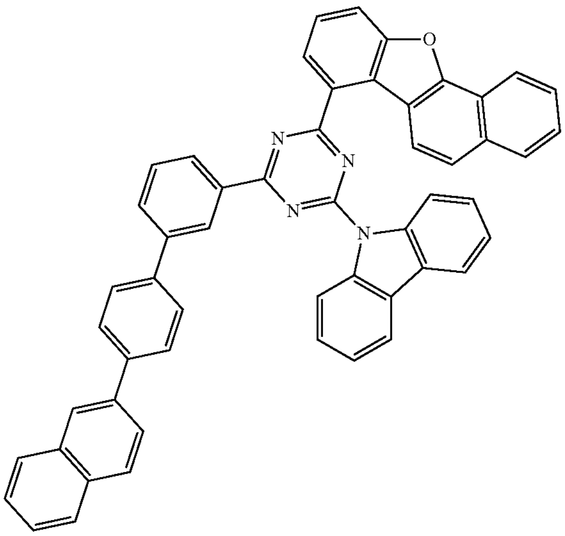
P-84
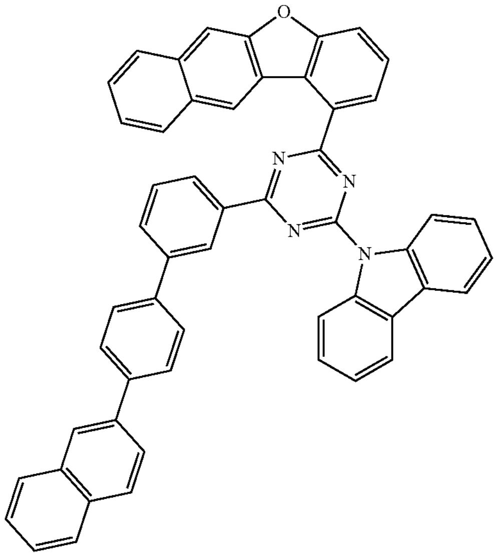

-continued
P-85
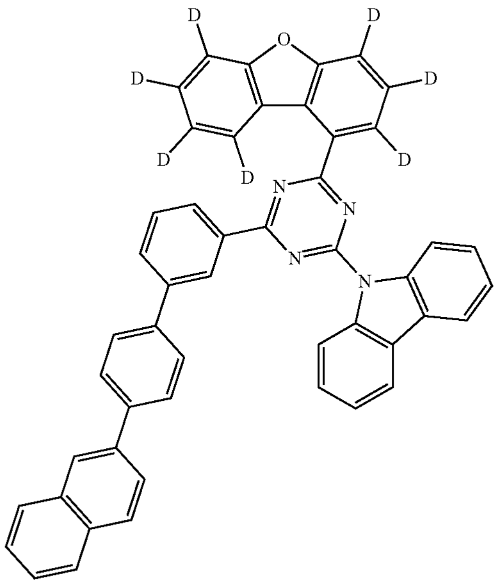
P-86
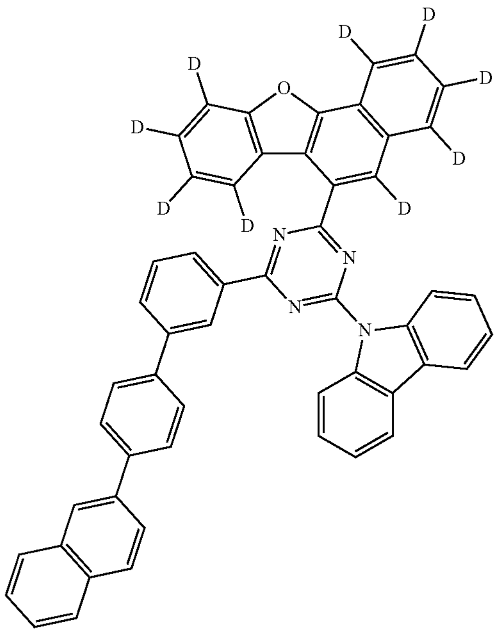
-continued
P-87
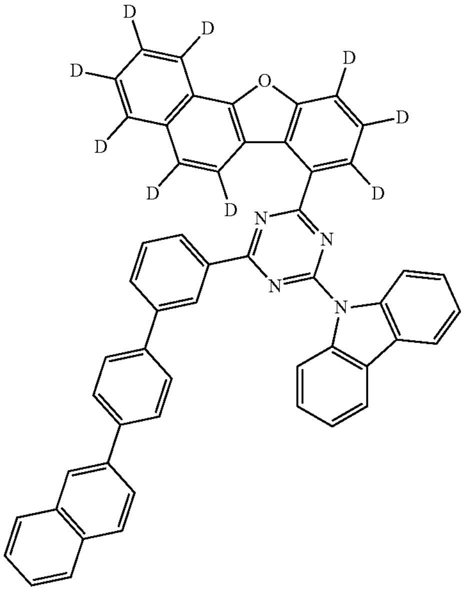
P-88
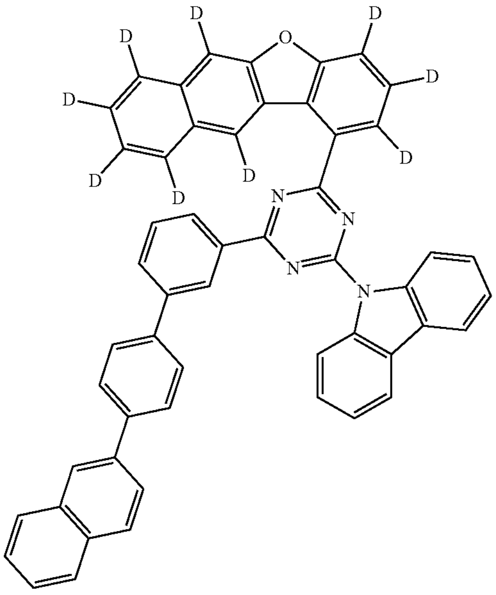

-continued
P-89
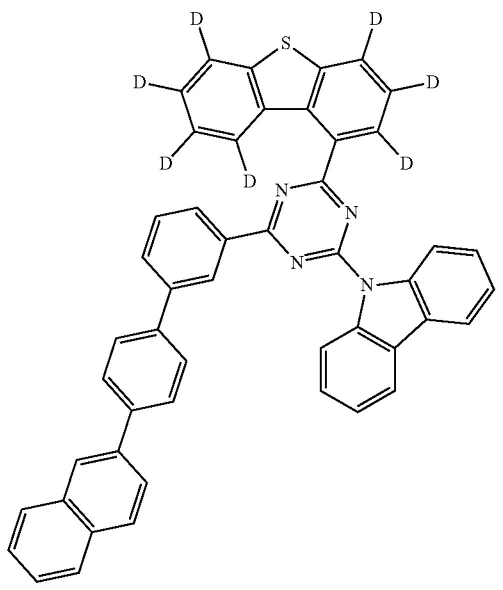
P-90
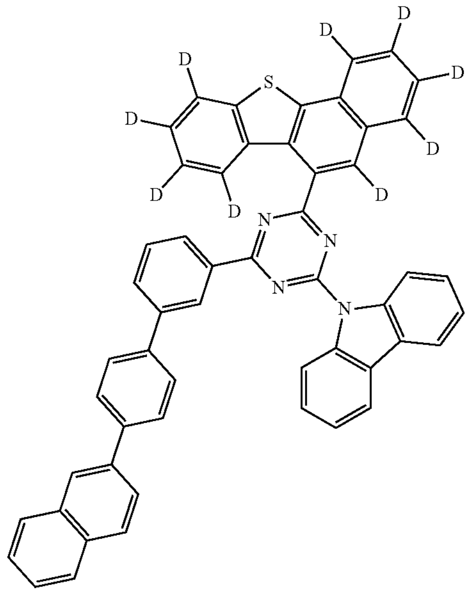
-continued
P-91
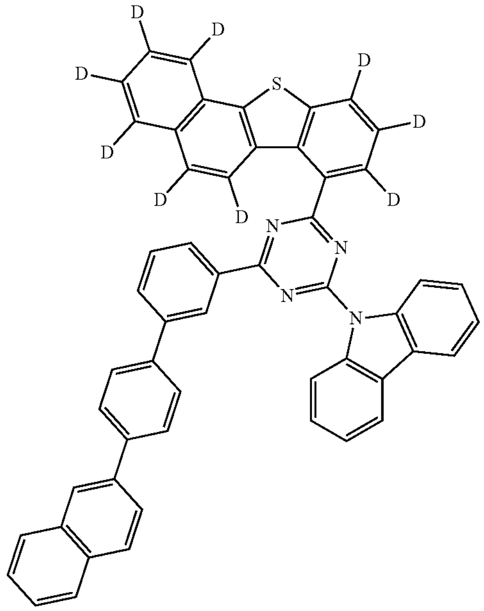
P-92
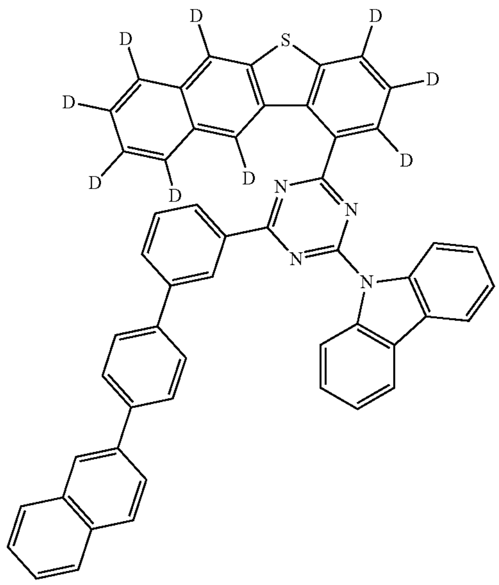

-continued
P-93
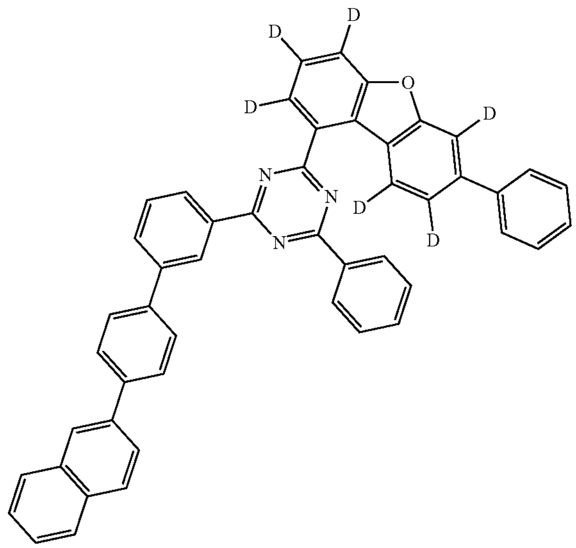
P-94
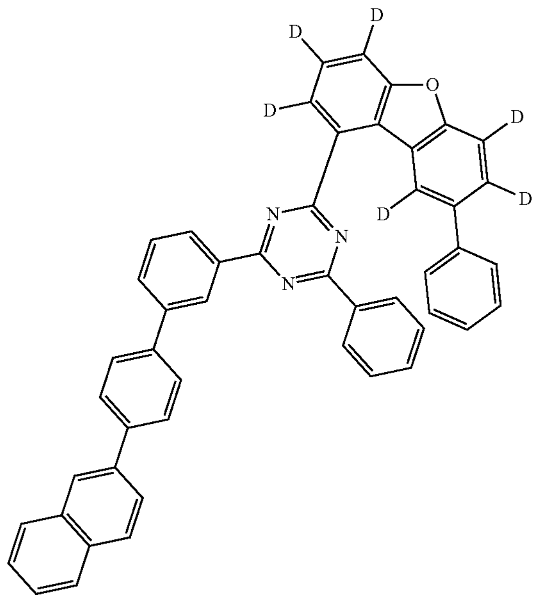
-continued
P-95
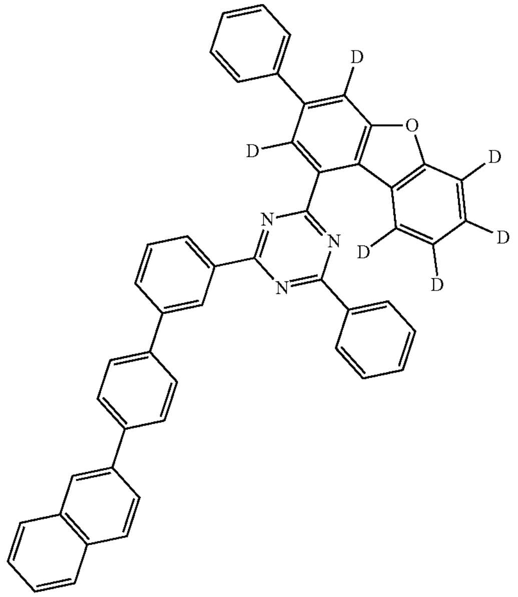
P-96
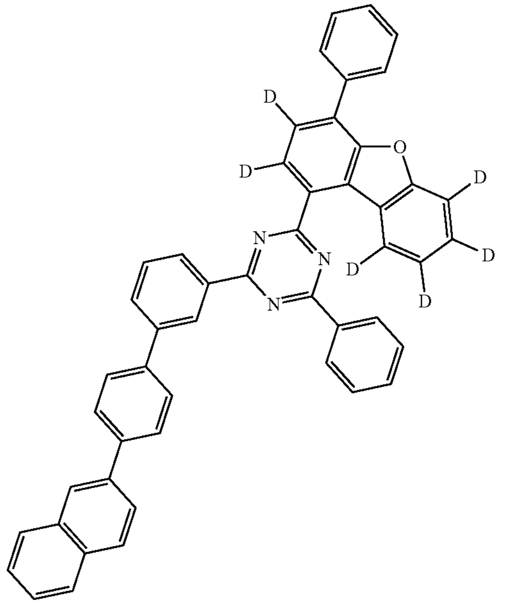

-continued
P-97
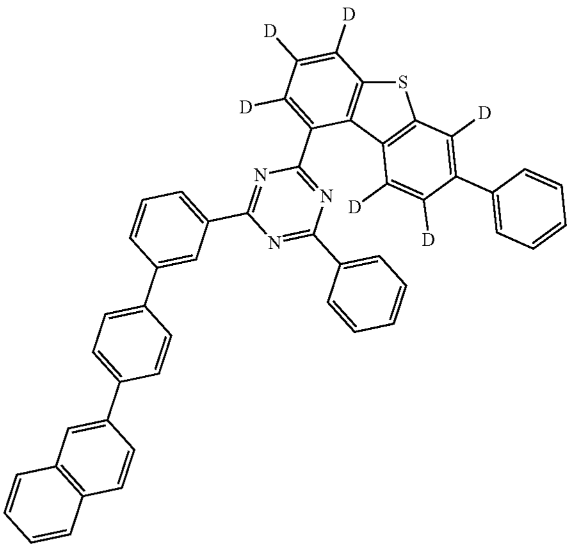
P-98
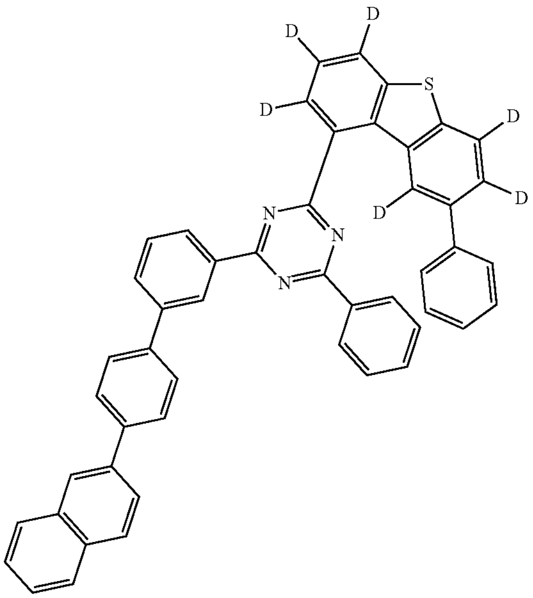
-continued
P-99
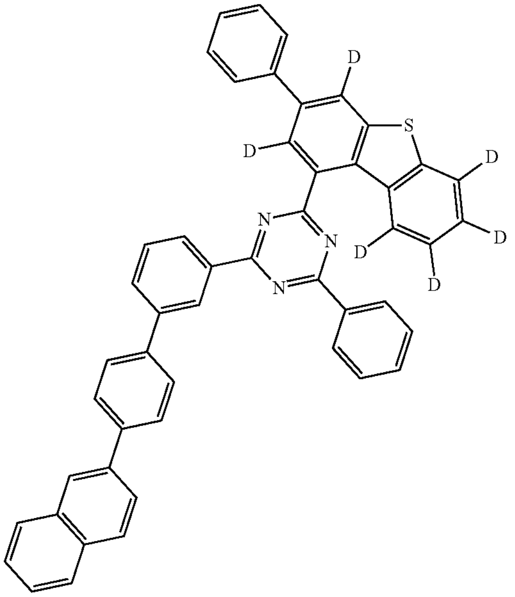
P-100
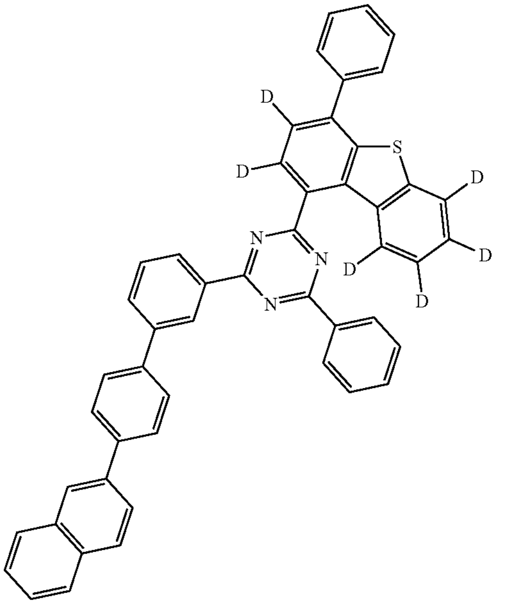

-continued
P-101
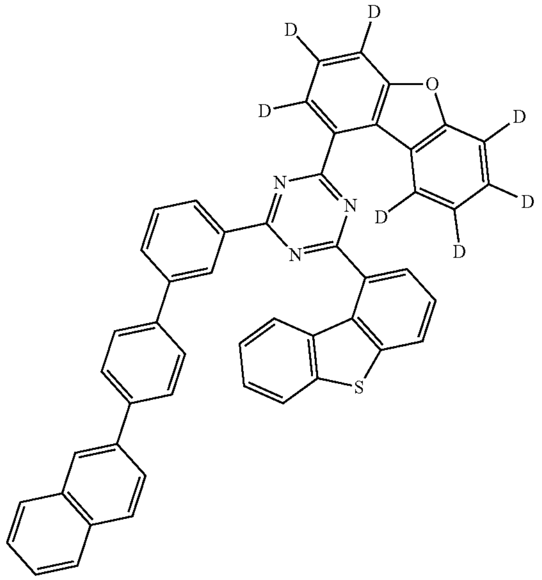
P-103
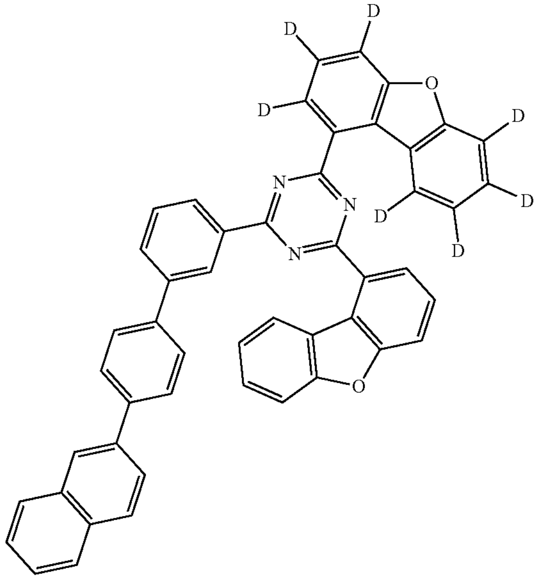
P-102
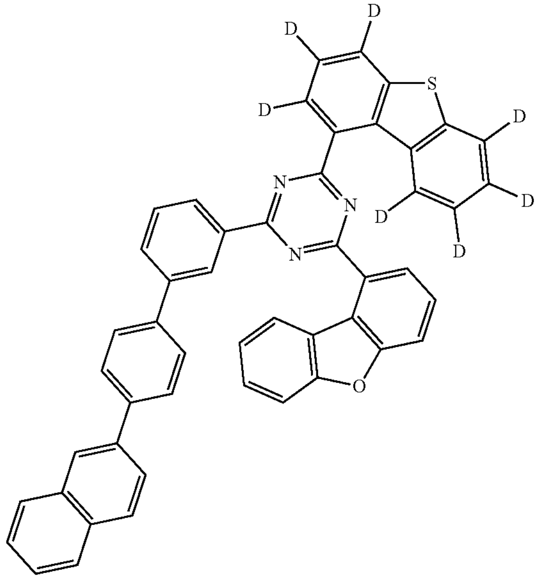
P-104
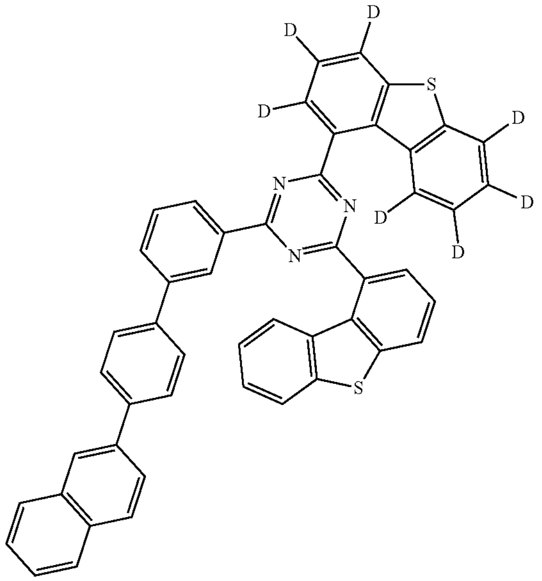

-continued
P-105
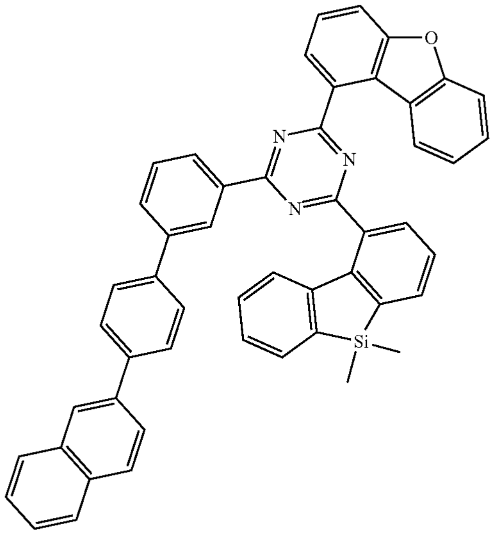
P-106
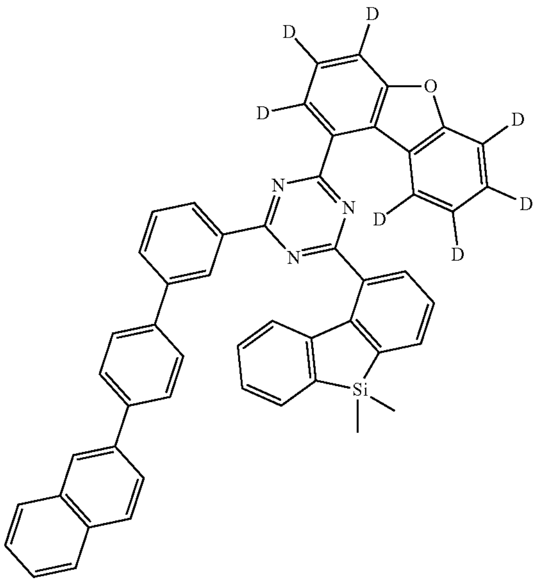
-continued
P-107
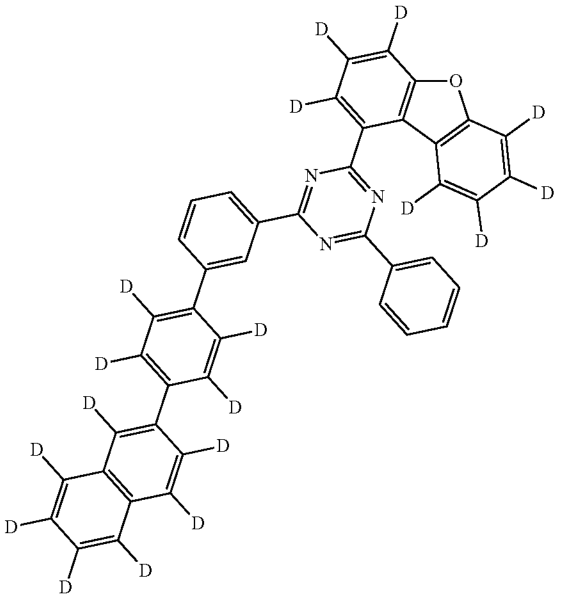
Also, Formula 4 is represented by any one of the following compounds H-1 to H-100.
H-1
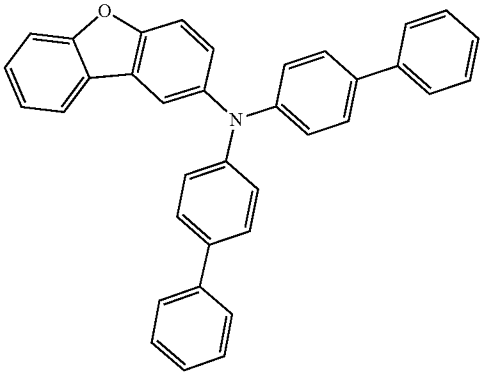
H-2
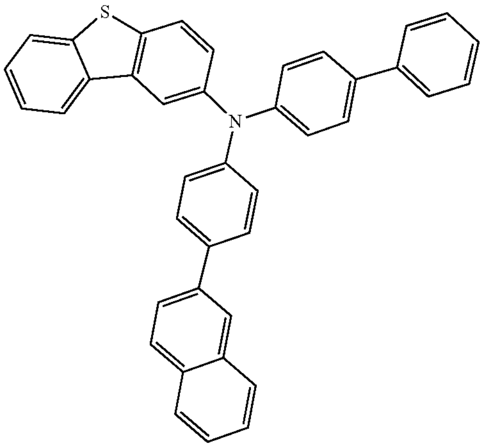

-continued
H-3
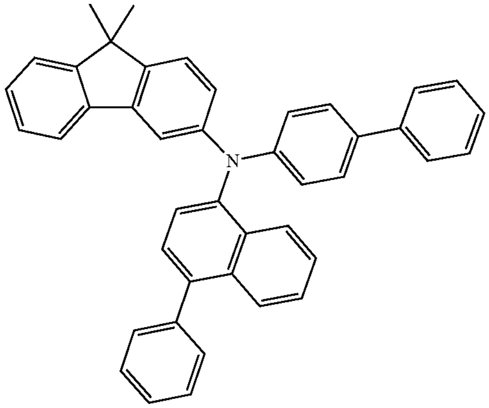
H-4
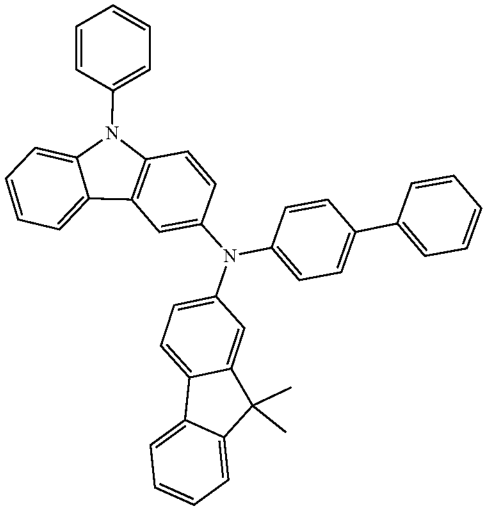
H-5
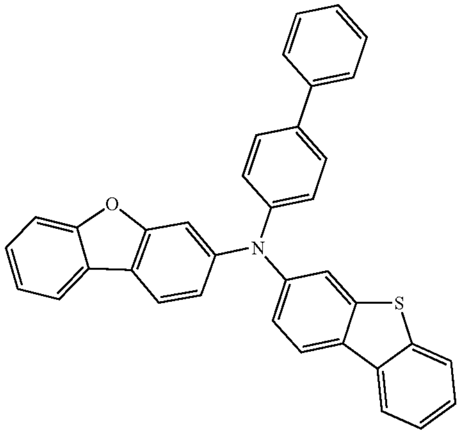
-continued
H-6
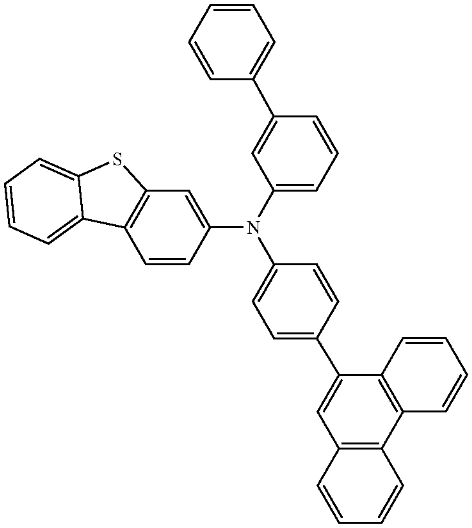
H-7
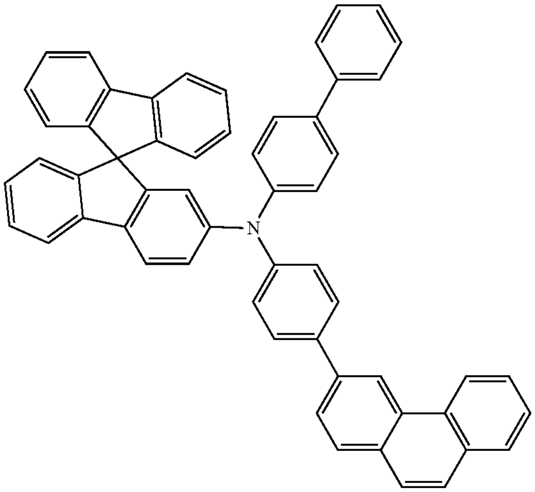
H-8
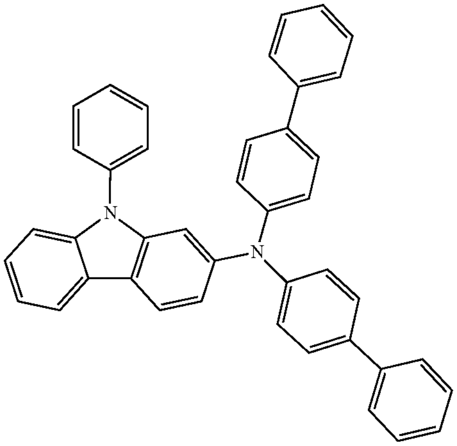

-continued
H-9
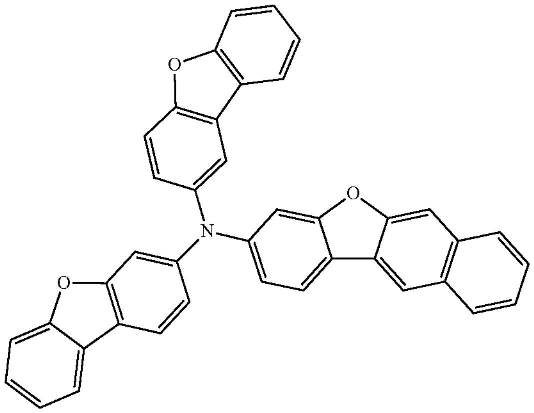
H-10
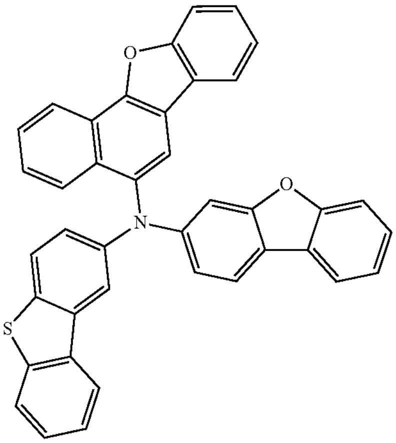
H-11
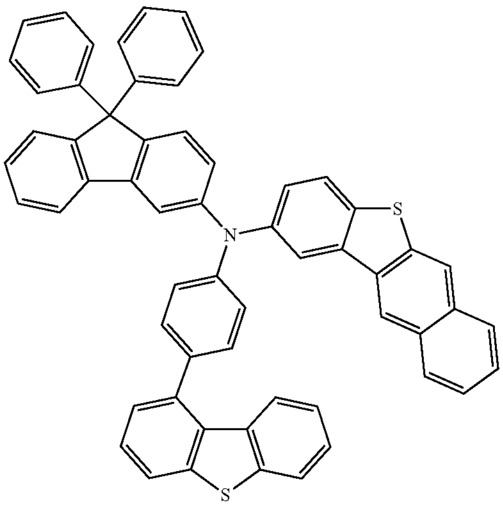
-continued
H-12
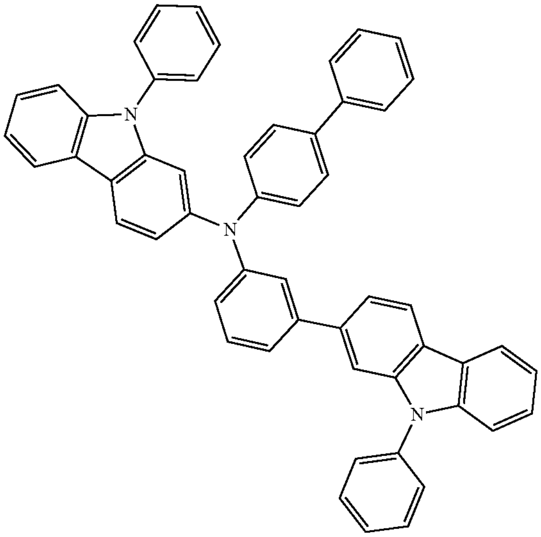
H-13
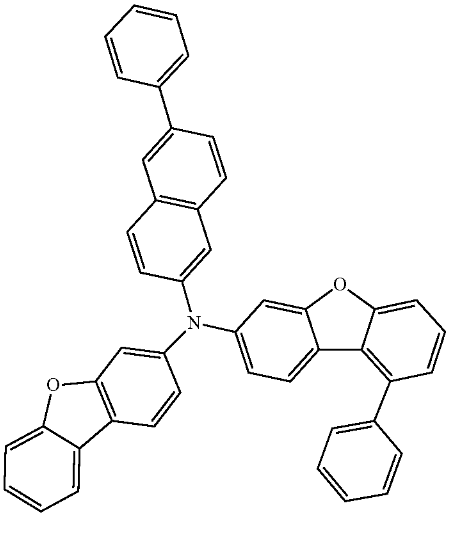
H-14
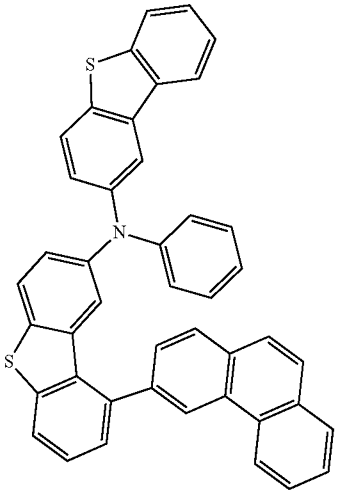

-continued
H-15
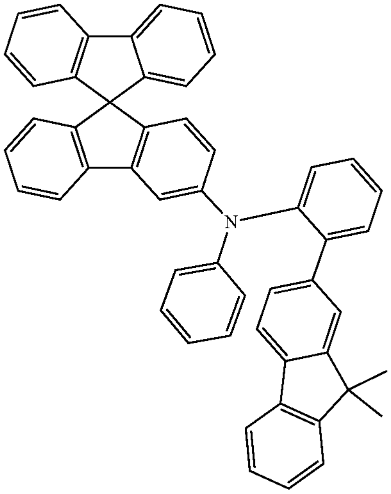
H-16
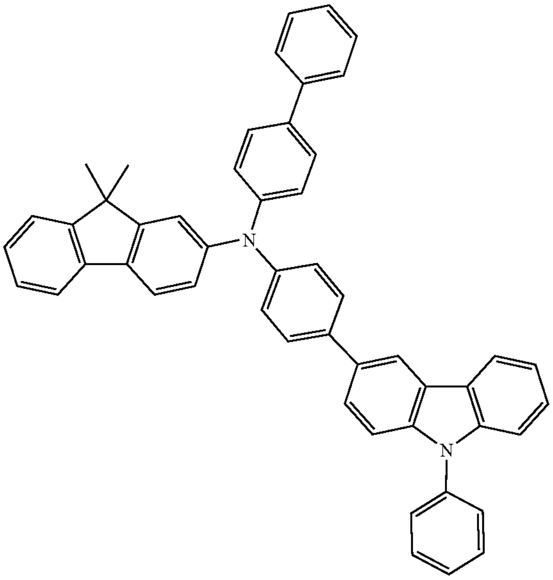
H-17
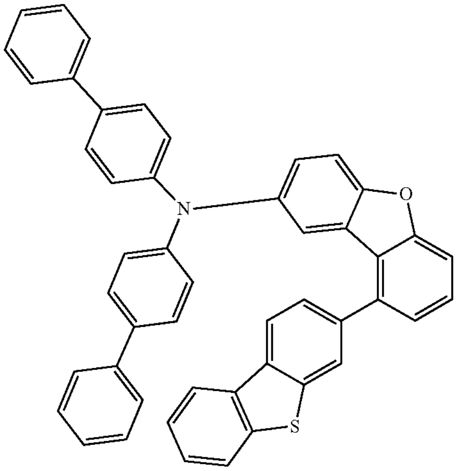
-continued
H-18
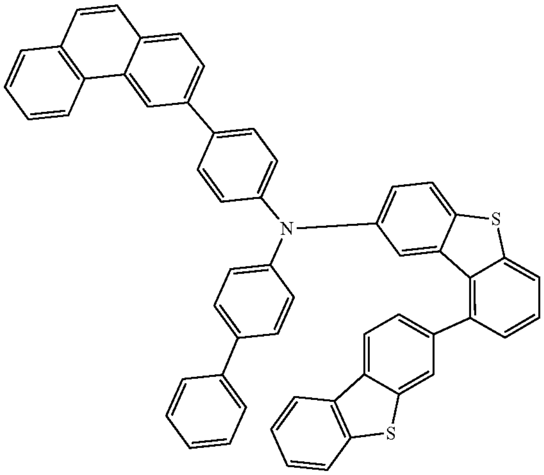
H-19
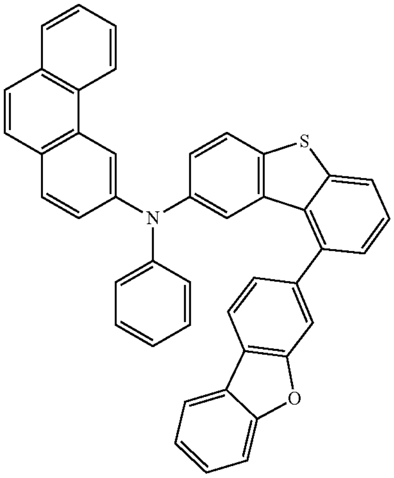
H-20
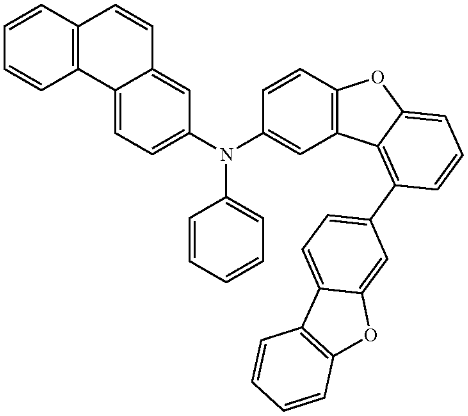

-continued
H-21
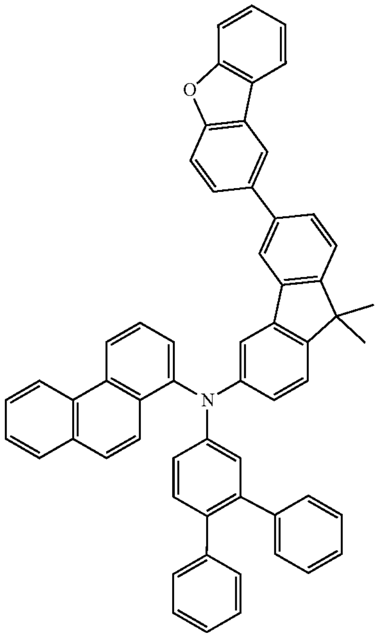
H-22
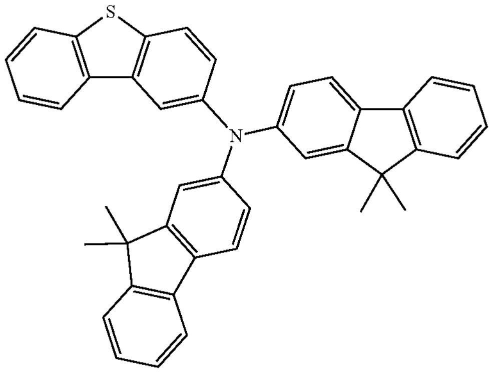
H-23
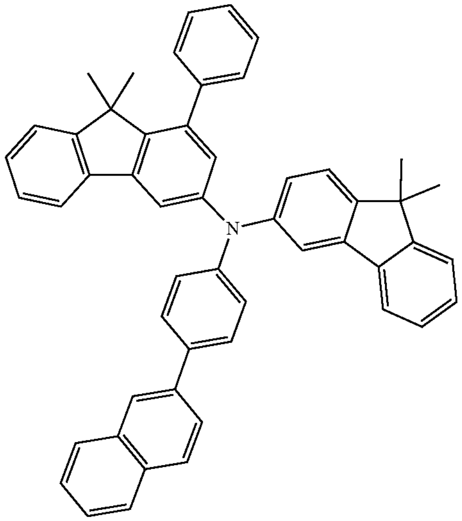
-continued
H-24
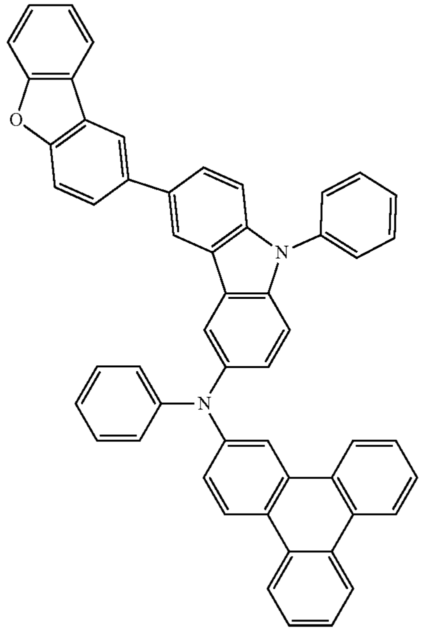
H-25
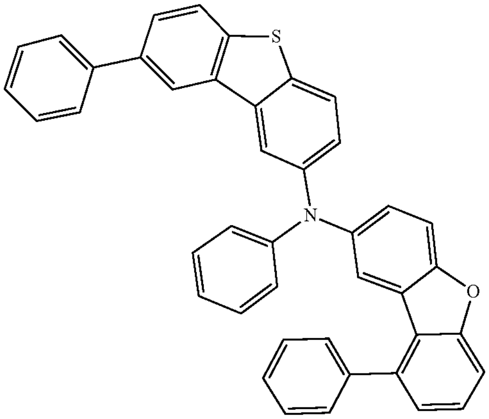
H-26
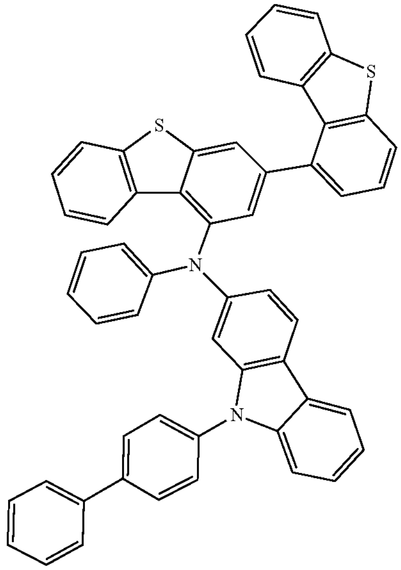

-continued
H-27
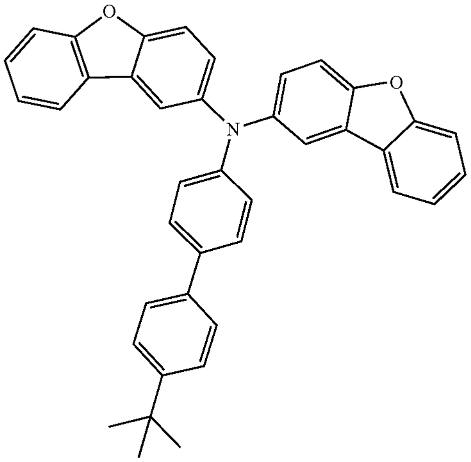
H-28
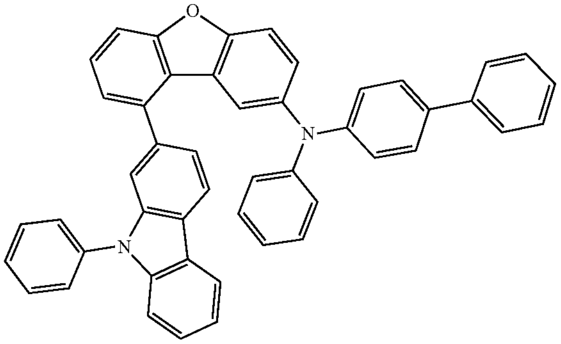
H-29
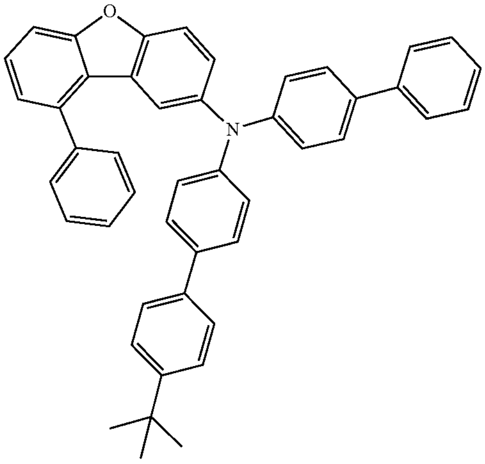
-continued
H-30
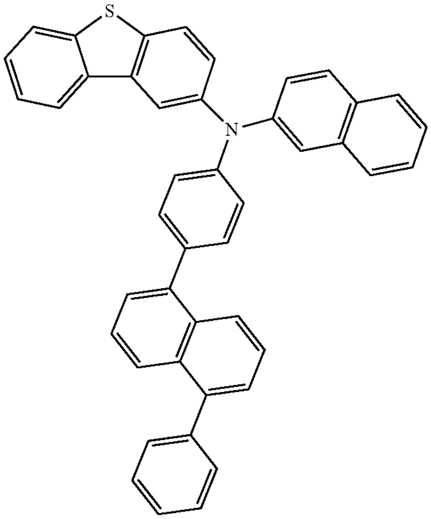
H-31
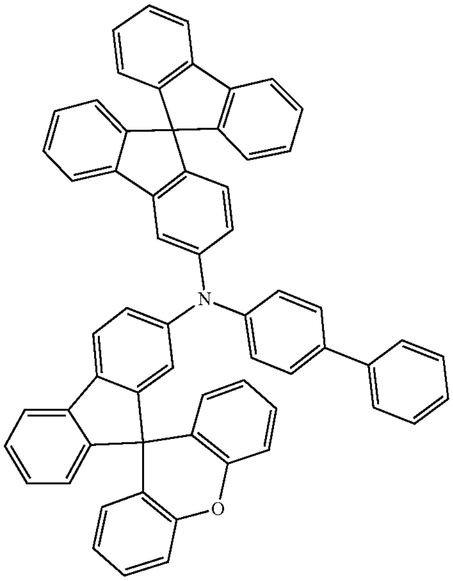

-continued
H-32
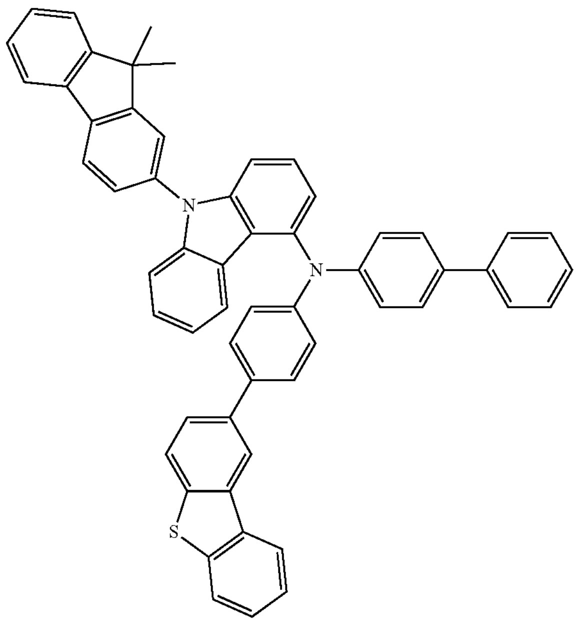
H-33
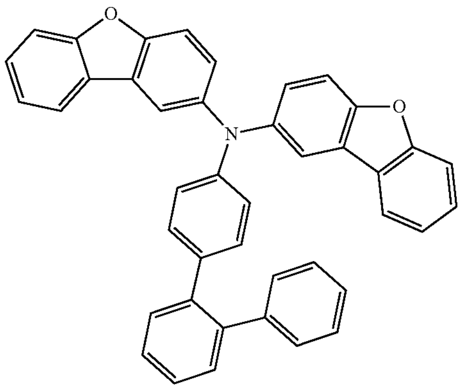
H-34
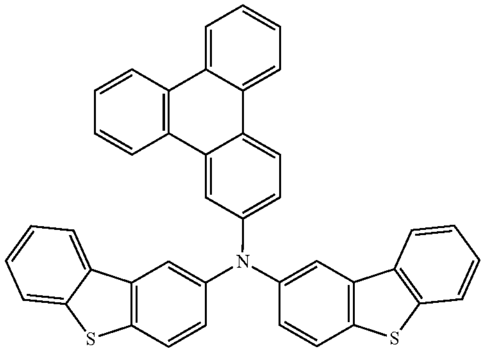
-continued
H-35
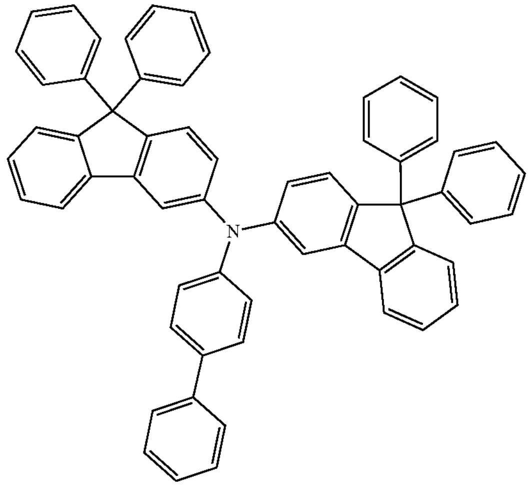
H-36
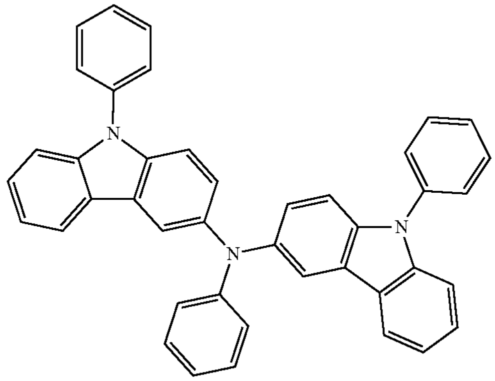
H-37
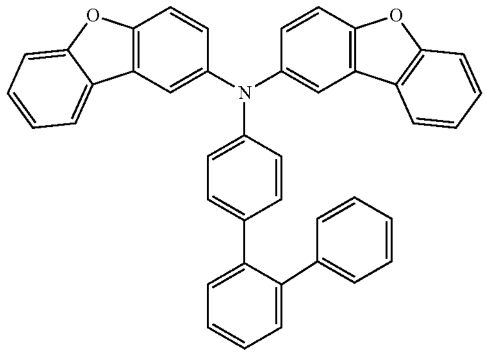

-continued
H-38
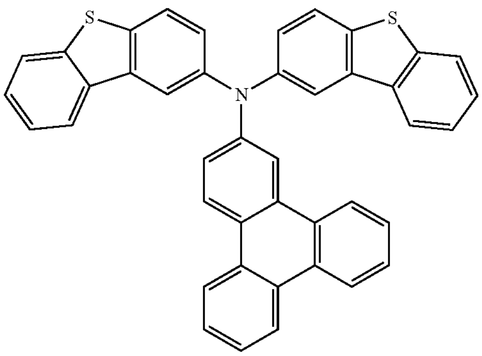
H-39
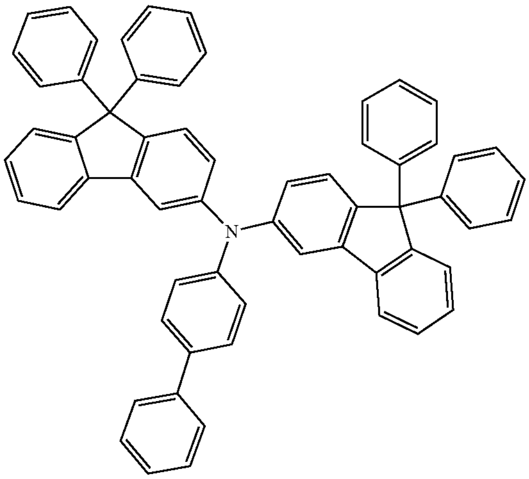
H-40
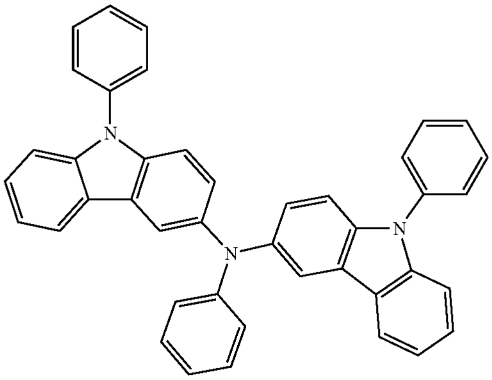
-continued
H-41
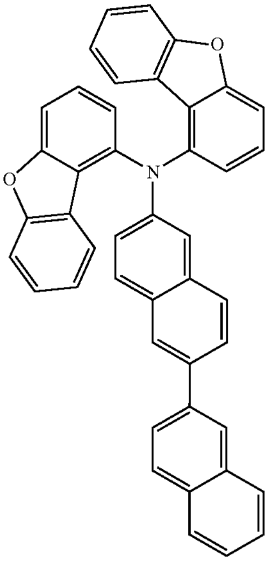
H-42
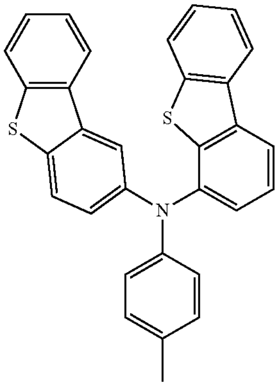
H-43
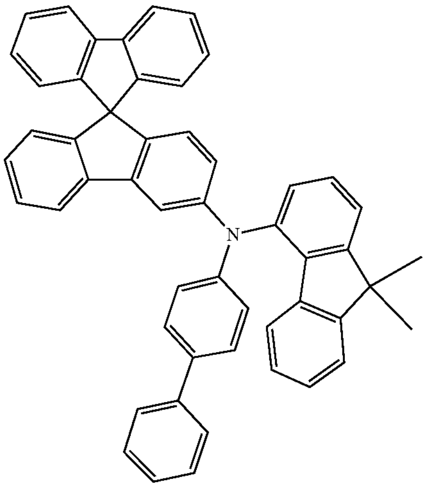

-continued
H-44
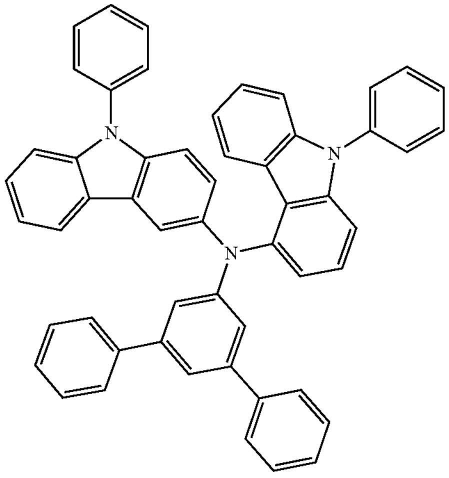
H-45
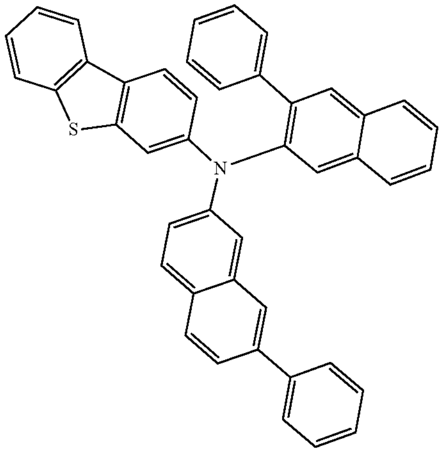
H-46
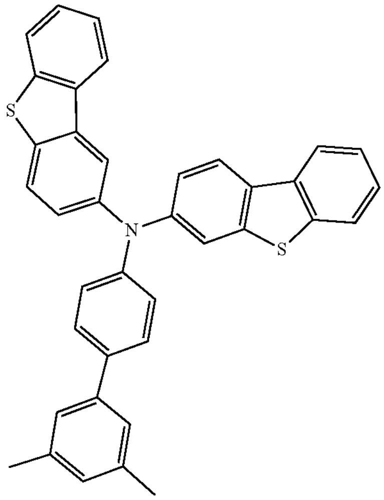
-continued
H-47
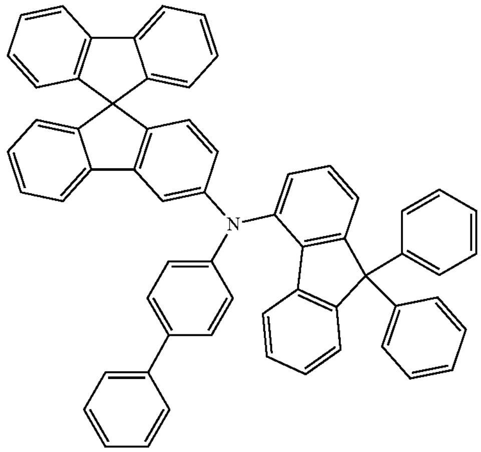
H-48
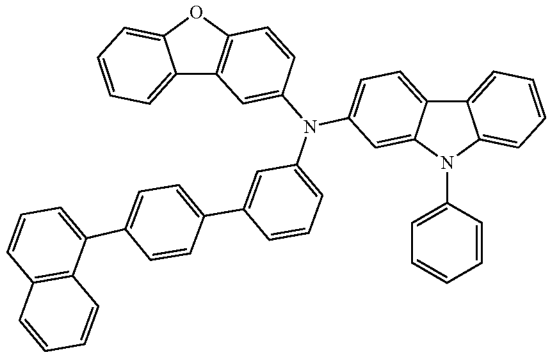
H-49
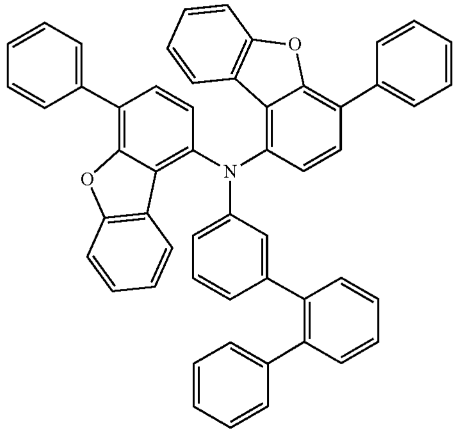

-continued
H-50
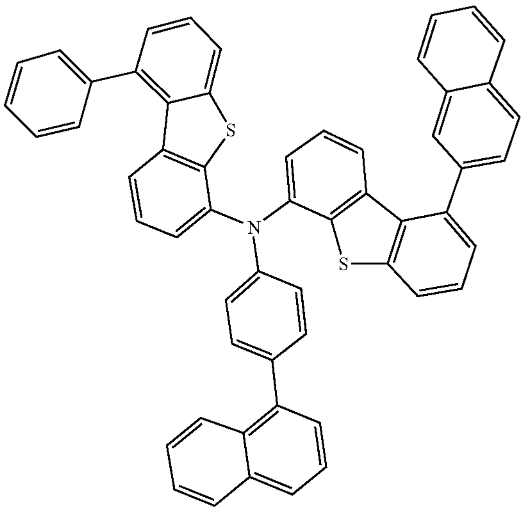
H-51
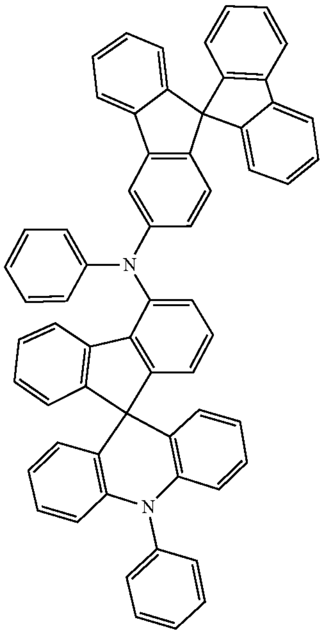
-continued
H-52
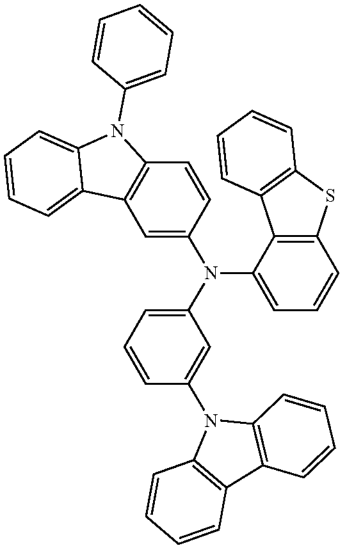
H-53
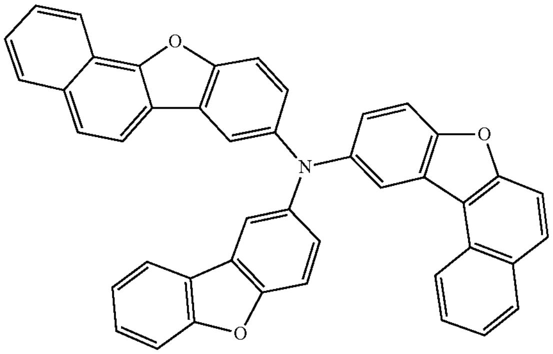
H-54
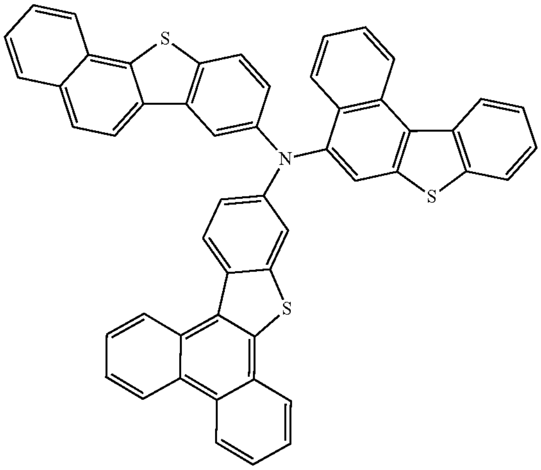

H-55
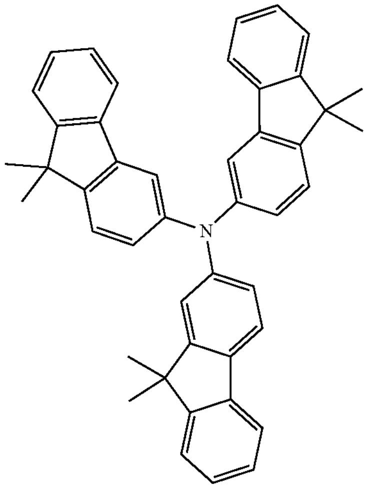
H-56
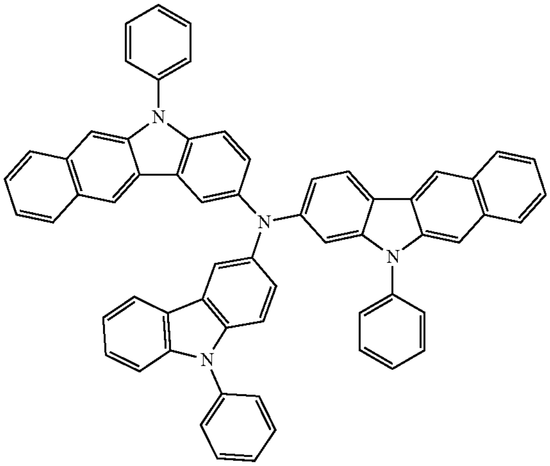
H-57
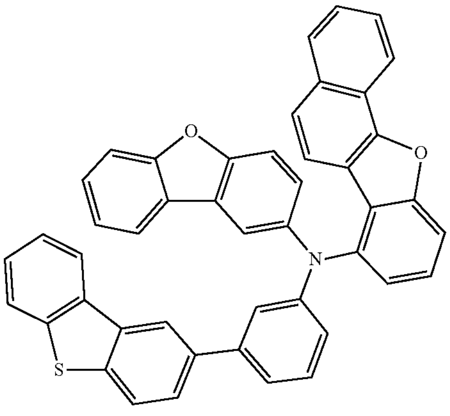
H-58
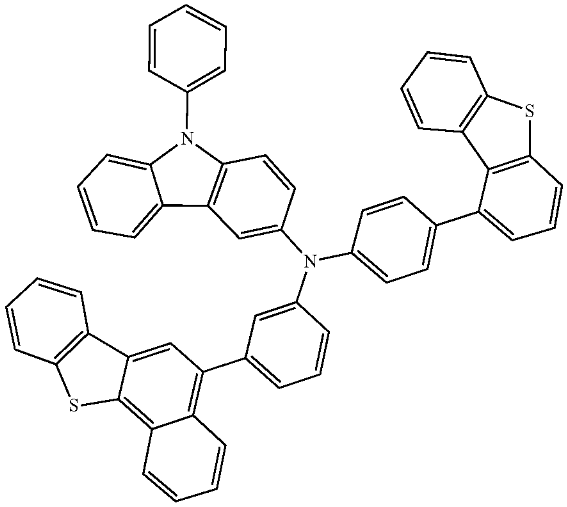
H-59
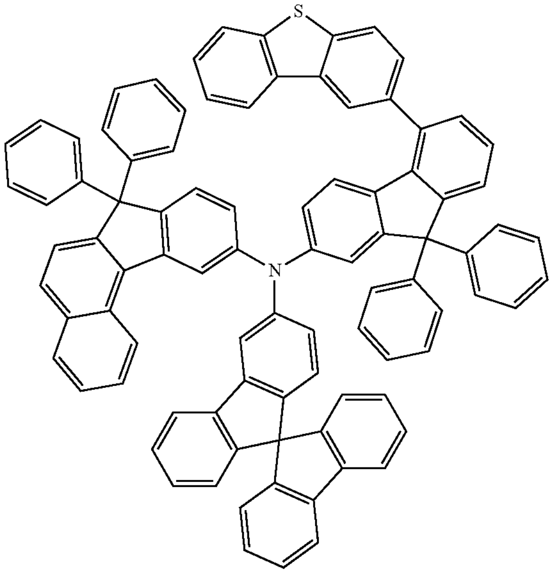
H-60
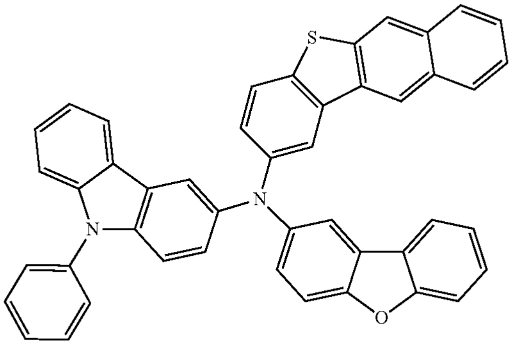

-continued
H-61
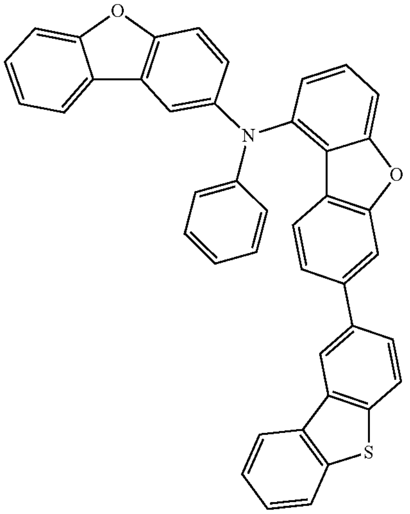
H-62
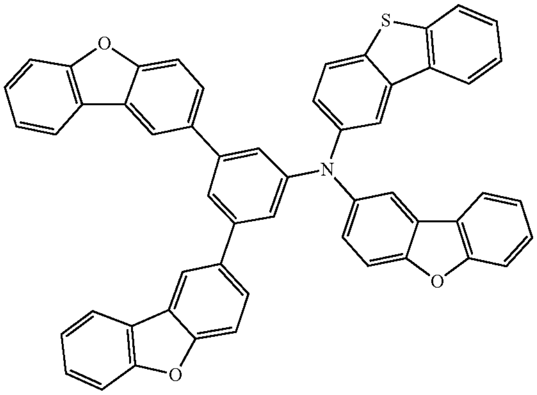
H-63
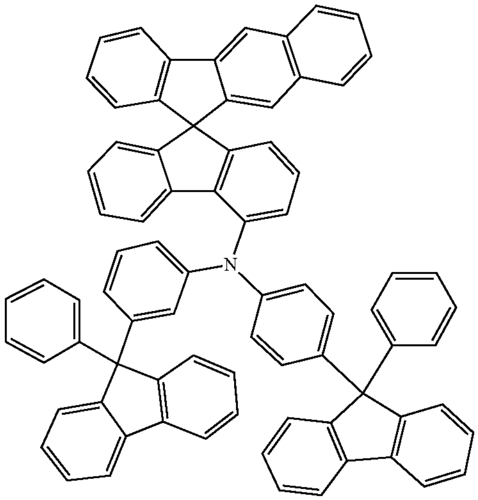
-continued
H-64
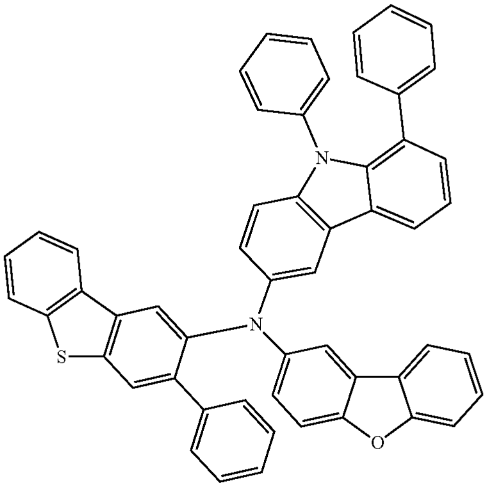
H-65
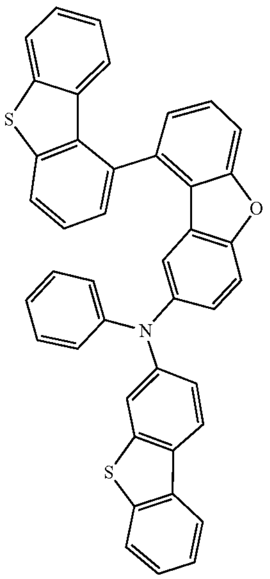
H-66
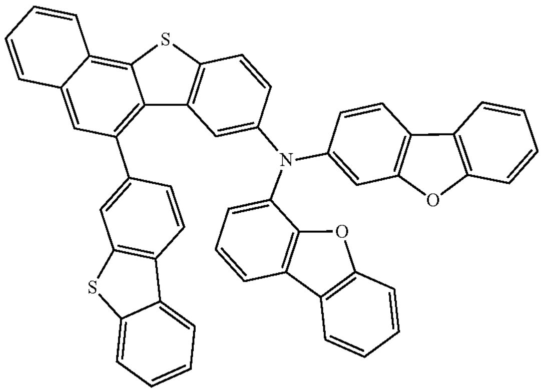

-continued
H-67
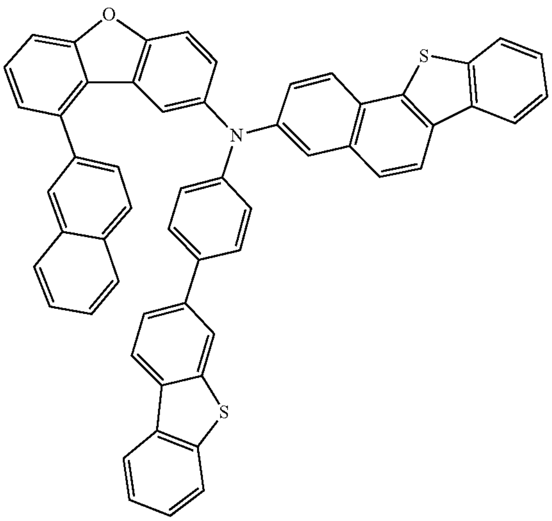
H-68
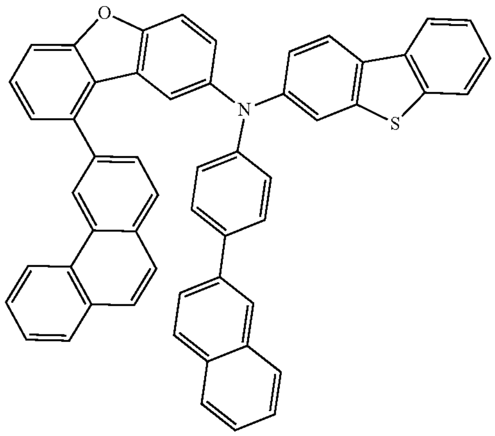
H-69
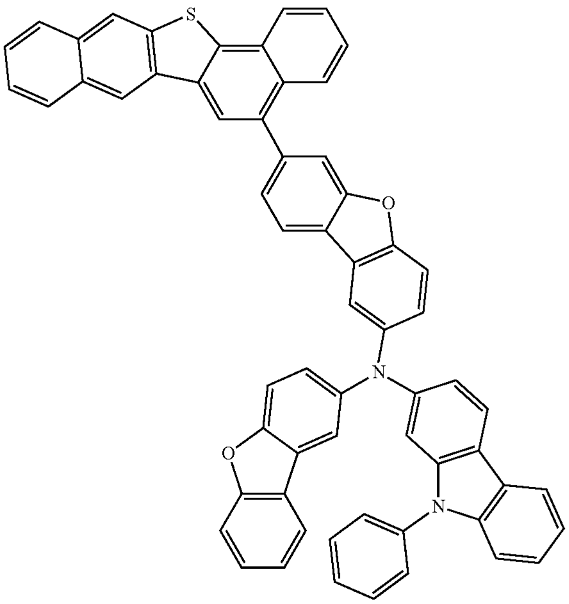
-continued
H-70
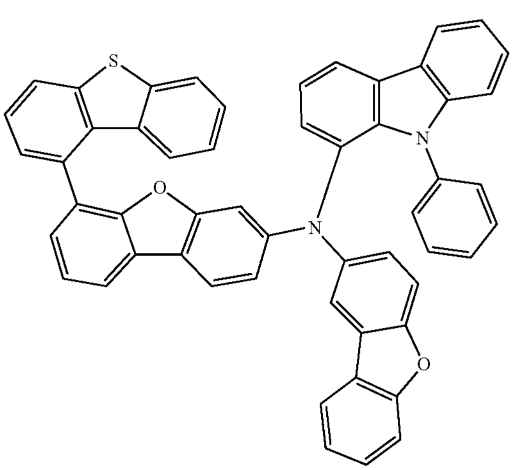
H-71
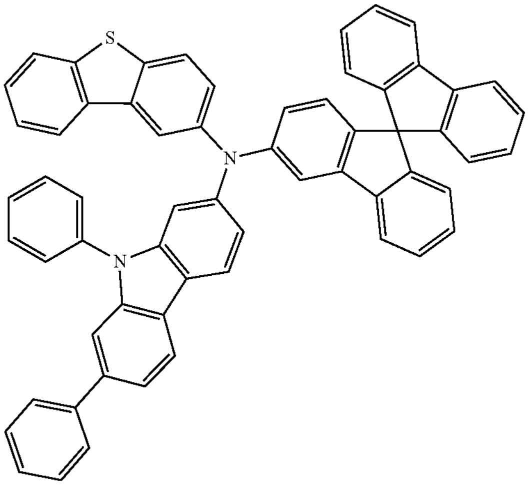
H-72
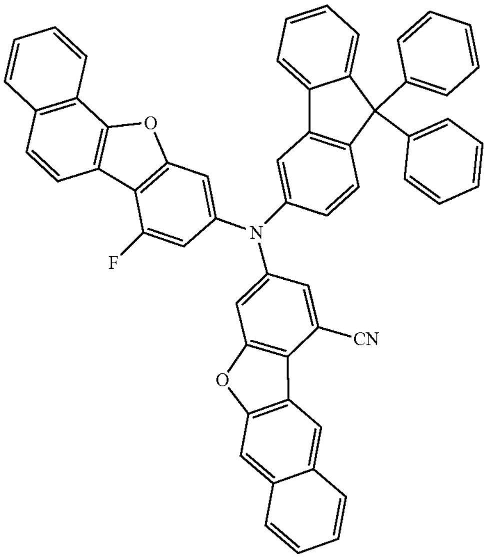

-continued
H-73
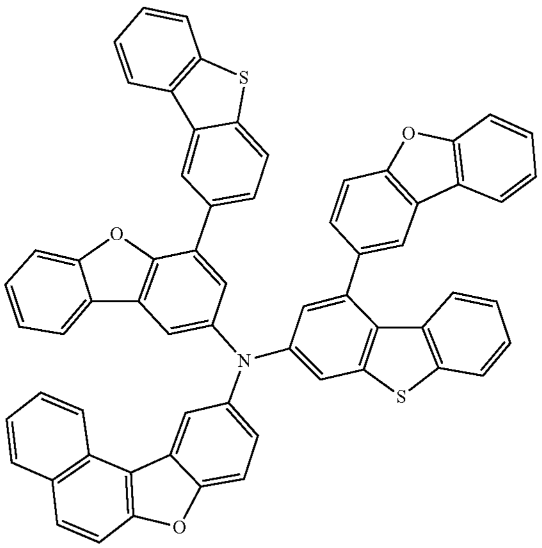
H-74
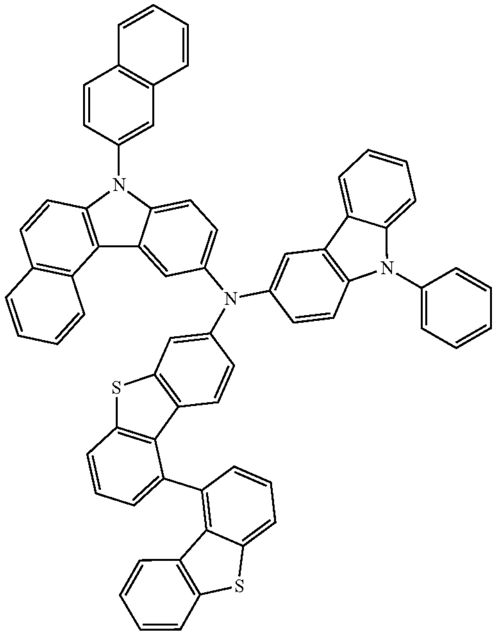
-continued
H-75
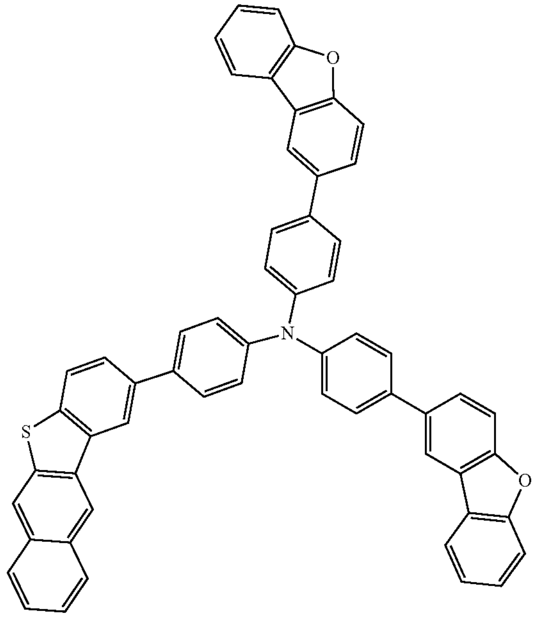
H-76
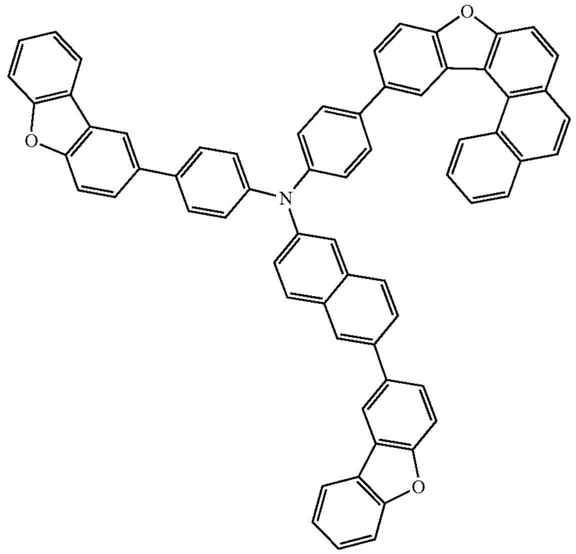

-continued
H-77
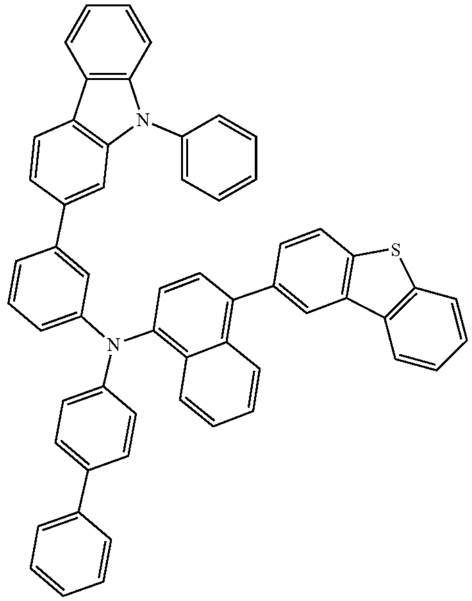
H-78
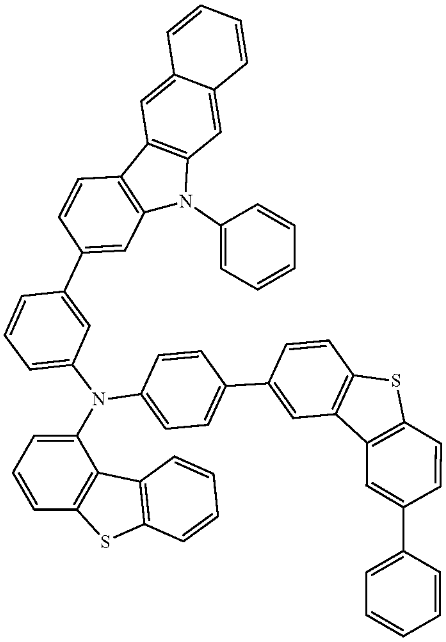
-continued
H-79
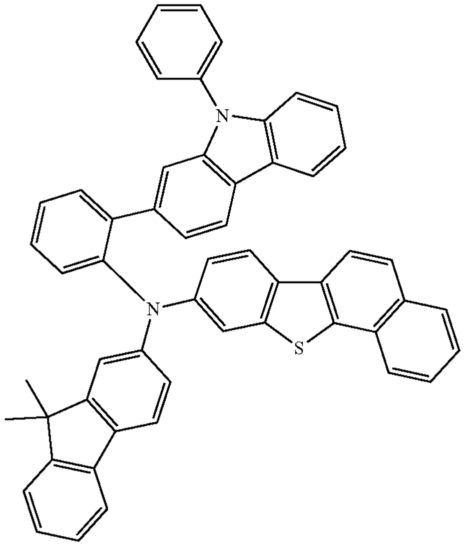
H-80
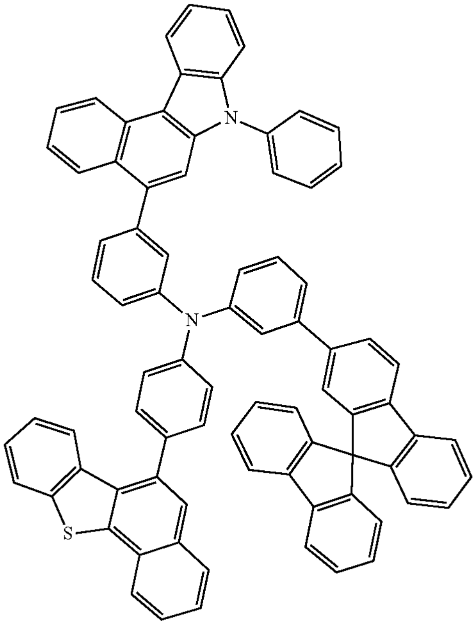

-continued
H-81
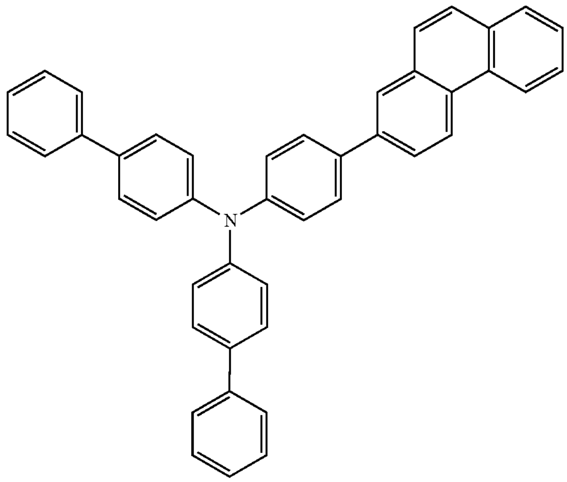
H-82
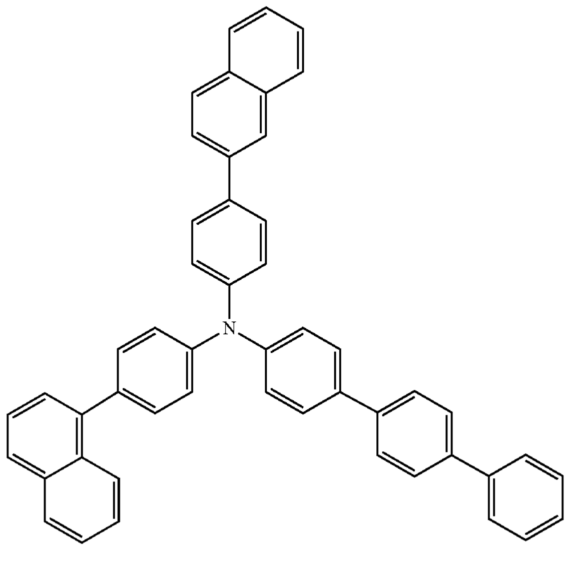
-continued
H-83
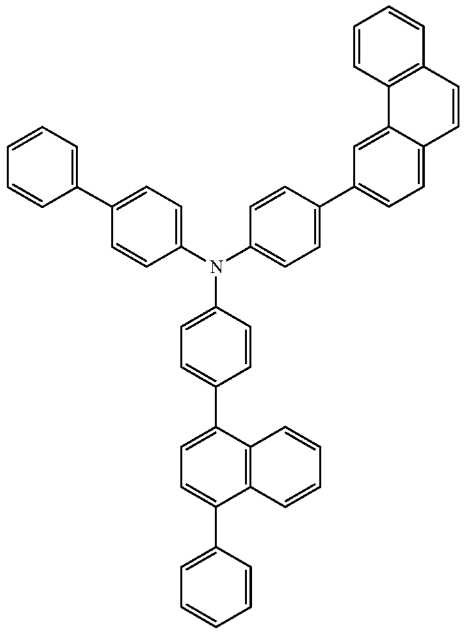
H-84
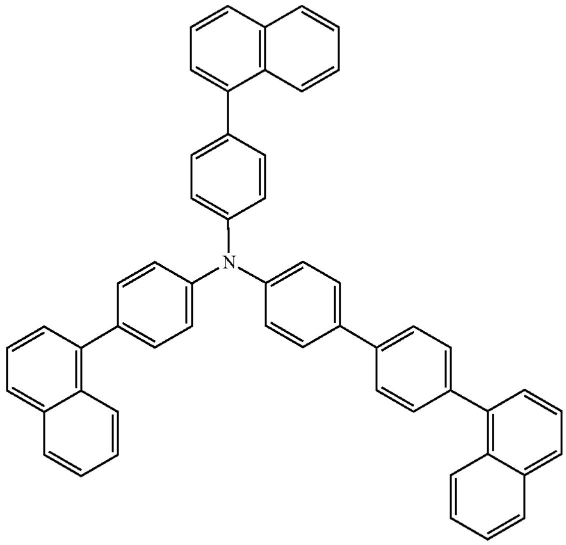

-continued
H-85
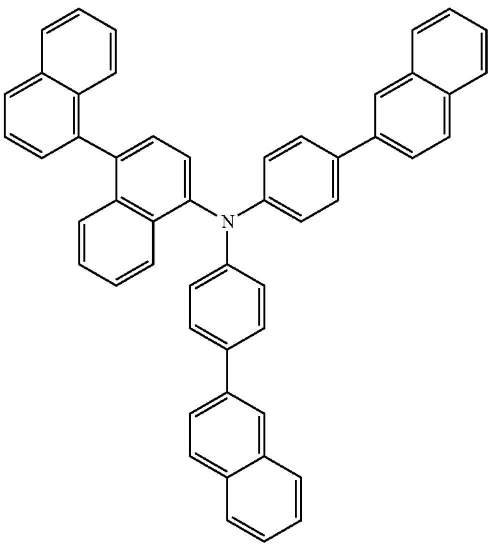
H-86
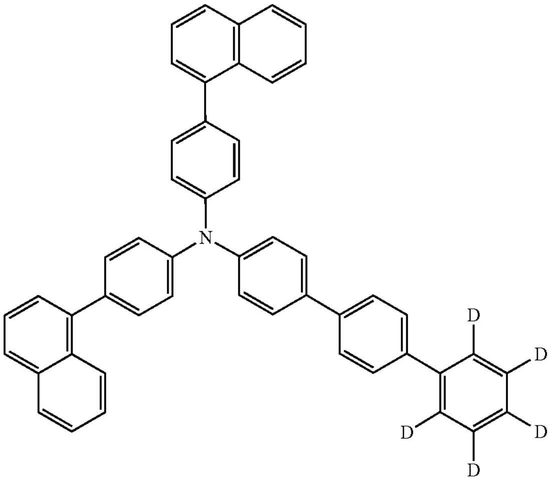
H-87
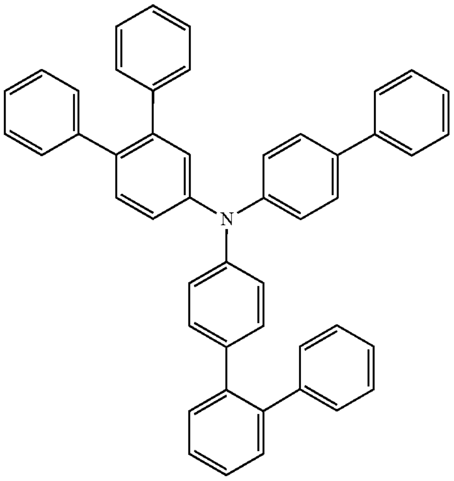
-continued
H-88
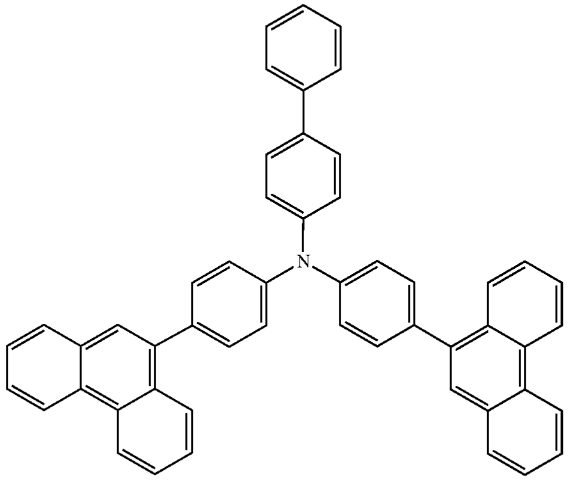
H-89
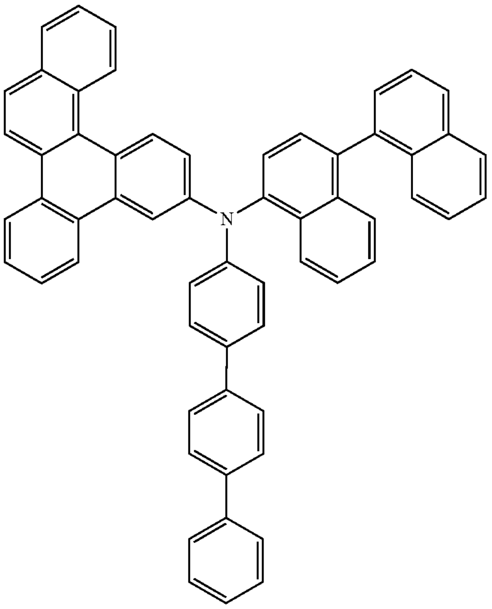
H-90
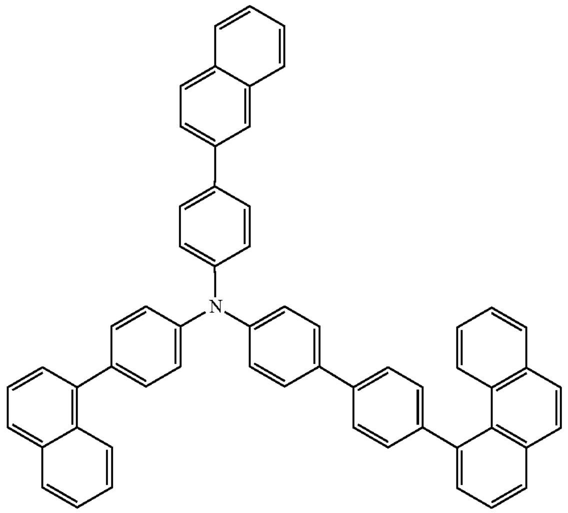

-continued
H-91
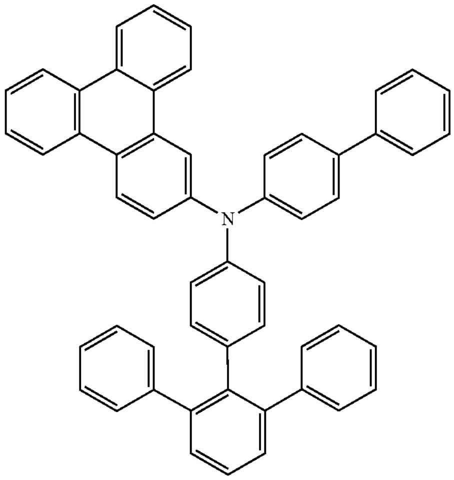
H-92
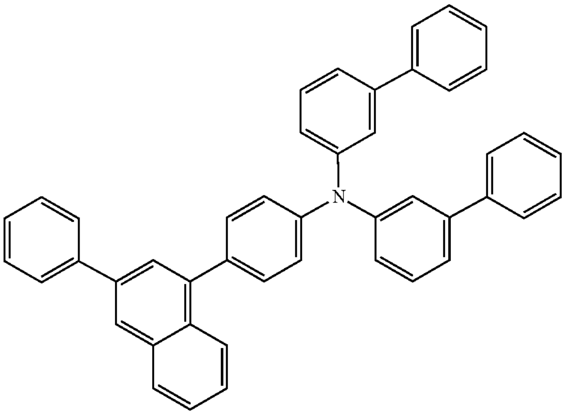
H-93
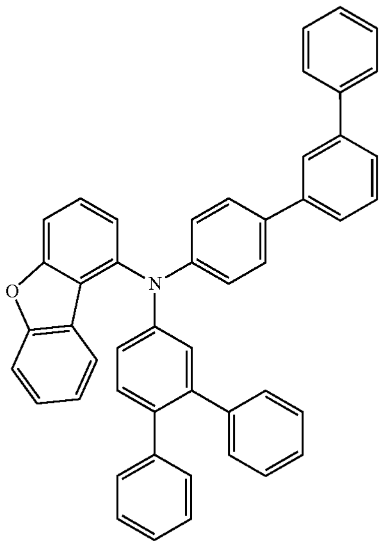
-continued
H-94
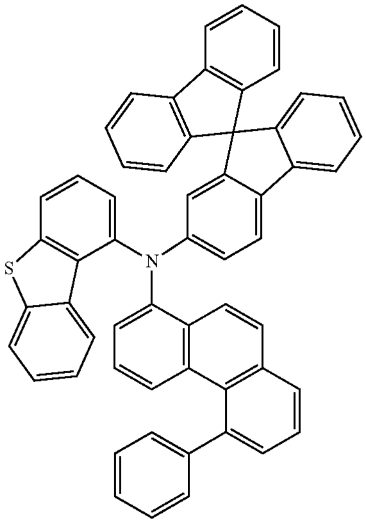
H-95
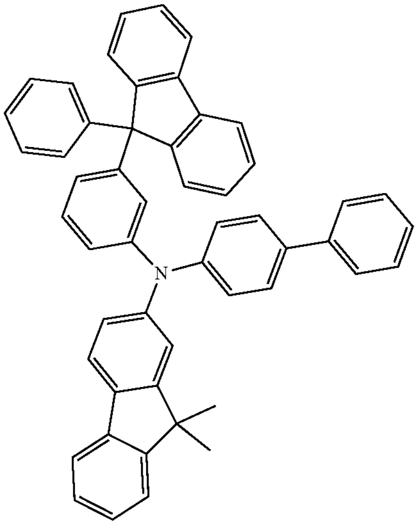
H-96
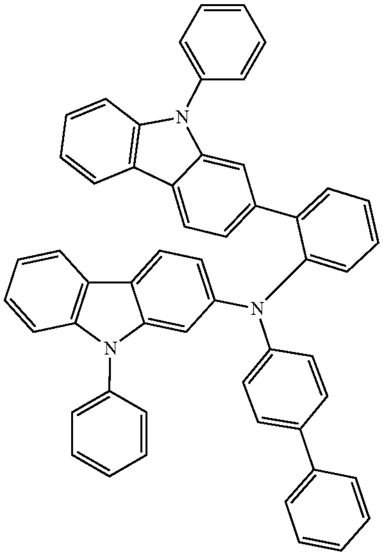

-continued
H-97
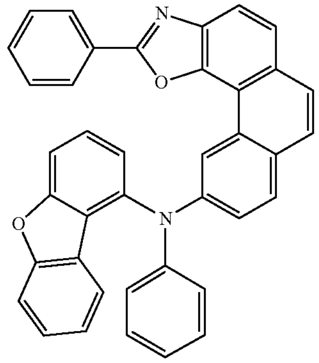
H-98
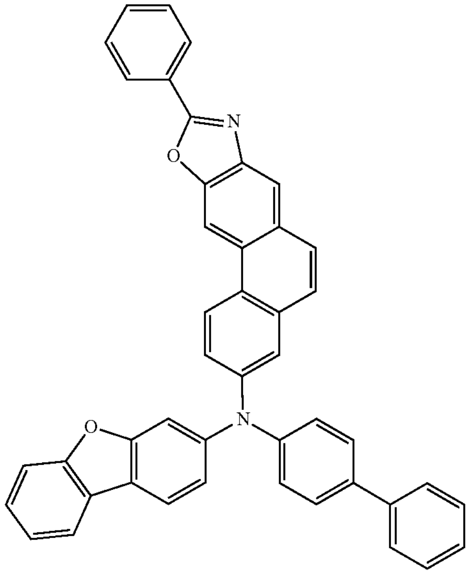
H-99
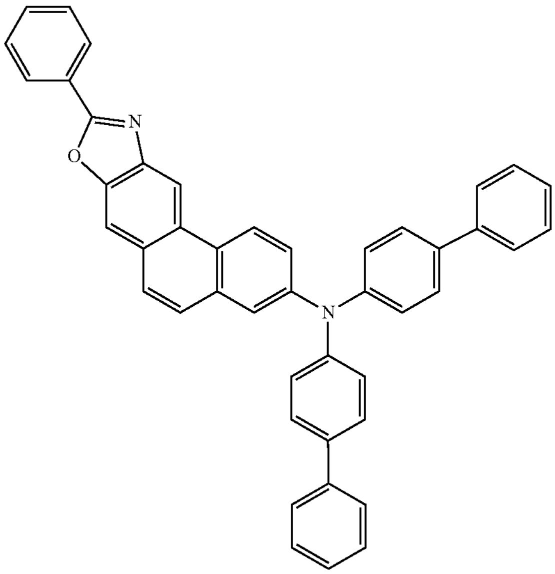
-continued
H-100
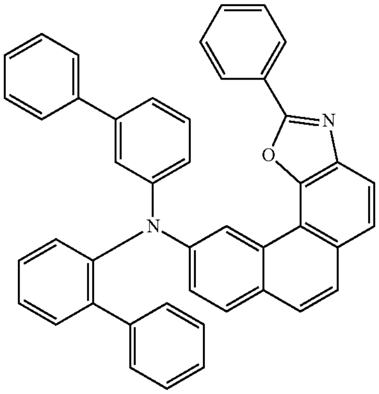
Also, Formula 5 is represented by any one of the following compounds S-1 to S-108.
S-1
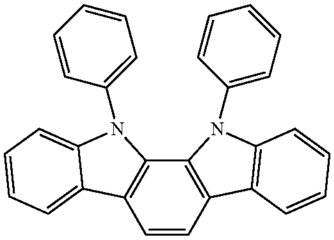
S-2
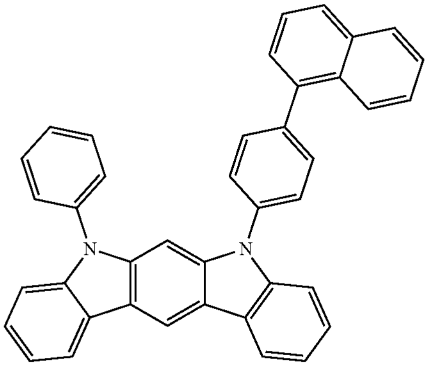
S-3
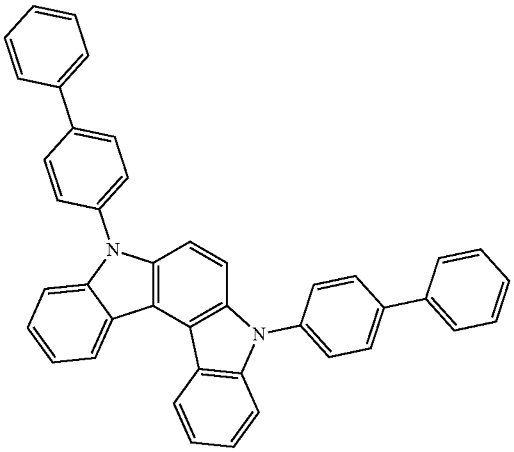

-continued
S-4
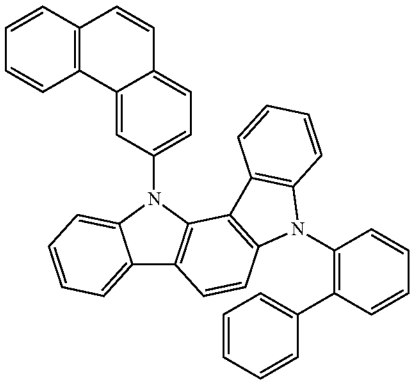
S-5
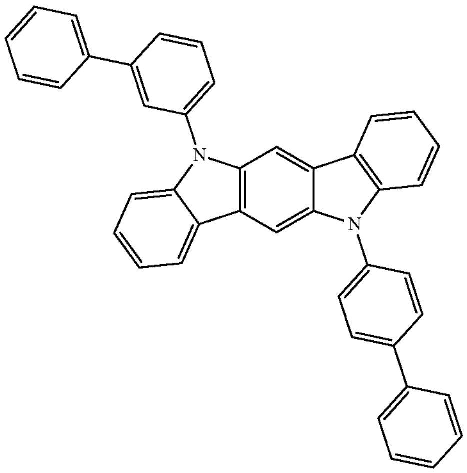
S-6
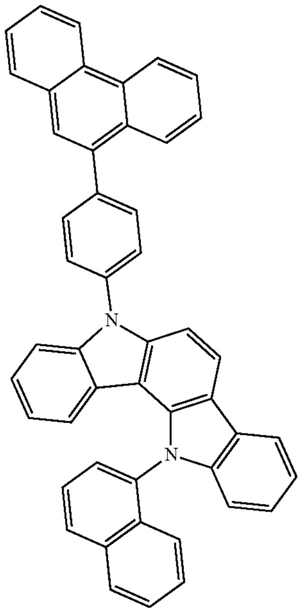
-continued
S-7
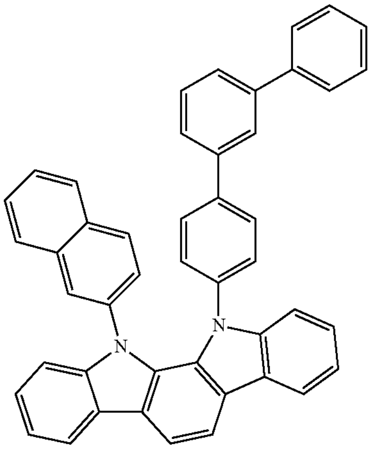
S-8
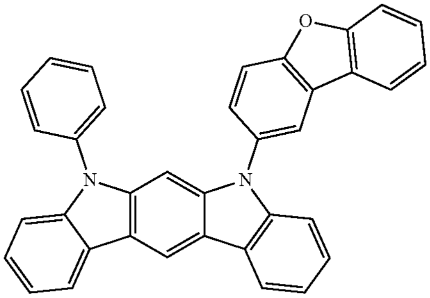
S-9
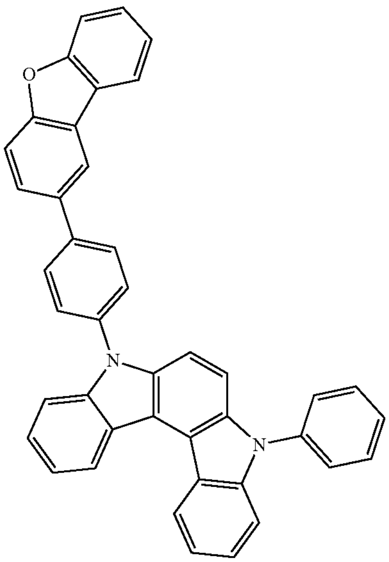

-continued
S-10
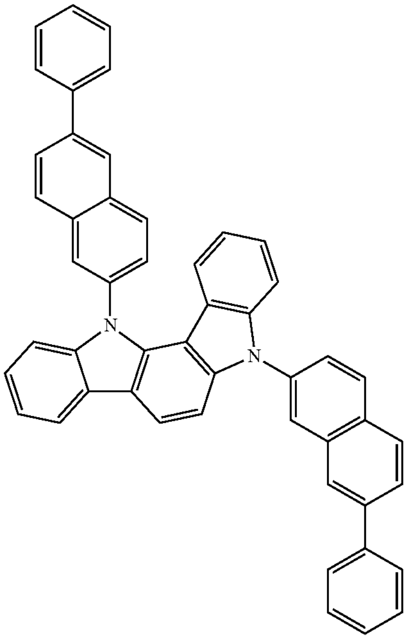
S-11
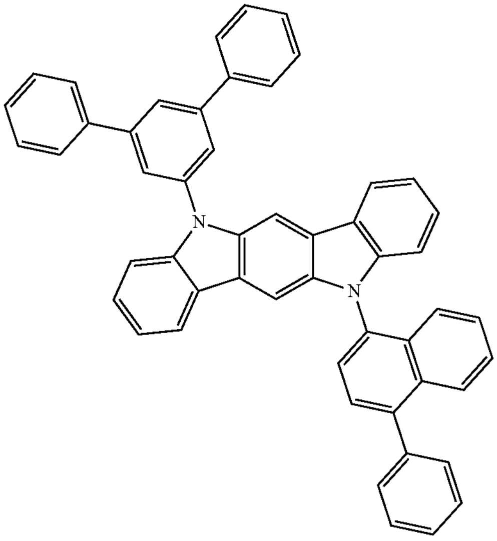
-continued
S-12
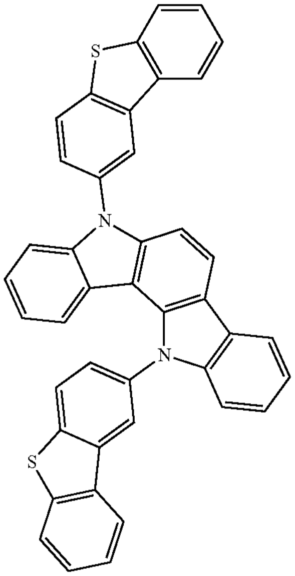
S-13
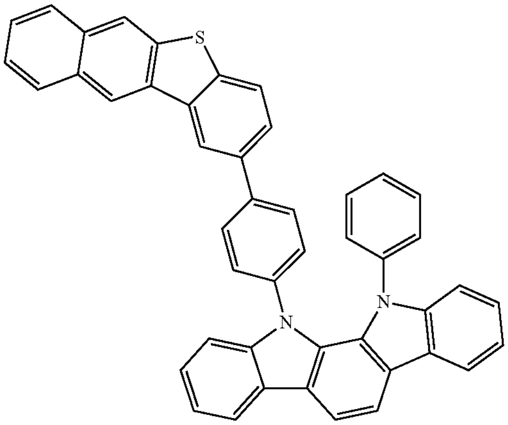
S-14
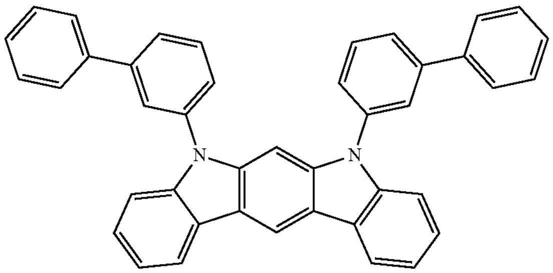
S-15
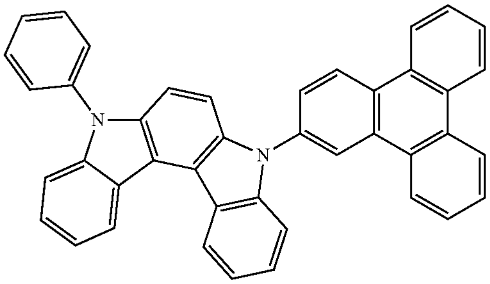

-continued
S-16
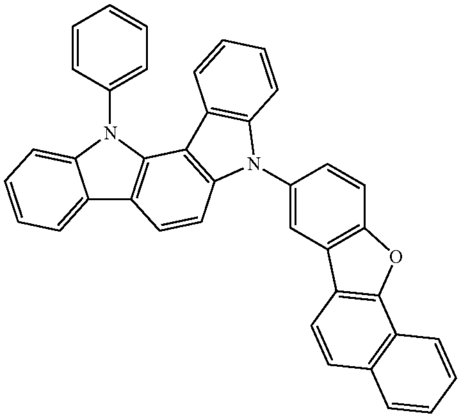
S-17
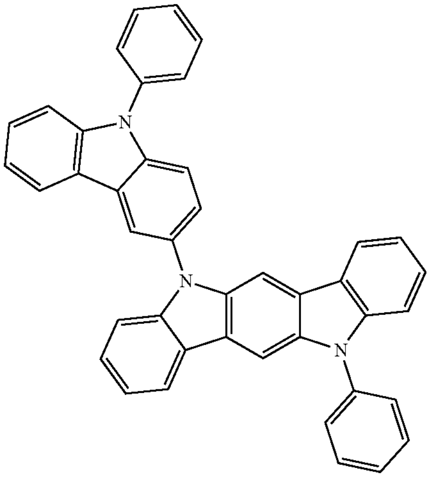
S-18
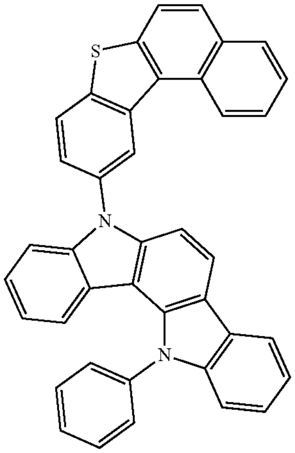
-continued
S-19
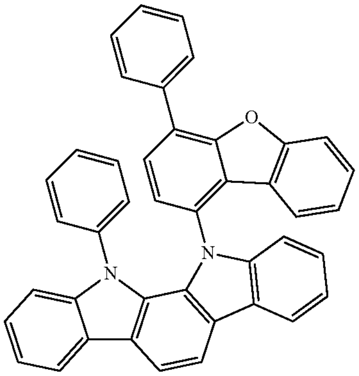
S-20
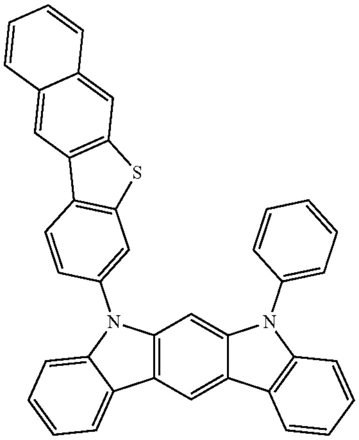
S-21
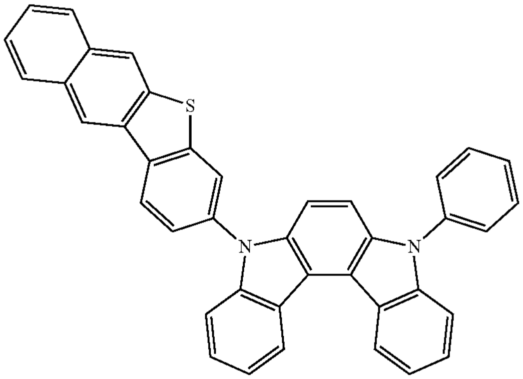

-continued
S-22
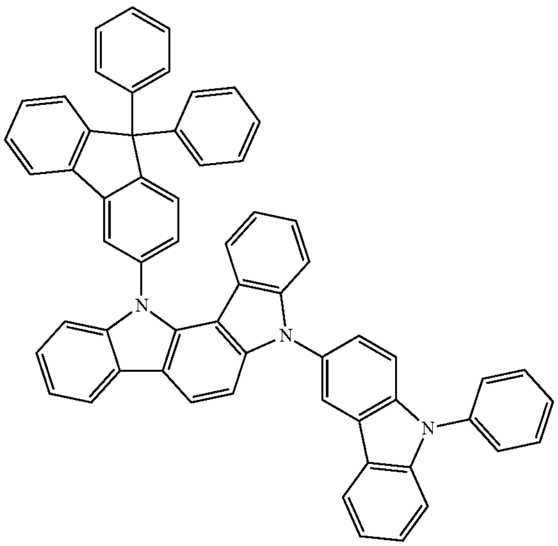
S-23
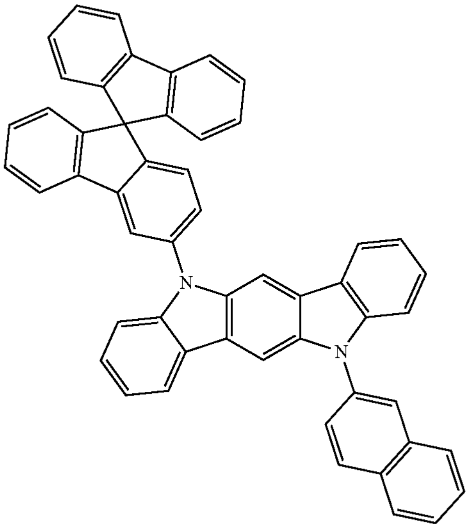
-continued
S-24
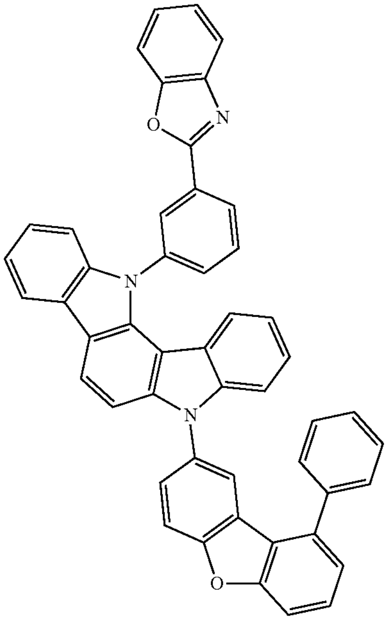
S-25
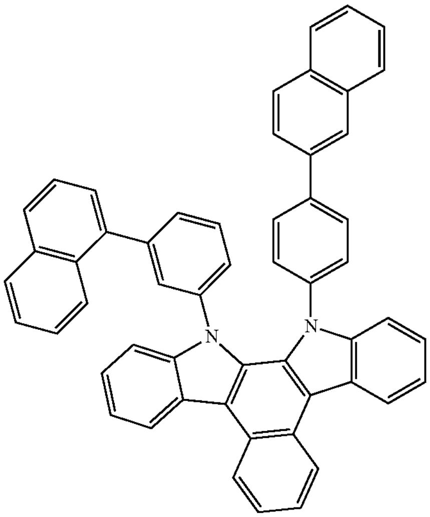
S-26
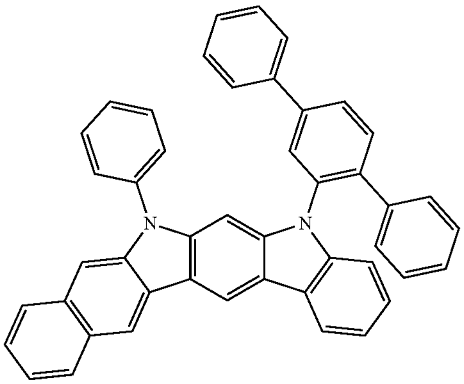

-continued
S-27
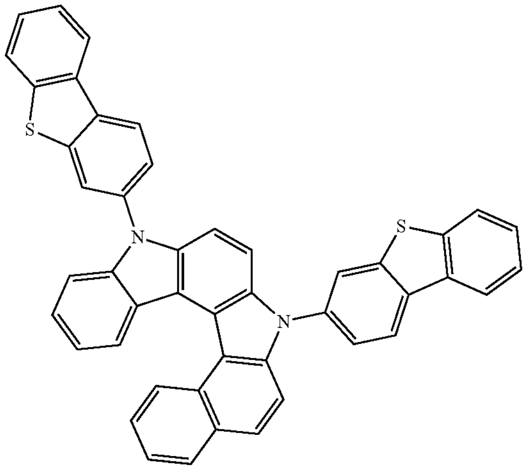
S-28
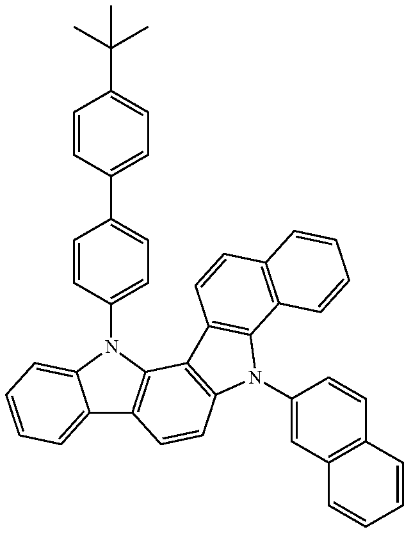
S-29
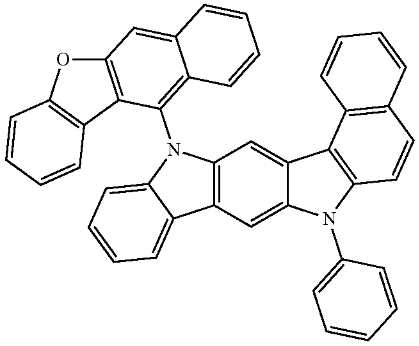
-continued
S-30
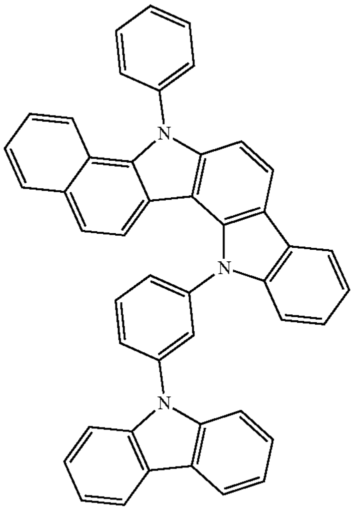
S-31
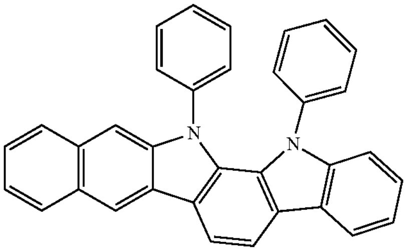
S-32
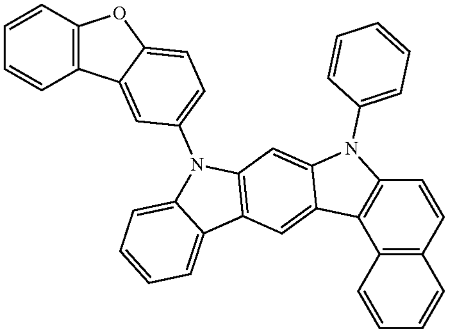
S-33
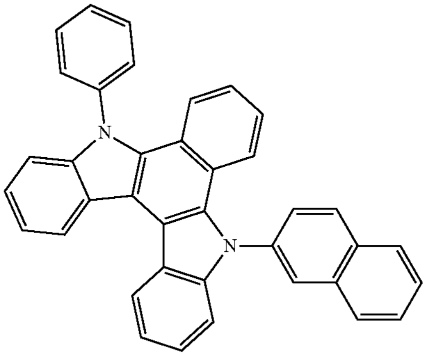

-continued
S-34
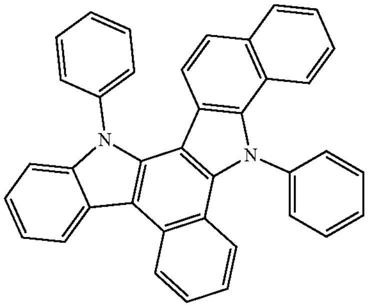
S-35
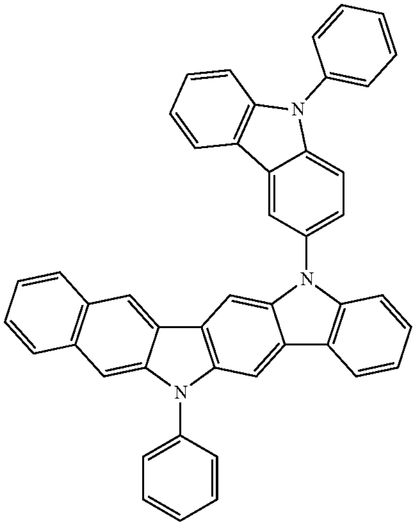
S-36
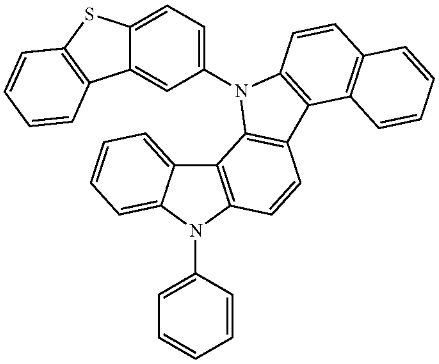
S-37
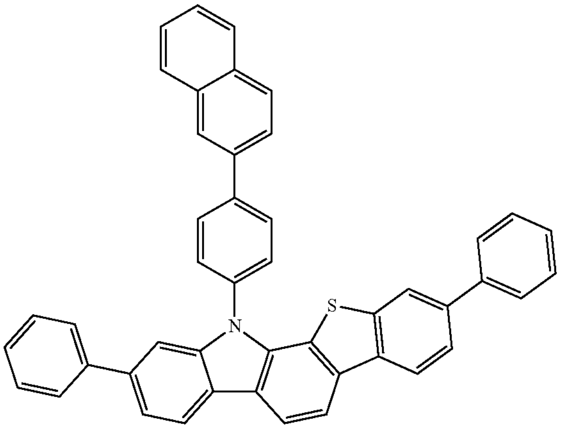
-continued
S-38
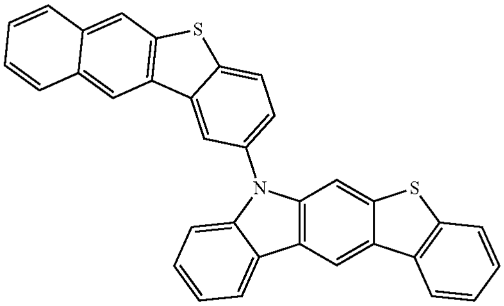
S-39
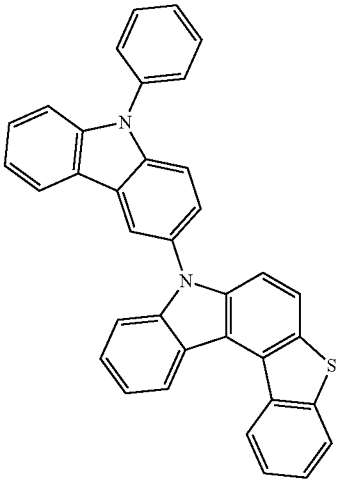
S-40
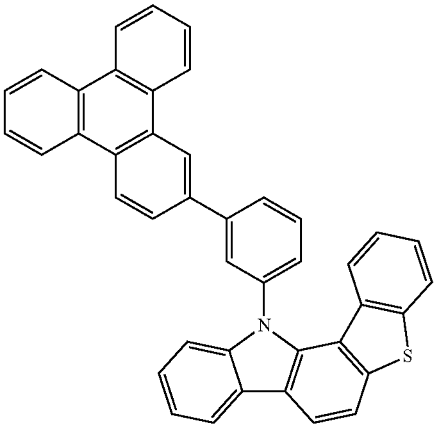

-continued
S-41
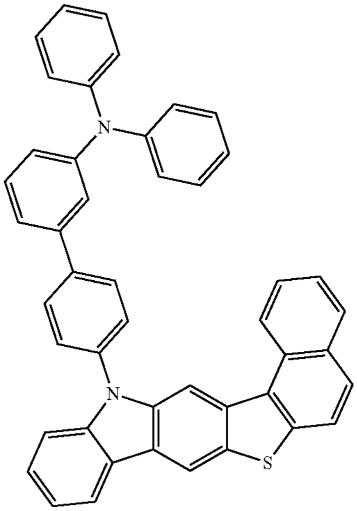
S-42
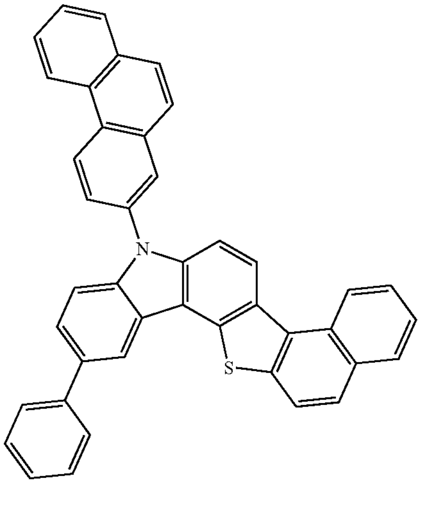
S-43
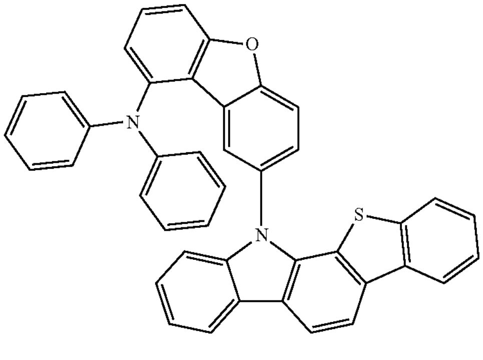
-continued
S-44
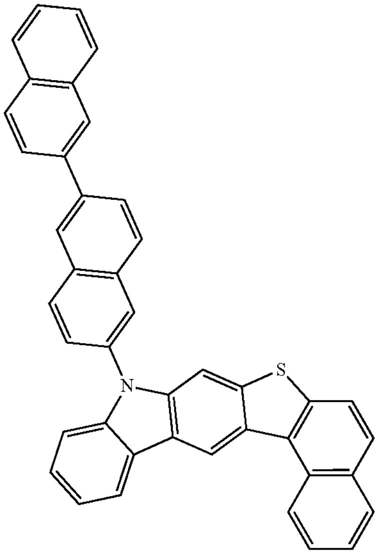
S-45
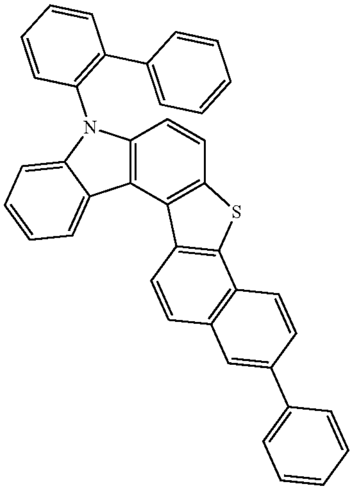
S-46
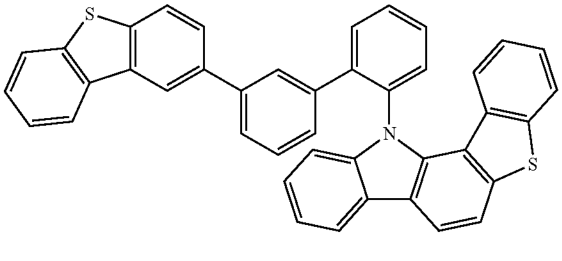

S-47
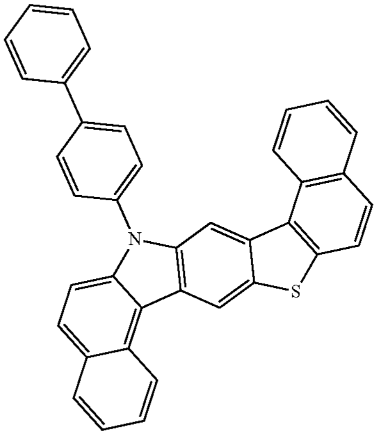
S-48
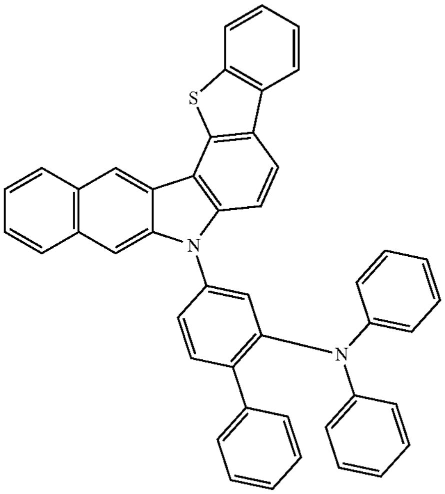
S-49
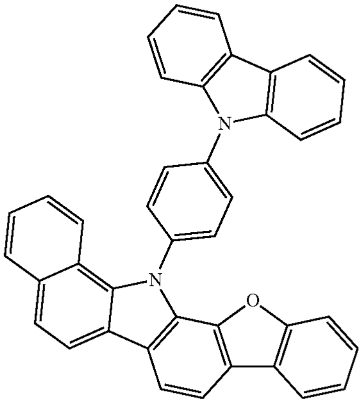
S-50
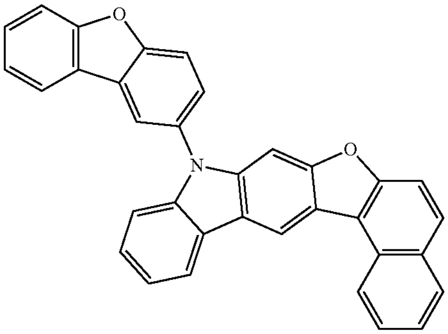
S-51
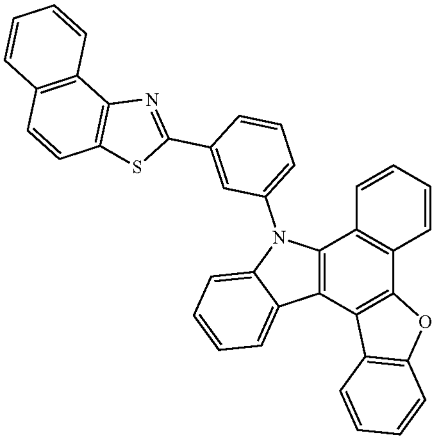
S-52
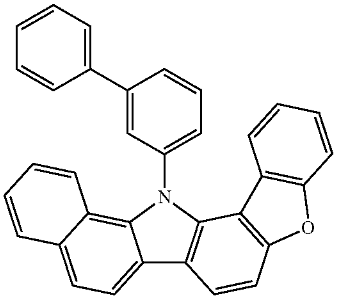
S-53
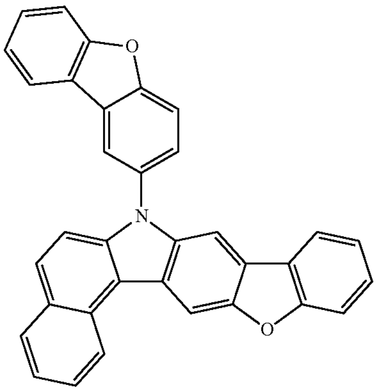

-continued
S-54
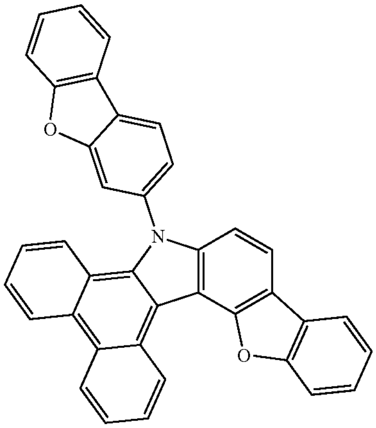
S-55
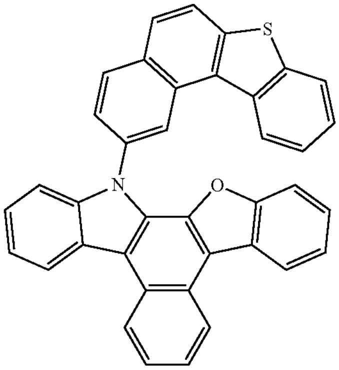
S-56
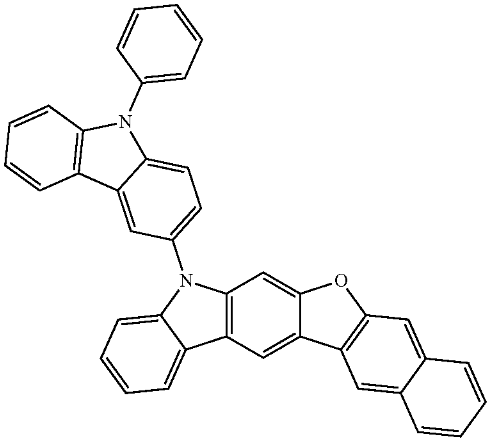
S-57
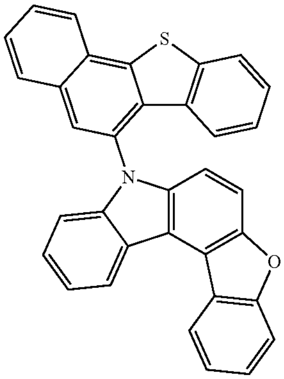
-continued
S-58
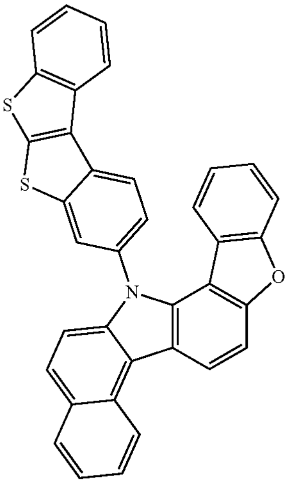
S-59
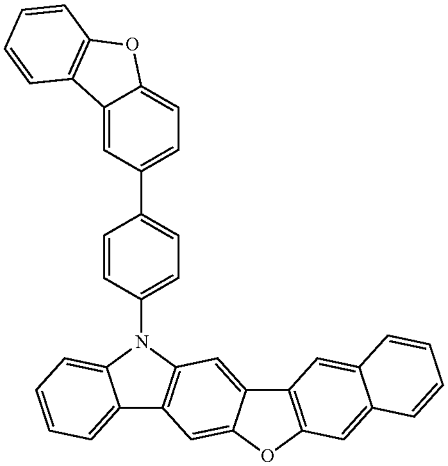
S-60
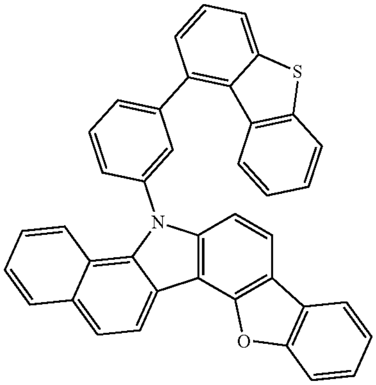

-continued
S-61
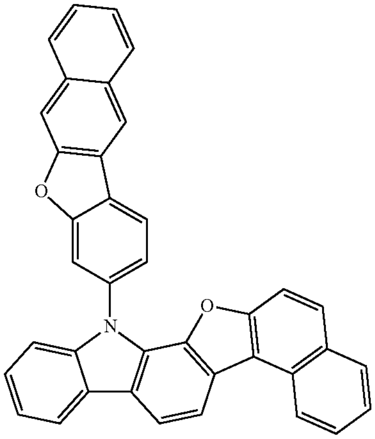
S-62
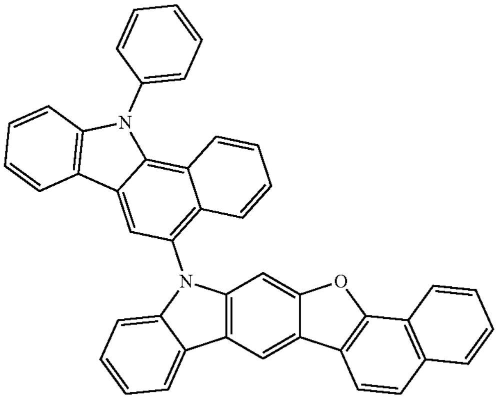
S-63
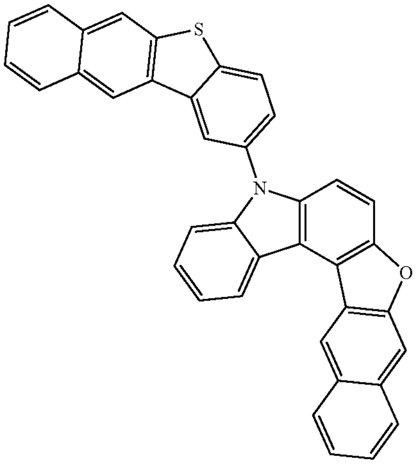
-continued
S-64
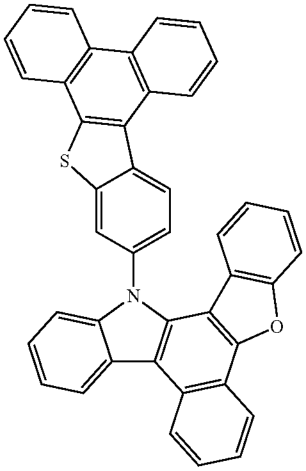
S-65
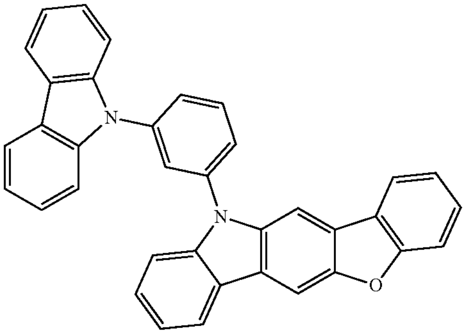
S-66
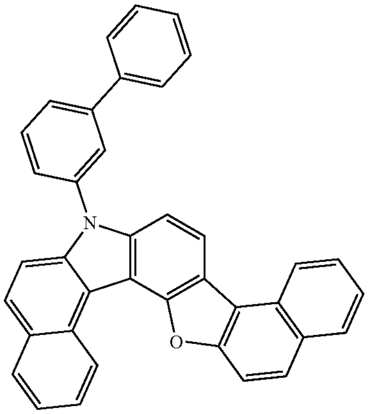
S-67
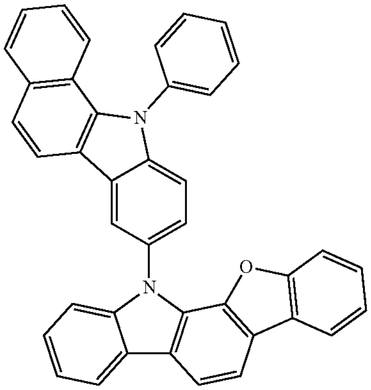

-continued
S-68
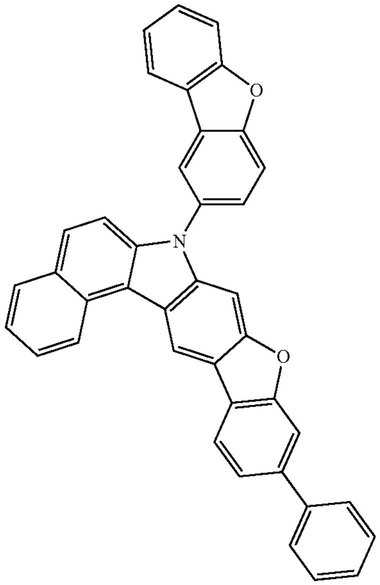
S-69
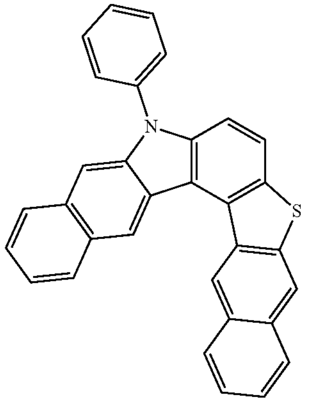
S-70
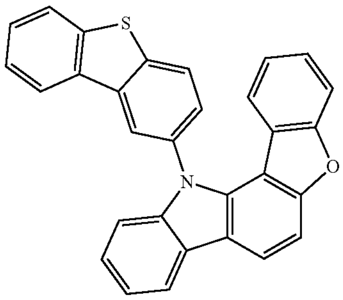
-continued
S-71
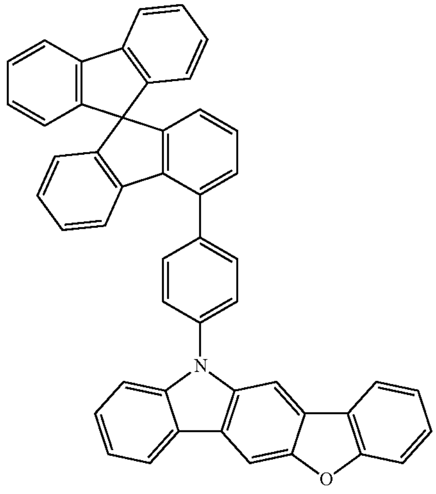
S-72
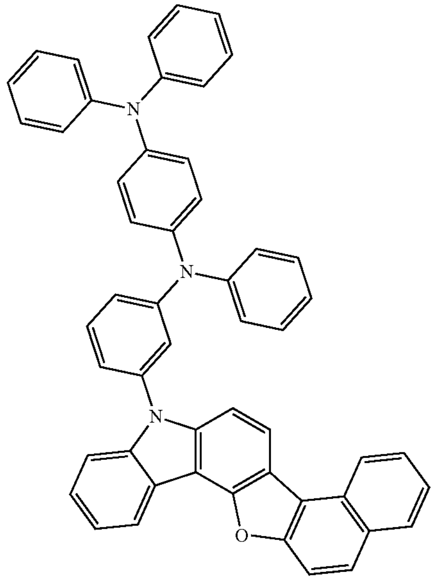
S-73
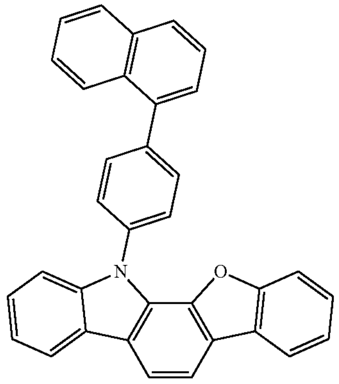

-continued
S-74
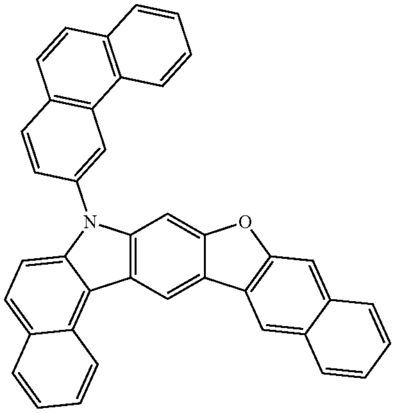
S-75
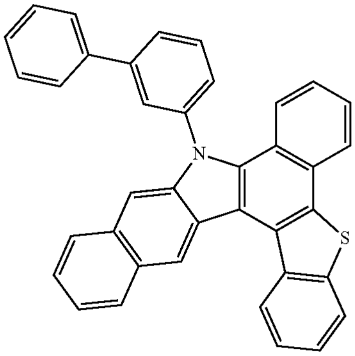
S-76
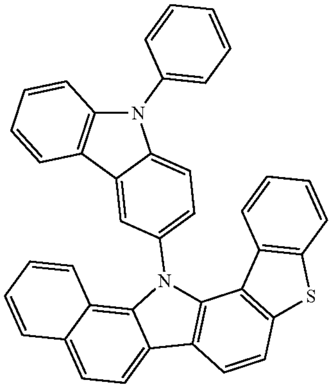
S-77
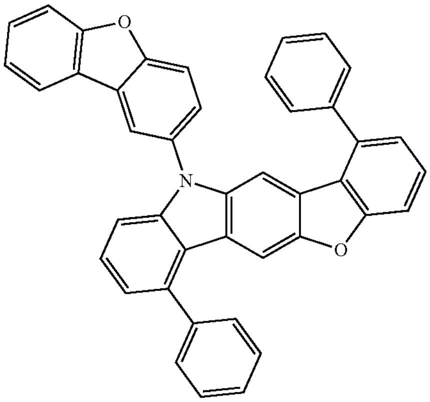
-continued
S-78
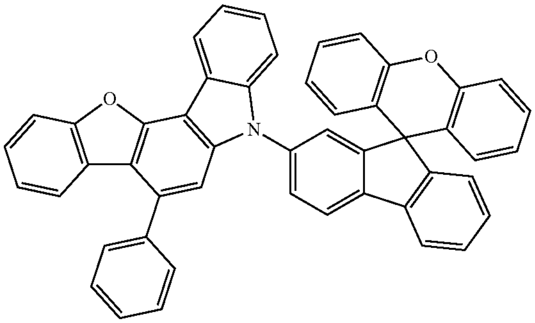
S-79
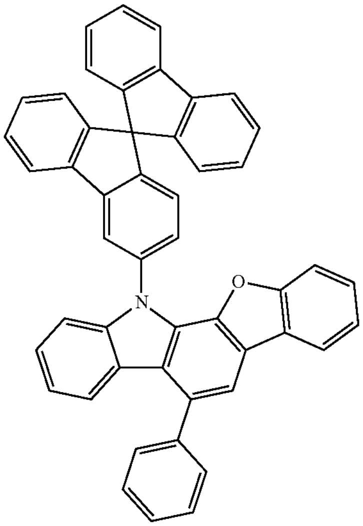
S-80
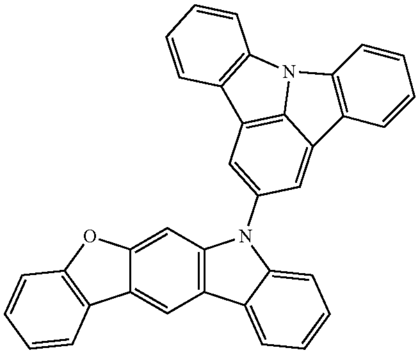
S-81
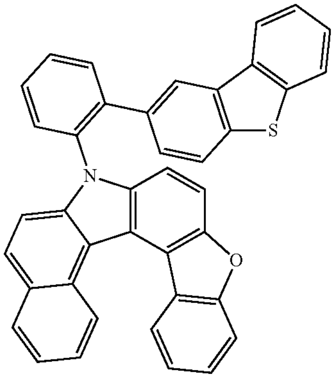

-continued
S-82
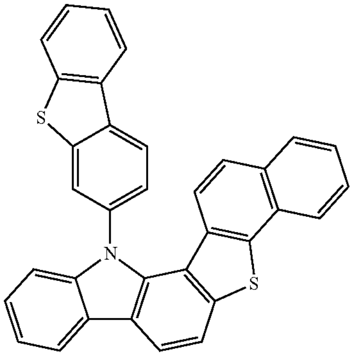
S-83
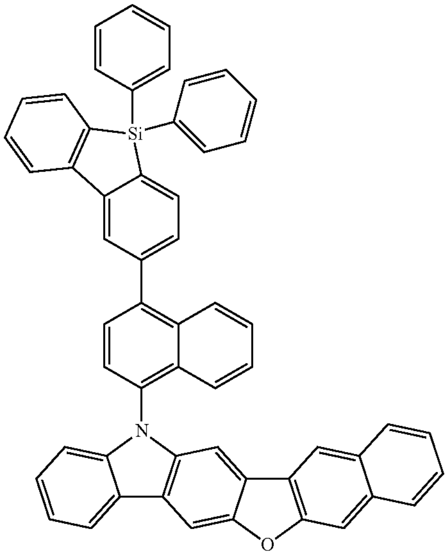
S-84
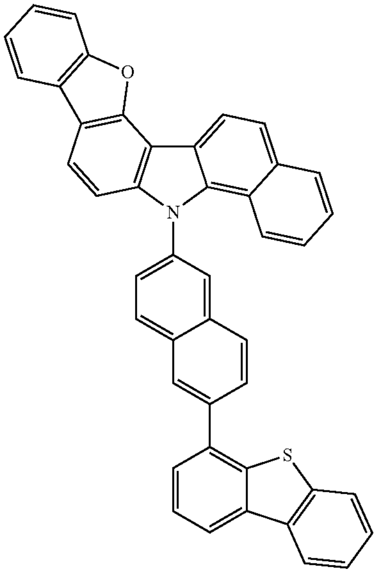
-continued
S-85
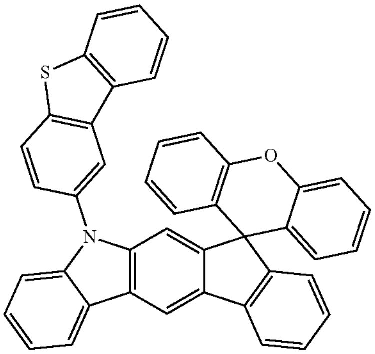
S-86
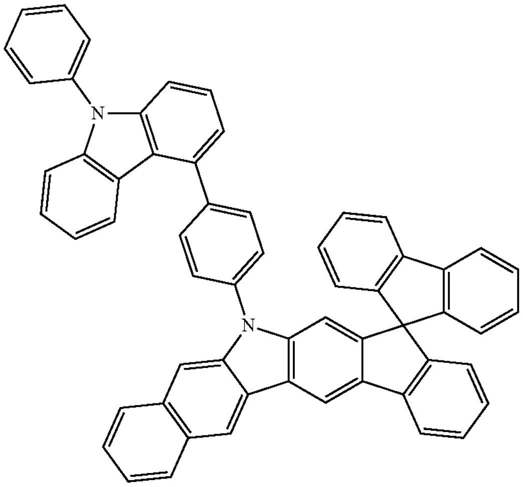
S-87
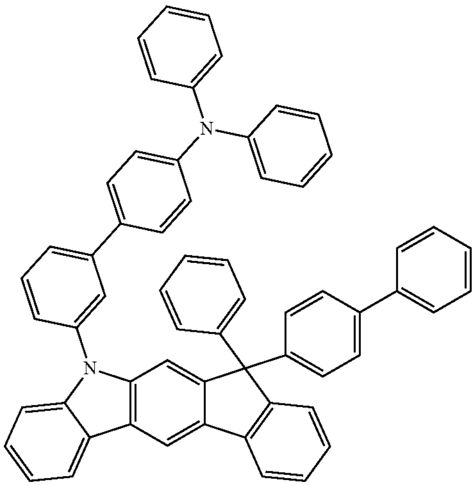

-continued
S-88
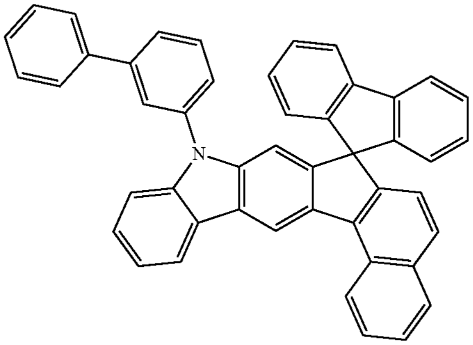
S-89
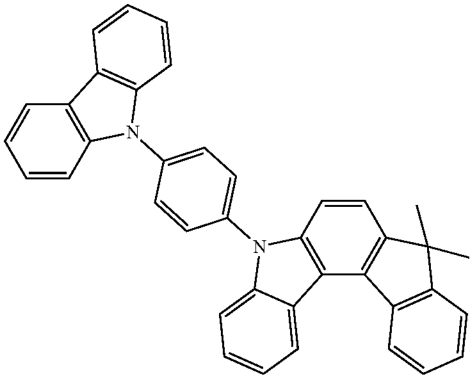
S-90
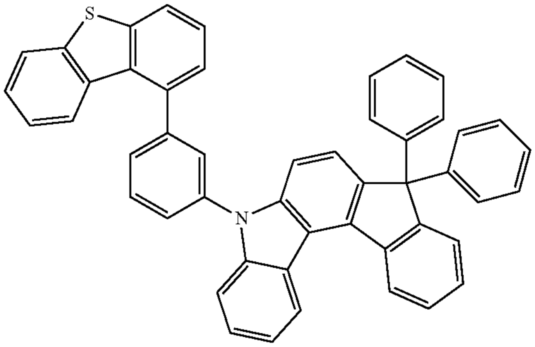
S-91
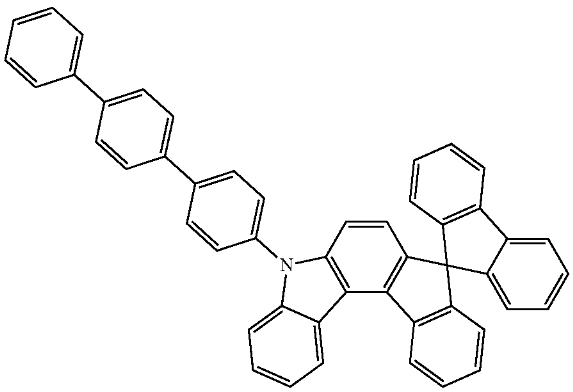
-continued
S-92
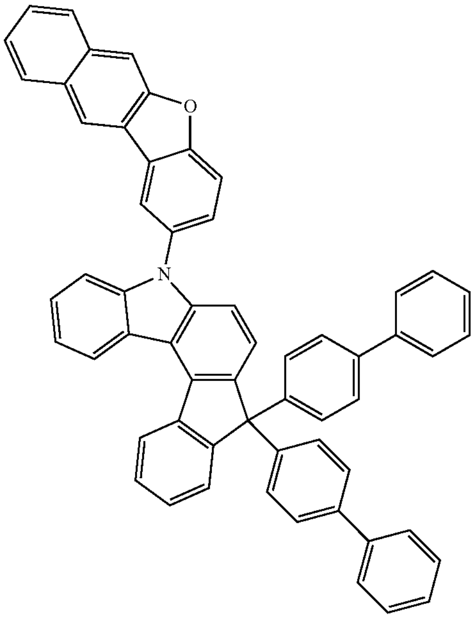
S-93
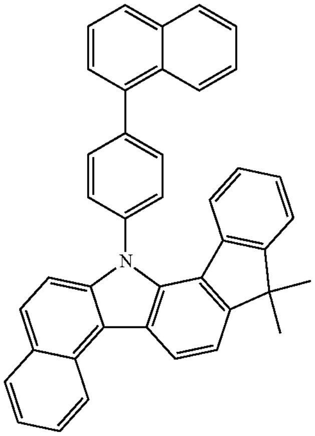
S-94
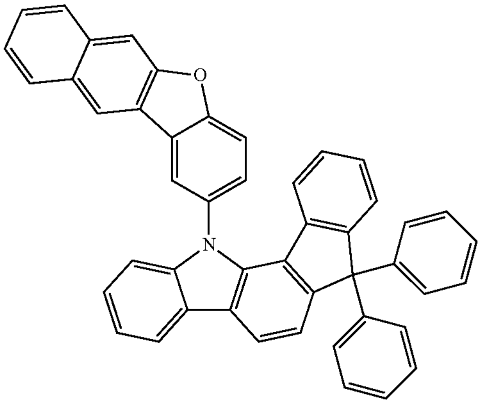

-continued
S-95
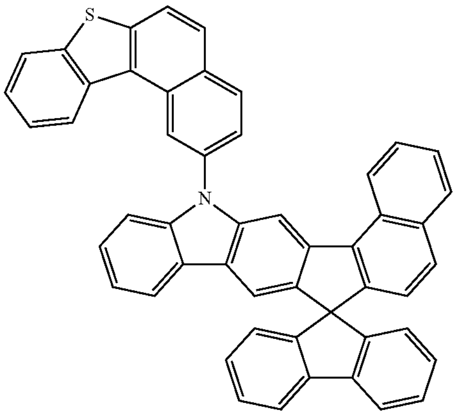
S-96
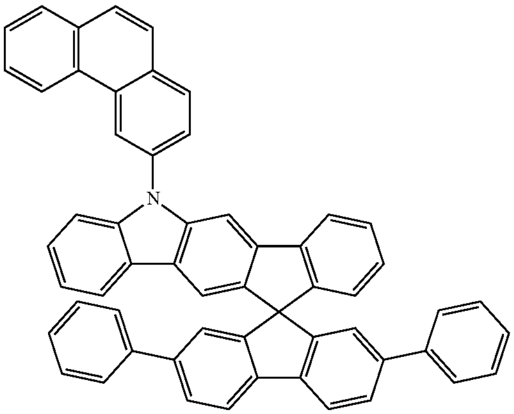
S-97
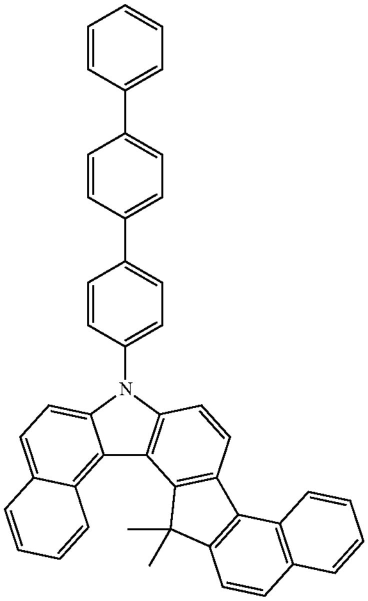
-continued
S-98
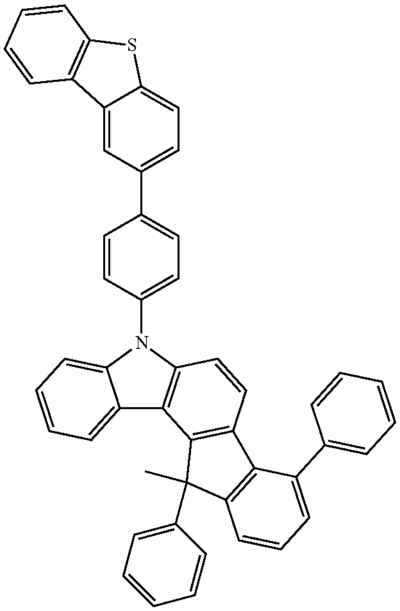
S-99
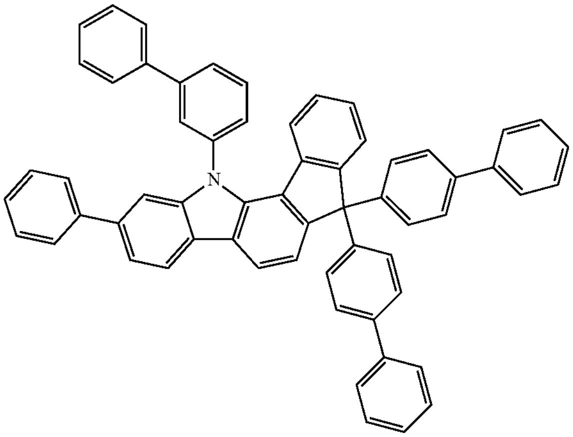
S-100
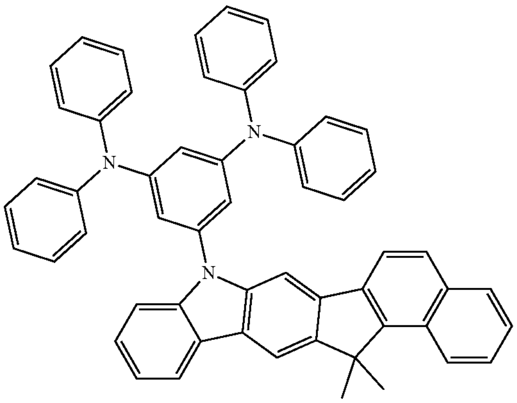

-continued
S-101
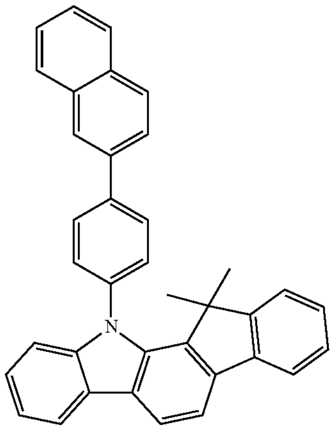
S-102
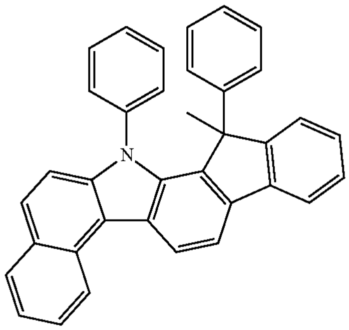
S-103
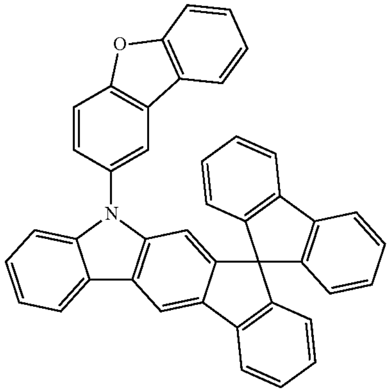
S-104
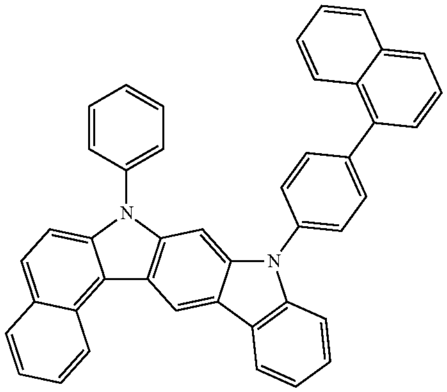
-continued
S-105
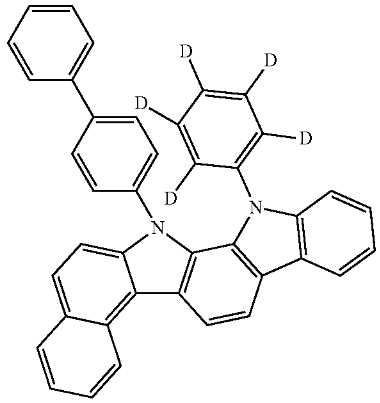
S-106
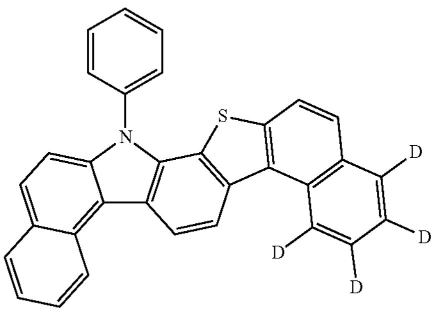
S-107
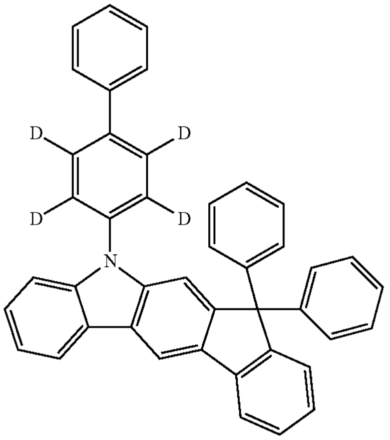
S-108
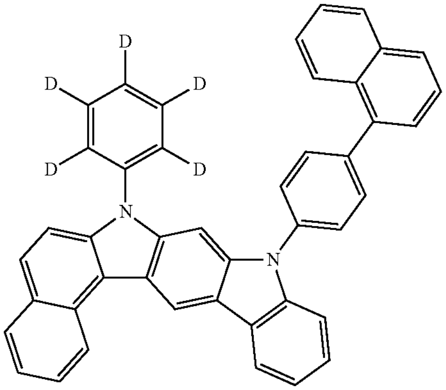
In another aspect, the present invention provides a compound represented by Formula 1.

Formula 1

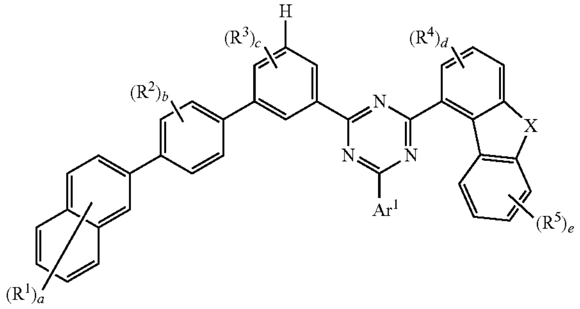

Wherein, $R^1$, $R^2$, $R^3$, $R^4$, $R^5$, X, $Ar^1$, a, b, c, d and e are the same as defined above.

Also, $Ar^1$ is represented by any one of Formulas Ar-1 to Ar-12.

Formula Ar-1

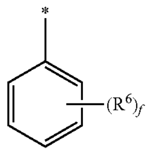

Formula Ar-2

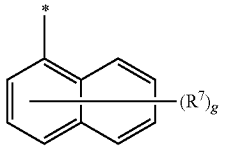

Formula Ar-3

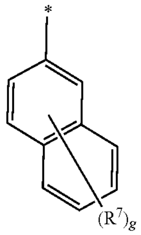

Formula Ar-4

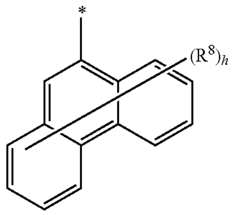

Formula Ar-5

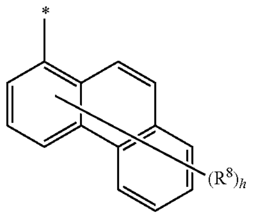

-continued

Formula Ar-6

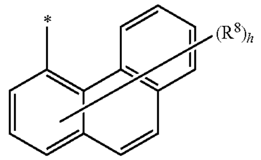

Formula Ar-7

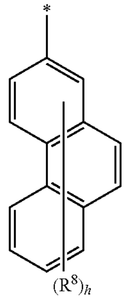

Formula Ar-8

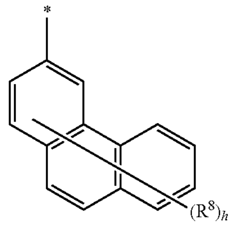

Formula Ar-9

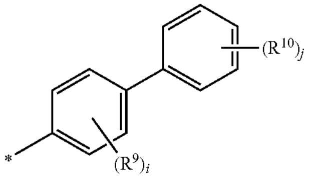

Formula Ar-10

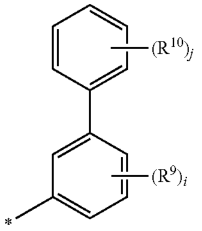

Formula Ar-11

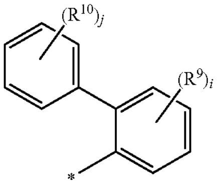

Formula Ar-12

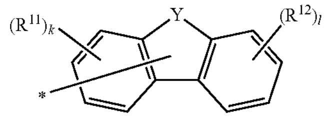

Wherein, $R^6$, $R^7$, $R^8$, $R^9$, $R^{10}$, $R^{11}$, $R^{12}$, Y, f, g, h, i, j, k, l and * are the same as defined above.

$R^1$, $R^2$ and $R^3$ in Formula 1 may preferably be deuterium.

Also, $R^4$ and $R^5$ in Formula 1 may preferably be deuterium.

Formula 1 may preferably be a compound represented by any one of Formulas 1-1 to 1-4.
Wherein, $R^1$, $R^2$, $R^3$, $R^4$, $R^5$, a, b, c, d, e, X and $Ar^1$ are the same as defined in Formula 1.
Formula 1-1
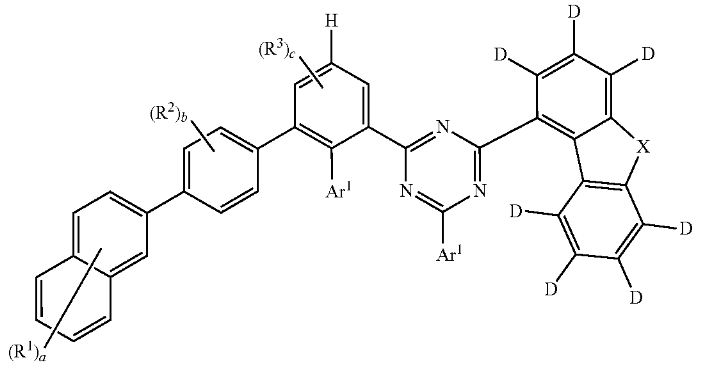
Formula 1-2
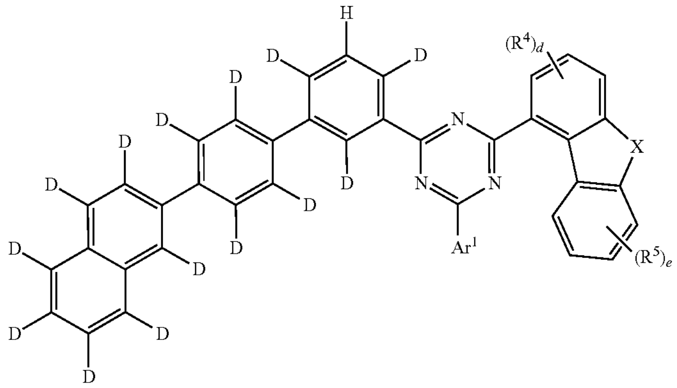
Formula 1-3
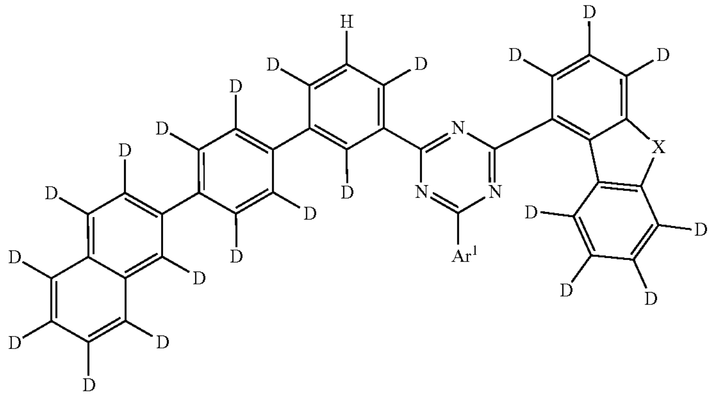
Formula 1-4
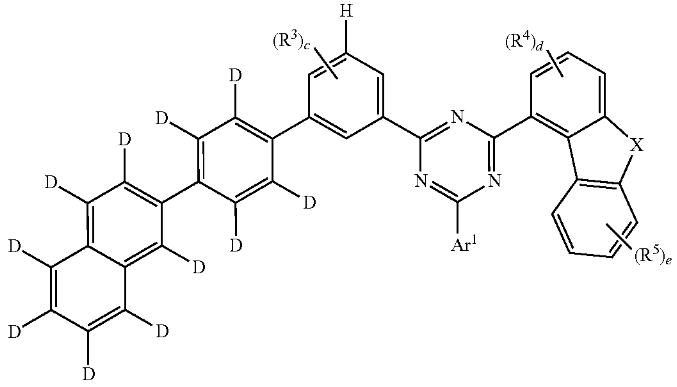

Also, Formula 1 is represented by any one of the following compounds P-1 to P-107.
P-1
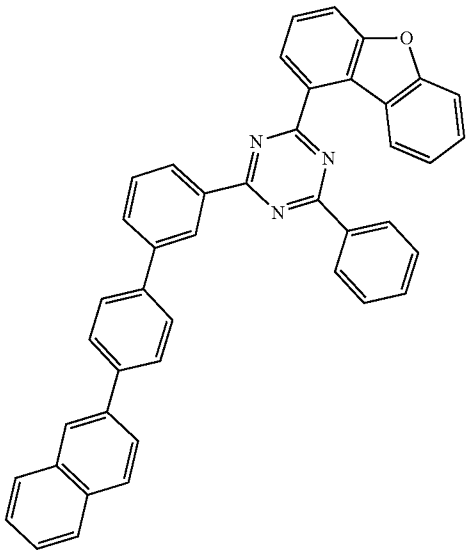
P-2
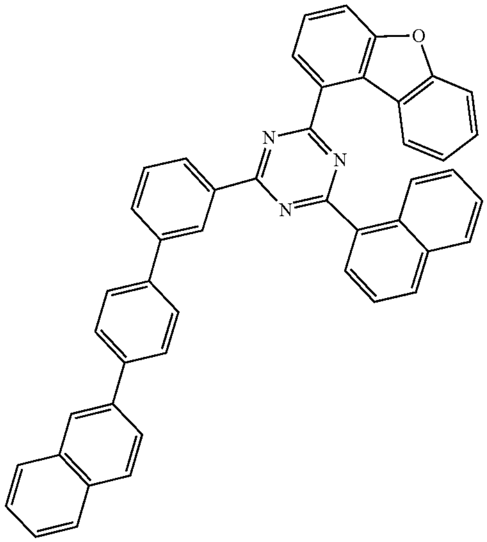
-continued
P-3
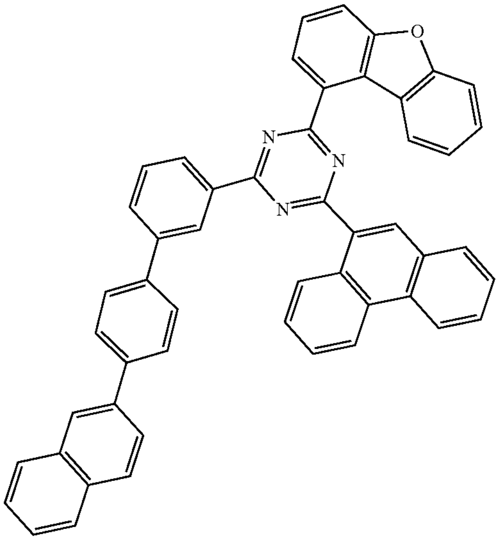
P-4
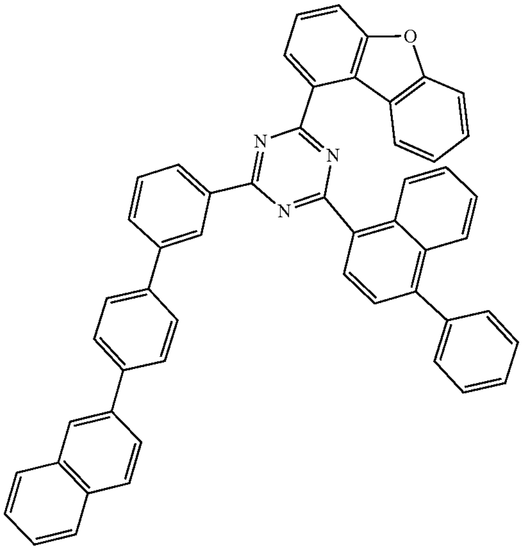
P-5
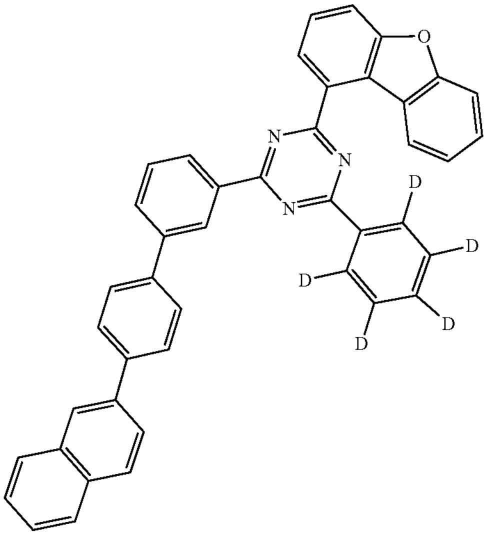

-continued
P-6
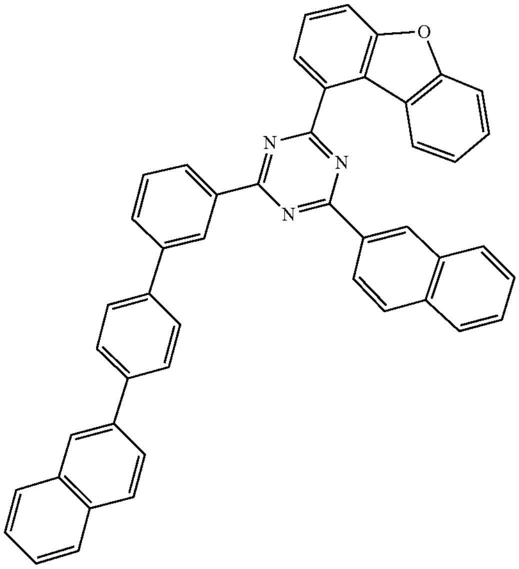
P-7
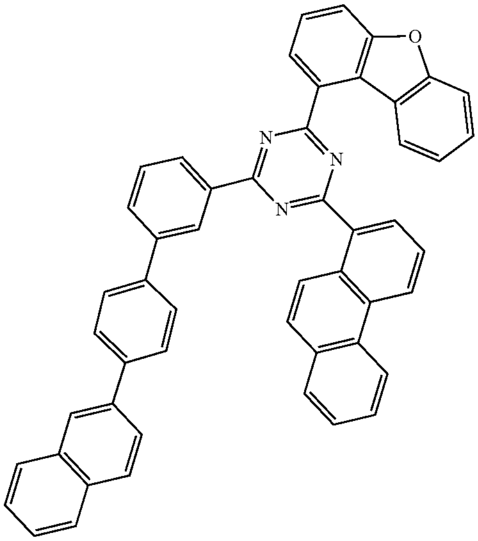
P-8
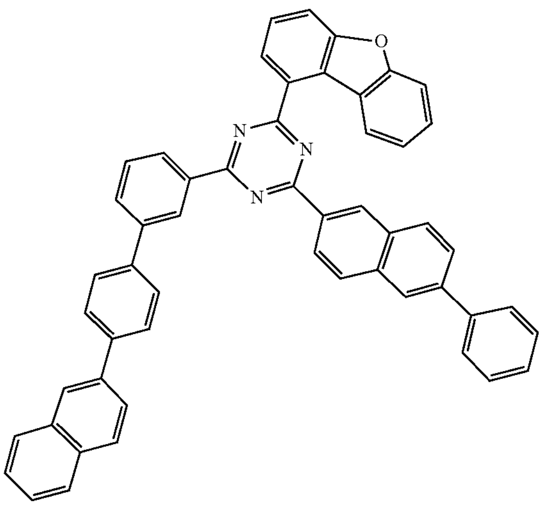
-continued
P-9
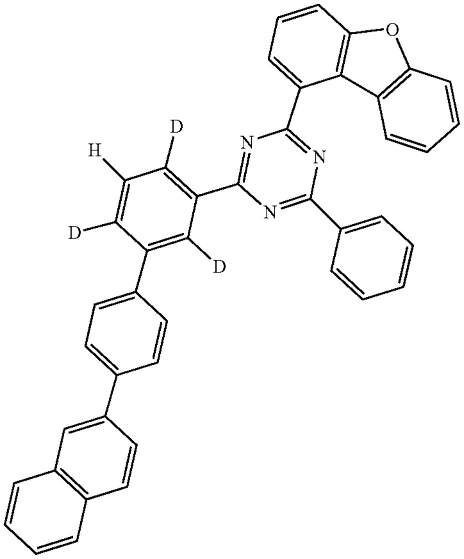
P-10
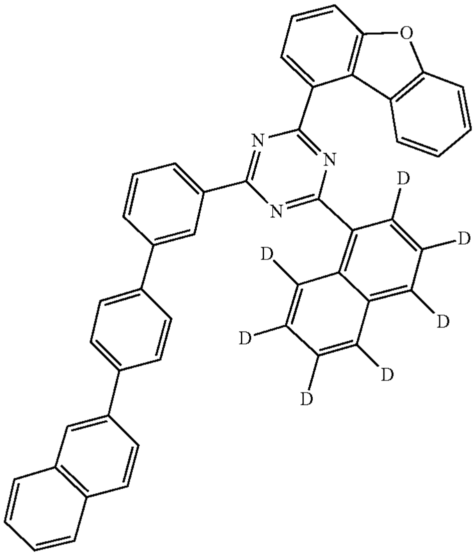

-continued
P-11
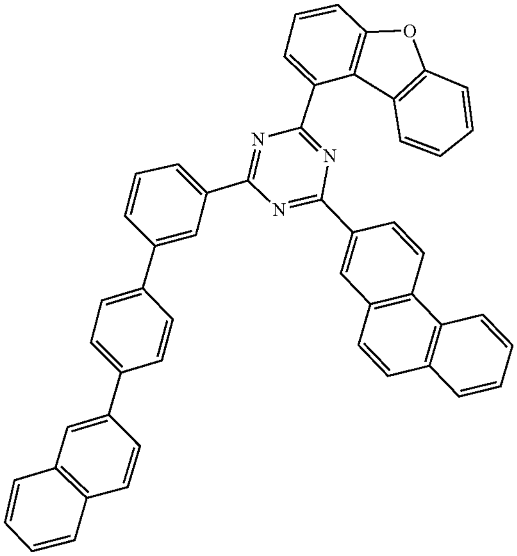
P-12
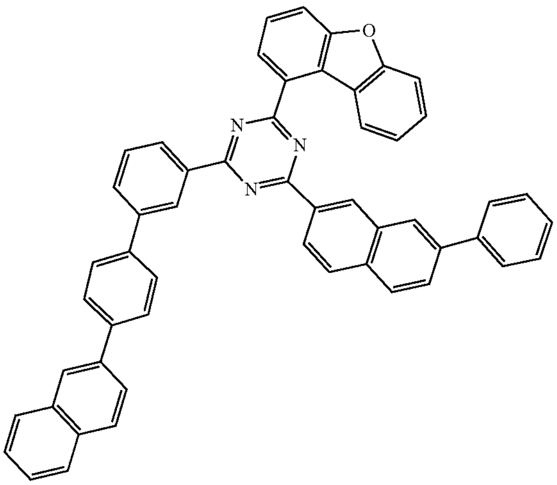
-continued
P-13
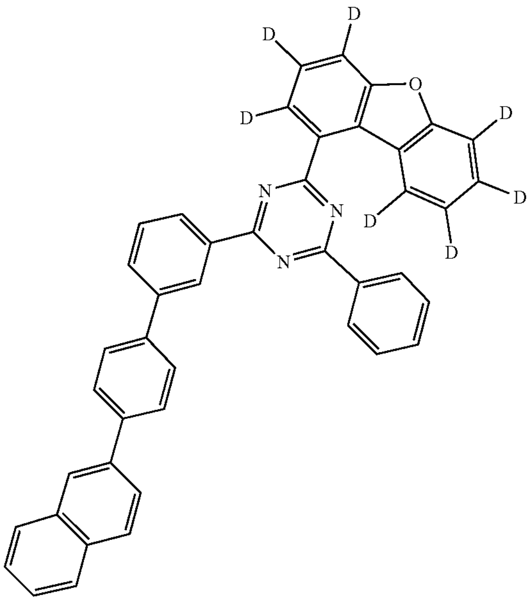
P-14
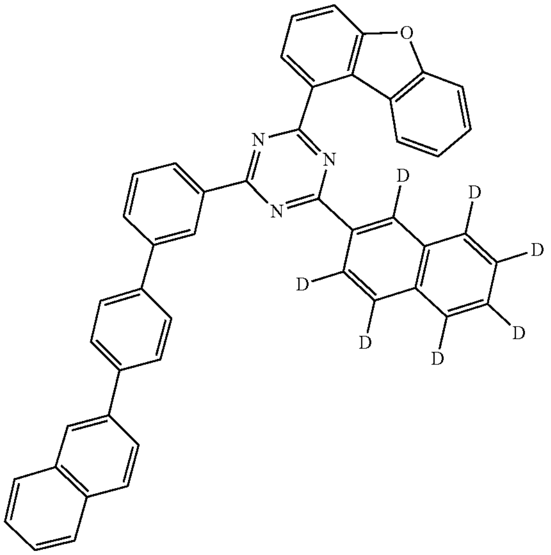

-continued
P-15
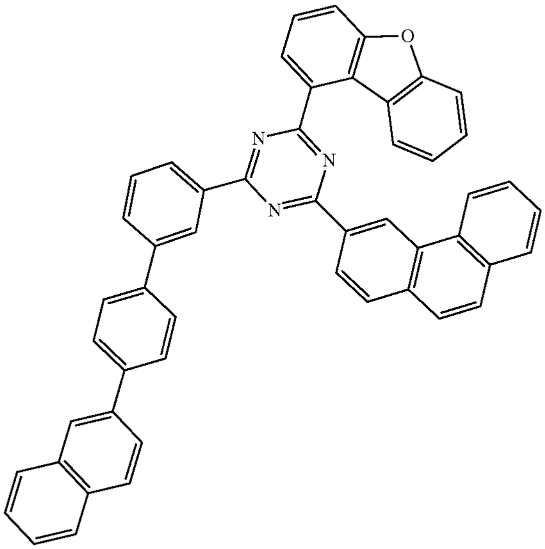
P-16
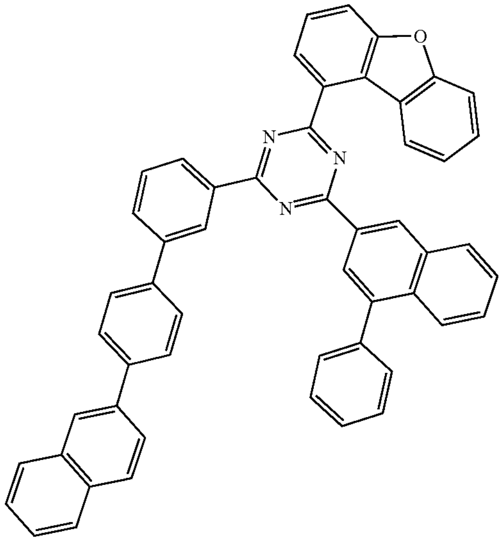
-continued
P-17
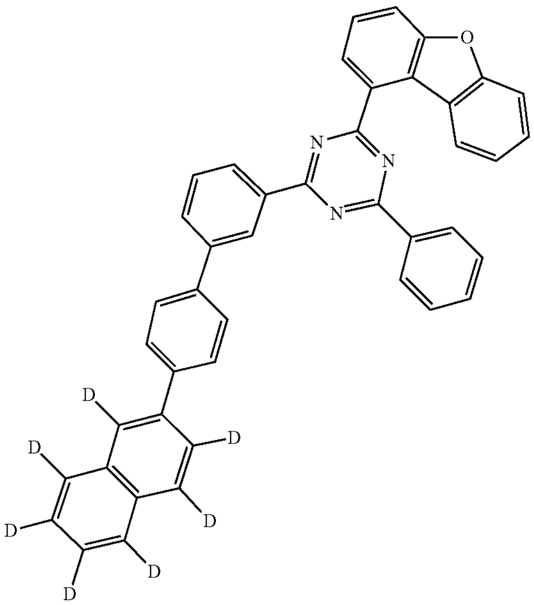
P-18
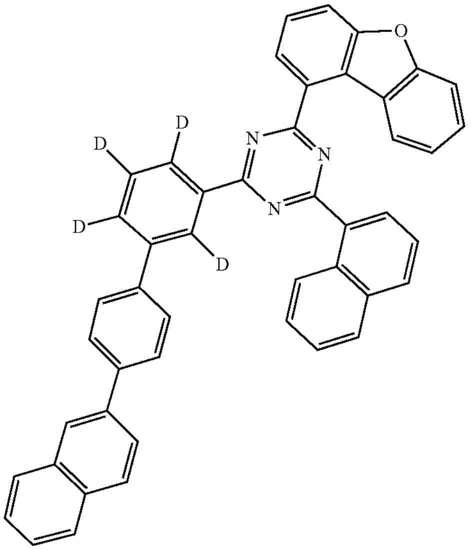

-continued
P-19
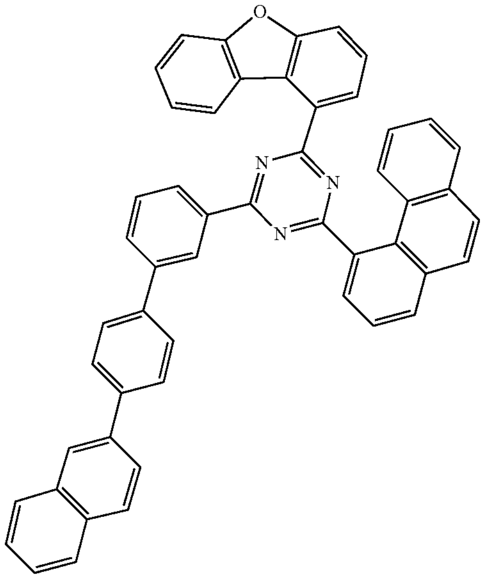
P-20
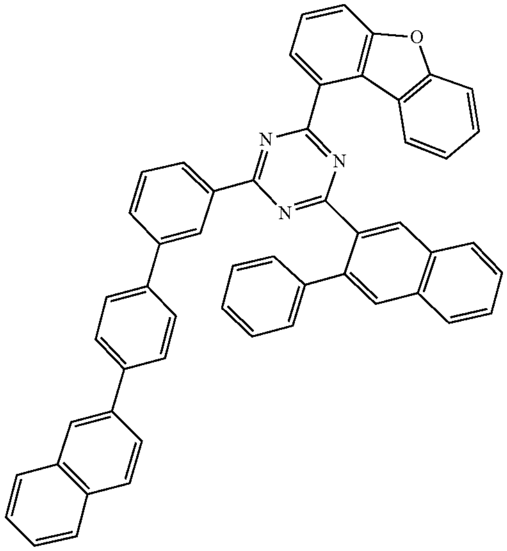
-continued
P-21
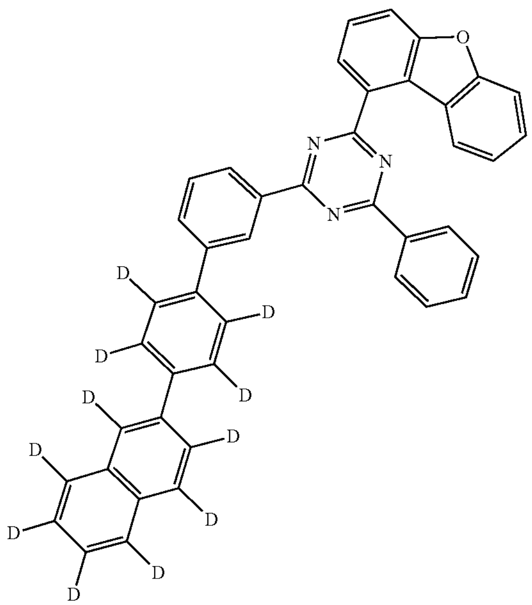
P-22
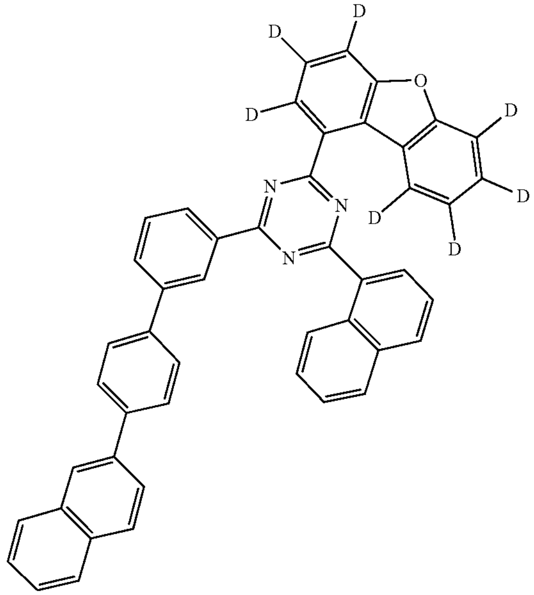

-continued
P-23
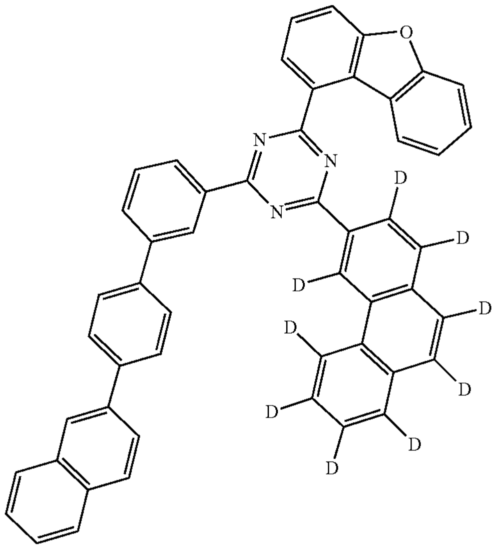
P-24
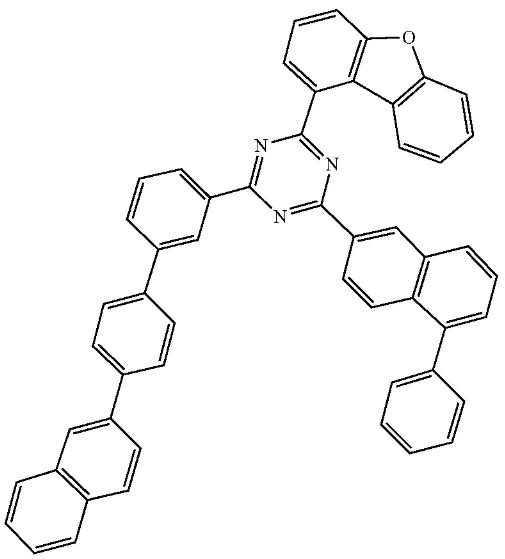
-continued
P-25
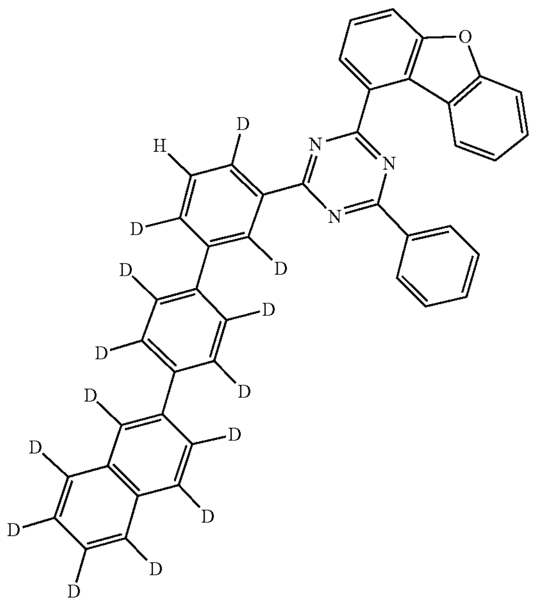
P-26
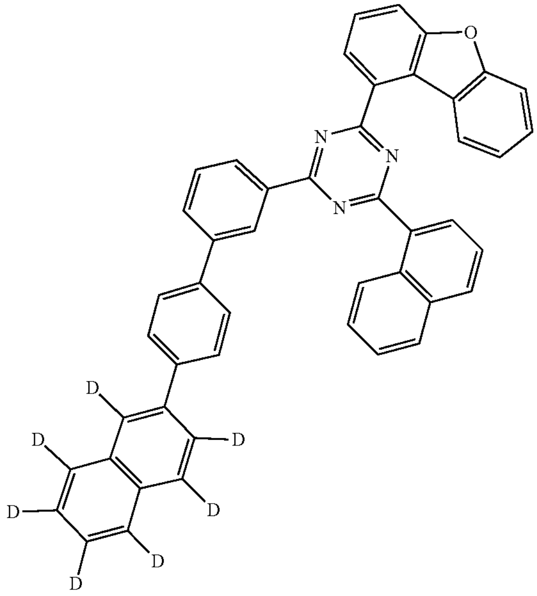

-continued
P-27
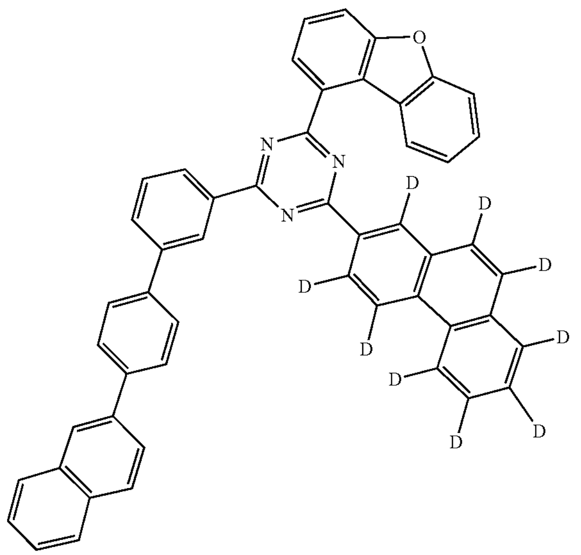
P-28
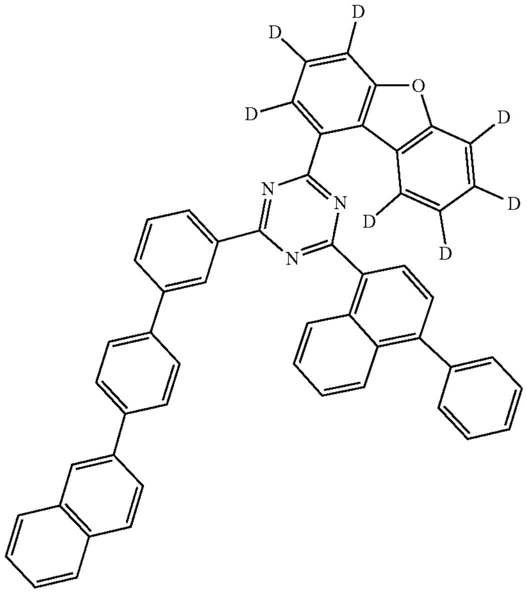
-continued
P-29
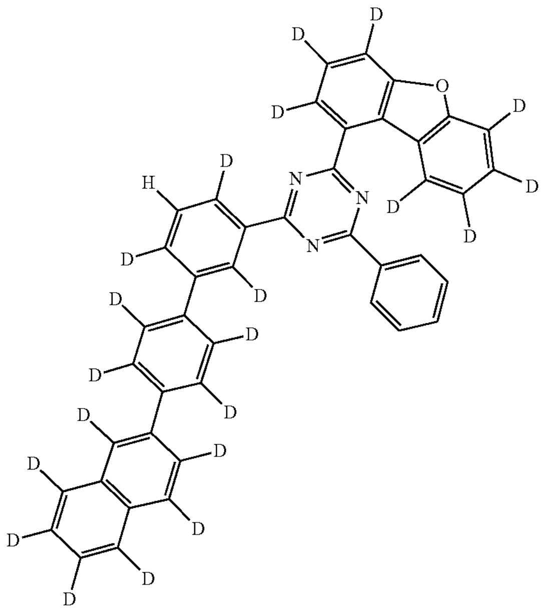
P-30
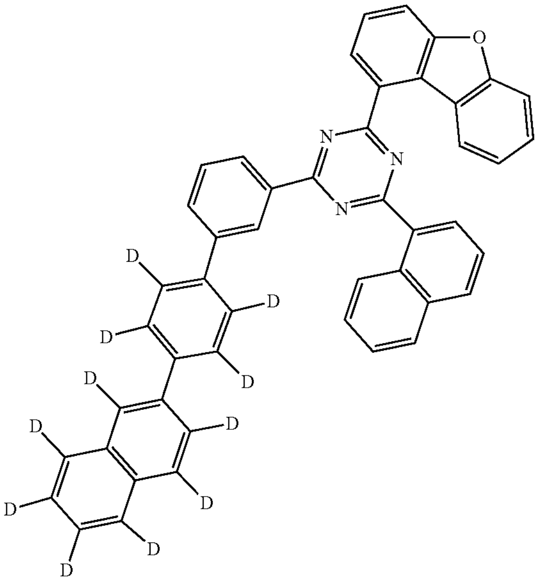

-continued
P-31
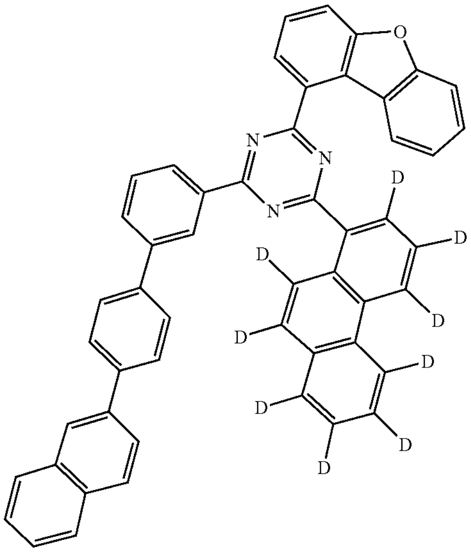
P-32
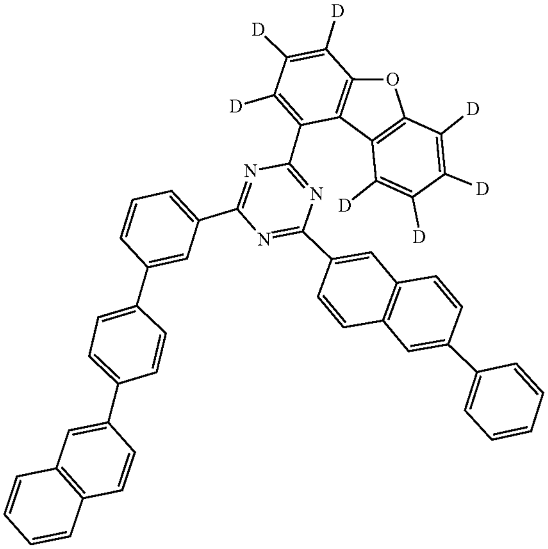
-continued
P-33
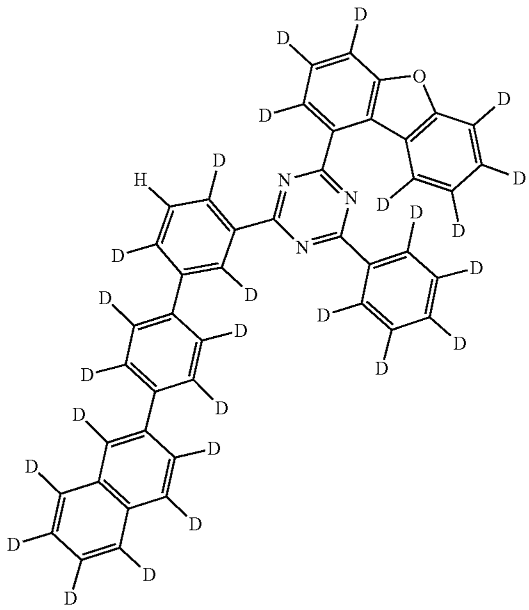
P-34
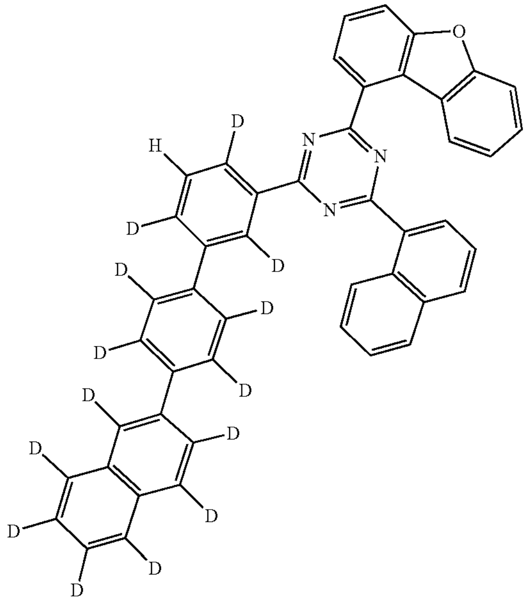

-continued
P-35
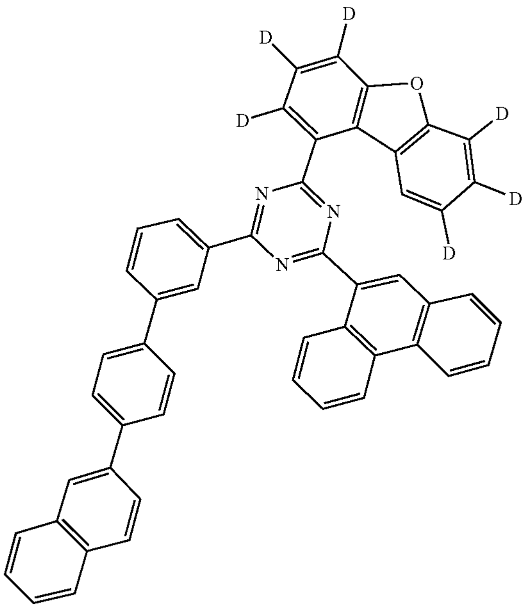
P-36
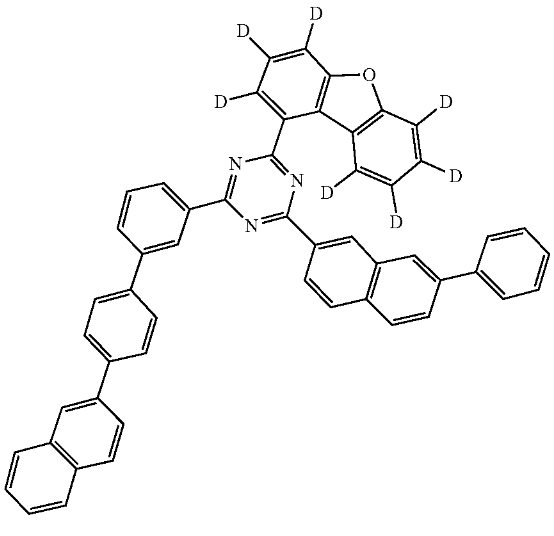
-continued
P-37
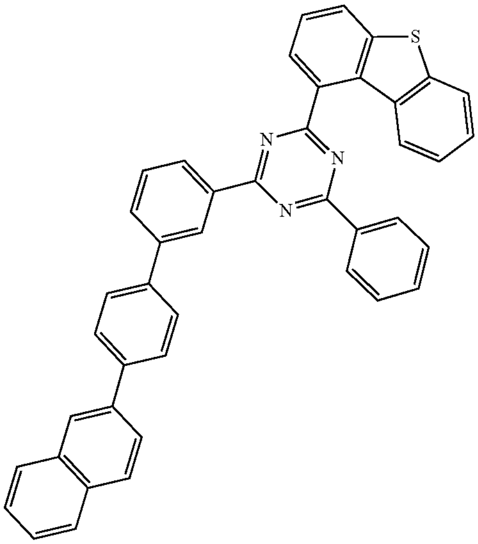
P-38
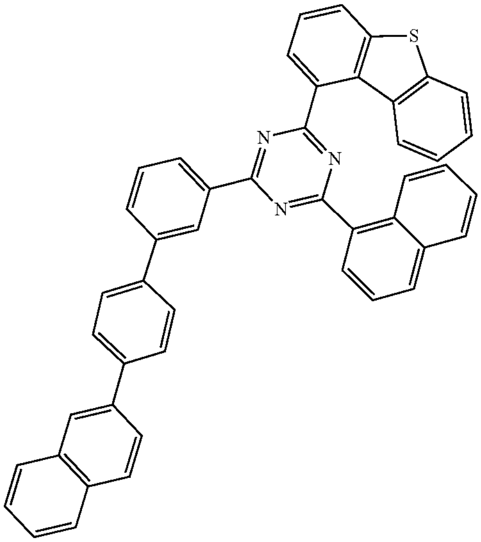
P-39
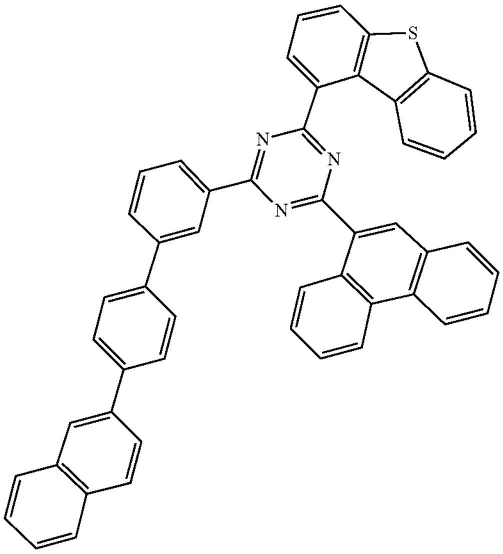

-continued
P-40
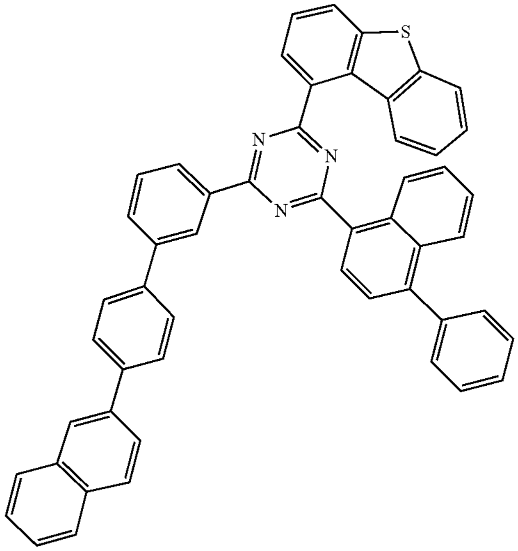
P-41
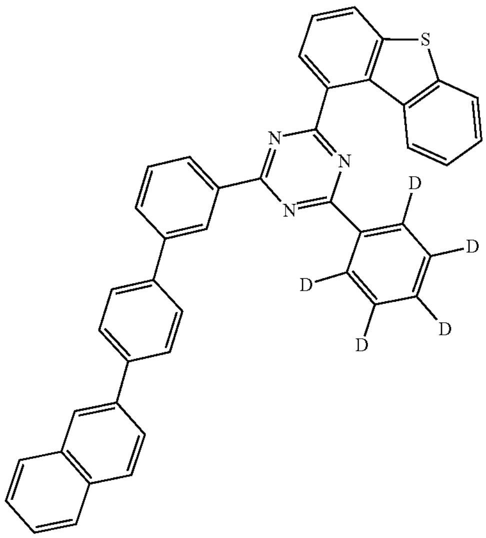
-continued
P-42
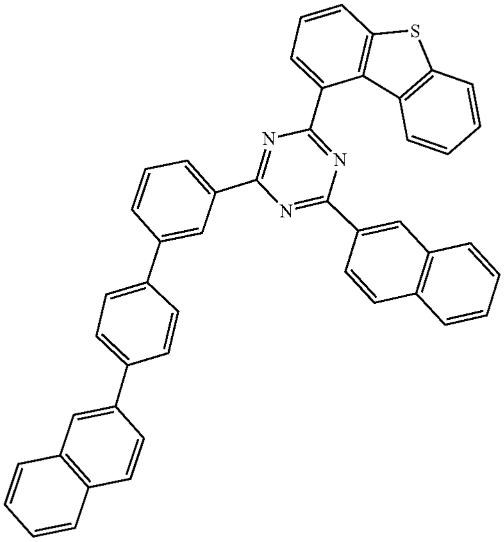
P-43
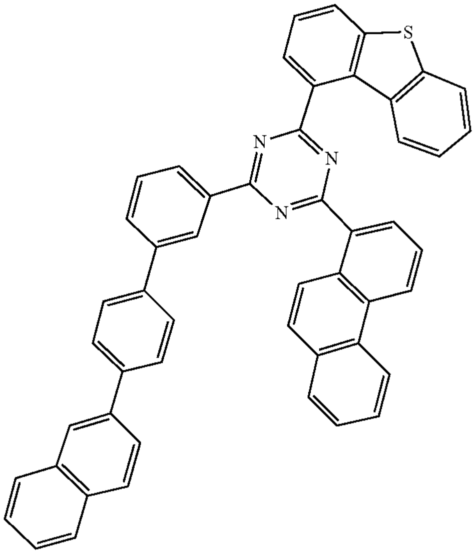
P-44
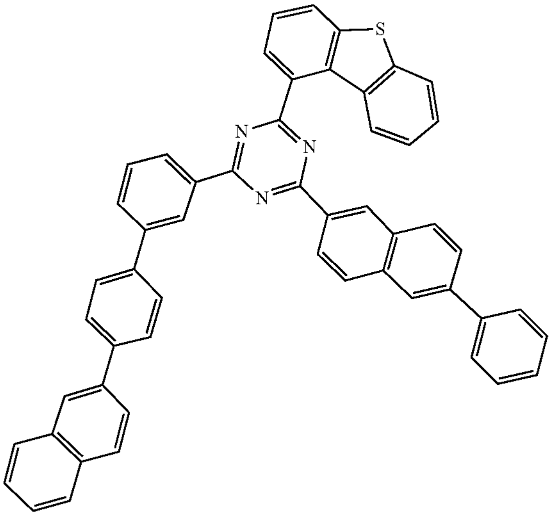

-continued
P-45
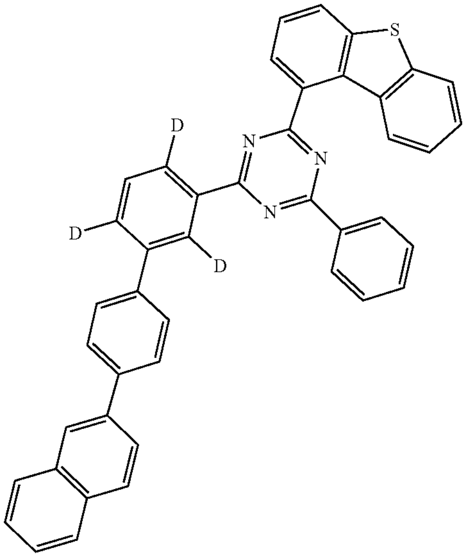
P-46
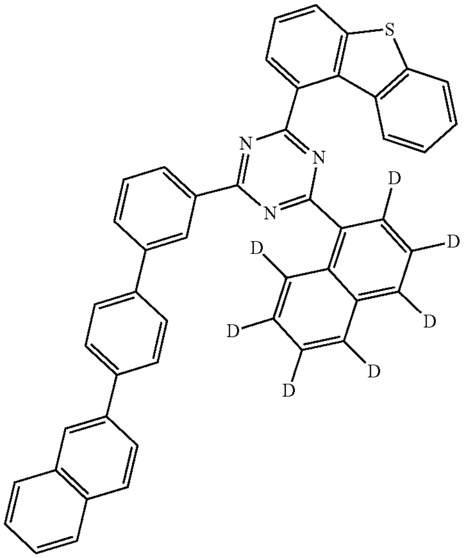
-continued
P-47
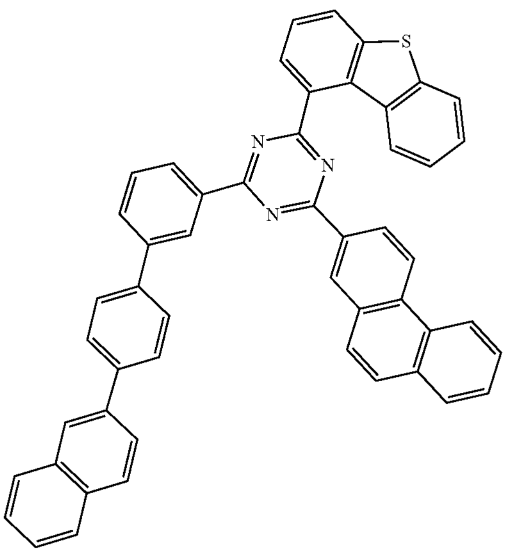
P-48
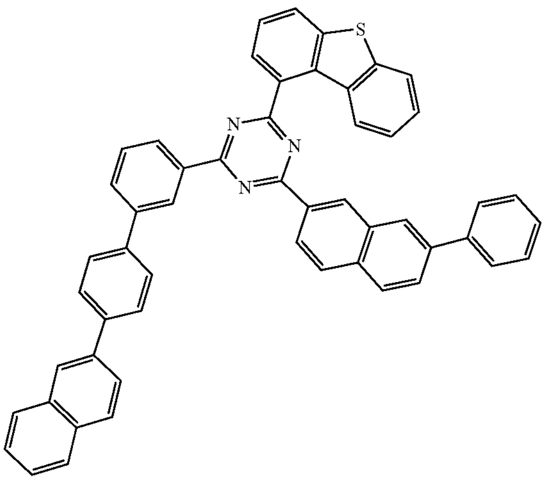

-continued
P-49
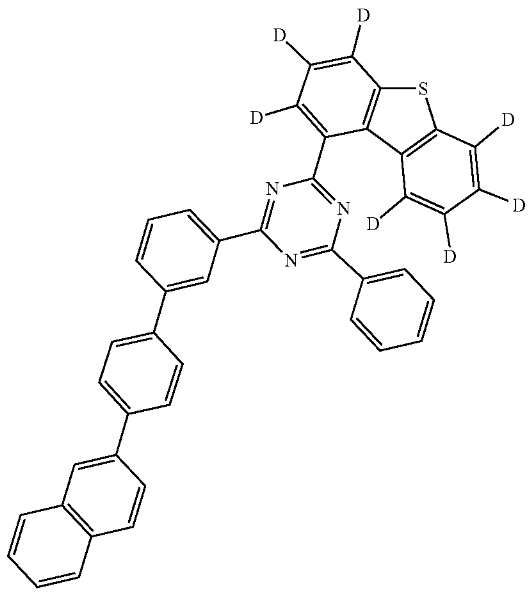
P-50
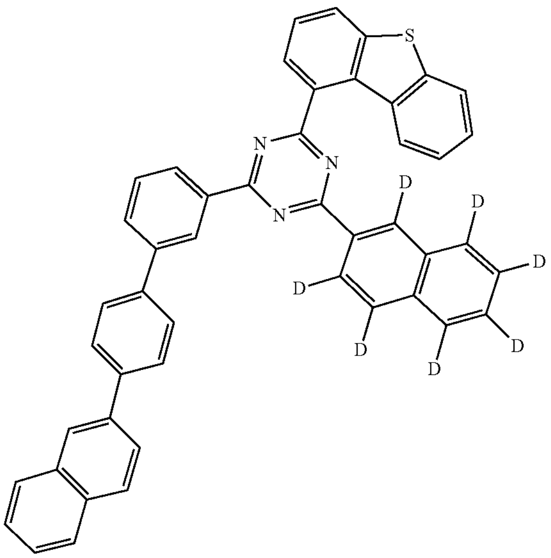
-continued
P-51
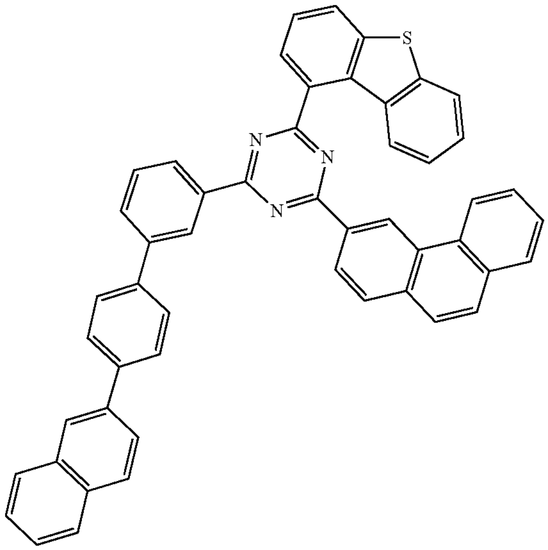
P-52
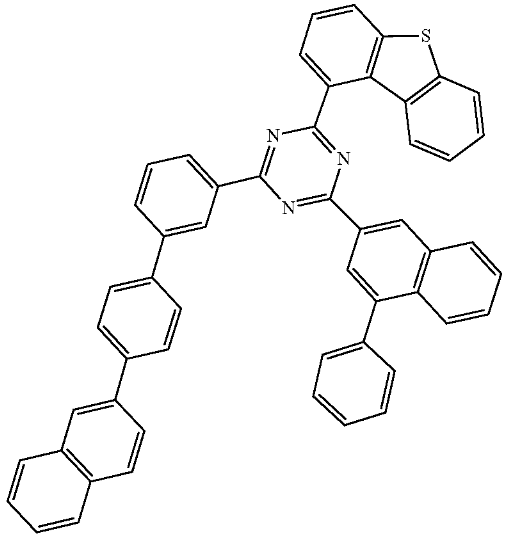

-continued
P-53
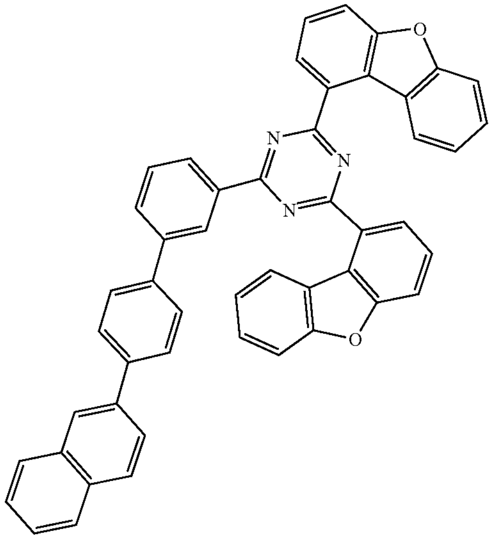
P-54
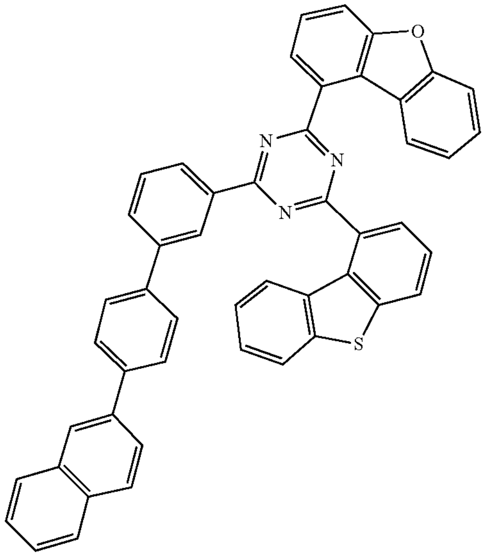
-continued
P-55
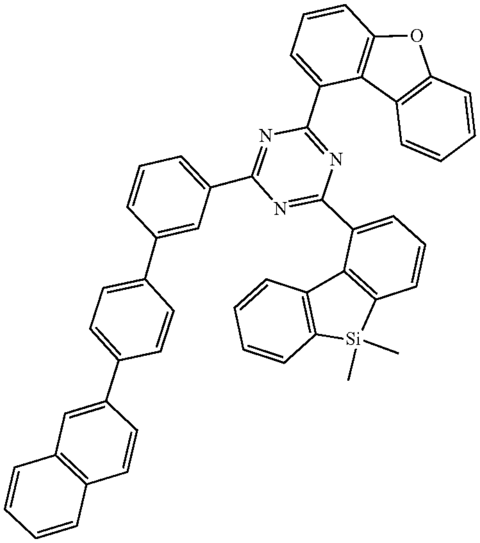
P-56
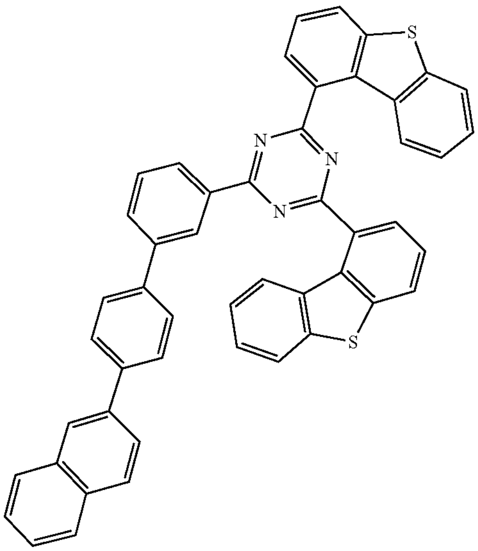

-continued
P-57
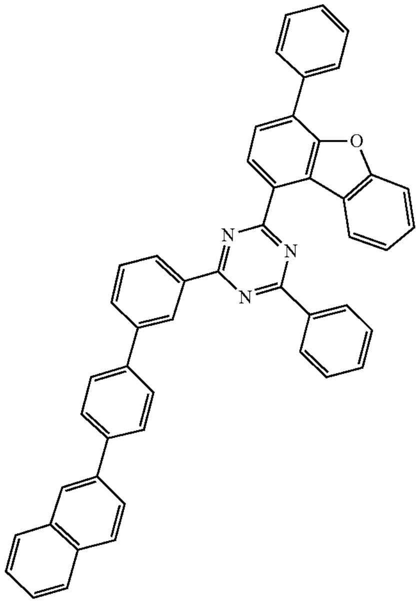
P-58
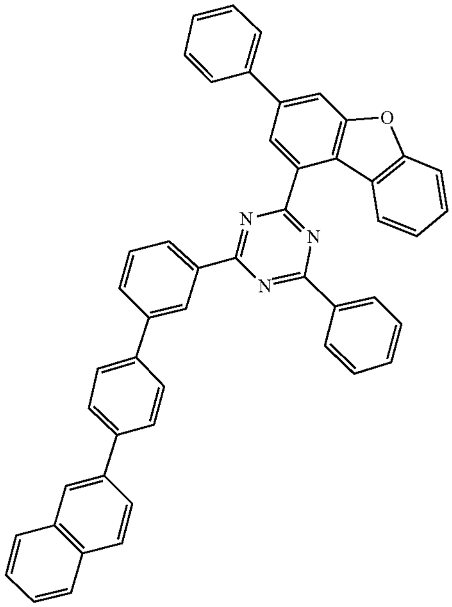
-continued
P-59
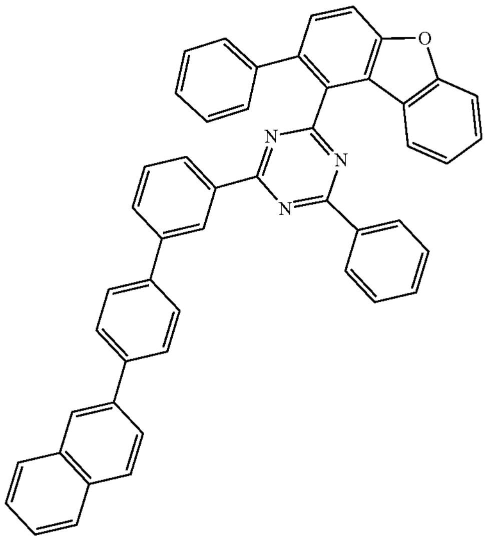
P-60
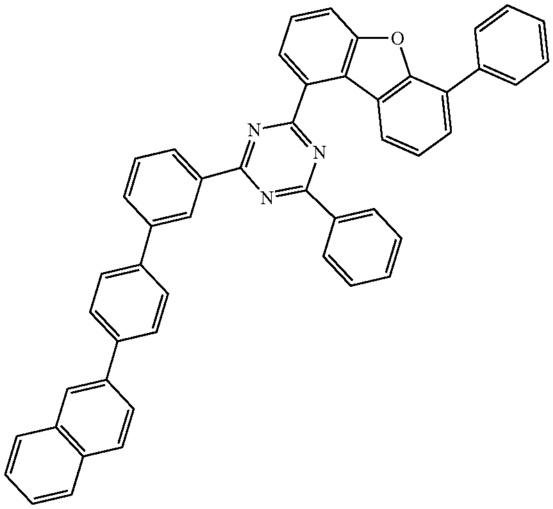
P-61
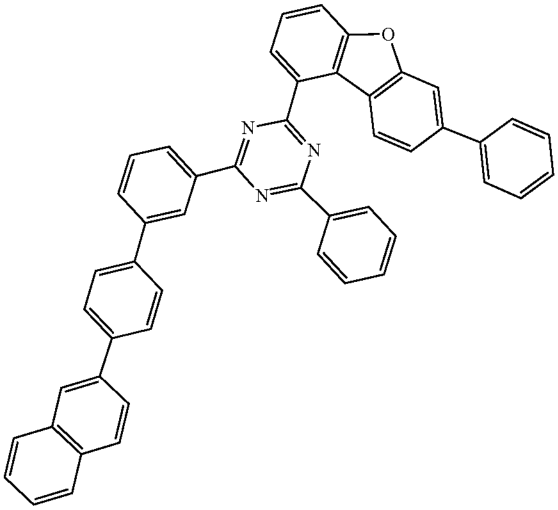

-continued
P-62
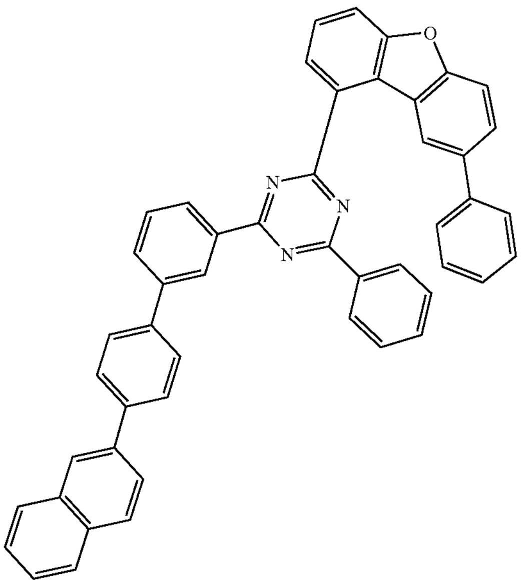
P-63
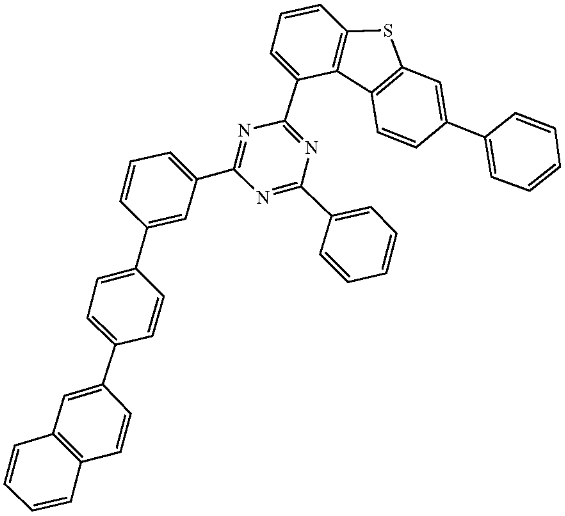
-continued
P-64
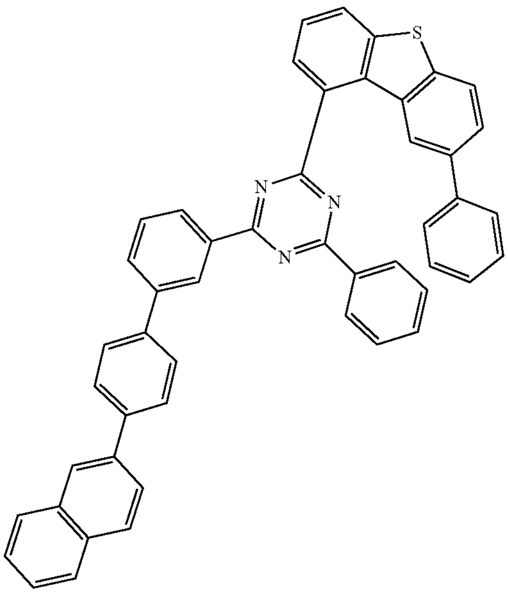
P-65
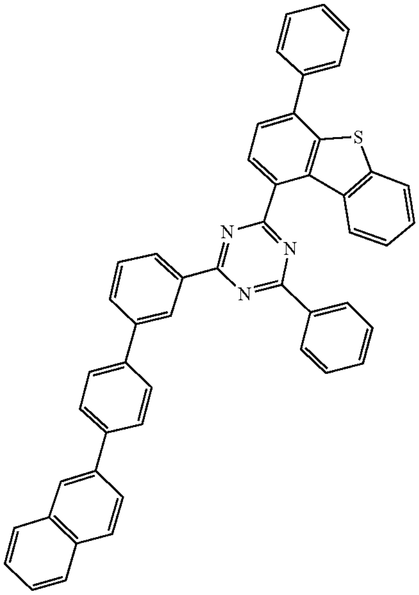

-continued
P-66
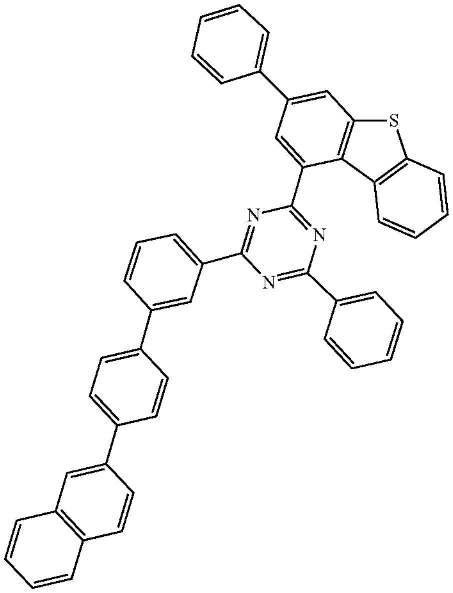
P-67
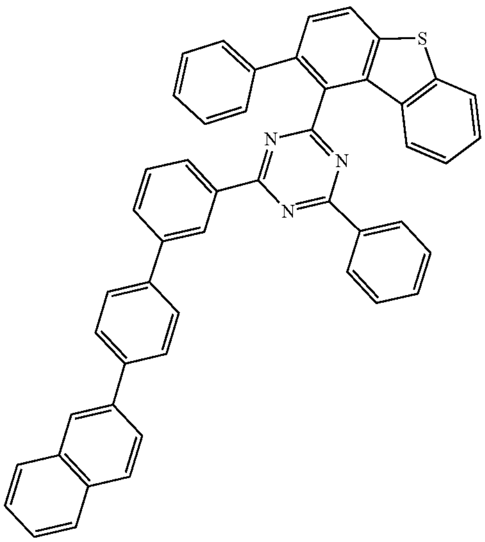
-continued
P-68
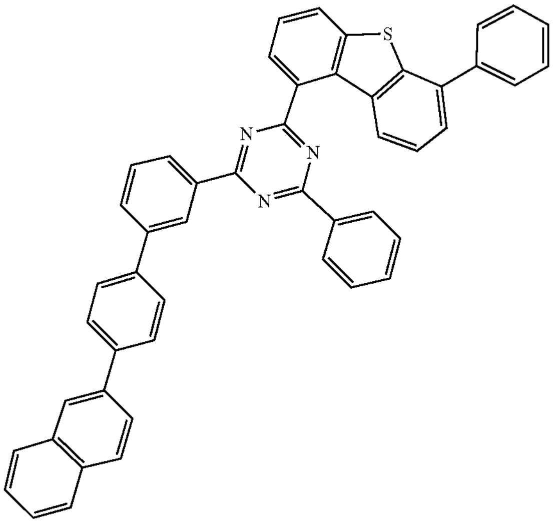
P-69
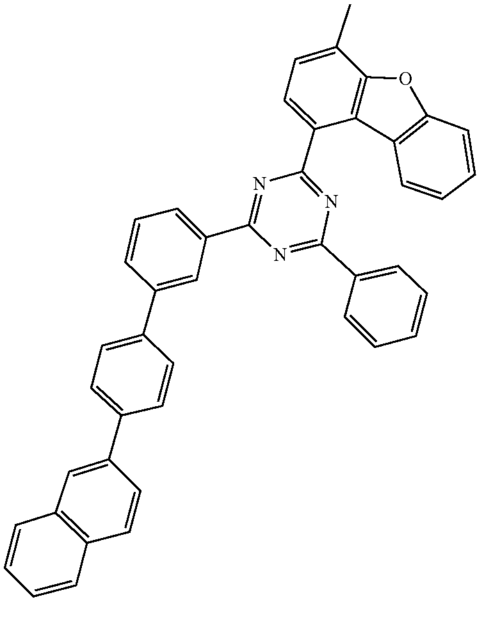

-continued
P-70
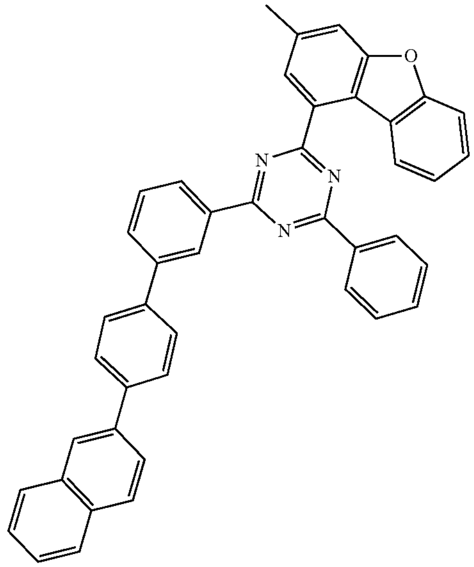
P-71
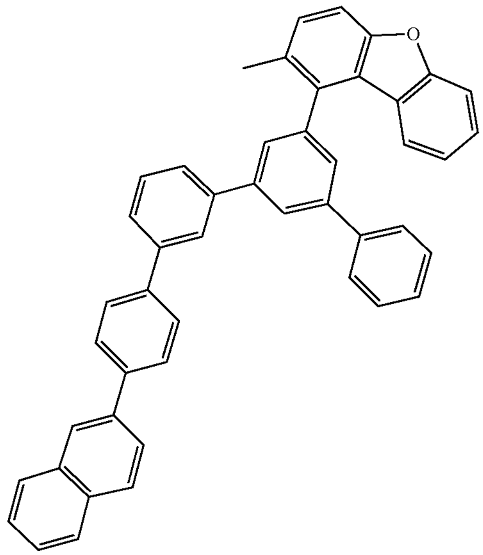
-continued
P-72
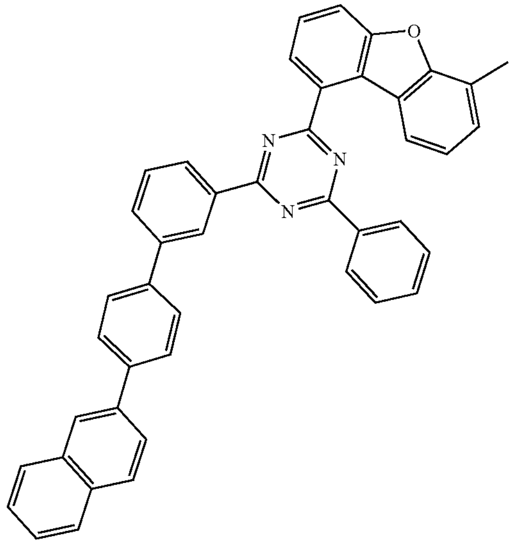
P-73
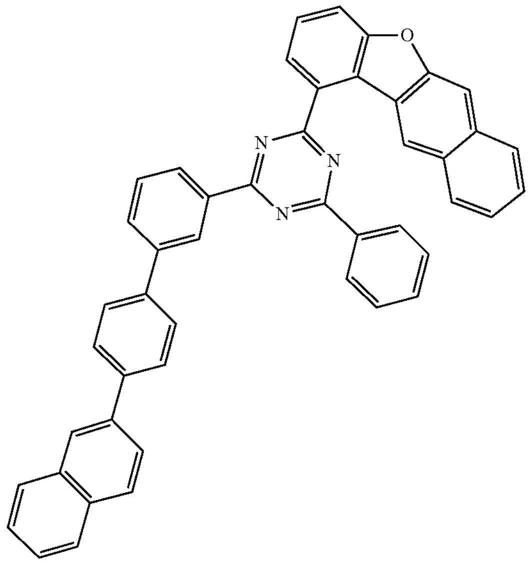

-continued
P-74
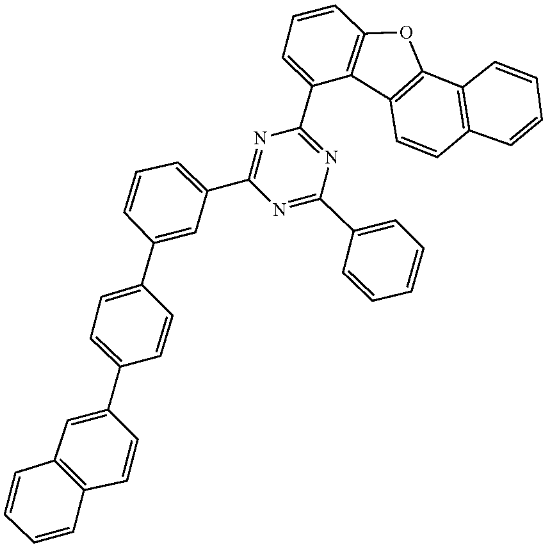
P-75
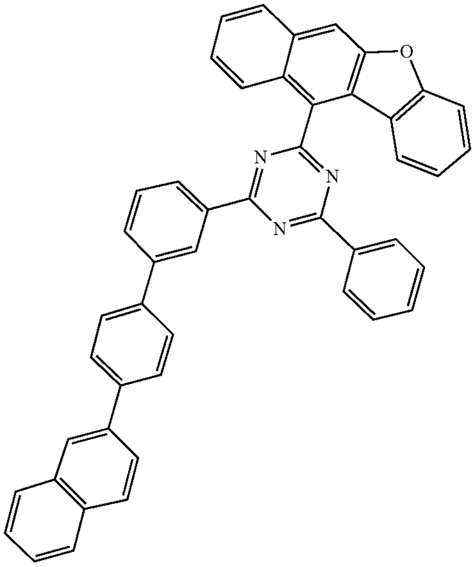
-continued
P-76
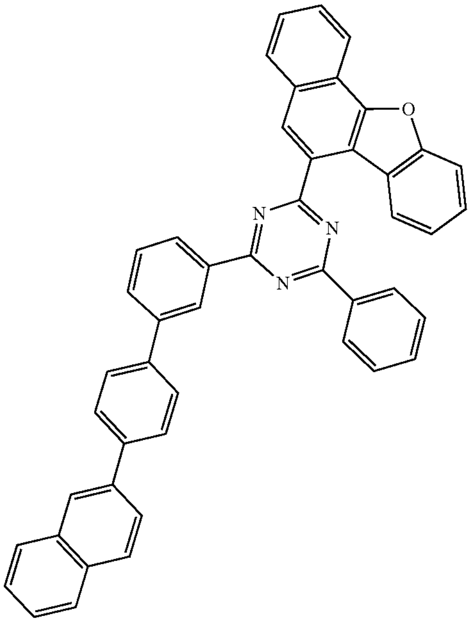
P-77
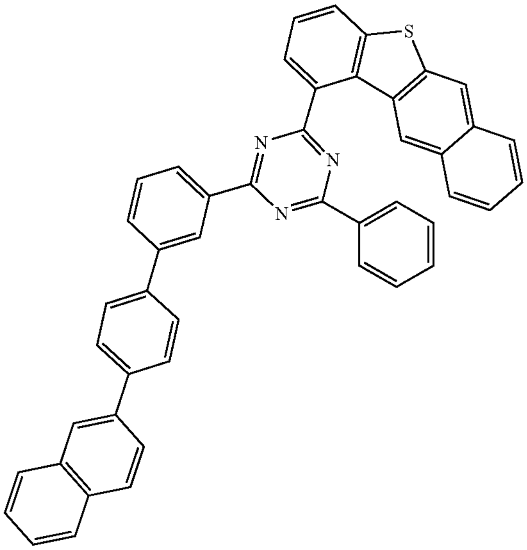

-continued
P-78
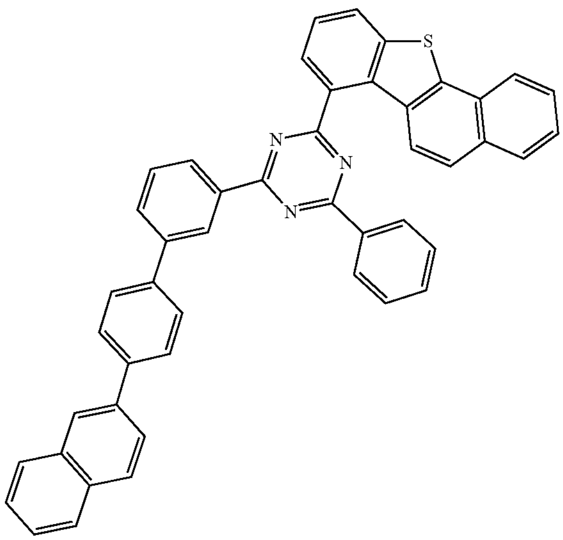
P-80
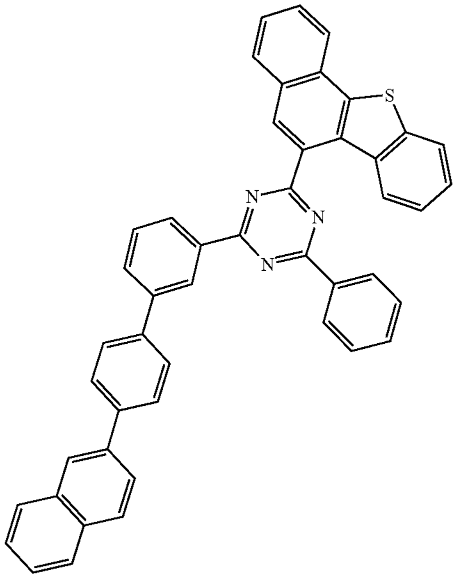
P-79
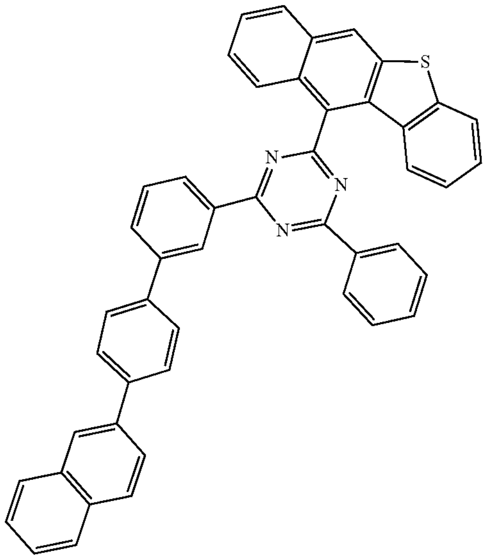
P-81
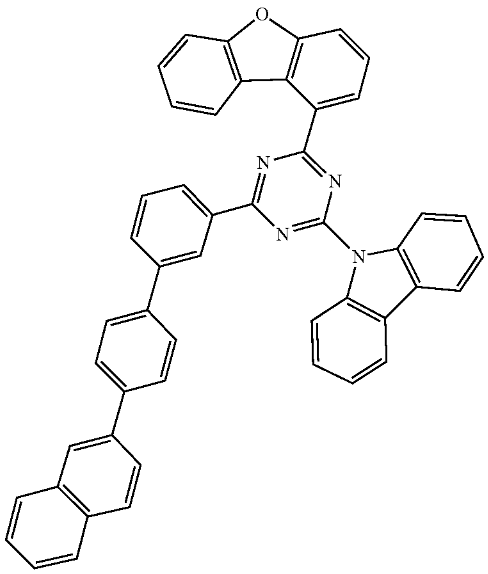

-continued
P-82
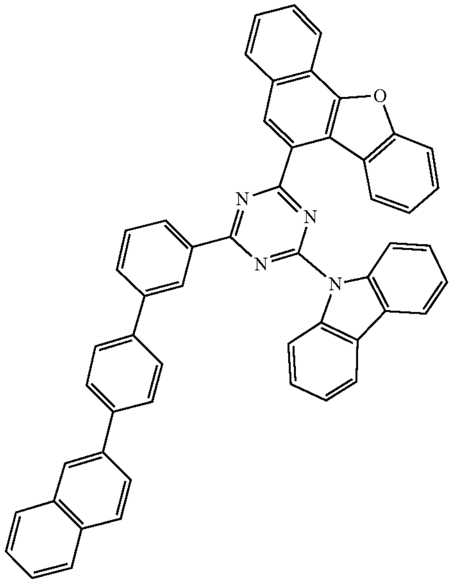
-continued
P-84
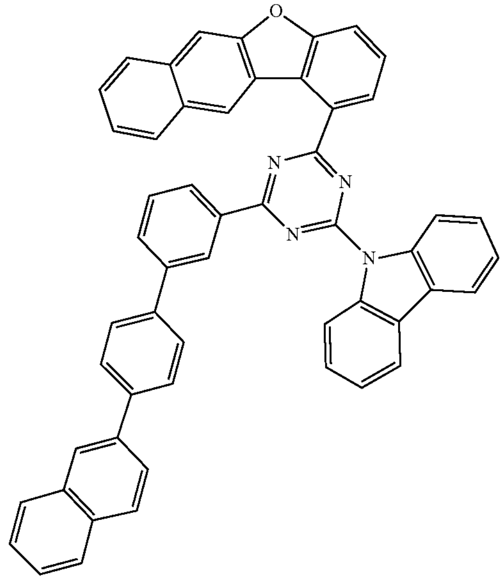
P-83
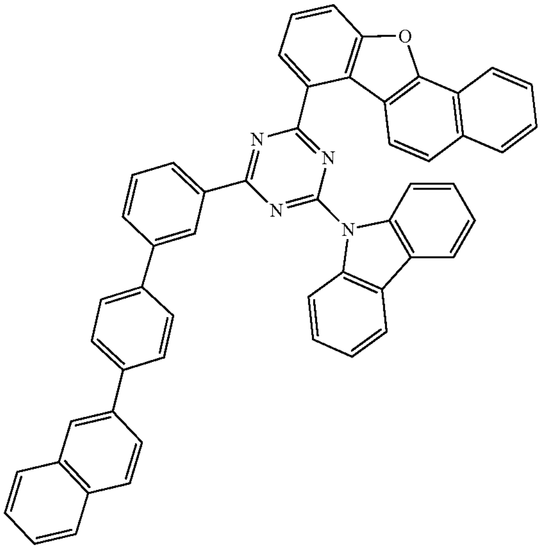
P-85
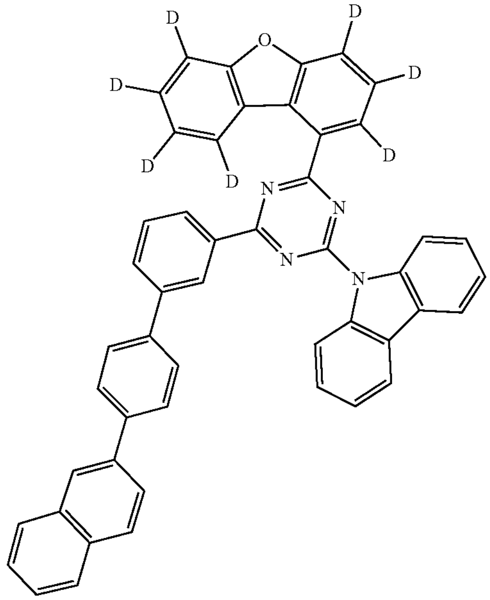

-continued
P-86
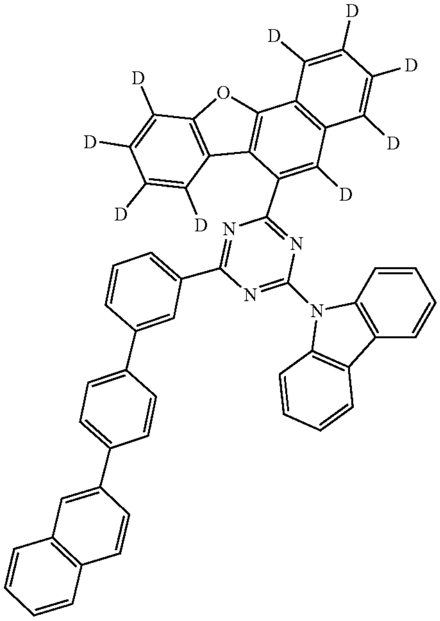
P-87
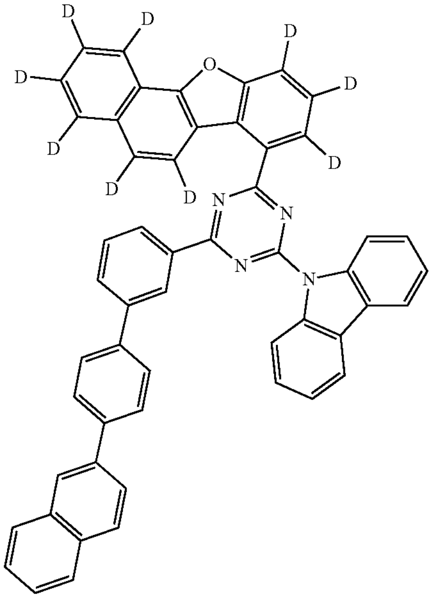
-continued
P-88
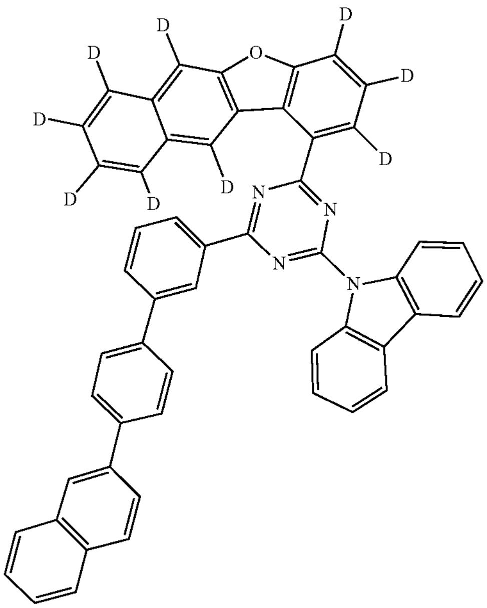
P-89
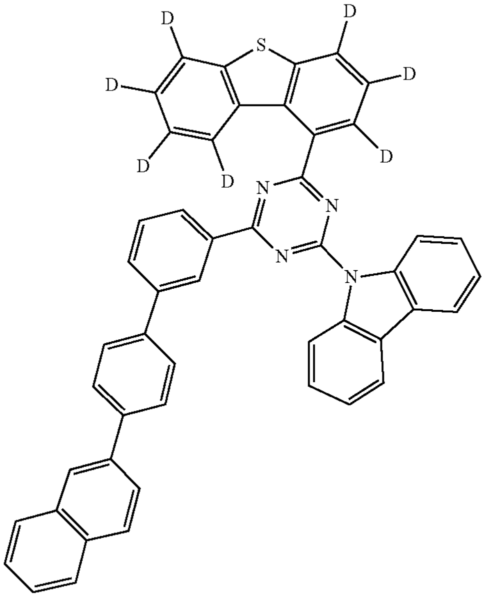

-continued
P-90
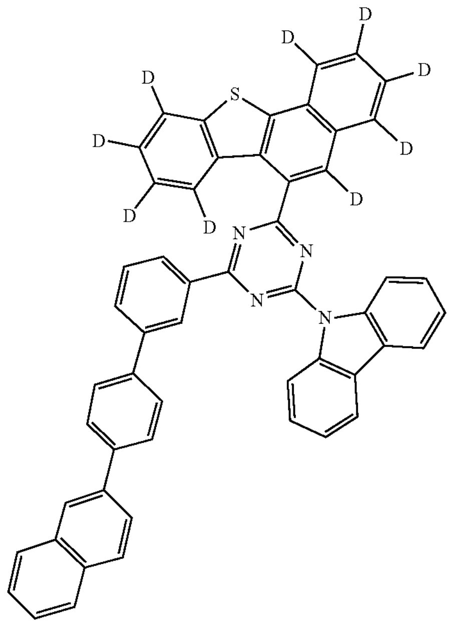
P-91
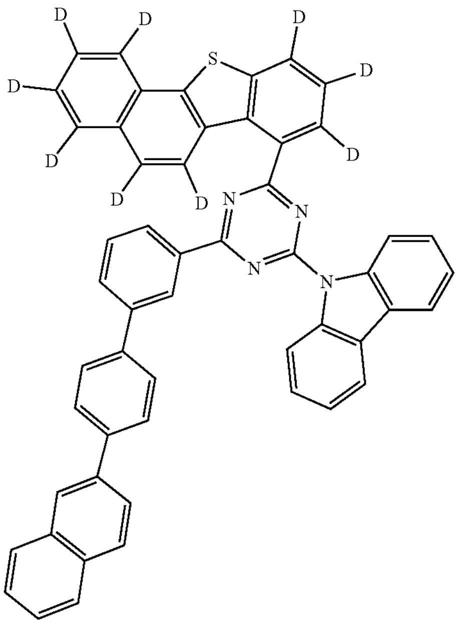
-continued
P-92
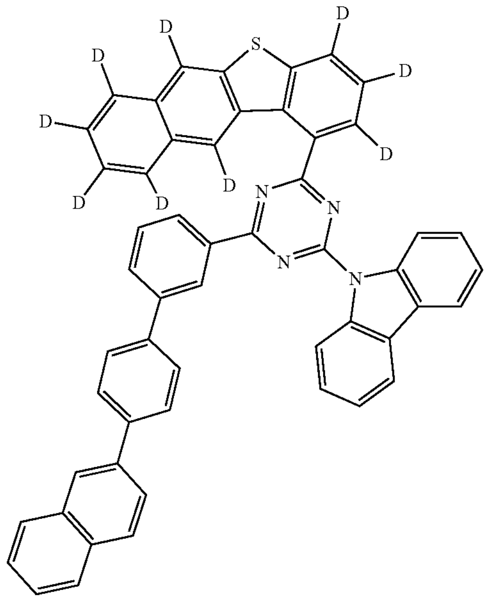
P-93
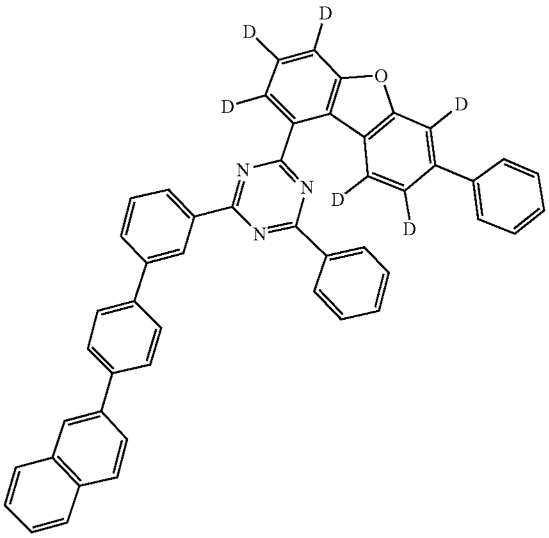

-continued
P-94
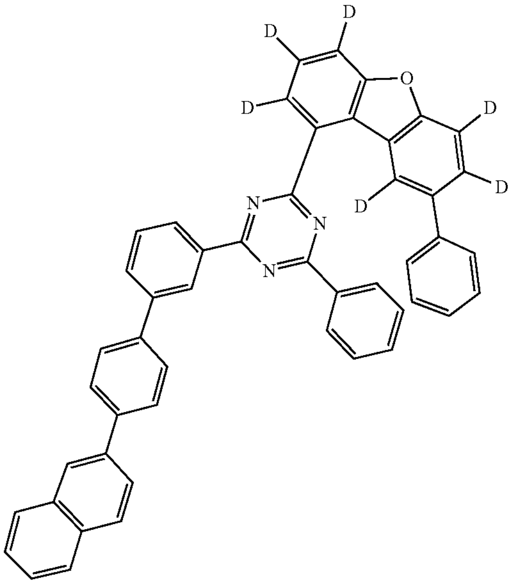
P-95
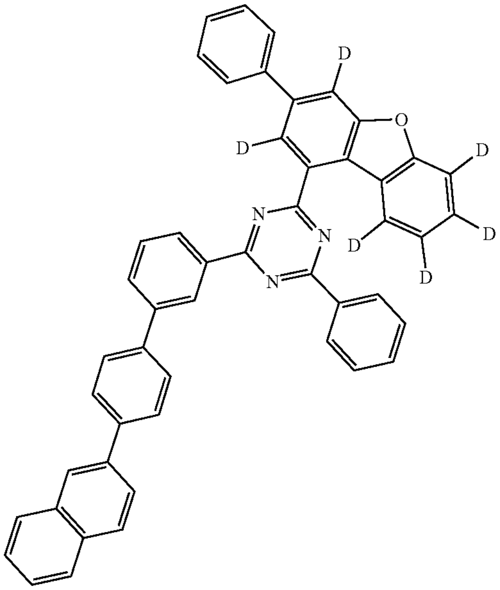
-continued
P-96
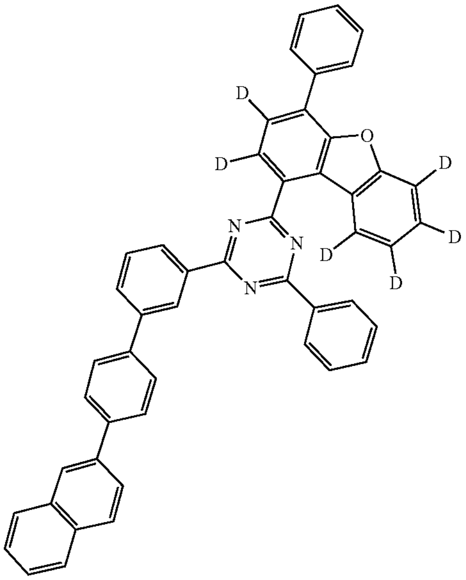
P-97
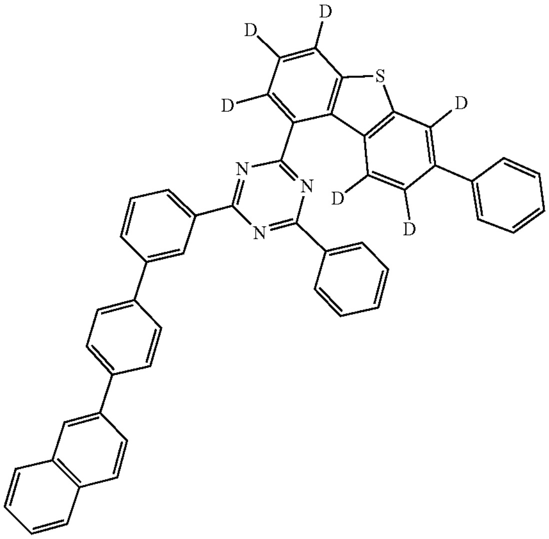

-continued
P-98
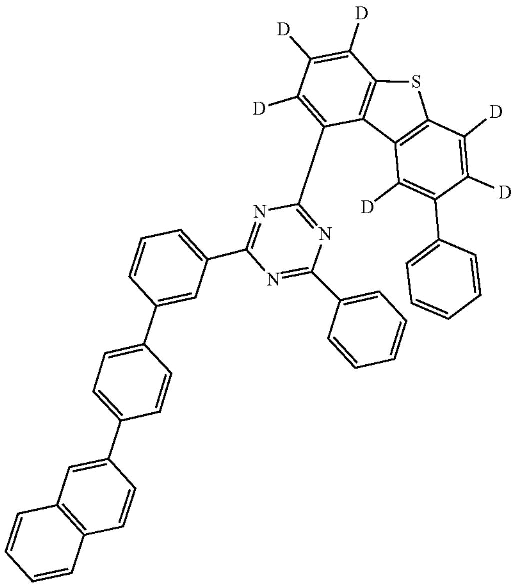
P-99
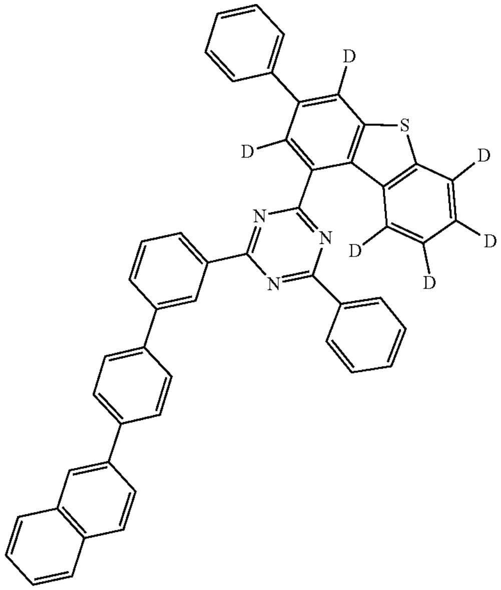
-continued
P-100
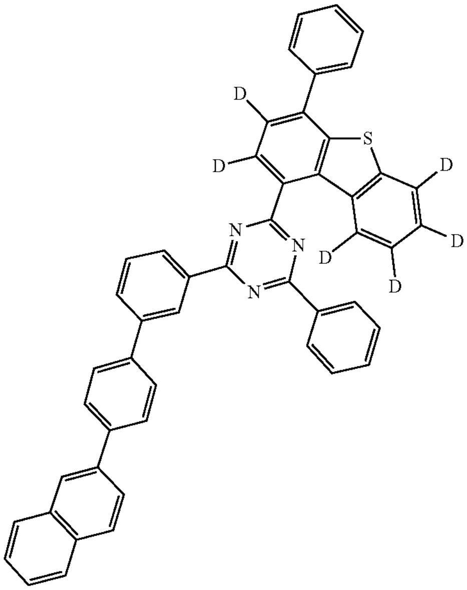
P-101
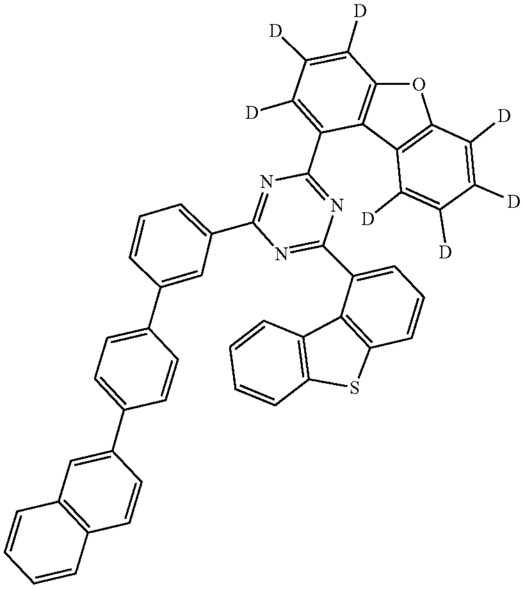

-continued
P-102
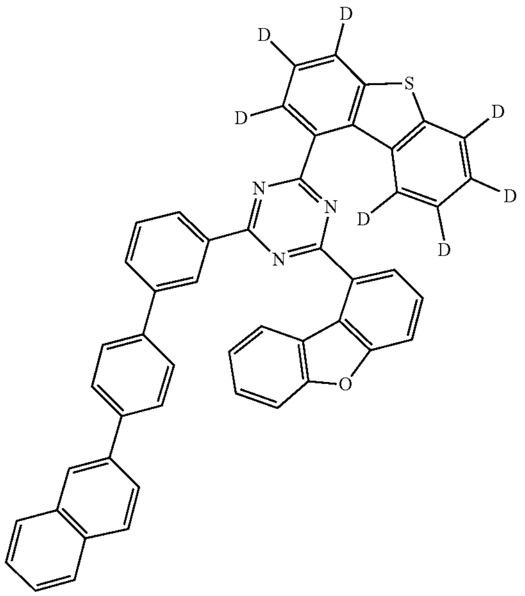
P-103
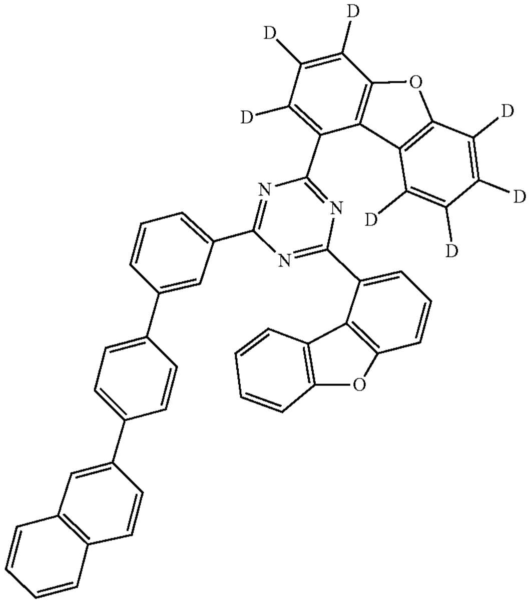
-continued
P-104
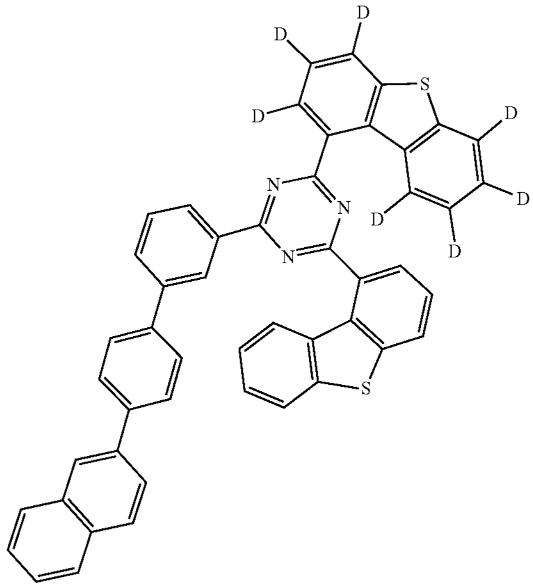
P-105
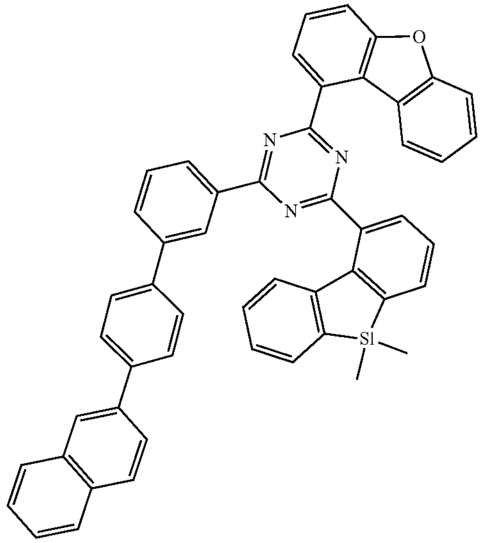

-continued

P-106

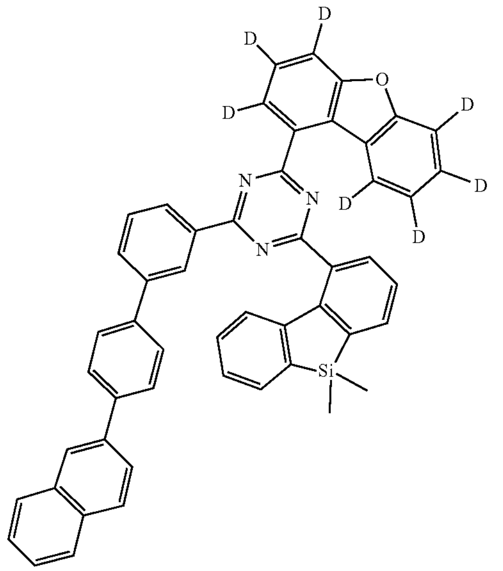

P-107

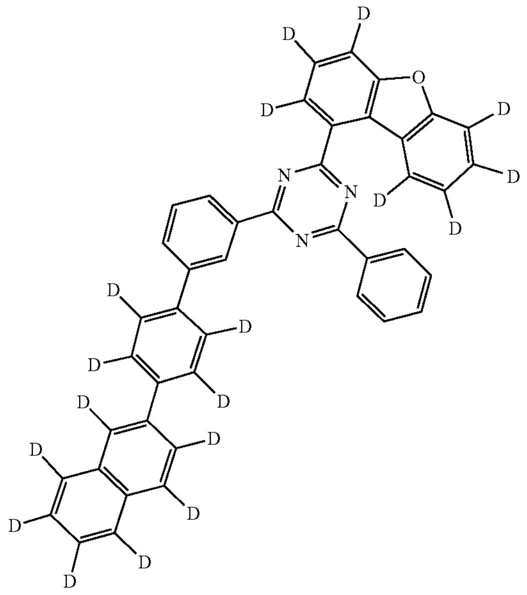

In another aspect, the present invention provides a method for reusing the compound represented by Formula 1, comprising:

a step of depositing an organic light emitting material including the compound represented by Formula 1;

a step of removing impurities from the crude organic light emitting material recovered from the deposition apparatus;

a step of recovering the removed impurities; and a step of purifying the recovered impurities to a purity of 99.9% or higher.

The step of removing impurities from the crude organic light emitting material recovered from the deposition apparatus may preferably include a step of performing a pre-purification process to obtain a purity of 98% or more by recrystallization in a recrystallization solvent.

The recrystallization solvent may be preferably a polar solvent having a polarity index (PI) of 5.5 to 7.2.

The recrystallization solvent may preferably be used by mixing a polar solvent having a polarity index of 5.5 to 7.2 and a non-polar solvent having a polarity index of 2.0 to 4.7.

When a mixture of a polar solvent and a non-polar solvent is used for the recrystallization solvent, the non-polar solvent may be used in an amount of 15% (v/v) or less relative to the polar solvent.

The recrystallization solvent may preferably be used by mixing N-Methylpyrrolidone (NMP) single solvent; or a polar solvent mixed any one selected from the group consisting of 1,3-Dimethyl-2-imidazolidinone, 2-pyrrolidone, N,N-Dimethyl formamide, Dimethyl acetamide, and Dimethyl sulfoxide with N-Methylpyrrolidone; or single solvents selected from the group consisting of Toluene, Dichloromethane (DCM), Dichloroethane (DCE), Tetrahydrofuran (THF), Chloroform, Ethyl acetate and Butanone; a two or more mixed non-polar solvent selected from the group consisting of Toluene, Dichloromethane (DCM), Dichloroethane (DCE), Tetrahydrofuran (THF), Chloroform, Ethyl acetate and Butanone; or mixed non-polar solvents: or a mixed solvent of a polar solvent and a non-polar solvent;

The pre-purification process may comprise a step of precipitating crystals of by cooling to 0° C. to 5° C. after dissolving the crude organic light emitting material recovered from the deposition apparatus in a polar solvent at 90° C. to 120° C.

The pre-purification process may comprise a step of precipitating crystals by cooling to 35° C. to 40° C., adding a non-polar solvent, and then cooling to 0° C. to 5° C. after dissolving the crude organic light emitting material recovered from the deposition apparatus in a polar solvent at 90° C. to 120° C.

The pre-purification process may comprise a step of precipitating crystals while concentrating the solvent and removing the non-polar solvent, after dissolving the crude organic light emitting material recovered from the deposition apparatus in a non-polar solvent.

The pre-purification process may comprise a step of recrystallizing again with a non-polar solvent after recrystallizing first with a polar solvent.

The step of purifying the recovered impurities to a purity of 99.9% or higher may comprise performing an adsorption separation process to adsorb and remove impurities by adsorbing on the adsorbent.

The adsorbent may be activated carbon, silica gel, alumina, or a material for known adsorption purposes.

The step of purifying the recovered impurities to a purity of 99.9% or higher may comprise performing sublimation purification.

The present invention may further include a light efficiency enhancing layer may be formed on at least one surface of the first electrode and the second electrode, the surface being opposite to the organic material layer.

Also, the organic material layer may include 2 or more stacks comprising a hole transport layer, an emitting layer, and an electron transport layer sequentially formed on the first electrode and may further comprise a charge generation layer formed between the 2 or more stacks In another aspect, the present invention also provides an electronic device comprising a display device comprising the organic electronic element; and a control unit for driving the display device. Here, the organic electronic element is at least one of an OLED, an organic solar cell, an organic photo conductor, an organic transistor (organic TFT) and an element for monochromic or white illumination.

Hereinafter, Synthesis examples of compounds represented by Formulas 1, 4 and 5 according to the present invention and examples of manufacturing an organic electronic element will be described in detail with examples, but the present invention is not limited to the following examples.

[Synthesis Example 1] Compound Represented by Formula 1

The compound (final products) represented by Formula 1 according to the present invention may be prepared by reacting as in Reaction Scheme 1, but is not limited thereto.

<Reaction Scheme 1>

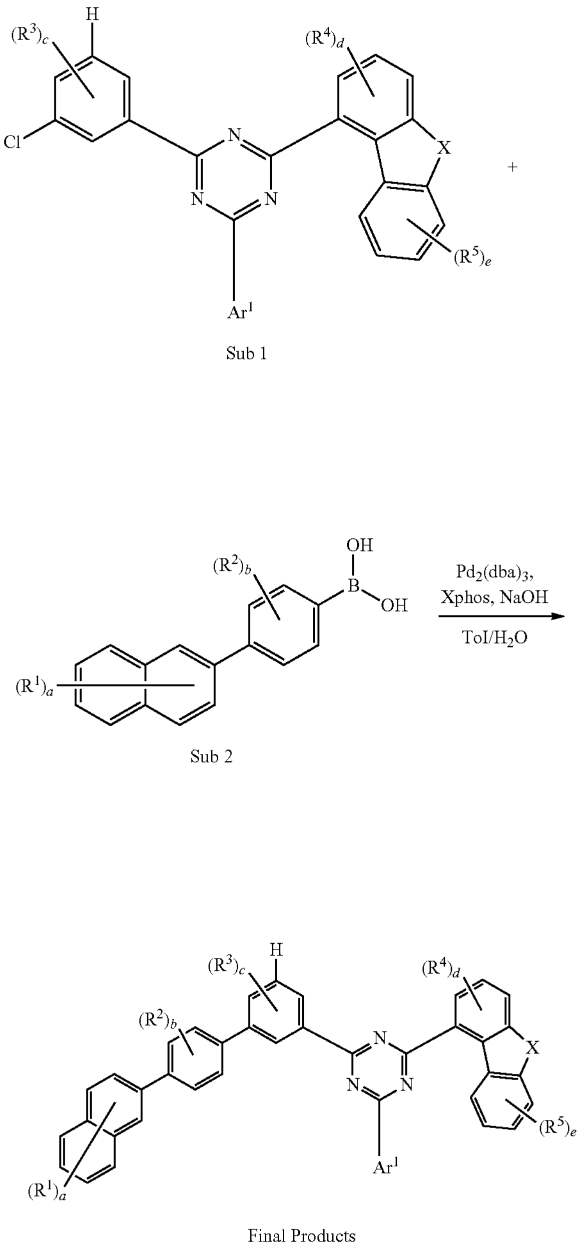

Sub 1

Sub 2

Final Products

Wherein, $R^1$, $R^2$, $R^3$, $R^4$, $R^5$, a, b, c, d, e, $Ar^1$ and X are the same as defined in Formula 1.

1. Synthesis of Sub 1

Sub 1 of Reaction Scheme 1 may be synthesized by the reaction pathway of Reaction Scheme 2, but is not limited thereto.

<Reaction Scheme 2>

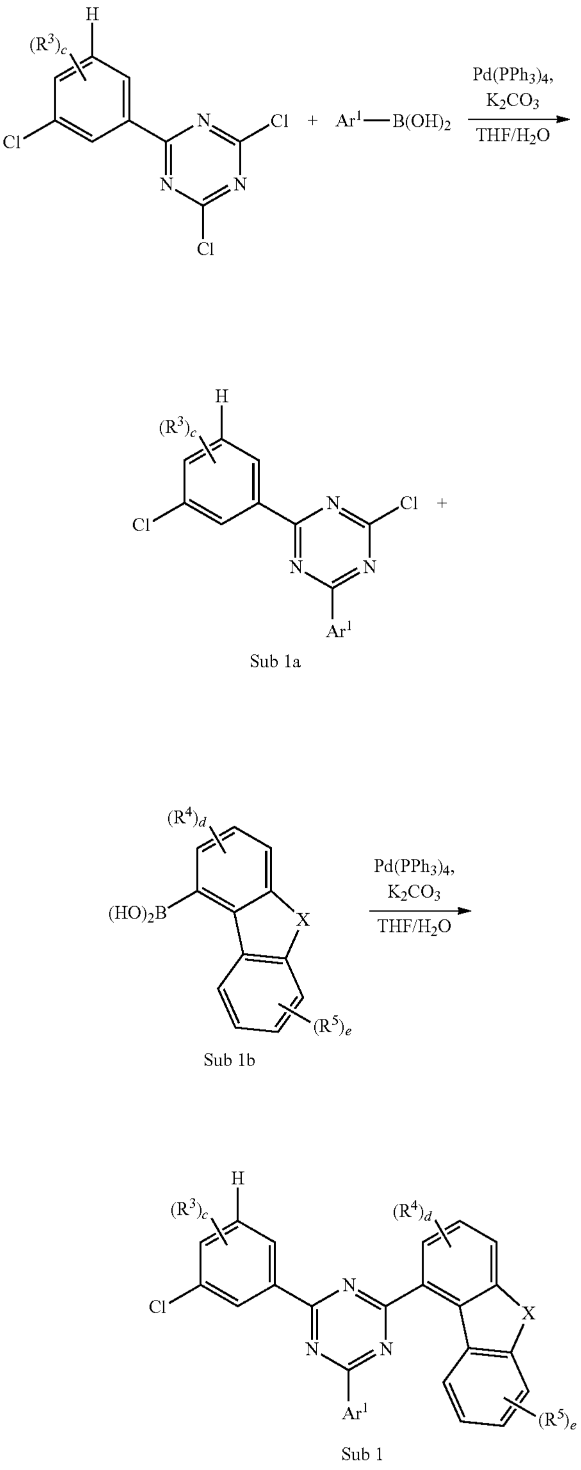

Sub 1a

Sub 1b

Sub 1

Wherein, $R^3$, $R^4$, $R^5$, c, d, e, $Ar^1$ and X are the same as defined in Formula 1.

1. Synthesis Example of Sub 1-1

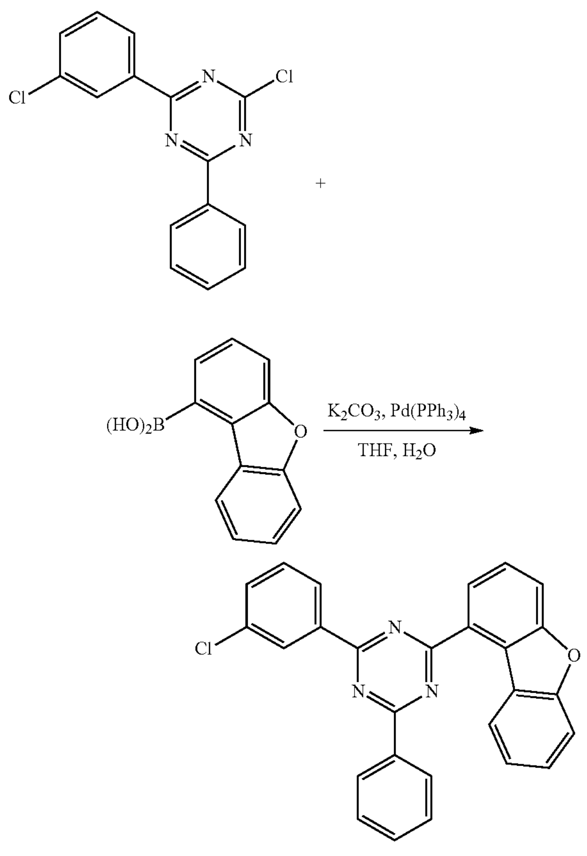

Sub 1-1 dibenzo[b,d]furan-1-ylboronic acid (20 g, 66.40 mmol), 2-chloro-4-(3-chlorophenyl)-6-phenyl-1,3,5-triazine (22.07 g, 73.04 mmol), $Pd(PPh_3)_4$ (2.30 g, 1.99 mmol), $K_2CO_3$ (13.7 g, 99.60 mmol) were dissolved in anhydrous THF (150 mL) and $H_2O$ (70 mL), the mixture was stirred for 8 hours at 60° C. After completion of the reaction, extraction was performed with $CH_2Cl_2$ and water, and the organic layer was treated with $MgSO_4$, concentrated, applied to Silicagel, and subjected to column and recrystallization to obtain 23 g of Sub 1-1 (yield: 75%).

2. Synthesis Example of Sub 1-6

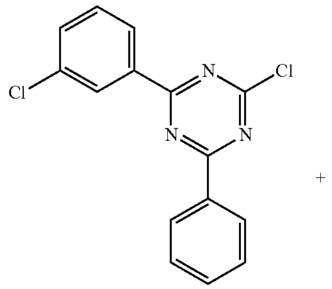

-continued

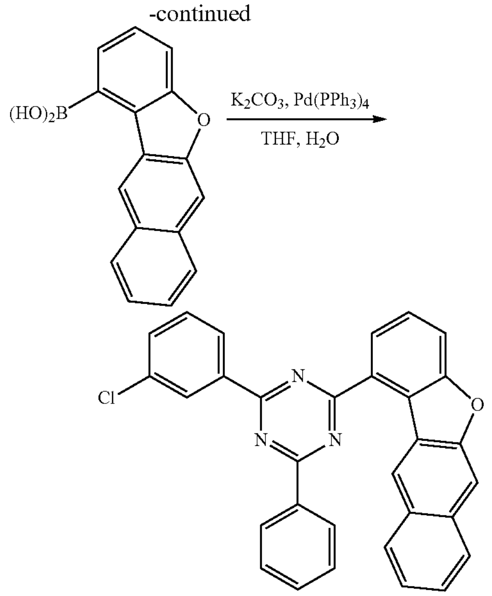

Sub 1-6 naphtho[2,3-b]benzofuran-1-ylboronic acid (20 g, 66.40 mmol), 2-chloro-4-(3-chlorophenyl)-6-(naphthalen-1-yl)-1,3,5-triazine (22.07 g, 73.04 mmol), $Pd(PPh_3)_4$ (2.30 g, 1.99 mmol), $K_2CO_3$ (13.7 g, 99.60 mmol) were dissolved in anhydrous THF (150 mL) and $H_2O$ (70 mL), the mixture was stirred for 8 hours at 60° C. After completion of the reaction, extraction was performed with $CH_2Cl_2$ and water, and the organic layer was treated with $MgSO_4$, concentrated, applied to Silicagel, and subjected to column and recrystallization to obtain 20 g of Sub 1-6 (yield: 68%).

3. Synthesis Example of Sub 1-21

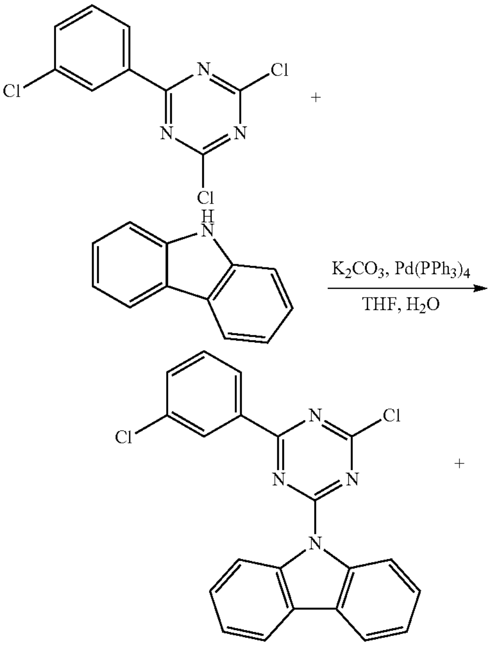

Sub 1a-1

-continued

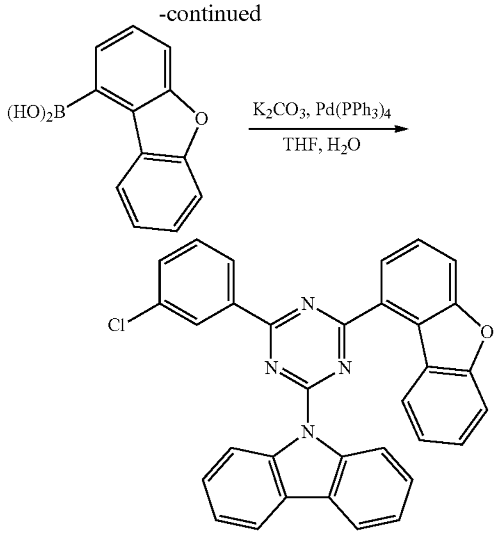

Sub 1-21

(1) Synthesis of Sub 1a-1

2,4-dichloro-6-(3-chlorophenyl)-1,3,5-triazine (34.27 g, 131.57 mmol), Carbazole (20 g, 119.61 mmol), $Pd(PPh_3)_4$ (4.15 g, 3.59 mmol), $K_2CO_3$ (24.8 g, 179.42 mmol) were placed in a round bottom flask and dissolving in anhydrous THF (265 mL) and water (132 mL), the mixture was stirred at 50° C. for 12 hours. When the reaction was completed, the reactant was cooled to room temperature, extracted with $CH_2Cl_2$ and water, and treated with $MgSO_4$. The product produced by concentrating the organic solvent was recrystallized using a Silicagel Column to obtain 28.07 g (60%) of Sub1a-1.

(2) Synthesis of Sub 1-21 dibenzo[b,d]furan-1-ylboronic acid (20 g, 66.40 mmol 9-(4-chloro-6-(3-chlorophenyl)-1,3,5-triazin-2-yl)-9H-carbazole (22.07 g, 73.04 mmol), $Pd(PPh_3)_4$ (2.30 g, 1.99 mmol), $K_2CO_3$ (13.7 g, 99.60 mmol) were dissolved in anhydrous THF (150 mL) and $H_2O$ (70 mL), the mixture was stirred for 8 hours at 60° C. After completion of the reaction, extraction was performed with $CH_2Cl_2$ and water, and the organic layer was treated with $MgSO_4$, concentrated, applied to Silicagel, and subjected to column and recrystallization to obtain 21 g of Sub 1-21 (yield: 72%).

The compound belonging to Sub 1 may be the following compounds, but is not limited thereto, and Table 1 shows the FD-MS (Field Desorption-Mass Spectrometry) values of the compounds belonging to Sub 1.

Sub 1-1

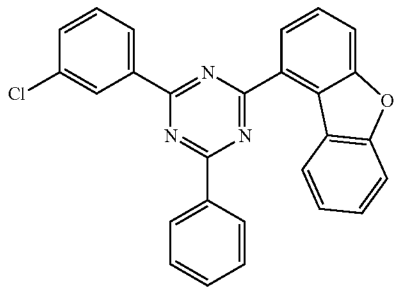

-continued

Sub 1-2

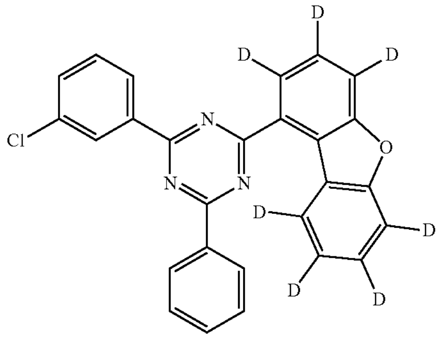

Sub 1-3

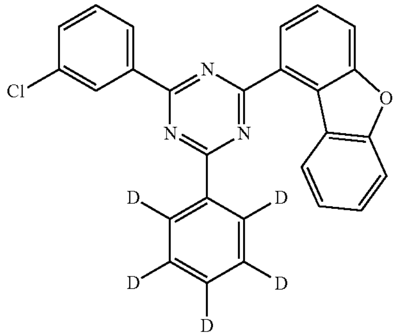

Sub 1-4

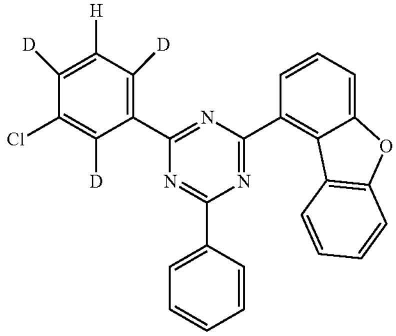

Sub 1-5

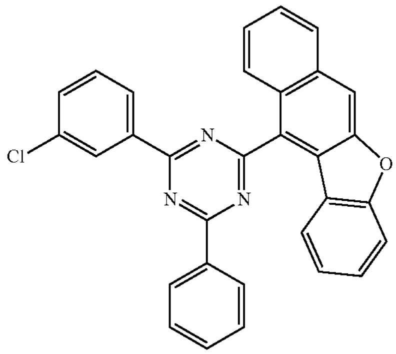

-continued
Sub 1-6
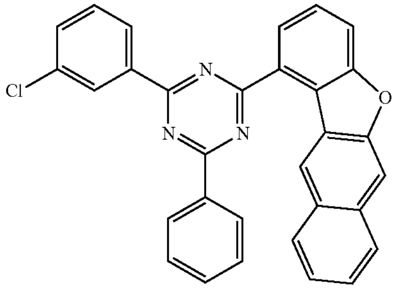
Sub 1-7
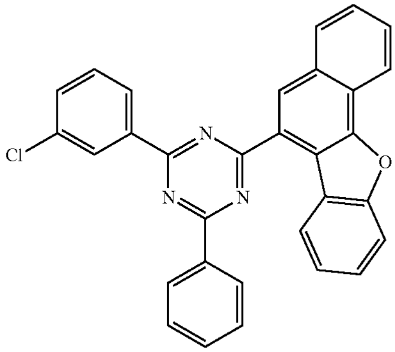
Sub 1-8
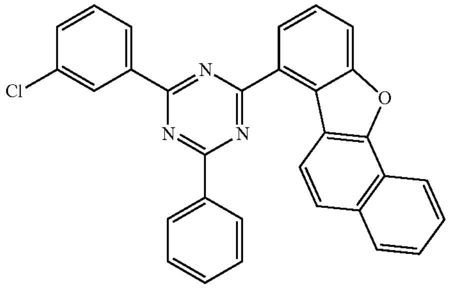
Sub 1-9
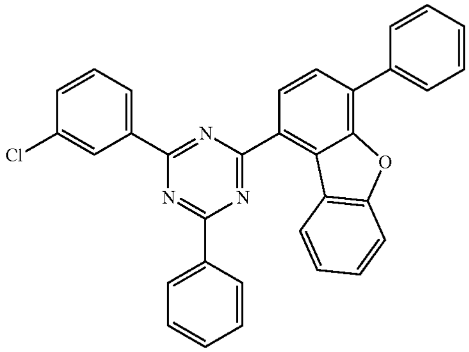
-continued
Sub 1-10
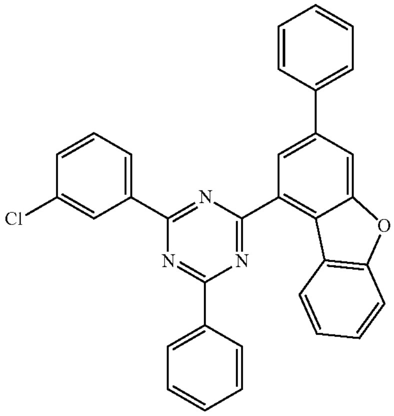
Sub 1-11
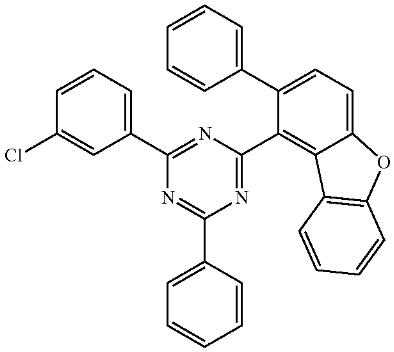
Sub 1-12
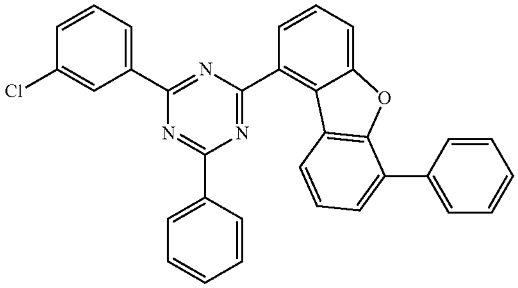
Sub 1-13
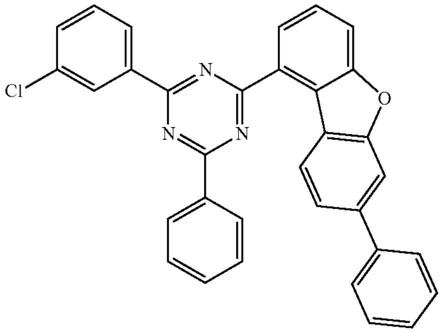

-continued
Sub 1-14
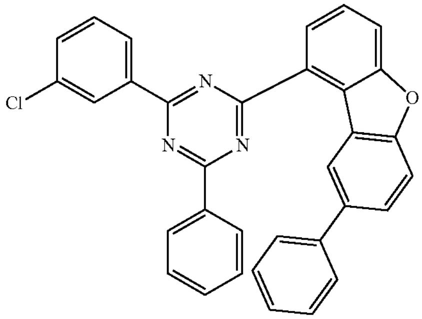
Sub 1-15
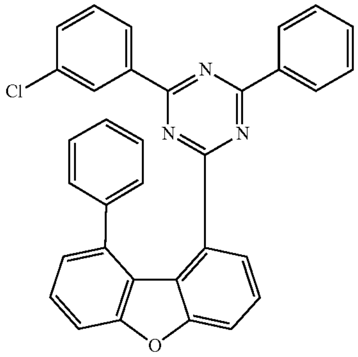
Sub 1-16
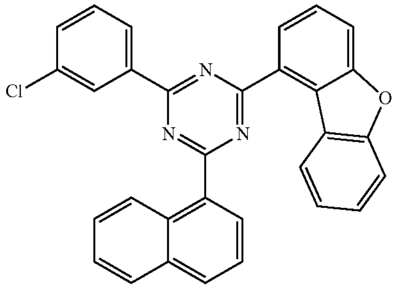
Sub 1-17
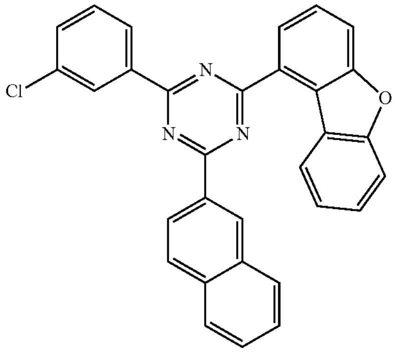
-continued
Sub 1-18
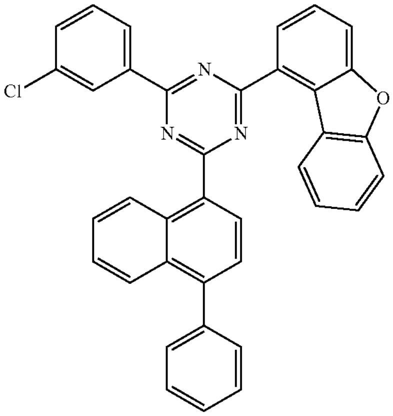
Sub 1-19
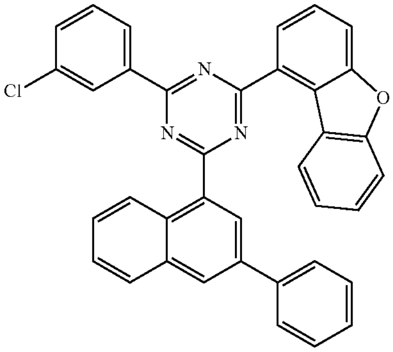
Sub 1-20
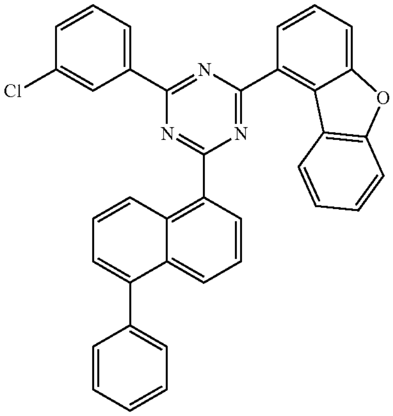
Sub 1-21
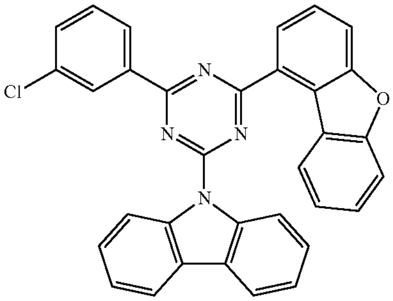

-continued
Sub 1-22
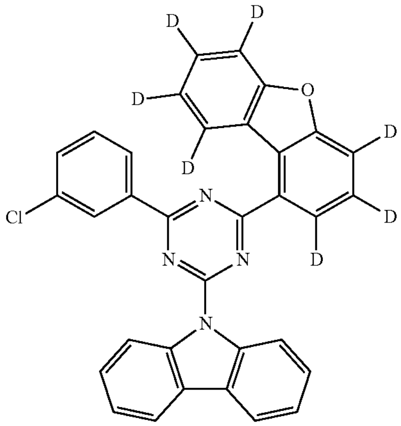
Sub 1-23
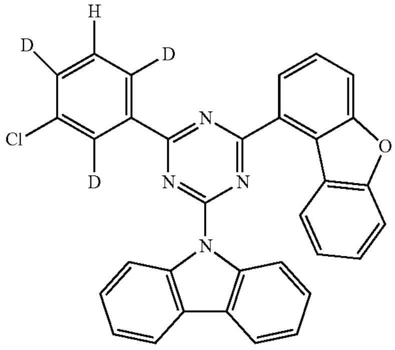
Sub 1-24
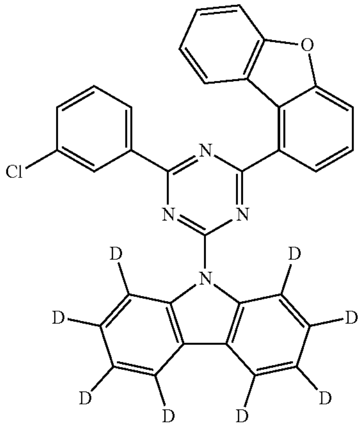
Sub 1-25
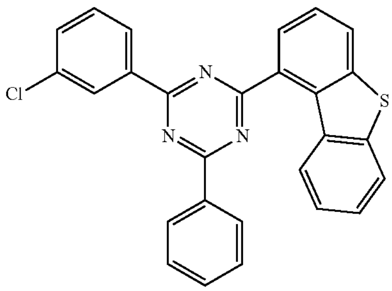
-continued
Sub 1-26
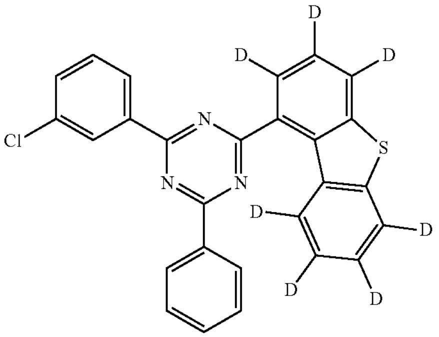
Sub 1-27
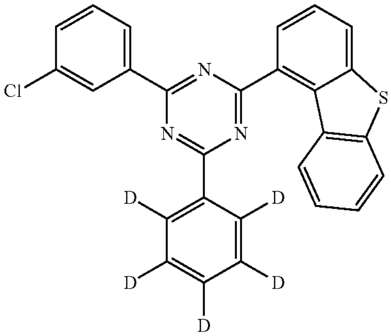
Sub 1-28
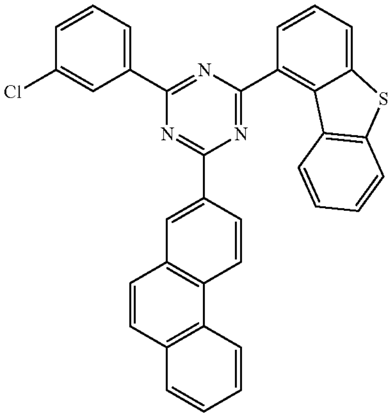
Sub 1-29
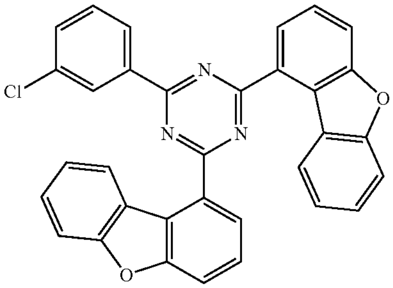

-continued

Sub 1-30

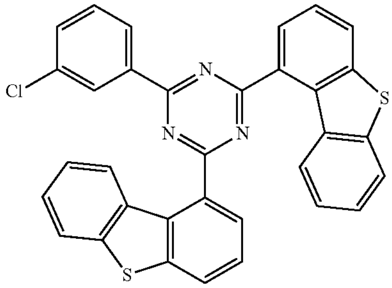

Sub 1-31

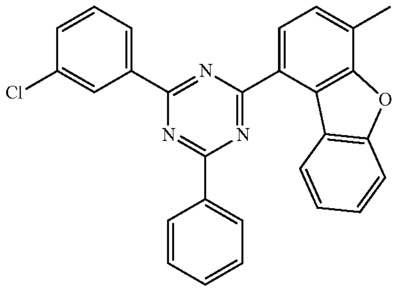

TABLE 1

| Compound | FD-MS | Compound | FD-MS |
|---|---|---|---|
| Sub1-1 | m/z = 433.10 ($C_{27}H_{16}ClN_3O$ = 433.89) | Sub1-2 | m/z = 440.14 ($C_{27}H_9D_7ClN_3O$ = 440.94) |
| Sub1-3 | m/z = 438.13 ($C_{27}H_{11}D_5ClN_3O$ = 438.93) | Sub1-4 | m/z = 436.12 ($C_{27}H_{13}D_3ClN_3O$ = 436.91) |
| Sub1-5 | m/z = 483.11 ($C_{31}H_{18}ClN_3O$ = 483.95) | Sub1-6 | m/z = 483.11 ($C_{31}H_{18}ClN_3O$ = 483.95) |
| Sub1-7 | m/z = 483.11 ($C_{31}H_{18}ClN_3O$ = 483.95) | Sub1-8 | m/z = 483.11 ($C_{31}H_{18}ClN_3O$ = 483.95) |
| Sub1-9 | m/z = 509.13 ($C_{33}H_{20}ClN_3O$ = 509.99) | Sub1-10 | m/z = 509.13 ($C_{33}H_{20}ClN_3O$ = 509.99) |
| Sub1-11 | m/z = 509.13 ($C_{33}H_{20}ClN_3O$ = 509.99) | Sub1-12 | m/z = 509.13 ($C_{33}H_{20}ClN_3O$ = 509.99) |
| Sub1-13 | m/z = 509.13 ($C_{33}H_{20}ClN_3O$ = 509.99) | Sub1-14 | m/z = 509.13 ($C_{33}H_{20}ClN_3O$ = 509.99) |
| Sub1-15 | m/z = 509.13 ($C_{33}H_{20}ClN_3O$ = 509.99) | Sub1-16 | m/z = 483.11 ($C_{31}H_{18}ClN_3O$ = 483.95) |
| Sub1-17 | m/z = 483.11 ($C_{31}H_{18}ClN_3O$ = 483.95) | Sub1-18 | m/z = 559.15 ($C_{37}H_{22}ClN_3O$ = 560.05) |
| Sub1-19 | m/z = 559.15 ($C_{37}H_{22}ClN_3O$ = 560.05) | Sub1-20 | m/z = 559.15 ($C_{37}H_{22}ClN_3O$ = 560.05) |
| Sub1-21 | m/z = 522.12 ($C_{33}H_{19}ClN_4O$ = 522.99) | Sub1-22 | m/z = 529.17 ($C_{33}H_{12}D_7ClN_4O$ = 530.03) |
| Sub1-23 | m/z = 525.14 ($C_{33}H_{16}D_3ClN_4O$ = 526.01) | Sub1-24 | m/z = 530.17 ($C_{33}H_{11}D_8ClN_4O$ = 531.04) |
| Sub1-25 | m/z = 449.08 ($C_{27}H_{16}ClN_3S$ = 449.96) | Sub1-26 | m/z = 456.12 ($C_{27}H_9D_7ClN_3S$ = 457.00) |
| Sub1-27 | m/z = 454.11 ($C_{27}H_{11}D_5ClN_3S$ = 454.99) | Sub1-28 | m/z = 549.11 ($C_{35}H_{20}ClN_3S$ = 550.08) |
| Sub1-29 | m/z = 523.11 ($C_{33}H_{18}ClN_3O_2$ = 523.98) | Sub1-30 | m/z = 555.06 ($C_{33}H_{18}ClN_3S_2$ = 556.10) |
| Sub1-31 | m/z = 447.11 ($C_{28}H_{18}ClN_3O$ = 447.92) | | |

II. Synthesis of Sub 2

Sub 2 of Reaction Scheme 1 may be synthesized by the reaction pathway of Reaction Scheme 3, but is not limited thereto.

<Reaction Scheme 3>

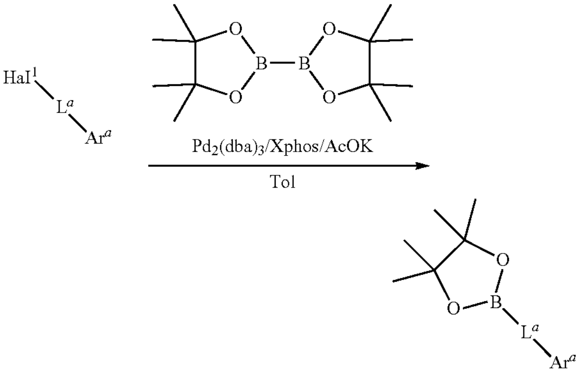

Sub 2

1. Synthesis Example of Sub 2-2

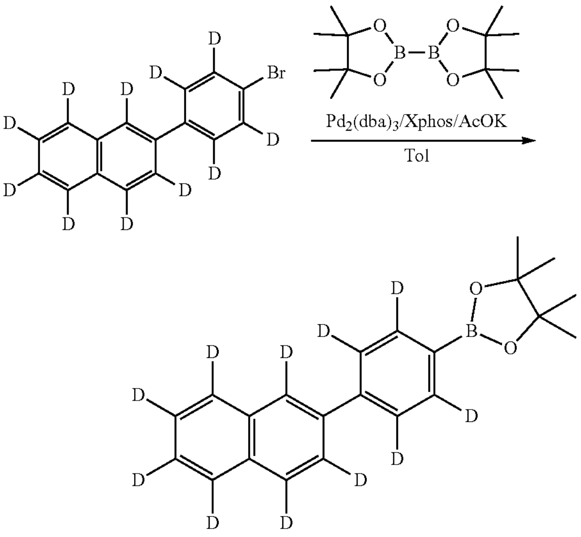

Sub 2-2

2-(4-bromophenyl-2,3,5,6-d4)naphthalene-1,3,4,5,6,7,8-d7 (10.00 g, 33.99 mmol) in 4,4,4',4',5,5,5',5'-octamethyl-2,2'-bi(1,3,2-dioxaborolane) (12.95 g, 50.98 mmol), $Pd_2(dba)_3$ (0.93 g, 1.02 mmol), Xphos (0.97 g, 2.04 mmol), AcOK (6.67 g, 67.97 mmol) were added to Toluene (85 mL) and stirred at 120° C. for 4 h. After the reaction was completed, the reaction solvent was removed, and the concentrated organic material was subjected to silica gel column or recrystallization to obtain 6.95 g (60%) of the product Sub2-2.

Compounds belonging to Sub 2 may be the following compounds, but are not limited thereto, and Table 2 shows FD-MS (Field Desorption-Mass Spectrometry) values of compounds belonging to Sub 2.

Sub 2-1

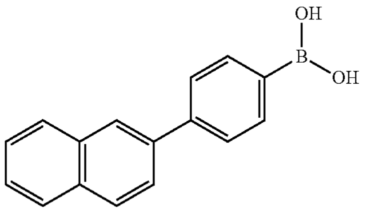

Sub 2-2

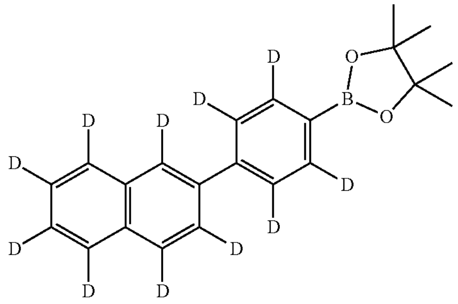

Sub 2-3

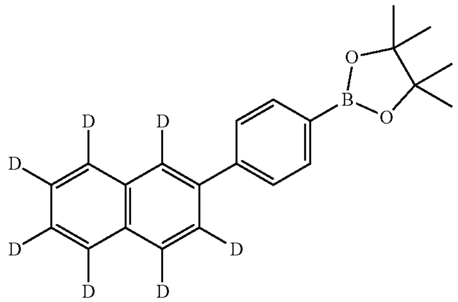

TABLE 2

| compound | FD-MS | compound | FD-MS |
|---|---|---|---|
| Sub2-1 | m/z = 248.10 ($C_{16}H_{13}BO_2$ = 248.09) | Sub2-2 | m/z = 341.25 ($C_{22}H_{12}D_{11}BO_2$ = 341.30) |
| Sub2-3 | m/z = 337.22 ($C_{22}H_{16}D_7BO_2$ = 337.28) | | |

1. Synthesis Example of P-1

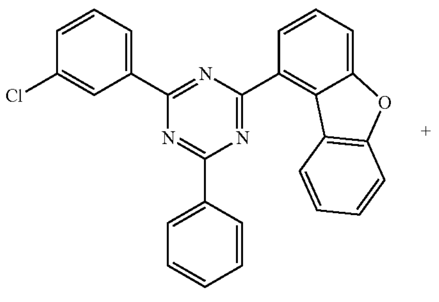

Sub 1-1

-continued

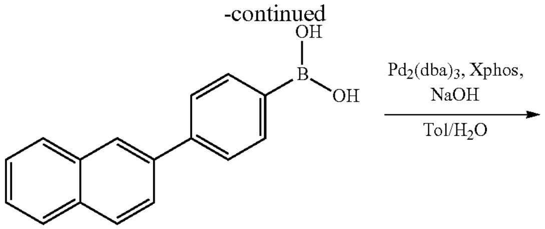

Sub 2-1

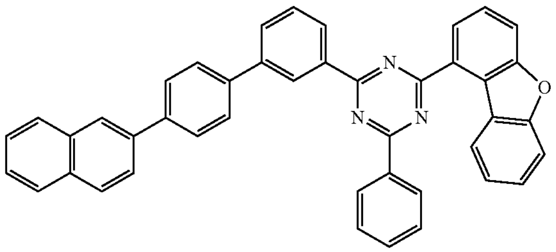

P-1

After dissolving Sub 1-1 (17.49 g, 40.31 mmol), Sub 2-1 (10 g, 40.31 mmol), $Pd_2(dba)_3$ (1.11 g, 1.21 mmol), Xphos (1.15 g, 2.42 mmol), NaOH (3.22 g, 80.62 mmol) in Toluene (90 mL), EtOH (5 mL), and $H_2O$ (50 mL) in a round bottom flask, the mixture was stirred at 120° C. After the reaction was completed, the produced solid was obtained by filtering, and the filtered solid was dissolved in toluene and silica filter was performed while heating. After concentrating the filtered solution, the resulting compound was recrystallized to obtain 16.9 g (yield: 70%) of product P-1.

2. Synthesis Example of P-6

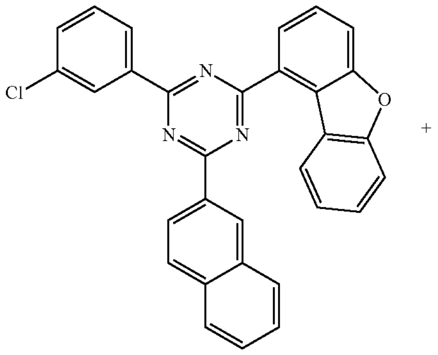

Sub 1-17

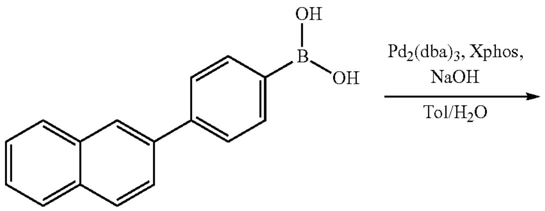

Sub 2-1

-continued

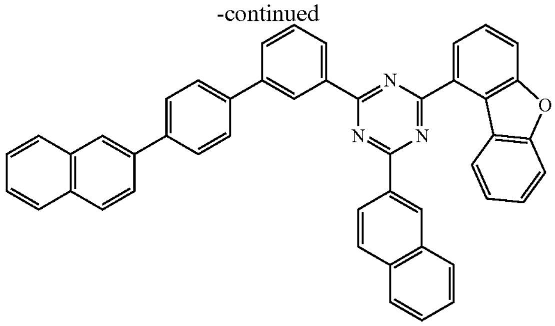

P-6

After dissolving Sub 1-17 (19.51 g, 40.31 mmol), Sub 2-1 (10 g, 40.31 mmol), $Pd_2(dba)_3$ (1.11 g, 1.21 mmol), Xphos (1.15 g, 2.42 mmol), NaOH (3.22 g, 80.62 mmol) in Toluene (90 mL), EtOH (5 mL), and $H_2O$ (50 mL) in a round bottom flask, the mixture was stirred at 120° C. After the reaction was completed, the produced solid was obtained by filtering, and the filtered solid was dissolved in toluene and silica filter was performed while heating. After concentrating the filtered solution, the resulting compound was recrystallized to obtain 17.2 g (yield: 72%) of product P-6.

3. Synthesis Example of P-13

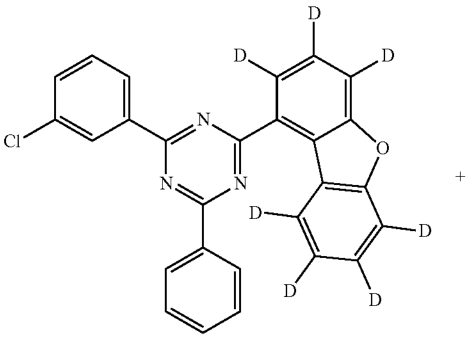

Sub 1-2

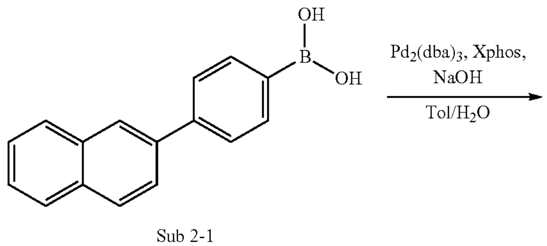

Sub 2-1

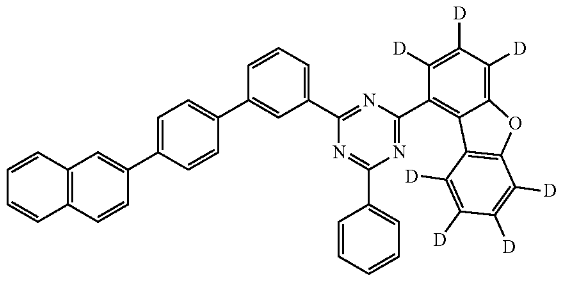

P-13

After dissolving Sub 1-2 (17.77 g, 40.31 mmol), Sub 2-1 (10 g, 40.31 mmol), $Pd_2(dba)_3$ (1.11 g, 1.21 mmol), Xphos (1.15 g, 2.42 mmol), NaOH (3.22 g, 80.62 mmol) in Toluene (90 mL), EtOH (5 mL), and $H_2O$ (50 mL) in a round bottom flask, the mixture was stirred at 120° C. After the reaction was completed, the produced solid was obtained by filtering, and the filtered solid was dissolved in toluene and silica filter was performed while heating. After concentrating the filtered solution, the resulting compound was recrystallized to obtain 16.9 g (yield: 70%) of product P-13.

4. Synthesis Example of P-21

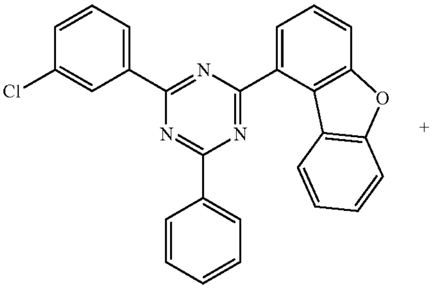

Sub 1-1

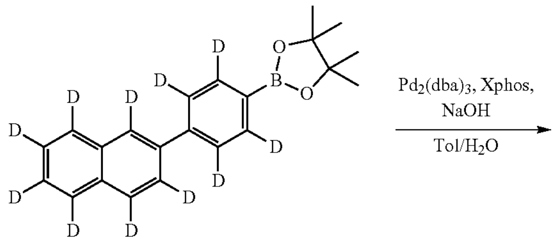

Sub 2-2

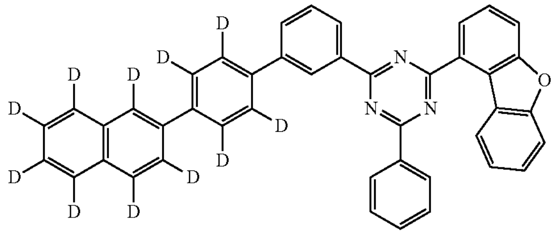

P-21

After dissolving Sub 1-1 (17.77 g, 40.31 mmol), Sub 2-2 (10 g, 40.31 mmol), $Pd_2(dba)_3$ (1.11 g, 1.21 mmol), Xphos (1.15 g, 2.42 mmol), NaOH (3.22 g, 80.62 mmol) in Toluene (90 mL), EtOH (5 mL), and $H_2O$ (50 mL) in a round bottom flask, the mixture was stirred at 120° C. After the reaction was completed, the produced solid was obtained by filtering, and the filtered solid was dissolved in toluene and silica filter was performed while heating. After concentrating the filtered solution, the resulting compound was recrystallized to obtain 17.1 g (yield: 70%) of product P-21.

5. Synthesis Example of P-37

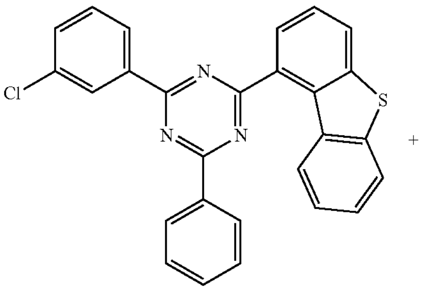

Sub 1-25

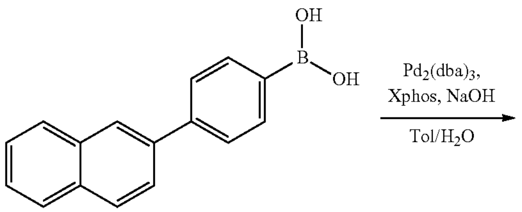

Sub 2-1

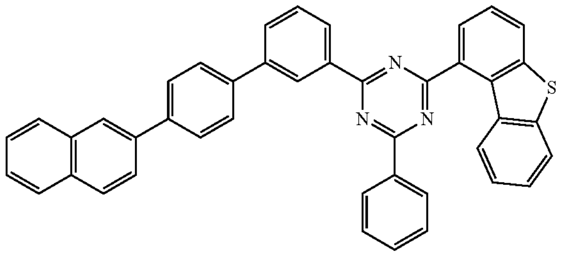

P-37

After dissolving Sub 1-25 (18.14 g, 40.31 mmol), Sub 2-1 (10 g, 40.31 mmol), $Pd_2(dba)_3$ (1.11 g, 1.21 mmol), Xphos (1.15 g, 2.42 mmol), NaOH (3.22 g, 80.62 mmol) in Toluene (90 mL), EtOH (5 mL), and $H_2O$ (50 mL) in a round bottom flask, the mixture was stirred at 120° C. After the reaction was completed, the produced solid was obtained by filtering, and the filtered solid was dissolved in toluene and silica filter was performed while heating. After concentrating the filtered solution, the resulting compound was recrystallized to obtain 16.18 g (yield: 65%) of product P-37.

6. Synthesis Example of P-47

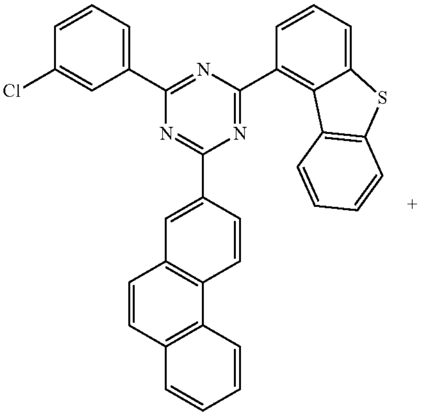

Sub 1-28

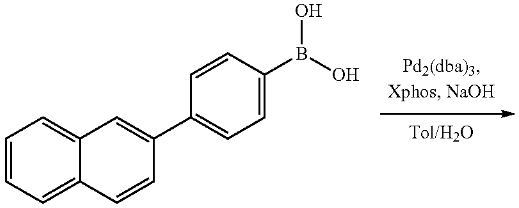

Sub 2-1

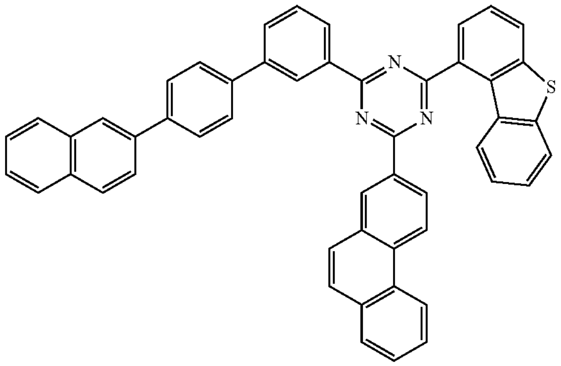

P-47

After dissolving Sub 1-28 (17.49 g, 40.31 mmol), Sub 2-1 (10 g, 40.31 mmol), $Pd_2(dba)_3$ (1.11 g, 1.21 mmol), Xphos (1.15 g, 2.42 mmol), NaOH (3.22 g, 80.62 mmol) in Toluene (90 mL), EtOH (5 mL), and $H_2O$ (50 mL) in a round bottom flask, the mixture was stirred at 120° C. After the reaction was completed, the produced solid was obtained by filtering, and the filtered solid was dissolved in toluene and silica filter was performed while heating. After concentrating the filtered solution, the resulting compound was recrystallized to obtain 16.9 g (yield: 70%) of product P-47.

7. Synthesis Example of P-53

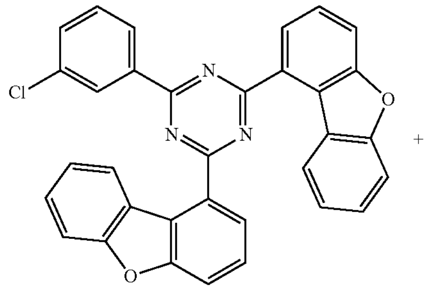

Sub 1-29

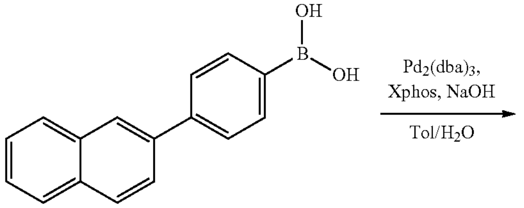

Sub 2-1

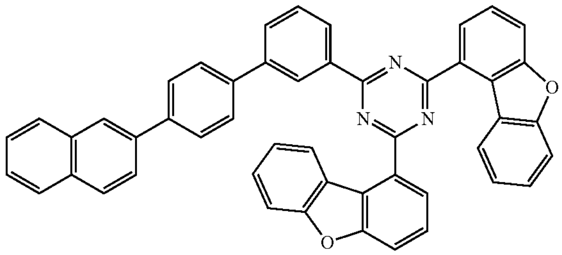

P-53

After dissolving Sub 1-29 (21.12 g, 40.31 mmol), Sub 2-1 (10 g, 40.31 mmol), $Pd_2(dba)_3$ (1.11 g, 1.21 mmol), Xphos (1.15 g, 2.42 mmol), NaOH (3.22 g, 80.62 mmol) in Toluene (90 mL), EtOH (5 mL), and $H_2O$ (50 mL) in a round bottom flask, the mixture was stirred at 120° C. After the reaction was completed, the produced solid was obtained by filtering, and the filtered solid was dissolved in toluene and silica filter was performed while heating. After concentrating the filtered solution, the resulting compound was recrystallized to obtain 20.63 g (yield: 75%) of product P-53.

8. Synthesis Example of P-62

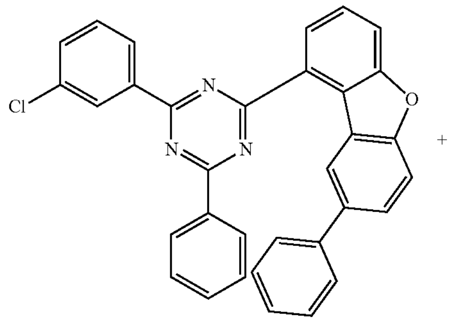

Sub 1-14

-continued

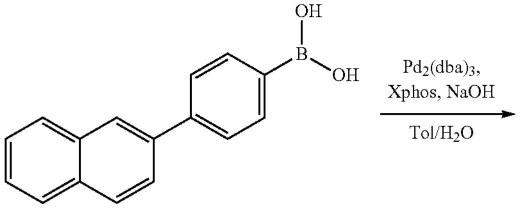

Sub 2-1

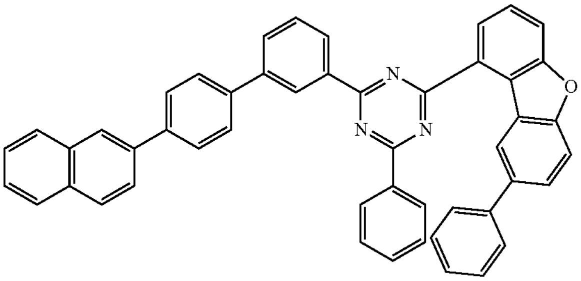

P-62

After dissolving Sub 1-14 (20.56 g, 40.31 mmol), Sub 2-1 (10 g, 40.31 mmol), $Pd_2(dba)_3$ (1.11 g, 1.21 mmol), Xphos (1.15 g, 2.42 mmol), NaOH (3.22 g, 80.62 mmol) in Toluene (90 mL), EtOH (5 mL), and $H_2O$ (50 mL) in a round bottom flask, the mixture was stirred at 120° C. After the reaction was completed, the produced solid was obtained by filtering, and the filtered solid was dissolved in toluene and silica filter was performed while heating. After concentrating the filtered solution, the resulting compound was recrystallized to obtain 18.27 g (yield: 68%) of product P-62.

9. Synthesis Example of P-69

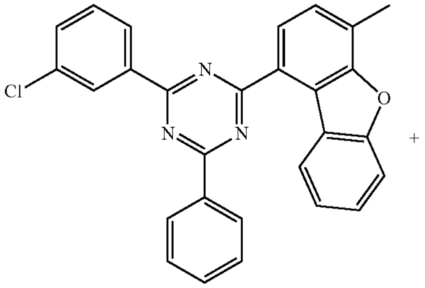

Sub 1-31

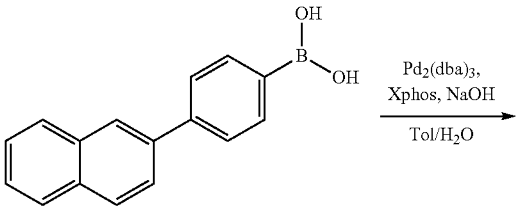

Sub 2-1

-continued

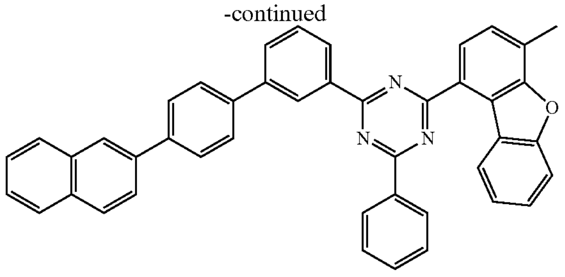

P-69

After dissolving Sub 1-31 (18.05 g, 40.31 mmol), Sub 2-1 (10 g, 40.31 mmol), $Pd_2(dba)_3$ (1.11 g, 1.21 mmol), Xphos (1.15 g, 2.42 mmol), NaOH (3.22 g, 80.62 mmol) in Toluene (90 mL), EtOH (5 mL), and $H_2O$ (50 mL) in a round bottom flask, the mixture was stirred at 120° C. After the reaction was completed, the produced solid was obtained by filtering, and the filtered solid was dissolved in toluene and silica filter was performed while heating. After concentrating the filtered solution, the resulting compound was recrystallized to obtain 17.12 g (yield: 69%) of product P-69.

10. Synthesis Example of P-73

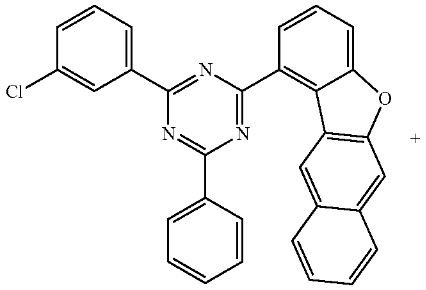

Sub 1-6

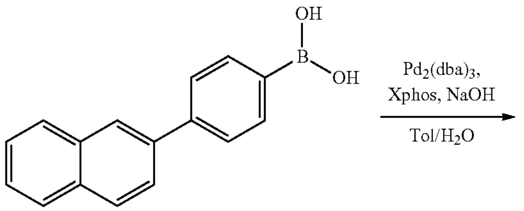

Sub 2-1

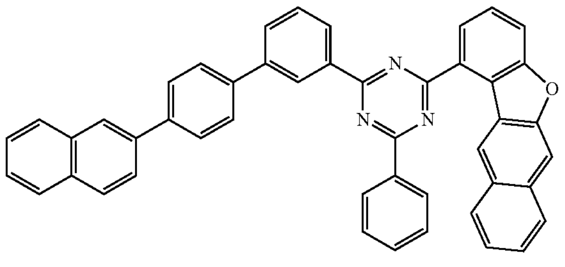

P-73

After dissolving Sub 1-6 (19.51 g, 40.31 mmol), Sub 2-1 (10 g, 40.31 mmol), $Pd_2(dba)_3$ (1.11 g, 1.21 mmol), Xphos (1.15 g, 2.42 mmol), NaOH (3.22 g, 80.62 mmol) in Toluene (90 mL), EtOH (5 mL), and $H_2O$ (50 mL) in a round bottom flask, the mixture was stirred at 120° C. After the reaction was completed, the produced solid was obtained by filtering, and the filtered solid was dissolved in toluene and silica filter was performed while heating. After concentrating the filtered solution, the resulting compound was recrystallized to obtain 18.3 g (yield: 70%) of product P-73.

11. Synthesis Example of P-81

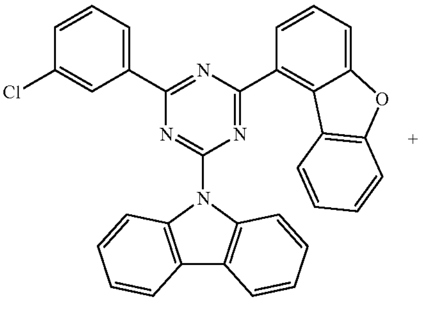

Sub 1-21

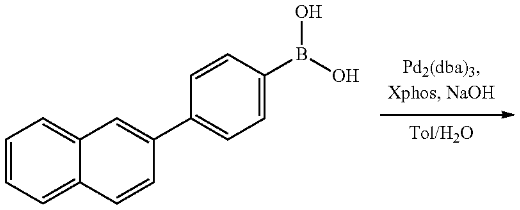

Sub 2-1

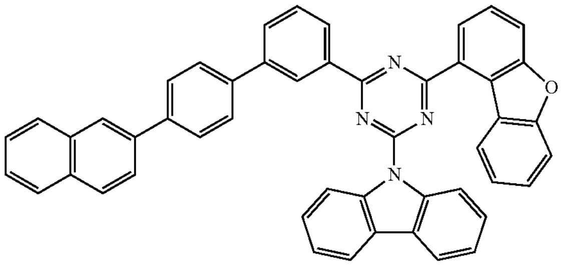

P-81

After dissolving Sub 1-21 (21.08 g, 40.31 mmol), Sub 2-1 (10 g, 40.31 mmol), $Pd_2(dba)_3$ (1.11 g, 1.21 mmol), Xphos (1.15 g, 2.42 mmol), NaOH (3.22 g, 80.62 mmol) in Toluene (90 mL), EtOH (5 mL), and $H_2O$ (50 mL) in a round bottom flask, the mixture was stirred at 120° C. After the reaction was completed, the produced solid was obtained by filtering, and the filtered solid was dissolved in toluene and silica filter was performed while heating. After concentrating the filtered solution, the resulting compound was recrystallized to obtain 17.82 g (yield: 64%) of product P-81.

12. Synthesis Example of P-107

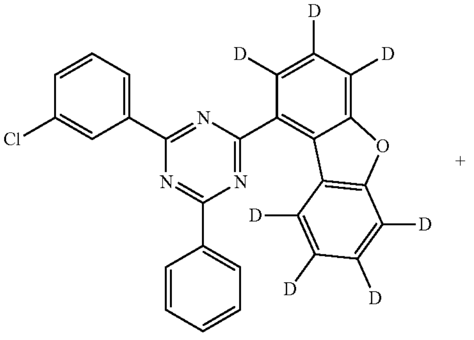

Sub 1-2

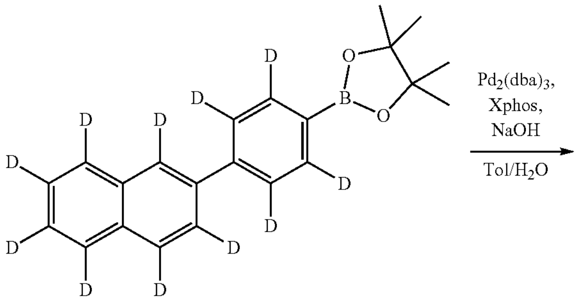

Sub 2-2

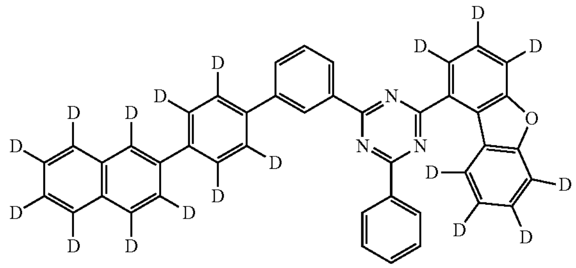

P-107

After dissolving Sub 1-2 (25.84 g, 58.60 mmol), Sub 2-2 (20 g, 58.60 mmol), $Pd_2(dba)_3$ (1.61 g, 1.76 mmol), Xphos (1.68 g, 3.52 mmol), NaOH (4.69 g, 117.20 mmol) in Toluene (130 mL), EtOH (6 mL), and $H_2O$ (60 mL) in a round bottom flask, the mixture was stirred at 120° C. After the reaction was completed, the produced solid was obtained by filtering, and the filtered solid was dissolved in toluene and silica filter was performed while heating. After concentrating the filtered solution, the resulting compound was recrystallized to obtain 21.7 g (yield: 60%) of product P-107.

Otherwise, the FD-MS values of the compounds P-1 to P-107 of the present invention prepared according to the Synthesis Example as described above are shown in Table 3.

TABLE 3

| Compound | FD-MS | Compound | FD-MS |
|---|---|---|---|
| P-1 | m/z = 601.22 ($C_{43}H_{27}N_3O$ = 601.71) | P-2 | m/z = 651.23 ($C_{47}H_{29}N_3O$ = 651.77) |
| P-3 | m/z = 701.25 ($C_{51}H_{31}N_3O$ = 701.83) | P-4 | m/z = 727.26 ($C_{53}H_{33}N_3O$ = 727.87) |
| P-5 | m/z = 606.25 ($C_{43}H_{22}D_5N_3O$ = 606.74) | P-6 | m/z = 651.23 ($C_{47}H_{29}N_3O$ = 651.77) |
| P-7 | m/z = 701.25 ($C_{51}H_{31}N_3O$ = 701.83) | P-8 | m/z = 727.26 ($C_{53}H_{33}N_3O$ = 727.87) |
| P-9 | m/z = 604.23 ($C_{43}H_{24}D_3N_3O$ = 604.73) | P-10 | m/z = 658.27 ($C_{47}H_{22}D_7N_3O$ = 658.81) |
| P-11 | m/z = 701.25 ($C_{51}H_{31}N_3O$ = 701.83) | P-12 | m/z = 727.26 ($C_{53}H_{33}N_3O$ = 727.87) |
| P-13 | m/z = 608.26 ($C_{43}H_{20}D_7N_3O$ = 608.75) | P-14 | m/z = 658.27 ($C_{47}H_{22}D_7N_3O$ = 658.81) |
| P-15 | m/z = 701.25 ($C_{51}H_{31}N_3O$ = 701.83) | P-16 | m/z = 727.26 ($C_{53}H_{33}N_3O$ = 727.87) |
| P-17 | m/z = 608.26 ($C_{43}H_{20}D_7N_3O$ = 608.75) | P-18 | m/z = 655.26 ($C_{47}H_{25}D_4N_3O$ = 655.79) |
| P-19 | m/z = 701.25 ($C_{51}H_{31}N_3O$ = 701.83) | P-20 | m/z = 727.26 ($C_{53}H_{33}N_3O$ = 727.87) |
| P-21 | m/z = 612.28 ($C_{43}H_{16}D_{11}N_3O$ = 612.78) | P-22 | m/z = 658.27 ($C_{47}H_{22}D_7N_3O$ = 658.81) |
| P-23 | m/z = 710.30 ($C_{51}H_{22}D_9N_3O$ = 710.88) | P-24 | m/z = 727.26 ($C_{53}H_{33}N_3O$ = 727.87) |
| P-25 | m/z = 615.30 ($C_{43}H_{13}D_{14}N_3O$ = 615.79) | P-26 | m/z = 658.27 ($C_{47}H_{22}D_7N_3O$ = 658.81) |
| P-27 | m/z = 710.30 ($C_{51}H_{22}D_9N_3O$ = 710.88) | P-28 | m/z = 734.31 ($C_{53}H_{26}D_7N_3O$ = 734.91) |
| P-29 | m/z = 622.35 ($C_{43}H_6D_{21}N_3O$ = 622.84) | P-30 | m/z = 662.30 ($C_{47}H_{18}D_{11}N_3O$ = 662.84) |
| P-31 | m/z = 710.30 ($C_{51}H_{22}D_9N_3O$ = 710.88) | P-32 | m/z = 734.31 ($C_{53}H_{26}D_7N_3O$ = 734.91) |
| P-33 | m/z = 627.38 ($C_{43}HD_{26}N_3O$ = 627.87) | P-34 | m/z = 665.32 ($C_{47}H_{15}D_{14}N_3O$ = 665.85) |
| P-35 | m/z = 707.28 ($C_{51}H_{25}D_6N_3O$ = 707.87) | P-36 | m/z = 734.31 ($C_{53}H_{26}D_7N_3O$ = 734.91) |
| P-37 | m/z = 617.19 ($C_{43}H_{27}NS$ = 617.77) | P-38 | m/z = 667.21 ($C_{47}H_{29}N_3S$ = 667.83) |
| P-39 | m/z = 717.22 ($C_{51}H_{31}N_3S$ = 717.89) | P-40 | m/z = 743.24 ($C_{53}H_{33}N_3S$ = 743.93) |
| P-41 | m/z = 622.22 ($C_{43}H_{22}D_5N_3S$ = 622.80) | P-42 | m/z = 667.21 ($C_{47}H_{29}N_3S$ = 667.83) |
| P-43 | m/z = 717.22 ($C_{51}H_{31}N_3S$ = 717.89) | P-44 | m/z = 743.24 ($C_{53}H_{33}N_3S$ = 743.93) |
| P-45 | m/z = 620.21 ($C_{43}H_{24}D_3N_3S$ = 620.79) | P-46 | m/z = 674.25 ($C_{47}H_{22}D_7N_3S$ = 674.87) |
| P-47 | m/z = 717.22 ($C_{51}H_{31}N_3S$ = 717.89) | P-48 | m/z = 743.24 ($C_{53}H_{33}N_3S$ = 743.93) |
| P-49 | m/z = 624.24 ($C_{43}H_{20}D_7N_3S$ = 624.81) | P-50 | m/z = 674.25 ($C_{47}H_{22}D_7N_3S$ = 674.87) |
| P-51 | m/z = 717.22 ($C_{51}H_{31}N_3S$ = 717.89) | P-52 | m/z = 743.24 ($C_{53}H_{33}N_3S$ = 743.93) |
| P-53 | m/z = 691.23 ($C_{49}H_{29}N_3O_2$ = 691.79) | P-54 | m/z = 707.20 ($C_{49}H_{29}N_3OS$ = 707.85) |
| P-55 | m/z = 733.25 ($C_{51}H_{35}N_3OSi$ = 733.95) | P-56 | m/z = 723.18 ($C_{49}H_{29}N_3S_2$ = 723.91) |
| P-57 | m/z = 677.25 ($C_{49}H_{31}N_3O$ = 677.81) | P-58 | m/z = 677.25 ($C_{49}H_{31}N_3O$ = 677.81) |
| P-59 | m/z = 677.25 ($C_{49}H_{31}N_3O$ = 677.81) | P-60 | m/z = 677.25 ($C_{49}H_{31}N_3O$ = 677.81) |
| P-61 | m/z = 677.25 ($C_{49}H_{31}N_3O$ = 677.81) | P-62 | m/z = 677.25 ($C_{49}H_{31}N_3O$ = 677.81) |
| P-63 | m/z = 693.22 ($C_{49}H_{31}N_3S$ = 693.87) | P-64 | m/z = 693.22 ($C_{49}H_{31}N_3S$ = 693.87) |
| P-65 | m/z = 693.22 ($C_{49}H_{31}N_3S$ = 693.87) | P-66 | m/z = 693.22 ($C_{49}H_{31}N_3S$ = 693.87) |
| P-67 | m/z = 693.22 ($C_{49}H_{31}N_3S$ = 693.87) | P-68 | m/z = 693.22 ($C_{49}H_{31}N_3S$ = 693.87) |
| P-69 | m/z = 615.23 ($C_{44}H_{29}N_3O$ = 615.74) | P-70 | m/z = 615.23 ($C_{44}H_{29}N_3O$ = 615.74) |
| P-71 | m/z = 615.23 ($C_{44}H_{29}N_3O$ = 615.74) | P-72 | m/z = 615.23 ($C_{44}H_{29}N_3O$ = 615.74) |
| P-73 | m/z = 651.23 ($C_{47}H_{29}N_3O$ = 651.77) | P-74 | m/z = 651.23 ($C_{47}H_{29}N_3O$ = 651.77) |
| P-75 | m/z = 651.23 ($C_{47}H_{29}N_3O$ = 651.77) | P-76 | m/z = 651.23 ($C_{47}H_{29}N_3O$ = 651.77) |
| P-77 | m/z = 667.21 ($C_{47}H_{29}N_3S$ = 667.83) | P-78 | m/z = 667.21 ($C_{47}H_{29}N_3S$ = 667.83) |
| P-79 | m/z = 667.21 ($C_{47}H_{29}N_3S$ = 667.83) | P-80 | m/z = 667.21 ($C_{47}H_{29}N_3S$ = 667.83) |

TABLE 3-continued

| Compound | FD-MS | Compound | FD-MS |
|---|---|---|---|
| P-81 | m/z = 690.24 ($C_{49}H_{30}N_4O$ = 690.81) | P-82 | m/z = 740.26 ($C_{53}H_{32}N_4O$ = 740.87) |
| P-83 | m/z = 740.26 ($C_{53}H_{32}N_4O$ = 740.87) | P-84 | m/z = 740.26 ($C_{53}H_{32}N_4O$ = 740.87) |
| P-85 | m/z = 697.59 ($C_{49}H_{20}D_7N_4O$ = 697.85) | P-86 | m/z = 749.31 ($C_{53}H_{23}D_9N_4$) = 749.92) |
| P-87 | m/z = 749.31 ($C_{53}H_{23}D_9N_4O$ = 749.92) | P-88 | m/z = 749.31 ($C_{53}H_{23}D_9N_4O$ = 749.92) |
| P-89 | m/z = 713.26 ($C_{49}H_{23}D_7N_4S$ = 713.91) | P-90 | m/z = 765.29 ($C_{53}H_{23}D_9N_4S$ = 765.98) |
| P-91 | m/z = 765.29 ($C_{53}H_{23}D_9N_4S$ = 765.98) | P-92 | m/z = 765.29 ($C_{53}H_{23}D_9N_4S$ = 765.98) |
| P-93 | m/z = 683.28 ($C_{49}H_{25}D_6N_3O$ = 683.84) | P-94 | m/z = 683.28 ($C_{49}H_{25}D_6N_3O$ = 683.84) |
| P-95 | m/z = 683.28 ($C_{49}H_{25}D_6N_3O$ = 683.84) | P-96 | m/z = 683.28 ($C_{49}H_{25}D_6N_{30}$ = 683.84) |
| P-97 | m/z = 699.26 ($C_{49}H_{25}D_6N_3S$ = 699.90) | P-98 | m/z = 699.26 ($C_{49}H_{25}D_6N_3S$ = 699.90) |
| P-99 | m/z = 699.26 ($C_{49}H_{25}D_6N_3S$ = 699.90) | P-100 | m/z = 699.26 ($C_{49}H_{25}D_6N_3S$ = 699.90) |
| P-101 | m/z = 714.25 ($C_{49}H_{22}D_7N_3OS$ = 714.89) | P-102 | m/z = 714.25 ($C_{49}H_{22}D_7N_3OS$ = 714.89) |
| P-103 | m/z = 698.27 ($C_{49}H_{22}D_7N_3O_2$ = 698.83) | P-104 | m/z = 730.22 ($C_{49}H_{22}D_7N_3S_2$ = 730.95) |
| P-105 | m/z = 733.25 ($C_{51}H_{35}N_3OSi$ = 733.95) | P-106 | m/z = 740.30 ($C_{51}H_{28}D_7N_3OSi$ = 740.99) |
| P-107 | m/z = 619.33 ($C_{43}H_9D_{18}N_3O$ = 619.82) | | |

Synthesis Example 2

1. Synthesis Example of H-12

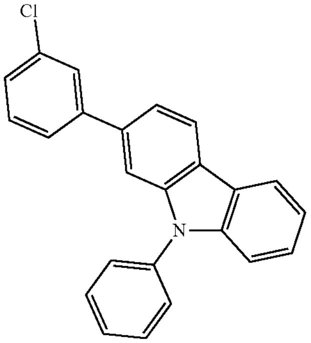
H-12a

+

-continued

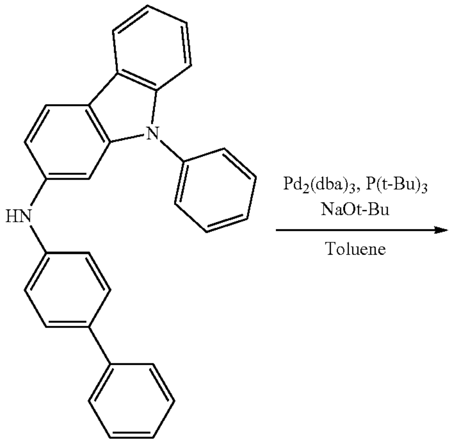

H-12b

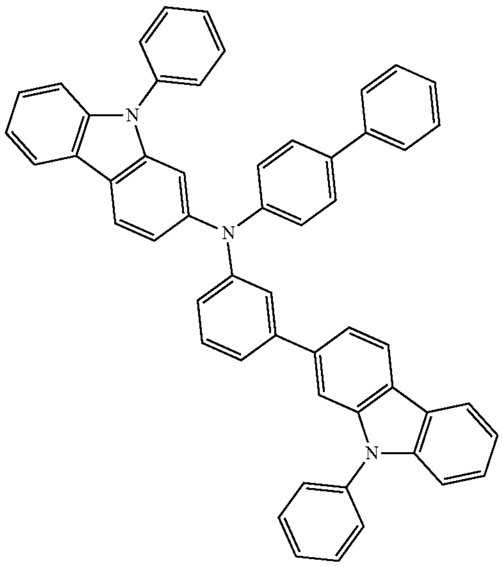
H-12

After dissolving H-12a (30 g, 0.08 mol) in Toluene (170 mL) in a round bottom flask, H-12b (34.8 g, 0.08 mol), $Pd_2(dba)_3$ (2.3 g, 0.003 mol), NaOt-Bu (24.5 g, 0.25 mol) and $P(t\text{-}Bu)_3$ (2.1 g, 0.005 mol) were added and stirred at 135° C. for 6 hours. When the reaction was completed, the reactant was extracted with $CH_2Cl_2$ and water, and the organic layer was dried over MgSO4, concentrated, and the resulting compound was recrystallized using a silicagel column to obtain 53 g of the product. (Yield: 85.8%)

2. Synthesis Example of H-19

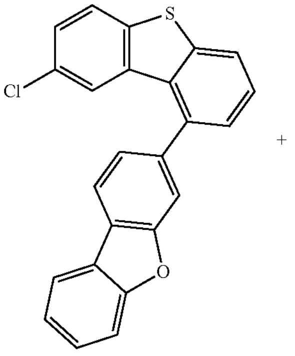

H-19a

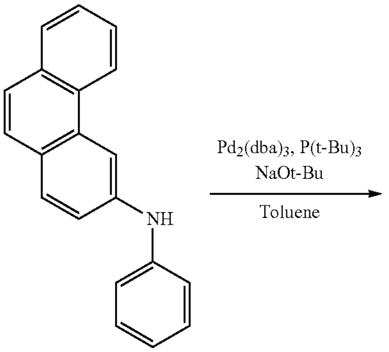

H-19b

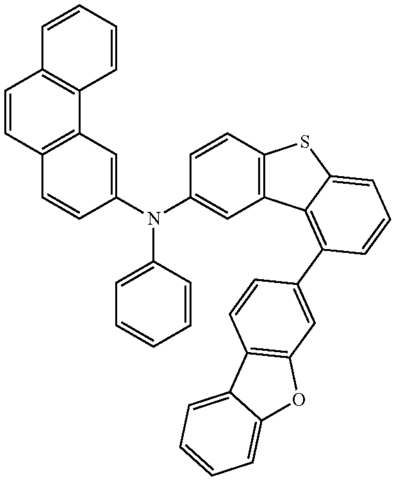

H-19

H-19a (50 g, 0.13 mol), H-19b (35 g, 0.13 mol), $Pd_2(dba)_3$ (3.6 g, 0.004 mol), NaOt-Bu (37.6 g, 0.40 mol), $P(t-Bu)_3$ (3.2 g, 0.008 mol), Toluene (260 mL) were added to a round bottom flask in the same manner as in H-12 to obtain 67 g of product. (Yield: 83.4%)

3. Synthesis Example of S-32

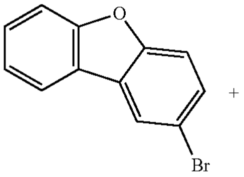

S-32a

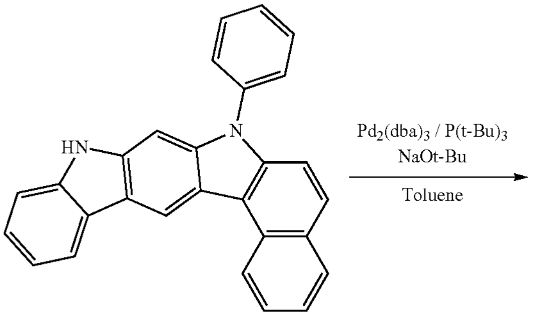

S-32b

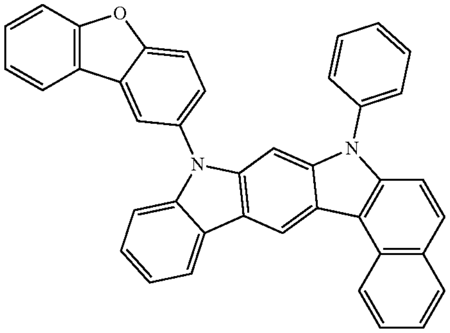

S-32

S-32a (10 g, 0.04 mol), S-32b (15.6 g, 0.04 mol), $Pd_2(dba)_3$ (1.1 g, 0.001 mol), NaOt-Bu (11.7 g, 0.12 mol), $P(t-Bu)_3$ (1.0 g, 0.002 mol), Toluene (80 mL) were added to a round bottom flask in the same manner as in H-12 to obtain 18 g of product. (Yield: 80.8%)

4. Synthesis Example of S-74

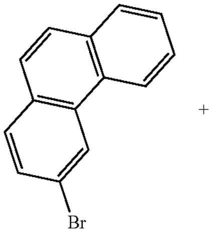

S-74a

-continued

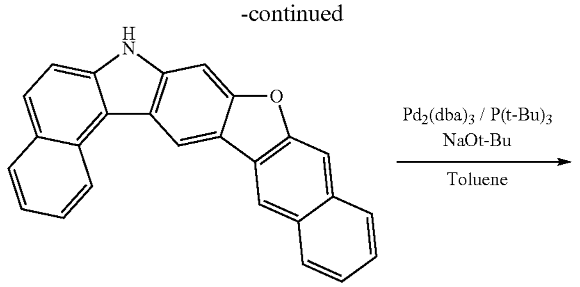

S-74b

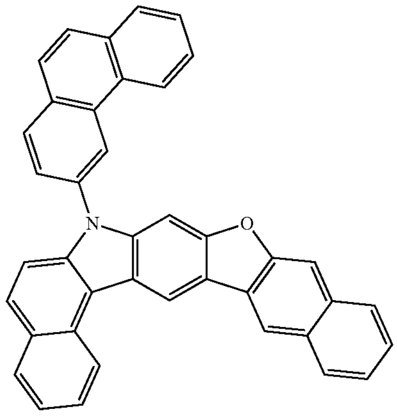

S-74

S-74a (15 g, 0.06 mol), S-74b (20.9 g, 0.06 mol), $Pd_2(dba)_3$ (1.6 g, 0.002 mol), NaOt-Bu (16.9 g, 0.18 mol), $P(t\text{-}Bu)_3$ (1.4 g, 0.004 mol), Toluene (120 mL) were added to a round bottom flask in the same manner as in H-12 to obtain 27 g of product. (Yield: 86.4%)

5. Synthesis Example of S-104

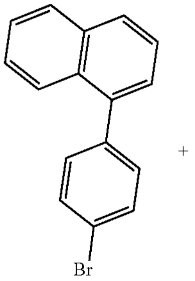

S-104a

-continued

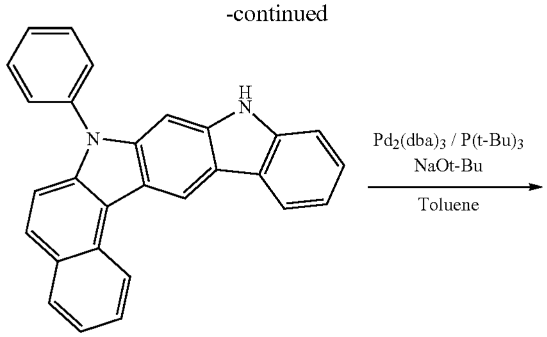

S-104b

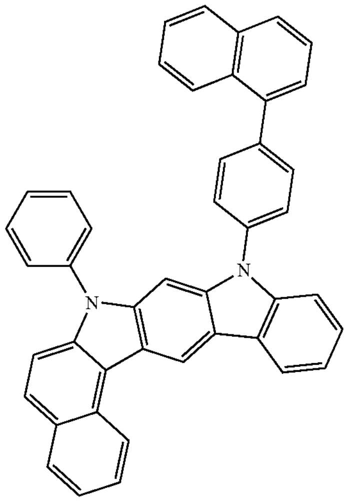

S-104

S-104a (30 g, 0.13 mol), S-104b (48.2.9 g, 0.13 mol), $Pd_2(dba)_3$ (3.5 g, 0.004 mol), NaOt-Bu (36.4 g, 0.38 mol), $P(t\text{-}Bu)_3$ (3.1 g, 0.008 mol), Toluene (250 mL) were added to a round bottom flask in the same manner as in H-12 to obtain 60 g of product. (Yield: 81.5%)

Otherwise, the ED-MS values of the compounds H-1 to H-100 and S-1 to S-108 of the present invention prepared according to the synthesis examples as described above are shown in Tables 4 and 5.

TABLE 4

| Compound | FD-MS | Compound | FD-MS |
|---|---|---|---|
| H-1 | m/z = 487.19($C_{36}H_{25}NO$ = 487.6) | H-2 | m/z = 553.19($C_{40}H_{27}NS$ = 553.72) |
| H-3 | m/z = 563.26($C_{43}H_{33}N$ = 563.74) | H-4 | m/z = 602.27($C_{45}H_{34}N_2$ = 602.78) |
| H-5 | m/z = 517.15($C_{36}H_{23}NOS$ = 517.65) | H-6 | m/z = 603.2($C_{44}H_{29}NS$ = 603.78) |
| H-7 | m/z = 735.29($C_{57}H_{37}N$ = 735.93) | H-8 | m/z = 562.24($C_{42}H_{30}N_2$ = 562.72) |
| H-9 | m/z = 565.17($C_{40}H_{23}NO_3$ = 565.63) | H-10 | m/z = 581.14($C_{40}H_{23}NO_2S$ = 581.69) |
| H-11 | m/z = 823.24($C_{59}H_{37}NS_2$ = 824.07) | H-12 | m/z = 727.3($C_{54}H_{37}N_3$ = 727.91) |
| H-13 | m/z = 627.22($C_{46}H_{29}NO_2$ = 627.74) | H-14 | m/z = 633.16($C_{44}H_{27}NS_2$ = 633.83) |
| H-15 | m/z = 675.29($C_{52}H_{37}N$ = 675.88) | H-16 | m/z = 678.3($C_{51}H_{38}N_2$ = 678.88) |
| H-17 | m/z = 669.21($C_{48}H_{31}NOS$ = 669.84) | H-18 | m/z = 785.22($C_{56}H_{35}NS_2$ = 786.02) |
| H-19 | m/z = 617.18($C_{44}H_{27}NOS$ = 617.77) | H-20 | m/z = 601.2($C_{44}H_{27}NO_2$ = 601.71) |

TABLE 4-continued

| Compound | FD-MS | Compound | FD-MS |
|---|---|---|---|
| H-21 | m/z = 779.32($C_{59}H_{41}NO$ = 779.98) | H-22 | m/z = 583.23($C_{42}H_{33}NS$ = 583.79) |
| H-23 | m/z = 679.32($C_{52}H_{41}N$ = 679.91) | H-24 | m/z = 726.27($C_{54}H_{34}N_2O$ = 726.88) |
| H-25 | m/z = 593.18($C_{42}H_{27}NOS$ = 593.74) | H-26 | m/z = 774.22($C_{54}H_{34}N_2S_2$ = 775) |
| H-27 | m/z = 557.24($C_{40}H_{31}NO_2$ = 557.69) | H-28 | m/z = 652.25($C_{48}H_{32}N_2O$ = 652.8) |
| H-29 | m/z = 619.29($C_{46}H_{37}NO$ = 619.81) | H-30 | m/z = 603.2($C_{44}H_{29}NS$ = 603.78) |
| H-31 | m/z = 813.3($C_{62}H_{39}NO$ = 814) | H-32 | m/z = 784.29($C_{57}H_{40}N_2S$ = 785.02) |
| H-33 | m/z = 577.2($C_{42}H_{27}NO_2$ = 577.68) | H-34 | m/z = 607.14($C_{42}H_{25}NS_2$ = 607.79) |
| H-35 | m/z = 801.34($C_{62}H_{43}N$ = 802.03) | H-36 | m/z = 575.24($C_{42}H_{29}N_3$ = 575.72) |
| H-37 | m/z = 577.2($C_{42}H_{27}NO_2$ = 577.68) | H-38 | m/z = 607.14($C_{42}H_{25}NS_2$ = 607.79) |
| H-39 | m/z = 801.34($C_{62}H_{43}N$ = 802.03) | H-40 | m/z = 575.24($C_{42}H_{29}N_3$ = 575.72) |
| H-41 | m/z = 601.2($C_{44}H_{27}NO_2$ = 601.71) | H-42 | m/z = 471.11($C_{31}H_{21}NS_2$ = 471.64) |
| H-43 | m/z = 675.29($C_{52}H_{37}N$ = 675.88) | H-44 | m/z = 727.3($C_{54}H_{37}N_3$ = 727.91) |
| H-45 | m/z = 603.2($C_{44}H_{29}NS$ = 603.78) | H-46 | m/z = 561.16($C_{38}H_{27}NS_2$ = 561.76) |
| H-47 | m/z = 799.32($C_{62}H_{41}N$ = 800.02) | H-48 | m/z = 702.27($C_{52}H_{34}N_2O$ = 702.86) |
| H-49 | m/z = 729.27($C_{54}H_{35}NO_2$ = 729.88) | H-50 | m/z = 785.22($C_{56}H_{35}NS_2$ = 786.02) |
| H-51 | m/z = 812.32($C_{62}H_{40}N_2$ = 813.02) | H-52 | m/z = 681.22($C_{48}H_{31}N_3S$ = 681.86) |
| H-53 | m/z = 615.18($C_{44}H_{25}NO_3$ = 615.69) | H-54 | m/z = 763.15($C_{52}H_{29}NS_3$ = 763.99) |
| H-55 | m/z = 593.31($C_{45}H_{39}N$ = 593.81) | H-56 | m/z = 840.33($C_{62}H_{40}N_4$ = 841.03) |
| H-57 | m/z = 657.18($C_{46}H_{27}NO_2S$ = 657.79) | H-58 | m/z = 824.23($C_{58}H_{36}N_2S_2$ = 825.06) |
| H-59 | m/z = 1195.42($C_{91}H_{57}NS$ = 1196.52) | H-60 | m/z = 656.19($C_{46}H_{28}N_2OS$ = 656.8) |
| H-61 | m/z = 607.16($C_{42}H_{25}NO_2S$ = 607.73) | H-62 | m/z = 773.2($C_{54}H_{31}NO_3S$ = 773.91) |
| H-63 | m/z = 1013.4($C_{79}H_{51}N$ = 1014.28) | H-64 | m/z = 758.24($C_{54}H_{34}N_2OS$ = 758.94) |
| H-65 | m/z = 623.14($C_{42}H_{25}NOS_2$ = 623.79) | H-66 | m/z = 763.16($C_{52}H_{29}NO_2S_2$ = 763.93) |
| H-67 | m/z = 799.2($C_{56}H_{33}NOS_2$ = 800.01) | H-68 | m/z = 743.23($C_{54}H_{33}NOS$ = 743.92) |
| H-69 | m/z = 872.25($C_{62}H_{36}N_2O_2S$ = 873.04) | H-70 | m/z = 772.22($C_{54}H_{32}N_2O_2S$ = 772.92) |
| H-71 | m/z = 830.28($C_{61}H_{38}N_2S$ = 831.05) | H-72 | m/z = 808.25($C_{58}H_{33}FN_2O_2$ = 808.91) |
| H-73 | m/z = 929.21($C_{64}H_{35}NO_3S_2$ = 930.11) | H-74 | m/z = 963.27($C_{68}H_{41}N_3S_2$ = 964.22) |
| H-75 | m/z = 809.24($C_{58}H_{35}NO_2S$ = 809.98) | H-76 | m/z = 893.29($C_{66}H_{39}NO_3$ = 894.04) |
| H-77 | m/z = 794.28($C_{58}H_{38}N_2S$ = 795.02) | H-78 | m/z = 900.26($C_{64}H_{40}N_2S_2$ = 901.16) |
| H-79 | m/z = 758.28($C_{55}H_{38}N_2S$ = 758.98) | H-80 | m/z = 1082.37($C_{81}H_{50}N_2S$ = 1083.37) |
| H-81 | m/z = 573.25($C_{44}H_{31}N$ = 573.74) | H-82 | m/z = 649.28($C_{50}H_{35}N$ = 649.84) |
| H-83 | m/z = 699.29($C_{54}H_{37}N$ = 699.9) | H-84 | m/z = 699.29($C_{54}H_{37}N$ = 699.9) |
| H-85 | m/z = 673.28($C_{52}H_{35}N$ = 673.86) | H-86 | m/z = 649.28($C_{50}H_{35}N$ = 649.84) |
| H-87 | m/z = 625.28($C_{48}H_{35}N$ = 625.82) | H-88 | m/z = 673.28($C_{52}H_{35}N$ = 673.86) |
| H-89 | m/z = 773.31($C_{60}H_{39}N$ = 773.98) | H-90 | m/z = 749.31($C_{58}H_{39}N$ = 749.96) |
| H-91 | m/z = 699.29($C_{54}H_{37}N$ = 699.9) | H-92 | m/z = 599.26($C_{46}H_{33}N$ = 599.78) |
| H-93 | m/z = 639.26($C_{48}H_{33}NO$ = 639.8) | H-94 | m/z = 765.25($C_{57}H_{35}NS$ = 765.97) |
| H-95 | m/z = 677.31($C_{52}H_{39}N$ = 677.89) | H-96 | m/z = 727.3($C_{54}H_{37}N_3$ = 727.91) |
| H-97 | m/z = 552.18($C_{39}H_{24}N_2O_2$ = 552.63) | H-98 | m/z = 628.22($C_{45}H_{28}N_2O_2$ = 628.73) |
| H-99 | m/z = 614.24($C_{45}H_{30}N_2O$ = 614.75) | H-100 | m/z = 614.24($C_{45}H_{30}N_2O$ = 614.75) |

TABLE 5

| Compound | FD-MS | Compound | FD-MS |
|---|---|---|---|
| S-1 | m/z = 408.16($C_{30}H_{20}N_2$ = 408.5) | S-2 | m/z = 534.21($C_{40}H_{26}N_2$ = 534.66) |
| S-3 | m/z = 560.23($C_{42}H_{28}N_2$ = 560.7) | S-4 | m/z = 584.23($C_{44}H_{28}N_2$ = 584.72) |
| S-5 | m/z = 560.23($C_{42}H_{28}N_2$ = 560.7) | S-6 | m/z = 634.24($C_{48}H_{30}N_2$ = 634.78) |
| S-7 | m/z = 610.24($C_{46}H_{30}N_2$ = 610.76) | S-8 | m/z = 498.17($C_{36}H_{22}N_2O$ = 498.59) |
| S-9 | m/z = 574.2($C_{42}H_{26}N_2O$ = 574.68) | S-10 | m/z = 660.26($C_{50}H_{32}N_2$ = 660.82) |
| S-11 | m/z = 686.27($C_{52}H_{34}N_2$ = 686.86) | S-12 | m/z = 620.14($C_{42}H_{24}N_2S_2$ = 620.79) |
| S-13 | m/z = 640.2($C_{46}H_{28}N_2S$ = 640.8) | S-14 | m/z = 560.23($C_{42}H_{28}N_2$ = 560.7) |
| S-15 | m/z = 558.21($C_{42}H_{26}N_2$ = 558.68) | S-16 | m/z = 548.19($C_{40}H_{24}N_2O$ = 548.65) |
| S-17 | m/z = 573.22($C_{42}H_{27}N_3$ = 573.7) | S-18 | m/z = 564.17($C_{40}H_{24}N_2S$ = 564.71) |
| S-19 | m/z = 574.2($C_{42}H_{26}N_2O$ = 574.68) | S-20 | m/z = 564.17($C_{40}H_{24}N_2S$ = 564.71) |
| S-21 | m/z = 564.17($C_{40}H_{24}N_2S$ = 564.71) | S-22 | m/z = 813.31($C_{61}H_{39}N_3$ = 814) |
| S-23 | m/z = 696.26($C_{53}H_{32}N_2$ = 696.85) | S-24 | m/z = 691.23($C_{49}H_{29}N_3O_2$ = 691.79) |
| S-25 | m/z = 710.27($C_{54}H_{34}N_2$ = 710.88) | S-26 | m/z = 610.24($C_{46}H_{30}N_2$ = 610.76) |
| S-27 | m/z = 670.15($C_{46}H_{26}N_2S_2$ = 670.85) | S-28 | m/z = 640.29($C_{48}H_{36}N_2$ = 640.83) |
| S-29 | m/z = 598.2($C_{44}H_{26}N_2O$ = 598.71) | S-30 | m/z = 623.24($C_{46}H_{29}N_3$ = 623.76) |
| S-31 | m/z = 458.18($C_{34}H_{22}N_2$ = 458.56) | S-32 | m/z = 548.19($C_{40}H_{24}N_2O$ = 548.65) |
| S-33 | m/z = 508.19($C_{38}H_{24}N_2$ = 508.62) | S-34 | m/z = 508.19($C_{38}H_{24}N_2$ = 508.62) |
| S-35 | m/z = 623.24($C_{46}H_{29}N_3$ = 623.76) | S-36 | m/z = 564.17($C_{40}H_{24}N_2S$ = 564.71) |
| S-37 | m/z = 627.2($C_{46}H_{29}NS$ = 627.81) | S-38 | m/z = 505.1($C_{34}H_{19}NS_2$ = 505.65) |
| S-39 | m/z = 514.15($C_{36}H_{22}N_2S$ = 514.65) | S-40 | m/z = 575.17($C_{42}H_{25}NS$ = 575.73) |
| S-41 | m/z = 642.21($C_{46}H_{30}N_2S$ = 642.82) | S-42 | m/z = 575.17($C_{42}H_{25}NS$ = 575.73) |
| S-43 | m/z = 606.18($C_{42}H_{26}N_2OS$ = 606.74) | S-44 | m/z = 575.17($C_{42}H_{25}NS$ = 575.73) |
| S-45 | m/z = 551.17($C_{40}H_{25}NS$ = 551.71) | S-46 | m/z = 607.14($C_{42}H_{25}NS_2$ = 607.79) |
| S-47 | m/z = 525.16($C_{38}H_{23}NS$ = 525.67) | S-48 | m/z = 642.21($C_{46}H_{30}N_2S$ = 642.82) |
| S-49 | m/z = 548.19($C_{40}H_{24}N_2O$ = 548.65) | S-50 | m/z = 473.14($C_{34}H_{19}NO_2$ = 473.53) |
| S-51 | m/z = 566.15($C_{39}H_{22}N_2OS$ = 566.68) | S-52 | m/z = 459.16($C_{34}H_{21}NO$ = 459.55) |

TABLE 5-continued

| Compound | FD-MS | Compound | FD-MS |
|---|---|---|---|
| S-53 | m/z = 473.14($C_{34}H_{19}NO_2$ = 473.53) | S-54 | m/z = 523.16($C_{38}H_{21}NO_2$ = 523.59) |
| S-55 | m/z = 539.13($C_{38}H_{21}NOS$ = 539.65) | S-56 | m/z = 548.19($C_{40}H_{24}N_2O$ = 548.65) |
| S-57 | m/z = 489.12($C_{34}H_{19}NOS$ = 489.59) | S-58 | m/z = 545.09($C_{36}H_{19}NOS_2$ = 545.67) |
| S-59 | m/z = 549.17($C_{40}H_{23}NO_2$ = 549.63) | S-60 | m/z = 565.15($C_{40}H_{23}NOS$ = 565.69) |
| S-61 | m/z = 523.16($C_{38}H_{21}NO_2$ = 523.59) | S-62 | m/z = 598.2($C_{44}H_{26}N_2O$ = 598.71) |
| S-63 | m/z = 539.13($C_{38}H_{21}NOS$ = 539.65) | S-64 | m/z = 589.15($C_{42}H_{23}NOS$ = 589.71) |
| S-65 | m/z = 498.17($C_{36}H_{22}N_2O$ = 498.59) | S-66 | m/z = 509.18($C_{38}H_{23}NO$ = 509.61) |
| S-67 | m/z = 548.19($C_{40}H_{24}N_2O$ = 548.65) | S-68 | m/z = 549.17($C_{40}H_{23}NO_2$ = 549.63) |
| S-69 | m/z = 449.12($C_{32}H_{19}NS$ = 449.57) | S-70 | m/z = 439.1($C_{30}H_{17}NOS$ = 439.53) |
| S-71 | m/z = 647.22($C_{49}H_{29}NO$ = 647.78) | S-72 | m/z = 717.28($C_{52}H_{35}N_3O$ = 717.87) |
| S-73 | m/z = 459.16($C_{34}H_{21}NO$ = 459.55) | S-74 | m/z = 533.18($C_{40}H_{23}NO$ = 533.63) |
| S-75 | m/z = 525.16($C_{38}H_{23}NS$ = 525.67) | S-76 | m/z = 564.17($C_{40}H_{24}N_2S$ = 564.71) |
| S-77 | m/z = 575.19($C_{42}H_{25}NO_2$ = 575.67) | S-78 | m/z = 663.22($C_{49}H_{29}NO_2$ = 663.78) |
| S-79 | m/z = 647.22($C_{49}H_{29}NO$ = 647.78) | S-80 | m/z = 496.16($C_{36}H_{20}N_2O$ = 496.57) |
| S-81 | m/z = 565.15($C_{40}H_{23}NOS$ = 565.69) | S-82 | m/z = 505.1($C_{34}H_{19}NS_2$ = 505.65) |
| S-83 | m/z = 765.25($C_{56}H_{35}NOSi$ = 765.99) | S-84 | m/z = 615.17($C_{44}H_{25}NOS$ = 615.75) |
| S-85 | m/z = 603.17($C_{43}H_{25}NOS$ = 603.74) | S-86 | m/z = 772.29($C_{59}H_{36}N_2$ = 772.95) |
| S-87 | m/z = 802.33($C_{61}H_{42}N_2$ = 803.02) | S-88 | m/z = 607.23($C_{47}H_{29}N$ = 607.76) |
| S-89 | m/z = 524.23($C_{39}H_{28}N_2$ = 524.67) | S-90 | m/z = 665.22($C_{49}H_{31}NS$ = 665.85) |
| S-91 | m/z = 633.25($C_{49}H_{31}N$ = 633.79) | S-92 | m/z = 775.29($C_{59}H_{37}NO$ = 775.95) |
| S-93 | m/z = 535.23($C_{41}H_{29}N$ = 535.69) | S-94 | m/z = 623.22($C_{47}H_{29}NO$ = 623.76) |
| S-95 | m/z = 687.2($C_{51}H_{29}NS$ = 687.86) | S-96 | m/z = 735.29($C_{57}H_{37}N$ = 735.93) |
| S-97 | m/z = 611.26($C_{47}H_{33}N$ = 611.79) | S-98 | m/z = 679.23($C_{50}H_{33}NS$ = 679.88) |
| S-99 | m/z = 787.32($C_{61}H_{41}N$ = 788.01) | S-100 | m/z = 743.33($C_{55}H_{41}N_3$ = 743.95) |
| S-101 | m/z = 485.21($C_{37}H_{27}N$ = 485.63) | S-102 | m/z = 471.2($C_{36}H_{25}N$ = 471.6) |
| S-103 | m/z = 571.19($C_{43}H_{25}NO$ = 571.68) | S-104 | m/z = 584.23($C_{44}H_{28}N_2$ = 584.72) |
| S-105 | m/z = 539.24($C_{40}H_{21}D_5N_2$ = 539.69) | S-106 | m/z = 453.15($C_{32}H_{15}NS$ = 471.6) |
| S-107 | m/z = 563.26($C_{43}H_{26}D_4NO$ = 563.74) | S-108 | m/z = 589.26($C_{44}H_{23}D_5N_2$ = 584.72) |

Otherwise, the synthesis examples of the present invention represented by the Formula 1, Formula 4 and Formula 5 have been described, but these are all based on the Buchwald-Hartwig cross coupling reaction, Miyaura boration reaction, Suzuki cross-coupling reaction, Intramolecular acid-induced cyclization reaction (*J. mater. Chem.* 1999, 9, 2095), Pd(II)-catalyzed oxidative cyclization reaction (*Org. Lett.* 2011, 13, 5504), and $PPh_3$-mediated reductive cyclization reaction (*J. Org. Chem.* 2005, 70, 5014), and those skilled in the art will easily understand that the reaction proceeds even when other substituents defined in Formula 1, Formula 4 and Formula 5 are bonded in addition to the substituents specified in the specific synthesis examples.

Manufacturing Evaluation of Organic Electronic Elements

[Example 1] Red Organic Light Emitting Device (Phosphorescent Host)

After vacuum depositing $N^1$-(naphthalen-2-yl)-$N^4$,$N^4$-bis(4-(naphthalen-2-yl(phenyl)amino)phenyl)-$N^1$-phenylbenzene-1,4-diamine (hereinafter abbreviated as 2-TNATA) on the ITO layer (anode) formed on the glass substrate to form a hole injection layer with a thickness of 60 nm, a hole transport layer was formed by vacuum depositing N,N'-bis(1-naphthalenyl)-N,N'-bis-phenyl-(1,1'-biphenyl)-4,4'-diamine (hereinafter abbreviated as NPB) to a thickness of 60 nm on the hole injection layer. Subsequently, tris(4-(9H-carbazol-9-yl)phenyl)amine (hereinafter abbreviated as TCTA) was vacuum-deposited to a thickness of 10 nm on the hole transport layer to form an emitting-auxiliary layer. Then, the host of the emitting layer uses P-1, the compound of the present invention as a first host, H-17, the compound of the present invention as a second host, but a mixture obtained by mixing the first host and the second host in a weight ratio of 5:5 is used, and bis-(1-phenylisoquinolyl) iridium(III) acetylacetonate (hereinafter abbreviated as $(piq)_2$ Ir(acac)) was used as a dopant, but the dopant was doped so that the weight ratio of the host and the dopant was 95:5 to form an emitting layer having a thickness of 30 nm.

Next, (1,1'-biphenyl-4-olato)bis(2-methyl-8-quinolinolato)aluminum (hereinafter abbreviated as BAlq) was vacuum deposited on the emitting layer to form a hole blocking layer having a thickness of 10 nm, Tris(8-hydroxyquinolinato)aluminium (hereinafter abbreviated as $ALq_3$) was vacuum deposited on the hole blocking layer to a thickness of 35 nm to form an electron transport layer. Thereafter, 8-quinolinolato lithium (hereinafter abbreviated as Liq) was deposited on the electron transport layer to form an electron injection layer having a thickness of 0.2 nm, and then Al was deposited to form a cathode having a thickness of 150 nm.

[Example 2] to [Example 40]

An organic light emitting device was manufactured in the same manner as in Example 1, except that the compound of the present invention described in Table 6 was used as the host material of the emitting layer.

[Comparative Example 1] and [Comparative Example 2]

An organic light emitting device was manufactured in the same manner as in Example 1, except that Comparative Compound A or Comparative Compound B was used as the first host as the host material of the emitting layer.

[Comparative Compound A]

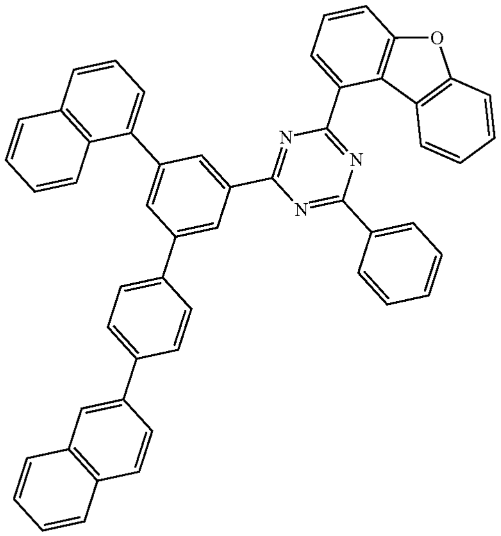

-continued

[Comparative Compound B]

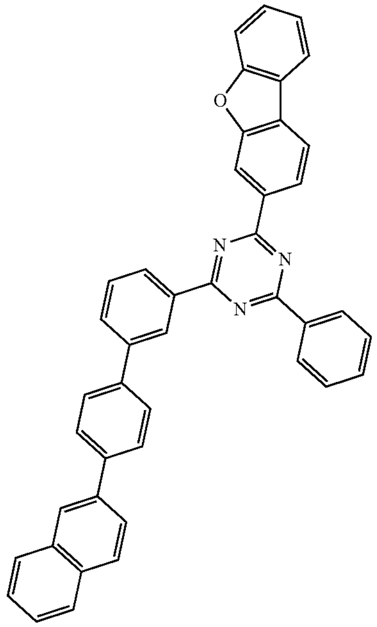

To the organic electroluminescent device manufactured by Examples 1 to 40, Comparative Example 1 and Comparative Example 2 of the present invention, Electroluminescence (EL) characteristics were measured with a PR-650 of Photoresearch Co., by applying a forward bias DC voltage. As a result of the measurement, T95 life was measured at a standard luminance of 2,500 cd/$m^2$ through life measuring apparatus manufactured by McScience. Table 6 shows the results of device fabrication and evaluation.

This measuring apparatus is unaffected by possible daily fluctuations in deposition rate, vacuum quality or other parameters, and can evaluate the performance of a new material compared to a comparative compound under the same conditions.

In the evaluation, since one batch contains 4 identically prepared OLEDs including the comparative compound, and the performance of a total of 12 OLEDs is evaluated in 3 batches, the experimental results obtained in this way show statistical significance.

TABLE 6

| | Frist host | Second host | Voltage | Current Density (mA/$cm^2$) | Brightness (cd/$m^2$) | Efficiency (cd/A) | T (95) |
|---|---|---|---|---|---|---|---|
| Comparative Example 1 | Comparative Compound A | H-17 | 5.5 | 10.2 | 2500.0 | 24.5 | 101.9 |
| Comparative example 2 | Comparative Compound B | H-17 | 5.7 | 11.2 | 2500.0 | 22.4 | 99.7 |
| Example 1 | P-1 | H-17 | 4.8 | 7.7 | 2500.0 | 32.3 | 121.3 |
| Example 2 | P-5 | H-17 | 4.8 | 7.7 | 2500.0 | 32.4 | 122.3 |
| Example 3 | P-8 | H-17 | 4.9 | 7.9 | 2500.0 | 31.6 | 120.6 |
| Example 4 | P-13 | H-17 | 4.8 | 7.5 | 2500.0 | 33.4 | 130.7 |
| Example 5 | P-15 | H-17 | 4.9 | 8.0 | 2500.0 | 31.2 | 120.5 |
| Example 6 | P-21 | H-17 | 4.8 | 7.7 | 2500.0 | 32.5 | 122.9 |
| Example 7 | P-23 | H-17 | 4.9 | 7.8 | 2500.0 | 32.1 | 122.7 |
| Example 8 | P-33 | H-17 | 4.9 | 7.6 | 2500.0 | 33.0 | 131.1 |
| Example 9 | P-37 | H-17 | 5.0 | 8.2 | 2500.0 | 30.6 | 121.0 |
| Example 10 | P-49 | H-17 | 5.0 | 7.9 | 2500.0 | 31.6 | 129.9 |
| Example 11 | P-53 | H-17 | 4.9 | 8.0 | 2500.0 | 31.4 | 122.4 |
| Example 12 | P-64 | H-17 | 5.0 | 8.1 | 2500.0 | 30.9 | 122.2 |
| Example 13 | P-74 | H-17 | 5.0 | 7.8 | 2500.0 | 31.9 | 121.8 |
| Example 14 | P-87 | H-17 | 5.1 | 8.1 | 2500.0 | 30.8 | 126.9 |

TABLE 6-continued

| | Frist host | Second host | Voltage | Current Density (mA/cm$^2$) | Brightness (cd/m$^2$) | Efficiency (cd/A) | T (95) |
|---|---|---|---|---|---|---|---|
| Example 15 | P-107 | H-17 | 5.0 | 7.8 | 2500.0 | 32.1 | 130.9 |
| Example 16 | P-1 | H-84 | 4.9 | 7.9 | 2500.0 | 31.7 | 120.7 |
| Example 17 | P-13 | H-84 | 4.9 | 7.6 | 2500.0 | 32.9 | 129.5 |
| Example 18 | P-37 | H-84 | 5.1 | 7.7 | 2500.0 | 32.5 | 120.9 |
| Example 19 | P-49 | H-84 | 5.1 | 8.1 | 2500.0 | 30.9 | 129.0 |
| Example 20 | P-53 | H-84 | 5.0 | 8.1 | 2500.0 | 31.0 | 121.9 |
| Example 21 | P-107 | H-84 | 5.1 | 7.9 | 2500.0 | 31.8 | 130.0 |
| Example 22 | P-1 | H-98 | 4.8 | 7.8 | 2500.0 | 32.0 | 122.1 |
| Example 23 | P-13 | H-98 | 4.8 | 7.6 | 2500.0 | 33.1 | 130.8 |
| Example 24 | P-37 | H-98 | 5.0 | 7.6 | 2500.0 | 32.9 | 121.3 |
| Example 25 | P-49 | H-98 | 5.1 | 8.0 | 2500.0 | 31.4 | 130.4 |
| Example 26 | P-53 | H-98 | 5.1 | 7.9 | 2500.0 | 31.5 | 122.6 |
| Example 27 | P-107 | H-98 | 4.9 | 7.8 | 2500.0 | 32.1 | 131.2 |
| Example 28 | P-1 | S-16 | 5.0 | 7.8 | 2500.0 | 31.9 | 123.3 |
| Example 29 | P-13 | S-16 | 5.0 | 7.7 | 2500.0 | 32.3 | 136.9 |
| Example 30 | P-37 | S-16 | 5.2 | 7.8 | 2500.0 | 32.0 | 123.5 |
| Example 31 | P-49 | S-16 | 5.1 | 7.7 | 2500.0 | 32.3 | 135.4 |
| Example 32 | P-53 | S-16 | 5.2 | 8.1 | 2500.0 | 30.9 | 124.0 |
| Example 33 | P-107 | S-16 | 5.0 | 7.9 | 2500.0 | 31.6 | 137.1 |
| Example 34 | P-1 | S-108 | 5.0 | 7.9 | 2500.0 | 31.5 | 124.9 |
| Example 35 | P-13 | S-108 | 5.0 | 7.8 | 2500.0 | 32.0 | 137.7 |
| Example 36 | P-33 | S-108 | 5.0 | 7.8 | 2500.0 | 31.9 | 137.2 |
| Example 37 | P-37 | S-108 | 5.1 | 8.3 | 2500.0 | 30.1 | 124.1 |
| Example 38 | P-53 | S-108 | 5.2 | 8.2 | 2500.0 | 30.4 | 124.9 |
| Example 39 | P-64 | S-108 | 5.3 | 8.1 | 2500.0 | 30.9 | 124.5 |
| Example 40 | P-107 | S-108 | 5.1 | 8.0 | 2500.0 | 31.3 | 137.5 |

As can be seen from the results of Table 6, when a red organic light emitting device was manufactured by using the material for an organic light emitting device of the present invention as a host material of the emitting layer, the driving voltage, luminous efficiency and lifespan of the organic light emitting device can be improved compared to Comparative Example using Comparative Compound A or Comparative Compound B having a similar basic skeleton to the compound of the present invention.

Comparative Compound A and Comparative Compound B are similar to the compounds of the present invention in that triazines are substituted with dibenzofuran or dibenzothiophene and groups containing the skeleton of 'phenyl-phenyl-naphthyl', but in the case of Comparative Compound A, an aryl group is further substituted on the 'phenyl-phenyl-naphthyl' skeleton, and in the case of Comparative Compound B, the substitution position of dibenzofuran or dibenzothiophene is different from that of the compound of the present invention.

Comparing the compound P-1 of the present invention and Comparative compound A in terms of structure, Comparative Compound A has a lower packing density than the compound of the present invention during device deposition as additional aryl groups are substituted on the 'phenyl-phenyl-naphthyl' skeleton, therefore when manufacturing a device, the distance between compounds becomes longer, so the mobility of holes and electrons is relatively lowered. As a result, energy transfer from the host to the dopant is not easily performed, which seems to affect device performance.

Next, although the types of substituents are similar, in order to confirm the energy level of the compound according to the substitution position of the substituent, the electronic energy of Comparative Compound B and Compound P-1 of the present invention having a high similarity thereto was measured using the DFT method (B3LYP/6-31 g(D)) of a Gaussian program, and the measurement data are shown in Table 7.

TABLE 7

| | P-1 | Comparative compound B |
|---|---|---|
| T1 (eV) | 2.5844 | 2.5851 |
| S1 (eV) | 3.0990 | 3.2156 |
| ΔST(eV) | 0.5146 | 0.6305 |

As can be seen from the results of Table 7, although the elements constituting the substituents are similar, it can be confirmed that the physical properties of the molecule change remarkably depending on the position in which the constituents are substituted.

More specifically, since the compound P-1 of the present invention has a smaller ΔST (eV) value than the comparative compound B, Compound P-1 of the present invention is more easily transferred from the host to the dopant than the comparative compound B, so that the luminous efficiency of the device is increased, and it was confirmed that the lifespan also significantly increased by well transitioning the unstable excited state energy.

Figure 5:
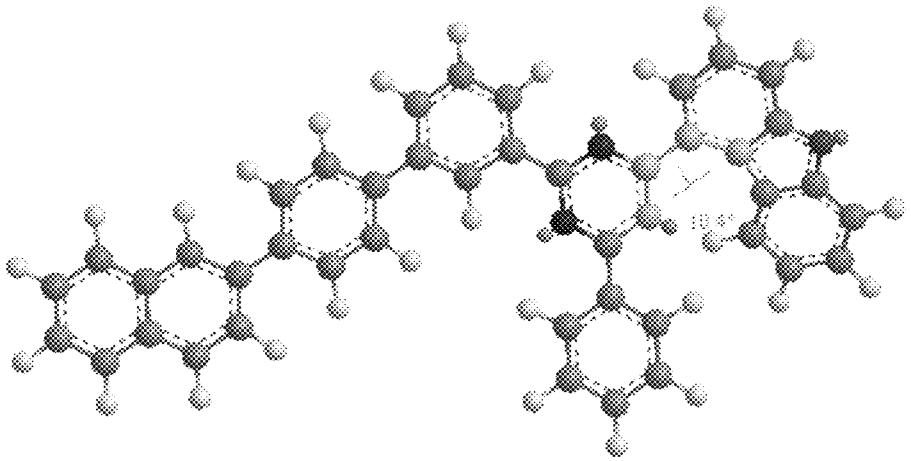
FIG. 5 is a measuring result of the dihedral angle of the compound P-1 of the present invention.
Figure 6:
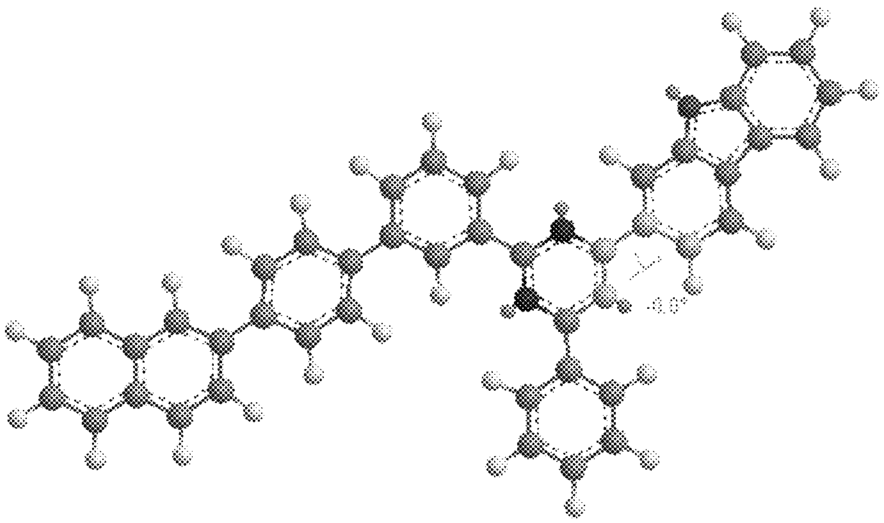
FIG. 6 is a measuring result of the dihedral angle of Comparative Compound B.

Additionally, to confirm the change in Dihedral angle according to the substitution position of the substituent, Dihedral angle of Comparative Compound B and Compound P-1 of the present invention having high similarity thereto was measured through MM2 Minimize energy calculation of Perkinelmer's Chem3D program, the measurement data are shown in FIGS. 5 and 6.

As can be seen from FIGS. 5 and 6, Dihedral angle values between triazine and dibenzofuran in Compound P-1 of the present invention and Comparative Compound B are 10.4° and 0°, respectively. More specifically, Comparative Compound B, which has a very high planar structure, is a compound with a crystalline structure and has a Tc, that is, a crystallization temperature, causing problems such as clogging of the mask and material accumulation during the device deposition process. On the contrary, the compound P-1 of the present invention has an amorphous structure and does not cause the above-mentioned problems, so device fabrication is smooth, and this difference affects device performance.

Among the examples of the present invention, in the case of a structure in which deuterium is substituted at the $R^4$ and $R^5$ positions of Formula 1, it can be confirmed that the lifespan is significantly increased compared to the structure in which deuterium is substituted at other $R^1$ to $R^3$. In this way, the reason why the lifespan of the device is maximized is that as the part with relatively weak carbon-hydrogen bond dissociation energy is replaced by deuterium, molecular hardcore volume is reduced, as a result, the electrical polarizability is reduced and the stability of the structure itself is greatly increased.

Figure 7:
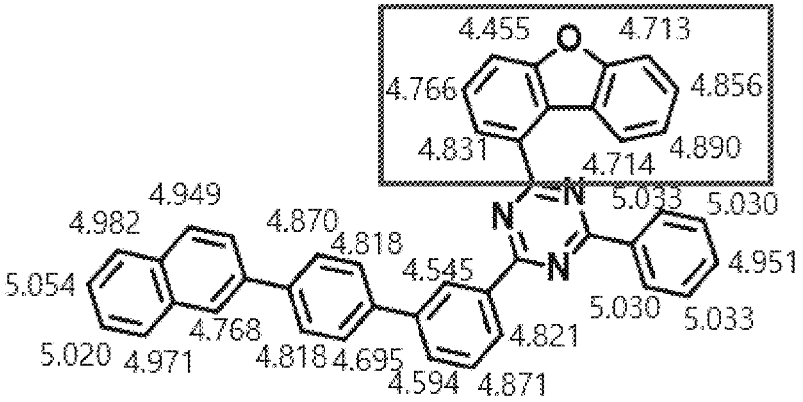
FIG. 7 is a measuring result of Bond-Dissociation energy E of the compound P-1 of the present invention in Anion state.

To interpret the above results, the bond dissociation energy E (hereinafter referred to as BDE, unit: eV) of the compound P-1 of the present invention in the anion state was measured using molecular simulation (Schrodinger Materials Science Suite 4.9.128), and the result is shown in FIG. 7.

As can be seen through FIG. 7, since the BDE value of the triazine-substituted dibenzofuran moiety is relatively smaller than the BDE value of other parts, when deuterium is substituted in the dibenzofuran moiety, as described above, the stability of the structure itself is maximized compared to when deuterium is substituted at other positions.

That is, as can be seen from the results of Tables 6, 7, and FIGS. 5 to 7, even if the compound has a similar composition, it can be seen that the compound of the present invention, which satisfies all complex factors such as the type of specific substituent and the specific substitution position of the substituent, exhibits a remarkable effect compared to other comparative compounds in organic electronic elements. Through this, it can be seen that the compound of the present invention exhibits a remarkable effect in organic electronic elements compared to other compounds having similar structures not described herein.

In other words, these results suggests that even for compounds with similar molecular components, the properties of compounds such as hole properties, light efficiency properties, energy level, hole injection and mobility properties of molecules, charge balance between holes and electrons, volume density and distance between molecules, etc. can vary significantly to the extent that it is difficult to predict, depending on the type and position of the substituent to be substituted, and also the performance of the device may vary due to complex factors, rather than one configuration affecting the overall result of the device.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

What is claimed is:

1. An organic electronic element comprising:

a first electrode, a second electrode, and an organic material layer formed between the first electrode and the second electrode, wherein the organic material layer comprises an emitting layer, wherein the emitting layer is a phosphorescent emitting layer and comprises a first host compound represented by Formula 1 and a second host compound represented by Formula 4 or Formula 5:

Formula 1

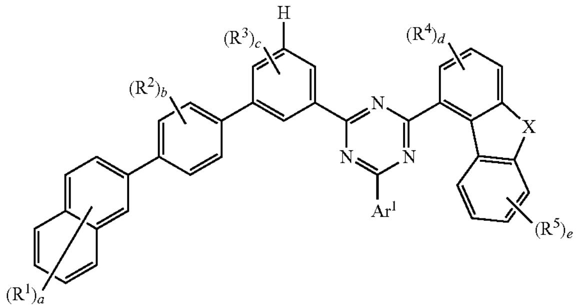

Formula 4

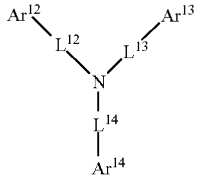

Formula 5

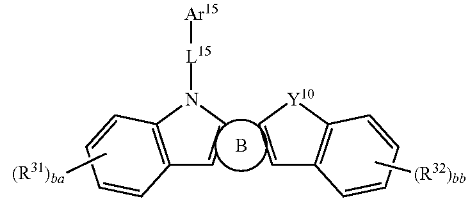

wherein:

$R^1$, $R^2$ and $R^3$ are the same or different from each other, and each independently hydrogen or deuterium, $R^4$ and $R^5$ are each the same or different, and each independently selected from the group consisting of hydrogen; deuterium; a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring; a $C_3$-$C_{60}$ aliphatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; and a $C_6$-$C_{30}$ aryloxy group; or an adjacent plurality of $R^4$ or plurality of $R^5$ may be bonded to each other to form a ring, X is O or S, $Ar^1$ is each independently selected from the group consisting of a $C_6$-$C_{60}$ aryl group; a fluorenyl group; a $C_2$-$C_{60}$ heterocyclic group including at least one hetero atom of O, N, S, Si or P; and a fused ring group of a $C_3$-$C_{60}$ aliphatic ring and a $C_6$-$C_{60}$ aromatic ring, a is an integer from 0 to 7, b and e are each independently an integer from 0 to 4, c and d are each independently an integer from 0 to 3, Ring B is an $C_6$-$C_{20}$ aryl group, $Y^{10}$ is O, S, $CR^{51}R^{52}$ or $NR^{53}$, $Ar^{12}$, $Ar^{13}$ and $Ar^{14}$ are each independently selected from the group consisting of an $C_6$-$C_{60}$ aryl group; a fluorenyl group; a $C_2$-$C_{60}$ heterocyclic group including at least one heteroatom of O, N, S, Si or P; and a fused ring group of a $C_3$-$C_{60}$ aliphatic ring and a $C_6$-$C_{60}$ aromatic ring, $Ar^{15}$ is each independently selected from the group consisting of an $C_6$-$C_{60}$ aryl group; a fluorenyl group; a $C_2$-$C_{60}$ heterocyclic group including at least one heteroatom of O, N, S, Si or P; and a fused ring group of a $C_3$-$C_{60}$ aliphatic ring and a $C_6$-$C_{60}$ aromatic ring; and -L"-$NR^fR^g$, $L^{12}$, $L^{13}$, $L^{14}$, $L^{15}$ and L" are each independently selected from the group consisting of single bond; a $C_6$-$C_{60}$ arylene group; a fluorenylene group; a fused ring group of a $C_3$-$C_{60}$ aliphatic ring and a $C_6$-$C_{60}$ aromatic ring; a $C_2$-$C_{60}$ heterocyclic group including at least one heteroatom of O, N, S, Si or P, $R^{31}$ and $R^{32}$ are each the same or different, and each independently selected from the group consisting of hydrogen; deuterium; halogen; cyano group; nitro group; a $C_6$-$C_{60}$ aryl group; fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; or an adjacent plurality of $R^{31}$ or a plurality of $R^{32}$ may be bonded to each other to form a ring, $R^{51}$, $R^{52}$ and $R^{53}$ are each independently selected from the group consisting of a $C_6$-$C_{60}$ aryl group; fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{60}$ alkyl group; a $C_2$-$C_{60}$ alkenyl group; a $C_2$-$C_{60}$ alkynyl group; a $C_1$-$C_{60}$ alkoxy group; and a $C_6$-$C_{60}$ aryloxy group; or $R^{51}$ and $R^{52}$ may be bonded to each other to form a ring, $R^f$ and $R^g$ are each independently selected from the group consisting of a $C_6$-$C_{60}$ aryl group; fluorenyl group; a $C_2$-$C_{60}$ heterocyclic group including at least one heteroatom of O, N, S, Si or P; and a $C_3$-$C_{60}$ aliphatic ring, ba and bb are each independently an integer from 0 to 4, wherein the aryl group, arylene group, heterocyclic group, fluorenyl group, fluorenylene group, aliphatic ring group, fused ring group, alkyl group, alkenyl group, alkynyl group, alkoxyl group and aryloxy group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxy group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$~$C_{20}$ heterocyclic group; $C_3$-$C_{20}$ cycloalkyl group; $C_7$-$C_{20}$ arylalkyl group; and $C_8$-$C_{20}$ arylalkenyl group; also the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

2. The organic electronic element of claim 1, wherein $Ar^1$ is represented by any one of Formulas (Ar-1) to (Ar-12):

Formula (Ar-1)

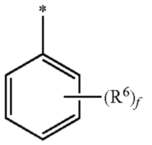

-continued

Formula (Ar-2)

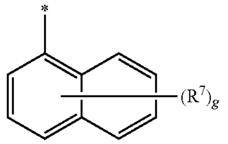

Formula (Ar-3)

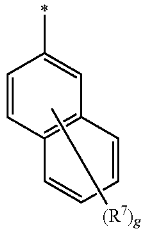

Formula (Ar-4)

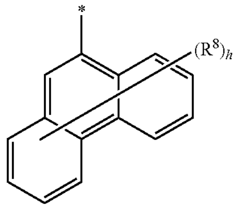

Formula (Ar-5)

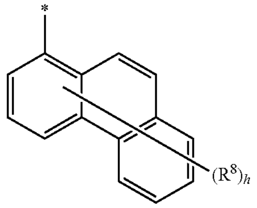

Formula (Ar-6)

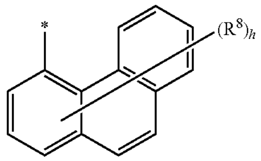

Formula (Ar-7)

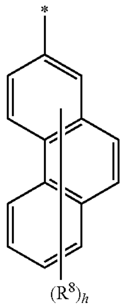

Formula (Ar-8)

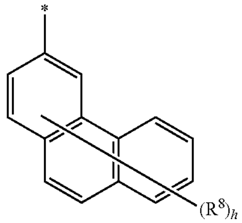

-continued

Formula (Ar-9)

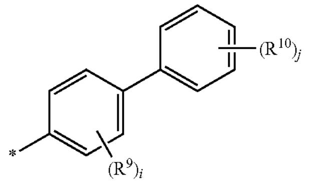

Formula (Ar-10)

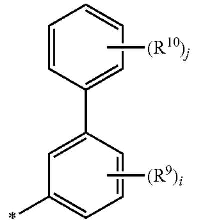

Formula (Ar-11)

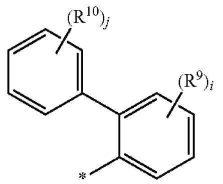

Formula (Ar-12)

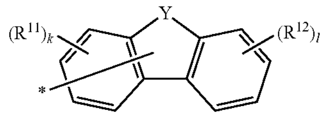

wherein:

$R^6$, $R^7$, $R^8$, $R^9$, $R^{10}$, $R^{11}$ and $R^{12}$ are the same as the definition of $R^4$ in claim 1, or an adjacent plurality of $R^6$, or plurality of $R^7$, or plurality of $R^8$, or plurality of $R^9$, or plurality of $R^{10}$, or plurality of $R^{11}$, or plurality of $R^{12}$ may be bonded to each other to form a ring, Y is O, S, $CR^{13}R^{14}$, $NR^{15}$ or $SiR^{16}R^{17}$, provided that when Y is bonded to Formula 1, it is $-L^1$-N, $R^{13}$, $R^{14}$, $R^{15}$, $R^{16}$ and $R^{17}$ are each independently selected from the group consisting of hydrogen; deuterium; a $C_1$-$C_{60}$ alkyl group; a $C_6$-$C_{60}$ aryl group; and a $C_2$-$C_{60}$ heterocyclic group including at least one hetero atom of O, N, S, Si or P; alternatively, $R^{13}$ and $R^{14}$ or $R^{16}$ and $R^{17}$ may be bonded to each other to form a spiro, $L^1$ is each independently selected from the group consisting of single bond; a $C_6$-$C_{60}$ arylene group; a fluorenylene group; a fused ring group of a $C_3$-$C_{60}$ aliphatic ring and a $C_6$-$C_{60}$ aromatic ring; a $C_2$-$C_{60}$ heteroarylene group including at least one heteroatom of O, N, S, Si or P;

f and j are each independently an integer from 0 to 5, g is an integer from 0 to 7, h is an integer from 0 to 9, i, k and l are an integer from 0 to 4, and

* means the position to be bonded.

3. The organic electronic element of claim 1, wherein Formula 1 is represented by any one of compounds P-1 to P-107:

P-1

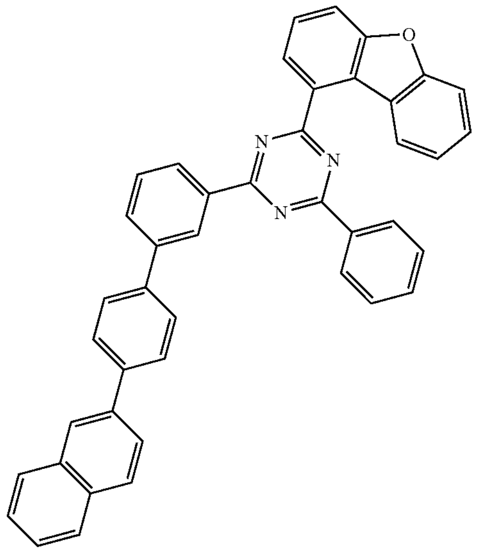

P-2

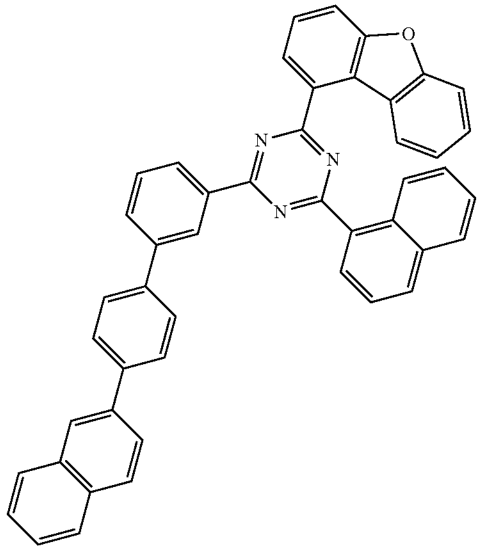

-continued
P-3
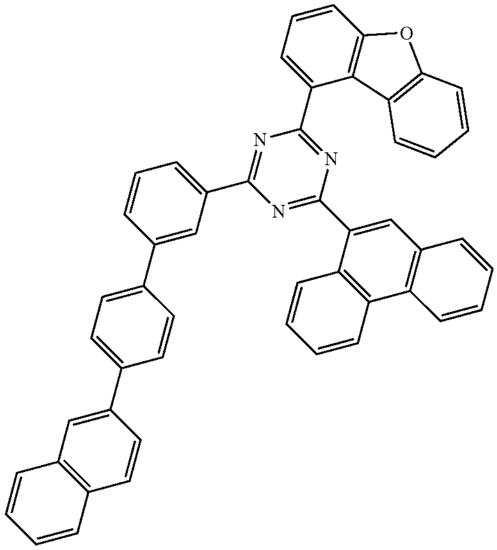
P-4
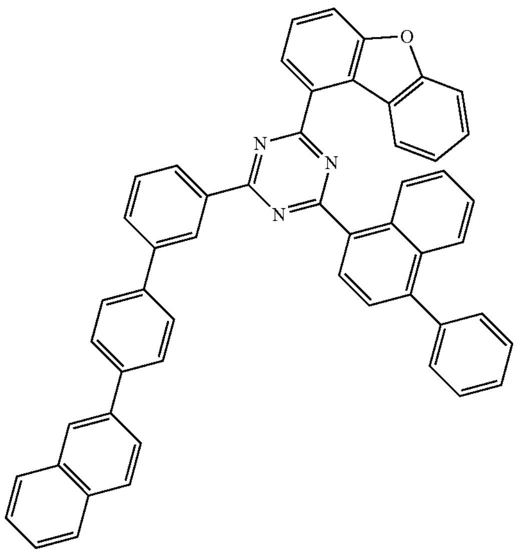
-continued
P-5
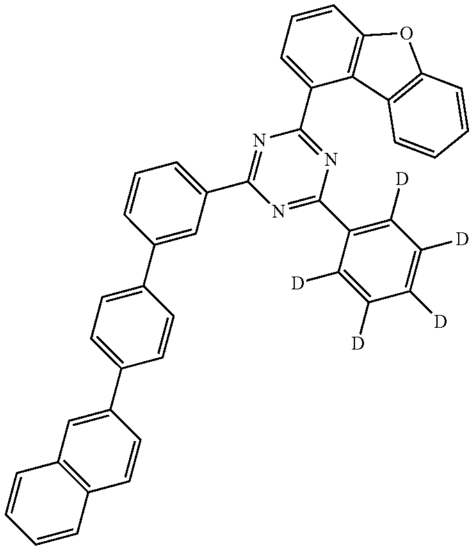
P-6
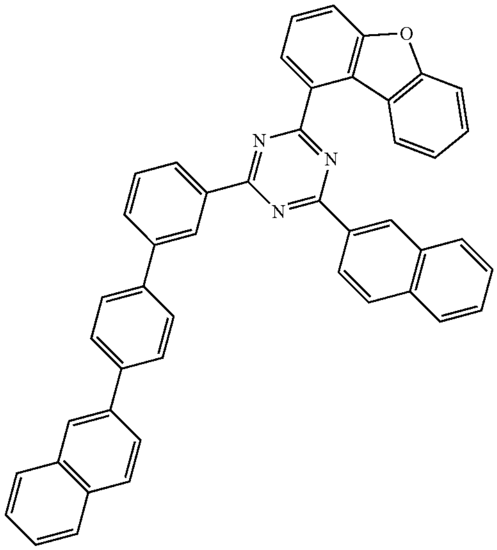
P-7
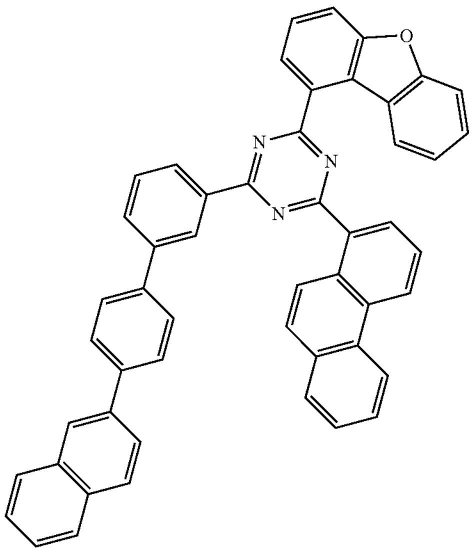

-continued
P-8
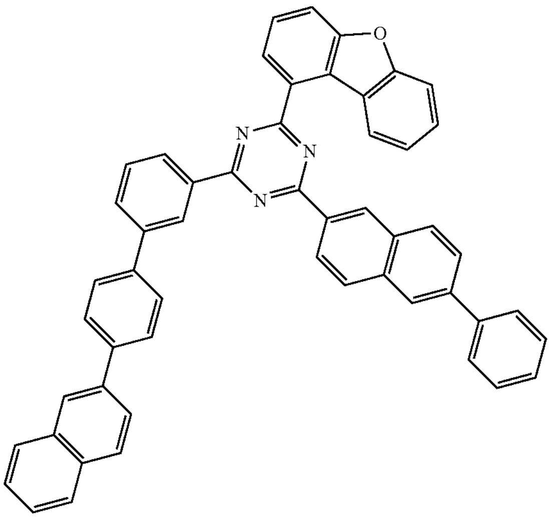
P-9
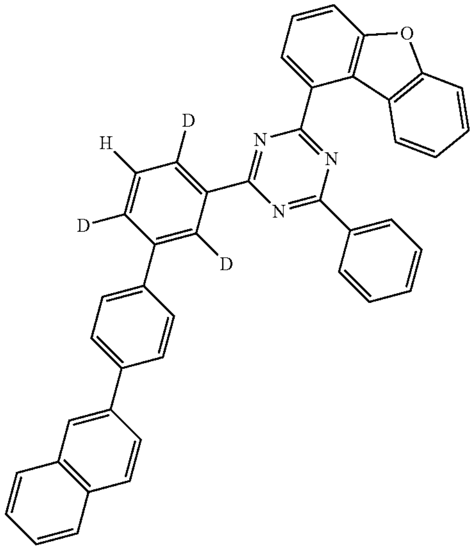
P-10
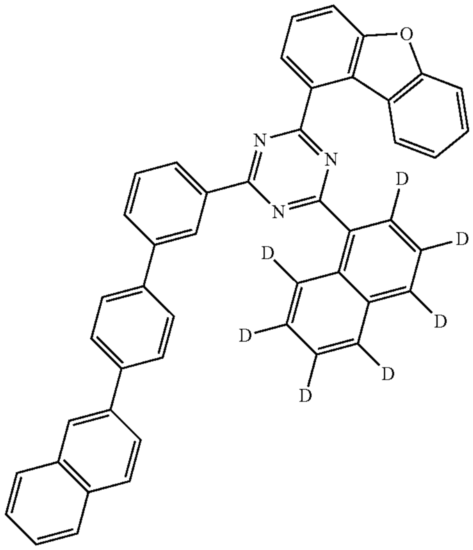
-continued
P-11
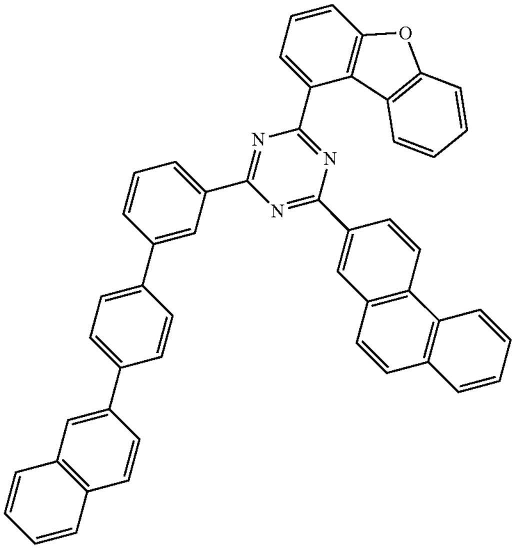
P-12
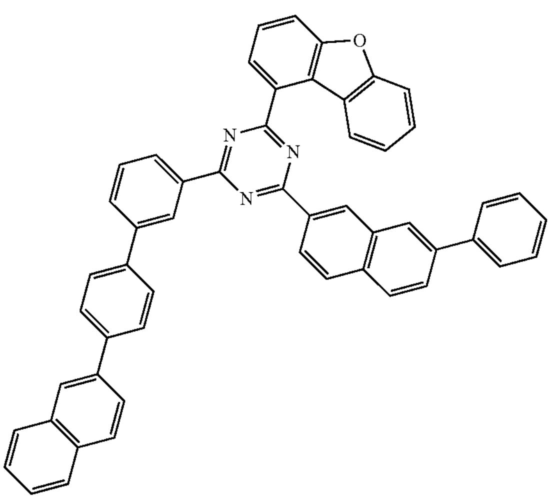

P-13
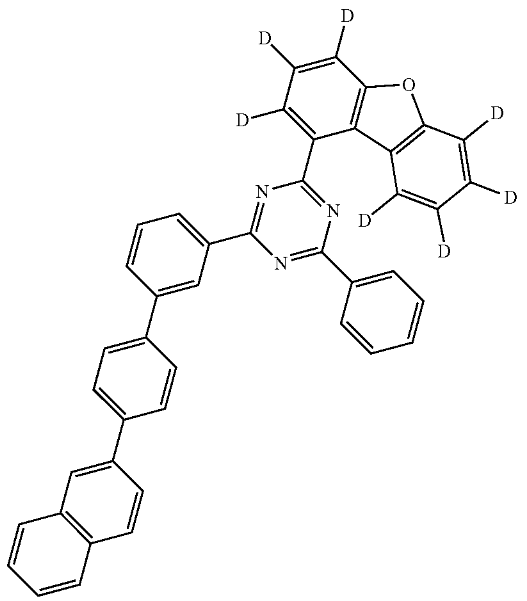
P-14
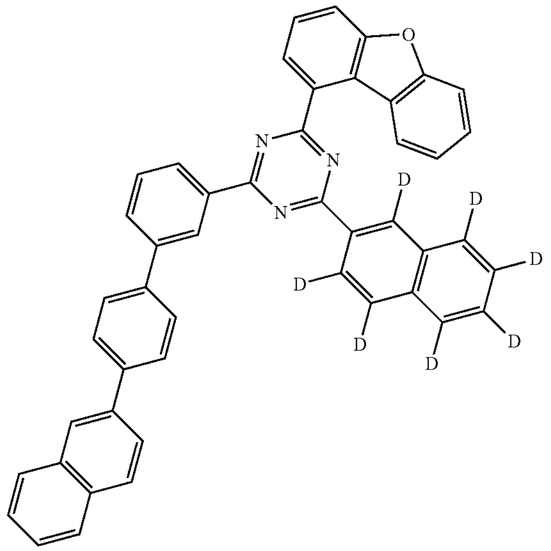
P-15
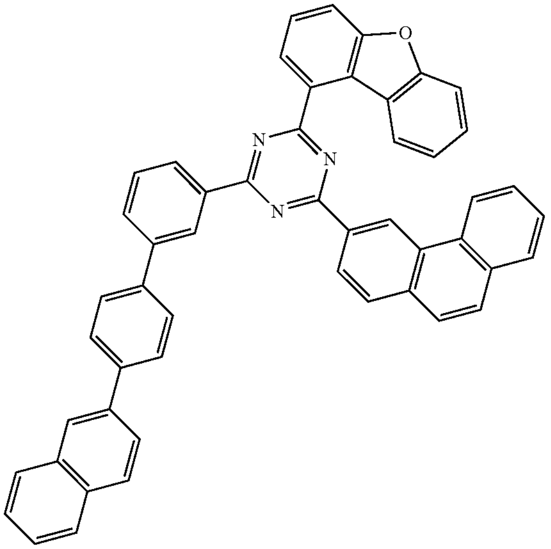
P-16
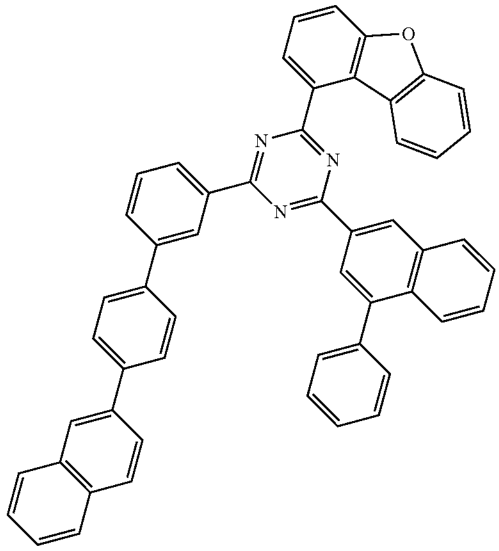

-continued
P-17
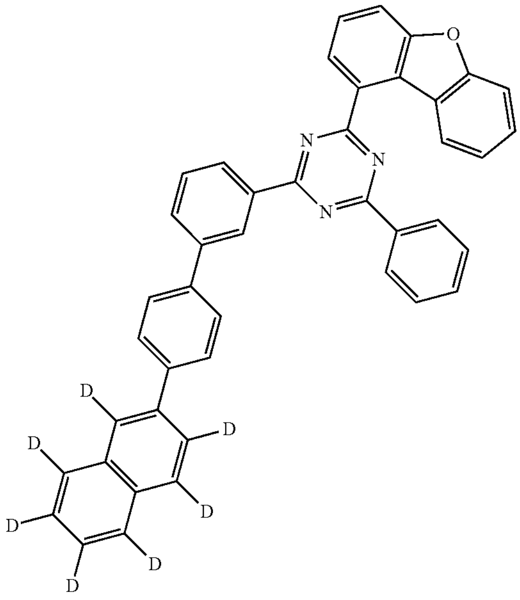
P-18
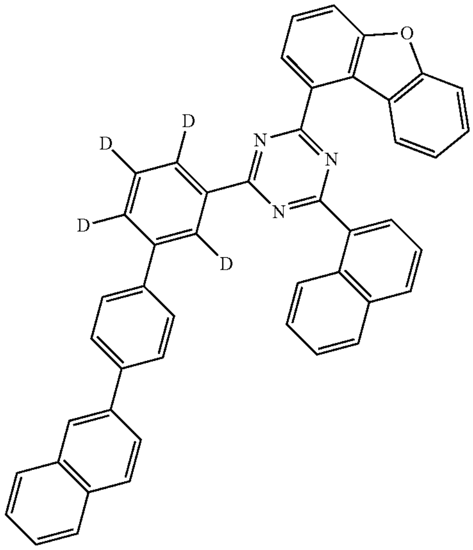
-continued
P-19
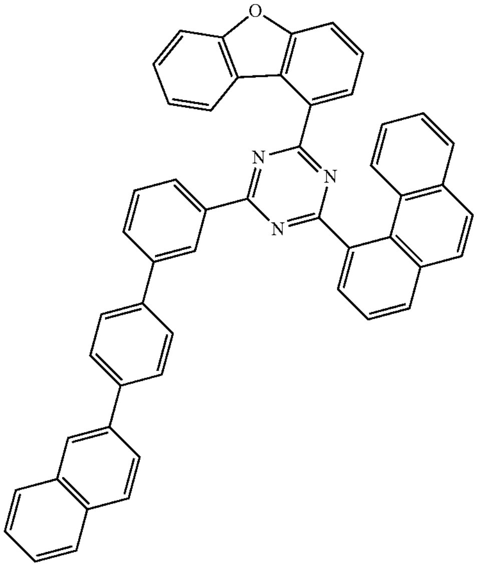
P-20
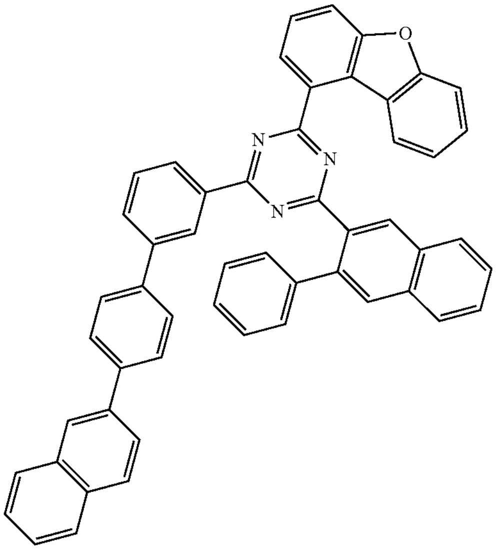

-continued
P-21
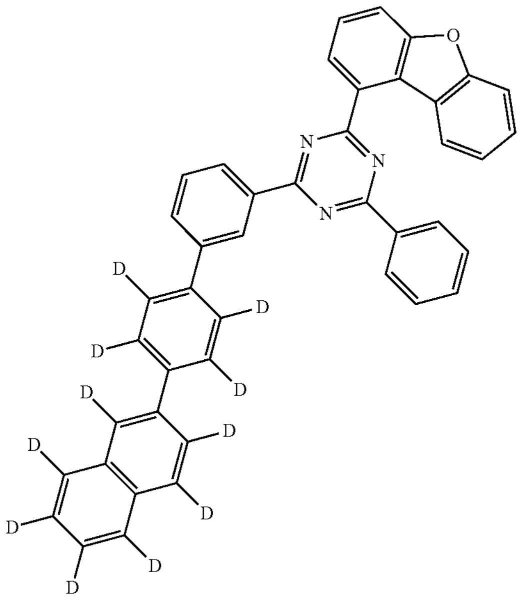
P-22
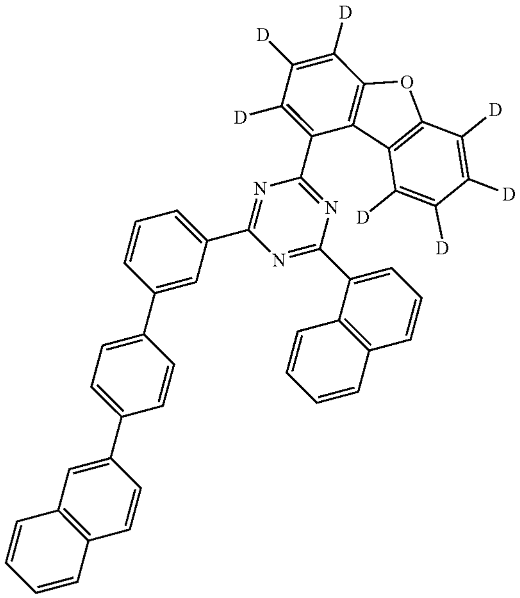
-continued
P-23
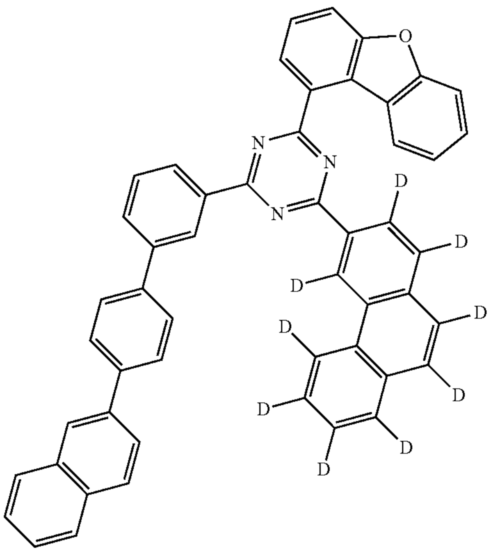
P-24
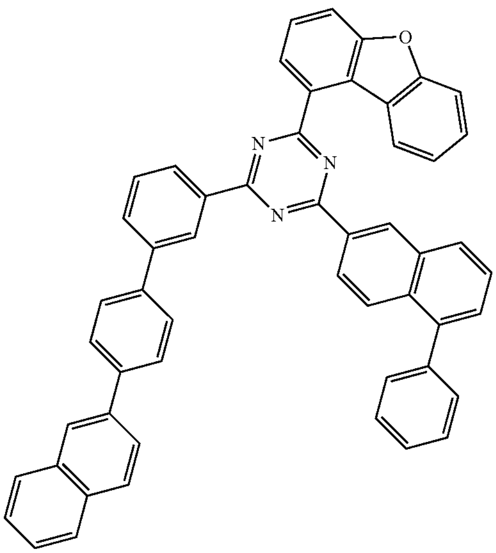

-continued
P-25
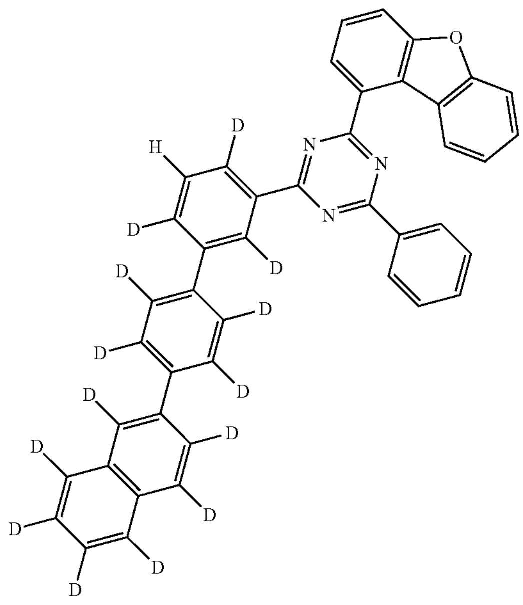
P-26
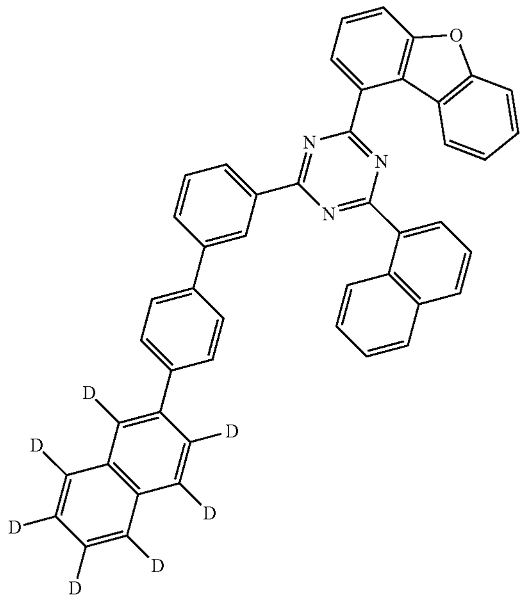
-continued
P-27
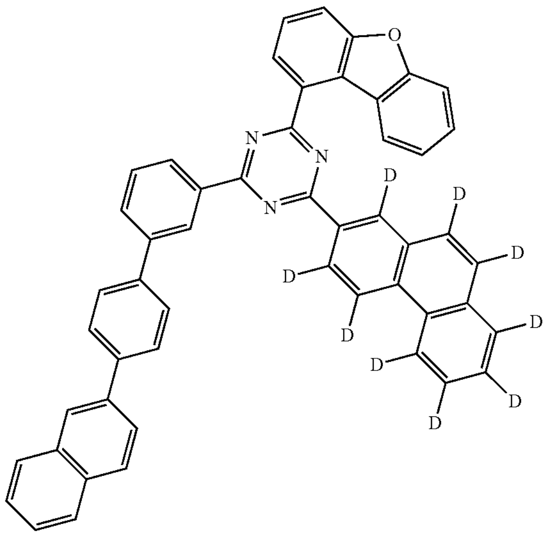
P-28
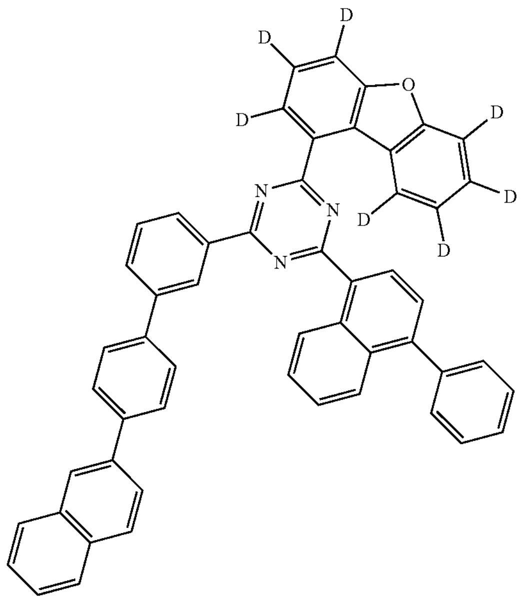

-continued
P-29
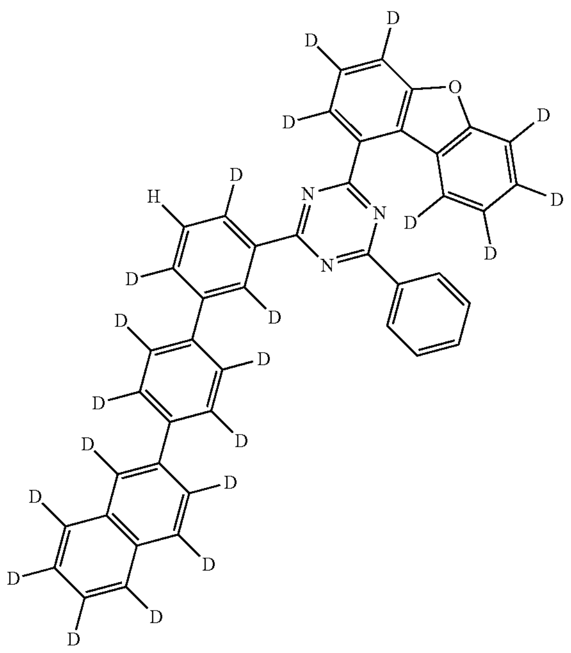
P-30
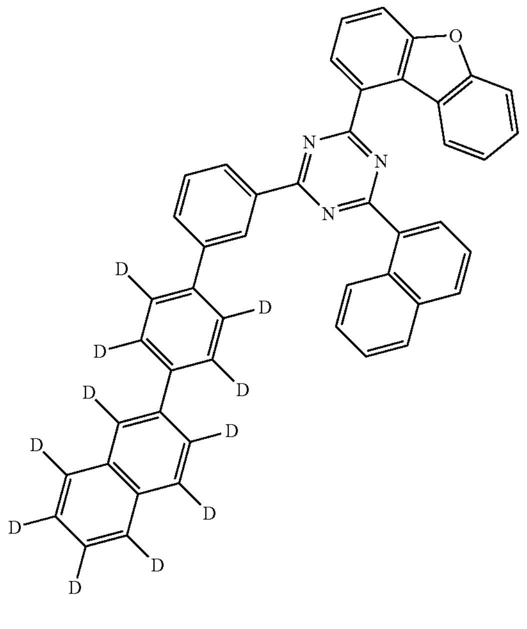
-continued
P-31
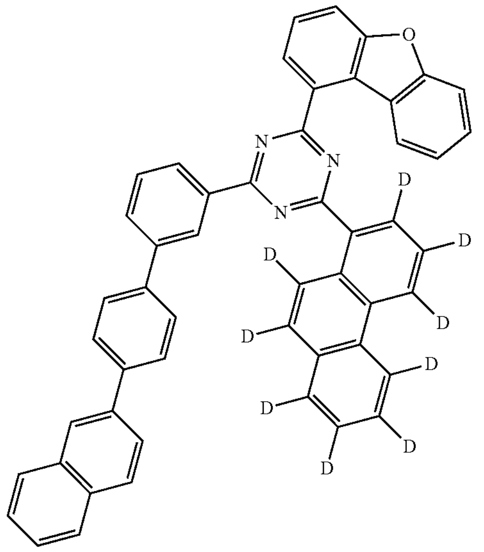
P-32
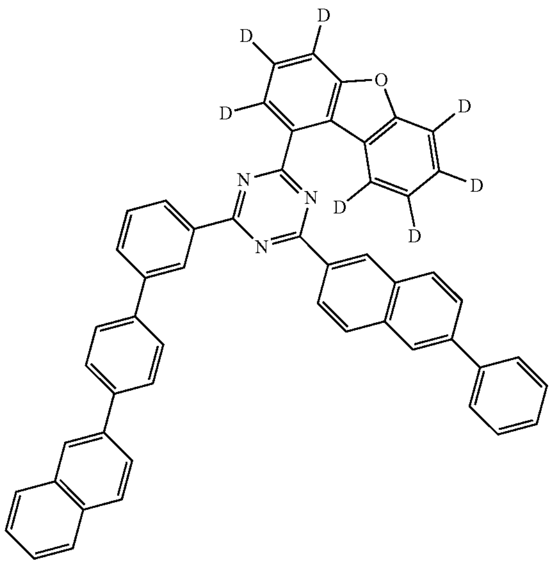

-continued
P-33
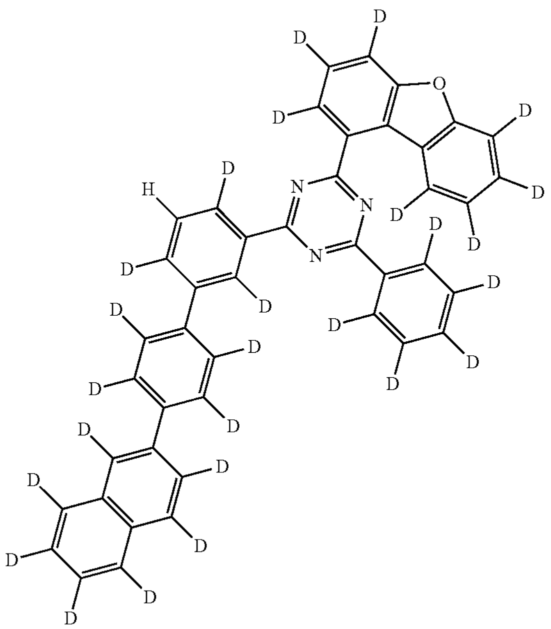
P-34
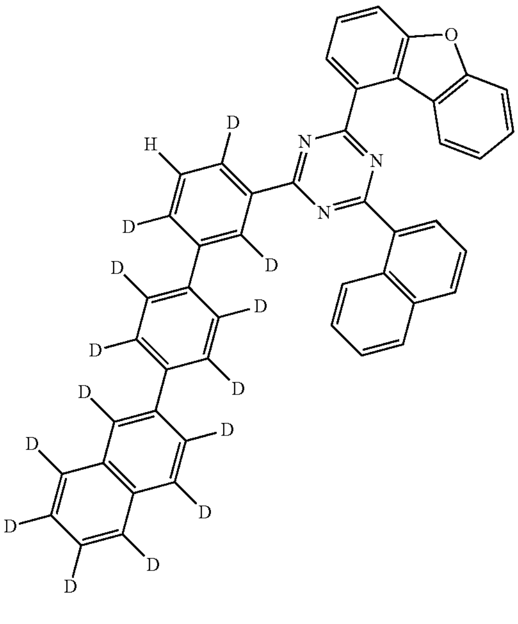
-continued
P-35
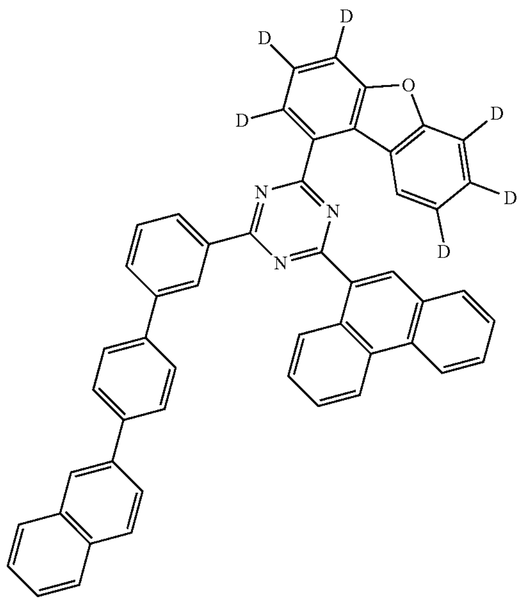
P-36
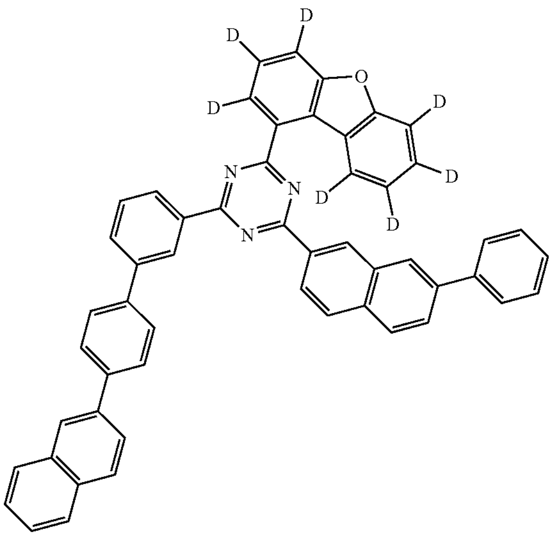

-continued
P-37
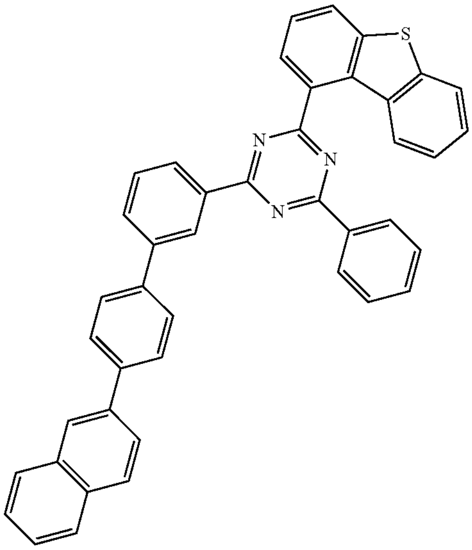
P-38
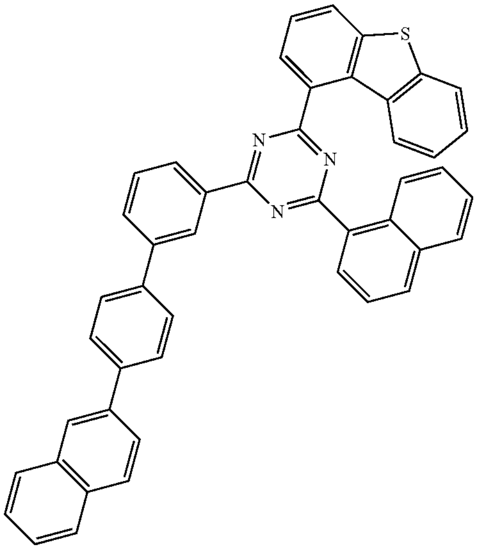
P-39
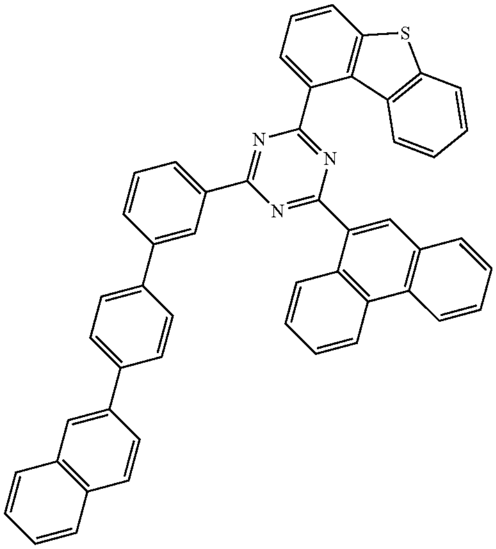
-continued
P-40
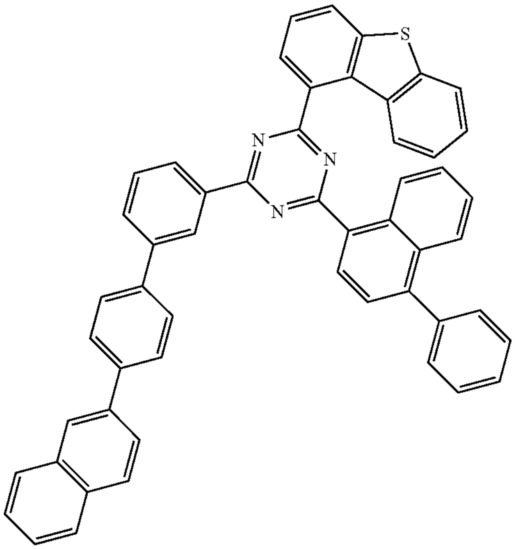
P-41
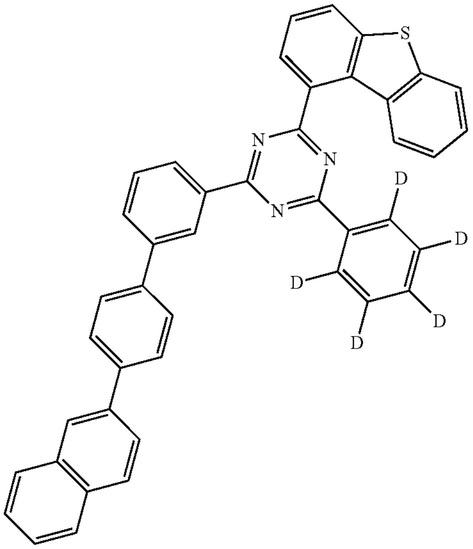

-continued
P-42
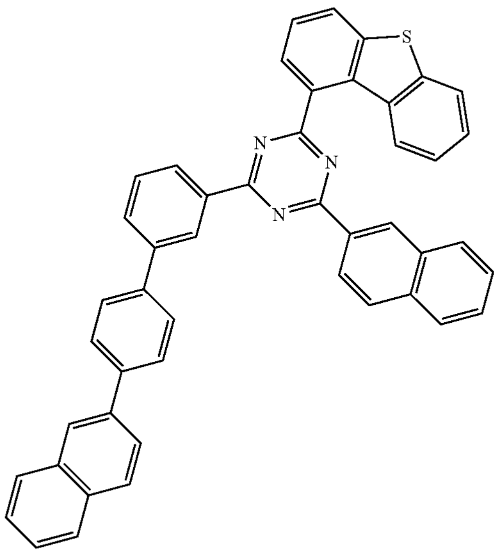
P-43
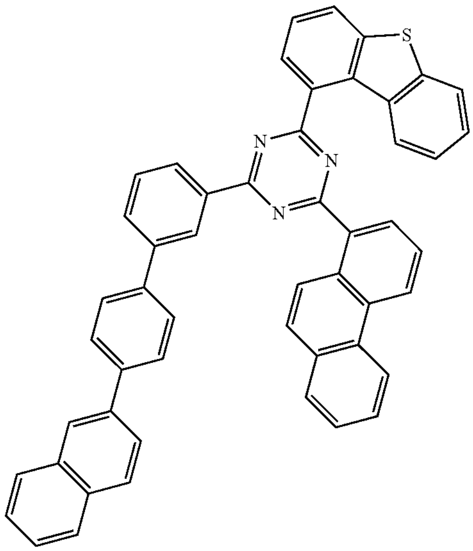
P-44
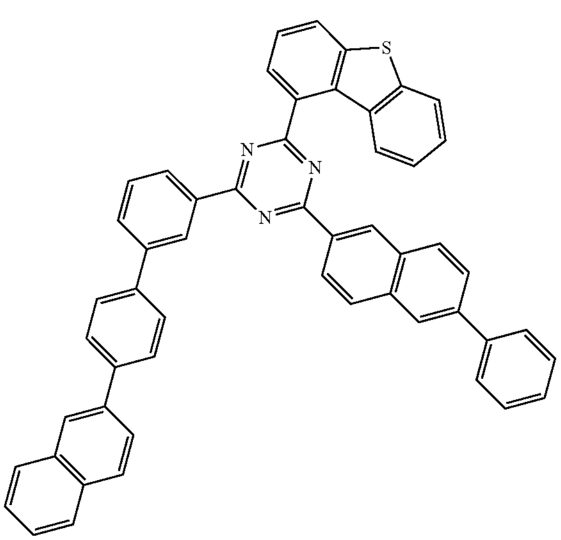
-continued
P-45
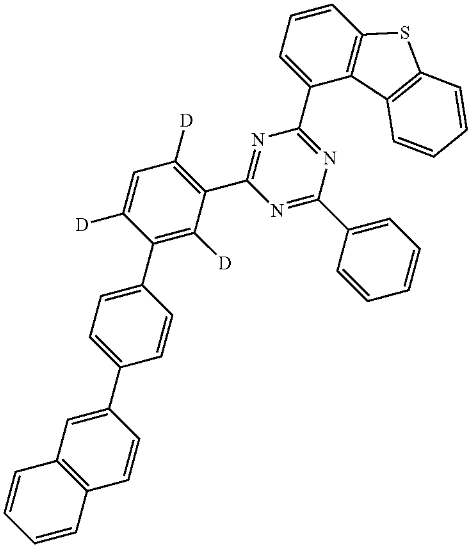
P-46
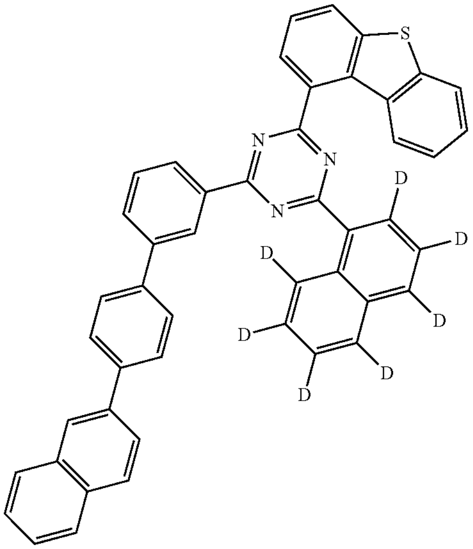
P-47
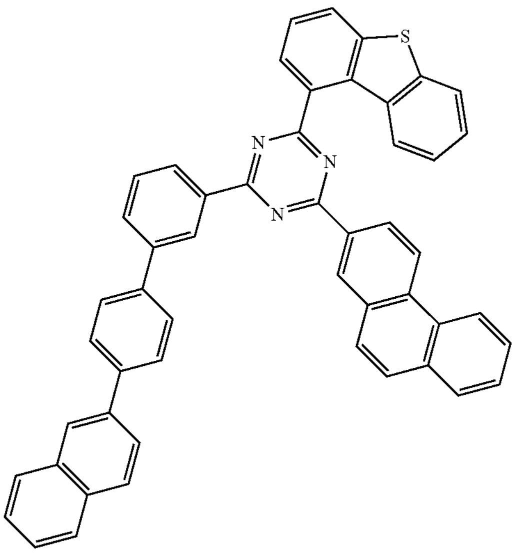

-continued
P-48
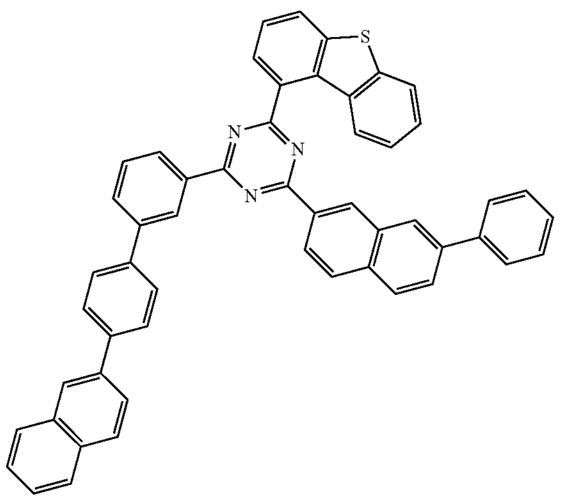
P-49
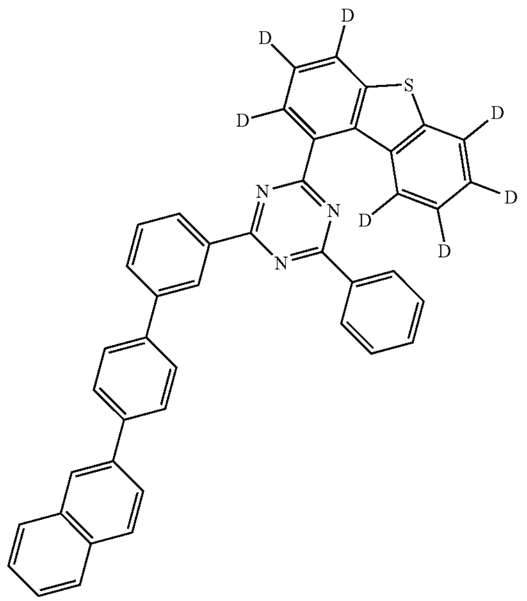
-continued
P-50
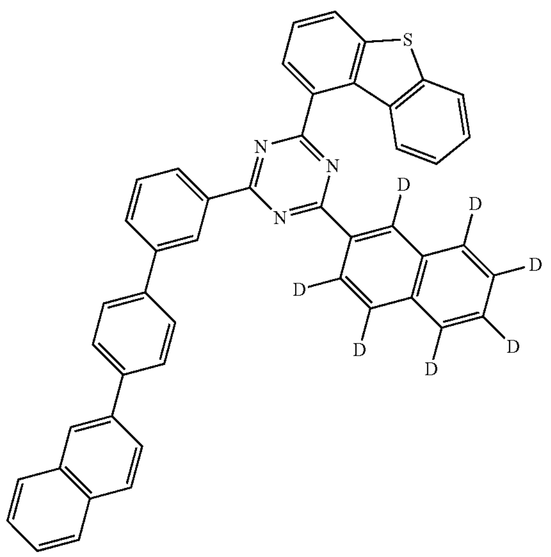
P-51
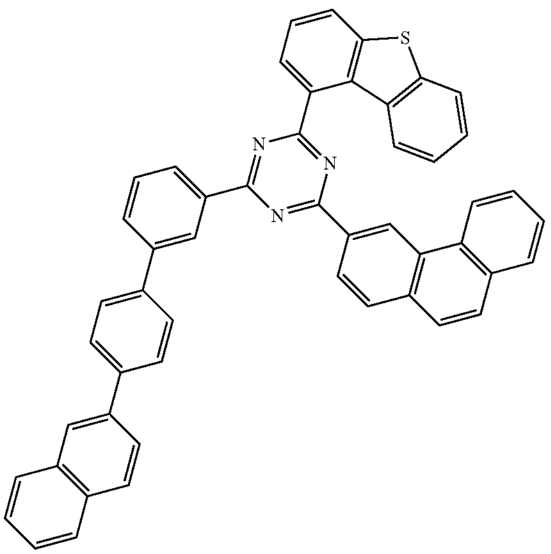

-continued
P-52
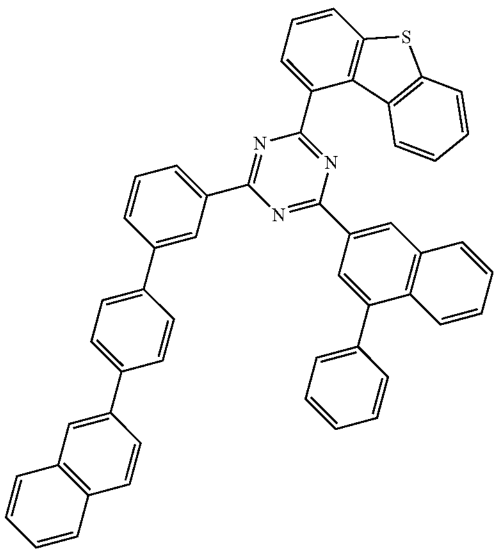
P-53
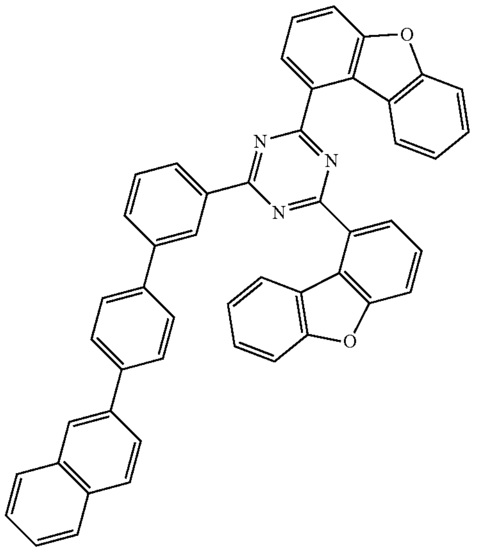
P-54
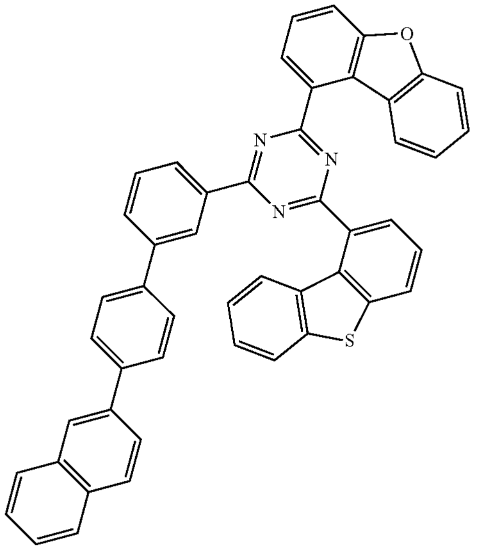
-continued
P-55
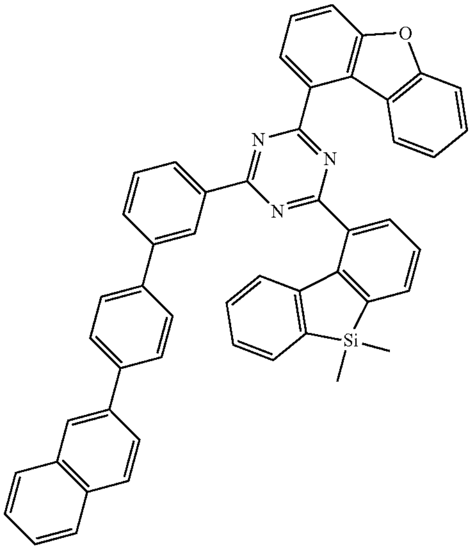
P-56
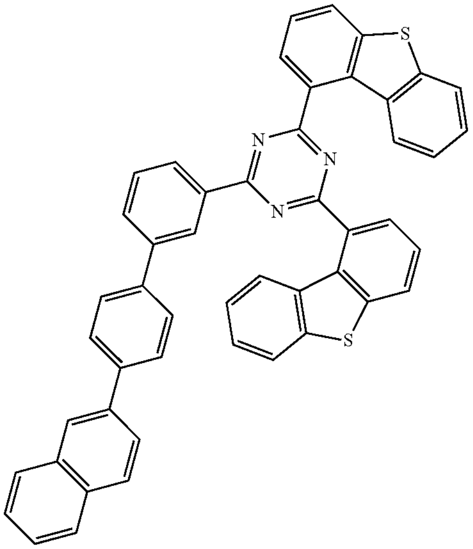

-continued
P-57
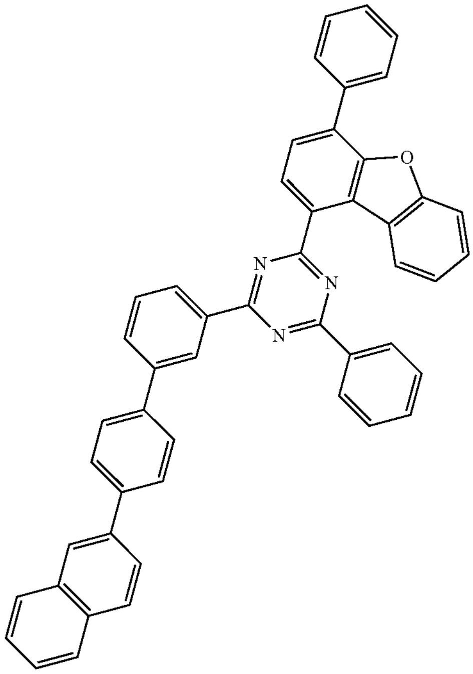
P-58
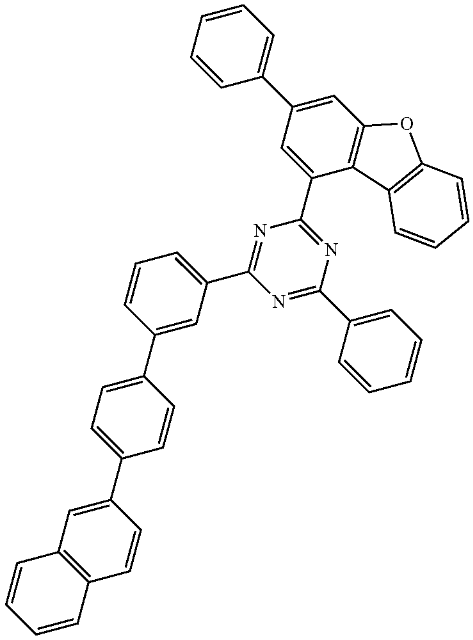
-continued
P-59
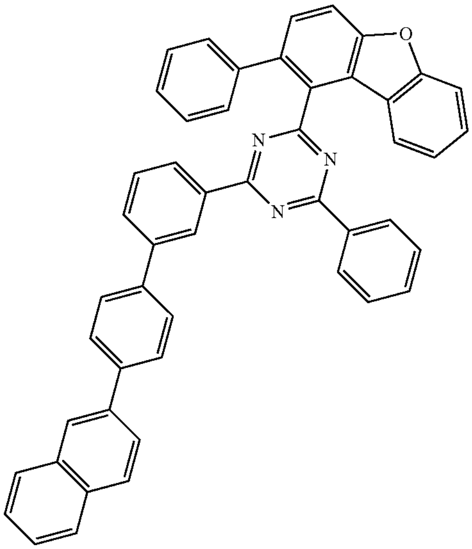
P-60
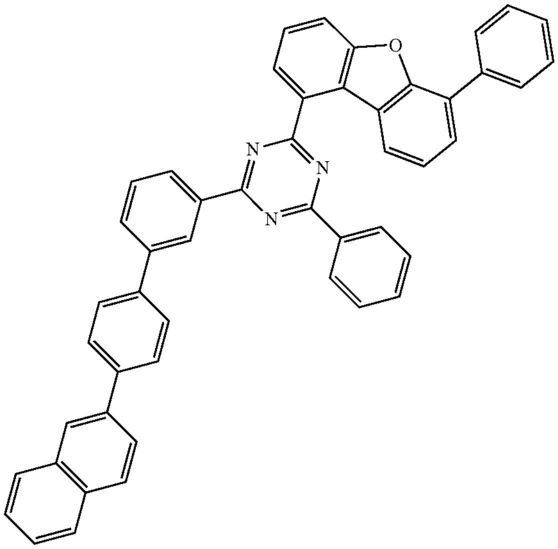
P-61
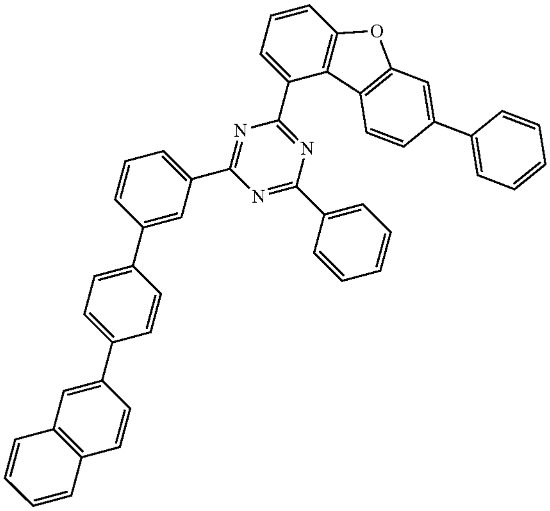

-continued
P-62
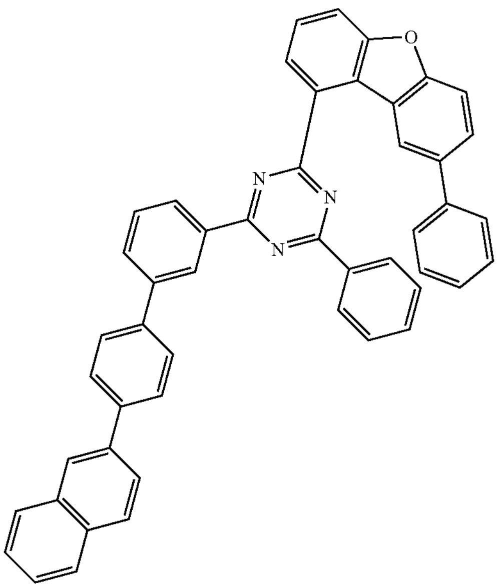
P-63
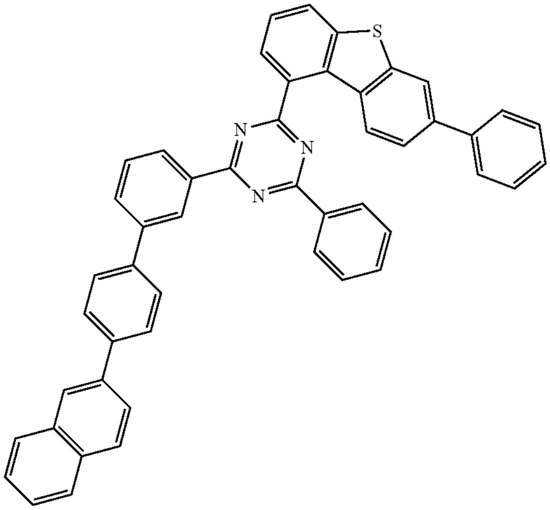
-continued
P-64
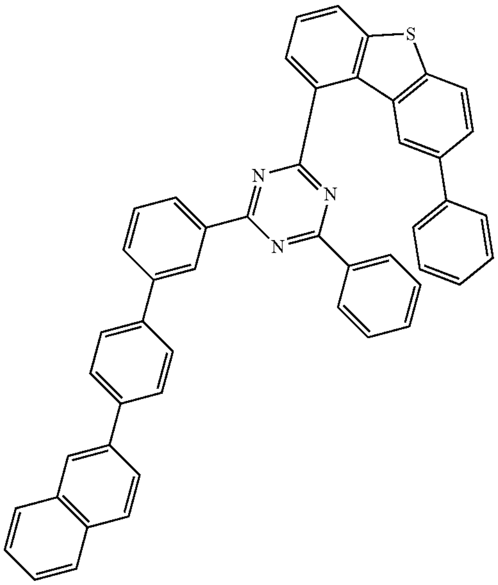
P-65
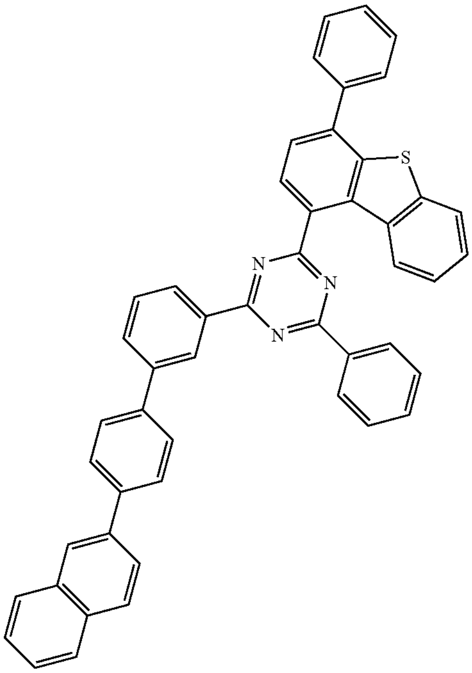

-continued
P-66
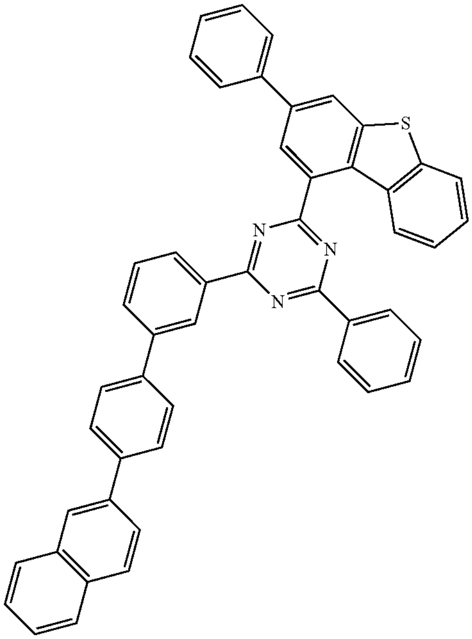
P-67
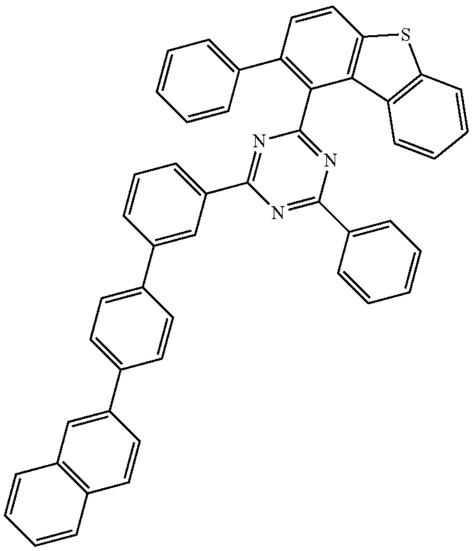
-continued
P-68
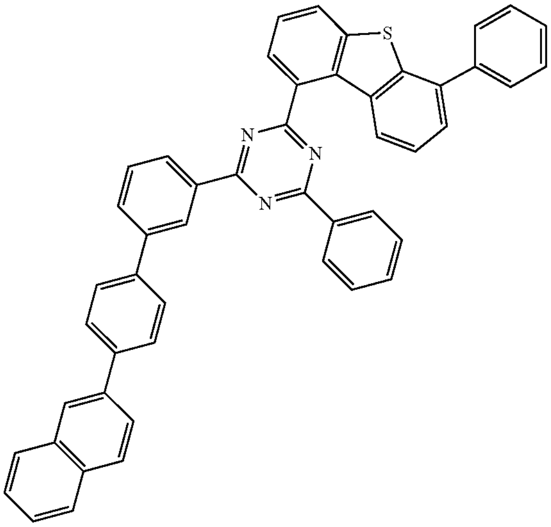
P-69
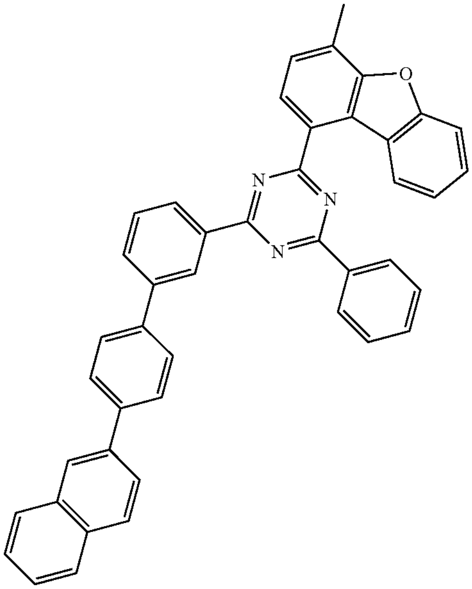

-continued
P-70
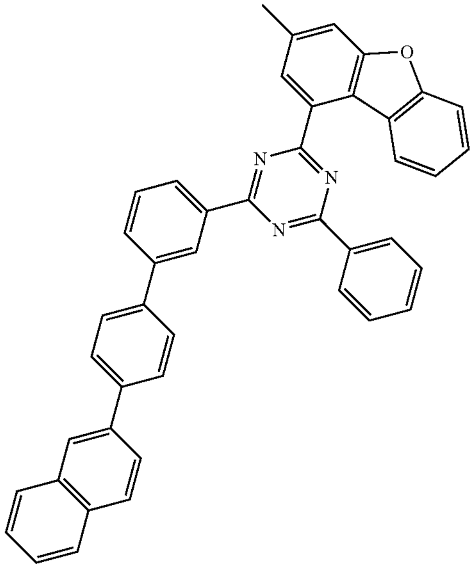
P-71
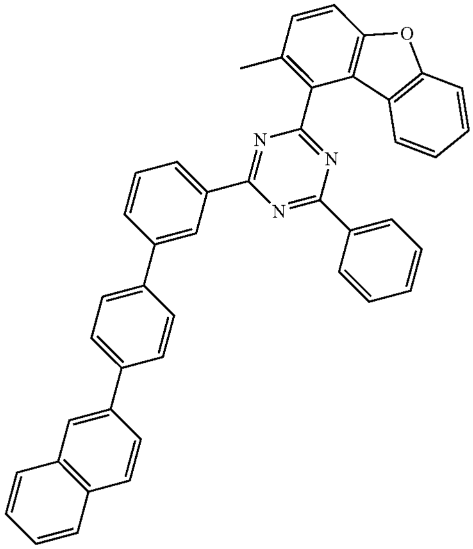
-continued
P-72
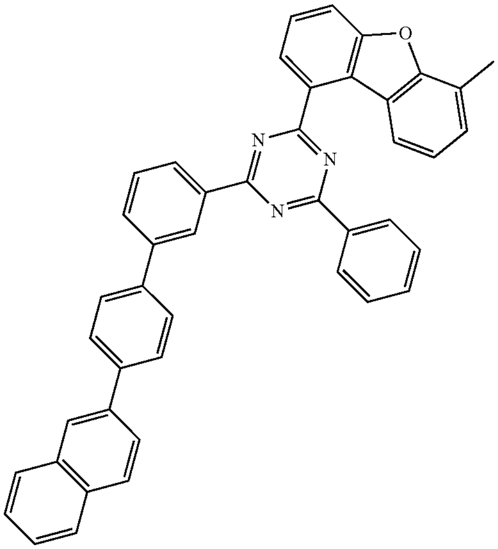
P-73
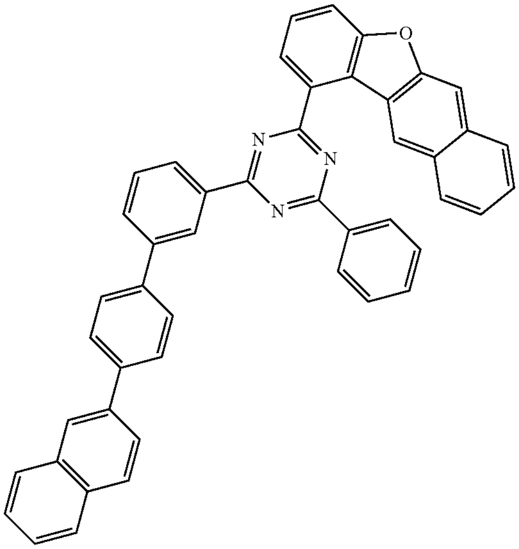

-continued
P-74
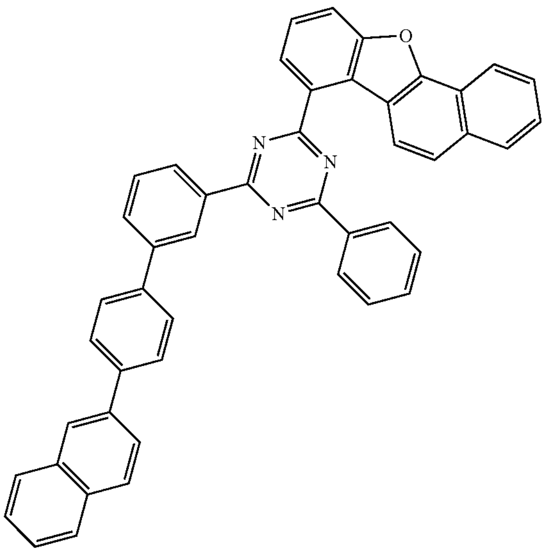
P-75
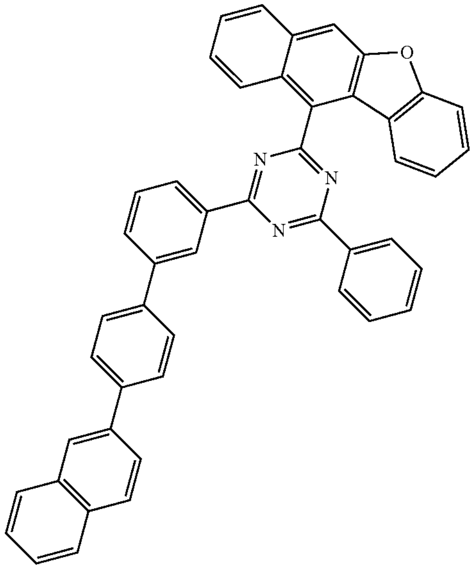
-continued
P-76
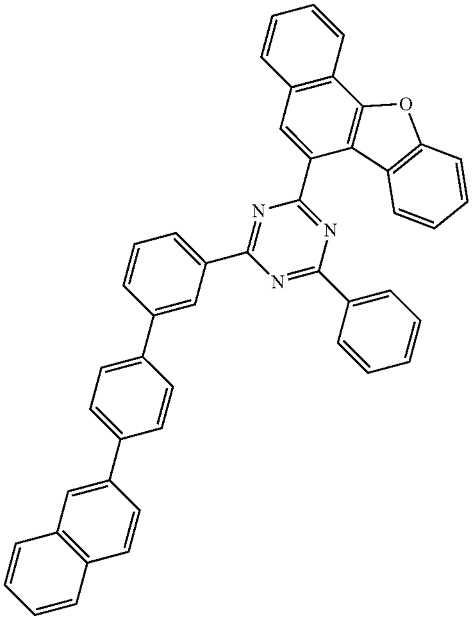
P-77
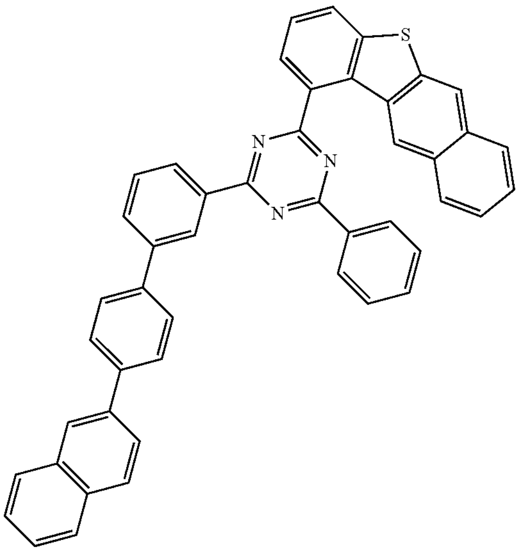

-continued
P-78
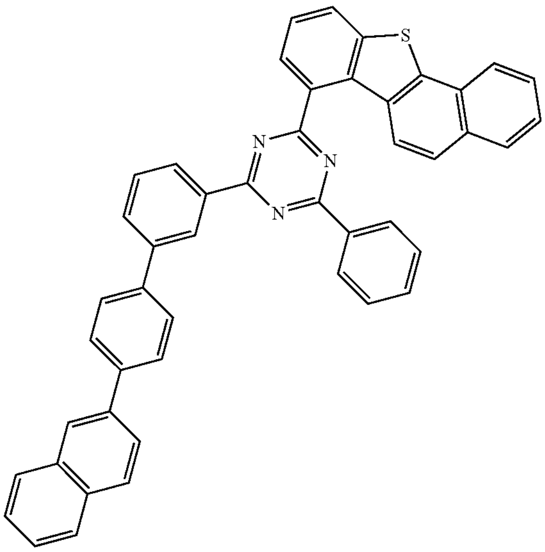
P-79
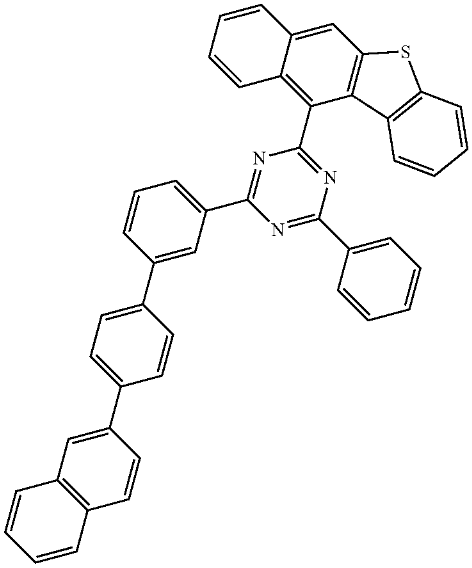
-continued
P-80
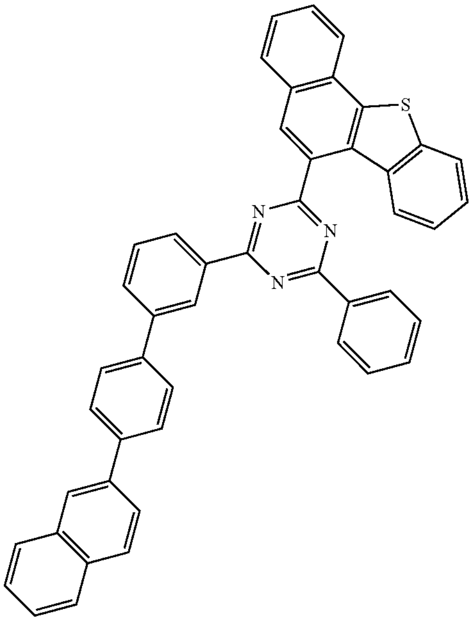
P-81
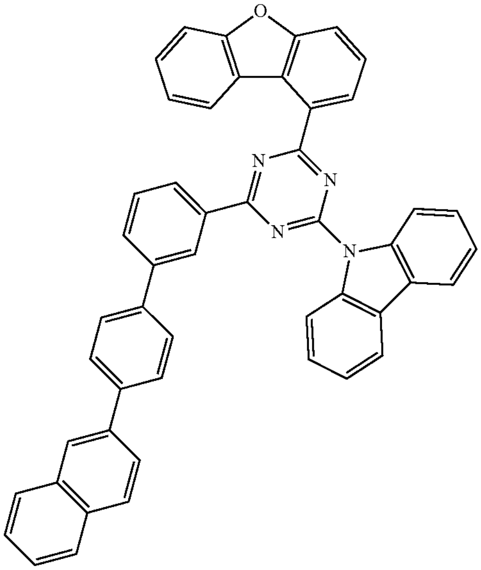

-continued
P-82
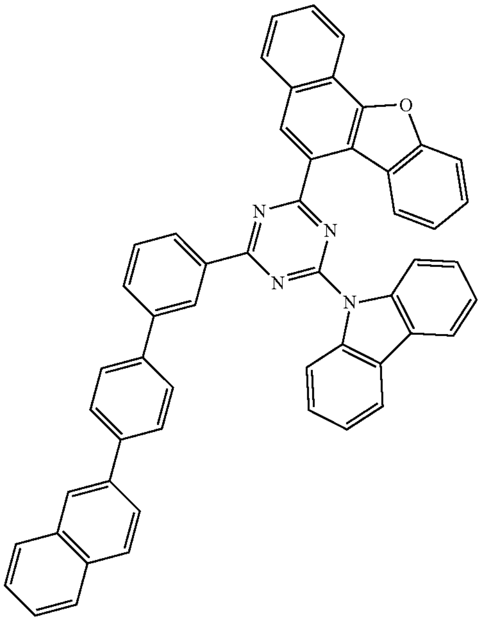
P-83
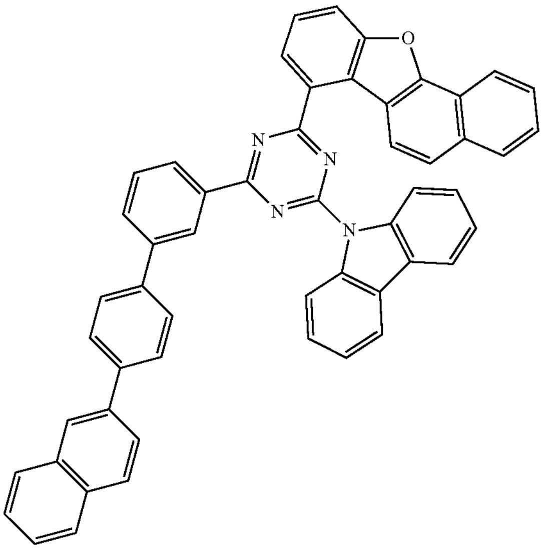
-continued
P-84
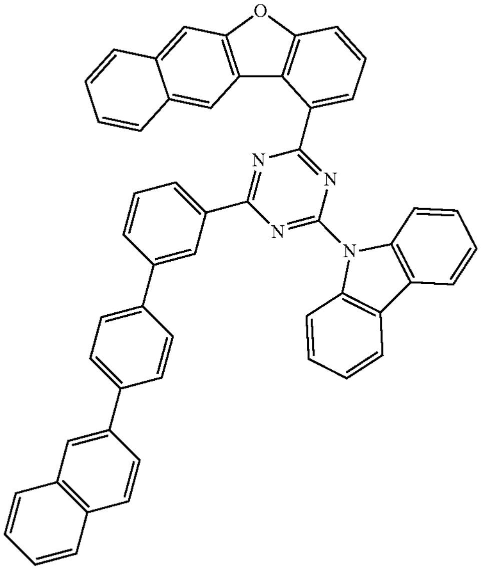
P-85
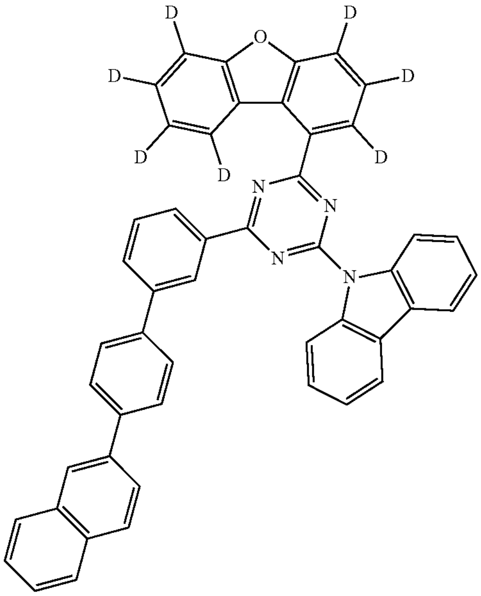

-continued
P-86
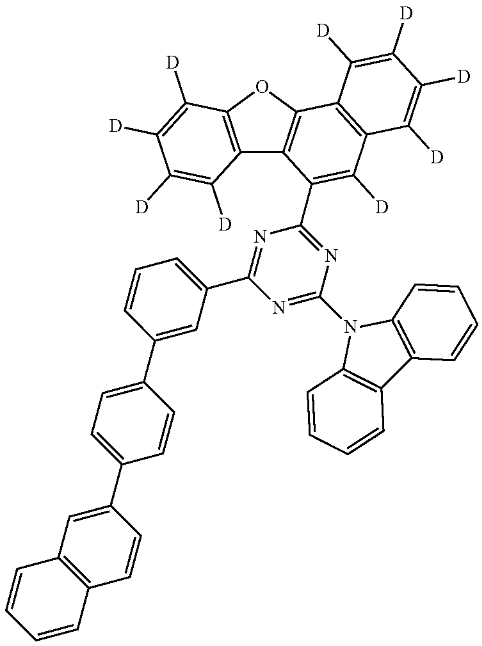
P-87
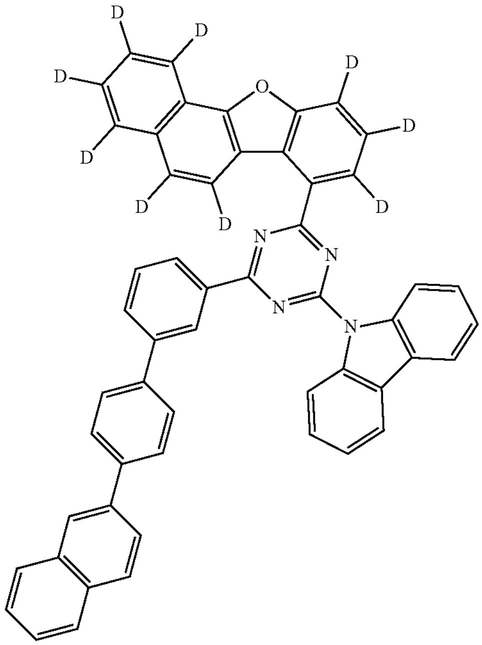
-continued
P-88
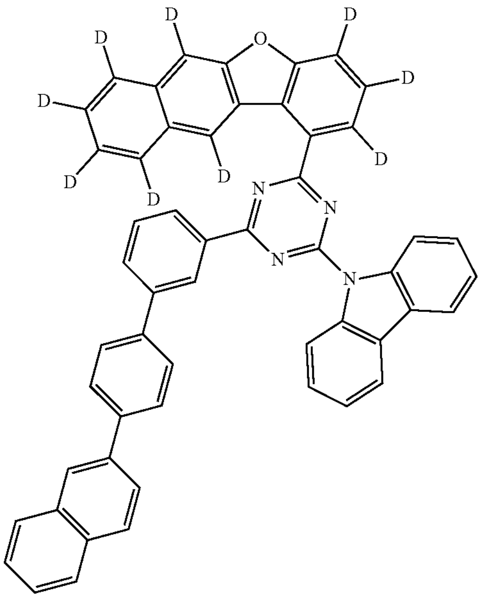
P-89
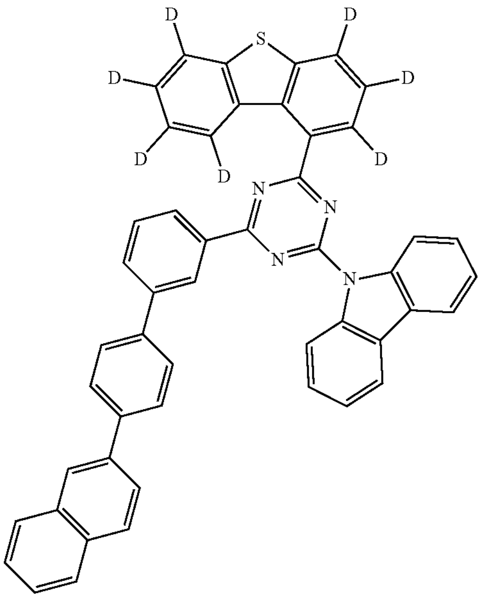

P-90
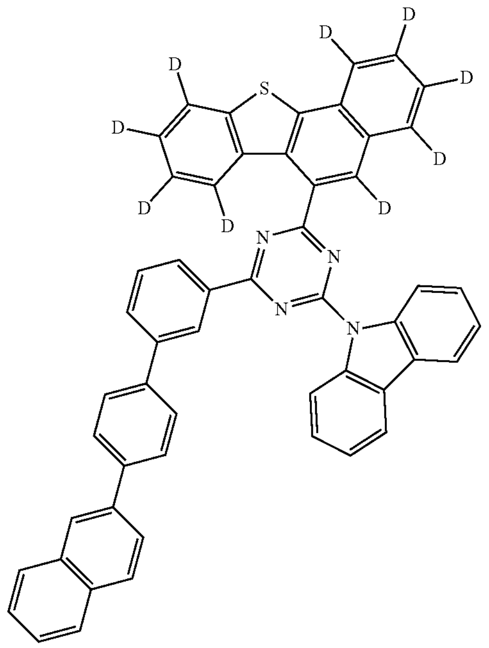
P-91
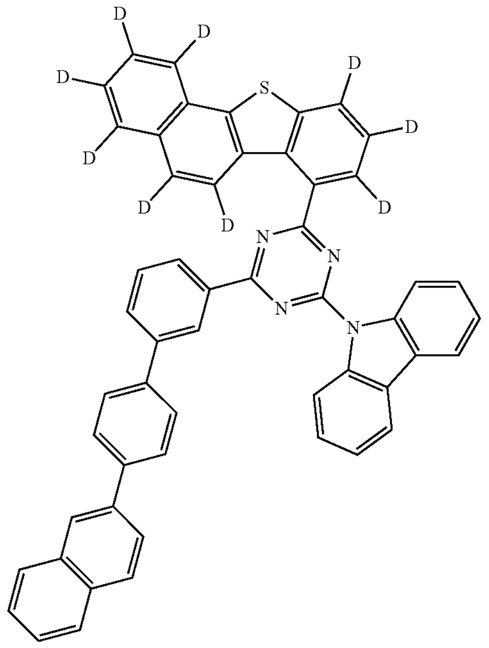
P-92
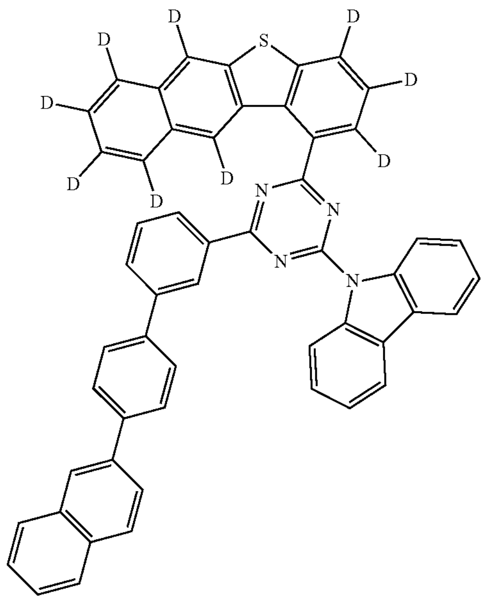
P-93
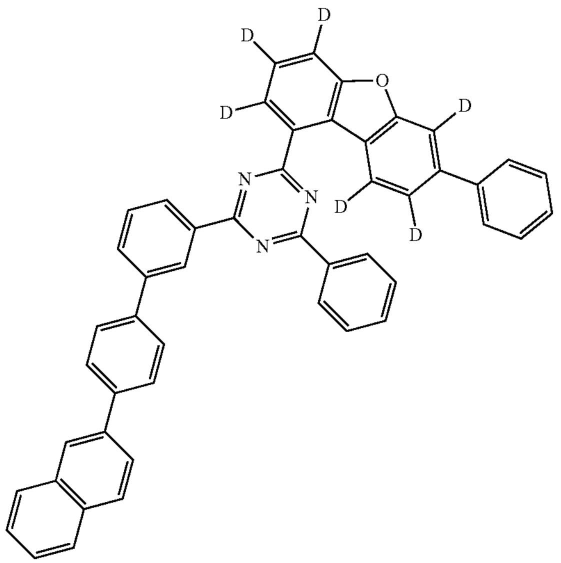

-continued
P-94
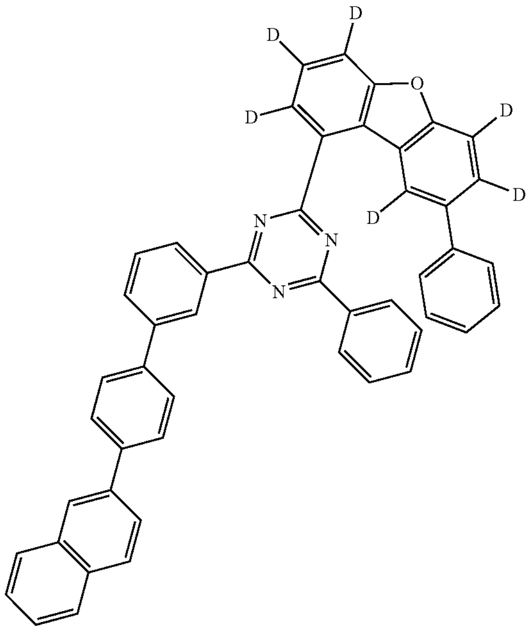
P-95
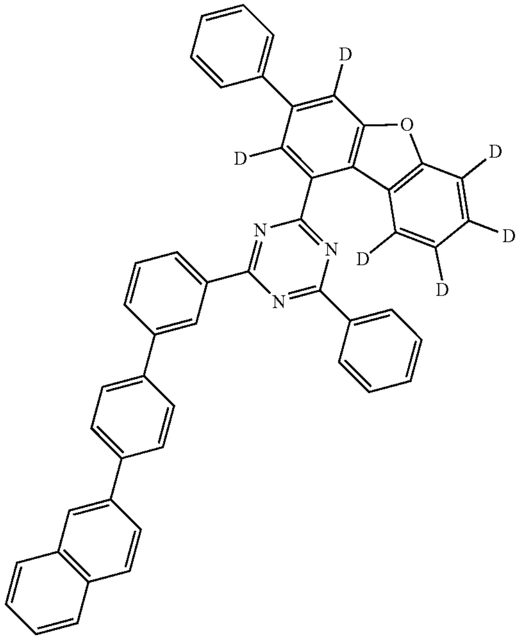
-continued
P-96
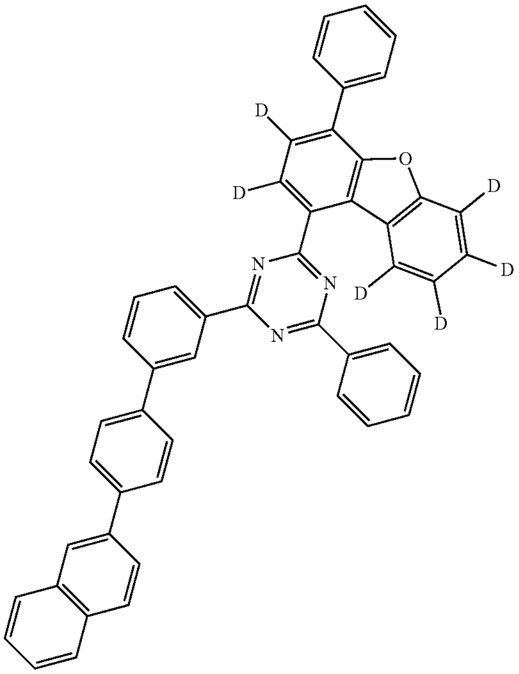
P-97
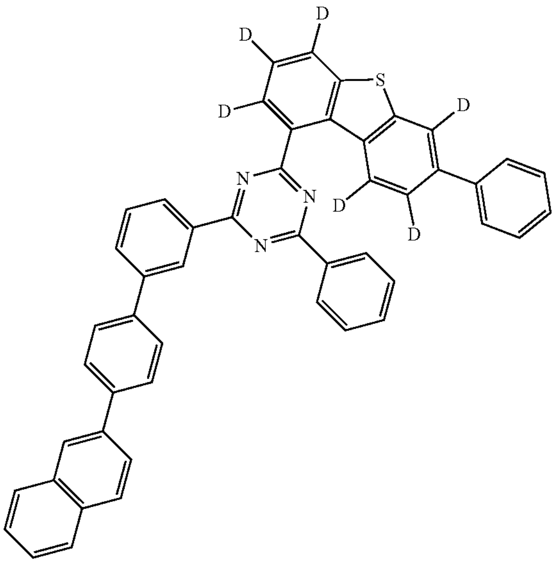

-continued
P-98
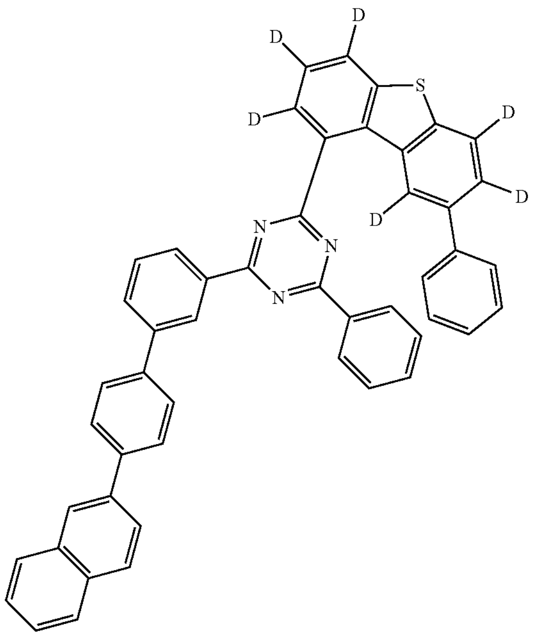
P-99
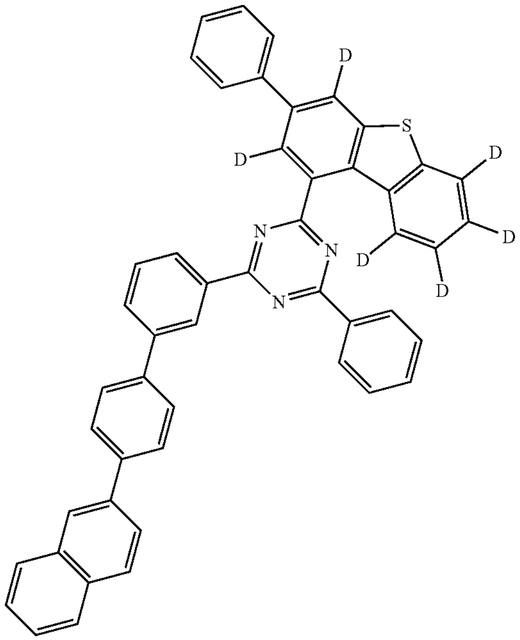
-continued
P-100
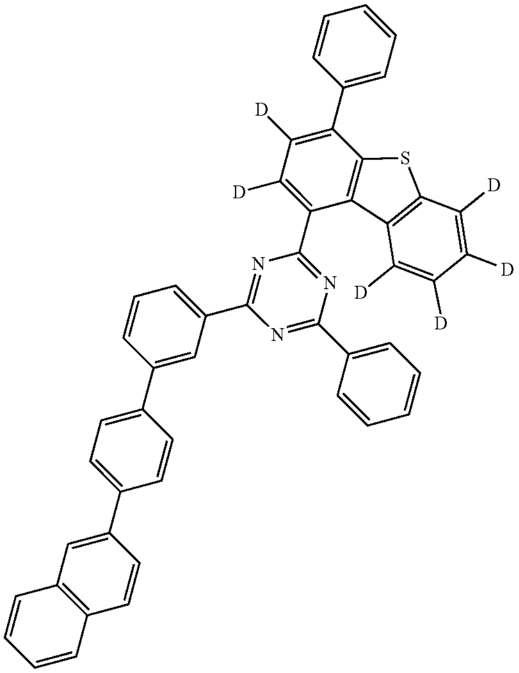
P-101
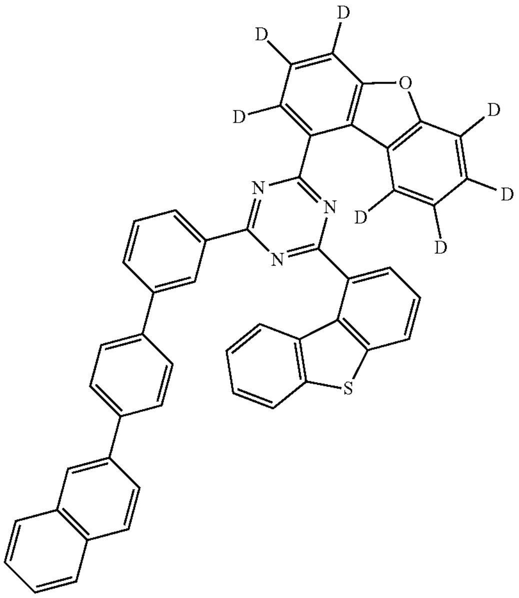

P-102
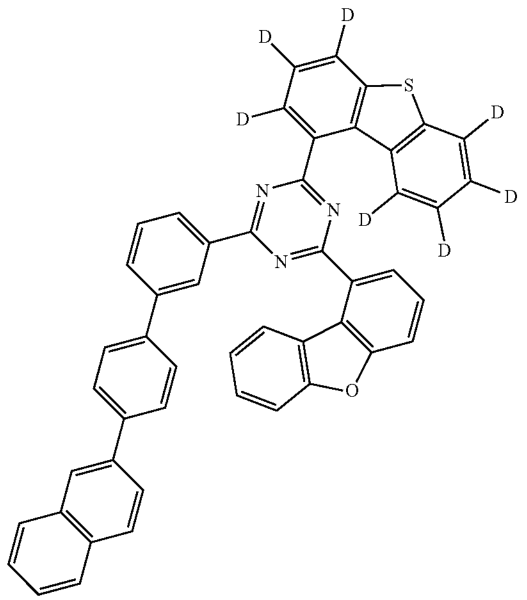
P-103
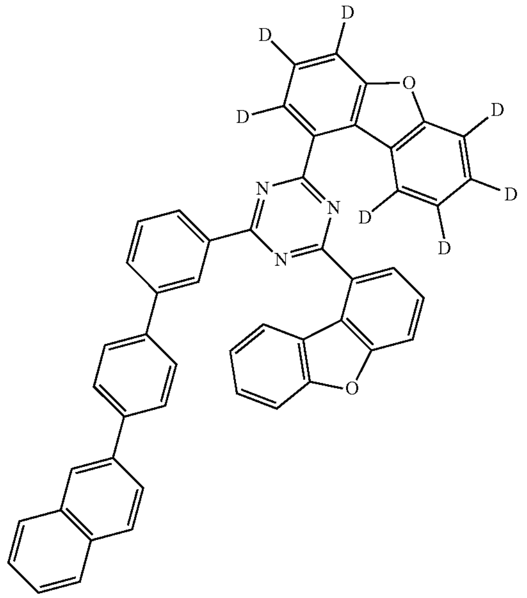
P-104
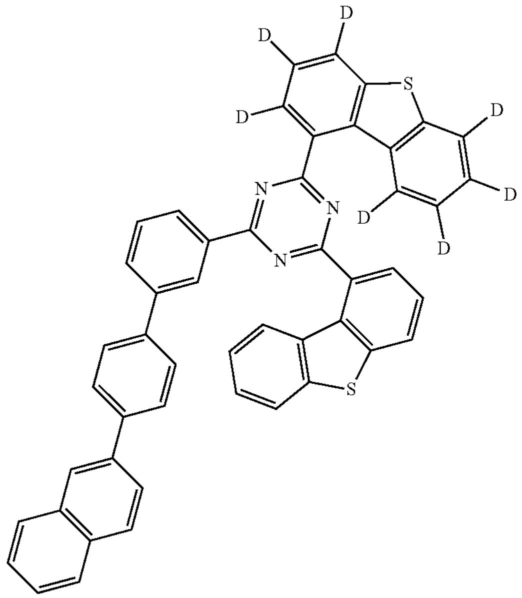
P-105
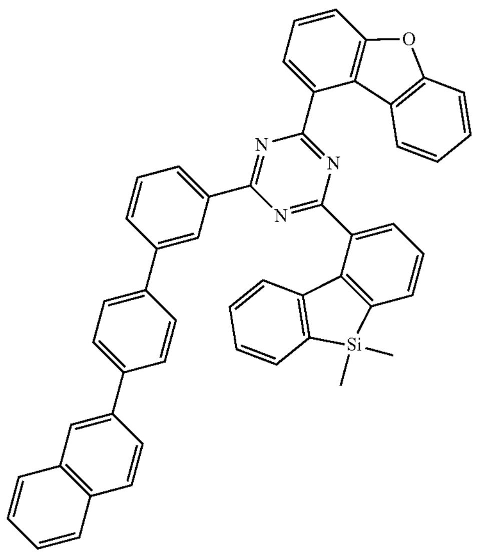

-continued
P-106
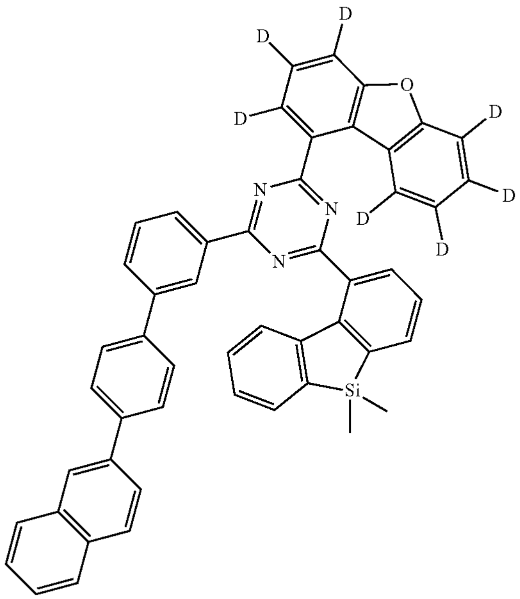
P-107
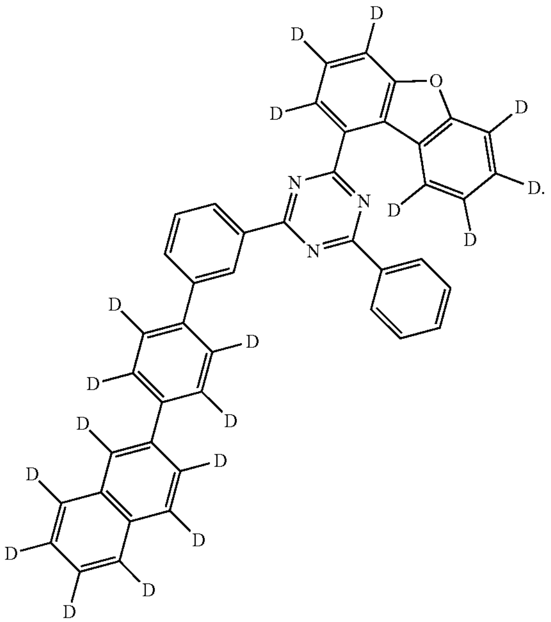
4. The organic electronic element of claim 1, wherein Formula 4 is represented by any one of compounds H-1 to H-108:
H-1
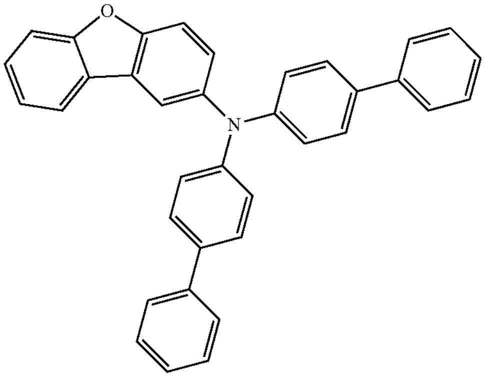
H-2
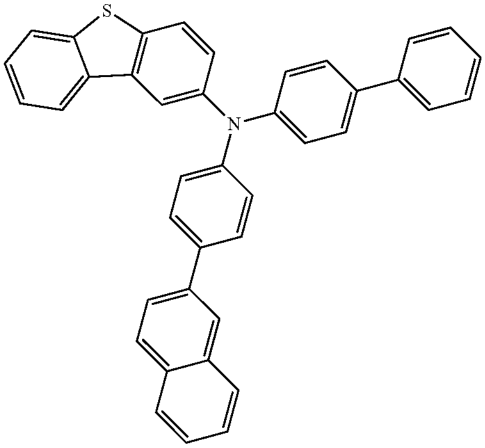
H-3
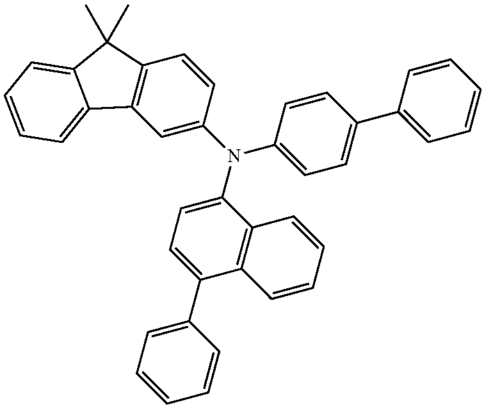

-continued
H-4
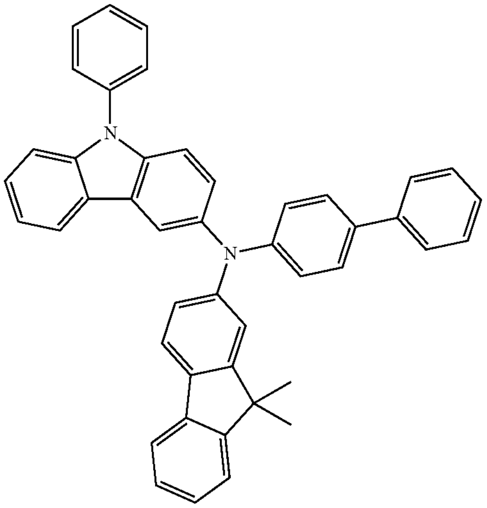
H-5
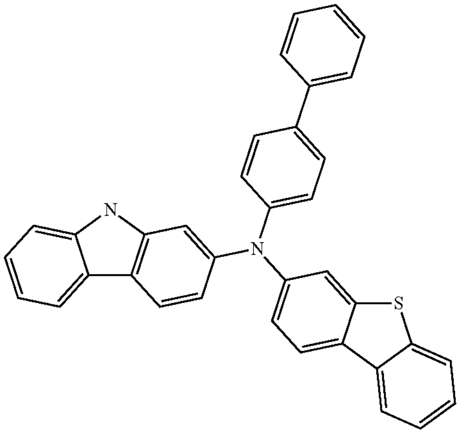
H-6
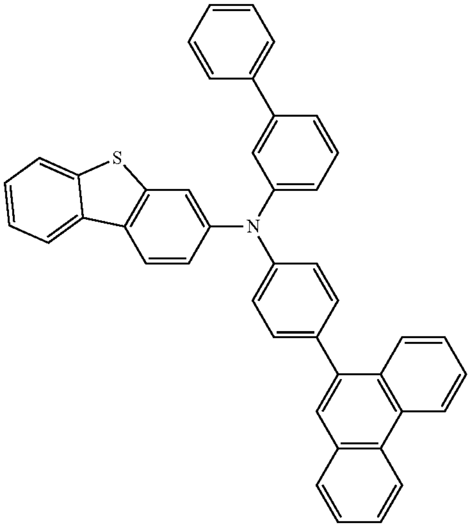
-continued
H-7
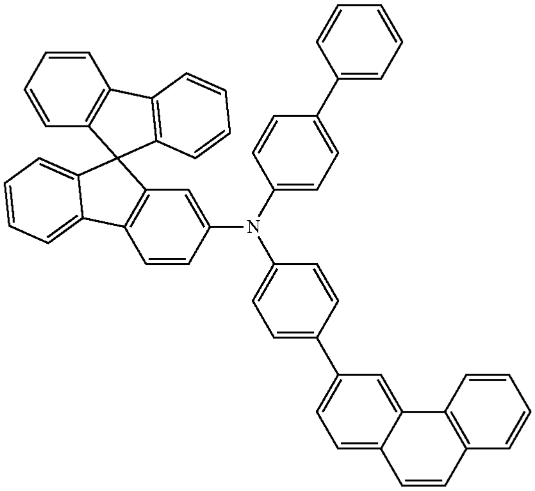
H-8
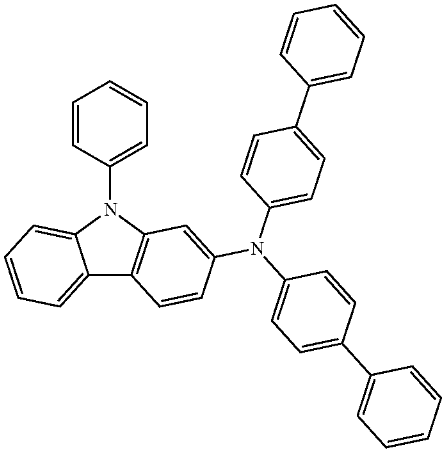
H-9
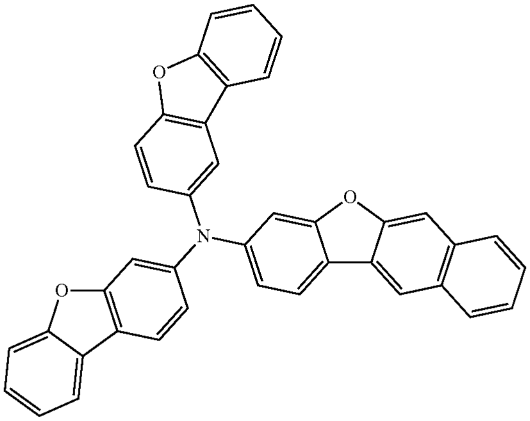

-continued
H-10
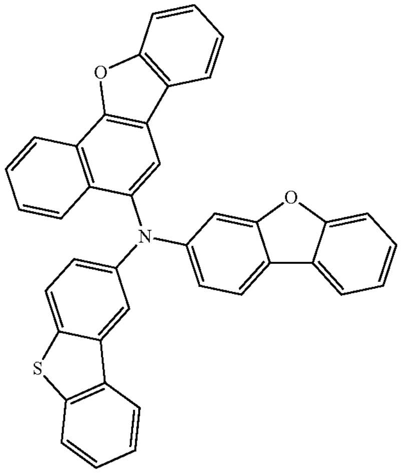
H-11
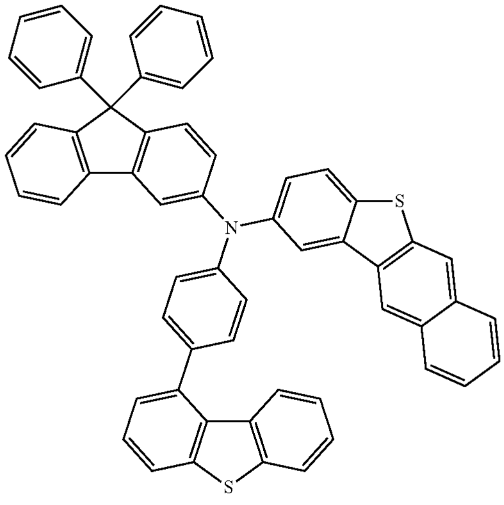
H-12
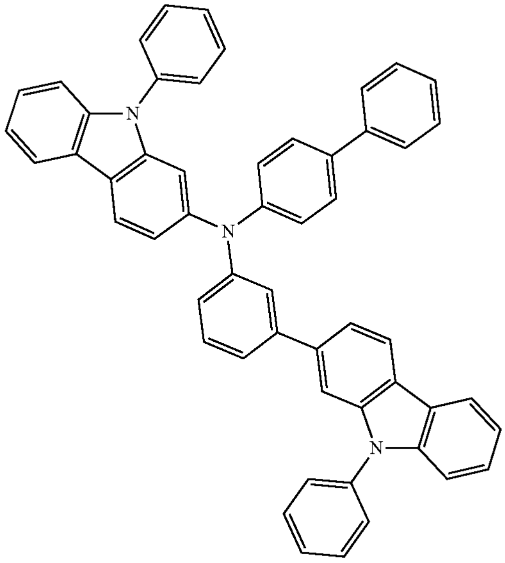
-continued
H-13
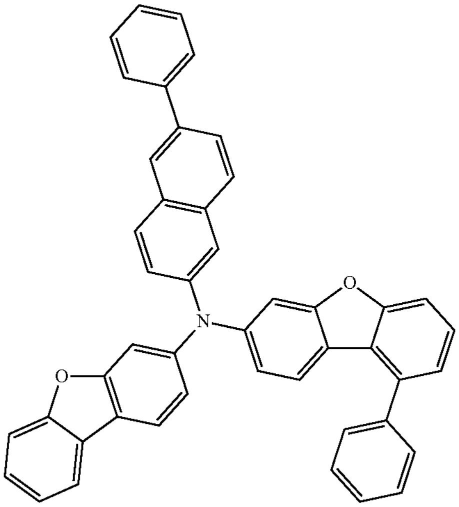
H-14
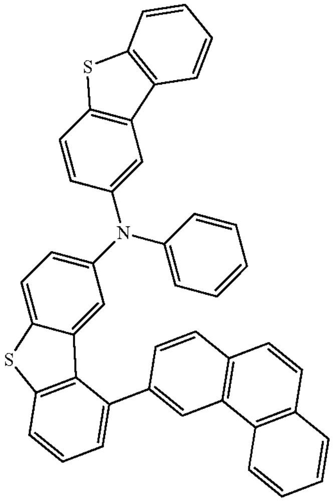
H-15
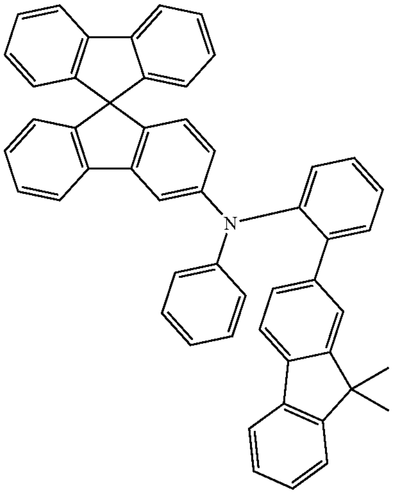

-continued
H-16
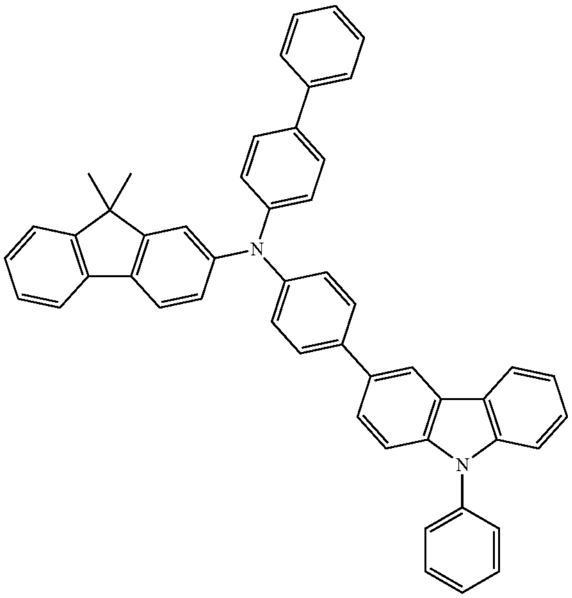
H-17
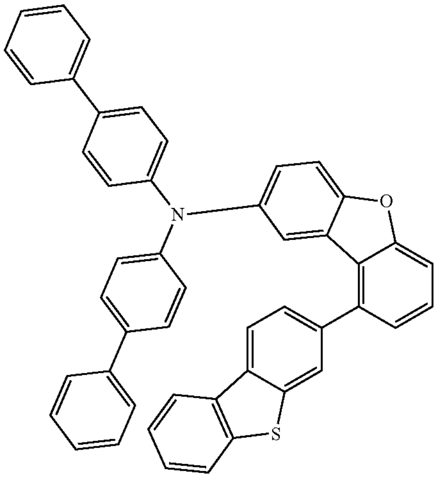
H-18
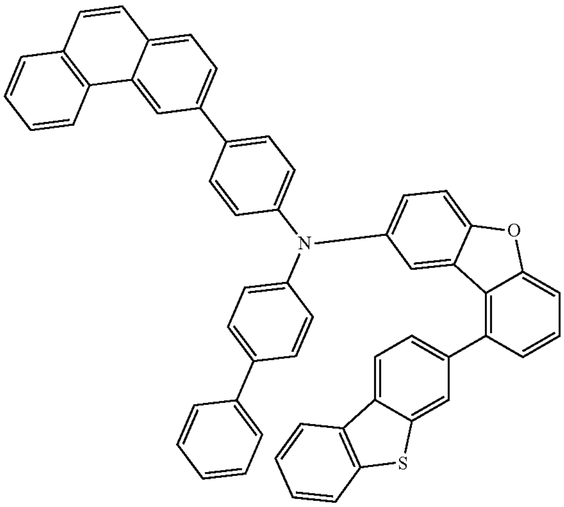
-continued
H-19
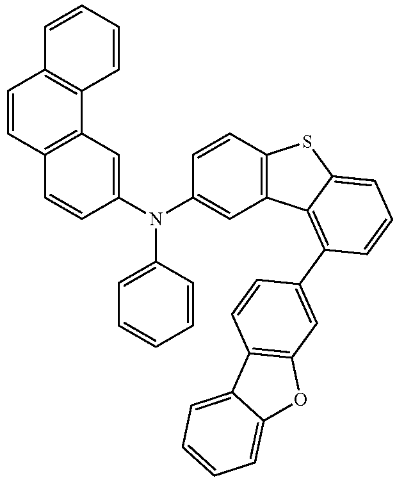
H-20
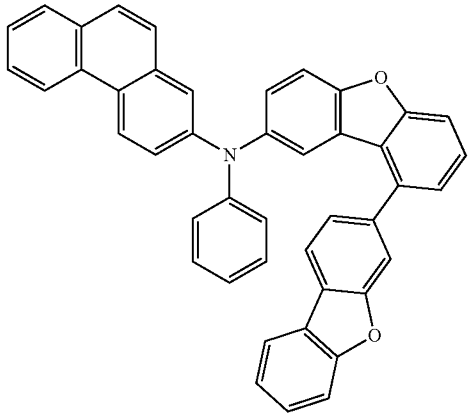
H-21
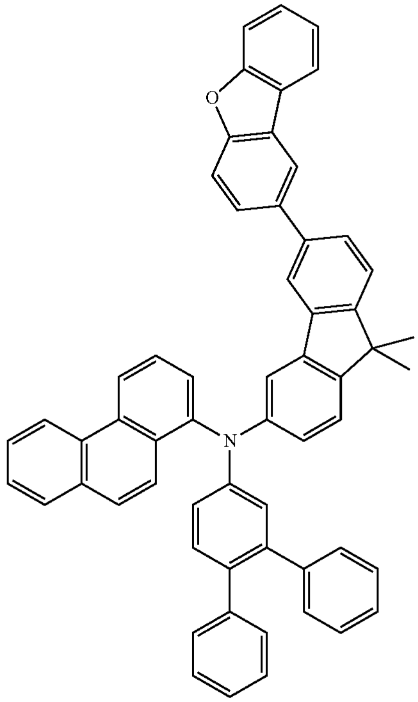

-continued
H-22
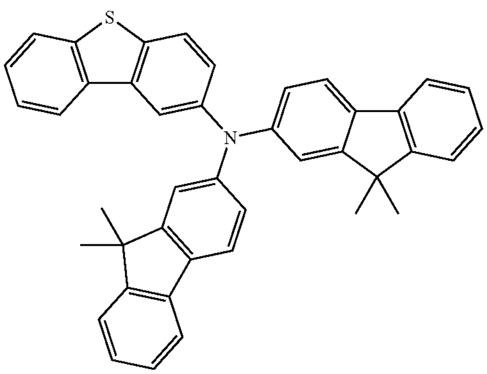
H-23
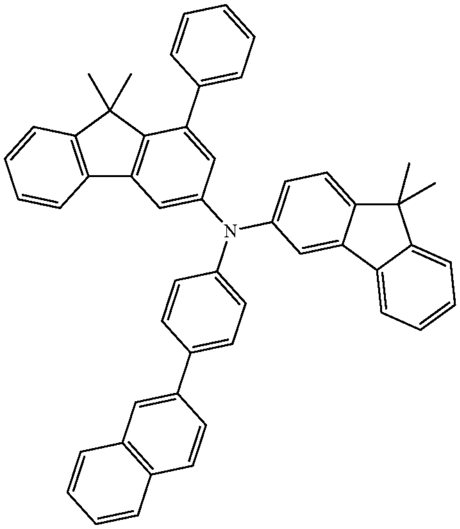
H-24
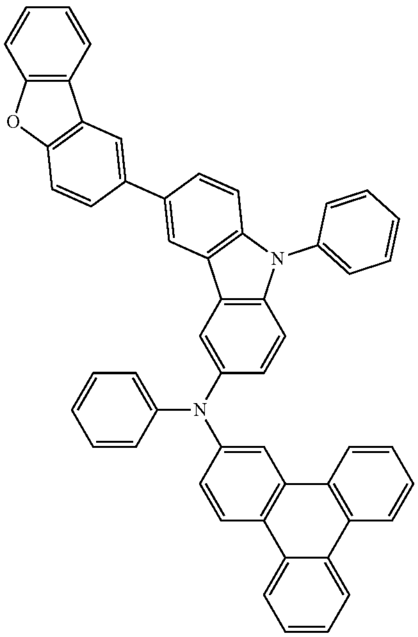
-continued
H-25
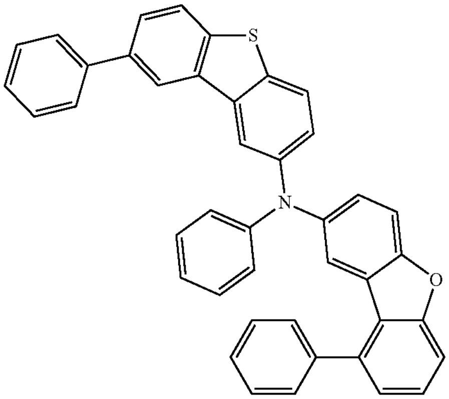
H-26
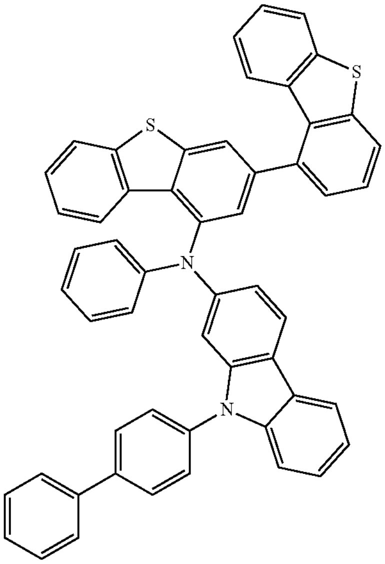
H-27
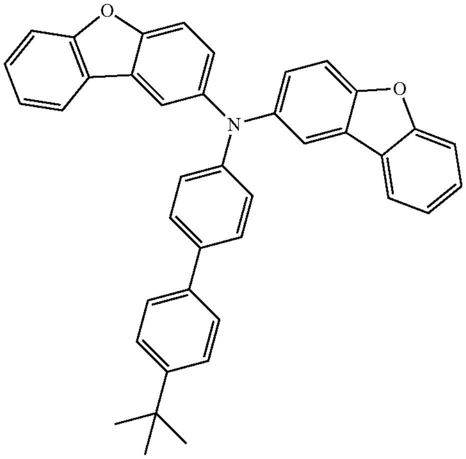

-continued
H-28
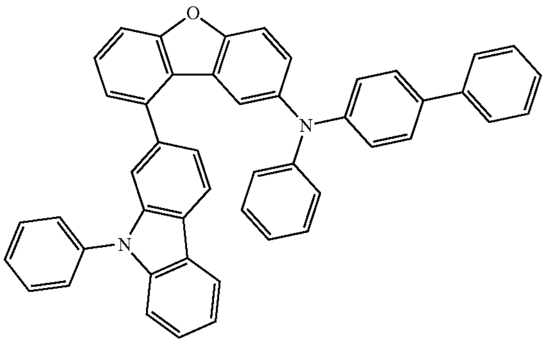
H-29
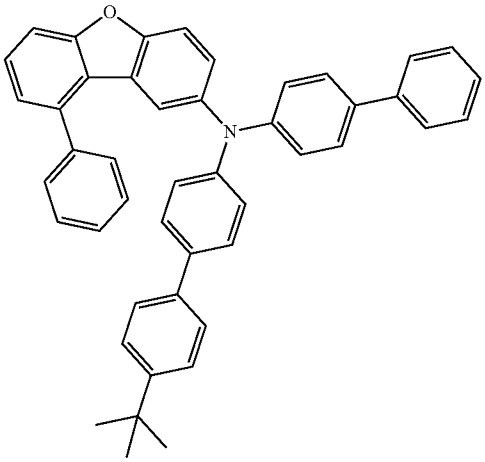
H-30
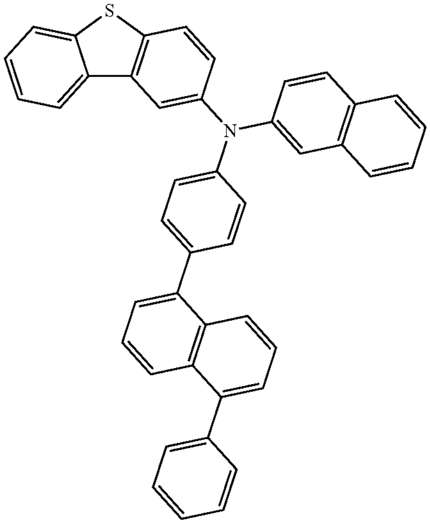
-continued
H-31
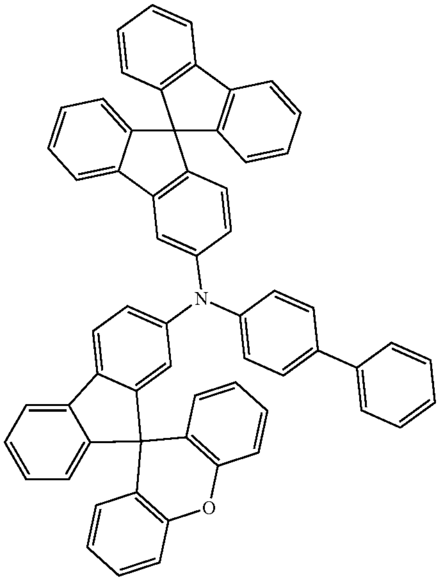
H-32
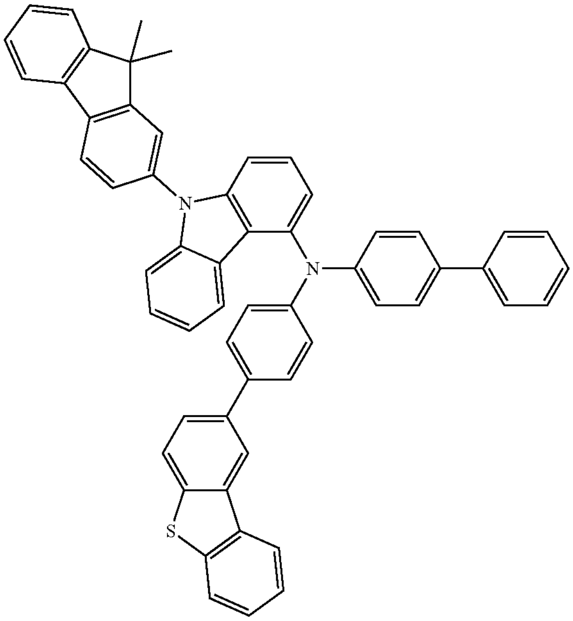
H-33
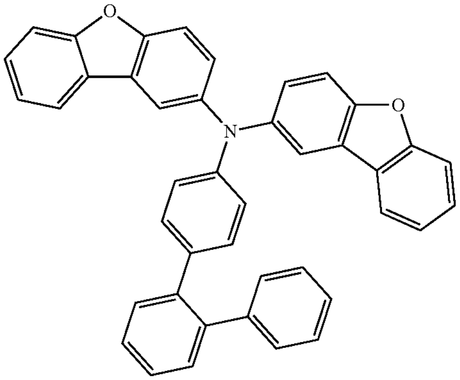

-continued
H-34
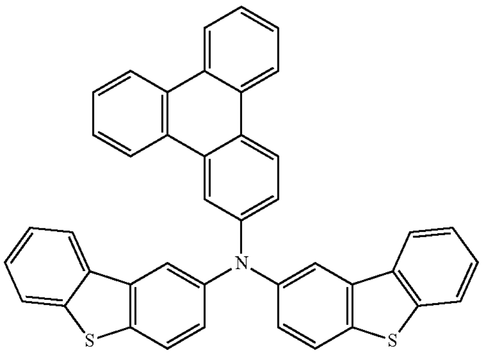
H-35
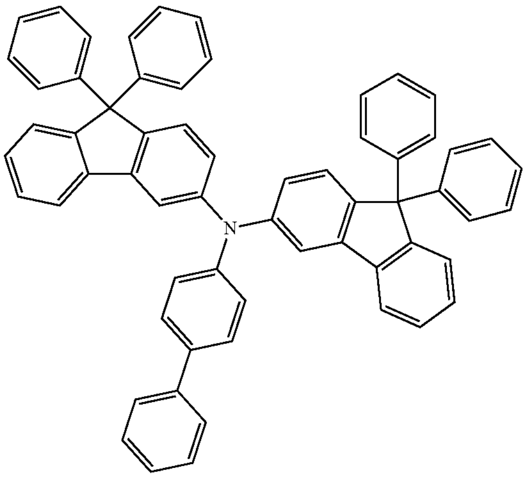
H-36
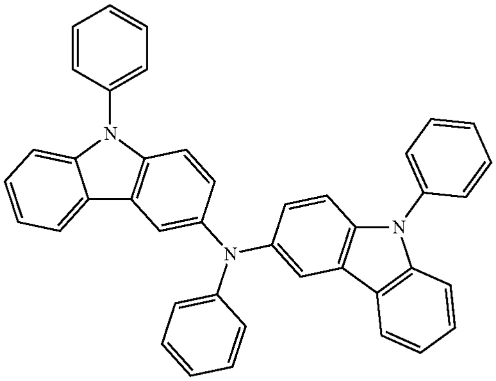
H-37
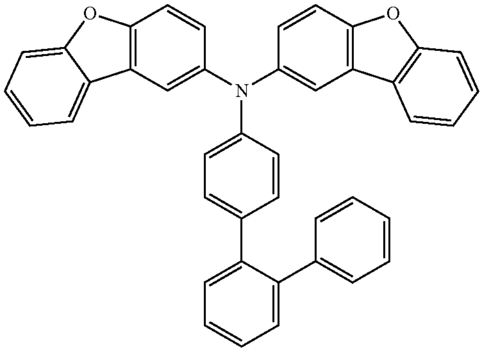
-continued
H-38
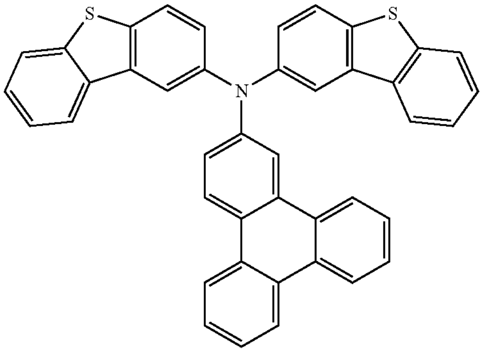
H-39
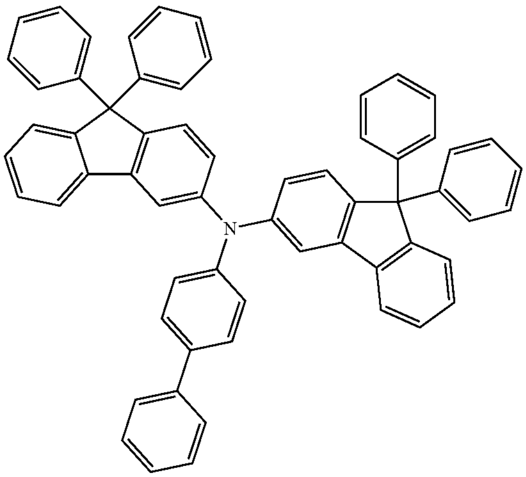
H-40
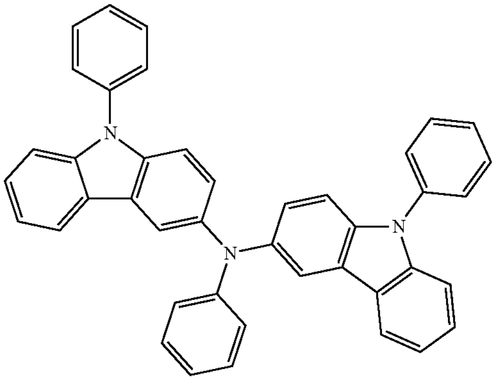

-continued
H-41
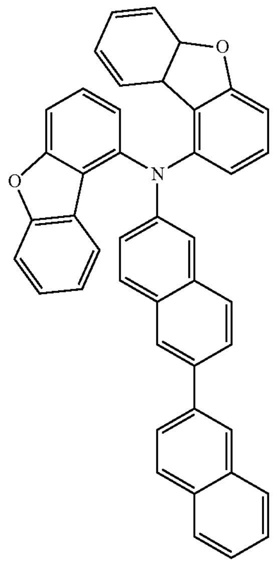
H-42
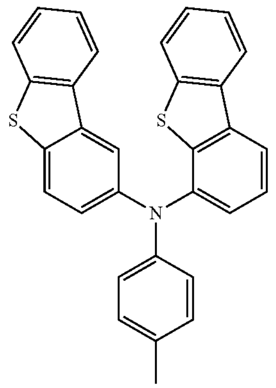
H-43
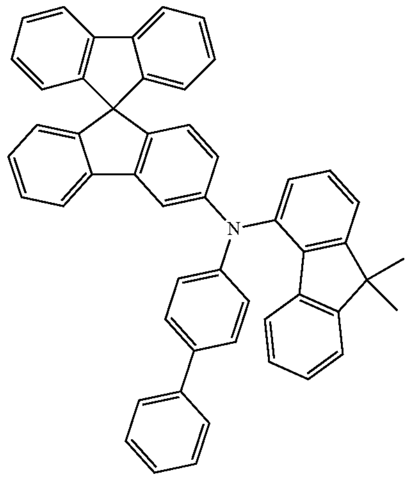
-continued
H-44
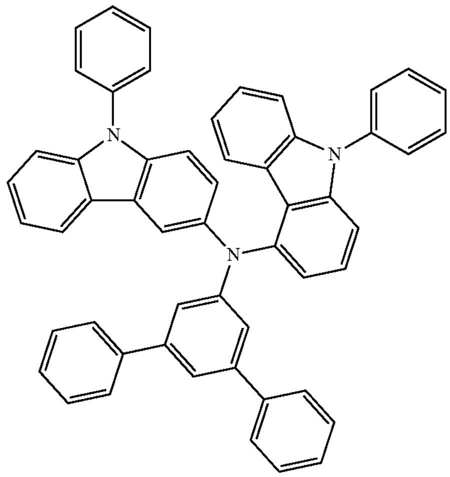
H-45
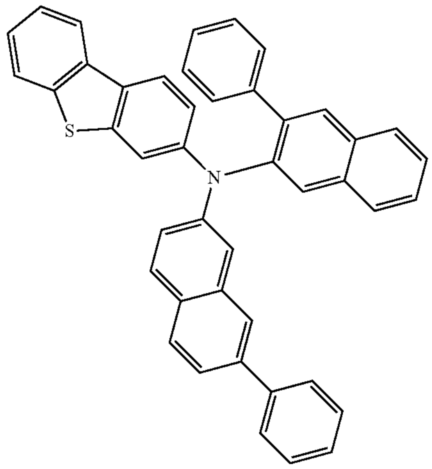
H-46
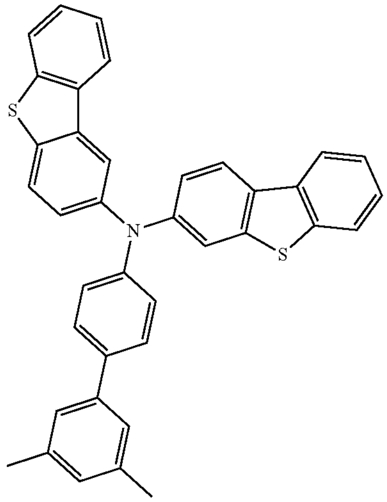

-continued
H-47
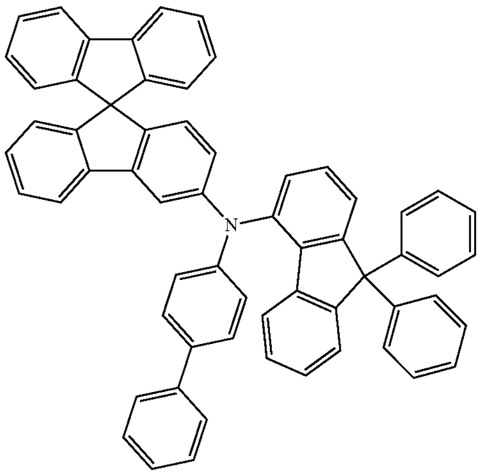
H-48
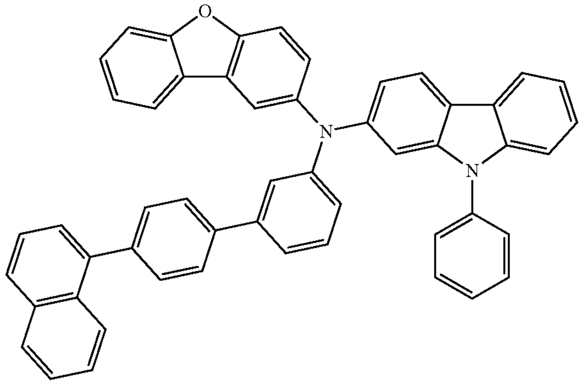
H-49
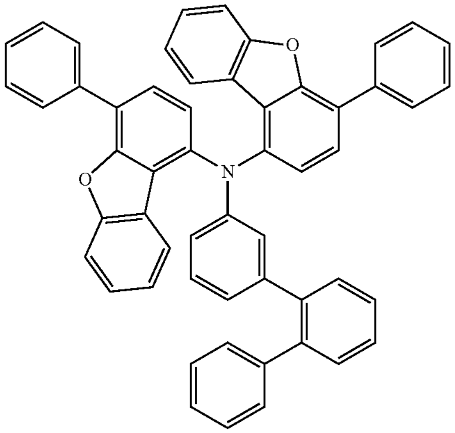
-continued
H-50
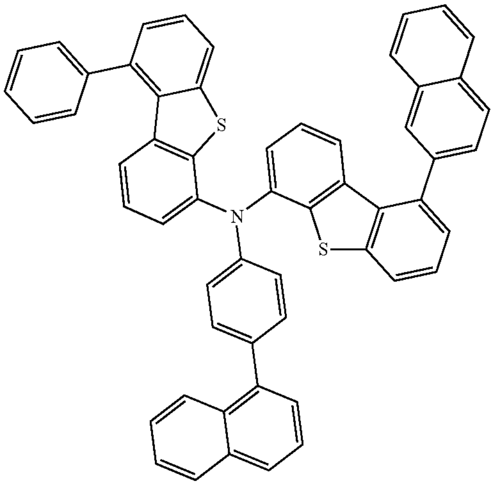
H-51
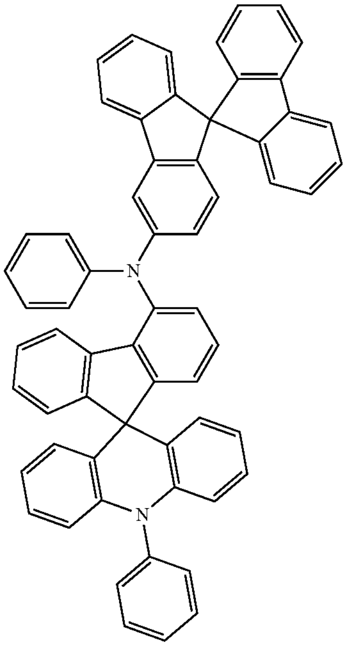

-continued
H-52
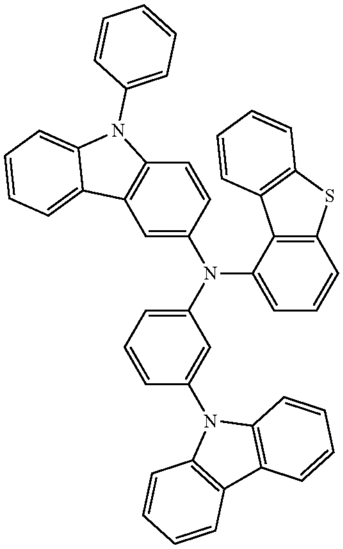
H-53
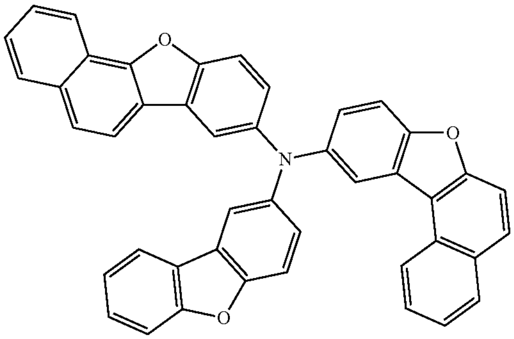
H-54
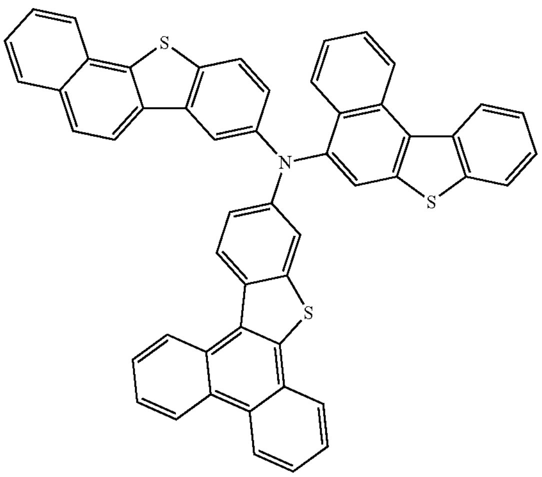
-continued
H-55
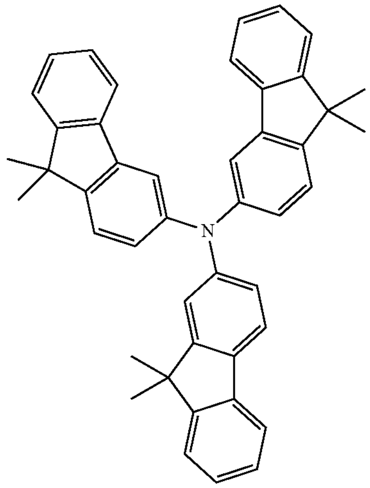
H-56
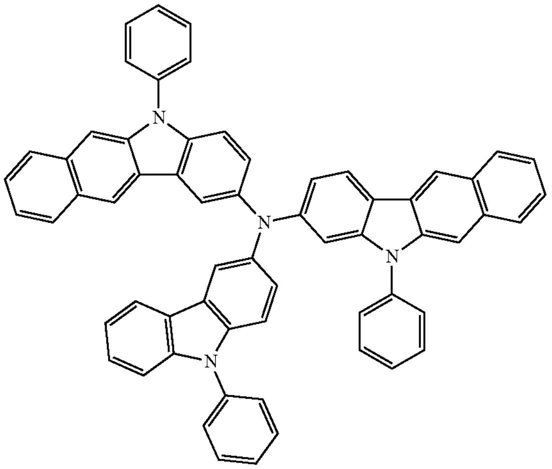
H-57
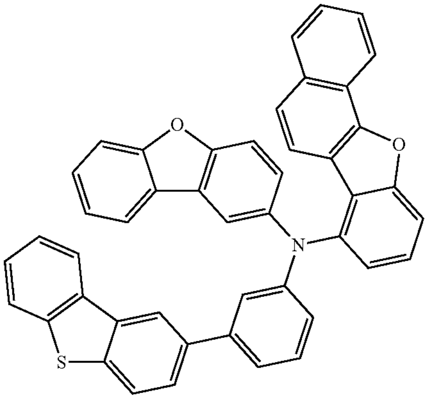

-continued
H-58
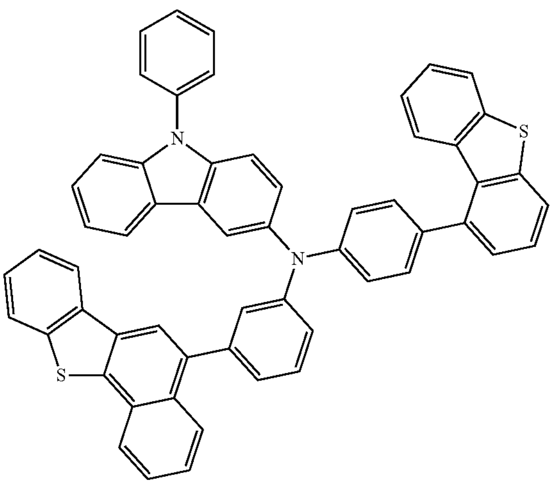
H-59
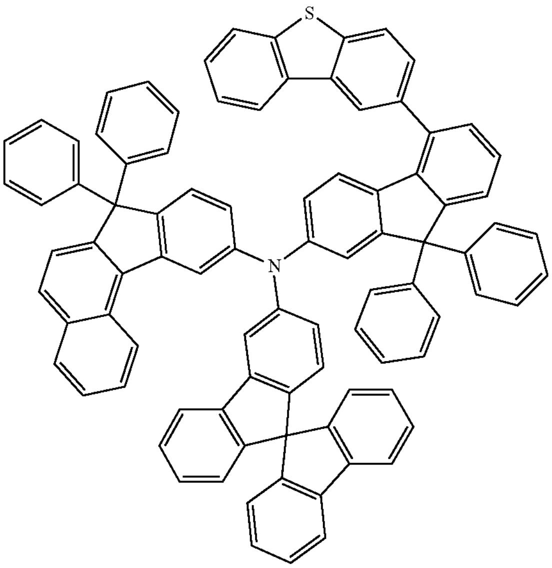
H-60
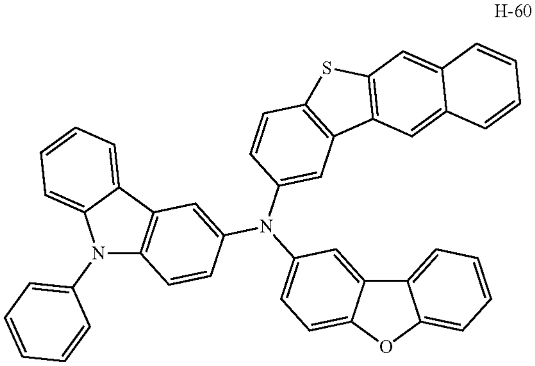
-continued
H-61
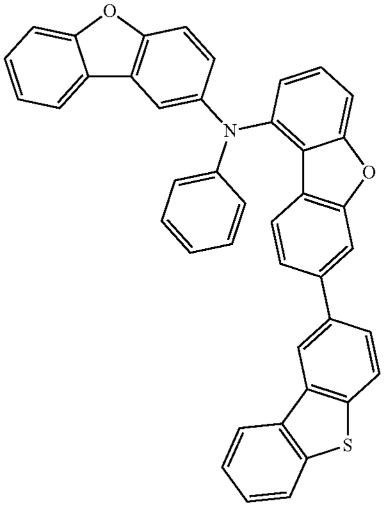
H-62
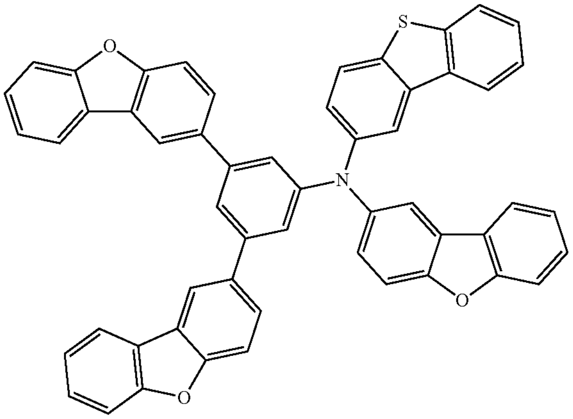
H-63
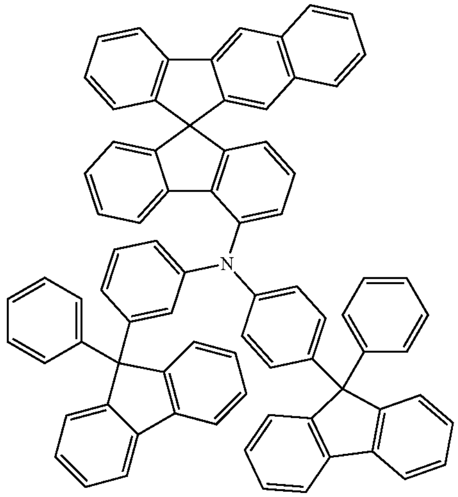

H-64
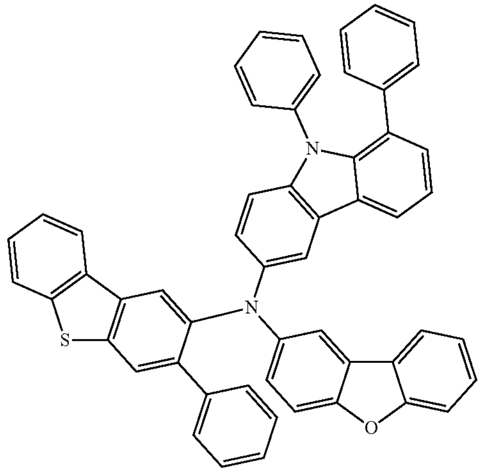
H-65
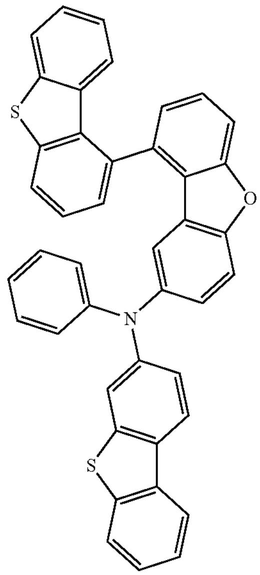
H-66
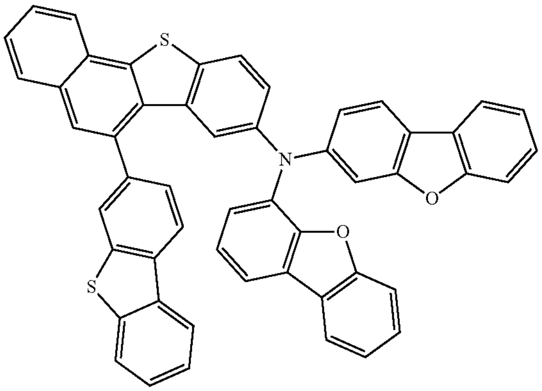
H-67
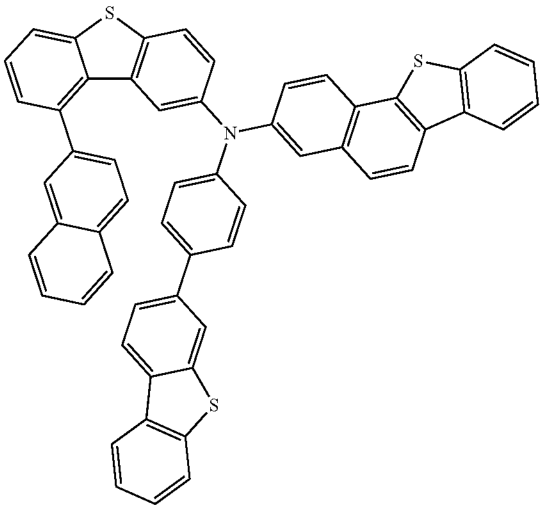
H-68
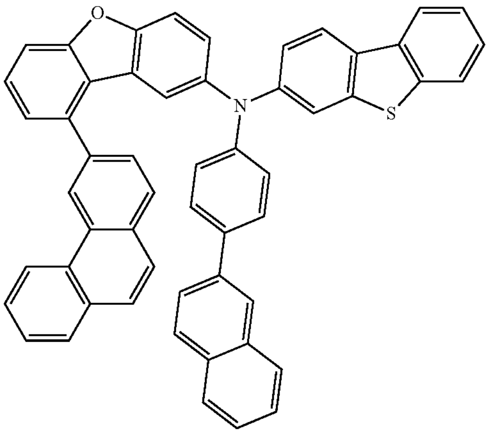
H-69
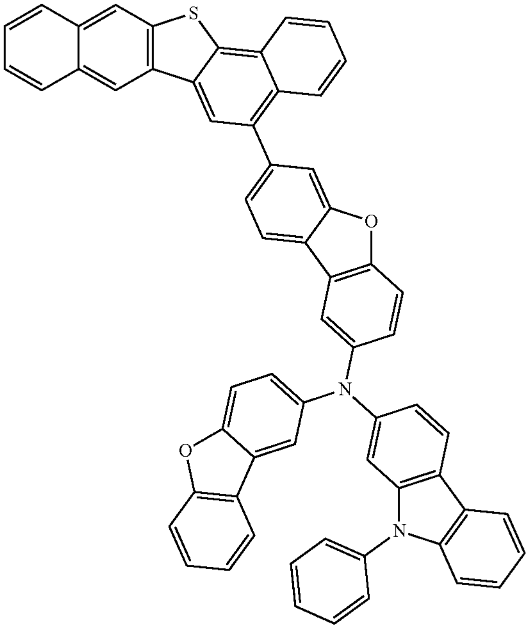

-continued
H-70
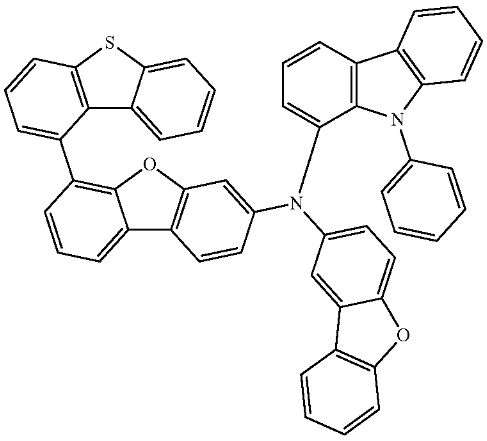
H-71
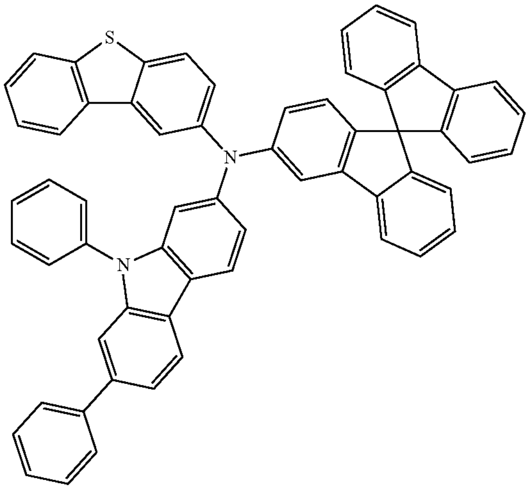
H-72
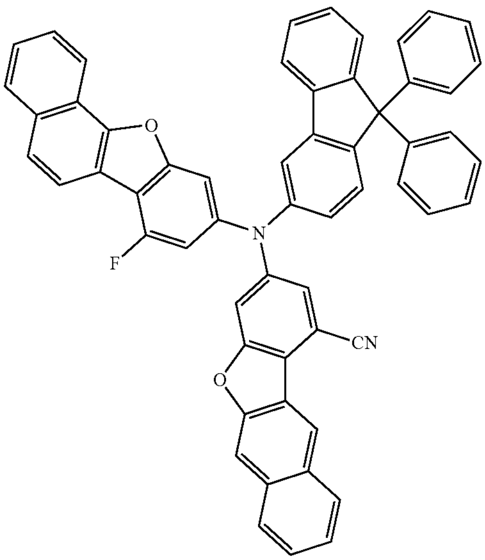
-continued
H-73
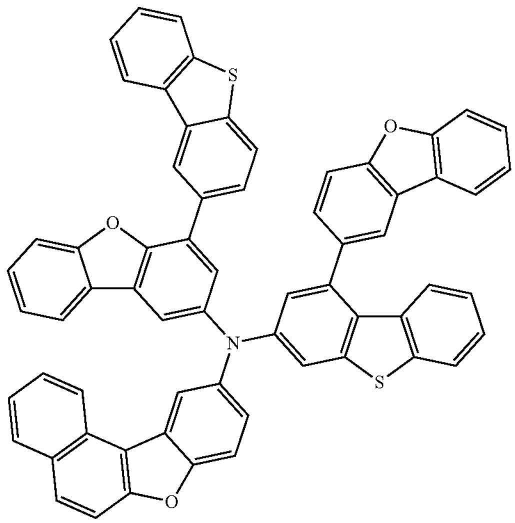
H-74
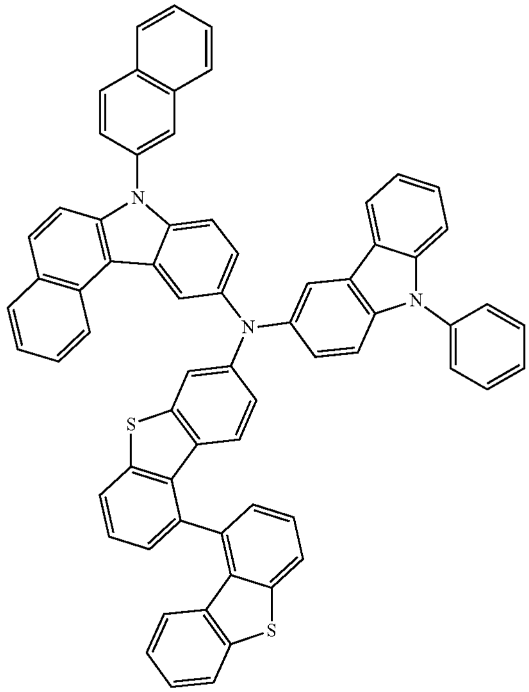

-continued
H-75
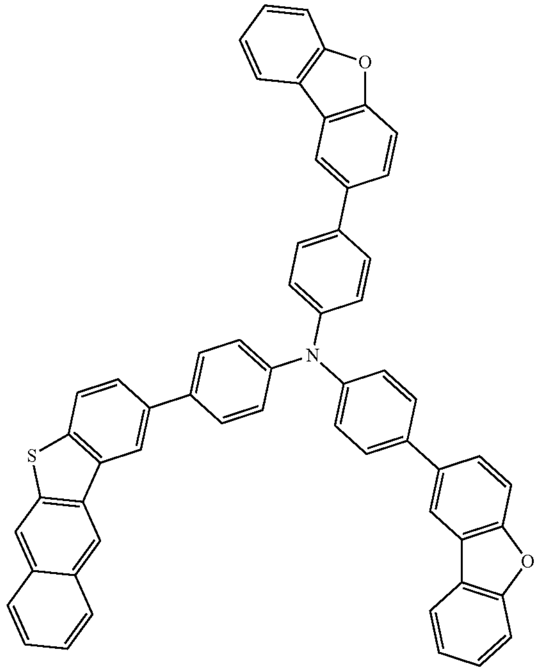
H-76
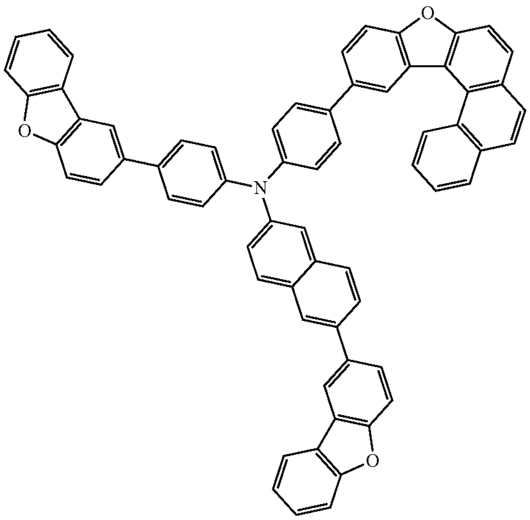
-continued
H-77
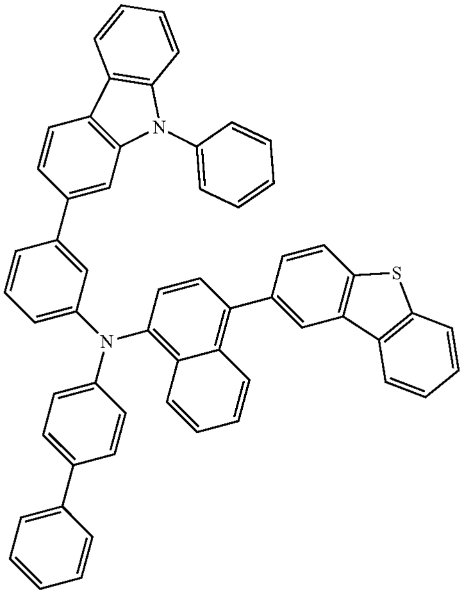
H-78
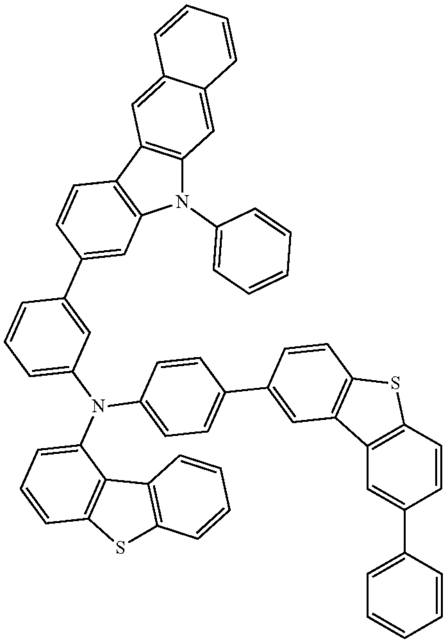

-continued
H-79
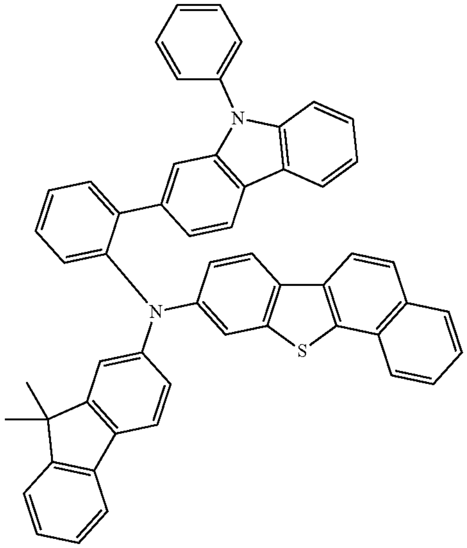
H-80
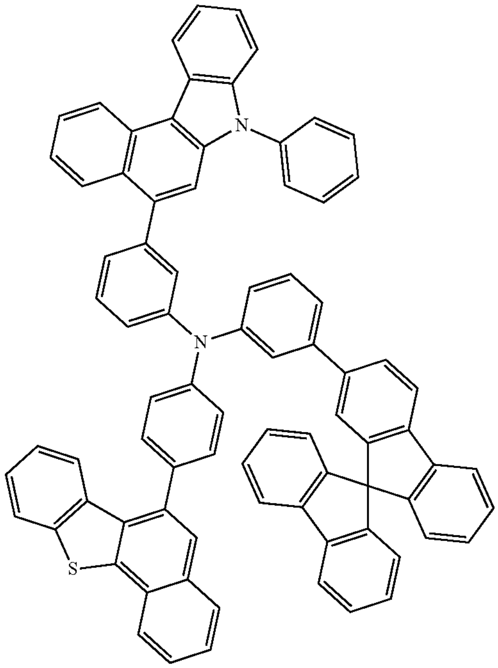
-continued
H-81
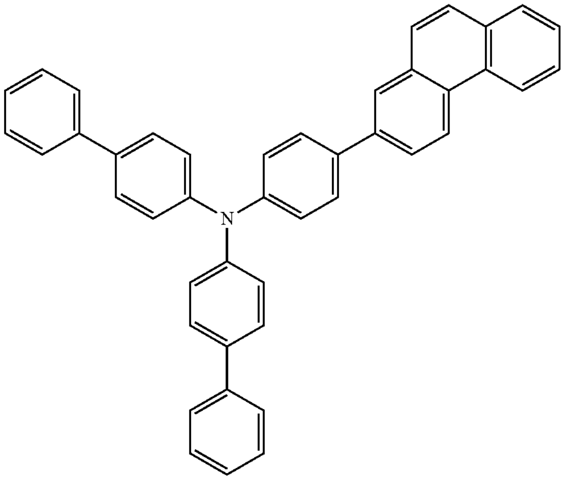
H-82
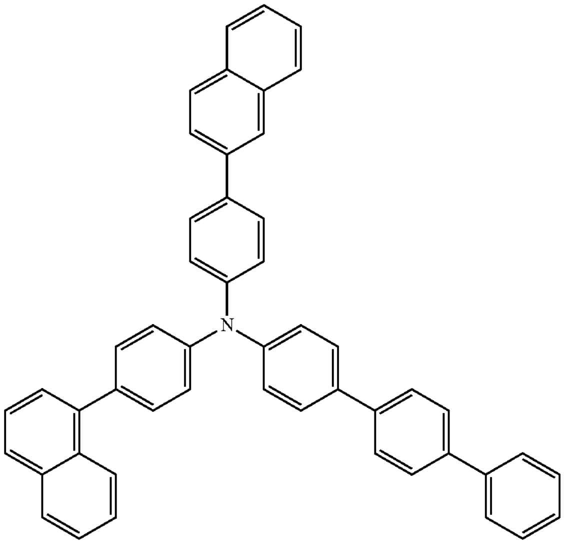

-continued
H-83
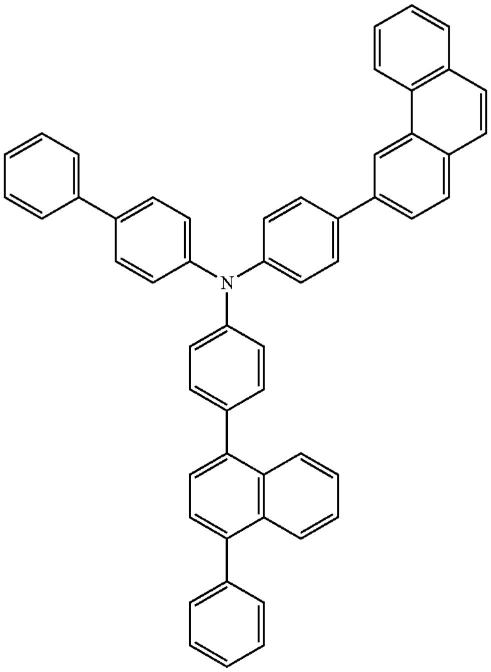
H-84
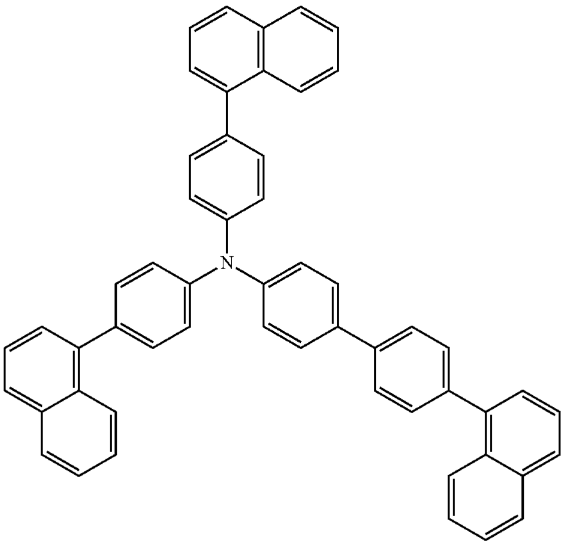
-continued
H-85
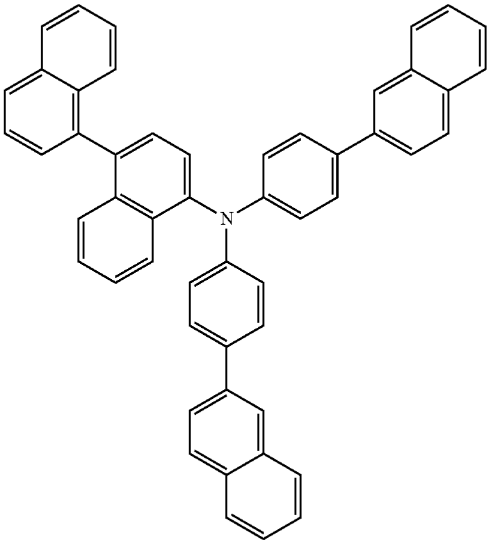
H-86
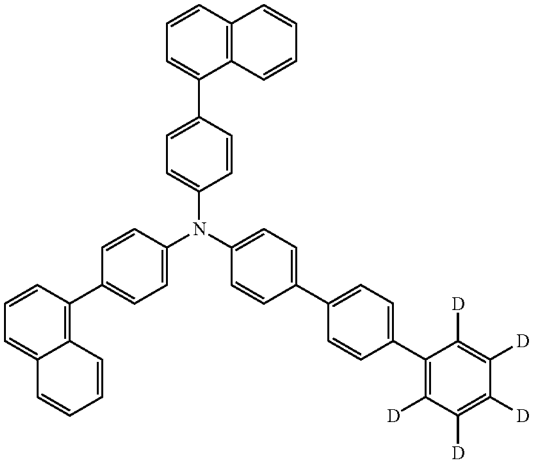
H-87
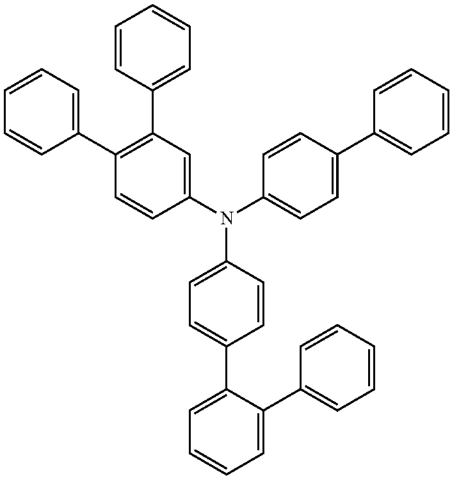

-continued
H-88
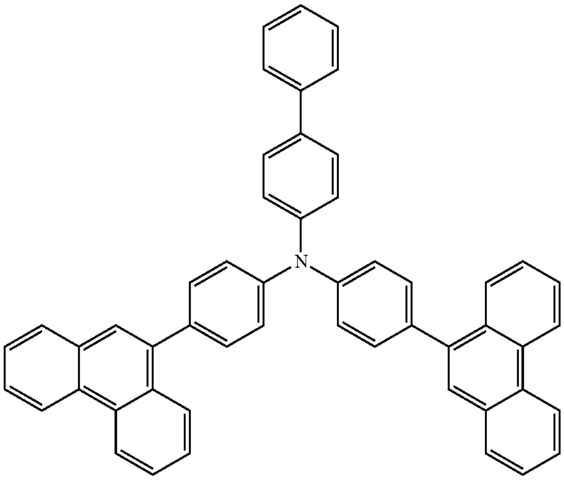
H-89
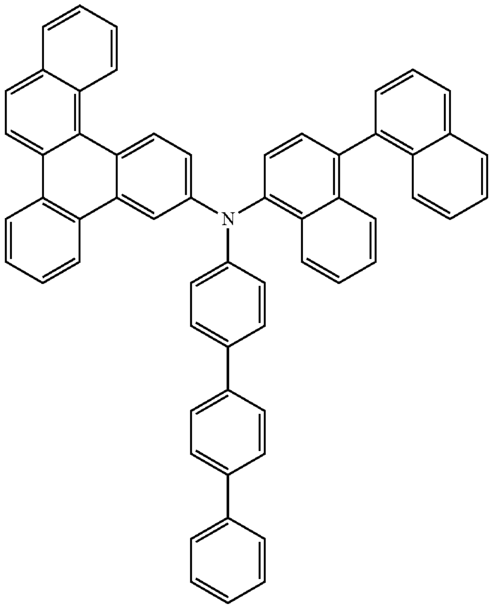
H-90
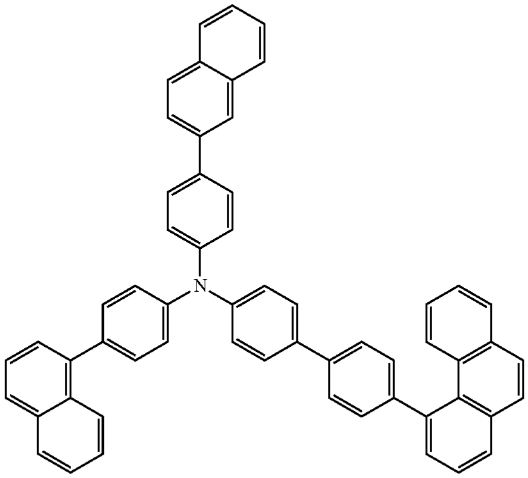
-continued
H-91
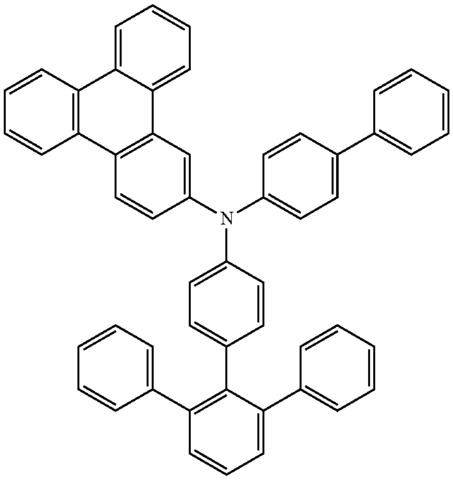
H-92
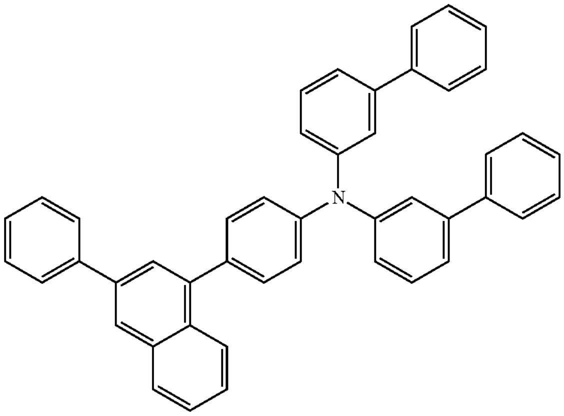
H-93
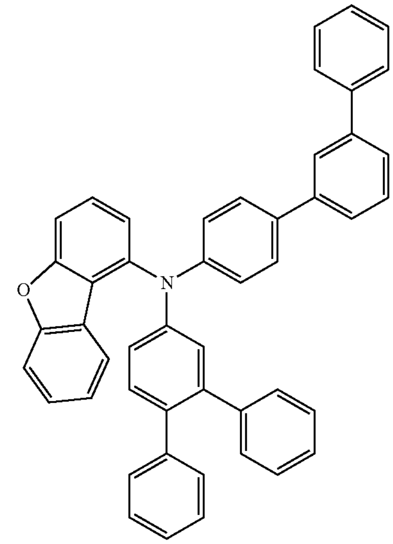

-continued
H-94
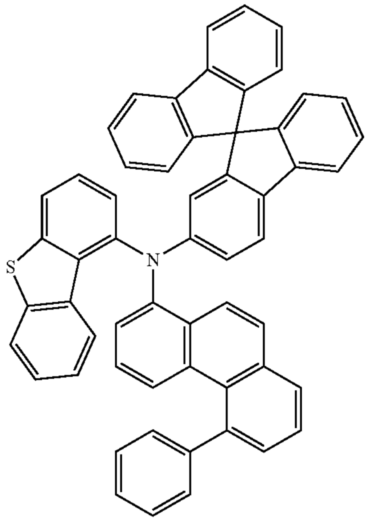
H-95
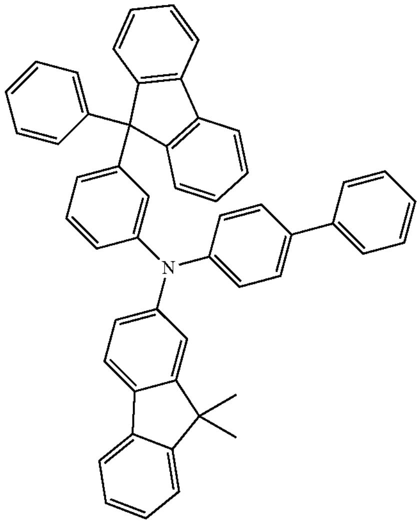
H-96
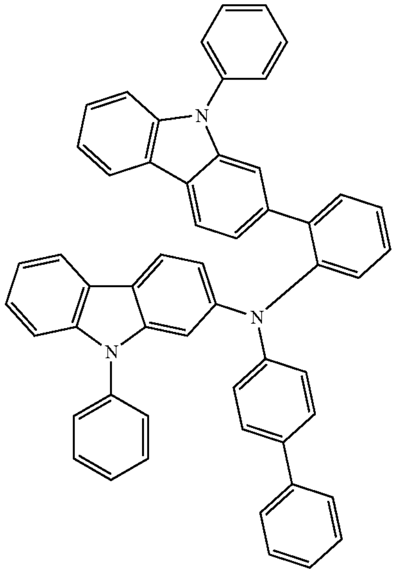
-continued
H-97
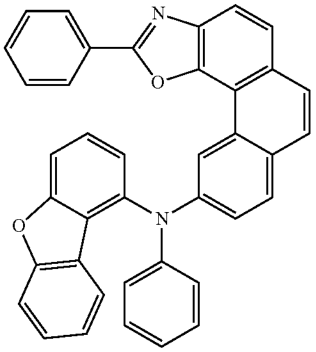
H-98
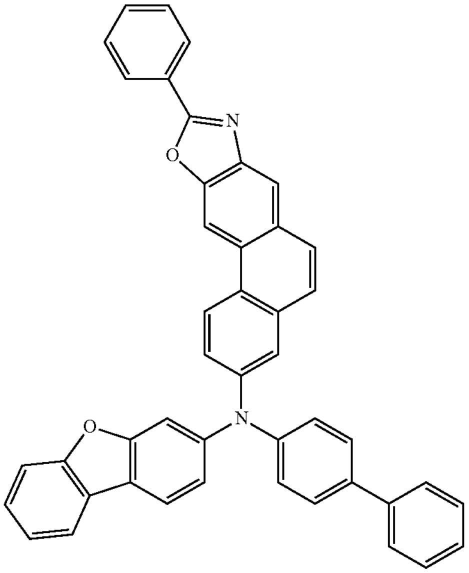
H-99
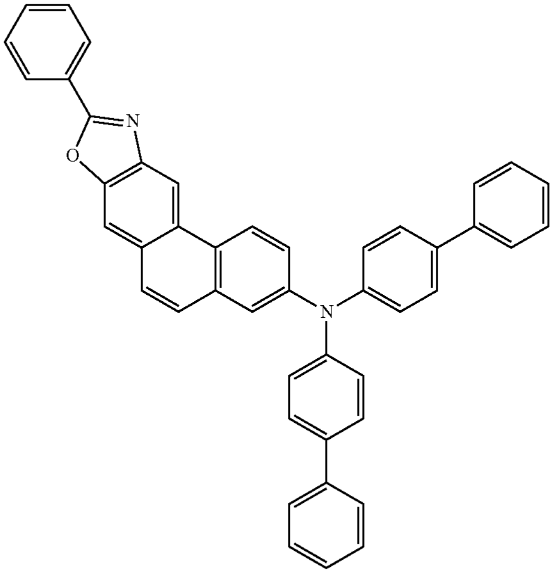

-continued
H-100
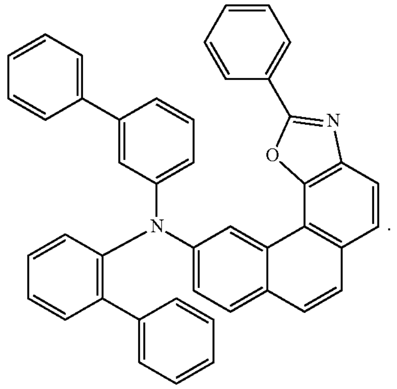
5. The organic electronic element of claim 1, wherein Formula 5 is represented by any one of compounds S-1 to S-108:
S-1
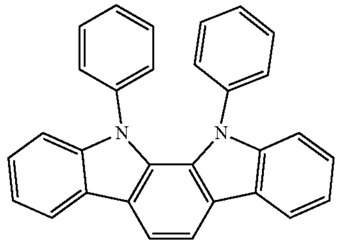
S-2
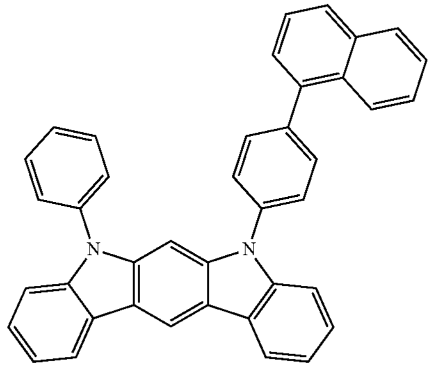
S-3
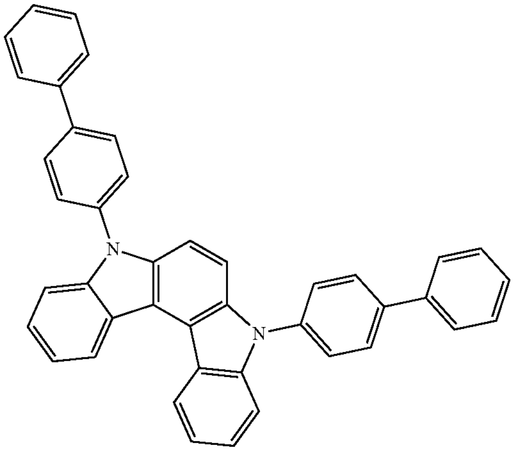
-continued
S-4
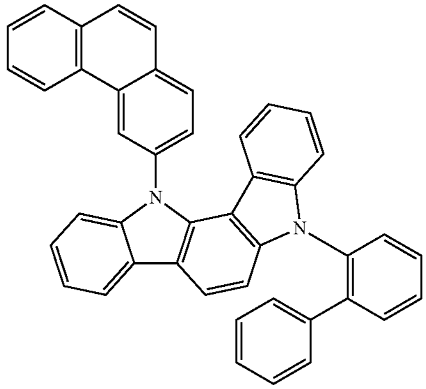
S-5
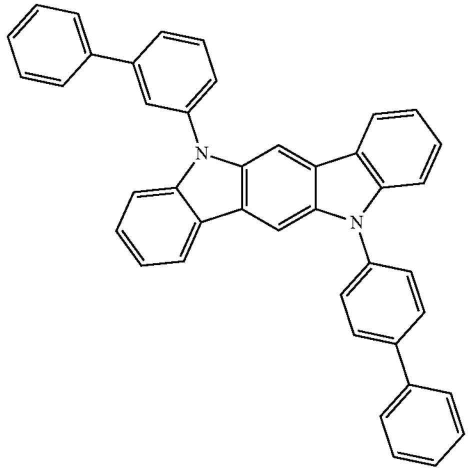
S-6
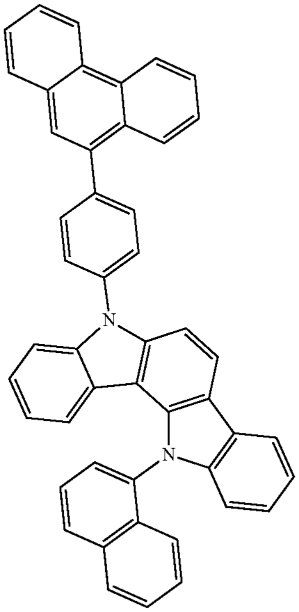

-continued
S-7
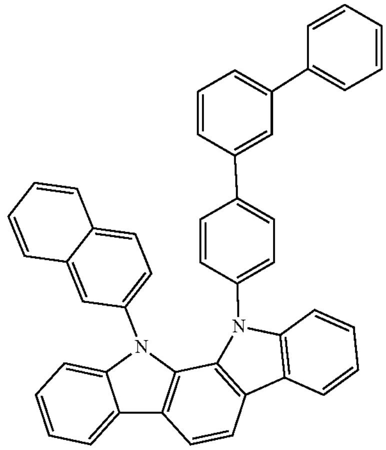
S-8
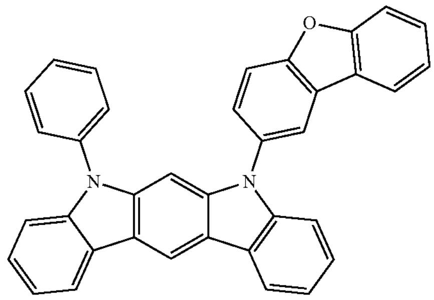
S-9
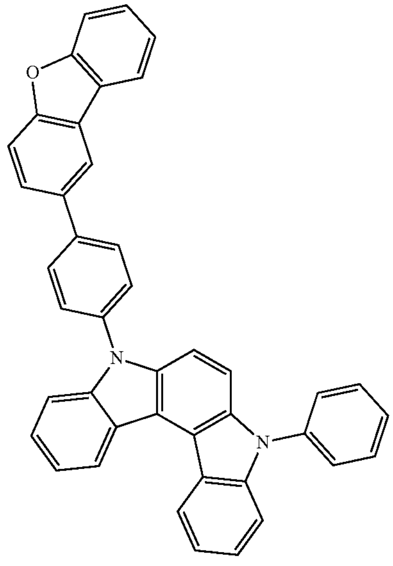
-continued
S-10
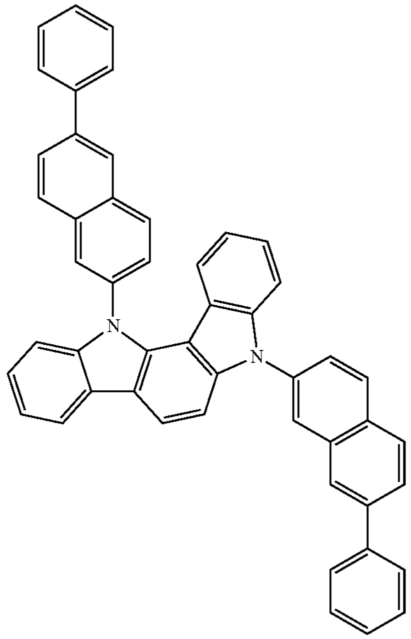
S-11
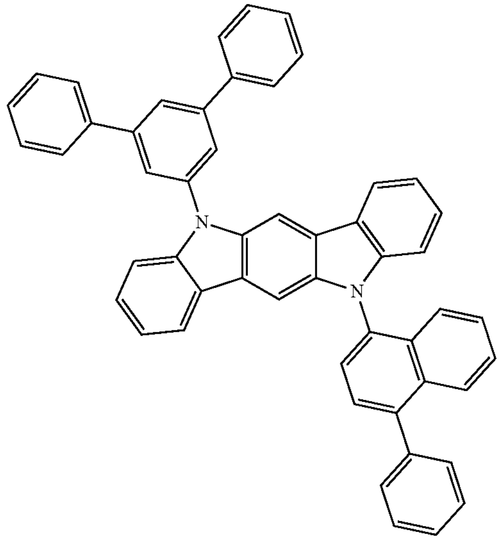

-continued
S-12
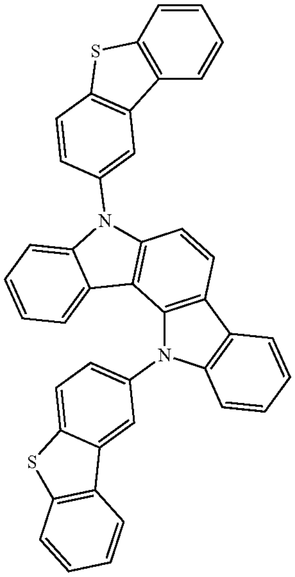
S-13
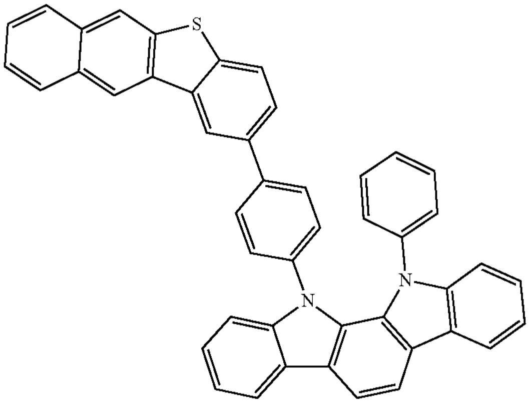
S-14
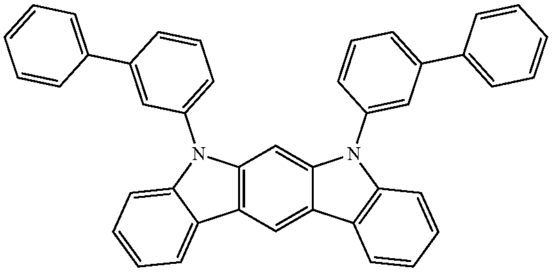
S-15
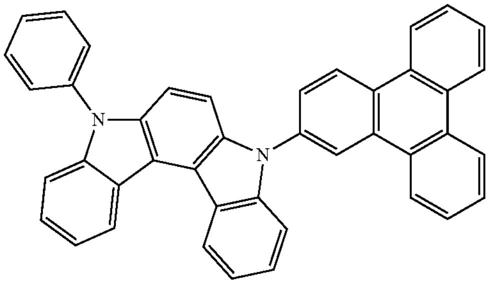
-continued
S-16
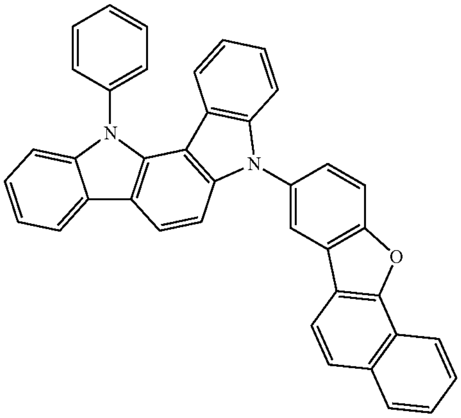
S-17
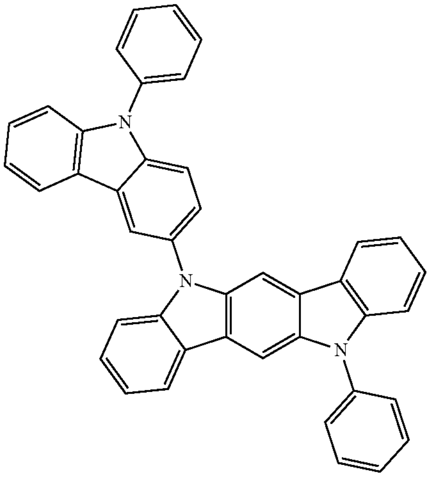
S-18
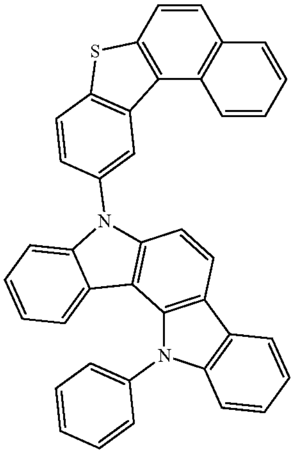

-continued
S-19
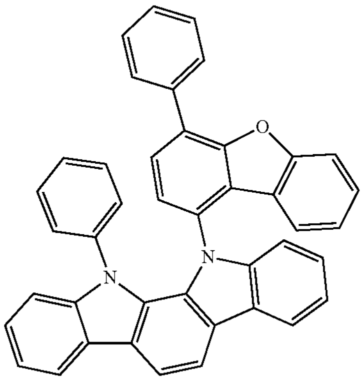
S-20
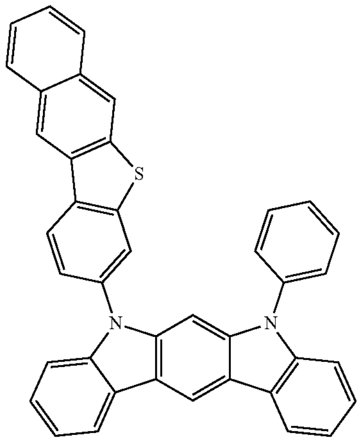
S-21
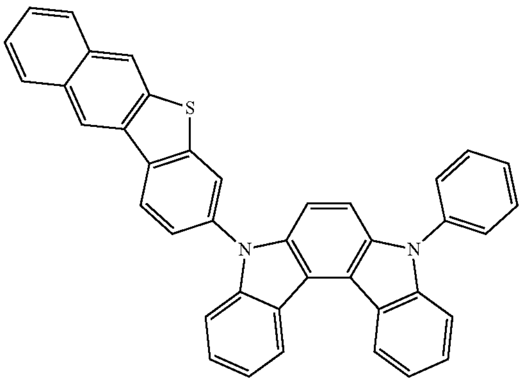
-continued
S-22
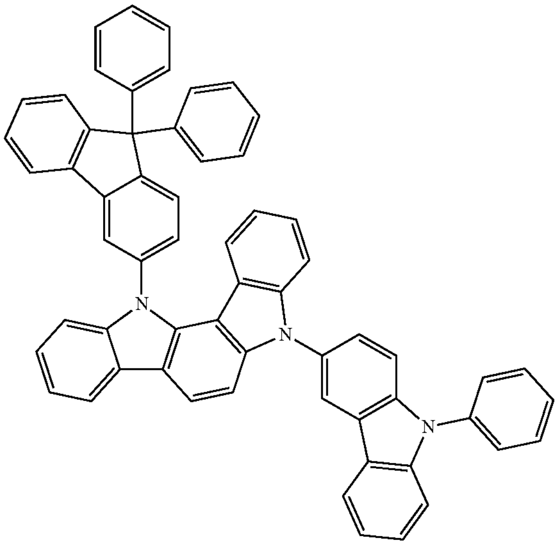
S-23
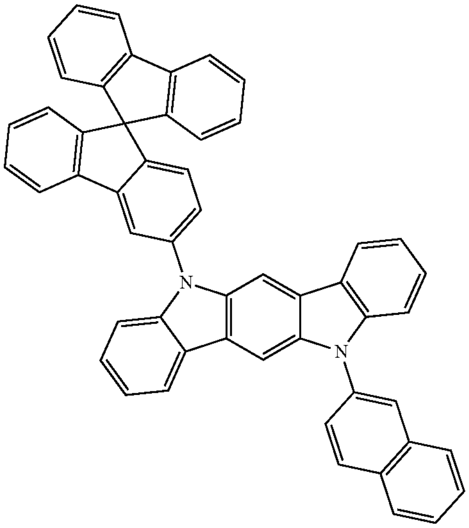

-continued
S-24
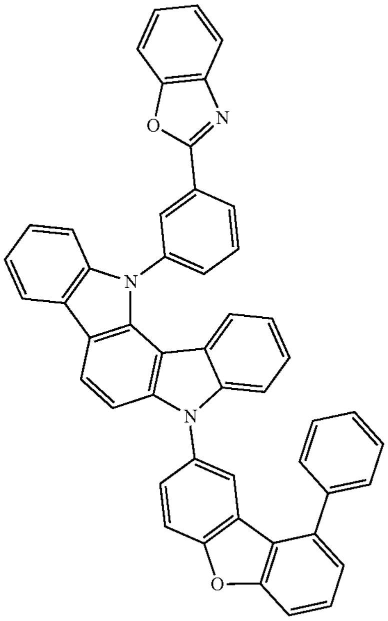
S-25
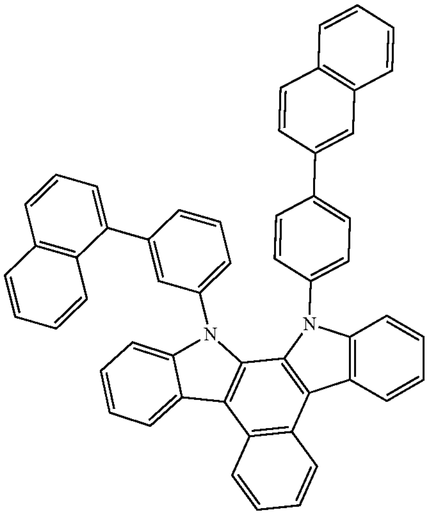
S-26
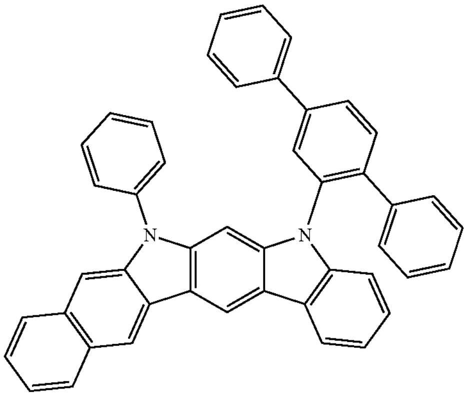
-continued
S-27
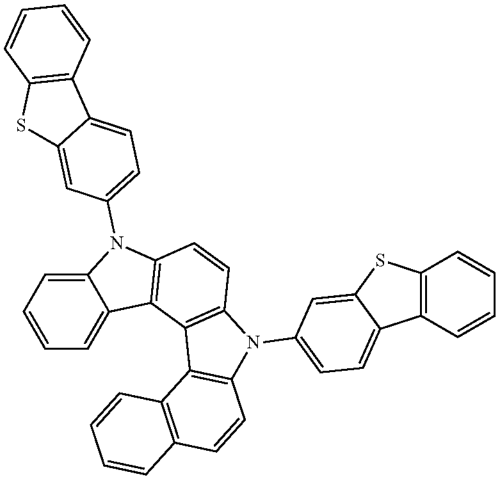
S-28
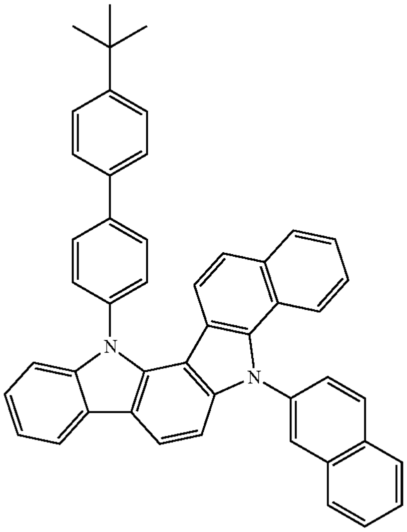
S-29
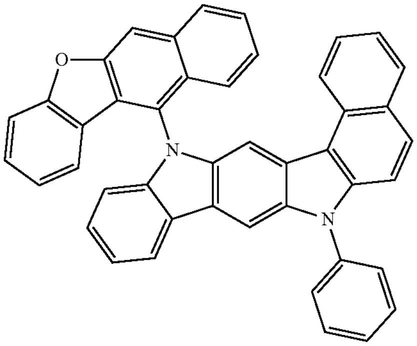

-continued
S-30
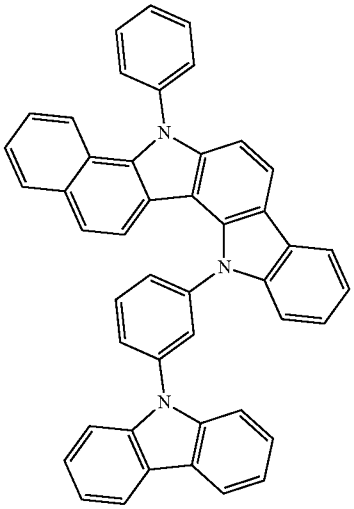
S-31
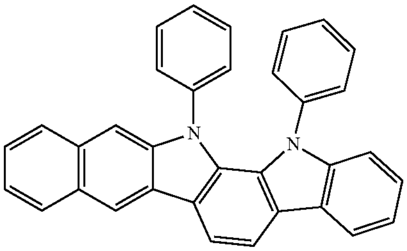
S-32
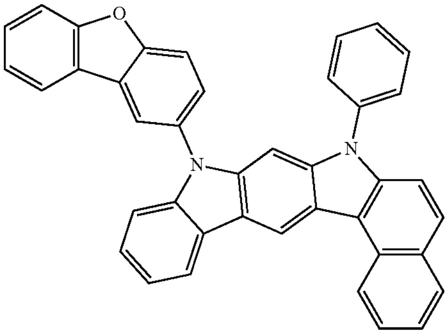
S-33
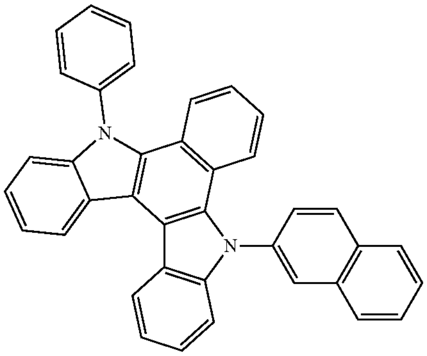
-continued
S-34
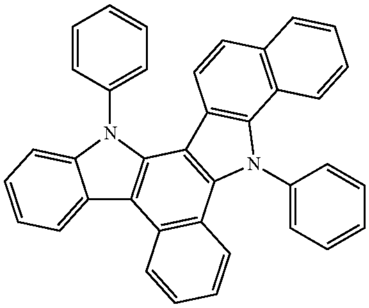
S-35
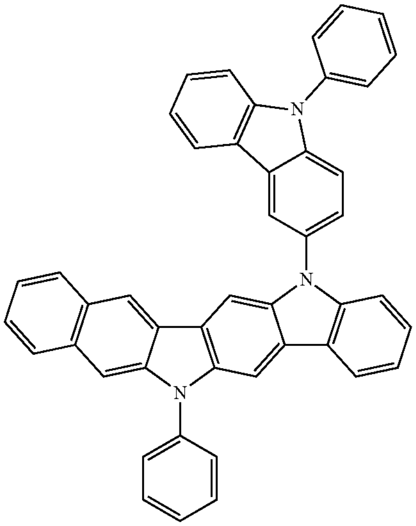
S-36
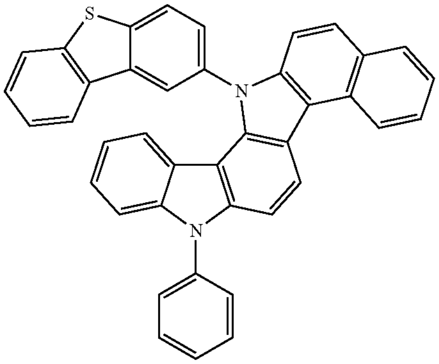
S-37
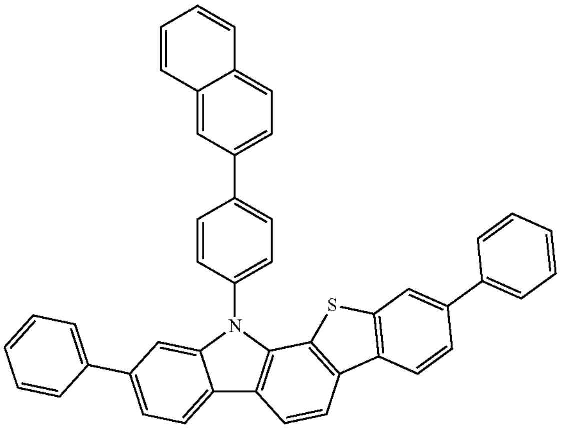

-continued
S-38
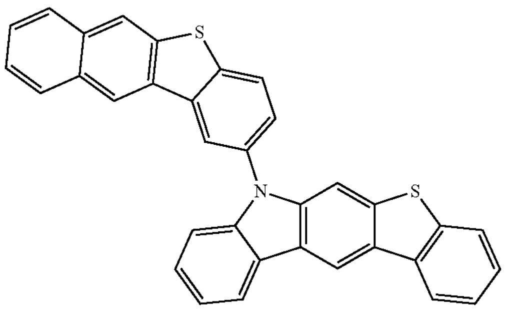
S-39
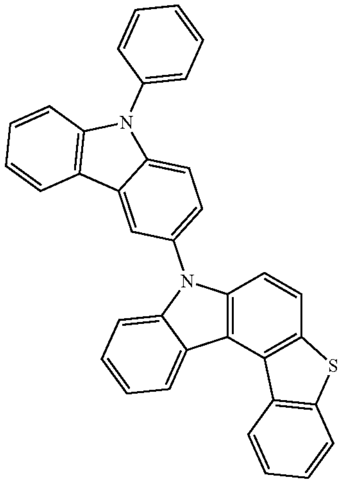
S-40
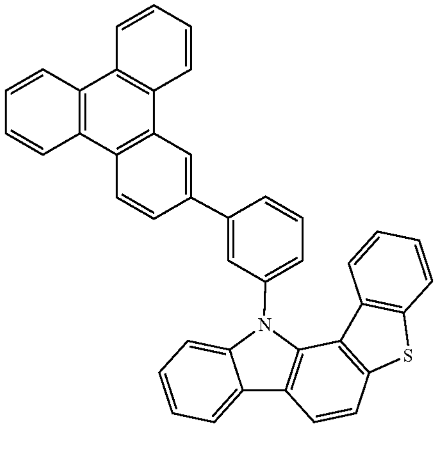
-continued
S-41
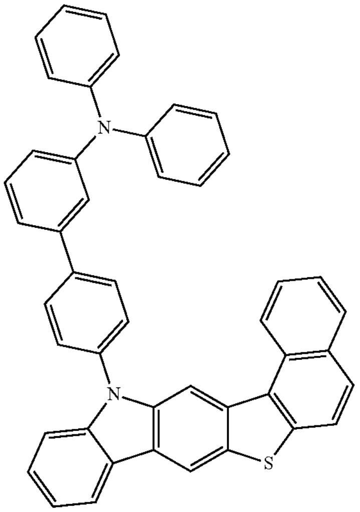
S-42
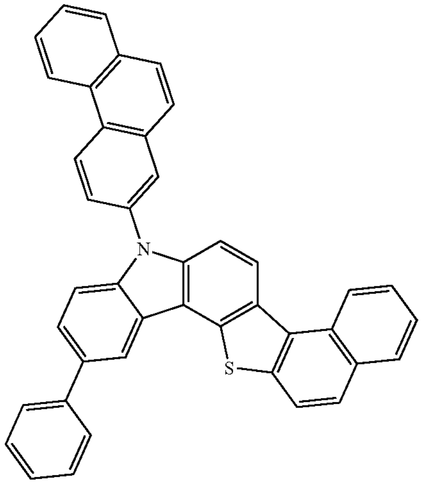
S-43
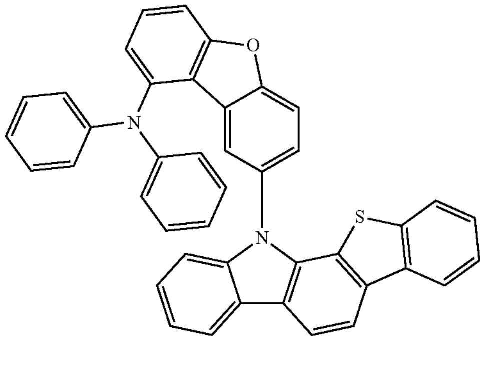

-continued
S-44
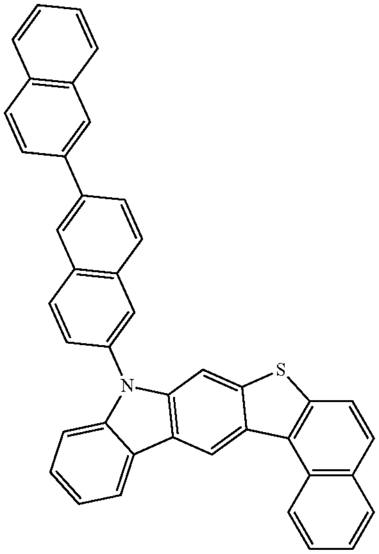
S-45
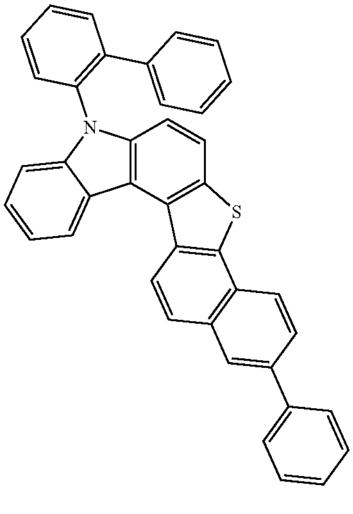
S-46
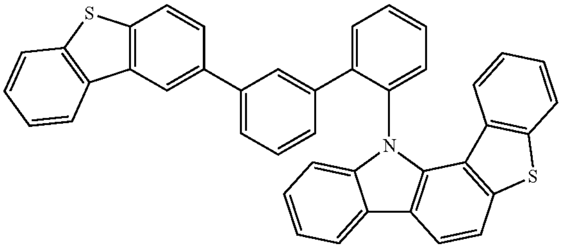
-continued
S-47
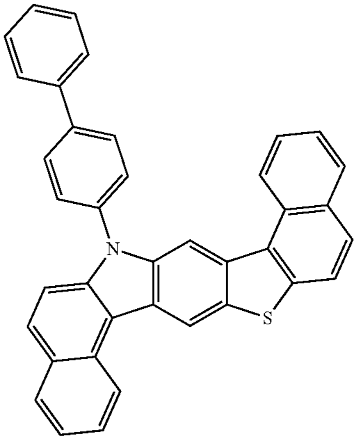
S-48
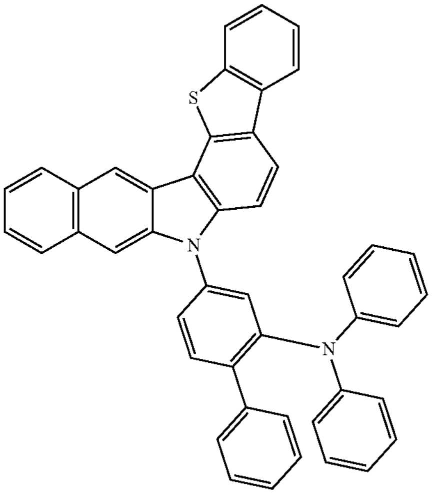
S-49
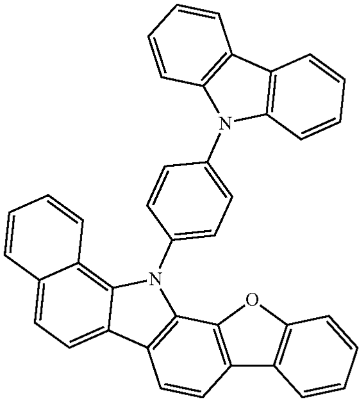

S-50
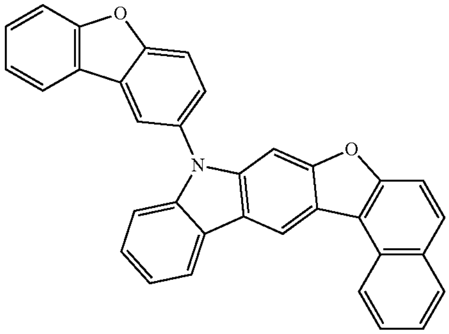
S-51
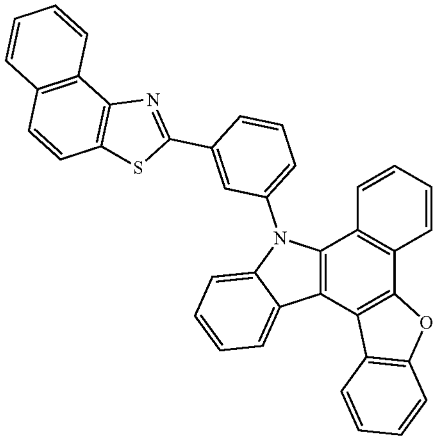
S-52
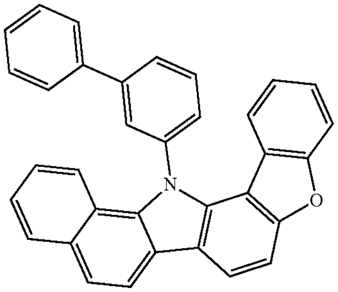
S-53
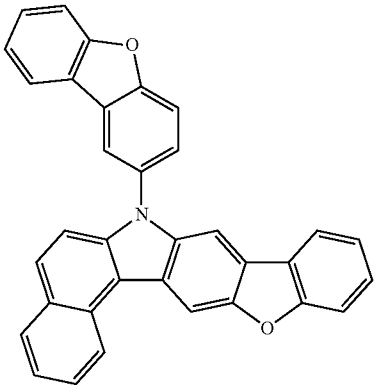
S-54
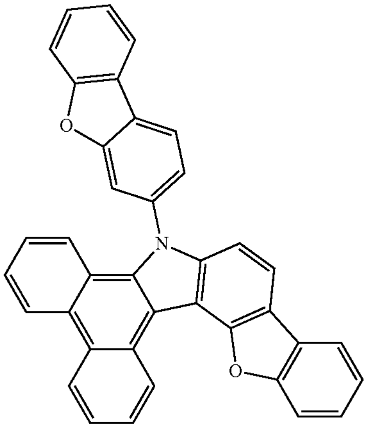
S-55
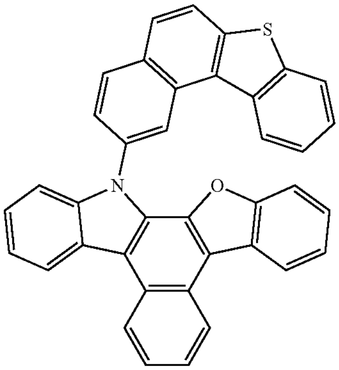
S-56
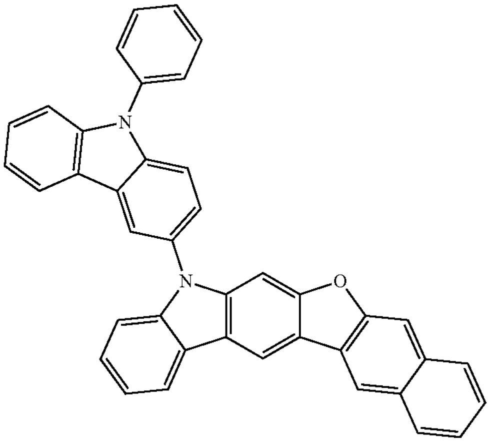
S-57
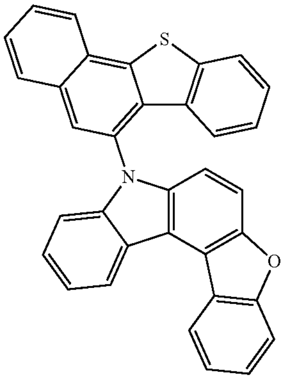

-continued
S-58
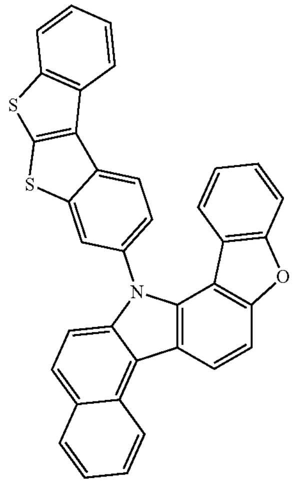
S-59
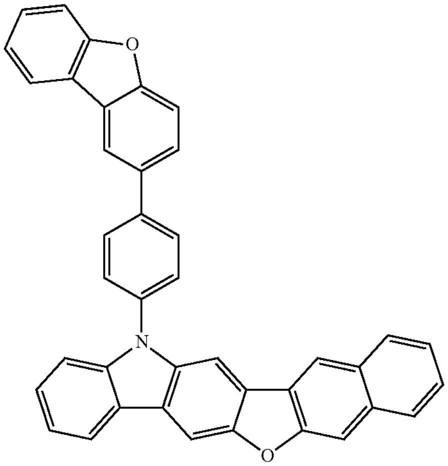
S-60
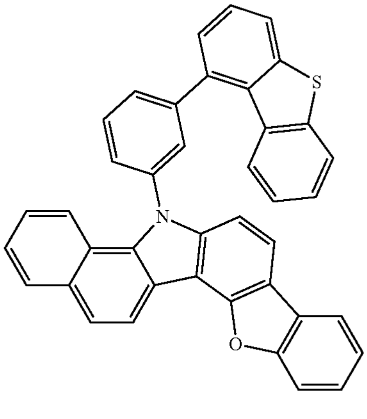
-continued
S-61
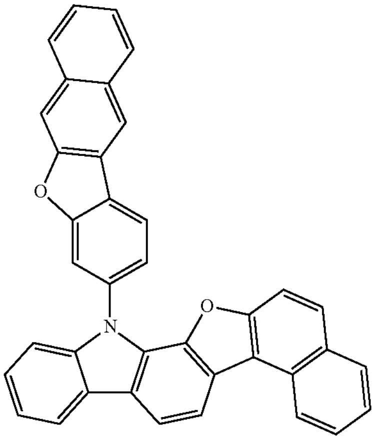
S-62
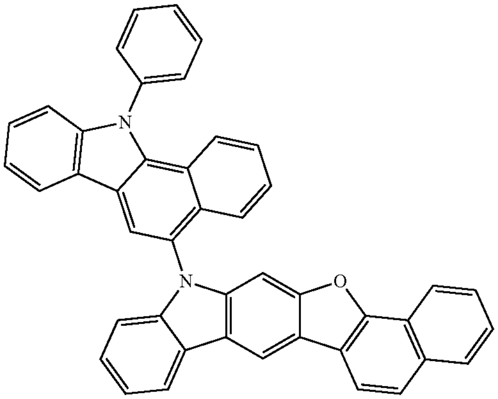
S-63
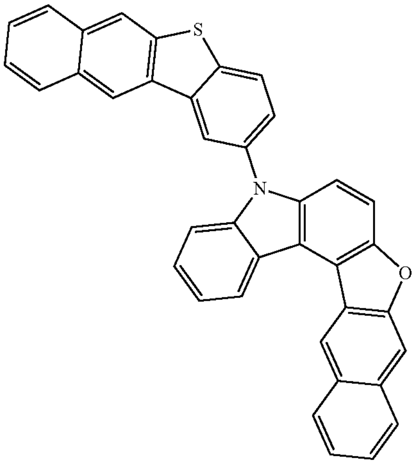

-continued
S-64
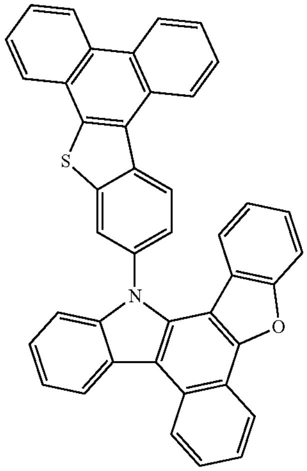
S-65
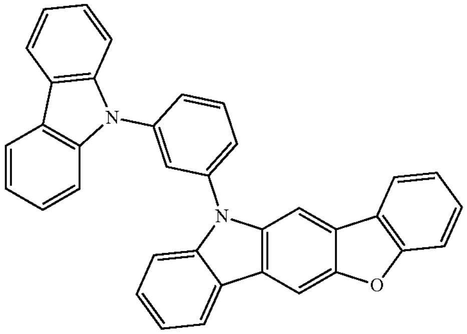
S-66
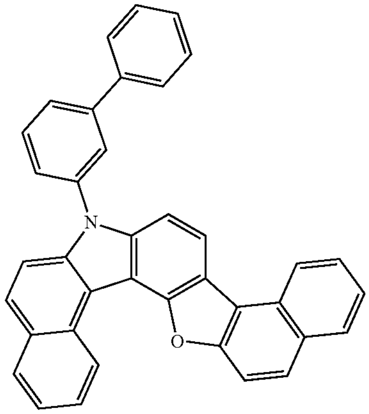
S-67
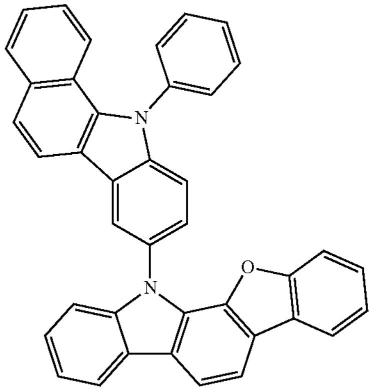
-continued
S-68
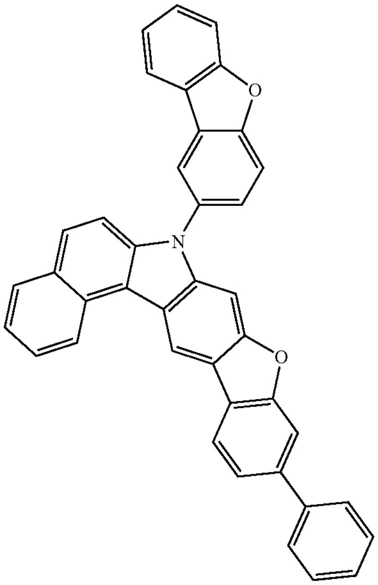
S-69
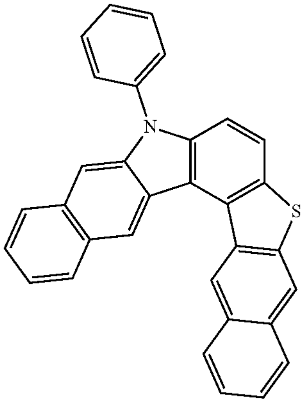
S-70
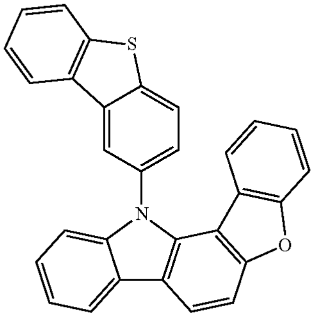

-continued
S-71
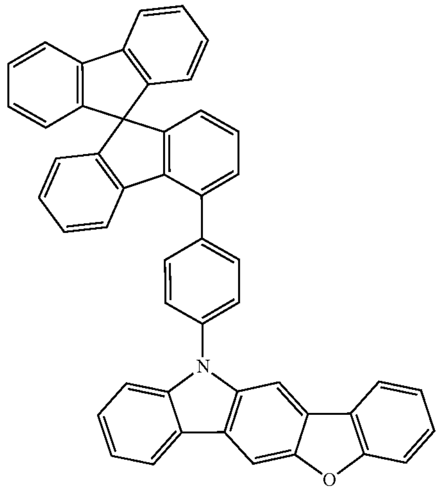
S-72
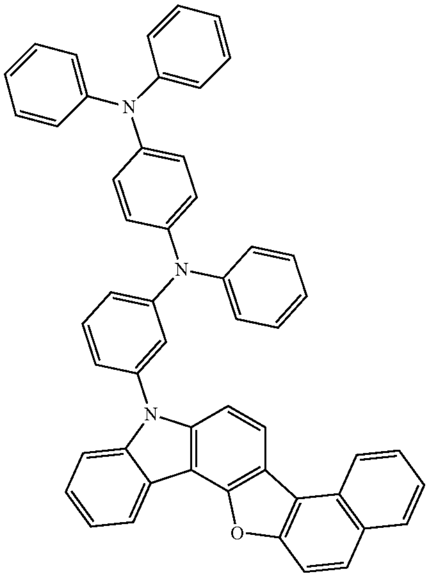
S-73
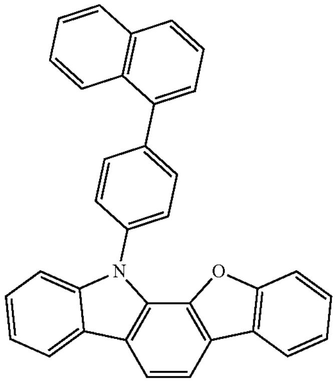
-continued
S-74
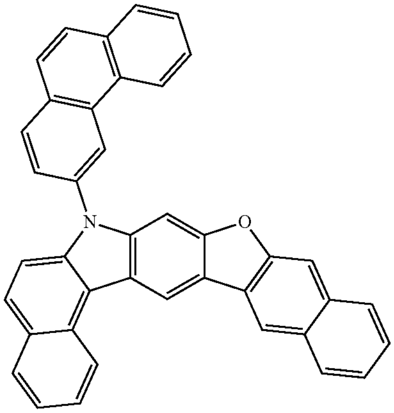
S-75
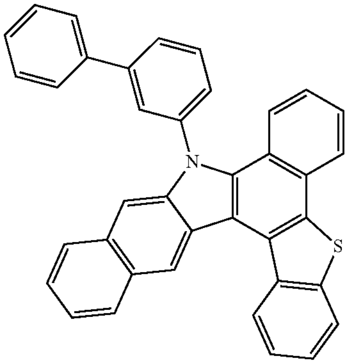
S-76
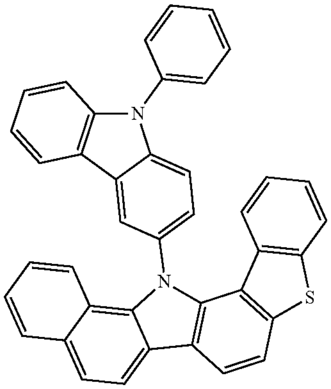
S-77
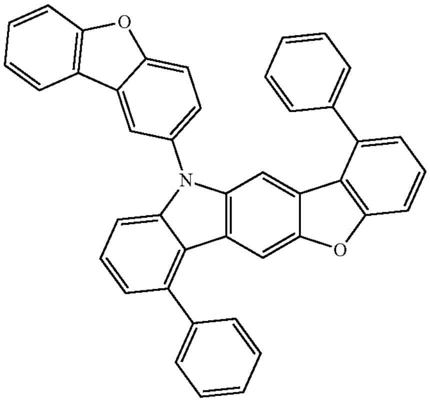

-continued
S-78
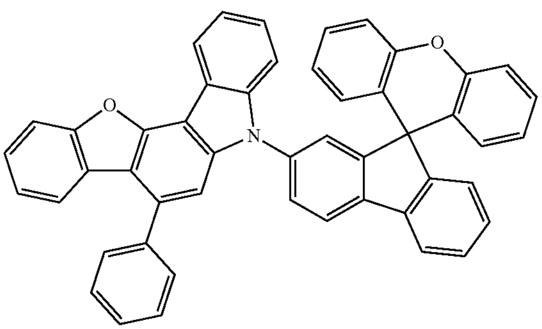
S-79
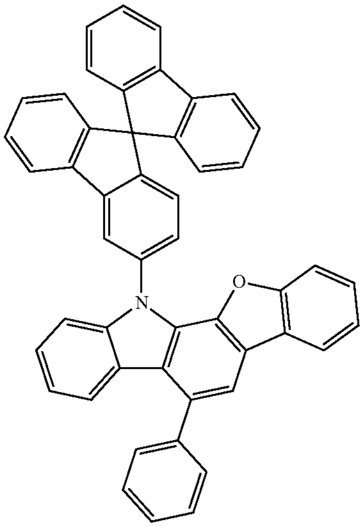
S-80
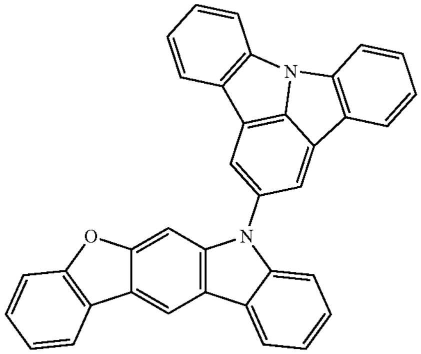
S-81
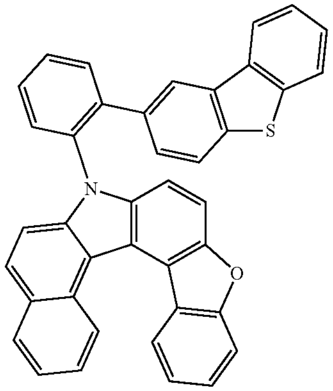
-continued
S-82
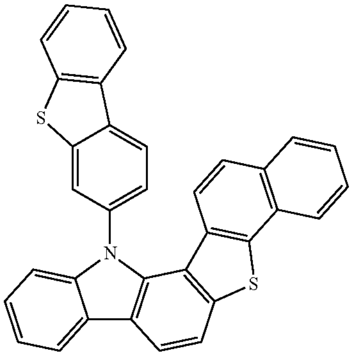
S-83
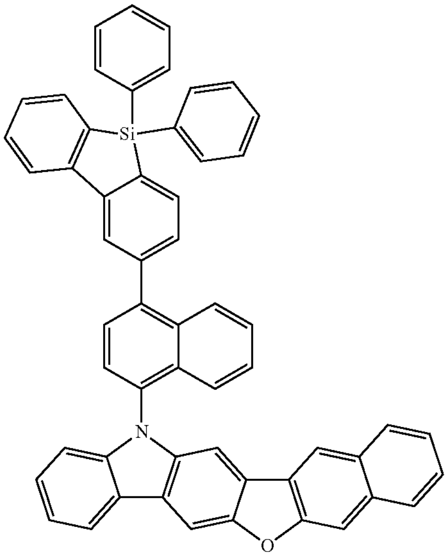
S-84
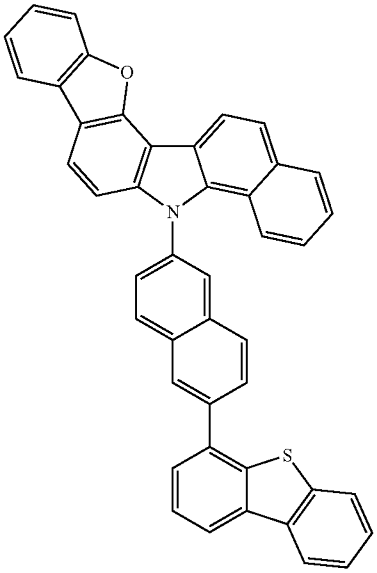

-continued
S-85
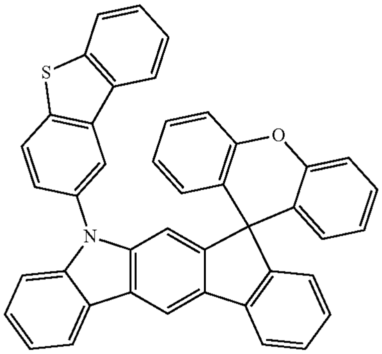
S-86
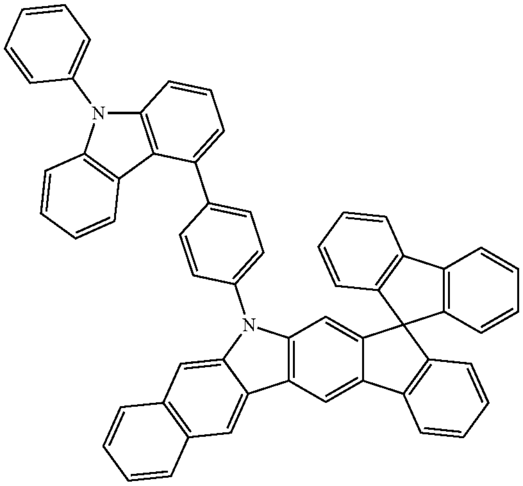
S-87
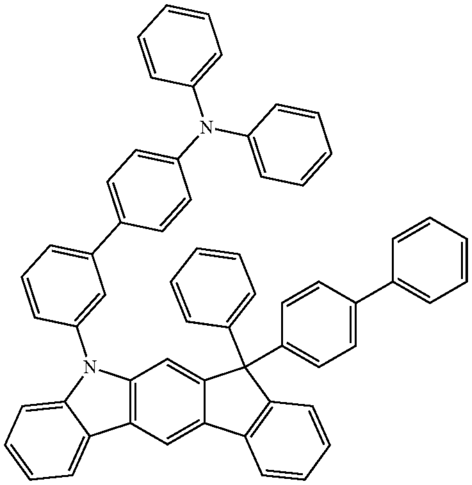
-continued
S-88
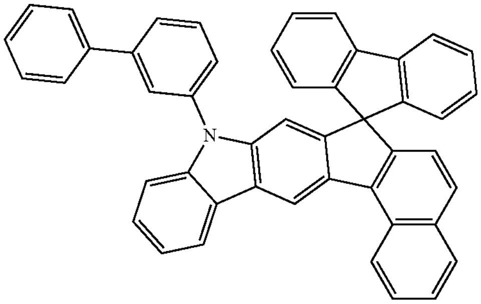
S-89
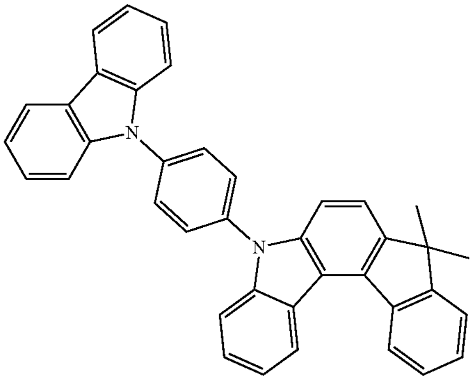
S-90
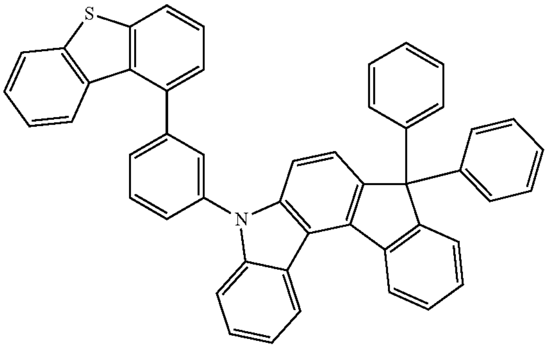
S-91
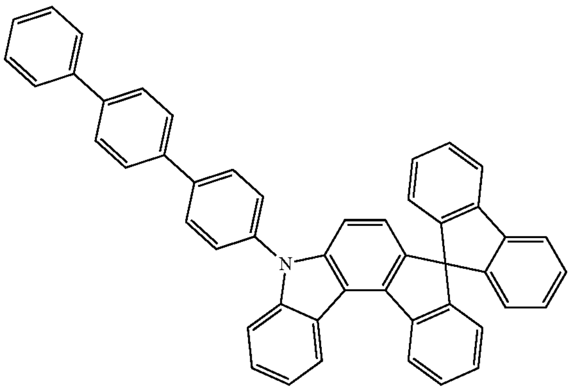

S-92
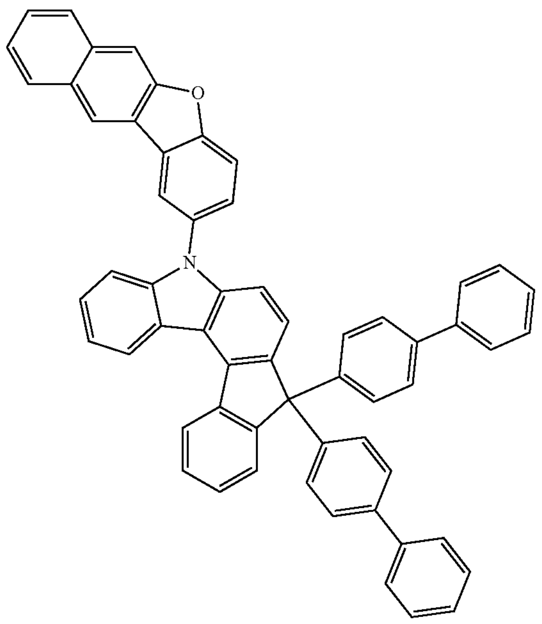
S-93
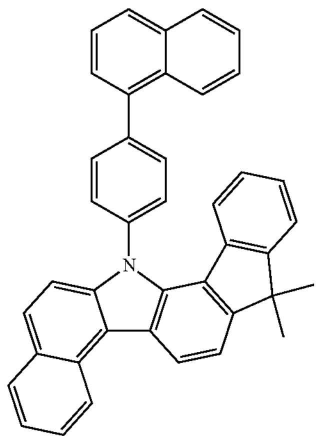
S-94
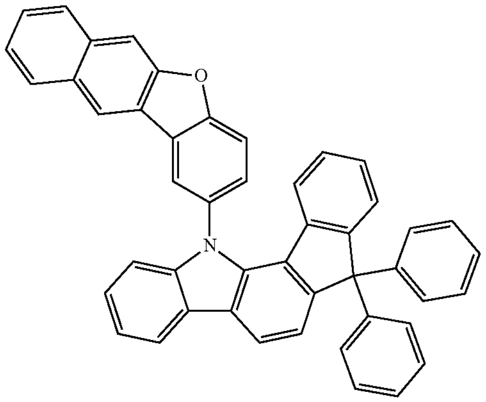
S-95
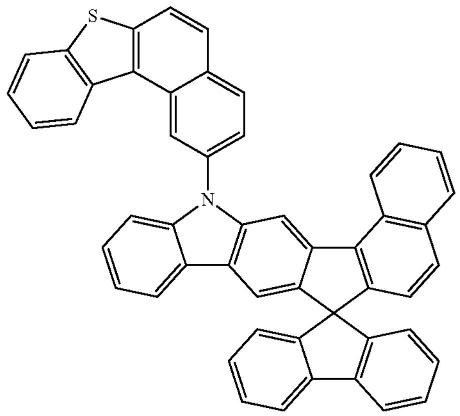
S-96
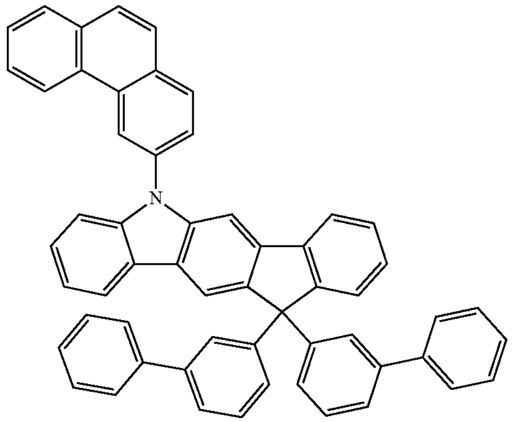
S-97
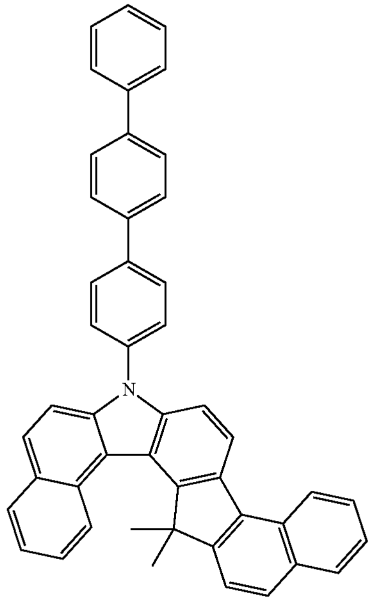

-continued
S-98
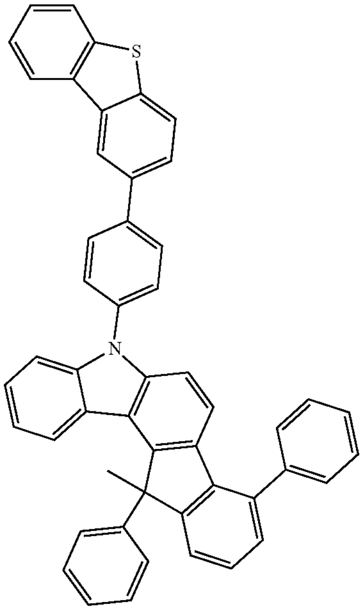
S-99
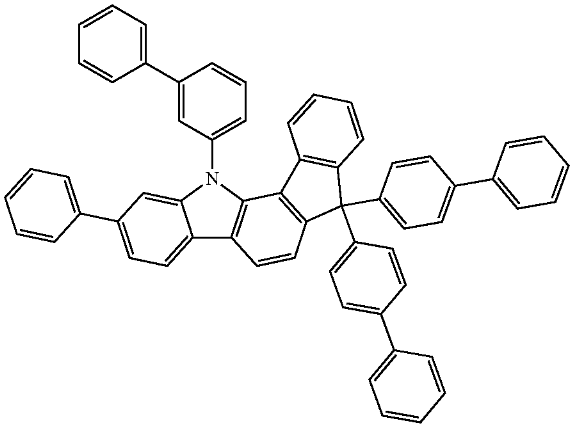
S-100
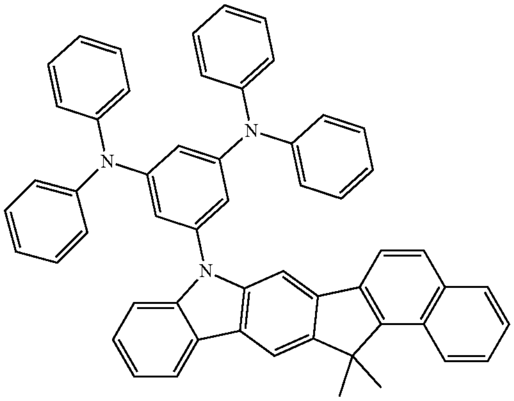
-continued
S-101
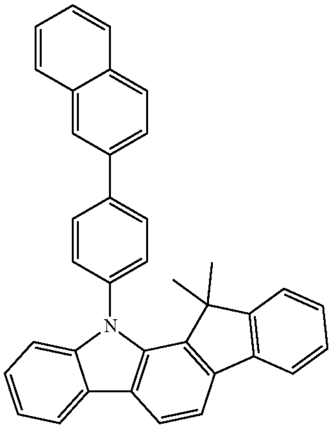
S-102
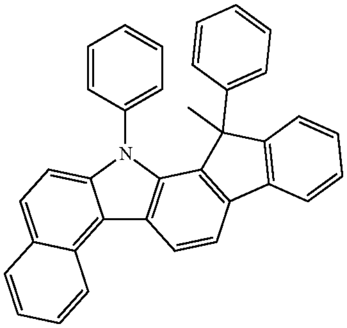
S-103
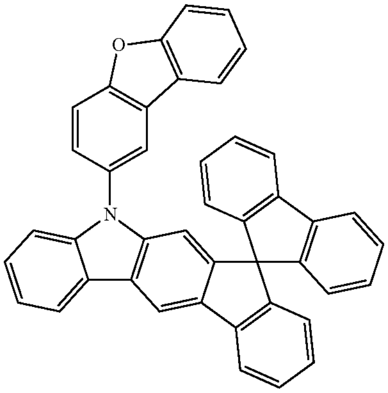
S-104
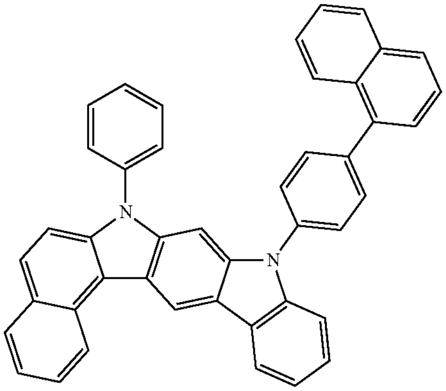

-continued

S-105

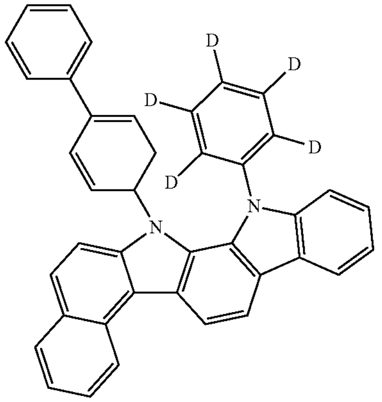

S-106

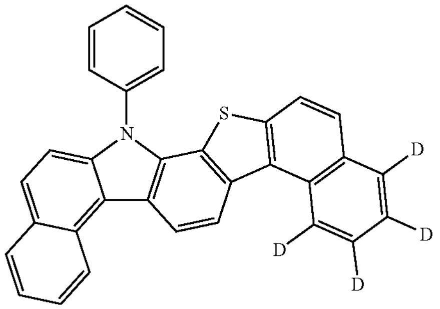

S-107

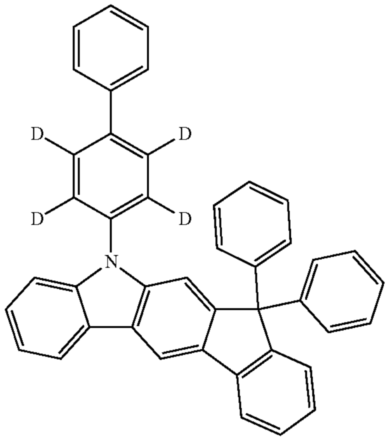

S-108

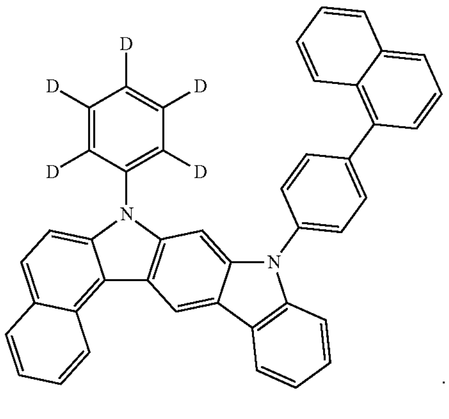

.

6. A compound represented by Formula 1:

Formula 1

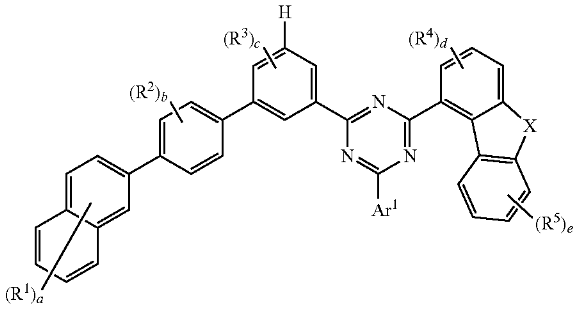

wherein:

$R^1$, $R^2$ and $R^3$ are each the same or different, and each independently hydrogen; or deuterium, $R^4$ and $R^5$ are each the same or different, and each independently selected from the group consisting of hydrogen; deuterium; a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring; a $C_3$-$C_{60}$ aliphatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; and a $C_6$-$C_{30}$ aryloxy group; or an adjacent plurality of $R^4$ or plurality of $R^5$ may be bonded to each other to form a ring, X is O or S, $Ar^1$ is each independently selected from the group consisting of a $C_6$-$C_{60}$ aryl group; a fluorenyl group; a $C_2$-$C_{60}$ heterocyclic group including at least one hetero atom of O, N, S, Si or P; and a fused ring group of a $C_3$-$C_{60}$ aliphatic ring and a $C_6$-$C_{60}$ aromatic ring, a is an integer from 0 to 7, b and e are each independently an integer from 0 to 4, c and d are each independently an integer from 0 to 3, wherein the aryl group, arylene group, heterocyclic group, fluorenyl group, fluorenylene group, aliphatic ring group, fused ring group, alkyl group, alkenyl group, alkynyl group, alkoxyl group and aryloxy group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxy group; $C_1$-$C_{20}$ alkyl group;

$C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$~$C_{20}$ heterocyclic group; $C_3$-$C_{20}$ cycloalkyl group; $C_7$-$C_{20}$ arylalkyl group; and $C_1$-$C_{20}$ arylalkenyl group; also the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

7. The compound of claim 6, wherein $Ar^1$ is represented by any one of Formulas (Ar-1) to (Ar-12):

Formula (Ar-1)

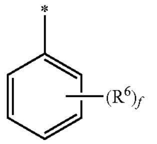

-continued

Formula (Ar-2)

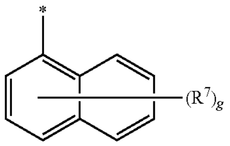

Formula (Ar-3)

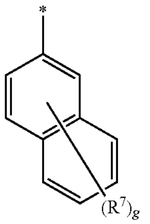

Formula (Ar-4)

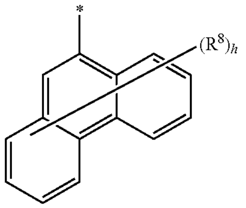

Formula (Ar-5)

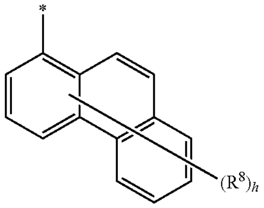

Formula (Ar-6)

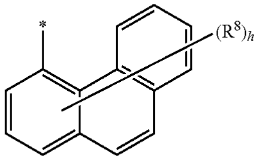

Formula (Ar-7)

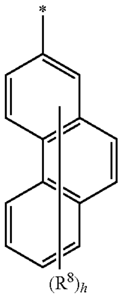

Formula (Ar-8)

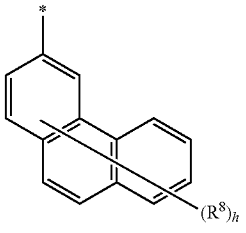

-continued

Formula (Ar-9)

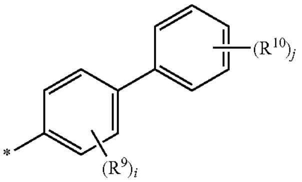

Formula (Ar-10)

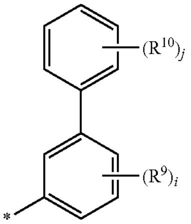

Formula (Ar-11)

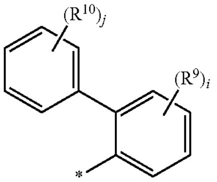

Formula (Ar-12)

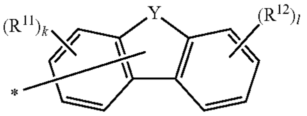

wherein:

$R^6$, $R^7$, $R^8$, $R^9$, $R^{10}$, $R^{11}$ and $R^{12}$ are the same as the definition of $R^4$ in claim 6, or an adjacent plurality of $R^6$, or plurality of $R^7$, or plurality of $R^8$, or plurality of $R^9$, or plurality of $R^{10}$, or plurality of $R^{11}$, or plurality of $R^{12}$ may be bonded to each other to form a ring, Y is O, S, $CR^{13}R^{14}$, $NR^{15}$ or $SiR^{16}R^{17}$, provided that when Y is bonded to Formula 1, it is $-L^1-N$, $R^{13}$, $R^{14}$, $R^{15}$, $R^{16}$ and $R^{17}$ are each independently selected from the group consisting of hydrogen; deuterium; a $C_1$-$C_{60}$ alkyl group; a $C_6$-$C_{60}$ aryl group; and a $C_2$-$C_{60}$ heterocyclic group including at least one hetero atom of O, N, S, Si or P; alternatively, $R^{13}$ and $R^{14}$ or $R^{16}$ and $R^{17}$ may be bonded to each other to form a spiro, $L^1$ is each independently selected from the group consisting of single bond; a $C_6$-$C_{60}$ arylene group; a fluorenylene group; a fused ring group of a $C_3$-$C_{60}$ aliphatic ring and a $C_6$-$C_{60}$ aromatic ring; a $C_2$-$C_{60}$ heteroarylene group including at least one heteroatom of O, N, S, Si or P;

f and j are each independently an integer from 0 to 5, g is an integer from 0 to 7, h is an integer from 0 to 9, i, k and l are an integer from 0 to 4,

* means the position to be bonded.

8. The compound of claim 6, wherein $R^1$, $R^2$ and $R^3$ are deuterium.

9. The compound of claim 6, wherein $R^4$ and $R^5$ are deuterium.

10. The compound of claim 6, wherein Formula 1 is represented by any one of compounds P-1 to P-107:
P-1
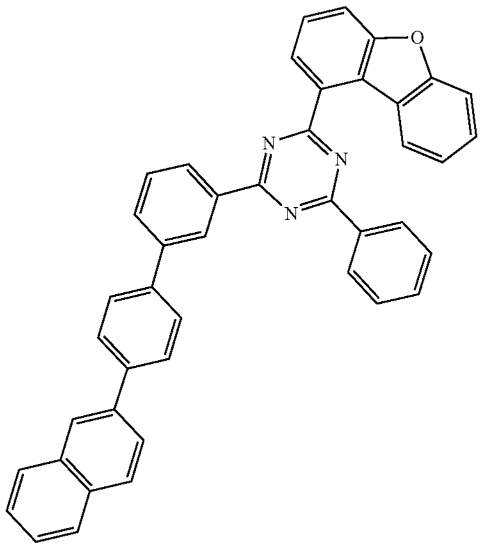
P-2
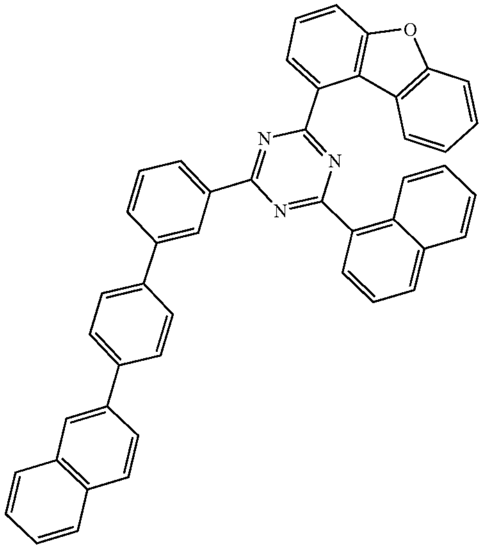
-continued
P-3
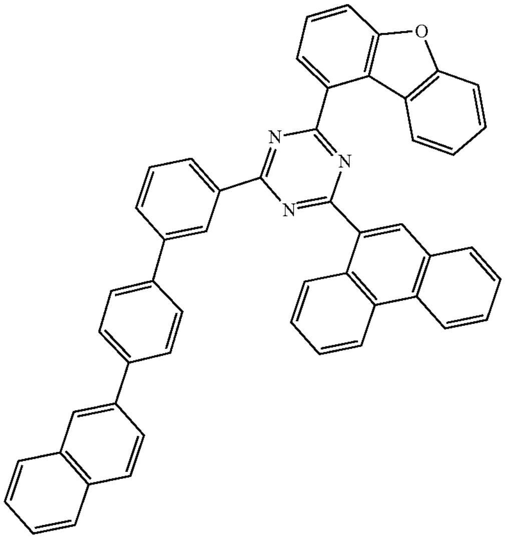
P-4
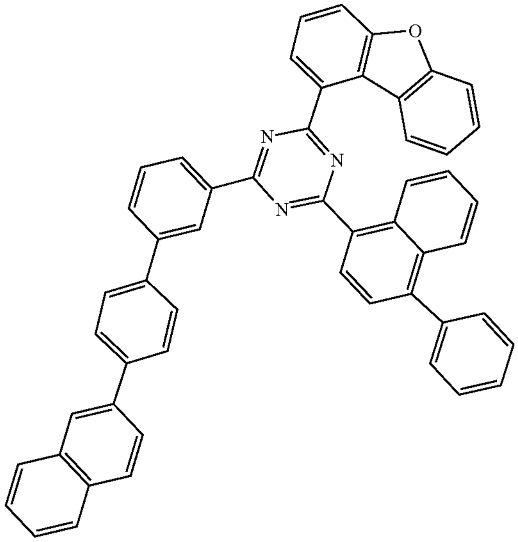

-continued
P-5
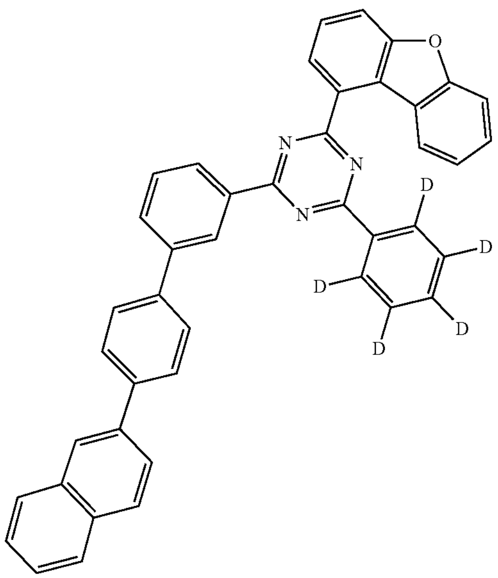
P-6
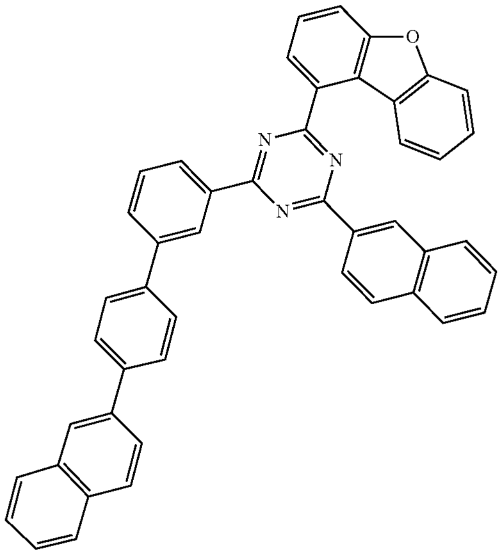
-continued
P-7
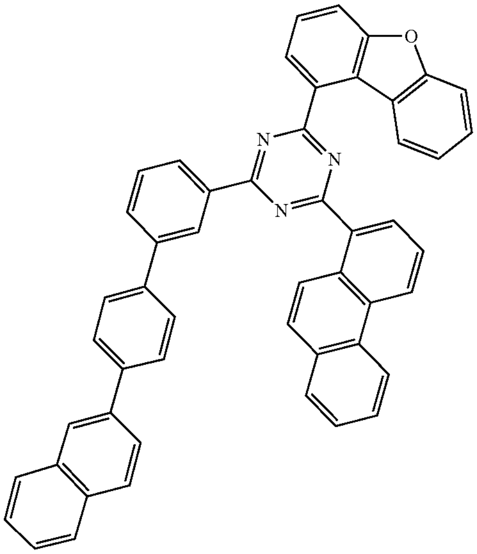
P-8
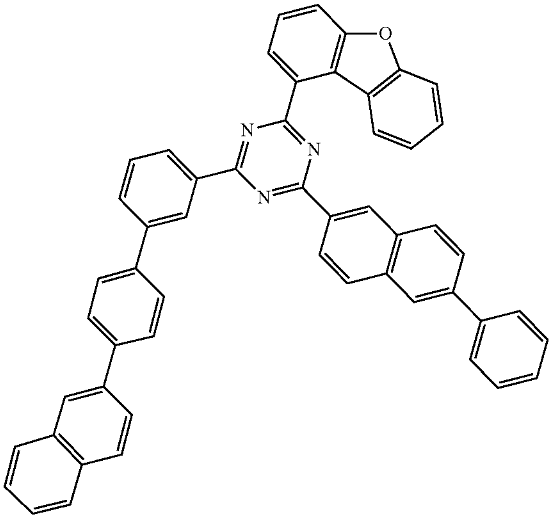
P-9
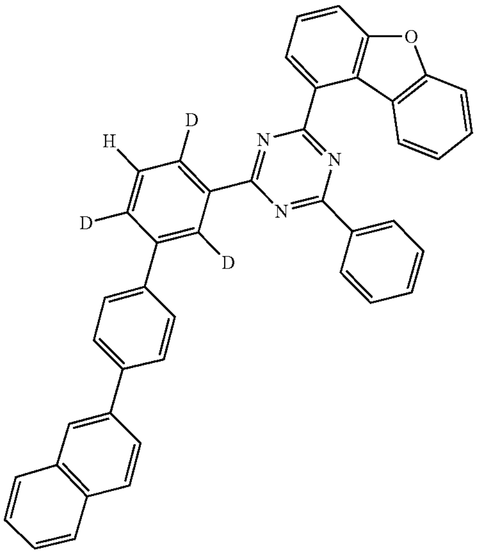

-continued
P-10
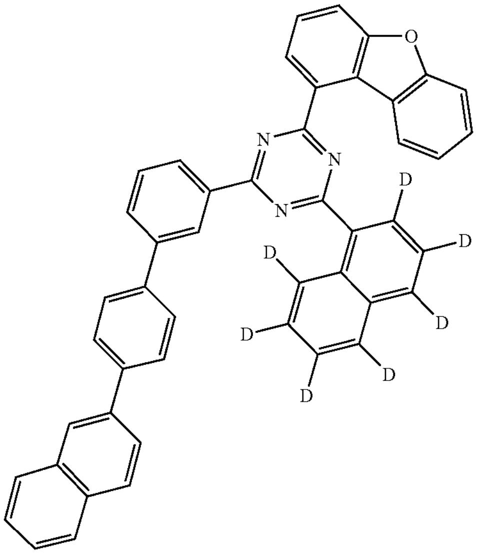
P-11
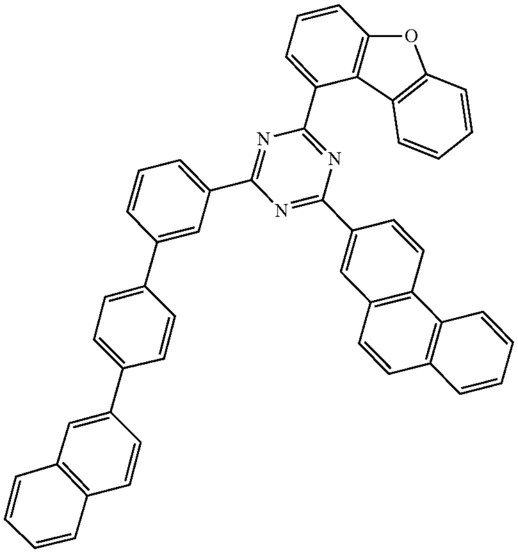
P-12
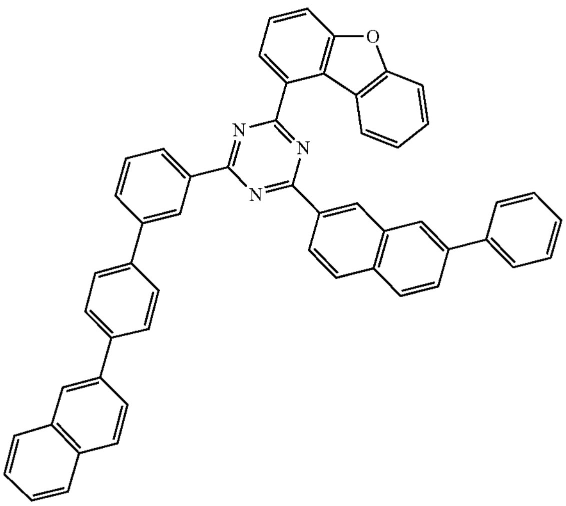
-continued
P-13
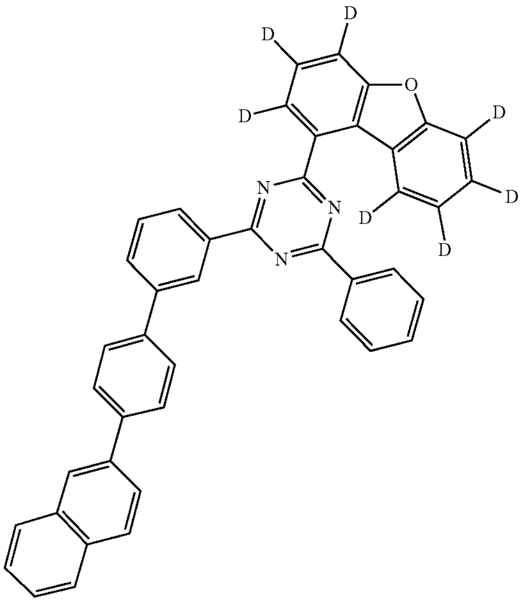
P-14
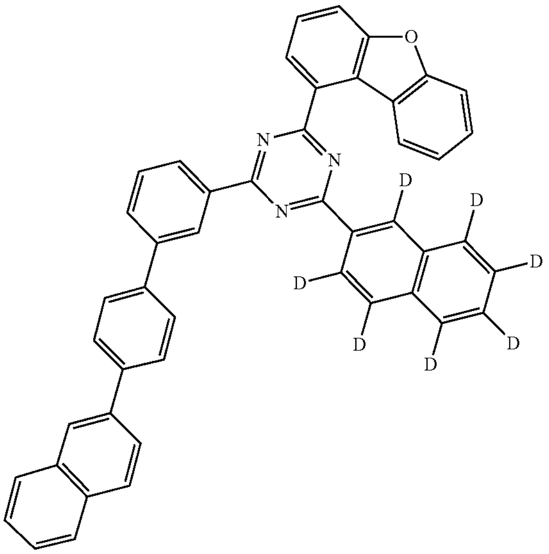

-continued
P-15
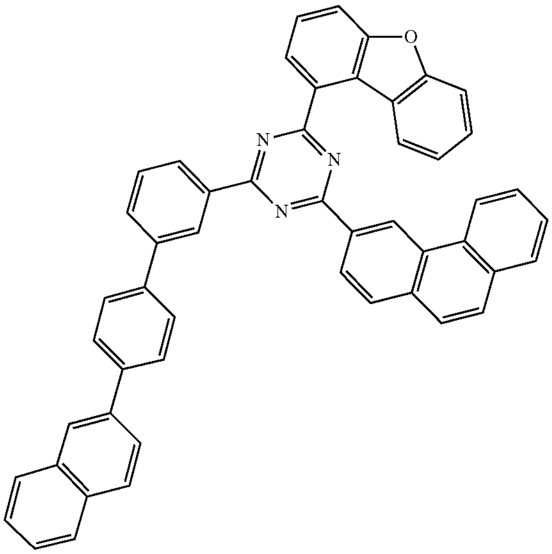
P-16
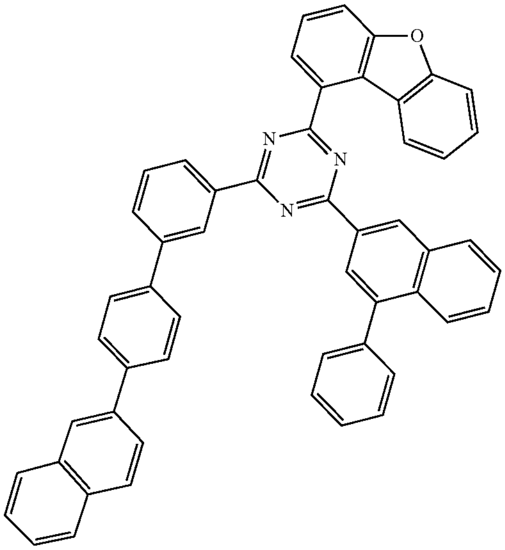
-continued
P-17
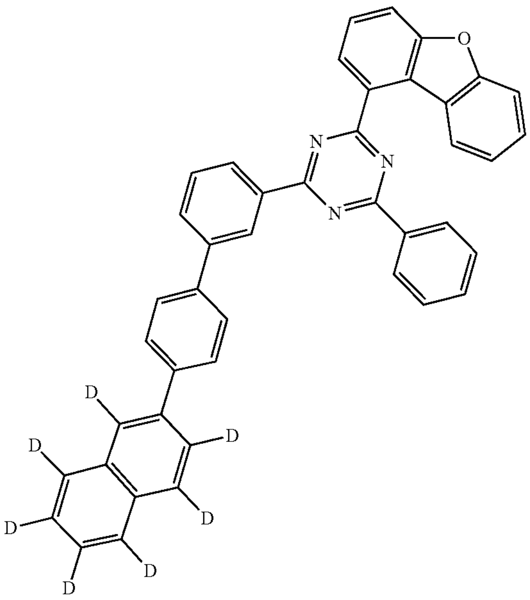
P-18
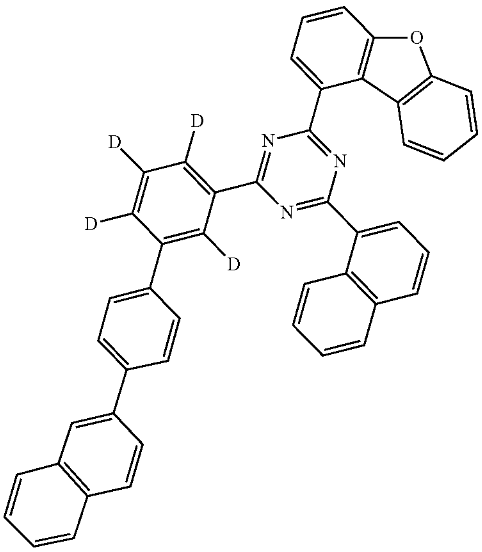

-continued
P-19
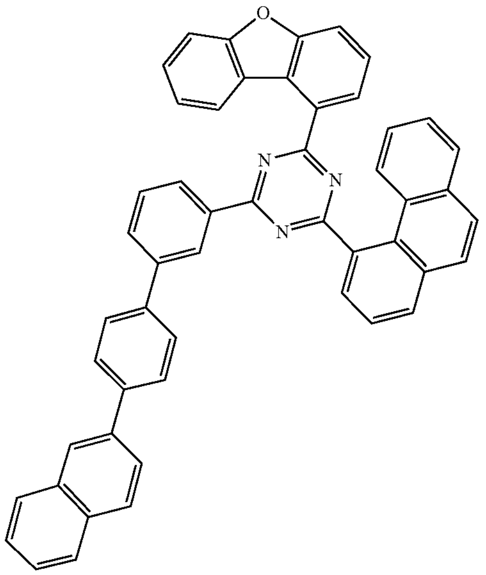
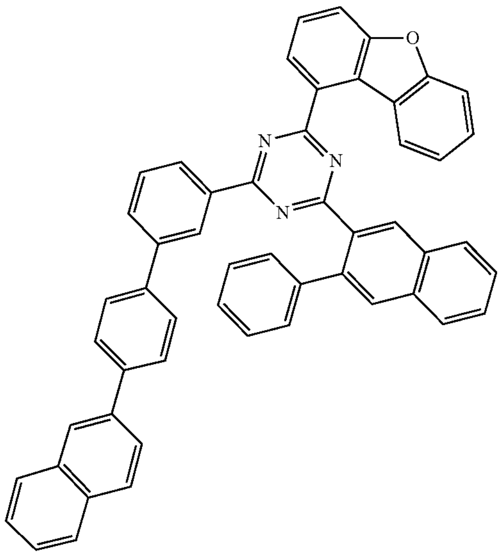
P-20
-continued
P-21
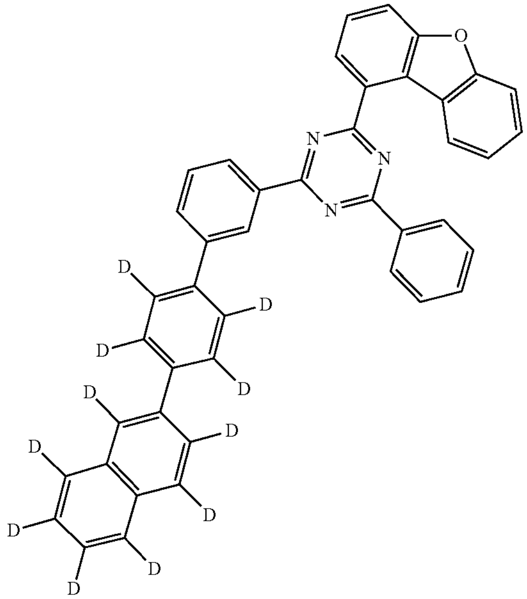
P-22
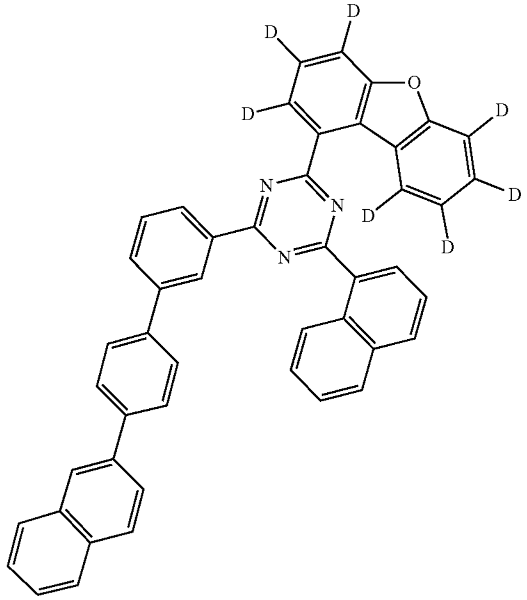

-continued
P-23
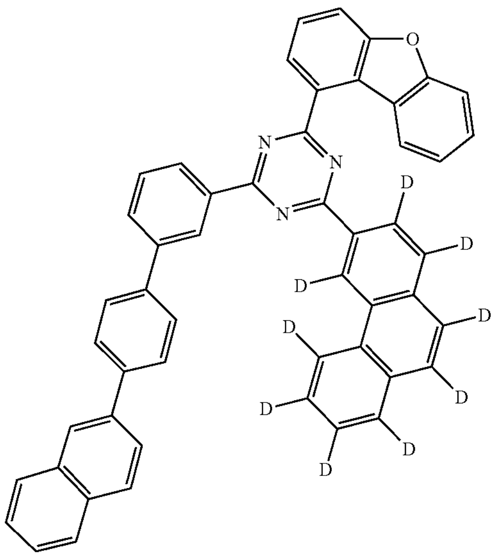
P-24
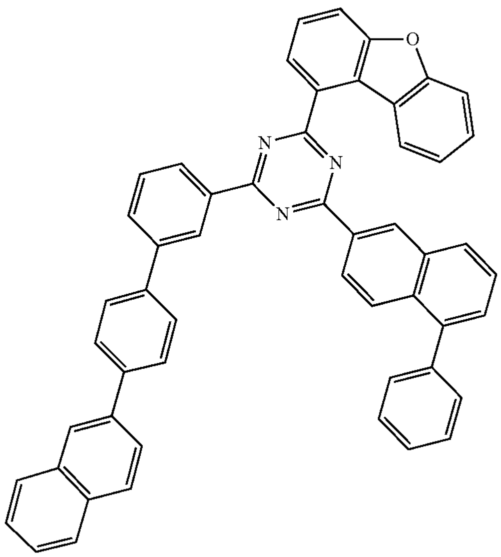
-continued
P-25
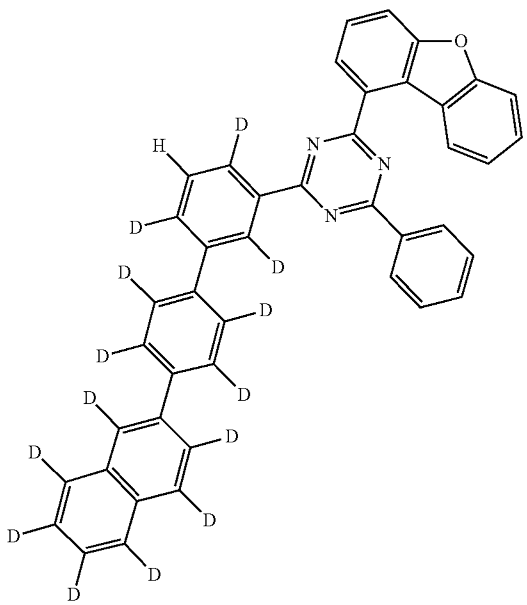
P-26
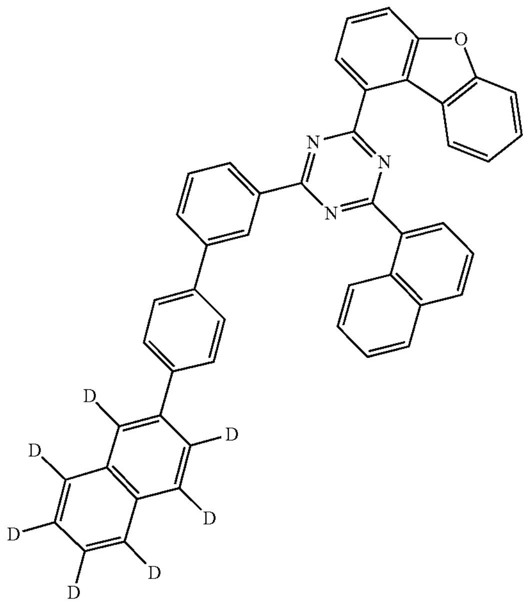

-continued
P-27
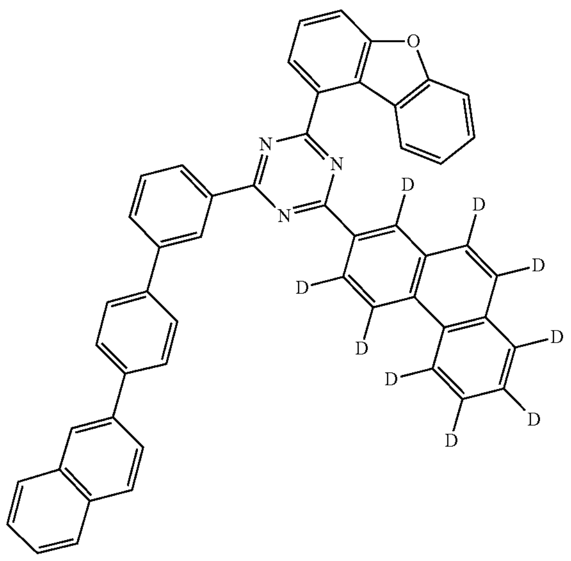
P-28
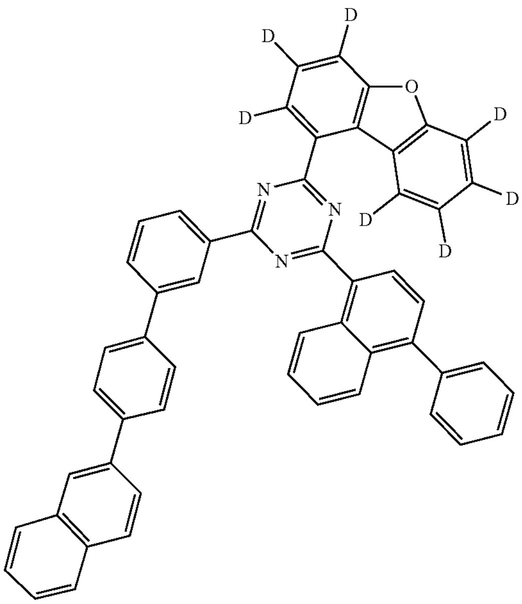
-continued
P-29
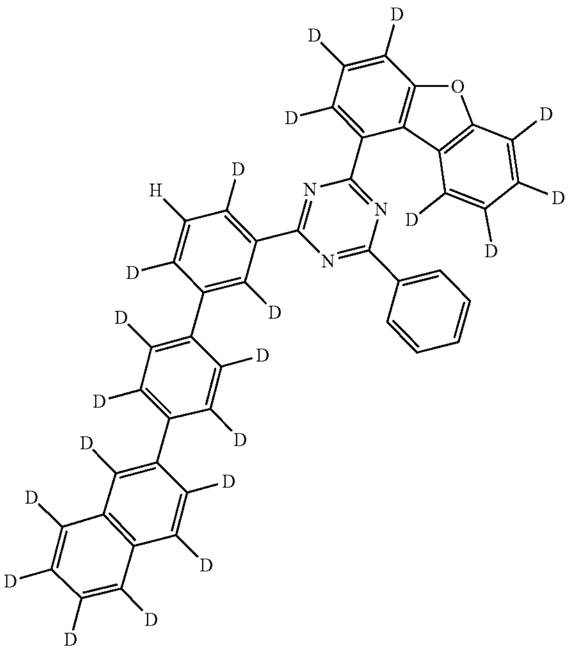
P-30
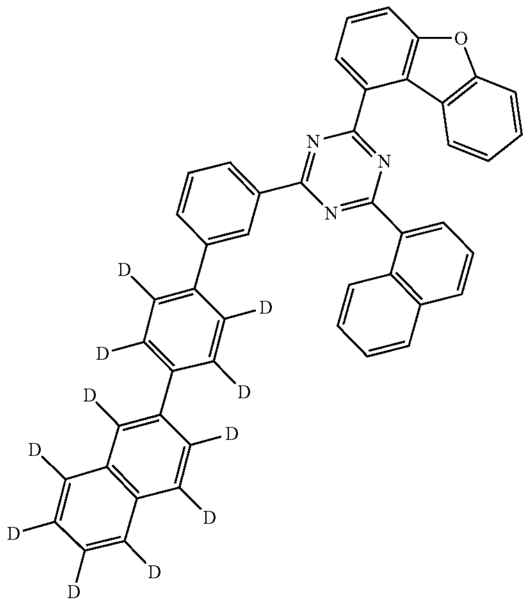

P-31
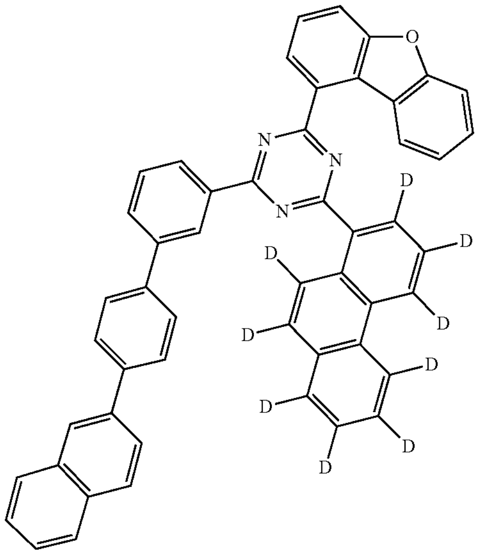
P-32
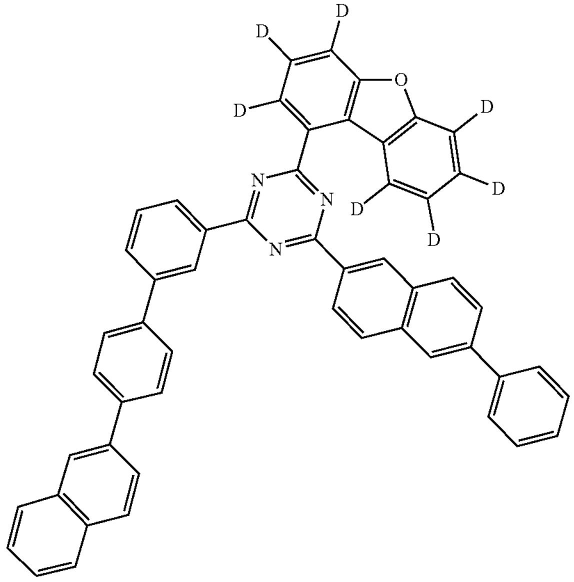
P-33
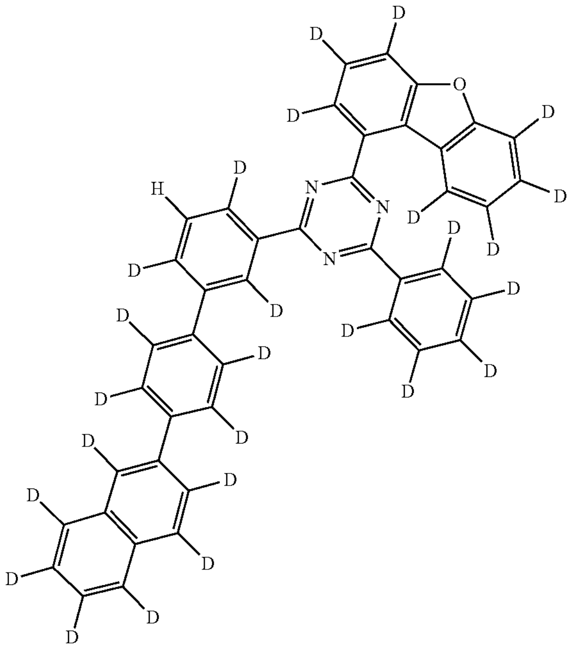
P-34
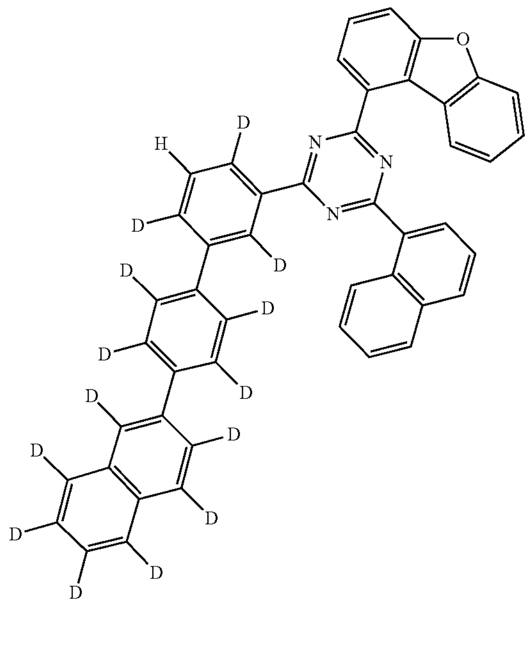

-continued
P-35
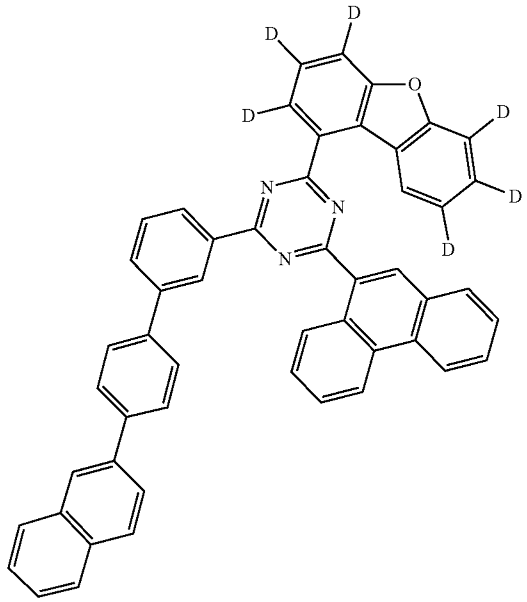
P-36
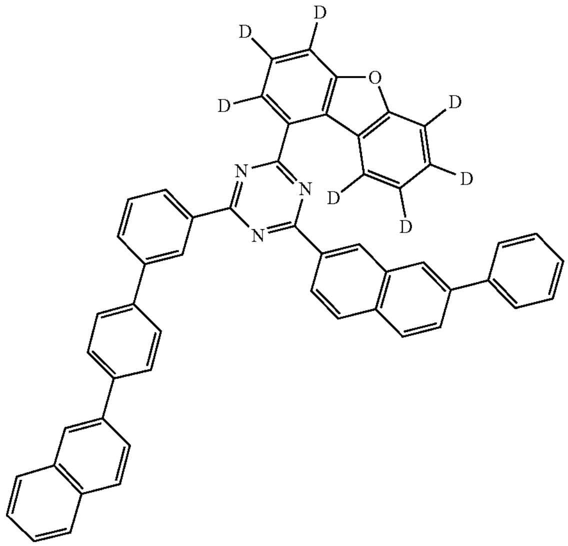
-continued
P-37
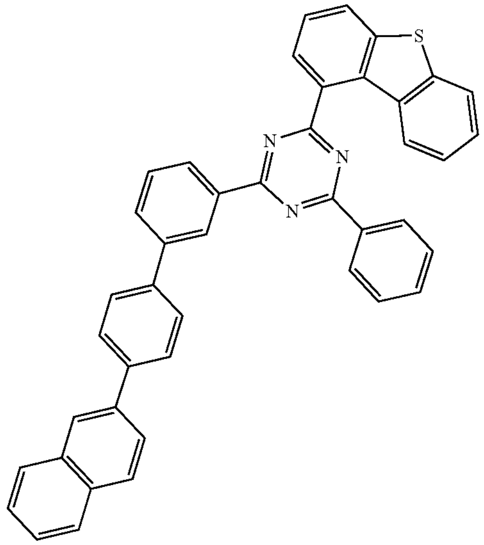
P-38
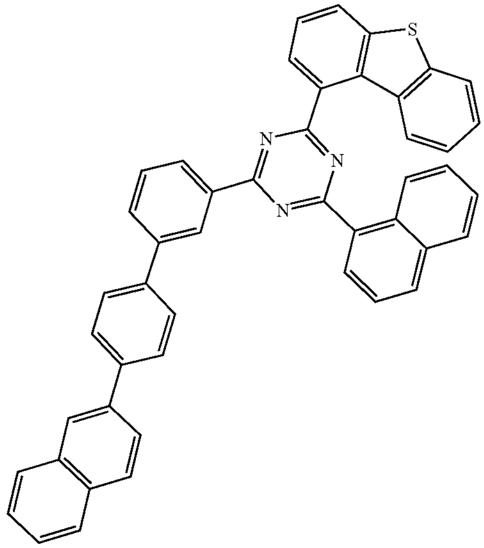
P-39
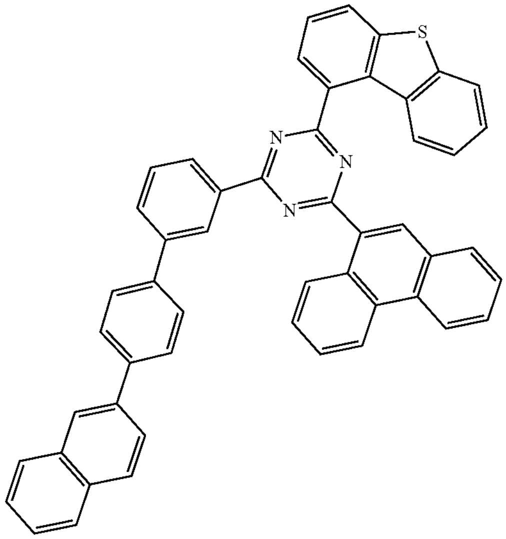

-continued
P-40
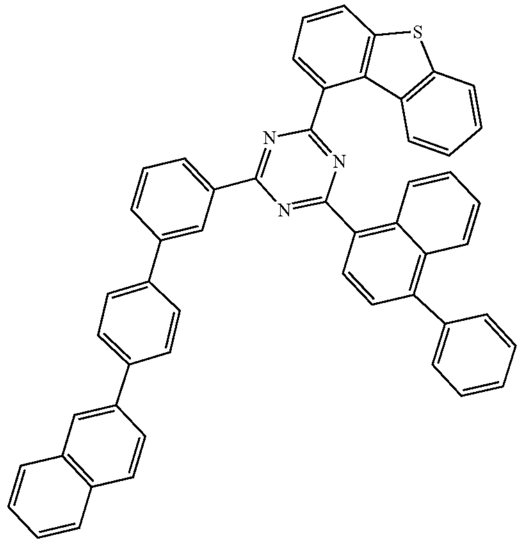
P-41
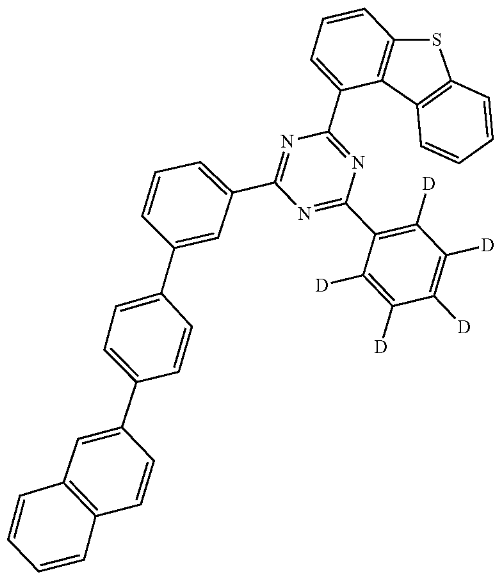
-continued
P-42
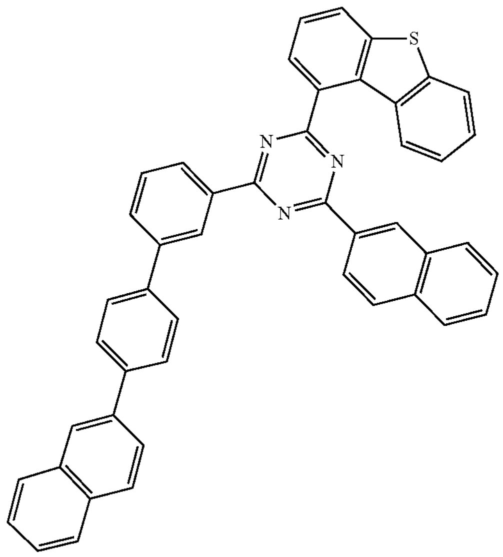
P-43
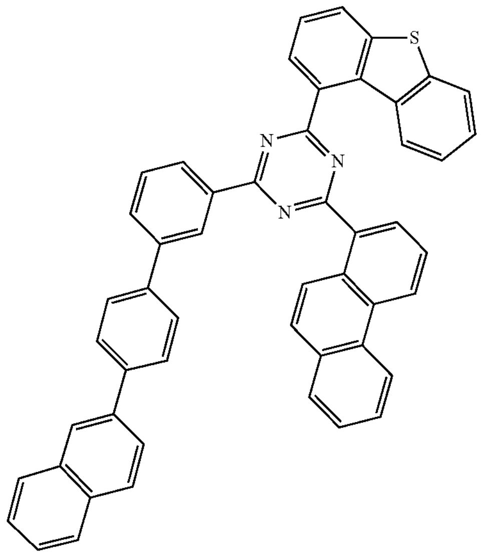
P-44
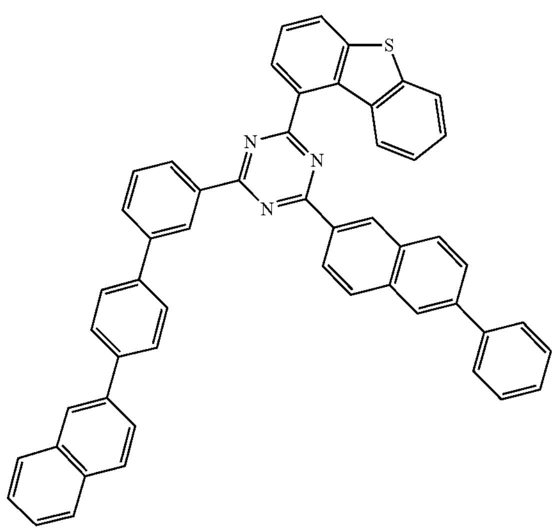

-continued
P-45
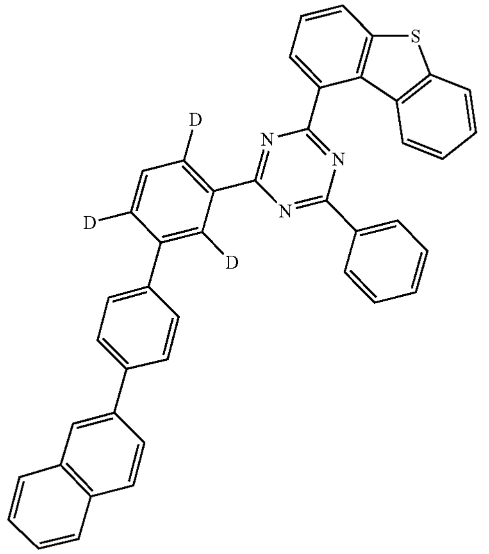
P-46
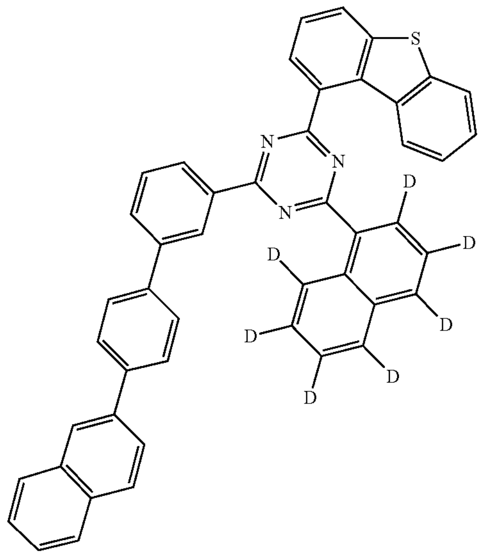
-continued
P-47
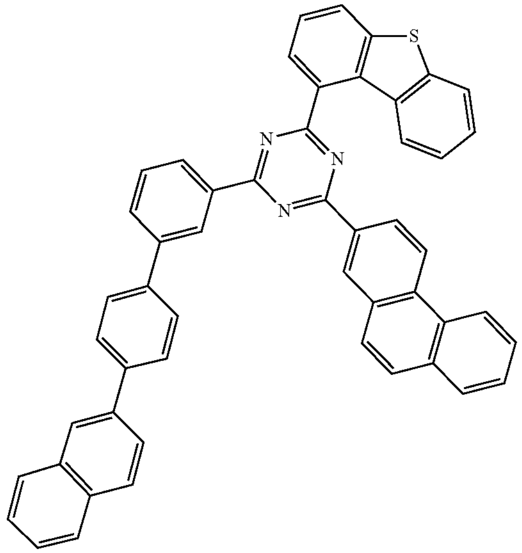
P-48
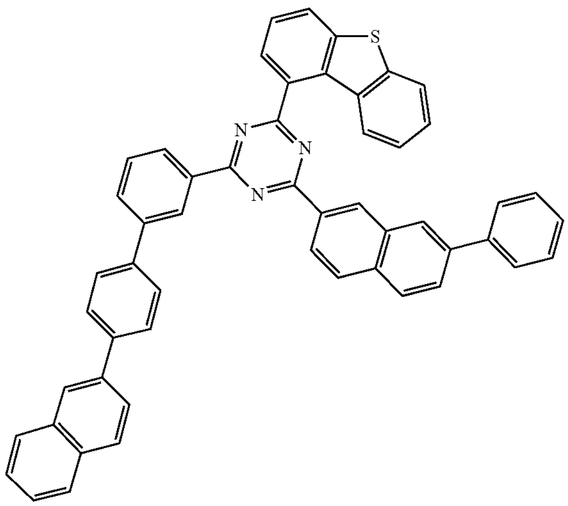

-continued
P-49
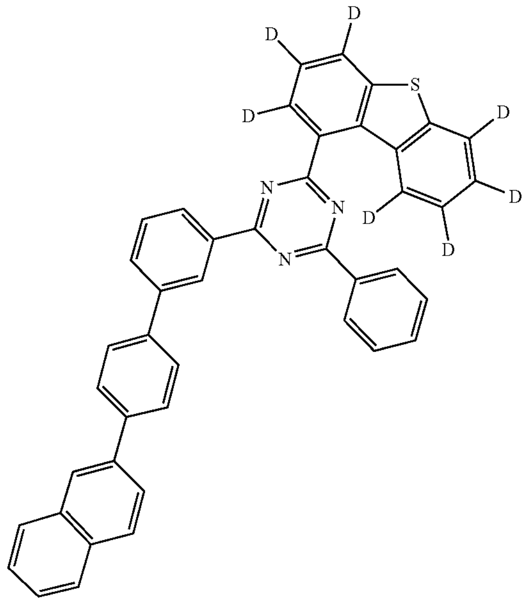
P-50
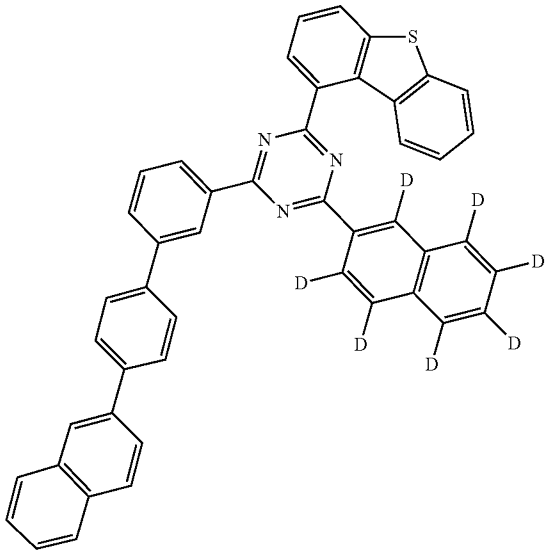
-continued
P-51
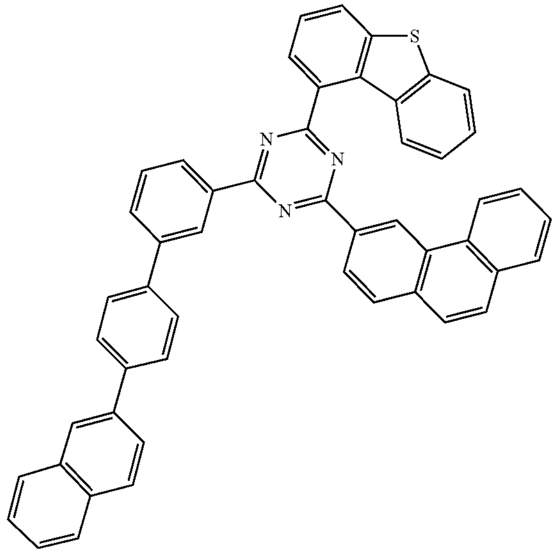
P-52
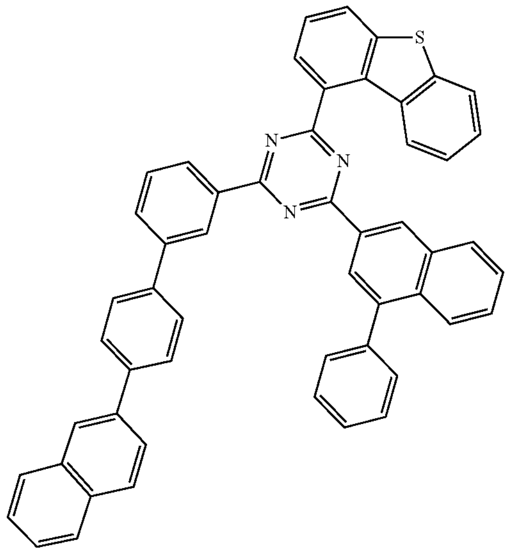

-continued
P-53
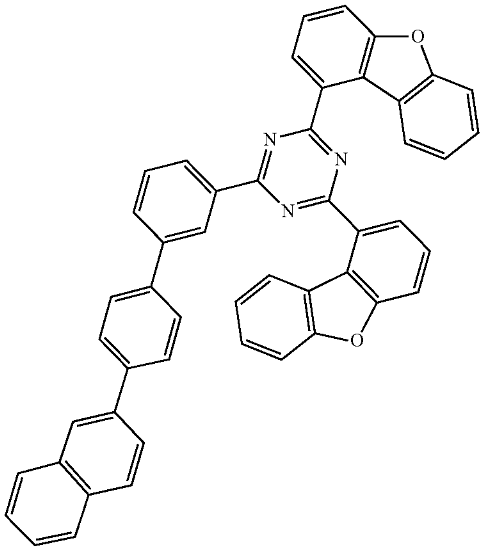
P-55
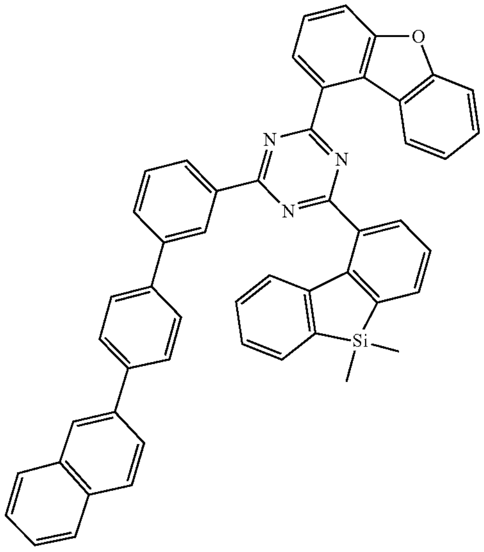
P-54
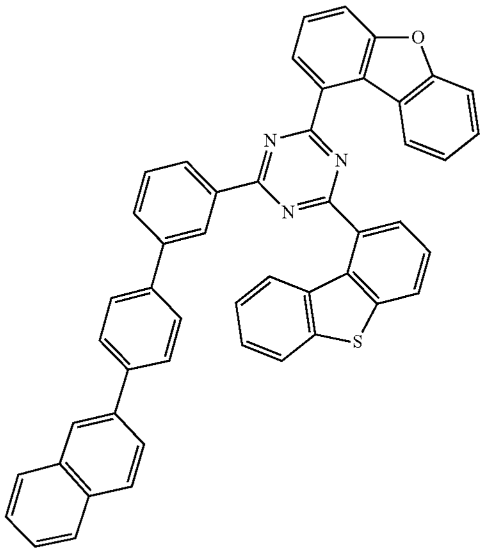
P-56
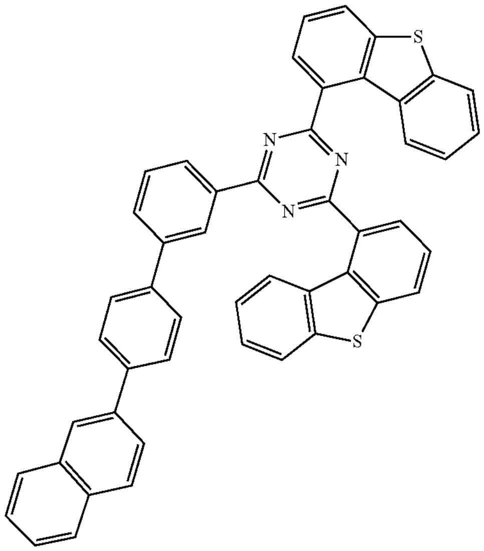

-continued
P-57
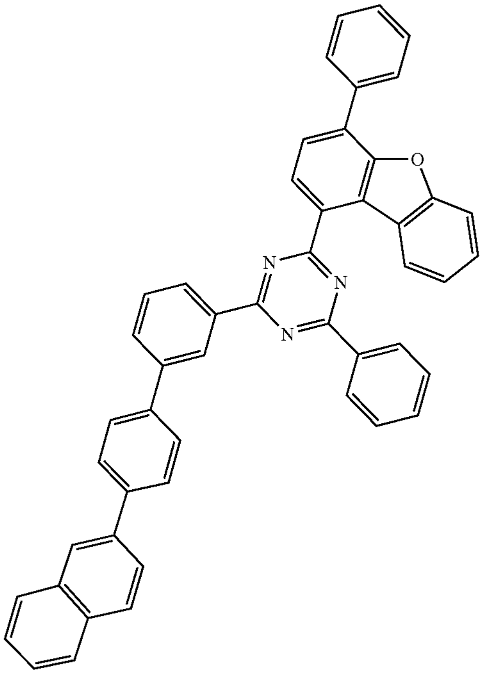
P-58
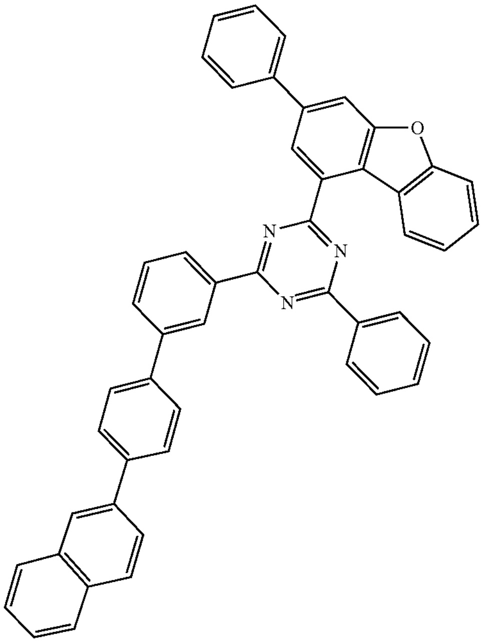
-continued
P-59
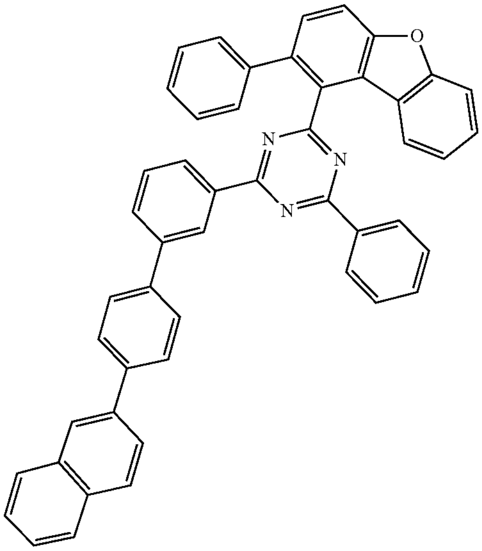
P-60
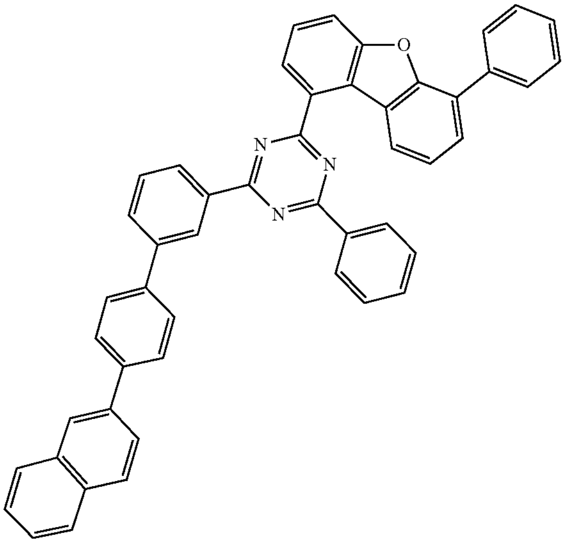

-continued
P-61
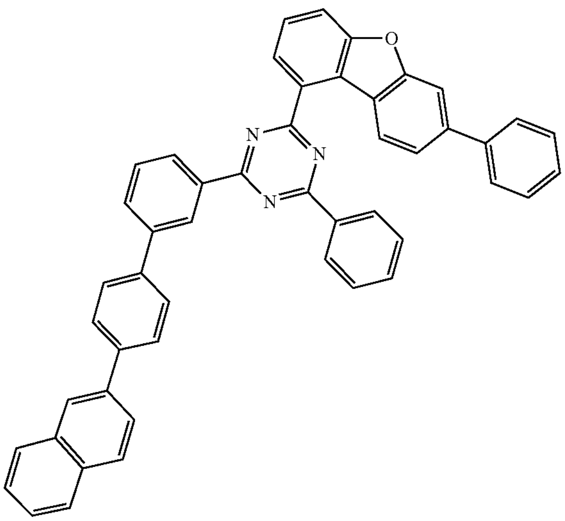
P-62
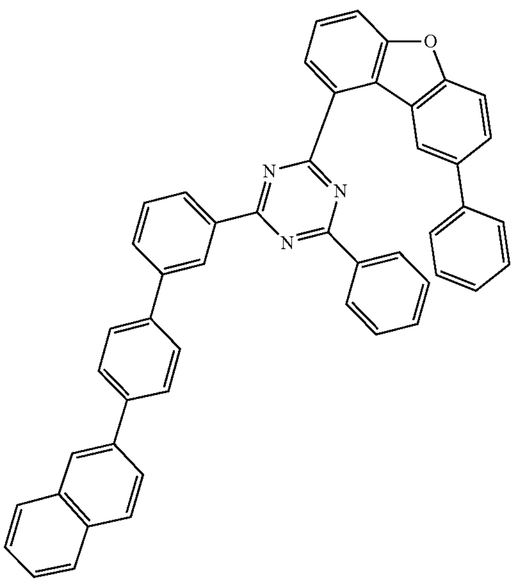
-continued
P-63
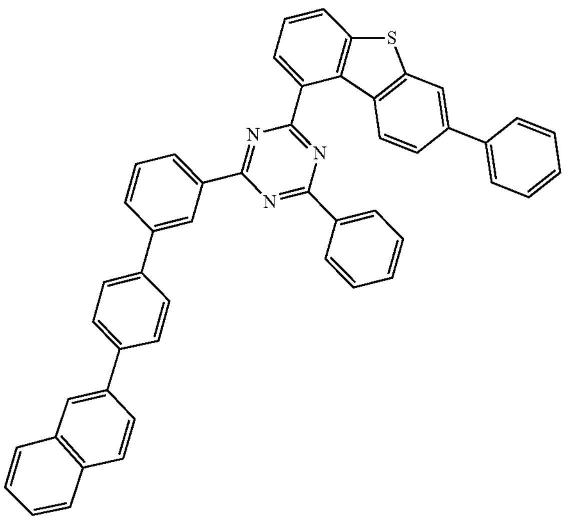
P-64
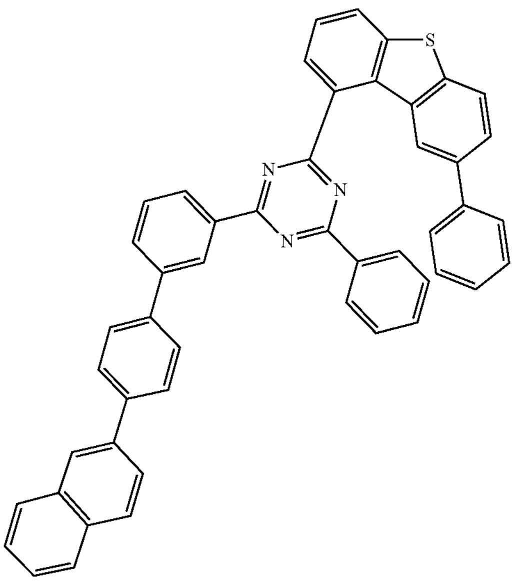

-continued
P-65
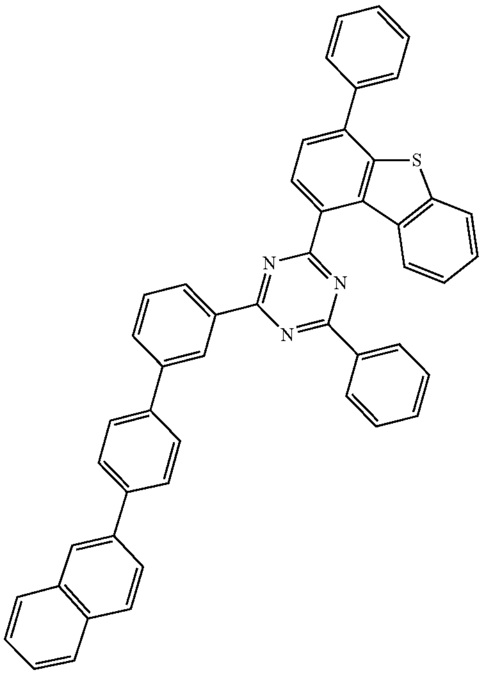
P-66
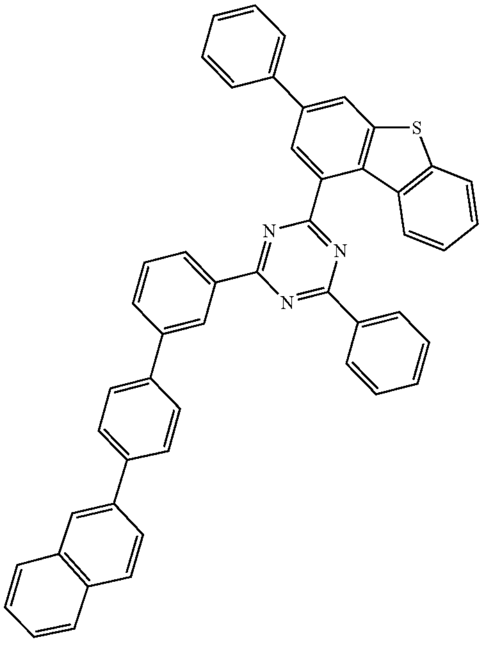
-continued
P-67
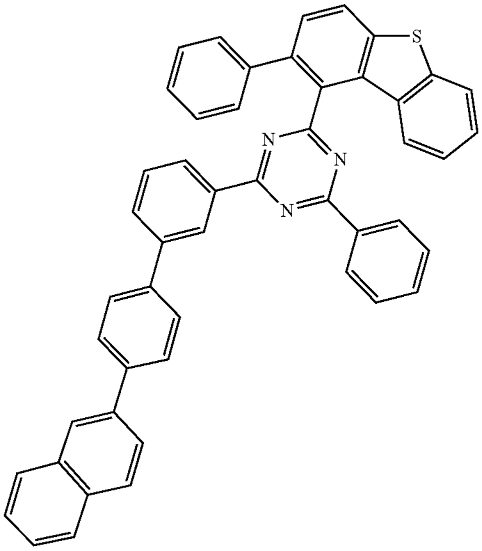
P-68
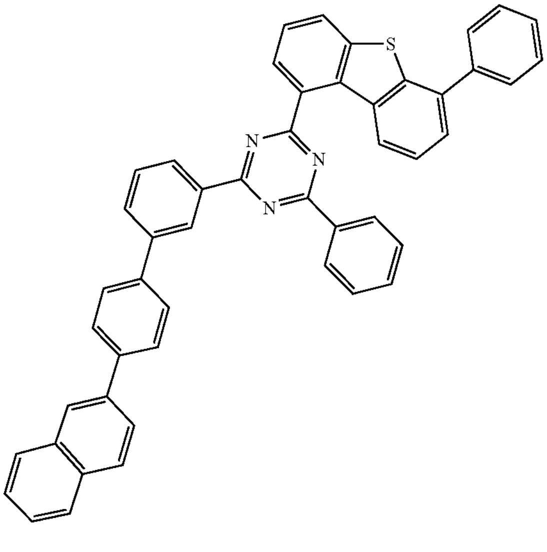

-continued
P-69
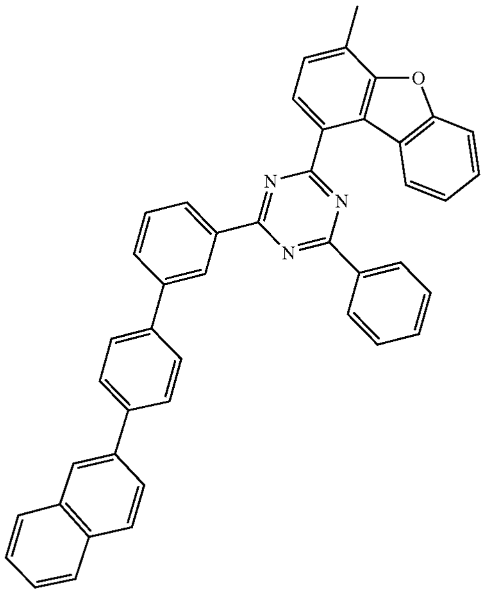
P-70
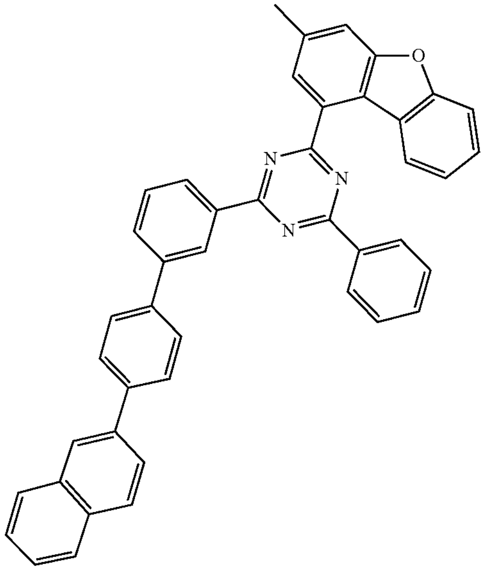
-continued
P-71
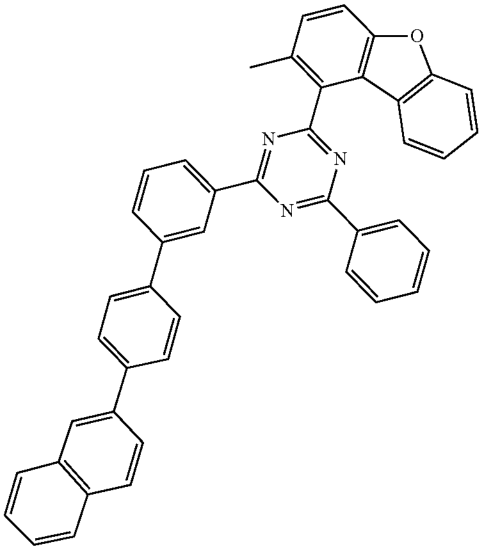
P-72
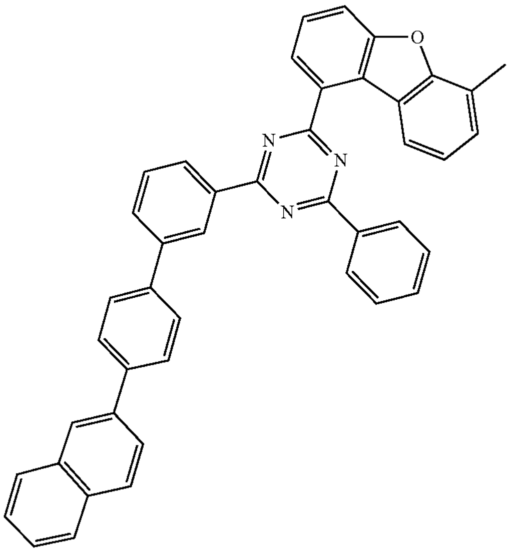

-continued
P-73
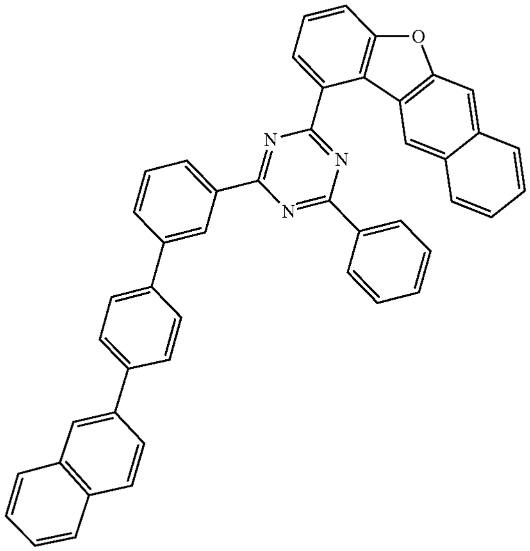
P-74
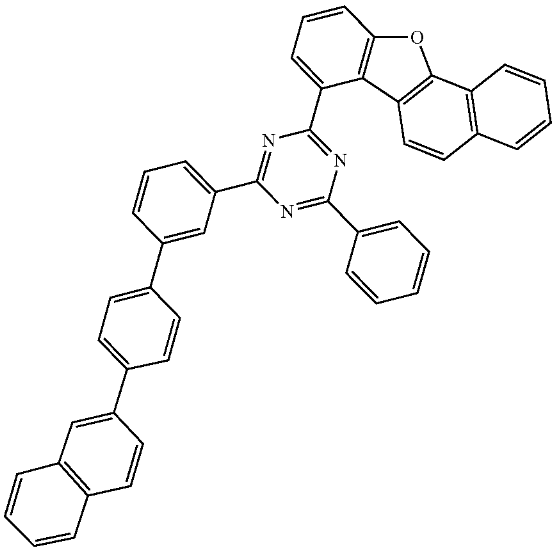
-continued
P-75
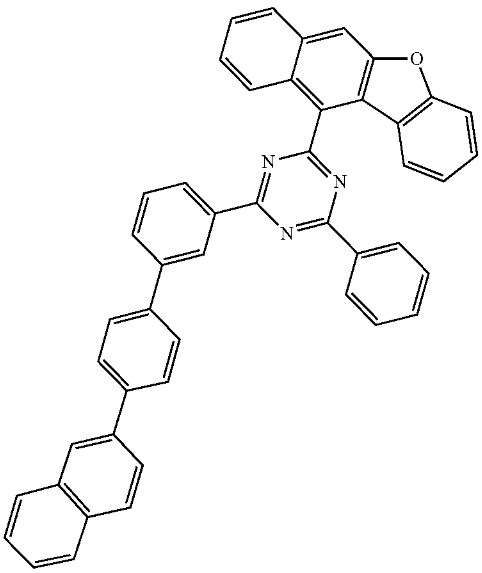
P-76
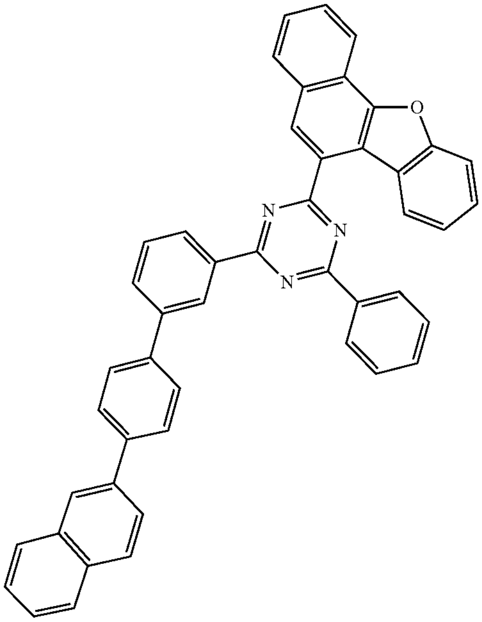

-continued
P-77
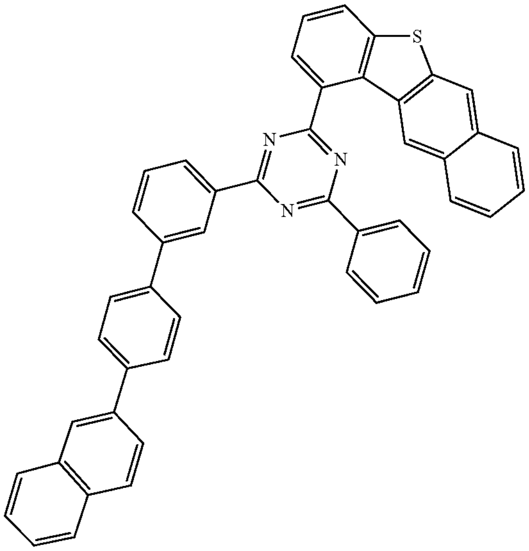
P-78
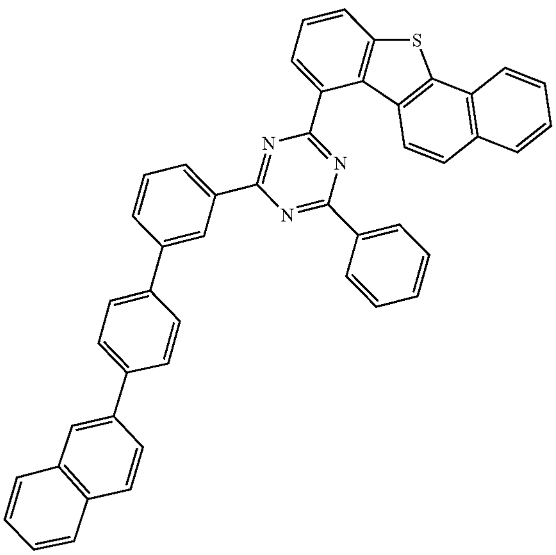
-continued
P-79
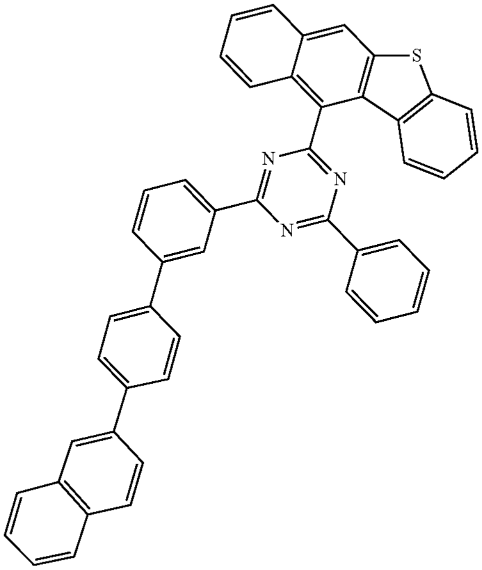
P-80
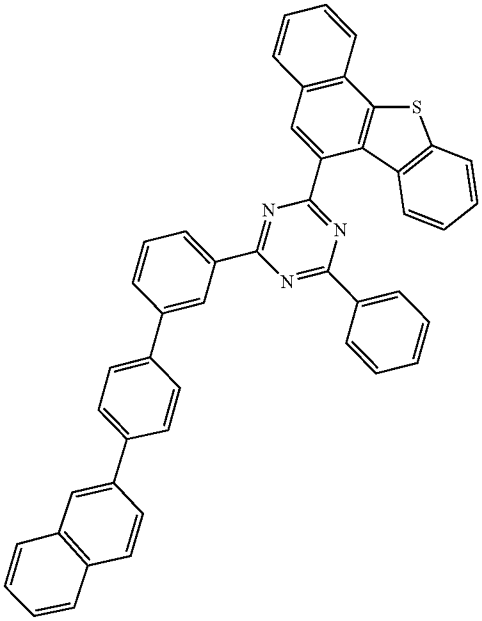

-continued
P-81
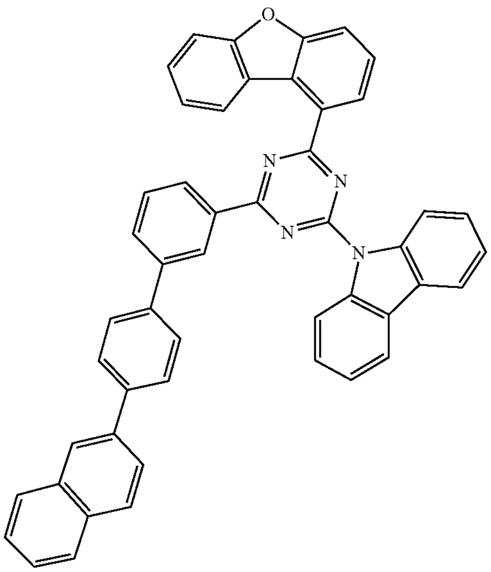
P-82
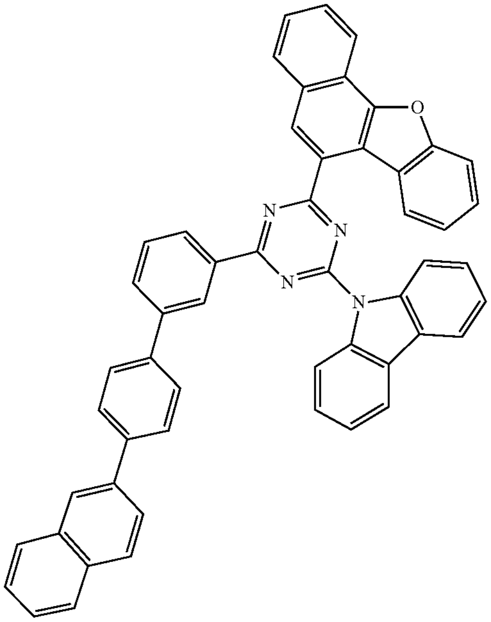
-continued
P-83
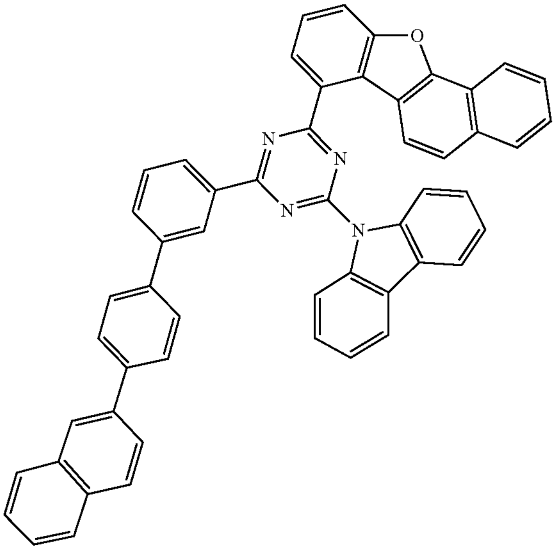
P-84
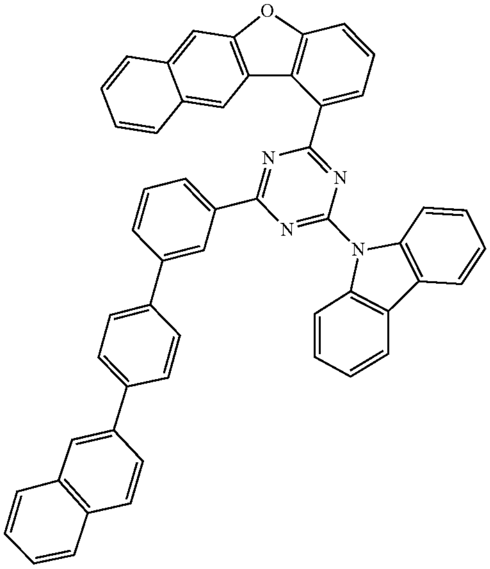

-continued
P-85
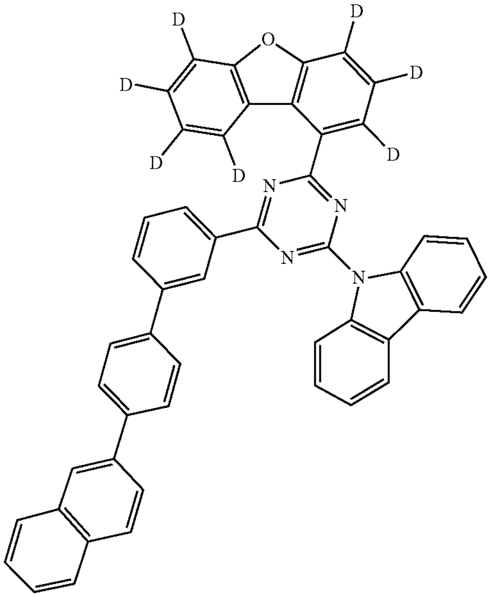
P-86
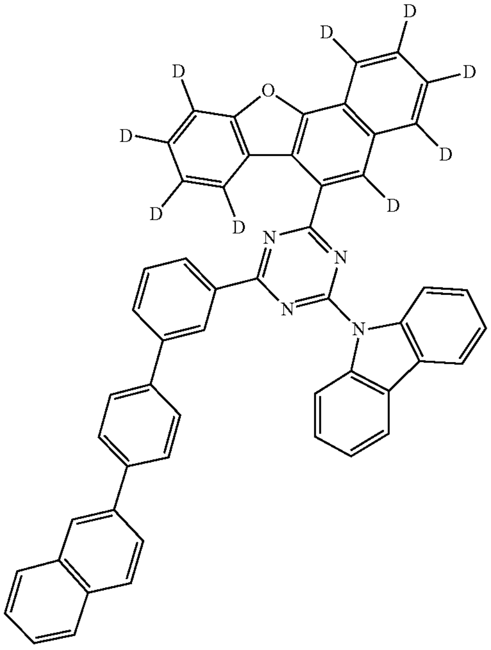
-continued
P-87
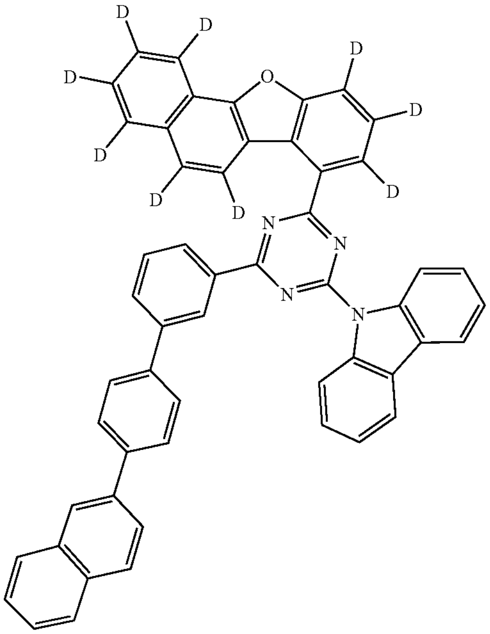
P-88
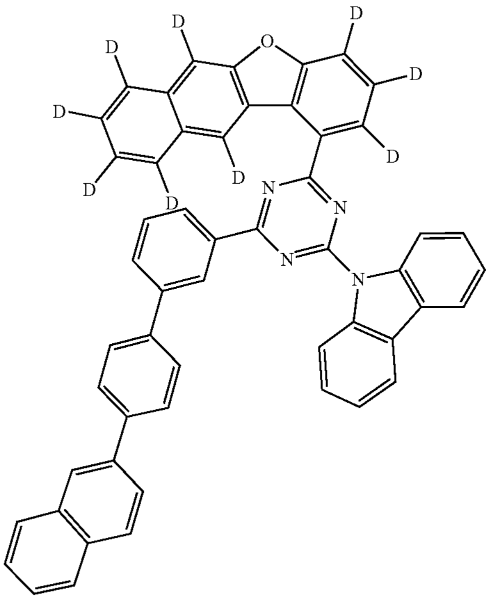

-continued
P-89
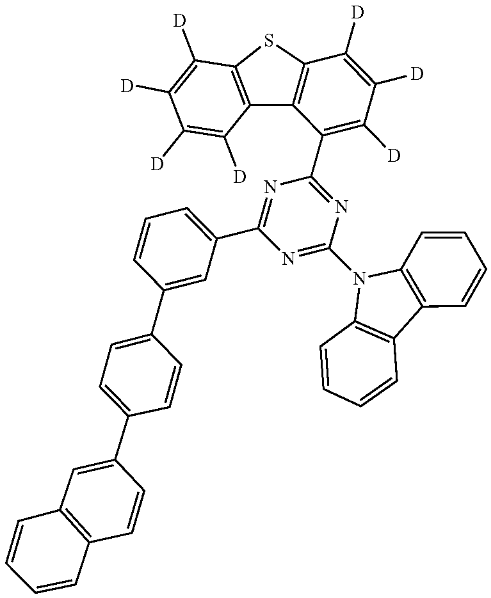
P-90
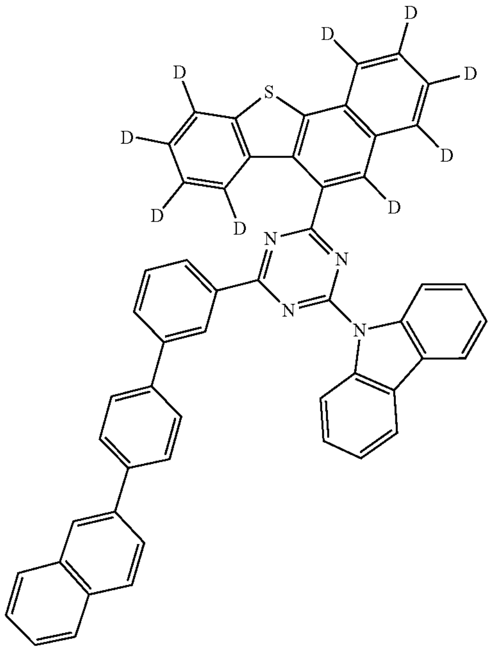
-continued
P-91
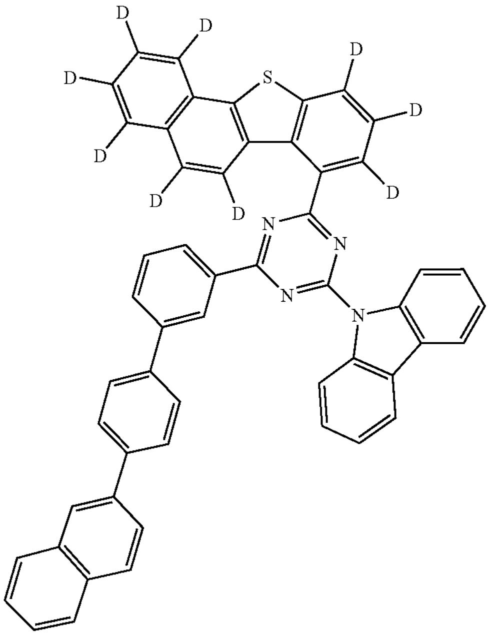
P-92
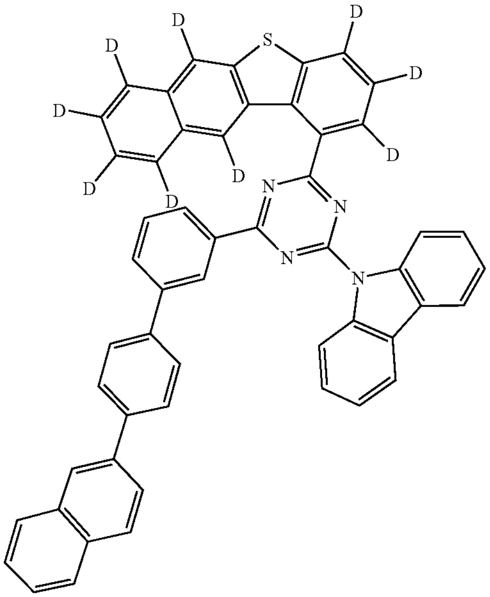

-continued
P-93
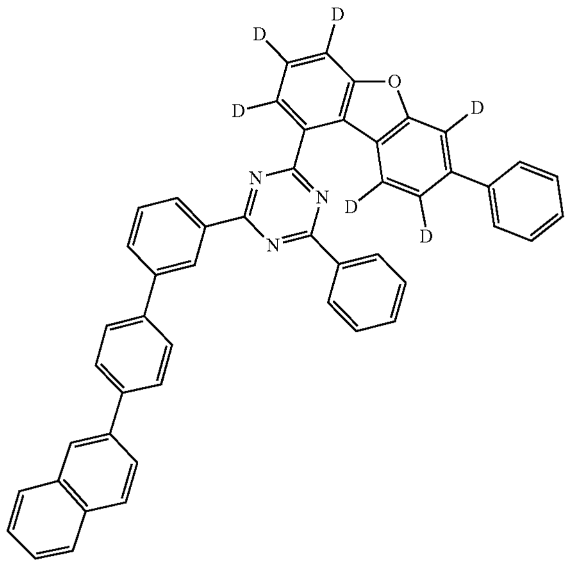
P-94
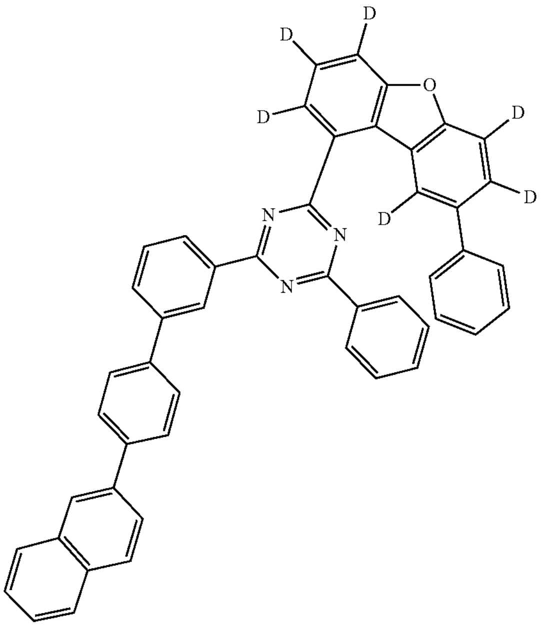
-continued
P-95
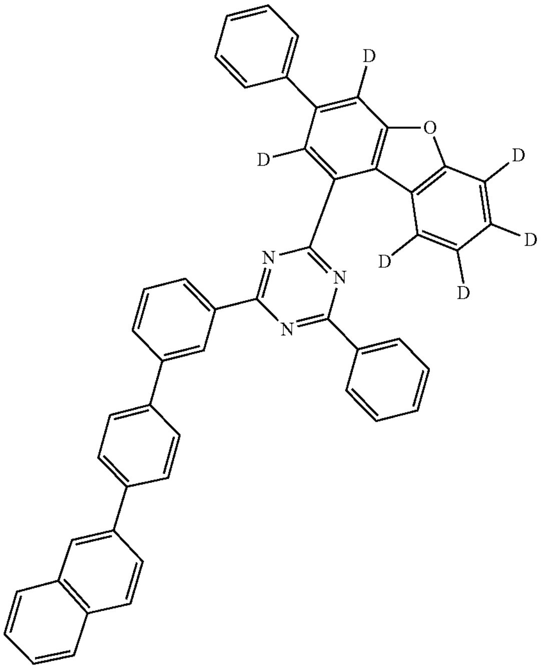
P-96
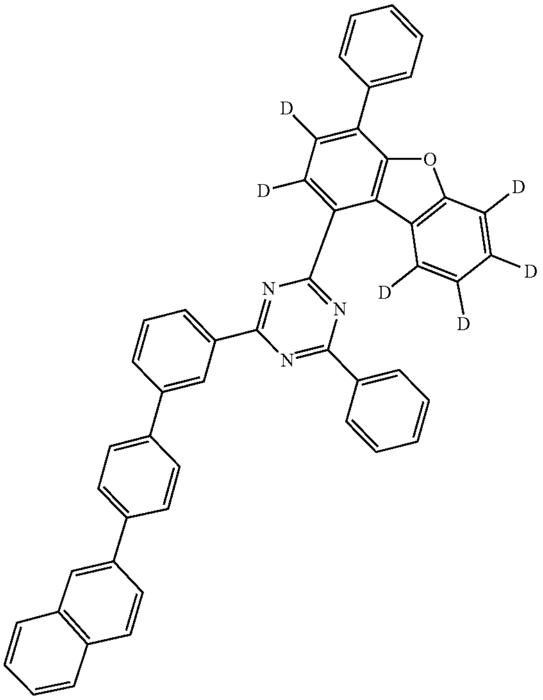

-continued
P-97
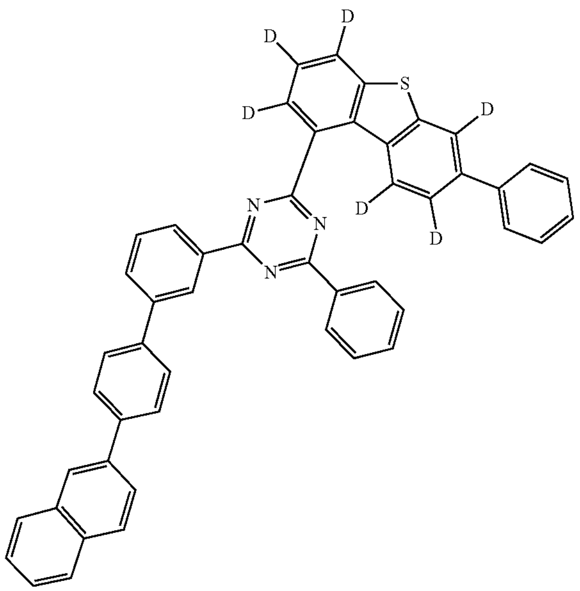
P-98
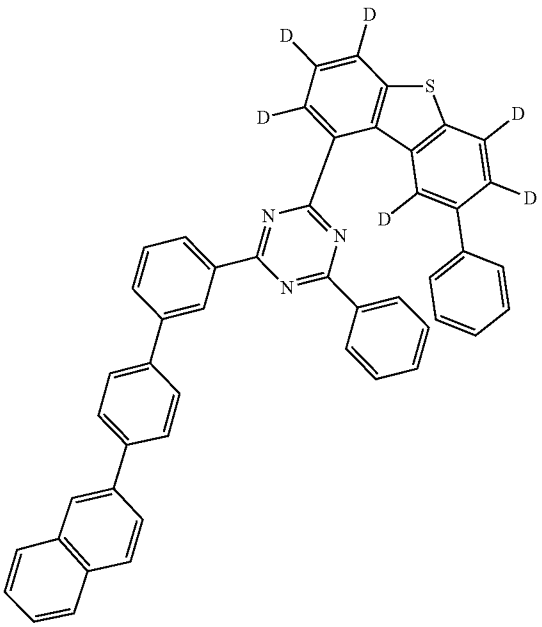
-continued
P-99
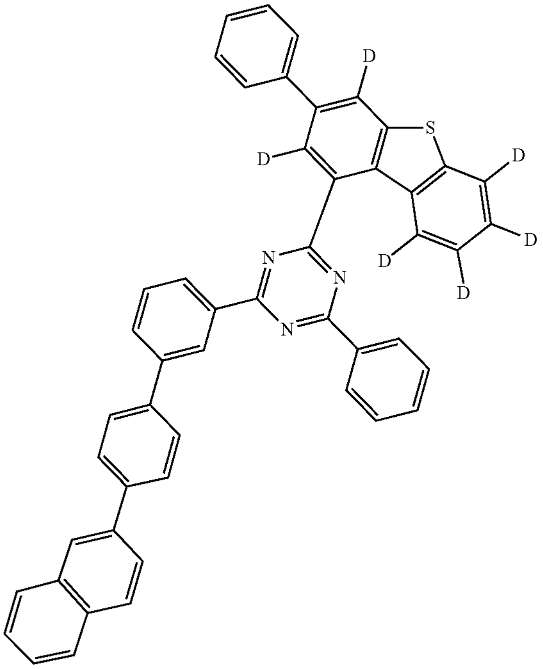
P-100
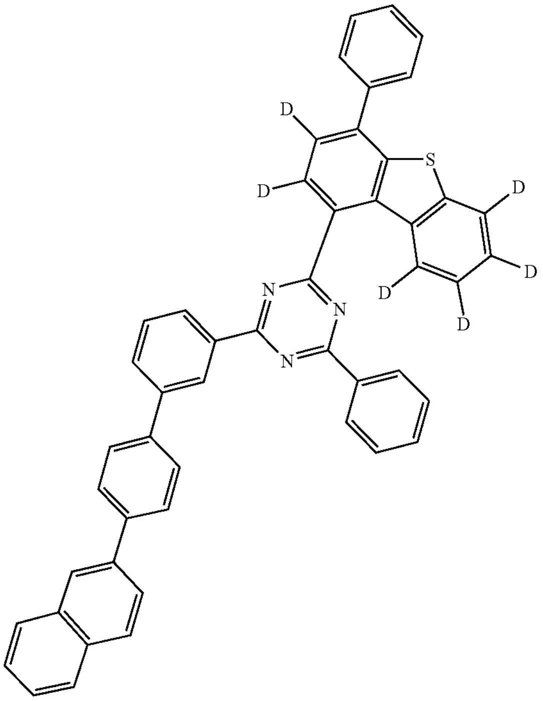

-continued
P-101
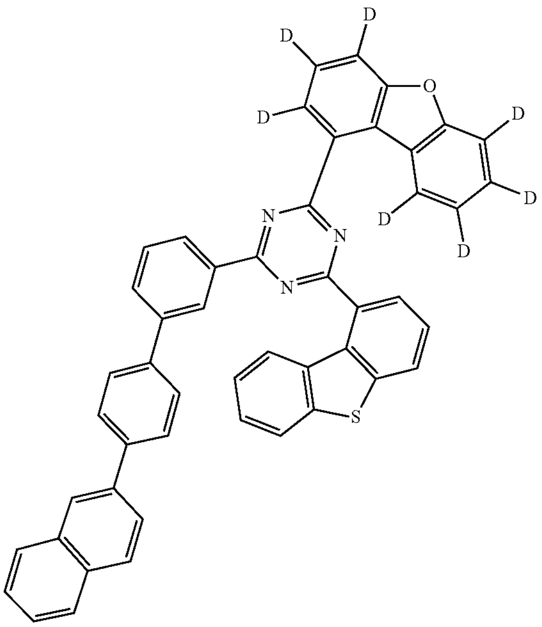
P-103
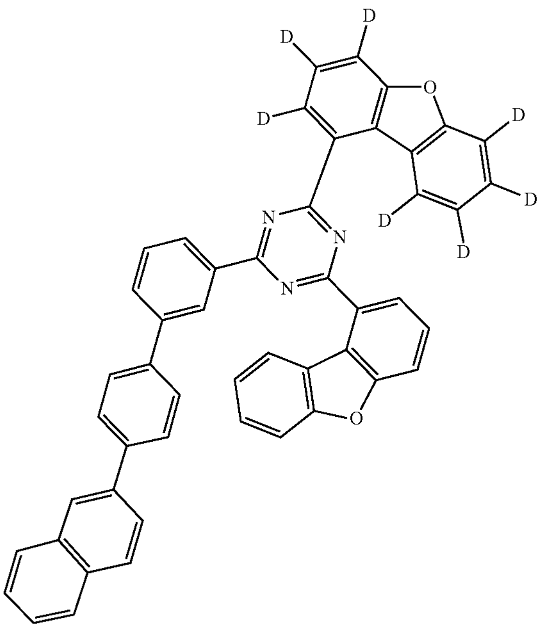
P-102
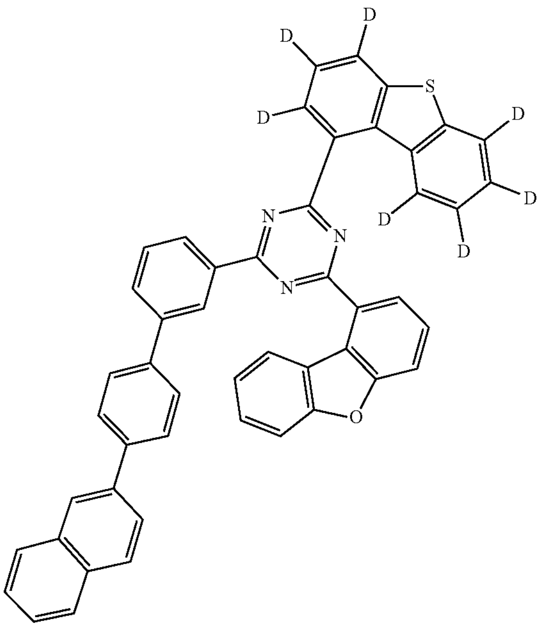
P-104
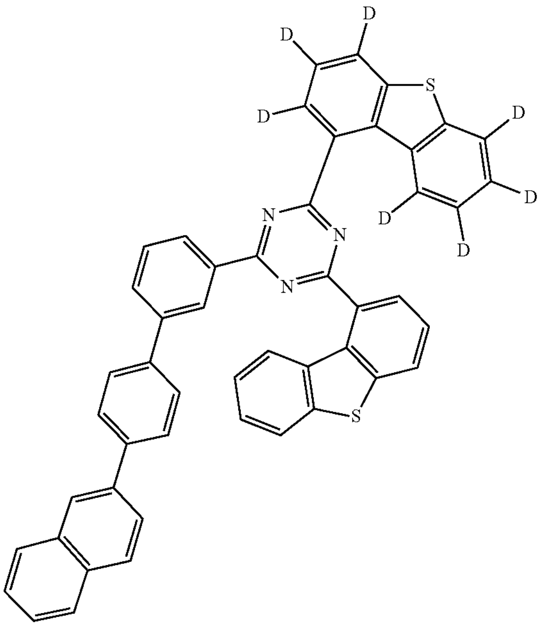

-continued

P-105

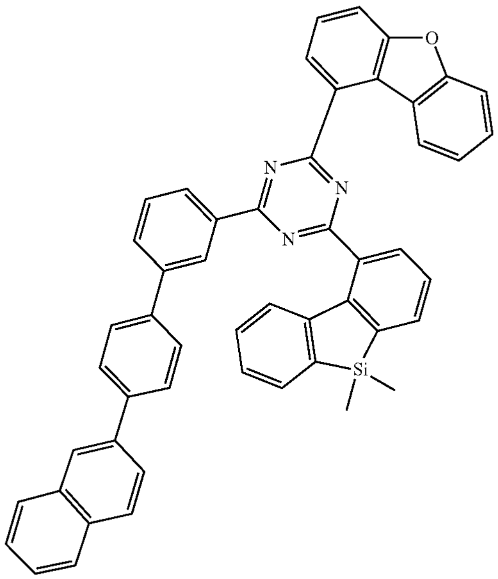

P-106

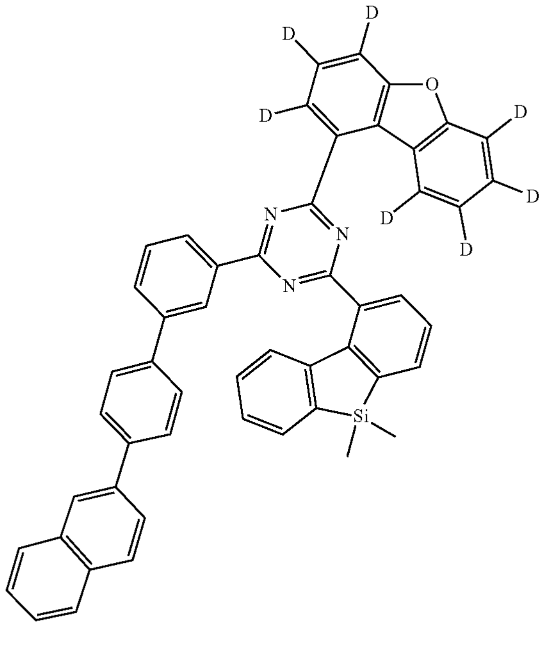

-continued

P-107

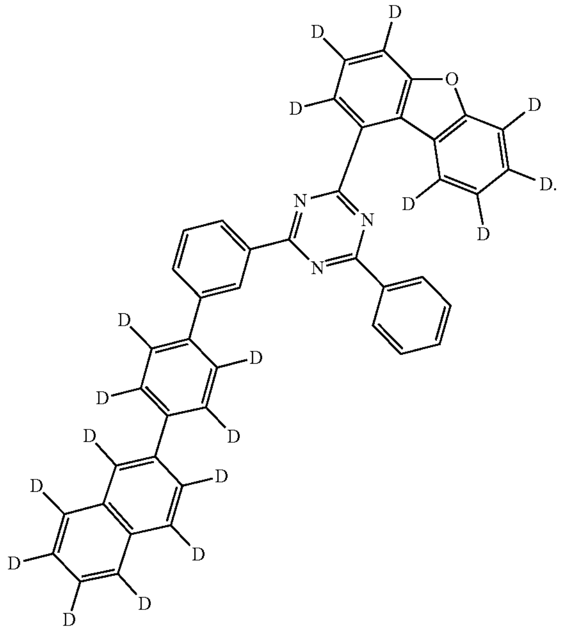

11. A method for reusing the compound represented by Formula 1 according to claim 6, comprising:

a step of depositing an organic light emitting material including the compound represented by Formula 1 in a manufacturing process of an organic light emitting device;

a step of removing impurities from the crude organic light emitting material recovered from the deposition apparatus;

a step of recovering the removed impurities; and a step of purifying the recovered impurities to a purity of 99.9% or higher.

12. The organic electronic element of claim 1, the organic electronic element further comprises a light efficiency enhancing layer formed on at least one surface of the first electrode and the second electrode, the surface being opposite to the organic material layer.

13. The organic electronic element of claim 1, wherein the organic material layer comprises 2 or more stacks comprising a hole transport layer, an emitting layer, and an electron transport layer sequentially formed on the first electrode.

14. The organic electronic element of claim 13, wherein the organic material layer further comprises a charge generation layer formed between the 2 or more stacks.

15. An electronic device comprising a display device comprising the organic electronic element of claim; and a control unit for driving the display device.

16. The electronic device according to claim 15, wherein the organic electronic element is at least one of n OLED, an organic solar cell, an organic photo conductor(OPC), organic transistor (organic TFT) and an element for monochromic or white illumination.

* * * * *